United States Patent
Altenbach et al.

(10) Patent No.: US 10,829,473 B2
(45) Date of Patent: Nov. 10, 2020

(54) MODULATORS OF THE CYSTIC FIBROSIS TRANSMEMBRANE CONDUCTANCE REGULATOR PROTEIN AND METHODS OF USE

(71) Applicants: AbbVie Overseas S.Á.R.L., Luxembourg (LU); Galapagos NV, Mechelen (BE)

(72) Inventors: Robert J. Altenbach, Chicago, IL (US); Andrew Bogdan, Evanston, IL (US); Sylvain Couty, Gentilly (FR); Nicolas Desroy, Massy (FR); Gregory A. Gfesser, Lindenhurst, IL (US); Christopher Gaëtan Housseman, Montreuil (FR); Philip R. Kym, Libertyville, IL (US); Bo Liu, Waukegan, IL (US); Thi Thu Trang Mai, Romainville (FR); Karine Fabienne Malagu, Saffron Walden (GB); Nuria Merayo Merayo, Paris (FR); Olivier Laurent Picolet, Romainville (FR); Mathieu Rafaël Pizzonero, Voisins le Bretonneaux (FR); Xenia B. Searle, Grayslake, IL (US); Steven Emiel Van der Plas, Steenhuffel (BE); Xueqing Wang, San Carlos, CA (US); Ming C. Yeung, Grayslake, IL (US)

(73) Assignees: AbbVie Overseas S.à.r.l., Luxembourg (LU); Galapagos NV, Mechelen (BE)

( * ) Notice: Subject to any disclaimer, the term of this patent is extended or adjusted under 35 U.S.C. 154(b) by 0 days.

(21) Appl. No.: 16/878,430

(22) Filed: May 19, 2020

(65) Prior Publication Data

US 2020/0277275 A1 Sep. 3, 2020

Related U.S. Application Data

(63) Continuation of application No. 16/129,458, filed on Sep. 12, 2018.

(60) Provisional application No. 62/608,846, filed on Dec. 21, 2017, provisional application No. 62/558,430, filed on Sep. 14, 2017.

(51) Int. Cl.
| | | |
|---|---|---|
| *C07D 401/04* | (2006.01) |
| *C07D 401/12* | (2006.01) |
| *C07D 401/14* | (2006.01) |
| *C07D 213/30* | (2006.01) |
| *C07D 213/64* | (2006.01) |
| *C07D 213/71* | (2006.01) |
| *C07D 215/36* | (2006.01) |
| *C07D 231/56* | (2006.01) |
| *C07D 235/28* | (2006.01) |
| *C07D 471/04* | (2006.01) |
| *A61P 1/00* | (2006.01) |
| *A61P 11/00* | (2006.01) |
| *C07C 311/45* | (2006.01) |

(52) U.S. Cl.
CPC .............. *C07D 401/04* (2013.01); *A61P 1/00* (2018.01); *A61P 11/00* (2018.01); *C07C 311/45* (2013.01); *C07D 213/30* (2013.01); *C07D 213/64* (2013.01); *C07D 213/71* (2013.01); *C07D 215/36* (2013.01); *C07D 231/56* (2013.01); *C07D 235/28* (2013.01); *C07D 401/12* (2013.01); *C07D 401/14* (2013.01); *C07D 471/04* (2013.01)

(58) Field of Classification Search
CPC .. C07D 401/04; C07D 401/12; C07D 401/14; C07D 213/30; C07D 213/64; C07D 213/71; C07D 215/35; C07D 231/56; C07D 235/28; C07D 471/04
See application file for complete search history.

(56) References Cited

U.S. PATENT DOCUMENTS

| | | | |
|---|---|---|---|
| 8,999,976 B2 | 4/2015 | Binch et al. |
| 2015/0287911 A1 | 10/2015 | Kim et al. |
| 2015/0287922 A1 | 10/2015 | Chen |
| 2016/0120841 A1 | 5/2016 | Kym et al. |

(Continued)

FOREIGN PATENT DOCUMENTS

| | | | |
|---|---|---|---|
| WO | 2005120497 A2 | 12/2005 |
| WO | 2006002421 A2 | 1/2006 |

(Continued)

OTHER PUBLICATIONS

Database CA, Database accession No. 1948.41879, XP002785989; & GB602426A, May 26, 1948, 3 pages.

(Continued)

*Primary Examiner* — Rebecca L Anderson
(74) *Attorney, Agent, or Firm* — Quarles & Brady LLP

(57) ABSTRACT

The invention discloses compounds of Formula (I),

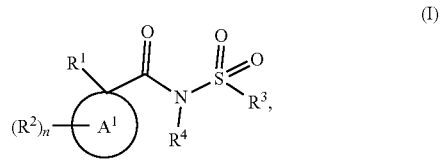

wherein $A^1$, $R^1$, $R^2$, $R^3$, $R^4$, and n are as defined herein. The present invention relates to compounds and their use in the treatment of cystic fibrosis, methods for their production, pharmaceutical compositions comprising the same, and methods of treating cystic fibrosis by administering a compound of the invention.

2 Claims, No Drawings

(56) References Cited

U.S. PATENT DOCUMENTS

| | | |
|---|---|---|
| 2016/0122331 A1 | 5/2016 | Kym et al. |
| 2017/0015675 A1 | 1/2017 | Altenbach et al. |
| 2017/0305891 A1 | 10/2017 | Altenbach et al. |
| 2018/0099931 A1 | 4/2018 | Altenbach et al. |
| 2018/0099932 A1 | 4/2018 | Altenbach et al. |

FOREIGN PATENT DOCUMENTS

| | | |
|---|---|---|
| WO | 2008127399 A2 | 10/2008 |
| WO | 2008147952 A1 | 12/2008 |
| WO | 2009074575 A2 | 6/2009 |
| WO | 2009076593 A1 | 6/2009 |
| WO | 2010048573 A1 | 4/2010 |
| WO | 2011072241 A1 | 6/2011 |
| WO | 2011113894 A1 | 9/2011 |
| WO | 2012048181 A1 | 4/2012 |
| WO | 2013038373 A1 | 3/2013 |
| WO | 2013038378 A1 | 3/2013 |
| WO | 2013038381 A1 | 3/2013 |
| WO | 2013038386 A1 | 3/2013 |
| WO | 2013038390 A1 | 3/2013 |
| WO | 2013043720 A1 | 3/2013 |
| WO | 2014180562 A1 | 11/2014 |
| WO | 2015018823 A1 | 2/2015 |
| WO | 2016193812 A1 | 12/2016 |
| WO | 2017060874 A1 | 4/2017 |
| WO | 2017208115 A1 | 12/2017 |

OTHER PUBLICATIONS

Database Registry, Database accession No. 1645455-76-0, 1645455-70-4, Feb. 8, 2015, XP002785994, 2 pages.

Database Registry, Database accession No. 1797711-38-6, Jul. 9, 2015, XP002785993, 1 page.

Database Registry, Database accession No. 1808652-56-3, Sep. 29, 2015, XP002785992, 1 page.

Database Registry, Database accession No. 2125927-23-1, 2125859-91-6, Sep. 7, 2017, XP002785991, 2 pages.

Database Registry, Database accession No. 2126568-04-3, 2126534-79-8, Sep. 8, 2017, XP002785990, 2 pages.

Enclosure to WO-ISA: Database Registry, Database accession Nos. 1436328-26-5 to 397848-28-1, Jun. 9, 2013 to Mar. 4, 2002, 5 pages.

Furniss et al., "Vogel's Textbook of Practical Organic Chemistry," 5th edition (1989), Longman Scientific & Technical, Essex CM20 2JE, England, 8 pages.

International Search Report and Written Opinion issued in corresponding International Application No. PCT/IB2018/057020, dated Nov. 12, 2018, 17 pages.

IUPAC Commission on Nomenclature of Organic Chemistry* Rules for the Nomenclature of Organic Chemistry Section E: Stereochemistry (Recommendations 1974) Pure & Appl. Chem., 1976, 45: 13-30.

Krasovskiy et al. "Convenient Titration Method for Organometallic Zinc, Magnesium, and Lanthanide Reagents" Synthesis 2006, 2006 (05), 0890-0891.

Registry No. 1333518-14-1, File Registry on STN Entered Sep. 28, 2011.

Registry No. 1371400-44-0, File Registry on STN Entered Apr. 30, 2012.

Registry No. 1625116-76-8, File Registry on STN Entered Sep. 24, 2014.

Veit G et al. (2012) "Proinflammatory cytokine secretion is suppressed by TMEM16A or CFTR channel activity in human cystic fibrosis bronchial epithelia" Mol Biol Cell. 23(21): Nov. 1, 2012, 4188-4202.

Yang et al. ""F508del-cystic fibrosis transmembrane regulator correctors for treatment of cystic fibrosis: a patent review"" Expert Opin. Ther. Patents, vol. 25, No. 9, May 14, 2015 (May 14, 2015), pp. 991-1002, XP055398070. ISSN: 1354-3776, DOI: 10.1517/13543776.2015.1045878.

MODULATORS OF THE CYSTIC FIBROSIS TRANSMEMBRANE CONDUCTANCE REGULATOR PROTEIN AND METHODS OF USE

CROSS REFERENCE TO RELATED APPLICATIONS

This application is a continuation of U.S. patent application Ser. No. 16/129,548, filed Sep. 12, 2018, which claims priority to U.S. Provisional Application No. 62/558,430, filed Sep. 14, 2017 and U.S. Provisional Application No. 62/608,846, filed Dec. 21, 2017, both of which are incorporated herein by reference for all purposes.

BACKGROUND OF THE INVENTION

Technical Field

The invention relates to substituted pyridine compounds that are modulators of the Cystic Fibrosis Transmembrane Conductance Regulator (CFTR) protein, useful in treating diseases and conditions mediated and modulated by CFTR. The invention also relates to compositions containing compounds of the invention, processes for their preparation, and methods of treatment using them.

Description of Related Technology

Cystic fibrosis (CF) is caused by a defect in genes which induce mutations in CFTR. Cystic fibrosis is the most common fatal genetic disease in humans, and affects 0.04% of white individuals, for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections. In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients. Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

In addition to cystic fibrosis, CFTR activity modulation may be beneficial for other diseases not directly caused by mutations in CFTR, such as chronic obstructive pulmonary disease (COPD), dry eye disease, and Sjögren's syndrome.

There is a need for novel compounds capable of modulating CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect the invention provides for compounds of Formula (I), and pharmaceutically acceptable salts thereof,

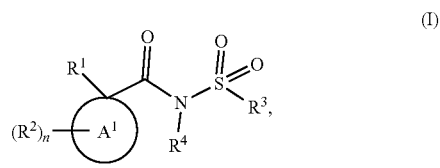

wherein
$A^1$ is selected from the group consisting of $C_3$-$C_7$ cycloalkyl, $C_4$-$C_7$ cycloalkenyl, and 4-7 membered heterocyclyl;
$R^1$ is selected from the group consisting of 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are substituted with two or more substituents independently selected from the group consisting of $R^7$, $OR^7$, $SR^7$, $C(O)R^7$, $OC(O)R^7$, $C(O)OR^7$, $SO_2R^7$, $C(O)NH_2$, $C(O)NHR^7$, $C(O)N(R^7)_2$, $NHC(O)R^7$, $NHR^7$, $N(R^7)_2$, $NH_2$, $C(O)OH$, $OH$, oxo, $CN$, $NO_2$, F, Cl, Br and I;
$R^2$ is independently selected from the group consisting of $R^8$, $OR^8$, $C(O)R^8$, $C(O)OR^8$, $SO_2R^8$, $NHR^8$, $N(R^8)_2$, $NH_2$, $C(O)OH$, $OH$, $CN$, $NO_2$, F, Cl, Br and I;
n is 0 or 1;
$R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_1$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^9$, $OR^9$, $SR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, $OH$, oxo, $CN$, $NO_2$, F, Cl, Br and I;
$R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $OR^{10}$, F, Cl, Br and I;
$R^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, $C_3$-$C_7$ cycloalkyl, OH, oxo, CN, $NO_2$, F, Cl, Br and I; wherein each $R^7$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{11}$, $OR^{11}$, $SR^{11}$, $C(O)OR^{11}$, $OC(O)R^{11}$, $C(O)R^{11}$, $SO_2R^{11}$, $C(O)NH_2$, $C(O)NHR^{11}$, $C(O)N(R^{11})_2$, $NHC(O)R^{11}$, $NHR^{11}$, $N(R^{11})_2$, $NH_2$, $C(O)OH$, OH, oxo, CN, $NO_2$, F, Cl, Br and I;

$R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{12}$, $OR^{12}$, $C(O)OR^{12}$, $NHR^{12}$, $N(R^{12})_2$, $NH_2$, $C(O)OH$, OH, CN, $NO_2$, F, Cl, Br and I;

$R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $C(O)R^{13}$, $OC(O)R^{13}$, $C(O)OR^{13}$, $SO_2R^{13}$, $C(O)NH_2$, $C(O)NHR^{13}$, $C(O)N(R^{13})_2$, $NHC(O)R^{13}$, $NHR^{13}$, $N(R^{13})_2$, $NH_2$, $C(O)OH$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{14}$, $OR^{14}$, $SR^{14}$, $C(O)R^{14}$, $OC(O)R^{14}$, $C(O)OR^{14}$, $SO_2R^{14}$, $C(O)NH_2$, $C(O)NHR^{14}$, $C(O)N(R^{14})_2$, $NHC(O)R^{14}$, $NHR^{14}$, $N(R^{14})_2$, $NH_2$, $C(O)OH$, OH, oxo, CN, $NO_2$, F, Cl, Br and I;

$R^{10}$, at each occurrence, is independently $C_1$-$C_4$ alkyl;

$R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of $C_1$-$C_6$ alkoxy, OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

$R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; $R^{13}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, cycloalkyl, $C_4$-$C_{11}$ cycloalkenyl, and 4-12 membered heterocyclyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I;

with the proviso that the compound is not 1-(3,4-dimethylphenyl)-N-(naphthalene-1-sulfonyl)cyclopentane-1-carboxamide.

These and other objects of the invention are described in the following paragraphs. These objects should not be deemed to narrow the scope of the invention.

DETAILED DESCRIPTION OF THE INVENTION

Described herein are compounds of Formula (I),

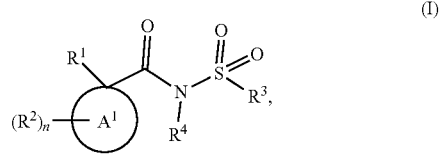

wherein $A^1$, $R^1$, $R^2$, $R^3$, $R^4$, and n are defined above in the Summary and below in the Detailed Description. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds; reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond.

The term "$C_2$-$C_6$ alkenyl" means an alkenyl group containing 2-6 carbon atoms. Non-limiting examples of $C_2$-$C_6$ alkenyl include buta-1,3-dienyl, ethenyl, 2-propenyl, 2-methyl-2-propenyl, 3-butenyl, 4-pentenyl, and 5-hexenyl.

The term "$C_1$-$C_6$ alkoxy" as used herein, means a $C_1$-$C_6$ alkyl group, as defined herein, appended to the parent molecular moiety through an oxygen atom. Non-limiting examples of alkoxy include methoxy, ethoxy, propoxy, 2-propoxy, butoxy, tert-butoxy, pentyloxy, and hexyloxy.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_4$ alkyl" means an alkyl substituent containing from 1 to 4 carbon atoms, and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl. The terms "alkyl," "$C_1$-$C_6$ alkyl," "$C_1$-$C_4$ alkyl," and "$C_1$-$C_3$ alkyl" used herein are unsubstituted, unless otherwise indicated.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —$CH_2$—, —$CH_2CH_2$—, —$C(CH_3)_2$—$CH_2CH_2CH_2$—, —$C(CH_3)_2$$CH_2CH_2$—, —$CH_2CH_2CH_2CH_2$—, and —$CH_2CH(CH_3)$$CH_2$—.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited, to acetylenyl, 1-propynyl, 2-propynyl, 3-butynyl, 2-pentynyl, and 1-butynyl.

The term "$C_3$-$C_{11}$ cycloalkyl" as used herein, means a hydrocarbon ring radical containing 3-11 carbon atoms, zero heteroatoms, and zero double bonds. The $C_3$-$C_{11}$ cycloalkyl group may be a single-ring (monocyclic) or have two or more rings (polycyclic or bicyclic). Monocyclic cycloalkyl groups typically contain from 3 to 8 carbon ring atoms ($C_3$-$C_8$ monocyclic cycloalkyl), and even more typically 3-7 carbon ring atoms ($C_3$-$C_7$ monocyclic cycloalkyl). Examples of monocyclic cycloalkyls include cyclopropyl, cyclobutyl, cyclopentyl, cyclohexyl, cycloheptyl, and cyclooctyl. Polycyclic cycloalkyl groups contain two or more rings, and bicyclic cycloalkyls contain two rings. In certain embodiments, the polycyclic cycloalkyl groups contain 2 or 3 rings. The rings within the polycyclic and the bicyclic cycloalkyl groups may be in a bridged, fused, or spiro orientation, or combinations thereof. In a spirocyclic cycloalkyl, one atom is common to two different rings. Examples of a spirocyclic cycloalkyl include spiro[2.5]octanyl and spiro[4.5]decanyl. In a bridged cycloalkyl, the rings share at least two non-adjacent atoms. Examples of bridged cycloalkyls include, but are not limited to bicyclo[1.1.1]pentanyl, bicyclo[2.2.2]octyl, bicyclo[3.2.1]octyl, bicyclo[3.1.1]heptyl, bicyclo[2.2.1]heptyl, bicyclo[3.2.2]nonyl, bicyclo[3.3.1]nonyl, and bicyclo[4.2.1]nonyl, tricyclo[3.3.1.0$^{3,7}$]nonyl (octahydro-2,5-methanopentalenyl or noradamantyl), tricyclo[3.3.1.1$^{3,7}$]decyl (adamantyl), and tricyclo[3.1.1$^{3,7}$]undecyl (homoadamantyl). In a fused ring cycloalkyl, the rings share one common bond. Examples of fused-ring cycloalkyl include, but are not limited to, decalin (decahydronaphthyl), bicyclo[3.1.0]hexanyl, and bicyclo[2.2.0]octyl.

The term "$C_3$-$C_7$ cycloalkyl" as used herein, means a hydrocarbon ring radical containing 3-7 carbon atoms, zero heteroatoms, and zero double bonds. The $C_3$-$C_7$ cycloalkyl group may be a single-ring (monocyclic) or have two rings (bicyclic).

The term "$C_4$-$C_{11}$ cycloalkenyl" as used herein, means a non-aromatic hydrocarbon ring radical containing 4-11 carbon atoms, zero heteroatoms, and one or more double bonds. The $C_4$-$C_{11}$ cycloalkenyl group may be a single-ring (monocyclic) or have two or more rings (polycyclic or bicyclic). Examples of monocyclic cycloalkenyl include cyclobutenyl, cyclopentenyl, cyclohexenyl, cyclohexadienyl, cycloheptyl, cyclooctenyl, and cyclooctadienyl. Examples of bicyclic cycloalkenyl include bicyclo[2.2.1]hept-2-enyl.

The term "$C_4$-$C_8$ monocyclic cycloalkenyl" as used herein, means cyclobutenyl, cyclopentenyl, cyclohexenyl, cyclohexadienyl, cycloheptenyl, cycloheptadienyl, cyclooctenyl, and cyclooctadienyl.

The term "$C_4$-$C_7$ monocyclic cycloalkenyl" as used herein, means cyclobutenyl, cyclopentenyl, cyclohexenyl, cyclohexadienyl, and cycloheptyl.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "4-12 membered heterocyclyl" as used herein, means a hydrocarbon ring radical of 4-12 carbon ring atoms wherein at least one carbon atom is replaced by a heteroatom(s) independently selected from the group consisting of 0, N, and S. The 4-12 membered heterocycle ring may be a single ring (monocyclic) or have two or more rings (bicyclic or polycyclic). In certain embodiments, the monocyclic heterocycle is a four-, five-, six-, seven-, or eight-membered hydrocarbon ring wherein at least one carbon ring atom is replaced by a heteroatom(s) independently selected from the group consisting of 0, N, and S. In certain embodiments, the monocyclic heterocycle is a 4-7 membered hydrocarbon ring wherein at least one carbon ring atom is replaced by a heteroatom(s). A four-membered monocyclic heterocycle contains zero or one double bond, and one heteroatom selected from the group consisting of 0, N, and S. A five-membered monocyclic heterocycle contains zero or one double bond and one, two, or three heteroatoms selected from the group consisting of 0, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, imidazolidinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of six-membered monocyclic heterocycles include dihydropyranyl, 1,4-dioxanyl, 1,3-dioxanyl, 1,4-dithianyl, hexahydropyrimidine, morpholinyl, 1,4-dihydropyridinyl, piperazinyl, piperidinyl, tetrahydropyranyl, 1,2,3,6-tetrahydropyridinyl, tetrahydrothiopyranyl, thiomorpholinyl, thioxanyl, and trithianyl. Seven- and eight-membered monocyclic heterocycles contains zero, one, two, or three double bonds and one, two, or three heteroatoms selected from the group consisting of O, N, and S. Examples of monocyclic heterocycles include, but are not limited to, azetidinyl, azepanyl, aziridinyl, 1,4-diazepanyl, dihydropyranyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxazepanyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. Polycyclic heterocycle groups contain two or more rings, and bicyclic heterocycles contain two rings. In certain embodiments, the polycyclic heterocycle groups contain 2 or 3 rings. The rings within the polycyclic and the bicyclic heterocycle groups may be in a bridged, fused, or spiro orientation, or combinations thereof. In a spirocyclic heterocycle, one atom is common to two different rings. Non limiting examples of the spirocyclic heterocycle include 6-oxaspiro[2.5]octanyl, 2-azaspiro[3.3]heptyl, 5-azaspiro[2.4]heptyl, 5-azaspiro[2.5]octyl, 2-azaspiro[3.5]nonyl, 2-azaspiro[3.4]octyl, 3-azaspiro[5.5]undecyl, 5-azaspiro[3.4]octyl, 2-oxaspiro[3.3]heptyl, 2-oxa-6-azaspiro[3.3]heptyl, 6-oxa-2-azaspiro[3.4]octyl, 6-azaspiro[3.4]octyl, 7-azaspiro[3.5]nonyl, 8-azaspiro[4.5]decyl, 1-oxa-7-azaspiro[4.4]nonyl, 1-oxa-7-azaspiro[3.5]nonyl, 1-oxa-8-azaspiro[4.5]decyl, 1-oxa-3,8-diazaspiro[4.5]decyl, 1-oxa-4,9-diazaspiro[5.5]undecyl, 2-oxa-7-azaspiro[3.5]nonyl, 5-oxa-2-azaspiro[3.5]nonyl, 6-oxa-2-azaspiro[3.5]nonyl, 7-oxa-2-azaspiro[3.5]nonyl, 8-oxa-2-azaspiro[4.5]decyl, 2,7-diazaspiro[4.4]nonyl, 1,4-dioxa-8-azaspiro[4.5]decyl, 1,3,8-triazaspiro[4.5]decyl. In a fused ring heterocycle, the rings share one common bond. Examples of fused bicyclic heterocycles are a 4-6 membered monocyclic heterocycle fused to a phenyl group, or a 4-6 membered monocyclic heterocycle fused to a $C_3$-$C_6$ monocyclic cycloalkyl, or a 4-6 membered monocyclic heterocycle fused to a $C_4$-$C_7$ monocyclic cycloalkenyl, or a 4-6 membered monocyclic heterocycle fused to a 4-7 membered monocyclic heterocycle. Examples of fused bicyclic heterocycles include, but are not limited to, 1,2-dihydrophthalazinyl, 3,4-dihydro-2H-benzo[b][1,4]dioxepinyl, chromanyl, chromenyl, isochromanyl, 2,3-dihydrobenzo[b][1,4]dioxinyl, isoindolinyl, 2,3-dihydrobenzo[b]thienyl, hexahydro-1H-cyclopenta[c]furanyl, 3-oxabicyclo[3.1.0]hexanyl, 3-azabicyclo[3.1.0]hexyl, benzopyranyl, benzothiopyranyl, indolinyl, decahydropyrrolo[3,4-b]azepinyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl, hexahydropyrrolo[3,4-c]pyrrol-2(1H)-yl, hexahydrocyclopenta[c]pyrrol-3a(1H)-yl, hexahydro-1H-oxazolo[3,4-a]pyrazinyl, octahydropyrrolo[3,4-b][1,4]oxazinyl, octahydroimidazo[1,5-a]pyrazinyl, octahydropyrrolo[1,2-a]pyrazinyl, octahydro-1H-pyrrolo[3,2-c]pyridinyl, and octahydropyrrolo[3,4-c]pyrrolyl. In a bridged heterocycle, the rings share at least two non-adjacent atoms. Examples of such bridged heterocycles include, but are not limited to, 8-oxabicyclo[3.2.1]octanyl, 7-oxabicyclo[2.2.1]heptanyl, azabicyclo[2.2.1]heptyl (including 2-azabicyclo[2.2.1]hept-2-yl), 8-azabicyclo[3.2.1]oct-8-yl, octahydro-2,5-epoxypentalene, 8-oxa-3-azabicyclo[3.2.1]octyl, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quaternized. Non limiting examples of the polycyclic heterocycle include 6,7-dihydro-[1,3]dioxolo[4,5-f]benzofuranyl.

The term "4-7 membered heterocyclyl" as used herein, means a hydrocarbon ring radical of 4-7 carbon ring atoms wherein at least one carbon atom is replaced by a heteroatom(s) independently selected from the group consisting of 0, N, and S.

The term "5-11 membered heteroaryl" as used herein, means a monocyclic heteroaryl and a bicyclic heteroaryl. The "5-6 membered heteroaryl" is a five- or six-membered ring. The five-membered ring contains two double bonds. The five membered ring may contain one heteroatom selected from 0 or S; or one, two, three, or four nitrogen atoms and optionally one oxygen or one sulfur atom. The six-membered ring contains three double bonds and one, two, three or four nitrogen atoms. Examples of 5-6 membered monocyclic heteroaryl include, but are not limited to, furanyl, imidazolyl, isoxazolyl, isothiazolyl, oxadiazolyl, 1,3-oxazolyl, pyridazinonyl, pyridinonyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a $C_3$-$C_6$ monocyclic cycloalkyl, or a monocyclic heteroaryl fused to $C_4$-$C_7$ monocyclic cycloalkenyl, or a monocyclic heteroaryl fused to a monocyclic heteroaryl, or a monocyclic heteroaryl fused to a 4-7 membered monocyclic heterocycle. Representative examples of bicyclic heteroaryl groups include, but are not limited to, 4H-furo[3,2-b]pyrrolyl, benzofuranyl, benzothienyl, benzoisoxazolyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 4,5,6,7-tetrahydropyrazolo[1,5-a]pyridinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The nitrogen atom in the heteroaryl rings may optionally be oxidized and may optionally be alkylated.

The term "6-10 membered aryl", as used herein, means a hydrocarbon ring radical containing 6-10 carbon atoms, zero heteroatoms, and one or more aromatic rings. The 6-10 membered aryl group may be a single-ring (monocyclic) or have two rings (bicyclic). The bicyclic aryl is naphthyl, or a phenyl fused to a monocyclic cycloalkyl, or a phenyl fused to a monocyclic cycloalkenyl. Representative examples of 6-10 membered aryl groups include, but are not limited to, phenyl, indenyl, tetrahydronaphthalenyl, dihydroindenyl (indanyl), naphthyl, and the like.

The aryls, the cycloalkyls, the cycloalkenyls, the heterocycles, and the heteroaryls, including the exemplary rings, are optionally substituted unless otherwise indicated; and are attached to the parent molecular moiety through any substitutable atom contained within the ring system.

The term "heteroatom" as used herein, means a nitrogen, oxygen, and sulfur.

The term "oxo" as used herein, means a =O group.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population.

The term "subject" is defined herein to refer to a human or patient. The terms "human," "patient," and "subject" are used interchangeably herein.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G, G1349D, S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10 kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326delITC, or 4279insA mutations. More particularly, Class VI mutation(s) refers to Rescued F508del mutations.

Compounds

Compounds of the invention have the general Formula (I) as described above.

Particular values of variable groups are as follows. Such values may be used where appropriate with any of the other values, definitions, claims or embodiments defined hereinbefore or hereinafter.

Certain embodiments pertain to compounds of Formula (I),

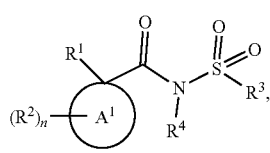

wherein
- $A^1$ is selected from the group consisting of $C_3$-$C_7$ cycloalkyl, $C_4$-$C_7$ cycloalkenyl, and 4-7 membered heterocyclyl;
- $R^1$ is selected from the group consisting of 6-10 membered aryl, 5-11 membered heteroaryl, $C_3$-$C_{11}$ cycloalkyl, cycloalkenyl, and 4-12 membered heterocyclyl; wherein the $R^1$ 6-10 membered aryl, 5-11 membered heteroaryl, $C_3$-$C_{11}$ cycloalkyl, cycloalkenyl, and 4-12 membered heterocyclyl are substituted with two or more substituents independently selected from the group consisting of $R^7$, $OR^7$, $SR^7$, $C(O)R^7$, $OC(O)R^7$, $C(O)OR^7$, $SO_2R^7$, $C(O)NH_2$, $C(O)NHR^7$, $C(O)N(R^7)_2$, $NHC(O)R^7$, $NHR^7$, $N(R^7)_2$, $NH_2$, $C(O)OH$, OH, oxo, CN, $NO_2$, F, Cl, Br and I;
- $R^2$ is independently selected from the group consisting of $R^8$, $OR^8$, $C(O)R^8$, $C(O)OR^8$, $SO_2R^8$, $NHR^8$, $N(R^8)_2$, $NH_2$, $C(O)OH$, OH, CN, $NO_2$, F, Cl, Br and I;
- n is 0 or 1;
- $R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_1$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^9$, $OR^9$, $SR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, OH, oxo, CN, $NO_2$, F, Cl, Br and I;
- $R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $OR^{10}$, F, Cl, Br and I;
- $R^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, $C_3$-$C_7$ cycloalkyl, OH, oxo, CN, $NO_2$, F, Cl, Br and I; wherein each $R^7$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{11}$, $OR^{11}$, $SR^{11}$, $C(O)OR^{11}$, $OC(O)R^{11}$, $C(O)R^{11}$, $SO_2R^{11}$, $C(O)NH_2$, $C(O)NHR^{11}$, $C(O)N(R^{11})_2$, $NHC(O)R^{11}$, $NHR^{11}$, $N(R^{11})_2$, $NH_2$, $C(O)OH$, OH, oxo, CN, $NO_2$, F, Cl, Br and I; at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{12}$, $OR^{12}$, $C(O)OR^{12}$, $NHR^{12}$, $N(R^{12})_2$, $NH_2$, $C(O)OH$, OH, CN, $NO_2$, F, Cl, Br and I;
- $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $C(O)R^{13}$, $OC(O)R^{13}$, $C(O)OR^{13}$, $SO_2R^{13}$, $C(O)NH_2$, $C(O)NHR^{13}$, $C(O)N(R^{13})_2$, $NHC(O)R^{13}$, $NHR^{13}$, $N(R^{13})_2$, $NH_2$, $C(O)OH$, OH, oxo, CN, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{14}$, $OR^{14}$, $SR^{14}$, $C(O)R^{14}$, $OC(O)R^{14}$, $C(O)OR^{14}$, $SO_2R^{14}$, $C(O)NH_2$, $C(O)NHR^{14}$, $C(O)N(R^{14})_2$, $NHC(O)R^{14}$, $NHR^{14}$, $N(R^{14})_2$, $NH_2$, $C(O)OH$, OH, oxo, CN, $NO_2$, F, Cl, Br and I;
- $R^{10}$, at each occurrence, is independently $C_1$-$C_4$ alkyl;
- $R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of $C_1$-$C_6$ alkoxy, OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;
- $R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl;
- $R^{13}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, cycloalkyl, $C_4$-$C_{11}$ cycloalkenyl, and 4-12 membered heterocyclyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I;

with the proviso that the compound is not 1-(3,4-dimethylphenyl)-N-(naphthalene-1-sulfonyl)cyclopentane-1-carboxamide.

In one embodiment of Formula (I), $A^1$ is selected from the group consisting of $C_3$-$C_7$ cycloalkyl, $C_4$-$C_7$ cycloalkenyl, and 4-7 membered heterocyclyl. In another embodiment of Formula (I), $A^1$ is $C_3$-$C_7$ cycloalkyl. In another embodiment of Formula (I), $A^1$ is $C_4$-$C_7$ cycloalkenyl. In another embodiment of Formula (I), $A^1$ is 4-7 membered heterocyclyl. In another embodiment of Formula (I), $A^1$ is cyclopropyl or cyclobutyl. In another embodiment of Formula (I), $A^1$ is cyclopropyl. In another embodiment of Formula (I), $A^1$ is cyclobutyl. In another embodiment of Formula (I), $A^1$ is cyclopentyl. In another embodiment of Formula (I), $A^1$ is tetrahydropyranyl. In another embodiment of Formula (I), $A^1$ is piperidinyl.

In one embodiment of Formula (I), $R^1$ is selected from the group consisting of 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are substituted with two or more substituents independently selected from the group consisting of $R^7$, $OR^7$, $SR^7$, $C(O)R^7$, $OC(O)R^7$, $C(O)OR^7$, $SO_2R^7$, $C(O)NH_2$, $C(O)NHR^7$, $C(O)N(R^7)_2$, $NHC(O)R^7$, $NHR^7$, $N(R^7)_2$, $NH_2$, $C(O)OH$, OH, oxo, CN, $NO_2$, F, Cl, Br and I. In another embodiment of Formula (I), $R^1$ is selected from the group consisting of 6-10 membered aryl, 5-11 membered heteroaryl, and 4-12 membered heterocyclyl; wherein the R' 6-10 membered aryl, 5-11 membered heteroaryl, and 4-12 membered heterocyclyl are substituted with two or more substituents independently selected from the group consisting of $R^7$, $OR^7$, $C(O)OR^7$, $N(R^7)_2$, CN, F, Cl, and Br. In another embodiment of Formula (I), $R^1$ is 6-10 membered aryl; wherein the $R^1$ 6-10 membered aryl is substituted with two or more substituents independently selected from the group consisting of $R^7$, $OR^7$, $C(O)OR^7$, $N(R^7)_2$, CN, F, Cl, and Br. In another embodiment of Formula (I), $R^1$ is 5-11 membered heteroaryl; wherein the $R^1$ 5-11 membered heteroaryl is substituted with two or more substituents independently selected from the group consisting of $R^7$, $OR^7$, $C(O)OR^7$, $N(R^7)_2$, $NH_2$, CN, F, Cl, and Br. In another embodiment of Formula (I), $R^1$ is 4-12 membered heterocyclyl; wherein the $R^1$ 4-12 membered heterocyclyl is substituted with two or more substituents independently selected from the group consisting of $R^7$, $OR^7$, $C(O)OR^7$, $N(R^7)_2$, $NH_2$, CN, F, Cl, and Br. In another embodiment of Formula (I), $R^1$ is phenyl; wherein the $R^1$ phenyl is substituted with two or more substituents independently selected from the group consisting of $R^7$, $OR^7$, $C(O)OR^7$, $N(R^7)_2$, $NH_2$, CN, F, Cl, and Br. In another embodiment of Formula (I), $R^1$ is selected from the group consisting of pyrazolyl, pyridinyl, quinolinyl, pyrimidinyl, and benzo[d][1,3]dioxolyl; wherein the $R^1$ pyrazolyl, pyridinyl, quinolinyl, pyrimidinyl, and benzo[d][1,3]dioxolyl are substituted with two or more substituents independently selected from the group consisting of $R^7$, $OR^7$, $C(O)OR^7$, $N(R^7)_2$, $NH_2$, CN, F, Cl, and Br.

In one embodiment of Formula (I), n is 0 or 1; and $R^2$ is independently selected from the group consisting of $R^8$, $OR^8$, $C(O)R^8$, $C(O)OR^8$, $SO_2R^8$, $NHR^8$, $N(R^8)_2$, $NH_2$, $C(O)OH$, OH, CN, $NO_2$, F, Cl, Br and I. In another embodiment of Formula (I), n is 1; and $R^2$ is independently selected from the group consisting of $R^8$ and $C(O)OR^8$. In another embodiment of Formula (I), n is 0. In another embodiment of Formula (I), n is 1; and $R^2$ is independently $R^8$. In another embodiment of Formula (I), n is 1; and $R^2$ is independently $C(O)OR^8$. In another embodiment of Formula (I), n is 1; and $R^2$ is independently $R^8$; and $R^8$ is independently $C_1$-$C_6$ alkyl. In another embodiment of Formula (I), n is 1; and $R^2$ is independently $C(O)OR^8$; and $R^8$ is independently $C_1$-$C_6$ alkyl.

In one embodiment of Formula (I), $R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_1$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^9$, $OR^9$, $SR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, OH, oxo, CN, $NO_2$, F, Cl, Br and I. In another embodiment of Formula (I), $R^3$ is selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein the $R^3$ $C_1$-$C_6$ alkyl is optionally substituted with one or more substituents independently selected from the group consisting of phenyl, F, and Cl; wherein the $R^3$ 6-10 membered aryl, 5-11 membered heteroaryl, $C_3$-$C_{11}$ cycloalkyl, and 4-12 membered heterocyclyl are optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br.

In another embodiment of Formula (I), $R^3$ is $C_1$-$C_6$ alkyl; wherein the $R^3$ $C_1$-$C_6$ alkyl is optionally substituted with one or more substituents independently selected from the group consisting of phenyl, F, and Cl. In another embodiment of Formula (I), $R^3$ is 6-10 membered aryl; wherein the $R^3$ 6-10 membered aryl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (I), $R^3$ is 5-11 membered heteroaryl; wherein the $R^3$ 5-11 membered heteroaryl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (I), $R^3$ is $C_3$-$C_{11}$ cycloalkyl; wherein the $R^3$ $C_3$-$C_{11}$ cycloalkyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (I), $R^3$ is 4-12 membered heterocyclyl; wherein the $R^3$ 4-12 membered heterocyclyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (I), $R^3$ is phenyl; wherein the $R^3$ phenyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (I), $R^3$ is napthyl; wherein the $R^3$ napthyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (I), $R^3$ is quinolinyl; wherein the $R^3$ quinolinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (I), $R^3$ is tetrahydroquinolinyl; wherein the $R^3$ tetrahydroquinolinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (I), $R^3$ is indazolyl; wherein the $R^3$ indazolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (I), $R^3$ is pyrazolo[1,5-a]pyridinyl; wherein the $R^3$ pyrazolo[1,5-a]pyridinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (I), $R^3$ is indolyl; wherein the $R^3$ indolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (I), $R^3$ is benzoimidazolyl; wherein the $R^3$ benzoimidazolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$.

In one embodiment of Formula (I), $R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $OR^{10}$, F, Cl, Br and I. In another embodiment of Formula (I), $R^4$ is selected from the group consisting of hydrogen and $C_1$-$C_6$ alkyl. In another embodiment of Formula (I), $R^4$ is hydrogen. In another embodiment of Formula (I), $R^4$ is $C_1$-$C_6$ alkyl. In another embodiment of Formula (I), $R^4$ is $CH_3$.

In one embodiment of Formula (I), $R^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, cycloalkyl, $C_4$-$C_{11}$ cycloalkenyl, and 4-12 membered heterocyclyl; wherein each 12_$^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, $C_3$-$C_7$ cycloalkyl, OH, oxo, CN, $NO_2$, F, Cl, Br and I; wherein each $R^7$ 6-10 membered aryl, 5-11 membered heteroaryl, cycloalkyl, $C_4$-$C_{11}$ cycloalkenyl, and 4-12 membered heterocyclyl is optionally substituted with one or more substituents independently selected from the group consisting of $R^{11}$, $OR^{11}$, $SR^{11}$, $C(O)R^{11}$, $OC(O)R^{11}$, $C(O)OR^{11}$, $SO_2R^{11}$, $C(O)NH_2$, $C(O)NHR^{11}$, $C(O)N(R^{11})_2$, $NHC(O)R^{11}$, $NHR^{11}$, $N(R^{11})_2$, $NH_2$, $C(O)OH$, $OH$, oxo, $CN$, $NO_2$, F, Cl, Br and I. In another embodiment of Formula (I), $R^7$, at each occurrence, is independently selected from the group consisting of $C_1$-$C_6$ alkyl, $C_3$-$C_{11}$ cycloalkyl, 5-11 membered heteroaryl, and 4-12 membered heterocyclyl; wherein each $R^7$ $C_1$-$C_6$ alkyl is optionally substituted with one or more substituents independently selected from the group consisting of $C_1$-$C_6$ alkoxy, $C_3$-$C_7$ cycloalkyl, OH and F; wherein each 127 $C_3$-$C_{11}$ cycloalkyl, 5-11 membered heteroaryl, and 4-12 membered heterocyclyl are optionally substituted with one or more substituents independently selected from the group consisting of $R^{11}$, $OR^{11}$, $NHR^{11}$, and $C(O)OR^{11}$.

In one embodiment of Formula (I), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $C(O)R^{13}$, $OC(O)R^{13}$, $C(O)OR^{13}$, $SO_2R^{13}$, $C(O)NH_2$, $C(O)NHR^{13}$, $C(O)N(R^{13})_2$, $NHC(O)R^{13}$, $NHR^{13}$, $N(R^{13})_2$, $NH_2$, $C(O)OH$, $OH$, oxo, $CN$, $NO_2$, F, Cl, Br and I; wherein each $R^9$ 6-10 membered aryl, 5-11 membered heteroaryl, cycloalkyl, $C_4$-$C_{11}$ cycloalkenyl, and 4-12 membered heterocyclyl is optionally substituted with one or more substituents independently selected from the group consisting of $R^{14}$, $OR^{14}$, $SR^{14}$, $C(O)R^{14}$, $OC(O)R^{14}$, $C(O)OR^{14}$, $SO_2R^{14}$, $C(O)NH_2$, $C(O)NHR^{14}$, $C(O)N(R^{14})_2$, $NHC(O)R^{14}$, $NHR^{14}$, $N(R^{14})_2$, $NH_2$, $C(O)OH$, $OH$, oxo, $CN$, $NO_2$, F, Cl, Br and I. In another embodiment of Formula (I), $R^9$, at each occurrence, is independently selected from the group consisting of $C_1$-$C_6$ alkyl, 5-11 membered heteroaryl, and 4-12 membered heterocyclyl; wherein each $R^9$ $C_1$-$C_6$ alkyl is optionally substituted with one or more substituents independently selected from the group consisting of $R^{13}$ and F; wherein each $R^9$ 5-11 membered heteroaryl and 4-12 membered heterocyclyl is optionally substituted with one or more oxo. In another embodiment of Formula (I), $R^9$, at each occurrence, is independently selected from the group consisting of 5-11 membered heteroaryl and 4-12 membered heterocyclyl; wherein each $R^9$ 5-11 membered heteroaryl and 4-12 membered heterocyclyl is optionally substituted with one or more oxo. In another embodiment of Formula (I), $R^9$, at each occurrence, is independently $C_1$-$C_6$ alkyl; wherein each $R^9$ $C_1$-$C_6$ alkyl is optionally substituted with one or more substituents independently selected from the group consisting of $R^{13}$ and F. In another embodiment of Formula (I), $R^9$, at each occurrence, is independently $C_1$-$C_6$ alkyl; wherein each $R^9$ $C_1$-$C_6$ alkyl is unsubstituted.

In one embodiment of Formula (I), $R^{10}$, at each occurrence, is independently $C_1$-$C_4$ alkyl.

In one embodiment of Formula (I), $R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of $C_1$-$C_6$ alkoxy, OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I. In another embodiment of Formula (I), $R^{11}$, at each occurrence, is independently $C_1$-$C_6$ alkyl; wherein each $R^{11}$ $C_1$-$C_6$ alkyl is optionally substituted with $C_1$-$C_6$ alkoxy.

In one embodiment of Formula (I), $R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl.

In one embodiment of Formula (I), $R^{13}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I. In another embodiment of Formula (I), $R^{13}$, at each occurrence, is $C_6$-$C_{10}$ membered aryl.

In one embodiment of Formula (I), $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I.

In one embodiment of Formula (I),
$A^1$ is selected from the group consisting of $C_3$-$C_7$ cycloalkyl and 4-7 membered heterocyclyl;
$R^1$ is selected from the group consisting of 6-10 membered aryl, 5-11 membered heteroaryl, and 4-12 membered heterocyclyl; wherein the $R^1$ 6-10 membered aryl, 5-11 membered heteroaryl, and 4-12 membered heterocyclyl are substituted with two or more substituents independently selected from the group consisting of $R^7$, $OR^7$, $C(O)OR^7$, $N(R^7)_2$, $NH_2$, CN, F, Cl, and Br;
$R^2$ is independently selected from the group consisting of $R^8$ and $C(O)OR^8$;
n is 0 or 1;
$R^3$ is selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein the $R^3$ $C_1$-$C_6$ alkyl is optionally substituted with one or more substituents independently selected from the group consisting of phenyl, F, and $C_1$; wherein the $R^3$ 6-10 membered aryl, 5-11 membered heteroaryl, $C_3$-$C_{11}$ cycloalkyl, and 4-12 membered heterocyclyl are optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, C(O)OH, OH, oxo, CN, $NO_2$, Cl, and Br;
$R^4$ is selected from the group consisting of hydrogen and $C_1$-$C_6$ alkyl;
$R^7$, at each occurrence, is independently selected from the group consisting of $C_1$-$C_6$ alkyl, 5-11 membered heteroaryl, $C_3$-$C_{11}$ cycloalkyl, and 4-12 membered heterocyclyl; wherein each $R^7$ $C_1$-$C_6$ alkyl is optionally substituted with one or more substituents independently selected from the group consisting of $C_1$-$C_6$ alkoxy, $C_3$-$C_7$ cycloalkyl, OH and F; wherein each $R^7$ 5-11 membered heteroaryl, $C_3$-$C_{11}$ cycloalkyl and 4-12 membered heterocyclyl is optionally substituted with one or more substituents independently selected from the group consisting of $R^{11}$, $OR^{11}$, $NHR^{11}$, and $C(O)OR^{11}$;

$R^8$ is independently $C_1$-$C_6$ alkyl;
$R^9$, at each occurrence, is independently selected from the group consisting of $C_1$-$C_6$ alkyl, 5-11 membered heteroaryl, and 4-12 membered heterocyclyl; wherein each $R^9$ $C_1$-$C_6$ alkyl is optionally substituted with one or more substituents independently selected from the group consisting of $R^{11}$ and F; wherein each $R^9$ 5-11 membered heteroaryl and 4-12 membered heterocyclyl is optionally substituted with one oxo;
$R^{11}$, at each occurrence, is independently $C_1$-$C_6$ alkyl; wherein each $R^{11}$ $C_1$-$C_6$ alkyl is optionally substituted with one $C_1$-$C_6$ alkoxy; and
$R^{13}$, at each occurrence, is independently $C_6$-$C_{10}$ membered aryl;
with the proviso that the compound is not 1-(3,4-dimethylphenyl)-N-(naphthalene-1-sulfonyl)cyclopentane-1-carboxamide.

Exemplary compounds of Formula (I) include, but are not limited to:
1-(5-bromo-2-methoxyphenyl)-N-(naphthalene-1-sulfonyl)cyclopropane-1-carboxamide;
1-(5-cyclobutyl-2-methoxyphenyl)-N-(naphthalene-1-sulfonyl)cyclopropane-1-carboxamide;
1-(5-cyclobutyl-2-methoxypyridin-3-yl)-N-(2-methylquinoline-5-sulfonyl)cyclopropane-1-carboxamide;
1-(5-cyclobutyl-2-methoxypyridin-3-yl)-N-(quinoline-5-sulfonyl)cyclopropane-1-carboxamide;
1-(5-cyclobutyl-2-methoxypyridin-3-yl)-N-(naphthalene-1-sulfonyl)cyclopropane-1-carboxamide;
1-(5-cyclobutyl-2-methoxypyridin-3-yl)-N-(1,2,3,4-tetrahydroquinoline-5-sulfonyl)cyclopropane-1-carboxamide;
1-(2,6-dimethoxyphenyl)-N-(naphthalene-1-sulfonyl)cyclopropane-1-carboxamide;
1-[2-methoxy-5-(trifluoromethyl)pyridin-3-yl]-N-(naphthalene-1-sulfonyl)cyclopropane-1-carboxamide;
1-(5-bromo-2-methoxyphenyl)-N-(1,2,3,4-tetrahydroquinoline-5-sulfonyl)cyclobutane-1-carboxamide;
1-(5-cyclobutyl-2-methoxyphenyl)-N-(1,2,3,4-tetrahydroquinoline-5-sulfonyl)cyclobutane-1-carboxamide;
1-(5-bromo-2-methoxyphenyl)-N-(1,2,3,4-tetrahydroquinoline-5-sulfonyl)cyclopropane-1-carboxamide;
1-(5-cyclopropyl-2-methoxyphenyl)-N-(naphthalene-1-sulfonyl)cyclopropane-1-carboxamide;
1-(5-cyclopropyl-2-methoxyphenyl)-N-(quinoline-5-sulfonyl)cyclopropane-1-carboxamide;
1-{2-methoxy-5-[(propan-2-yl)oxy]phenyl}-N-(quinoline-5-sulfonyl)cyclopropane-1-carboxamide;
1-(2-methoxy-5-methylpyridin-3-yl)-N-(naphthalene-1-sulfonyl)cyclopropane-1-carboxamide;
1-(5-cyclobutyl-2-methoxyphenyl)-N-(1,2,3,4-tetrahydroquinoline-5-sulfonyl)cyclopropane-1-carboxamide;
1-(5-cyclobutyl-2-methoxyphenyl)-N-(quinoline-5-sulfonyl)cyclopropane-1-carboxamide;
1-(5-bromo-2-methoxyphenyl)-N-(quinoline-5-sulfonyl)cyclopropane-1-carboxamide;
1-(5-cyclobutyl-2-methoxypyridin-3-yl)-N-(pyrazolo[1,5-a]pyridine-4-sulfonyl)cyclopropane-1-carboxamide;
1-(5-cyclobutyl-2-methoxypyridin-3-yl)-N-(1-methyl-1H-indole-7-sulfonyl)cyclopropane-1-carboxamide;
1-(5-cyclobutyl-2-methoxypyridin-3-yl)-N-(1H-indole-4-sulfonyl)cyclopropane-1-carboxamide;

N-(1H-indole-4-sulfonyl)-1-[2-methoxy-5-(trifluoromethyl)pyridin-3-yl]cyclopropane-1-carboxamide;
1-(5-cyclobutyl-2-methoxyphenyl)-N-(pyrazolo[1,5-a]pyridine-4-sulfonyl)cyclobutane-1-carboxamide;
1-(5-cyclobutyl-2-methoxyphenyl)-N-(1-methyl-1H-benzimidazole-7-sulfonyl)cyclobutane-1-carboxamide;
1-(5-cyclobutyl-2-methoxyphenyl)-N-(1-methyl-1H-indazole-7-sulfonyl)cyclobutane-1-carboxamide;
1-(5-cyclobutyl-2-methoxyphenyl)-N-(1H-indazole-4-sulfonyl)cyclobutane-1-carboxamide;
1-(5-cyclopropyl-2-methoxyphenyl)-N-(1,2,3,4-tetrahydroquinoline-5-sulfonyl)cyclobutane-1-carboxamide;
1-(2,5-dimethoxyphenyl)-N-(naphthalene-1-sulfonyl)cyclopropane-1-carboxamide;
1-(2,5-dimethoxyphenyl)-N-(quinoline-5-sulfonyl)cyclopropane-1-carboxamide;
1-[2-(dimethylamino)-5-(trifluoromethyl)pyridin-3-yl]-N-(naphthalene-1-sulfonyl)cyclopropane-1-carboxamide;
1-(5-ethoxy-2-methoxyphenyl)-N-(quinoline-5-sulfonyl)cyclopropane-1-carboxamide;
1-[5-(cyclobutyloxy)-2-methoxyphenyl]-N-(quinoline-5-sulfonyl)cyclopropane-1-carboxamide;
1-(5-cyclobutyl-2-methoxyphenyl)-N-(2-methylquinoline-5-sulfonyl)cyclobutane-1-carboxamide;
1-(5-tert-butyl-2-methoxyphenyl)-N-(quinoline-5-sulfonyl)cyclopropane-1-carboxamide;
1-[2-methoxy-5-(propan-2-yl)phenyl]-N-(quinoline-5-sulfonyl)cyclopropane-1-carboxamide;
1-[4-fluoro-2-methoxy-5-(propan-2-yl)phenyl]-N-(quinoline-5-sulfonyl)cyclopropane-1-carboxamide;
1-[2-methoxy-5-(trifluoromethyl)phenyl]-N-(quinoline-5-sulfonyl)cyclopropane-1-carboxamide;
1-[5-(bicyclo[1.1.1]pentan-1-yl)-2-methoxyphenyl]-N-(quinoline-5-sulfonyl)cyclopropane-1-carboxamide;
1-(5-tert-butyl-2-methoxyphenyl)-N-(1,2,3,4-tetrahydroquinoline-5-sulfonyl)cyclopropane-1-carboxamide;
1-(2,6-dimethoxy-3-methylphenyl)-N-(naphthalene-1-sulfonyl)cyclopropane-1-carboxamide;
1-(2,6-dimethoxy-3-methylphenyl)-N-(quinoline-5-sulfonyl)cyclopropane-1-carboxamide;
1-(2,6-dimethoxy-3-methylphenyl)-N-(1H-indole-4-sulfonyl)cyclopropane-1-carboxamide;
1-(2,6-dimethoxy-3-methylphenyl)-N-(2-methylquinoline-5-sulfonyl)cyclopropane-1-carboxamide;
1-(2-methoxy-5-methylphenyl)-N-(quinoline-5-sulfonyl)cyclopropane-1-carboxamide;
1-(2-ethoxy-6-methoxyphenyl)-N-(quinoline-5-sulfonyl)cyclopropane-1-carboxamide;
1-[2-(cyclopropylmethoxy)-6-methoxyphenyl]-N-(quinoline-5-sulfonyl)cyclopropane-1-carboxamide;
1-(6-methoxy-2,3-dimethylphenyl)-N-(quinoline-5-sulfonyl)cyclopropane-1-carboxamide;
1-(3-cyclopropyl-6-methoxy-2-methylphenyl)-N-(quinoline-5-sulfonyl)cyclopropane-1-carboxamide;
N-(1H-indole-4-sulfonyl)-1-(2-methoxy-5-methylphenyl)cyclopropane-1-carboxamide;
1-[2-methoxy-6-(propan-2-yl)phenyl]-N-(quinoline-5-sulfonyl)cyclopropane-1-carboxamide;
1-(2-cyclobutyl-6-methoxyphenyl)-N-(quinoline-5-sulfonyl)cyclopropane-1-carboxamide;
1-[2-methoxy-5-(2-methoxypropan-2-yl)phenyl]-N-(quinoline-5-sulfonyl)cyclopropane-1-carboxamide;
N-(1H-indazole-4-sulfonyl)-1-(2-methoxy-5-methylphenyl)cyclopropane-1-carboxamide;
1-(5-cyclobutyl-2-methoxyphenyl)-N-(2,3-dihydro-1H-indole-4-sulfonyl)cyclopropane-1-carboxamide;
1-(5-cyclobutyl-2-methoxyphenyl)-N-(1H-indole-4-sulfonyl)cyclopropane-1-carboxamide;
1-(5-cyclobutyl-2-methoxyphenyl)-N-(1H-indazole-4-sulfonyl)cyclopropane-1-carboxamide;
1-[2-(dimethylamino)-5-(trifluoromethyl)pyridin-3-yl]-N-(quinoline-5-sulfonyl)cyclopropane-1-carboxamide;
1-(5-cyclobutyl-2-methoxyphenyl)-N-(1-methyl-1H-indole-4-sulfonyl)cyclopropane-1-carboxamide;
1-(5-cyclobutyl-2-methoxyphenyl)-N-(1-methyl-1H-indole-7-sulfonyl)cyclopropane-1-carboxamide;
1-(5-cyclobutyl-2-methoxyphenyl)-N-(1-methyl-1H-indazole-7-sulfonyl)cyclopropane-1-carboxamide;
1-(5-cyclobutyl-2-methoxyphenyl)-N-(pyrazolo[1,5-a]pyridine-4-sulfonyl)cyclopropane-1-carboxamide;
1-(5-cyclobutyl-2-methoxyphenyl)-N-(2-methylquinoline-8-sulfonyl)cyclopropane-1-carboxamide;
1-(5-cyclobutyl-2-methoxyphenyl)-N-(2-methylquinoline-5-sulfonyl)cyclopropane-1-carboxamide;
1-(2-methoxy-5-methylphenyl)-N-(2-methylquinoline-5-sulfonyl)cyclopropane-1-carboxamide;
1-[5-(difluoromethoxy)-2-methoxyphenyl]-N-(quinoline-5-sulfonyl)cyclopropane-1-carboxamide;
1-(2,6-diethoxyphenyl)-N-(quinoline-5-sulfonyl)cyclopropane-1-carboxamide;
N-(2-aminoquinoline-5-sulfonyl)-1-(5-cyclobutyl-2-methoxyphenyl)cyclopropane-1-carboxamide;
1-(5-cyclopropyl-2-methoxyphenyl)-N-(2-methylquinoline-5-sulfonyl)cyclopropane-1-carboxamide;
1-(5-ethoxy-2-methoxyphenyl)-N-(2-methylquinoline-5-sulfonyl)cyclopropane-1-carboxamide;
1-(5-tert-butyl-2-methoxyphenyl)-N-(2-methylquinoline-5-sulfonyl)cyclopropane-1-carboxamide;
1-[2-methoxy-5-(propan-2-yl)phenyl]-N-(2-methylquinoline-5-sulfonyl)cyclopropane-1-carboxamide;
1-[2-(dimethylamino)-5-(trifluoromethyl)pyridin-3-yl]-N-(2-methylquinoline-5-sulfonyl)cyclopropane-1-carboxamide;
1-{2-methoxy-5-[1-(methoxymethyl)cyclopropyl]phenyl}-N-(quinoline-5-sulfonyl)cyclopropane-1-carboxamide;
1-{2-methoxy-5-[1-(methoxymethyl)cyclopropyl]phenyl}-N-(2-methylquinoline-5-sulfonyl)cyclopropane-1-carboxamide;
1-{5-methyl-2-[(propan-2-yl)oxy]phenyl}-N-(quinoline-5-sulfonyl)cyclopropane-1-carboxamide;
1-{5-methyl-2-[(propan-2-yl)oxy]phenyl}-N-(2-methylquinoline-5-sulfonyl)cyclopropane-1-carboxamide;
N-(2-aminoquinoline-5-sulfonyl)-1-(2-methoxy-5-methylphenyl)cyclopropane-1-carboxamide;
1-(4-cyclobutyl-2,6-dimethoxyphenyl)-N-(quinoline-5-sulfonyl)cyclopropane-1-carboxamide;
N-(2-aminoquinoline-5-sulfonyl)-1-(2,5-dimethylphenyl)cyclopropane-1-carboxamide;
1-(2-ethoxy-5-methylphenyl)-N-(quinoline-5-sulfonyl)cyclopropane-1-carboxamide;
1-(2-ethoxy-5-methylphenyl)-N-(2-methylquinoline-5-sulfonyl)cyclopropane-1-carboxamide;
1-(5-ethyl-2-methoxyphenyl)-N-(2-methylquinoline-5-sulfonyl)cyclopropane-1-carboxamide;
1-{2-methoxy-5-[1-(methylamino)cyclopropyl]phenyl}-N-(quinoline-5-sulfonyl)cyclopropane-1-carboxamide;
1-(4-cyclobutyl-2,6-dimethoxyphenyl)-N-(1H-indole-4-sulfonyl)cyclopropane-1-carboxamide;
N-(2-aminoquinoline-5-sulfonyl)-1-{5-methyl-2-[(propan-2-yl)oxy]phenyl}cyclopropane-1-carboxamide;
1-[2-methoxy-5-(1-methoxycyclobutyl)phenyl]-N-(quinoline-5-sulfonyl)cyclopropane-1-carboxamide;

N-(2-aminoquinoline-5-sulfonyl)-1-(2-ethoxy-5-methyl-phenyl)cyclopropane-1-carboxamide;
1-[2-methoxy-5-(oxetan-3-yl)phenyl]-N-(quinoline-5-sulfonyl)cyclopropane-1-carboxamide;
1-(2-ethoxy-5-methylphenyl)-N-(2-methyl-1H-indole-4-sulfonyl)cyclopropane-1-carboxamide;
N-(2-aminoquinoline-5-sulfonyl)-1-[2-methoxy-5-(2-methylpropoxy)pyridin-4-yl]cyclopropane-1-carboxamide;
1-{5-methyl-2-[(oxetan-3-yl)oxy]phenyl}-N-(quinoline-5-sulfonyl)cyclopropane-1-carboxamide;
1-[5-ethyl-2-(2-methylpropoxy)pyridin-3-yl]-N-(1H-indazole-4-sulfonyl)cyclopropane-1-carboxamide;
1-(2-{[(2R)-1-methoxypropan-2-yl]oxy}-5-methylphenyl)-N-(quinoline-5-sulfonyl)cyclopropane-1-carboxamide;
N-(2-aminoquinoline-5-sulfonyl)-1-[5-methyl-2-(2-methylpropoxy)pyridin-3-yl]cyclopropane-1-carboxamide;
N-(2-aminoquinoline-5-sulfonyl)-1-{5-methyl-2-[(propan-2-yl)oxy]pyridin-3-yl}cyclopropane-1-carboxamide;
N-(2-aminoquinoline-5-sulfonyl)-1-[5-ethyl-2-(2-methylpropoxy)pyridin-3-yl]cyclopropane-1-carboxamide;
1-[2-ethoxy-5-(2-ethoxypropan-2-yl)phenyl]-N-(quinoline-5-sulfonyl)cyclopropane-1-carboxamide;
1-[2-(difluoromethoxy)-5-methylphenyl]-N-(quinoline-5-sulfonyl)cyclopropane-1-carboxamide;
1-[2-ethoxy-5-(1-methoxy-2-methylpropan-2-yl)phenyl]-N-(quinoline-5-sulfonyl)cyclopropane-1-carboxamide;
1-[2-ethoxy-5-(1-methoxycyclobutyl)phenyl]-N-(quinoline-5-sulfonyl)cyclopropane-1-carboxamide;
1-[2-ethoxy-5-(2-ethoxypropan-2-yl)phenyl]-N-(2-methylquinoline-5-sulfonyl)cyclopropane-1-carboxamide;
1-[2-ethoxy-5-(2-methoxypropan-2-yl)phenyl]-N-(2-methylquinoline-5-sulfonyl)cyclopropane-1-carboxamide;
1-[2-ethoxy-5-(1-methoxycyclobutyl)phenyl]-N-(2-methylquinoline-5-sulfonyl)cyclopropane-1-carboxamide;
1-{5-methyl-2-[(oxetan-3-yl)oxy]phenyl}-N-(2-methylquinoline-5-sulfonyl)cyclopropane-1-carboxamide;
1-(2-{[(2R)-1-methoxypropan-2-yl]oxy}-5-methylphenyl)-N-(2-methylquinoline-5-sulfonyl)cyclopropane-1-carboxamide;
1-[3-(dimethylamino)-6-(2-methylpropoxy)pyridin-2-yl]-N-(quinoline-5-sulfonyl)cyclopropane-1-carboxamide;
1-[5-(dimethylamino)-2-(2-methylpropoxy)pyridin-3-yl]-N-(2-methylquinoline-5-sulfonyl)cyclopropane-1-carboxamide;
1-[2-methoxy-5-(1-methoxy-2-methylpropan-2-yl)phenyl]-N-(quinoline-5-sulfonyl)cyclopropane-1-carboxamide;
1-(5-ethyl-2-{[(2R)-1-methoxypropan-2-yl]oxy}phenyl)-N-(quinoline-5-sulfonyl)cyclopropane-1-carboxamide;
1-(5-ethyl-2-{[(2R)-1-methoxypropan-2-yl]oxy}phenyl)-N-(2-methylquinoline-5-sulfonyl)cyclopropane-1-carboxamide;
1-{2-[(2S)-2-methoxypropoxy]-5-methylphenyl}-N-(quinoline-5-sulfonyl)cyclopropane-1-carboxamide;
1-{2-[(2S)-2-methoxypropoxy]-5-methylphenyl}-N-(2-methylquinoline-5-sulfonyl)cyclopropane-1-carboxamide;
1-{2-[(2R)-2-methoxypropoxy]-5-methylphenyl}-N-(quinoline-5-sulfonyl)cyclopropane-1-carboxamide;
1-{2-[(2R)-2-methoxypropoxy]-5-methylphenyl}-N-(2-methylquinoline-5-sulfonyl)cyclopropane-1-carboxamide;
1-(5-ethyl-2-{[(3S)-oxolan-3-yl]oxy}phenyl)-N-(quinoline-5-sulfonyl)cyclopropane-1-carboxamide;
1-(5-ethyl-2-{[(3R)-oxolan-3-yl]oxy}phenyl)-N-(quinoline-5-sulfonyl)cyclopropane-1-carboxamide;
1-(5-ethyl-2-{[(3R)-oxolan-3-yl]oxy}phenyl)-N-(2-methylquinoline-5-sulfonyl)cyclopropane-1-carboxamide;
1-(5-methyl-2-{[(3R)-oxolan-3-yl]oxy}phenyl)-N-(quinoline-5-sulfonyl)cyclopropane-1-carboxamide;
1-(5-methyl-2-{[(3R)-oxolan-3-yl]oxy}phenyl)-N-(2-methylquinoline-5-sulfonyl)cyclopropane-1-carboxamide;
1-(5-methyl-2-{[(3S)-oxolan-3-yl]oxy}phenyl)-N-(2-methylquinoline-5-sulfonyl)cyclopropane-1-carboxamide;
1-(3-methoxy-4-methylphenyl)-N-(naphthalene-1-sulfonyl)cyclopropane-1-carboxamide;
1-(1-ethyl-3-methyl-1H-pyrazol-5-yl)-N-(naphthalene-1-sulfonyl)cyclopropane-1-carboxamide;
1-(1-ethyl-5-methyl-1H-pyrazol-3-yl)-N-(naphthalene-1-sulfonyl)cyclopropane-1-carboxamide;
1-[2-methoxy-5-(trifluoromethyl)pyridin-3-yl]-N-(quinoline-5-sulfonyl)cyclopropane-1-carboxamide;
1-[2-methoxy-5-(trifluoromethyl)pyridin-3-yl]-N-(1,2,3,4-tetrahydroquinoline-5-sulfonyl)cyclopropane-1-carboxamide;
1-[2-methoxy-5-(trifluoromethyl)pyridin-3-yl]-N-(2-methylquinoline-5-sulfonyl)cyclopropane-1-carboxamide;
1-(2-methoxy-5-methylpyridin-3-yl)-N-(1,2,3,4-tetrahydroquinoline-5-sulfonyl)cyclopropane-1-carboxamide;
1-(5-cyclobutyl-2-methoxypyridin-3-yl)-N-(1-methyl-1H-benzimidazole-7-sulfonyl)cyclopropane-1-carboxamide;
1-(5-cyclobutyl-2-methoxypyridin-3-yl)-N-(1-methyl-1H-indazole-7-sulfonyl)cyclopropane-1-carboxamide;
1-(5-cyclobutyl-2-methoxypyridin-3-yl)-N-(1-methyl-1H-indole-4-sulfonyl)cyclopropane-1-carboxamide;
1-(5-cyclobutyl-2-methoxypyridin-3-yl)-N-(1H-indazole-4-sulfonyl)cyclopropane-1-carboxamide;
1-(5-cyclobutyl-2-methoxypyridin-3-yl)-N-(3-methylimidazo[1,2-a]pyridine-5-sulfonyl)cyclopropane-1-carboxamide;
1-[2-methoxy-5-(trifluoromethyl)pyridin-3-yl]-N-(1-methyl-1H-indole-7-sulfonyl)cyclopropane-1-carboxamide;
1-[2-methoxy-5-(trifluoromethyl)pyridin-3-yl]-N-(1-methyl-1H-indole-4-sulfonyl)cyclopropane-1-carboxamide;
1-[2-methoxy-5-(trifluoromethyl)pyridin-3-yl]-N-(3-methylimidazo[1,2-a]pyridine-5-sulfonyl)cyclopropane-1-carboxamide;
1-[2-methoxy-5-(propan-2-yl)phenyl]-N-(1,2,3,4-tetrahydroquinoline-5-sulfonyl)cyclobutane-1-carboxamide;
1-(5-cyclopentyl-2-methoxyphenyl)-N-(1,2,3,4-tetrahydroquinoline-5-sulfonyl)cyclobutane-1-carboxamide;
1-[5-(butan-2-yl)-2-methoxyphenyl]-N-(1,2,3,4-tetrahydroquinoline-5-sulfonyl)cyclobutane-1-carboxamide;
1-{2-methoxy-5-[(oxolan-3-yl)oxy]phenyl}-N-(quinoline-5-sulfonyl)cyclopropane-1-carboxamide;
1-[2-chloro-5-(trifluoromethoxy)phenyl]-N-(quinoline-5-sulfonyl)cyclopropane-1-carboxamide;
1-[2-chloro-5-(trifluoromethoxy)phenyl]-N-(1,2,3,4-tetrahydroquinoline-5-sulfonyl)cyclopropane-1-carboxamide;
1-[2-methoxy-5-(propan-2-yl)phenyl]-N-(1,2,3,4-tetrahydroquinoline-5-sulfonyl)cyclopropane-1-carboxamide;
1-[4-fluoro-2-methoxy-5-(propan-2-yl)phenyl]-N-(1,2,3,4-tetrahydroquinoline-5-sulfonyl)cyclopropane-1-carboxamide;
1-[2-methoxy-5-(trifluoromethyl)phenyl]-N-(1,2,3,4-tetrahydroquinoline-5-sulfonyl)cyclopropane-1-carboxamide;
1-(5-bromo-2-methoxyphenyl)-N-(2-methylquinoline-5-sulfonyl)cyclobutane-1-carboxamide;
methyl 1-(4-methoxy-3-{1-[(quinoline-5-sulfonyl)carbamoyl]cyclopropyl}phenyl)cyclopropane-1-carboxylate;
methyl 4-methoxy-3-{1-[(quinoline-5-sulfonyl)carbamoyl]cyclopropyl}benzoate;

methyl 4-methoxy-3-{1-[(naphthalene-1-sulfonyl)carbamoyl]cyclopropyl}benzoate;

1-(5-cyclobutyl-2-methoxy-4-methylpyridin-3-yl)-N-(2-methylquinoline-5-sulfonyl)cyclopropane-1-carboxamide;

1-(5-bromo-2-methoxyphenyl)-N-(1-methyl-2,3-dihydro-1H-indole-4-sulfonyl)cyclopropane-1-carboxamide;

1-(2-methoxy-6-methylphenyl)-N-(quinoline-5-sulfonyl)cyclopropane-1-carboxamide;

1-(6-methoxy-2,3-dimethylphenyl)-N-(1,2,3,4-tetrahydroquinoline-5-sulfonyl)cyclopropane-1-carboxamide;

1-(3-cyclopropyl-6-methoxy-2-methylphenyl)-N-(1,2,3,4-tetrahydroquinoline-5-sulfonyl)cyclopropane-1-carboxamide;

1-(5-cyclobutyl-2-methoxy-4-methylpyridin-3-yl)-N-(1,2,3,4-tetrahydroquinoline-5-sulfonyl)cyclopropane-1-carboxamide;

1-(2,6-dimethoxy-3-methylphenyl)-N-(2-methylquinoline-8-sulfonyl)cyclopropane-1-carboxamide;

1-(5-cyclobutyl-2-methoxyphenyl)-N-(1-methyl-2,3-dihydro-1H-indole-4-sulfonyl)cyclopropane-1-carboxamide;

1-(5-cyclobutyl-2-methoxy-4-methylpyridin-3-yl)-N-(1-methyl-1H-indole-4-sulfonyl)cyclopropane-1-carboxamide;

1-(5-cyclobutyl-2-methoxy-4-methylpyridin-3-yl)-N-(1-methyl-1H-indole-7-sulfonyl)cyclopropane-1-carboxamide;

1-(5-cyclobutyl-2-methoxy-4-methylpyridin-3-yl)-N-(1-methyl-1H-indazole-7-sulfonyl)cyclopropane-1-carboxamide;

1-(5-cyclobutyl-2-methoxy-4-methylpyridin-3-yl)-N-(2-methylquinoline-8-sulfonyl)cyclopropane-1-carboxamide;

1-(2-methoxy-6-methylphenyl)-N-(2-methylquinoline-8-sulfonyl)cyclopropane-1-carboxamide;

1-(2-cyclobutyl-5-methoxyphenyl)-N-(quinoline-5-sulfonyl)cyclopropane-1-carboxamide;

1-(2-cyclobutyl-5-methoxyphenyl)-N-(2-methylquinoline-5-sulfonyl)cyclopropane-1-carboxamide;

1-[5-(hydroxymethyl)-2-methoxyphenyl]-N-(quinoline-5-sulfonyl)cyclopropane-1-carboxamide;

1-[2-methoxy-5-(methoxymethyl)phenyl]-N-(quinoline-5-sulfonyl)cyclopropane-1-carboxamide;

1-(2-methoxy-6-methylphenyl)-N-(2-methylquinoline-5-sulfonyl)cyclopropane-1-carboxamide;

1-(6-methoxy-2,3-dimethylphenyl)-N-(2-methylquinoline-5-sulfonyl)cyclopropane-1-carboxamide;

1-(3-cyclopropyl-6-methoxy-2-methylphenyl)-N-(2-methylquinoline-5-sulfonyl)cyclopropane-1-carboxamide;

1-(2-methoxy-6-methylphenyl)-N-(1,2,3,4-tetrahydroquinoline-5-sulfonyl)cyclopropane-1-carboxamide;

1-(3-chloro-2,6-dimethoxyphenyl)-N-(quinoline-5-sulfonyl)cyclopropane-1-carboxamide;

1-(5-methoxy-2-methylphenyl)-N-(quinoline-5-sulfonyl)cyclopropane-1-carboxamide;

1-(2-cyclopropyl-6-methoxyphenyl)-N-(quinoline-5-sulfonyl)cyclopropane-1-carboxamide;

1-[5-methoxy-2-(propan-2-yl)phenyl]-N-(quinoline-5-sulfonyl)cyclopropane-1-carboxamide;

1-(5-methoxy-2-propylphenyl)-N-(quinoline-5-sulfonyl)cyclopropane-1-carboxamide;

1-(2-cyclopropyl-6-methoxyphenyl)-N-(2-methylquinoline-5-sulfonyl)cyclopropane-1-carboxamide;

1-(2,5-dimethylphenyl)-N-(quinoline-5-sulfonyl)cyclopropane-1-carboxamide;

1-(5-ethyl-2-methoxyphenyl)-N-(quinoline-5-sulfonyl)cyclopropane-1-carboxamide;

1-(2-methoxy-4-methylphenyl)-N-(quinoline-5-sulfonyl)cyclopropane-1-carboxamide;

1-(2-methoxy-3-methylphenyl)-N-(quinoline-5-sulfonyl)cyclopropane-1-carboxamide;

1-(4-cyclobutyl-2,6-dimethoxyphenyl)-N-(1-methyl-1H-indole-4-sulfonyl)cyclopropane-1-carboxamide;

1-(4-cyclobutyl-2,6-dimethoxyphenyl)-N-(1-methyl-1H-indole-7-sulfonyl)cyclopropane-1-carboxamide;

1-(4-cyclobutyl-2,6-dimethoxyphenyl)-N-(1-methyl-1H-indazole-7-sulfonyl)cyclopropane-1-carboxamide;

1-(4-cyclobutyl-2,6-dimethoxyphenyl)-N-(pyrazolo[1,5-a]pyridine-4-sulfonyl)cyclopropane-1-carboxamide;

1-(4-cyclobutyl-2,6-dimethoxyphenyl)-N-(2-methylquinoline-5-sulfonyl)cyclopropane-1-carboxamide;

N-(2-aminoquinoline-5-sulfonyl)-1-(4-cyclobutyl-2,6-dimethoxyphenyl)cyclopropane-1-carboxamide;

N-(2-aminoquinoline-5-sulfonyl)-1-(5-ethyl-2-methoxyphenyl)cyclopropane-1-carboxamide;

1-(5-ethyl-2-methoxyphenyl)-N-(1H-indazole-4-sulfonyl)cyclopropane-1-carboxamide;

1-(2-ethyl-6-methoxyphenyl)-N-(quinoline-5-sulfonyl)cyclopropane-1-carboxamide;

1-(2-ethoxy-5-methylphenyl)-N-(1H-indazole-4-sulfonyl)cyclopropane-1-carboxamide;

N-(1H-indazole-4-sulfonyl)-1-{5-methyl-2-[(propan-2-yl)oxy]phenyl}cyclopropane-1-carboxamide;

1-(4-cyclobutyl-2,6-dimethoxyphenyl)-N-(1H-indazole-4-sulfonyl)cyclopropane-1-carboxamide;

N-(1H-indazole-4-sulfonyl)-1-(6-methoxy-2,3-dimethylphenyl)cyclopropane-1-carboxamide;

1-(3-cyclopropyl-6-methoxy-2-methylphenyl)-N-(1H-indazole-4-sulfonyl)cyclopropane-1-carboxamide;

N-(1H-indole-4-sulfonyl)-1-{5-methyl-2-[(propan-2-yl)oxy]phenyl}cyclopropane-1-carboxamide;

1-(2,5-dimethylphenyl)-N-(1H-indole-4-sulfonyl)cyclopropane-1-carboxamide;

1-(2-cyclopropyl-6-methoxyphenyl)-N-(1H-indazole-4-sulfonyl)cyclopropane-1-carboxamide;

N-(2-aminoquinoline-5-sulfonyl)-1-{2-methoxy-5-[1-(methoxymethyl)cyclopropyl]phenyl}cyclopropane-1-carboxamide;

1-(2-ethoxy-5-methylphenyl)-N-(2-methoxyquinoline-5-sulfonyl)cyclopropane-1-carboxamide;

1-(2-ethoxy-5-methylphenyl)-N-[2-(methylamino)quinoline-5-sulfonyl]cyclopropane-1-carboxamide;

1-(2-ethoxy-5-methylphenyl)-N-(1H-indole-4-sulfonyl)cyclopropane-1-carboxamide;

1-[2-methoxy-5-(2,2,2-trifluoro-1-methoxyethyl)phenyl]-N-(quinoline-5-sulfonyl)cyclopropane-1-carboxamide;

1-[2-methoxy-5-(1-methoxyethyl)phenyl]-N-(quinoline-5-sulfonyl)cyclopropane-1-carboxamide;

N-(1H-indole-4-sulfonyl)-1-[2-methoxy-5-(2-methoxypropan-2-yl)phenyl]cyclopropane-1-carboxamide;

1-[2-methoxy-5-(3-methyloxetan-3-yl)phenyl]-N-(quinoline-5-sulfonyl)cyclopropane-1-carboxamide;

N-(2-aminoquinoline-5-sulfonyl)-1-{5-methyl-2-[(oxetan-3-yl)oxy]phenyl}cyclopropane-1-carboxamide;

N-(1H-indazole-4-sulfonyl)-1-[2-methoxy-5-(2-methylpropoxy)pyridin-4-yl]cyclopropane-1-carboxamide;

1-(2-{[(2S)-1-methoxypropan-2-yl]oxy}-5-methylphenyl)-N-(quinoline-5-sulfonyl)cyclopropane-1-carboxamide;

1-[5-cyclopropyl-2-(2-methylpropoxy)pyridin-3-yl]-N-(2-methoxyquinoline-5-sulfonyl)cyclopropane-1-carboxamide;

1-[5-cyclobutyl-2-(2-methylpropoxy)pyridin-3-yl]-N-(2-methoxyquinoline-5-sulfonyl)cyclopropane-1-carboxamide;
1-{5-cyclopropyl-2-[(propan-2-yl)oxy]pyridin-3-yl}-N-(2-methoxyquinoline-5-sulfonyl)cyclopropane-1-carboxamide;
1-[5-(2-ethoxypropan-2-yl)-2-methoxyphenyl]-N-(quinoline-5-sulfonyl)cyclopropane-1-carboxamide;
1-[2-ethoxy-5-(2-methoxypropan-2-yl)phenyl]-N-(quinoline-5-sulfonyl)cyclopropane-1-carboxamide;
1-[2-(difluoromethoxy)-5-ethylphenyl]-N-(quinoline-5-sulfonyl)cyclopropane-1-carboxamide;
1-[2-methoxy-5-(2-methoxypropan-2-yl)phenyl]-N-(2-methylquinoline-5-sulfonyl)cyclopropane-1-carboxamide;
1-[2-methoxy-5-(1-methoxycyclobutyl)phenyl]-N-(2-methylquinoline-5-sulfonyl)cyclopropane-1-carboxamide;
1-[2-(difluoromethoxy)-5-methylphenyl]-N-(2-methylquinoline-5-sulfonyl)cyclopropane-1-carboxamide;
1-[5-chloro-2-(difluoromethoxy)phenyl]-N-(2-methylquinoline-5-sulfonyl)cyclopropane-1-carboxamide;
1-[2-(difluoromethoxy)-5-ethylphenyl]-N-(2-methylquinoline-5-sulfonyl)cyclopropane-1-carboxamide;
1-(2-{[(2S)-1-methoxypropan-2-yl]oxy}-5-methylphenyl)-N-(2-methylquinoline-5-sulfonyl)cyclopropane-1-carboxamide;
1-[2-ethoxy-5-(1-methoxy-2-methylpropan-2-yl)phenyl]-N-(2-methylquinoline-5-sulfonyl)cyclopropane-1-carboxamide;
1-[2-(difluoromethoxy)-5-(2-ethoxypropan-2-yl)phenyl]-N-(quinoline-5-sulfonyl)cyclopropane-1-carboxamide;
1-[2-(difluoromethoxy)-5-(2-ethoxypropan-2-yl)phenyl]-N-(2-methylquinoline-5-sulfonyl)cyclopropane-1-carboxamide;
1-[2-(difluoromethoxy)-5-(2-methoxypropan-2-yl)phenyl]-N-(quinoline-5-sulfonyl)cyclopropane-1-carboxamide;
1-[2-(difluoromethoxy)-5-(2-methoxypropan-2-yl)phenyl]-N-(2-methylquinoline-5-sulfonyl)cyclopropane-1-carboxamide;
1-[5-(1-ethoxy-2-methylpropan-2-yl)-2-methoxyphenyl]-N-(quinoline-5-sulfonyl)cyclopropane-1-carboxamide;
1-[5-(1-ethoxy-2-methylpropan-2-yl)-2-methoxyphenyl]-N-(2-methylquinoline-5-sulfonyl)cyclopropane-1-carboxamide;
1-[5-(dimethylamino)-2-(2-methylpropoxy)pyridin-3-yl]-N-(quinoline-5-sulfonyl)cyclopropane-1-carboxamide;
1-[2-methoxy-5-(1-methoxy-2-methylpropan-2-yl)phenyl]-N-(2-methylquinoline-5-sulfonyl)cyclopropane-1-carboxamide;
1-(5-ethyl-2-{[(3S)-oxolan-3-yl]oxy}phenyl)-N-(2-methylquinoline-5-sulfonyl)cyclopropane-1-carboxamide;
1-(5-methyl-2-{[(3S)-oxolan-3-yl]oxy}phenyl)-N-(quinoline-5-sulfonyl)cyclopropane-1-carboxamide;
N-(benzenesulfonyl)-1-(2,4-dichlorophenyl)cyclopropane-1-carboxamide;
1-(2,4-dichlorophenyl)-N-(2,3-dihydro-1H-indene-5-sulfonyl)cyclopropane-1-carboxamide;
N-(4-chlorobenzene-1-sulfonyl)-1-(2,4-dichlorophenyl)cyclopropane-1-carboxamide;
methyl 5-{[1-(2,4-dichlorophenyl)cyclopropane-1-carbonyl]sulfamoyl}-4-methoxythiophene-3-carboxylate;
1-(2,4-dichlorophenyl)-N-(3,5-dimethyl-1,2-oxazol-4-sulfonyl)cyclopropane-1-carboxamide;
1-(2,4-dichlorophenyl)-N-[2-(trifluoromethoxy)benzene-1-sulfonyl]cyclopropane-1-carboxamide;
1-(2,4-dichlorophenyl)-N-[4-(trifluoromethoxy)benzene-1-sulfonyl]cyclopropane-1-carboxamide;
1-(2,4-dichlorophenyl)-N-[3-(trifluoromethyl)benzene-1-sulfonyl]cyclopropane-1-carboxamide;
1-(2,4-dichlorophenyl)-N-[4-(2-oxopyrrolidin-1-yl)benzene-1-sulfonyl]cyclopropane-1-carboxamide;
1-(2,4-dichlorophenyl)-N-[5-(1,2-oxazol-5-yl)thiophene-2-sulfonyl]cyclopropane-1-carboxamide;
1-(2,4-dichlorophenyl)-N-[4-(pyrrolidine-1-sulfonyl)benzene-1-sulfonyl]cyclopropane-1-carboxamide;
N-(4-chlorobenzene-1-sulfonyl)-1-(2,4-dichlorophenyl)-N-methylcyclopropane-1-carboxamide;
1-(2,4-dichlorophenyl)-N-{4-[(propan-2-yl)oxy]benzene-1-sulfonyl}cyclopropane-1-carboxamide;
1-(2,4-dichlorophenyl)-N-[6-(morpholin-4-yl)pyridine-3-sulfonyl]cyclopropane-1-carboxamide;
benzyl 4-{[1-(2,4-dichlorophenyl)cyclopropane-1-carbonyl]sulfamoyl}piperidine-1-carboxylate;
1-(2,4-dichlorophenyl)-N-(4-methoxybenzene-1-sulfonyl)cyclopropane-1-carboxamide;
1-(2,4-dichlorophenyl)-N-(3,4-dimethoxybenzene-1-sulfonyl)cyclopropane-1-carboxamide;
N-(3-chlorobenzene-1-sulfonyl)-1-(2,4-dichlorophenyl)cyclopropane-1-carboxamide;
1-(2,4-dichlorophenyl)-N-(naphthalene-2-sulfonyl)cyclopropane-1-carboxamide;
N-(cyclopropanesulfonyl)-1-(2,4-dichlorophenyl)cyclopropane-1-carboxamide;
N-(benzenesulfonyl)-1-(3,4-dichlorophenyl)cyclopropane-1-carboxamide;
1-(2,4-dichlorophenyl)-N-(1,1-dioxo-1$\lambda^6$-thiolane-3-sulfonyl)cyclopropane-1-carboxamide;
1-(2,4-dichlorophenyl)-N-(4-methylbenzene-1-sulfonyl)cyclopropane-1-carboxamide;
N-(2-cyano-5-fluorobenzene-1-sulfonyl)-1-(2,4-dichlorophenyl)cyclopropane-1-carboxamide;
1-(2,4-dichlorophenyl)-N-(pyridine-3-sulfonyl)cyclopropane-1-carboxamide;
N-(6-chloropyridine-3-sulfonyl)-1-(2,4-dichlorophenyl)cyclopropane-1-carboxamide;
methyl 5-{[1-(2,4-dichlorophenyl)cyclopropane-1-carbonyl]sulfamoyl}furan-2-carboxylate;
N-(5-bromothiophene-2-sulfonyl)-1-(2,4-dichlorophenyl)cyclopropane-1-carboxamide;
1-(2,4-dichlorophenyl)-N-[3-(trifluoromethoxy)benzene-1-sulfonyl]cyclopropane-1-carboxamide;
methyl 2-{[1-(2,4-dichlorophenyl)cyclopropane-1-carbonyl]sulfamoyl}benzoate;
methyl 4-chloro-2-{[1-(2,4-dichlorophenyl)cyclopropane-1-carbonyl]sulfamoyl}benzoate;
2-{[1-(2,4-dichlorophenyl)cyclopropane-1-carbonyl]sulfamoyl}benzoic acid;
4-chloro-2-{[1-(2,4-dichlorophenyl)cyclopropane-1-carbonyl]sulfamoyl}benzoic acid;
benzyl 4-{[1-(3,4-dichlorophenyl)cyclopropane-1-carbonyl]sulfamoyl}piperidine-1-carboxylate;
1-(2,4-dichlorophenyl)-N-(piperidine-4-sulfonyl)cyclopropane-1-carboxamide;
N-(1-acetylpiperidine-4-sulfonyl)-1-(2,4-dichlorophenyl)cyclopropane-1-carboxamide;
1-(2,4-dichlorophenyl)-N-[1-(3-phenylpropanoyl)piperidine-4-sulfonyl]cyclopropane-1-carboxamide;
tert-butyl 4-{[1-(2,4-dichlorophenyl)cyclopropane-1-carbonyl]sulfamoyl}piperidine-1-carboxylate;
1-(2,4-dichlorophenyl)-N-(2-methylbenzene-1-sulfonyl)cyclopropane-1-carboxamide;
1-(3,4-dimethoxyphenyl)-N-(naphthalene-1-sulfonyl)cyclopentane-1-carboxamide;

1-(2,2-difluoro-2H-1,3-benzodioxol-5-yl)-N-(naphthalene-1-sulfonyl)cyclopropane-1-carboxamide;
4-(5-methoxy-2-methylphenyl)-1-methyl-N-(quinoline-5-sulfonyl)piperidine-4-carboxamide;
1-[2-methoxy-5-(trifluoromethyl)pyridin-3-yl]-N-(pyrazolo[1,5-a]pyridine-4-sulfonyl)cyclopropane-1-carboxamide;
1-[2-methoxy-5-(trifluoromethyl)pyridin-3-yl]-N-(1-methyl-1H-benzimidazole-7-sulfonyl)cyclopropane-1-carboxamide;
1-[2-methoxy-5-(trifluoromethyl)pyridin-3-yl]-N-(1-methyl-1H-indazole-7-sulfonyl)cyclopropane-1-carboxamide;
N-(1H-indazole-4-sulfonyl)-1-[2-methoxy-5-(trifluoromethyl)pyridin-3-yl]cyclopropane-1-carboxamide;
1-(5-cyano-2-methoxyphenyl)-N-(quinoline-5-sulfonyl)cyclopropane-1-carboxamide;
1-(5-cyano-2-methoxyphenyl)-N-(1,2,3,4-tetrahydroquinoline-5-sulfonyl)cyclopropane-1-carboxamide;
1-[5-(bicyclo[1.1.1]pentan-1-yl)-2-methoxyphenyl]-N-(1,2,3,4-tetrahydroquinoline-5-sulfonyl)cyclopropane-1-carboxamide;
1-(2-methoxy-6-methylphenyl)-N-(1-methyl-1H-indole-4-sulfonyl)cyclopropane-1-carboxamide;
1-(3,5-dichloro-2,6-dimethoxyphenyl)-N-(quinoline-5-sulfonyl)cyclopropane-1-carboxamide;
1-(2,4-dichlorophenyl)-N-(phenylmethanesulfonyl)cyclopropane-1-carboxamide;
1-(2,4-dichlorophenyl)-N-(trifluoromethane sulfonyl)cyclopropane-1-carboxamide;
1-(2,4-dichlorophenyl)-N-(2,2,2-trifluoroethane sulfonyl)cyclopropane-1-carboxamide;
1-(2,4-dichlorophenyl)-N-(propane-1-sulfonyl)cyclopropane-1-carboxamide;
N-(3-chloropropane-1-sulfonyl)-1-(2,4-dichlorophenyl)cyclopropane-1-carboxamide;
1-(2,4-dichlorophenyl)-N-(propane-2-sulfonyl)cyclopropane-1-carboxamide;
1-(3,4-dichlorophenyl)-N-(phenylmethanesulfonyl)cyclopropane-1-carboxamide;
N-(pentane-3-sulfonyl)-1-phenylcyclopropane-1-carboxamide;
1-(3,4-dimethoxyphenyl)-N-(naphthalene-1-sulfonyl)cyclobutane-1-carboxamide;
1-[2-methoxy-6-(1-methyl-1H-pyrazol-4-yl)phenyl]-N-(quinoline-5-sulfonyl)cyclopropane-1-carboxamide;
1-(4-cyclobutyl-2,6-dimethoxyphenyl)-N-(1-methyl-1H-benzimidazole-7-sulfonyl)cyclopropane-1-carboxamide;
1-(3-methoxy-6-methylpyridin-2-yl)-N-(quinoline-5-sulfonyl)cyclopropane-1-carboxamide;
1-(3-methoxy-6-methylpyridin-2-yl)-N-(naphthalene-1-sulfonyl)cyclopropane-1-carboxamide;
1-(3-methoxy-6-methylpyridin-2-yl)-N-(2-methylquinoline-5-sulfonyl)cyclopropane-1-carboxamide;
1-(2,5-dimethylphenyl)-N-(1H-indazole-4-sulfonyl)cyclopropane-1-carboxamide;
1-[2-methoxy-5-(3-methoxyoxetan-3-yl)phenyl]-N-(quinoline-5-sulfonyl)cyclopropane-1-carboxamide;
1-{2-methoxy-5-[(3-$^2$H)oxetan-3-yl]phenyl}-N-(quinoline-5-sulfonyl)cyclopropane-1-carboxamide;
N-(1H-indazole-4-sulfonyl)-1-[5-methyl-2-(2-methylpropoxy)pyridin-3-yl]cyclopropane-1-carboxamide;
N-(1H-indazole-4-sulfonyl)-1-{5-methyl-2-[(propan-2-yl)oxy]pyridin-3-yl}cyclopropane-1-carboxamide;
1-(2-ethyl-6-methoxyphenyl)-N-(1H-indazole-4-sulfonyl)cyclopropane-1-carboxamide;
1-(2-ethyl-6-methoxyphenyl)-N-(2-methylquinoline-5-sulfonyl)cyclopropane-1-carboxamide;
N-[2-(dimethylamino)quinoline-5-sulfonyl]-1-(2-ethoxy-5-methylphenyl)cyclopropane-1-carboxamide;
1-{5-bromo-2-[(propan-2-yl)oxy]pyridin-3-yl}-N-(quinoline-5-sulfonyl)cyclopropane-1-carboxamide
1-{5-bromo-2-[(propan-2-yl)oxy]pyridin-3-yl}-N-(1,2,3,4-tetrahydroquinoline-5-sulfonyl)cyclopropane-1-carboxamide;
1-(5-chloro-2-methoxypyridin-3-yl)-N-(naphthalene-1-sulfonyl)cyclopropane-1-carboxamide
1-[2-propyl-6-(trifluoromethyl)pyridin-3-yl]-N-(quinoline-5-sulfonyl)cyclopropane-1-carboxamide;
1-[2-cyclopropyl-6-(trifluoromethyl)pyridin-3-yl]-N-(quinoline-5-sulfonyl)cyclopropane-1-carboxamide;
1-[2-cyclopropyl-6-(trifluoromethyl)pyridin-3-yl]-N-(1,2,3,4-tetrahydroquinoline-5-sulfonyl)cyclopropane-1-carboxamide;
1-[2-(propan-2-yl)-6-(trifluoromethyl)pyridin-3-yl]-N-(quinoline-5-sulfonyl)cyclopropane-1-carboxamide;
1-[2-propyl-6-(trifluoromethyl)pyridin-3-yl]-N-(1,2,3,4-tetrahydroquinoline-5-sulfonyl)cyclopropane-1-carboxamide;
1-[2-(propan-2-yl)-6-(trifluoromethyl)pyridin-3-yl]-N-(1,2,3,4-tetrahydroquinoline-5-sulfonyl)cyclopropane-1-carboxamide;
1-[2-cyclobutyl-6-(trifluoromethyl)pyridin-3-yl]-N-(1,2,3,4-tetrahydroquinoline-5-sulfonyl)cyclopropane-1-carboxamide;
1-[2-cyclobutyl-6-(trifluoromethyl)pyridin-3-yl]-N-(naphthalene-1-sulfonyl)cyclopropane-1-carboxamide
1-[2-cyclopropyl-5-(2-methylpropoxy)pyridin-3-yl]-N-(quinoline-5-sulfonyl)cyclopropane-1-carboxamide;
1-{5-ethyl-2-[(propan-2-yl)oxy]pyridin-3-yl}-N-(quinoline-5-sulfonyl)cyclopropane-1-carboxamide;
1-{5-ethyl-2-[(propan-2-yl)oxy]pyridin-3-yl}-N-(1,2,3,4-tetrahydroquinoline-5-sulfonyl)cyclopropane-1-carboxamide;
1-[2-(pyrrolidin-1-yl)-6-(trifluoromethyl)pyridin-3-yl]-N-(quinoline-5-sulfonyl)cyclopropane-1-carboxamide;
1-{2-methoxy-5-[(propan-2-yl)oxy]pyridin-4-yl}-N-(quinoline-5-sulfonyl)cyclopropane-1-carboxamide;
1-{6-methoxy-4-[(propan-2-yl)oxy]pyridin-3-yl}-sulfonyl)cyclopropane-1-carboxamide;
1-{6-methoxy-4-[(propan-2-yl)oxy]pyridin-3-yl}-N-(2-methylquinoline-5-sulfonyl)cyclopropane-1-carboxamide;
1-[2-methoxy-5-(2-methylpropoxy)pyridin-4-yl]-N-(quinoline-5-sulfonyl)cyclopropane-1-carboxamide;
1-[2-methoxy-5-(2-methylpropoxy)pyridin-4-yl]-N-(2-methylquinoline-5-sulfonyl)cyclopropane-1-carboxamide;
N-(1H-indole-4-sulfonyl)-1-[2-methoxy-5-(2-methylpropoxy)pyridin-4-yl]cyclopropane-1-carboxamide;
1-{5-cyclobutyl-2-[(propan-2-yl)oxy]pyridin-3-yl}-sulfonyl)cyclopropane-1-carboxamide;
1-{5-cyclobutyl-2-[(propan-2-yl)oxy]pyridin-3-yl}-N-(2-methylquinoline-5-sulfonyl)cyclopropane-1-carboxamide;
1-{5-cyclobutyl-2-[(propan-2-yl)oxy]pyridin-3-yl}-N-(1H-indole-4-sulfonyl)cyclopropane-1-carboxamide;
1-{2-cyclobutyl-5-[(propan-2-yl)oxy]pyridin-4-yl}-N-(quinoline-5-sulfonyl)cyclopropane-1-carboxamide;
1-{2-cyclobutyl-5-[(propan-2-yl)oxy]pyridin-4-yl}-N-(2-methylquinoline-5-sulfonyl)cyclopropane-1-carboxamide;
1-{2-cyclobutyl-5-[(propan-2-yl)oxy]pyridin-4-yl}-N-(1H-indole-4-sulfonyl)cyclopropane-1-carboxamide;

1-[5-cyclobutyl-2-(pyrrolidin-1-yl)pyridin-3-yl]-N-(quinoline-5-sulfonyl)cyclopropane-1-carboxamide;
1-[5-cyclobutyl-2-(pyrrolidin-1-yl)pyridin-3-yl]-N-(2-methylquinoline-5-sulfonyl)cyclopropane-1-carboxamide;
1-[5-cyclobutyl-2-(pyrrolidin-1-yl)pyridin-3-yl]-N-(1H-indole-4-sulfonyl)cyclopropane-1-carboxamide;
1-[5-cyclobutyl-2-(pyrrolidin-1-yl)pyridin-3-yl]-N-(1,2,3,4-tetrahydroquinoline-5-sulfonyl)cyclopropane-1-carboxamide;
1-[5-cyclopropyl-2-(pyrrolidin-1-yl)pyridin-3-yl]-N-(quinoline-5-sulfonyl)cyclopropane-1-carboxamide;
1-[5-cyclopropyl-2-(pyrrolidin-1-yl)pyridin-3-yl]-N-(2-methylquinoline-5-sulfonyl)cyclopropane-1-carboxamide;
1-[5-cyclopropyl-2-(pyrrolidin-1-yl)pyridin-3-yl]-N-(1H-indole-4-sulfonyl)cyclopropane-1-carboxamide;
1-[5-chloro-2-(pyrrolidin-1-yl)pyridin-3-yl]-N-(quinoline-5-sulfonyl)cyclopropane-1-carboxamide;
1-[5-chloro-2-(pyrrolidin-1-yl)pyridin-3-yl]-N-(2-methylquinoline-5-sulfonyl)cyclopropane-1-carboxamide;
1-[5-ethyl-2-(pyrrolidin-1-yl)pyridin-3-yl]-N-(1H-indole-4-sulfonyl)cyclopropane-1-carboxamide;
1-{6-cyclobutyl-3-[(propan-2-yl)oxy]pyridin-2-yl}-N-(1H-indole-4-sulfonyl)cyclopropane-1-carboxamide;
1-{6-cyclobutyl-3-[(propan-2-yl)oxy]pyridin-2-yl}-N-(quinoline-5-sulfonyl)cyclopropane-1-carboxamide;
1-{5-ethyl-2-[(propan-2-yl)oxy]pyridin-3-yl}-N-(2-methylquinoline-5-sulfonyl)cyclopropane-1-carboxamide;
1-{5-ethyl-2-[(propan-2-yl)oxy]pyridin-3-yl}-N-(1H-indole-4-sulfonyl)cyclopropane-1-carboxamide;
1-[5-methyl-2-(2-methylpropoxy)pyridin-3-yl]-N-(quinoline-5-sulfonyl)cyclopropane-1-carboxamide;
1-[5-methyl-2-(2-methylpropoxy)pyridin-3-yl]-N-(2-methylquinoline-5-sulfonyl)cyclopropane-1-carboxamide;
N-(1H-indole-4-sulfonyl)-1-[5-methyl-2-(2-methylpropoxy)pyridin-3-yl]cyclopropane-1-carboxamide;
1-[5-ethyl-2-(2-methylpropoxy)pyridin-3-yl]-N-(quinoline-5-sulfonyl)cyclopropane-1-carboxamide;
1-[5-ethyl-2-(2-methylpropoxy)pyridin-3-yl]-N-(2-methylquinoline-5-sulfonyl)cyclopropane-1-carboxamide;
1-[5-ethyl-2-(2-methylpropoxy)pyridin-3-yl]-N-(1H-indole-4-sulfonyl)cyclopropane-1-carboxamide;
1-[5-cyclopropyl-2-(2-methylpropoxy)pyridin-3-yl]-N-(quinoline-5-sulfonyl)cyclopropane-1-carboxamide;
1-[5-cyclopropyl-2-(2-methylpropoxy)pyridin-3-yl]-N-(2-methylquinoline-5-sulfonyl)cyclopropane-1-carboxamide;
1-[5-cyclopropyl-2-(2-methylpropoxy)pyridin-3-yl]-N-(1H-indole-4-sulfonyl)cyclopropane-1-carboxamide;
1-[5-cyclobutyl-2-(2-methylpropoxy)pyridin-3-yl]-N-(quinoline-5-sulfonyl)cyclopropane-1-carboxamide;
1-[5-cyclobutyl-2-(2-methylpropoxy)pyridin-3-yl]-N-(1H-indole-4-sulfonyl)cyclopropane-1-carboxamide;
1-[5-cyclobutyl-2-(2-methylpropoxy)pyridin-3-yl]-N-(2-methylquinoline-5-sulfonyl)cyclopropane-1-carboxamide;
1-{6-ethyl-3-[(propan-2-yl)oxy]pyridin-2-yl}-N-(2-methylquinoline-5-sulfonyl)cyclopropane-1-carboxamide;
1-{6-ethyl-3-[(propan-2-yl)oxy]pyridin-2-yl}-N-(quinoline-5-sulfonyl)cyclopropane-1-carboxamide;
1-{6-ethyl-3-[(propan-2-yl)oxy]pyridin-2-yl}-N-(1H-indole-4-sulfonyl)cyclopropane-1-carboxamide;
1-[5-cyclobutyl-2-(4-methoxypiperidin-1-yl)pyridin-3-yl]-N-(1H-indole-4-sulfonyl)cyclopropane-1-carboxamide;
1-{5-methyl-2-[(propan-2-yl)oxy]pyridin-3-yl}-N-(2-methylquinoline-5-sulfonyl)cyclopropane-1-carboxamide;
N-(1H-indole-4-sulfonyl)-1-{5-methyl-2-[(propan-2-yl)oxy]pyridin-3-yl}cyclopropane-1-carboxamide;
1-{5-cyclopropyl-2-[(propan-2-yl)oxy]pyridin-3-yl}-N-(2-methylquinoline-5-sulfonyl)cyclopropane-1-carboxamide;
1-{5-cyclopropyl-2-[(propan-2-yl)oxy]pyridin-3-yl}-N-(1H-indole-4-sulfonyl)cyclopropane-1-carboxamide;
1-{2-[(propan-2-yl)oxy]-5-(pyrrolidin-1-yl)pyridin-3-yl}-N-(quinoline-5-sulfonyl)cyclopropane-1-carboxamide;
N-(2-methylquinoline-5-sulfonyl)-1-{2-[(propan-2-yl)oxy]-5-(pyrrolidin-1-yl)pyridin-3-yl}cyclopropane-1-carboxamide;
N-(1H-indole-4-sulfonyl)-1-{2-[(propan-2-yl)oxy]-5-(pyrrolidin-1-yl)pyridin-3-yl}cyclopropane-1-carboxamide;
1-{2,5-bis[(propan-2-yl)oxy]pyridin-3-yl}-N-(quinoline-5-sulfonyl)cyclopropane-1-carboxamide;
1-{2,5-bis[(propan-2-yl)oxy]pyridin-3-yl}-N-(1H-indole-4-sulfonyl)cyclopropane-1-carboxamide;
1-{2,5-bis[(propan-2-yl)oxy]pyridin-3-yl}-N-(2-methylquinoline-5-sulfonyl)cyclopropane-1-carboxamide;
1-[2-(2-methylpropoxy)-5-(pyrrolidin-1-yl)pyridin-3-yl]-N-(quinoline-5-sulfonyl)cyclopropane-1-carboxamide;
1-[2-(2-methylpropoxy)-5-(pyrrolidin-1-yl)pyridin-3-yl]-N-(2-methylquinoline-5-sulfonyl)cyclopropane-1-carboxamide;
N-(1H-indole-4-sulfonyl)-1-[2-(2-methylpropoxy)-5-(pyrrolidin-1-yl)pyridin-3-yl]cyclopropane-1-carboxamide;
1-{5-(dimethylamino)-2-[(propan-2-yl)oxy]pyridin-3-yl}-N-(quinoline-5-sulfonyl)cyclopropane-1-carboxamide;
1-{5-(dimethylamino)-2-[(propan-2-yl)oxy]pyridin-3-yl}-N-(2-methylquinoline-5-sulfonyl)cyclopropane-1-carboxamide;
1-{5-(dimethylamino)-2-[(propan-2-yl)oxy]pyridin-3-yl}-N-(1H-indole-4-sulfonyl)cyclopropane-1-carboxamide;
1-{5-methoxy-2-[(propan-2-yl)oxy]pyridin-3-yl}-N-(quinoline-5-sulfonyl)cyclopropane-1-carboxamide;
N-(1H-indole-4-sulfonyl)-1-{5-methoxy-2-[(propan-2-yl)oxy]pyridin-3-yl}cyclopropane-1-carboxamide;
1-{5-methoxy-2-[(propan-2-yl)oxy]pyridin-3-yl}-N-(2-methylquinoline-5-sulfonyl)cyclopropane-1-carboxamide;
1-[5-methoxy-2-(2-methylpropoxy)pyridin-3-yl]-N-(quinoline-5-sulfonyl)cyclopropane-1-carboxamide;
N-(1H-indole-4-sulfonyl)-1-[5-methoxy-2-(2-methylpropoxy)pyridin-3-yl]cyclopropane-1-carboxamide;
1-[5-methoxy-2-(2-methylpropoxy)pyridin-3-yl]-N-(2-methylquinoline-5-sulfonyl)cyclopropane-1-carboxamide;
1-{6-methyl-2-[(propan-2-yl)oxy]pyridin-3-yl}-N-(quinoline-5-sulfonyl)cyclopropane-1-carboxamide;
1-{6-methyl-2-[(propan-2-yl)oxy]pyridin-3-yl}-N-(2-methylquinoline-5-sulfonyl)cyclopropane-1-carboxamide;
N-(1H-indole-4-sulfonyl)-1-{6-methyl-2-[(propan-2-yl)oxy]pyridin-3-yl}cyclopropane-1-carboxamide;
1-{5-(azetidin-1-yl)-2-[(propan-2-yl)oxy]pyridin-3-yl}-N-(quinoline-5-sulfonyl)cyclopropane-1-carboxamide;
1-{5-(azetidin-1-yl)-2-[(propan-2-yl)oxy]pyridin-3-yl}-N-(2-methylquinoline-5-sulfonyl)cyclopropane-1-carboxamide;
1-{5-(azetidin-1-yl)-2-[(propan-2-yl)oxy]pyridin-3-yl}-N-(1H-indole-4-sulfonyl)cyclopropane-1-carboxamide;
1-{6-(2-methylpropoxy)-3-[(propan-2-yl)oxy]pyridin-2-yl}-N-(quinoline-5-sulfonyl)cyclopropane-1-carboxamide;
1-[2-(cyclopropylmethoxy)-5-methoxypyridin-3-yl]-N-(quinoline-5-sulfonyl)cyclopropane-1-carboxamide;

1-[2-(cyclopropylmethoxy)-5-methoxypyridin-3-yl]-N-(1H-indole-4-sulfonyl)cyclopropane-1-carboxamide;
N-(1H-indole-4-sulfonyl)-1-{6-(2-methylpropoxy)-3-[(propan-2-yl)oxy]pyridin-2-yl}cyclopropane-1-carboxamide;
1-{6-(2-methylpropoxy)-3-[(propan-2-yl)oxy]pyridin-2-yl}-N-(2-methylquinoline-5-sulfonyl)cyclopropane-1-carboxamide;
1-[5-(cyclopropylmethoxy)-2-methoxypyridin-4-yl]-N-(quinoline-5-sulfonyl)cyclopropane-1-carboxamide;
1-[2-(cyclopropylmethoxy)-5-methoxypyridin-3-yl]-N-(2-methylquinoline-5-sulfonyl)cyclopropane-1-carboxamide;
1-[5-(cyclopropylmethoxy)-2-methoxypyridin-4-yl]-N-(2-methylquinoline-5-sulfonyl)cyclopropane-1-carboxamide;
1-[5-cyclobutyl-2-(2-methoxyethoxy)pyridin-3-yl]-N-(2-methylquinoline-5-sulfonyl)cyclopropane-1-carboxamide;
1-[5-(cyclopropylmethoxy)-2-methoxypyridin-4-yl]-N-(1H-indole-4-sulfonyl)cyclopropane-1-carboxamide;
1-[2-(cyclopropylmethoxy)-5-methylpyridin-3-yl]-N-(quinoline-5-sulfonyl)cyclopropane-1-carboxamide;
1-[2-(cyclopropylmethoxy)-5-methylpyridin-3-yl]-N-(1H-indole-4-sulfonyl)cyclopropane-1-carboxamide;
1-[5-cyclobutyl-2-(cyclopropylmethoxy)pyridin-3-yl]-N-(1H-indole-4-sulfonyl)cyclopropane-1-carboxamide;
1-[5-cyclobutyl-2-(2-methoxyethoxy)pyridin-3-yl]-N-(1H-indole-4-sulfonyl)cyclopropane-1-carboxamide;
1-[5-cyclobutyl-2-(cyclopropylmethoxy)pyridin-3-yl]-N-(quinoline-5-sulfonyl)cyclopropane-1-carboxamide;
1-[2-(cyclopropylmethoxy)-5-methylpyridin-3-yl]-N-(2-methylquinoline-5-sulfonyl)cyclopropane-1-carboxamide;
1-(5-ethyl-2-{4-[(propan-2-yl)oxy]piperidin-1-yl}pyridin-3-yl)-N-(1H-indole-4-sulfonyl)cyclopropane-1-carboxamide;
1-(5-cyclobutyl-2-{4-[(propan-2-yl)oxy]piperidin-1-yl}pyridin-3-yl)-N-(1H-indole-4-sulfonyl)cyclopropane-1-carboxamide;
1-(5-cyclobutyl-2-{4-[(propan-2-yl)oxy]piperidin-1-yl}pyridin-3-yl)-N-(quinoline-5-sulfonyl)cyclopropane-1-carboxamide;
1-[2-(cyclopropylmethoxy)-5-ethylpyridin-3-yl]-N-(quinoline-5-sulfonyl)cyclopropane-1-carboxamide;
1-[2-(cyclopropylmethoxy)-5-ethylpyridin-3-yl]-N-(2-methylquinoline-5-sulfonyl)cyclopropane-1-carboxamide;
1-[2-(cyclopropylmethoxy)-5-ethylpyridin-3-yl]-N-(1H-indole-4-sulfonyl)cyclopropane-1-carboxamide;
1-[5-ethyl-2-(2-methoxyethoxy)pyridin-3-yl]-N-(1H-indole-4-sulfonyl)cyclopropane-1-carboxamide;
1-[5-cyclobutyl-2-(cyclopropylmethoxy)pyridin-3-yl]-N-(2-methylquinoline-5-sulfonyl)cyclopropane-1-carboxamide;
1-[5-cyclobutyl-2-(2-methoxyethoxy)pyridin-3-yl]-N-(quinoline-5-sulfonyl)cyclopropane-1-carboxamide;
1-[5-ethyl-2-(2-methoxyethoxy)pyridin-3-yl]-N-(quinoline-5-sulfonyl)cyclopropane-1-carboxamide;
1-(5-cyclobutyl-2-{4-[(propan-2-yl)oxy]piperidin-1-yl}pyridin-3-yl)-N-(2-methylquinoline-5-sulfonyl)cyclopropane-1-carboxamide;
1-(5-cyclobutyl-2-ethoxypyridin-3-yl)-N-(quinoline-5-sulfonyl)cyclopropane-1-carboxamide;
1-(5-cyclobutyl-2-ethoxypyridin-3-yl)-N-(2-methylquinoline-5-sulfonyl)cyclopropane-1-carboxamide;
1-(2-ethoxy-5-ethylpyridin-3-yl)-N-(quinoline-5-sulfonyl)cyclopropane-1-carboxamide;
1-(2-ethoxy-5-ethylpyridin-3-yl)-N-(2-methylquinoline-5-sulfonyl)cyclopropane-1-carboxamide;
1-{5-cyclobutyl-2-[4-(methoxymethyl)piperidin-1-yl]pyridin-3-yl}-N-(1H-indole-4-sulfonyl)cyclopropane-1-carboxamide;
1-{5-[1-(methoxymethyl)cyclopropyl]-2-[(propan-2-yl)oxy]pyridin-3-yl}-N-(naphthalene-1-sulfonyl)cyclopropane-1-carboxamide;
1-{5-ethyl-2-[4-(methoxymethyl)piperidin-1-yl]pyridin-3-yl}-N-(1H-indole-4-sulfonyl)cyclopropane-1-carboxamide;
1-{5-cyclobutyl-2-[4-(methoxymethyl)piperidin-1-yl]pyridin-3-yl}-N-(quinoline-5-sulfonyl)cyclopropane-1-carboxamide;
1-(2,4-dimethoxypyrimidin-5-yl)-N-(naphthalene-1-sulfonyl)cyclopropane-1-carboxamide;
N-(naphthalene-1-sulfonyl)-1-{2-[(propan-2-yl)oxy]pyridin-3-yl}cyclopropane-1-carboxamide;
1-{2-[(propan-2-yl)oxy]pyridin-3-yl}-N-(quinoline-5-sulfonyl)cyclopropane-1-carboxamide;
1-{2-[(propan-2-yl)oxy]pyridin-3-yl}-N-(1,2,3,4-tetrahydroquinoline-5-sulfonyl)cyclopropane-1-carboxamide;
1-[5-chloro-2-(trifluoromethyl)pyridin-3-yl]-N-(naphthalene-1-sulfonyl)cyclopropane-1-carboxamide;
1-(5-chloro-2-methoxypyridin-4-yl)-N-(quinoline-5-sulfonyl)cyclopropane-1-carboxamide,
1-(5-chloro-2-methoxypyridin-4-yl)-N-(1,2,3,4-tetrahydroquinoline-5-sulfonyl)cyclopropane-1-carboxamide;
1-[5-methyl-2-(morpholin-4-yl)pyridin-4-yl]-N-(quinoline-5-sulfonyl)cyclopropane-1-carboxamide;
1-[5-methyl-2-(pyrrolidin-1-yl)pyridin-4-yl]-N-(quinoline-5-sulfonyl)cyclopropane-1-carboxamide;
1-[2-methoxy-6-(trifluoromethyl)pyridin-3-yl]-N-(quinoline-5-sulfonyl)cyclopropane-1-carboxamide;
1-[2-(dimethylamino)-5-methylpyridin-4-yl]-N-(quinoline-5-sulfonyl)cyclopropane-1-carboxamide;
1-[2-methoxy-6-(trifluoromethyl)pyridin-3-yl]-N-(1,2,3,4-tetrahydroquinoline-5-sulfonyl)cyclopropane-1-carboxamide;
1-(2-methoxy-5-methylpyridin-4-yl)-N-(quinoline-5-sulfonyl)cyclopropane-1-carboxamide;
1-[2-cyclobutyl-6-(trifluoromethyl)pyridin-3-yl]-N-(quinoline-5-sulfonyl)cyclopropane-1-carboxamide;
1-(2-cyclopropyl-5-methoxypyridin-3-yl)-N-(quinoline-5-sulfonyl)cyclopropane-1-carboxamide;
1-{2-ethyl-5-[(propan-2-yl)oxy]pyridin-3-yl}-N-(quinoline-5-sulfonyl)cyclopropane-1-carboxamide;
1-(2-ethyl-5-methoxypyridin-3-yl)-N-(quinoline-5-sulfonyl)cyclopropane-1-carboxamide;
1-[6-(dimethylamino)-2-methoxypyridin-3-yl]-N-(quinoline-5-sulfonyl)cyclopropane-1-carboxamide;
1-(6-methoxy-2-methylpyridin-3-yl)-N-(naphthalene-1-sulfonyl)cyclopropane-1-carboxamide;
1-(4-ethylpyridin-3-yl)-N-(naphthalene-1-sulfonyl)cyclopropane-1-carboxamide;
1-(4-ethylpyridin-3-yl)-N-(1,2,3,4-tetrahydroquinoline-5-sulfonyl)cyclopropane-1-carboxamide;
1-(6-methoxy-4-methylpyridin-3-yl)-N-(naphthalene-1-sulfonyl)cyclopropane-1-carboxamide;
1-(6-methoxy-4-methylpyridin-3-yl)-N-(quinoline-5-sulfonyl)cyclopropane-1-carboxamide;
1-{6-methoxy-4-[(propan-2-yl)oxy]pyridin-3-yl}-N-(1,2,3,4-tetrahydroquinoline-5-sulfonyl)cyclopropane-1-carboxamide;
1-{5-cyclobutyl-2-[(propan-2-yl)oxy]pyridin-3-yl}-N-(1,2,3,4-tetrahydroquinoline-5-sulfonyl)cyclopropane-1-carboxamide;

1-{2-cyclobutyl-5-[(propan-2-yl)oxy]pyridin-4-yl}-N-(1,2,3,4-tetrahydroquinoline-5-sulfonyl)cyclopropane-1-carboxamide;
1-{5-cyclobutyl-3-[(propan-2-yl)oxy]pyridin-2-yl}-N-(quinoline-5-sulfonyl)cyclopropane-1-carboxamide;
1-[5-cyclobutyl-2-(morpholin-4-yl)pyridin-3-yl]-N-(quinoline-5-sulfonyl)cyclopropane-1-carboxamide;
1-[5-cyclopropyl-2-(pyrrolidin-1-yl)pyridin-3-yl]-N-(1,2,3,4-tetrahydroquinoline-5-sulfonyl)cyclopropane-1-carboxamide;
1-[5-ethyl-2-(pyrrolidin-1-yl)pyridin-3-yl]-N-(quinoline-5-sulfonyl)cyclopropane-1-carboxamide;
1-[5-ethyl-2-(pyrrolidin-1-yl)pyridin-3-yl]-N-(2-methylquinoline-5-sulfonyl)cyclopropane-1-carboxamide;
1-[5-ethyl-2-(morpholin-4-yl)pyridin-3-yl]-N-(2-methylquinoline-5-sulfonyl)cyclopropane-1-carboxamide;
1-[2-(pyrrolidin-1-yl)pyridin-3-yl]-N-(quinoline-5-sulfonyl)cyclopropane-1-carboxamide;
N-(2-methylquinoline-5-sulfonyl)-1-[2-(pyrrolidin-1-yl)pyridin-3-yl]cyclopropane-1-carboxamide;
1-[5-ethyl-2-(pyrrolidin-1-yl)pyridin-3-yl]-N-(1,2,3,4-tetrahydroquinoline-5-sulfonyl)cyclopropane-1-carboxamide;
1-[5-methyl-2-(pyrrolidin-1-yl)pyridin-3-yl]-N-(2-methylquinoline-5-sulfonyl)cyclopropane-1-carboxamide;
N-(1H-indole-4-sulfonyl)-1-[5-methyl-2-(pyrrolidin-1-yl)pyridin-3-yl]cyclopropane-1-carboxamide;
1-[5-methyl-2-(pyrrolidin-1-yl)pyridin-3-yl]-N-(quinoline-5-sulfonyl)cyclopropane-1-carboxamide;
1-(3-cyclopropyl-5-methylpyridin-2-yl)-N-(1H-indole-4-sulfonyl)cyclopropane-1-carboxamide;
1-[5-methoxy-2-(pyrrolidin-1-yl)pyridin-3-yl]-N-(quinoline-5-sulfonyl)cyclopropane-1-carboxamide;
1-[2-(dimethylamino)-5-methylpyridin-3-yl]-N-(quinoline-5-sulfonyl)cyclopropane-1-carboxamide;
1-[5-methoxy-2-(2-methoxyethoxy)pyridin-3-yl]-N-(2-methylquinoline-5-sulfonyl)cyclopropane-1-carboxamide;
N-(1H-indole-4-sulfonyl)-1-[5-methoxy-2-(2-methoxyethoxy)pyridin-3-yl]cyclopropane-1-carboxamide;
1-[5-methoxy-2-(2-methoxyethoxy)pyridin-3-yl]-N-(quinoline-5-sulfonyl)cyclopropane-1-carboxamide;
N-(1H-indole-4-sulfonyl)-1-[2-methoxy-5-(2-methoxyethoxy)pyridin-4-yl]cyclopropane-1-carboxamide;
1-[2-methoxy-5-(2-methoxyethoxy)pyridin-4-yl]-N-(2-methylquinoline-5-sulfonyl)cyclopropane-1-carboxamide;
1-[2-(dimethylamino)-5-ethylpyridin-3-yl]-N-(quinoline-5-sulfonyl)cyclopropane-1-carboxamide;
1-[2-(dimethylamino)-5-ethylpyridin-3-yl]-N-(2-methylquinoline-5-sulfonyl)cyclopropane-1-carboxamide;
1-[2-(dimethylamino)-5-ethylpyridin-3-yl]-N-(1H-indole-4-sulfonyl)cyclopropane-1-carboxamide;
1-[2-(2-methoxyethoxy)-5-methylpyridin-3-yl]-N-(2-methylquinoline-5-sulfonyl)cyclopropane-1-carboxamide;
1-{2-(dimethylamino)-6-[(propan-2-yl)oxy]pyridin-3-yl}-N-(quinoline-5-sulfonyl)cyclopropane-1-carboxamide;
1-[2-(2-methoxyethoxy)-5-methylpyridin-3-yl]-N-(quinoline-5-sulfonyl)cyclopropane-1-carboxamide;
N-(1H-indole-4-sulfonyl)-1-[2-(2-methoxyethoxy)-5-methylpyridin-3-yl]cyclopropane-1-carboxamide;
1-(5-ethyl-2-{4-[(propan-2-yl)oxy]piperidin-1-yl}pyridin-3-yl)-N-(quinoline-5-sulfonyl)cyclopropane-1-carboxamide;
1-(5-ethyl-2-{4-[(propan-2-yl)oxy]piperidin-1-yl}pyridin-3-yl)-N-(2-methylquinoline-5-sulfonyl)cyclopropane-1-carboxamide;
1-[5-ethyl-2-(2-methoxyethoxy)pyridin-3-yl]-N-(2-methylquinoline-5-sulfonyl)cyclopropane-1-carboxamide;
1-[5-ethyl-2-(4-methoxypiperidin-1-yl)pyridin-3-yl]-N-(quinoline-5-sulfonyl)cyclopropane-1-carboxamide;
1-[5-ethyl-2-(4-methoxypiperidin-1-yl)pyridin-3-yl]-N-(1H-indole-4-sulfonyl)cyclopropane-1-carboxamide;
1-{5-ethyl-2-[4-(methoxymethyl)piperidin-1-yl]pyridin-3-yl}-N-(quinoline-5-sulfonyl)cyclopropane-1-carboxamide;
1-[3-chloro-5-(trifluoromethyl)pyridin-2-yl]-N-(quinoline-5-sulfonyl)cyclopropane-1-carboxamide;
1-[5-chloro-2-(trifluoromethyl)pyridin-3-yl]-N-(quinoline-5-sulfonyl)cyclopropane-1-carboxamide;
N-(1H-indole-4-sulfonyl)-1-{6-methoxy-4-[(propan-2-yl)oxy]pyridin-3-yl}cyclopropane-1-carboxamide;
1-(3-cyclopropyl-5-methylpyridin-2-yl)-N-(quinoline-5-sulfonyl)cyclopropane-1-carboxamide;
1-[2-chloro-5-(2-methylpropoxy)pyridin-3-yl]-N-(quinoline-5-sulfonyl)cyclopropane-1-carboxamide;
1-(4-ethylpyridin-3-yl)-N-(quinoline-5-sulfonyl)cyclopropane-1-carboxamide;
1-(2-fluoro-5-methylpyridin-4-yl)-N-(1,2,3,4-tetrahydroquinoline-5-sulfonyl)cyclopropane-1-carboxamide;
1-(6-methoxy-2-methylpyridin-3-yl)-N-(quinoline-5-sulfonyl)cyclopropane-1-carboxamide;
1-[5-cyclopropyl-2-(4-methylpiperazin-1-yl)pyridin-3-yl]-N-(quinoline-5-sulfonyl)cyclopropane-1-carboxamide;
1-[5-cyclopropyl-2-(trifluoromethyl)pyridin-3-yl]-N-(quinoline-5-sulfonyl)cyclopropane-1-carboxamide;
1-[2-methoxy-5-(2-methoxyethoxy)pyridin-4-yl]-N-(quinoline-5-sulfonyl)cyclopropane-1-carboxamide;
1-(2,4-dimethoxypyrimidin-5-yl)-N-(1,2,3,4-tetrahydroquinoline-5-sulfonyl)cyclopropane-1-carboxamide;
1-{2-chloro-5-[(propan-2-yl)oxy]pyridin-3-yl}-N-(quinoline-5-sulfonyl)cyclopropane-1-carboxamide;
1-[5-(2,2-difluoroethoxy)-2-methoxypyridin-4-yl]-N-(2-methylquinoline-5-sulfonyl)cyclopropane-1-carboxamide;
1-(6-methoxy-2-methylpyridin-3-yl)-N-(1,2,3,4-tetrahydroquinoline-5-sulfonyl)cyclopropane-1-carboxamide;
1-(2-fluoro-5-methylpyridin-4-yl)-N-(quinoline-5-sulfonyl)cyclopropane-1-carboxamide;
1-(6-methoxy-4-methylpyridin-3-yl)-N-(1,2,3,4-tetrahydroquinoline-5-sulfonyl)cyclopropane-1-carboxamide;
1-[5-(2,2-difluoroethoxy)-2-methoxypyridin-4-yl]-N-(quinoline-5-sulfonyl)cyclopropane-1-carboxamide;
1-[5-(difluoromethoxy)-2-methoxypyridin-4-yl]-N-(quinoline-5-sulfonyl)cyclopropane-1-carboxamide;
1-[5-cyclopropyl-2-(morpholin-4-yl)pyridin-3-yl]-N-(2-methylquinoline-5-sulfonyl)cyclopropane-1-carboxamide;
1-[2-chloro-6-(trifluoromethyl)pyridin-3-yl]-N-(naphthalene-1-sulfonyl)cyclopropane-1-carboxamide;
1-[5-(difluoromethoxy)-2-methoxypyridin-4-yl]-N-(2-methylquinoline-5-sulfonyl)cyclopropane-1-carboxamide;
1-[5-ethyl-2-(morpholin-4-yl)pyridin-3-yl]-N-(quinoline-5-sulfonyl)cyclopropane-1-carboxamide;
1-(2,4-dimethoxypyrimidin-5-yl)-N-(quinoline-5-sulfonyl)cyclopropane-1-carboxamide;
1-[5-cyclopropyl-2-(morpholin-4-yl)pyridin-3-yl]-N-(quinoline-5-sulfonyl)cyclopropane-1-carboxamide;
1-[5-methyl-2-(4-methylpiperazin-1-yl)pyridin-3-yl]-N-(quinoline-5-sulfonyl)cyclopropane-1-carboxamide;
1-[5-cyclopropyl-2-(4-methylpiperazin-1-yl)pyridin-3-yl]-N-(2-methylquinoline-5-sulfonyl)cyclopropane-1-carboxamide;

1-[2-chloro-6-(trifluoromethyl)pyridin-3-yl]-N-(1,2,3,4-tetrahydroquinoline-5-sulfonyl)cyclopropane-1-carboxamide;

1-[2-chloro-6-(trifluoromethyl)pyridin-3-yl]-N-(quinoline-5-sulfonyl)cyclopropane-1-carboxamide;

1-(6-amino-2-methoxypyridin-3-yl)-N-(quinoline-5-sulfonyl)cyclopropane-1-carboxamide;

1-[5-cyclobutyl-2-(4-methylpiperazin-1-yl)pyridin-3-yl]-N-(quinoline-5-sulfonyl)cyclopropane-1-carboxamide;

1-[5-cyclobutyl-2-(4-methylpiperazin-1-yl)pyridin-3-yl]-N-(2-methylquinoline-5-sulfonyl)cyclopropane-1-carboxamide;

1-[5-ethyl-2-(4-methylpiperazin-1-yl)pyridin-3-yl]-N-(quinoline-5-sulfonyl)cyclopropane-1-carboxamide;

1-(5-chloro-2-fluoropyridin-3-yl)-N-(quinoline-5-sulfonyl)cyclopropane-1-carboxamide;

1-{5-(hydroxymethyl)-2-[(propan-2-yl)oxy]pyridin-3-yl}-N-(quinoline-5-sulfonyl)cyclopropane-1-carboxamide;

1-[5-cyclopropyl-2-(4-methylpiperazin-1-yl)pyridin-3-yl]-N-(1H-indole-4-sulfonyl)cyclopropane-1-carboxamide;

and pharmaceutically acceptable salts thereof.

Certain embodiments pertain to compounds of Formula (II),

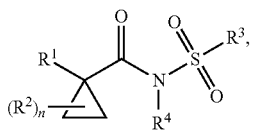

Formula (II)

wherein

R$^1$ is selected from the group consisting of 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the R$^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are substituted with two or more substituents independently selected from the group consisting of R$^7$, OR$^7$, C(O)R$^7$, OC(O)R$^7$, C(O)OR$^7$, SO$_2$R$^7$, C(O)NH$_2$, C(O)NHR$^7$, C(O)N(R$^7$)$_2$, NHC(O)R$^7$, NHR$^7$, N(R$^7$)$_2$, NH$_2$, C(O)OH, OH, oxo, CN, NO$_2$, F, Cl, Br and I;

R$^2$ is independently selected from the group consisting of hydrogen, R$^8$, OR$^8$, C(O)R$^8$, C(O)OR$^8$, SO$_2$R$^8$, NHR$^8$, N(R$^8$)$_2$, NH$_2$, C(O)OH, OH, NO$_2$, F, Cl, Br and I;

n is 0 or 1;

R$^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the R$^3$ $C_1$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, NO$_2$, F, Cl, Br and I; wherein the R$^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of R$^9$, OR$^9$, SR$^9$, C(O)R$^9$, OC(O)R$^9$, C(O)OR$^9$, SO$_2$R$^9$, C(O)NH$_2$, C(O)NHR$^9$, C(O)N(R$^9$)$_2$, NHC(O)R$^9$, NHR$^9$, N(R$^9$)$_2$, NH$_2$, C(O)OH, OH, oxo, CN, NO$_2$, F, Cl, Br and I;

R$^4$ is selected from the group consisting of hydrogen and $C_1$-$C_6$ alkyl; wherein the R$^4$ $C_1$-$C_6$ alkyl is optionally substituted with one or more substituents independently selected from the group consisting of OR$^{10}$, F, Cl, Br and I;

R$^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each R$^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, $C_3$-$C_7$ cycloalkyl, OH, oxo, CN, NO$_2$, F, Cl, Br and I; wherein each R$^7$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of R$^{11}$, OR$^{11}$, SR$^{11}$, C(O)OR$^{11}$, OC(O)R$^{11}$, C(O)R$^{11}$, SO$_2$R$^{11}$, C(O)NH$_2$, C(O)NHR$^{11}$, C(O)N(R$^{11}$)$_2$, NHC(O)R$^{11}$, NHR$^{11}$, N(R$^{11}$)$_2$, NH$_2$, C(O)OH, OH, oxo, CN, NO$_2$, F, Cl, Br and I;

R$^8$, at each occurrence, is independently selected from the group consisting of $C_1$-$C_6$ alkyl, $C_2$-$C_6$ alkenyl, and $C_2$-$C_6$ alkynyl; wherein each R$^8$ $C_1$-$C_6$ alkyl, $C_2$-$C_6$ alkenyl, and $C_2$-$C_6$ alkynyl is optionally substituted with one or more substituents independently selected from the group consisting of R$^{12}$, OR$^{12}$, C(O)O N$_{HR}$12 N(R12)$_2$, NH$_2$, C(O)OH, OH, CN, NO$_2$, F, Cl, Br and I;

R$^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each R$^9$ $C_1$-$C_6$ alkyl, $C_2$-$C_6$ alkenyl, and $C_2$-$C_6$ alkynyl is optionally substituted with one or more substituents independently selected from the group consisting of R$^{13}$, OR$^{13}$, SR$^{13}$, C(O)R$^{13}$, OC(O)R$^{13}$, C(O)OR$^{13}$, SO$_2$R$^{13}$, C(O)NH$_2$, C(O)NHR$^{13}$, C(O)N(R$^{13}$)$_2$, NHC(O)R$^{13}$, NHR$^{13}$, N(R$^{13}$)$_2$, NH$_2$, C(O)OH, OH, oxo, CN, NO$_2$, F, Cl, Br and I; wherein each R$^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of R$^{14}$, OR$^{14}$, SR$^{14}$, C(O)R$^{14}$, OC(O)R$^{14}$, C(O)OR$^{14}$, SO$_2$R$^{14}$, C(O)NH$_2$, C(O)NHR$^{14}$, C(O)N(R$^{14}$)$_2$, NHC(O)R$^{14}$, NHR$^{14}$, N(R$^{14}$)$_2$, NH$_2$, C(O)OH, OH, oxo, CN, NO$_2$, F, Cl, Br and I;

R$^{10}$, at each occurrence, is independently $C_1$-$C_4$ alkyl;

R$^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each R$^{11}$ $C_1$-$C_6$ alkyl and $C_1$-$C_6$ alkoxy is optionally substituted with one or more substituents independently selected from the group consisting of $C_1$-$C_6$ alkoxy, OH, oxo, CN, NO$_2$, F, Cl, Br and I; wherein each R$^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;

R$^{12}$, at each occurrence, is independently selected from the group consisting of $C_1$-$C_6$ alkyl, $C_1$-$C_6$ alkoxy, C$_6$-C$_{10}$ membered aryl, C$_3$-C$_{11}$ cycloalkyl, 4-12 membered heterocyclyl, C$_4$-C$_{11}$ cycloalkenyl, and 5-6 membered heteroaryl;

R$^{13}$, at each occurrence, is independently selected from the group consisting of C$_1$-C$_6$ alkyl, C$_2$-C$_6$ alkenyl, C$_2$-C$_6$ alkynyl, C$_6$-C$_{10}$ membered aryl, 5-11 membered heteroaryl, C$_3$-C$_{11}$ cycloalkyl, C$_4$-C$_{11}$ cycloalkenyl, and 4-12 membered heterocyclyl; wherein each R$^{13}$ C$_1$-C$_6$ alkyl, C$_2$-C$_6$ alkenyl, and C$_2$-C$_6$ alkynyl is optionally substituted with one or more substituents independently selected from the group consisting of OH, oxo, CN, NO$_2$, F, Cl, Br and I; wherein each R$^{13}$ C$_6$-C$_{10}$ membered aryl, 5-11 membered heteroaryl, C$_3$-C$_{11}$ cycloalkyl, C$_4$-C$_{11}$ cycloalkenyl, and 4-12 membered heterocyclyl is optionally substituted with one or more substituents independently selected from the group consisting of C$_1$-C$_6$ alkyl, C$_1$-C$_6$ alkoxy, 5-6 membered heteroaryl, OH, oxo, CN, NO$_2$, F, Cl, Br and I; and R$^{14}$, at each occurrence, is independently selected from the group consisting of C$_1$-C$_6$ alkyl, C$_2$-C$_6$ alkenyl, C$_2$-C$_6$ alkynyl, C$_6$-C$_{10}$ membered aryl, 5-11 membered heteroaryl, C$_3$-C$_{11}$ cycloalkyl, C$_4$-C$_{11}$ cycloalkenyl, and 4-12 membered heterocyclyl; wherein each R$^{11}$ C$_1$-C$_6$ alkyl, C$_2$-C$_6$ alkenyl, and C$_2$-C$_6$ alkynyl is optionally substituted with one or more substituents independently selected from the group consisting of C$_1$-C$_6$ alkyl, C$_1$-C$_6$ alkoxy, 5-6 membered heteroaryl, 4-12 membered heterocyclyl, OH, oxo, CN, NO$_2$, F, Cl, Br and I.

In one embodiment of Formula (II), R$^1$ is selected from the group consisting of 6-10 membered aryl, 5-11 membered heteroaryl, C$_3$-C$_{11}$ cycloalkyl, C$_4$-C$_{11}$ cycloalkenyl, and 4-12 membered heterocyclyl; wherein the R$^1$ 6-10 membered aryl, 5-11 membered heteroaryl, C$_3$-C$_{11}$ cycloalkyl, C$_4$-C$_{11}$ cycloalkenyl, and 4-12 membered heterocyclyl are substituted with two or more substituents independently selected from the group consisting of R$^7$, OR$^7$, SR$^7$, C(O)R$^7$, OC(O)R$^7$, C(O)OR$^7$, SO$_2$R$^7$, C(O)NH$_2$, C(O)NHR$^7$, C(O)N(R$^7$)$_2$, NHC(O)R$^7$, NHR$^7$, N(R$^7$)$_2$, NH$_2$, C(O)OH, OH, oxo, CN, NO$_2$, F, Cl, Br and I. In another embodiment of Formula (II), R$^1$ is selected from the group consisting of 6-10 membered aryl, 5-11 membered heteroaryl, and 4-12 membered heterocyclyl; wherein the R$^1$ 6-10 membered aryl, 5-11 membered heteroaryl, and 4-12 membered heterocyclyl are substituted with two or more substituents independently selected from the group consisting of R$^7$, OR$^7$, C(O)OR$^7$, N(R$^7$)$_2$, CN, F, Cl, and Br. In another embodiment of Formula (II), R$^1$ is 6-10 membered aryl; wherein the R$^1$ 6-10 membered aryl is substituted with two or more substituents independently selected from the group consisting of 127, OR$^7$, C(O)OR$^7$, N(R$^7$)$_2$, CN, F, Cl, and Br. In another embodiment of Formula (II), R$^1$ is 5-11 membered heteroaryl; wherein the R$^1$ 5-11 membered heteroaryl is substituted with two or more substituents independently selected from the group consisting of R$^7$, OR$^7$, C(O)OR$^7$, N(R$^7$)$_2$, NH$_2$, CN, F, C$_1$, and Br. In another embodiment of Formula (II), R$^1$ is 4-12 membered heterocyclyl; wherein the R$^1$ 4-12 membered heterocyclyl is substituted with two or more substituents independently selected from the group consisting of R$^7$, OR$^7$, C(O)OR$^7$, N(R$^7$)$_2$, NH$_2$, CN, F, Cl, and Br. In another embodiment of Formula (II), R$^1$ is phenyl; wherein the R$^1$ phenyl is substituted with two or more substituents independently selected from the group consisting of R$^7$, OR$^7$, C(O)OR$^7$, N(R$^7$)$_2$, NH$_2$, CN, F, Cl, and Br. In another embodiment of Formula (II), R$^1$ is selected from the group consisting of pyrazolyl, pyridinyl, quinolinyl, pyrimidinyl, and benzo[d][1,3]dioxolyl; wherein the R$^1$ pyrazolyl, pyridinyl, quinolinyl, pyrimidinyl, and benzo[d][1,3]dioxolyl are substituted with two or more substituents independently selected from the group consisting of R$^7$, OR$^7$, C(O)OR$^7$, N(R$^7$)$_2$, NH$_2$, CN, F, Cl, and Br.

In one embodiment of Formula (II), n is 0 or 1; and R$^2$ is independently selected from the group consisting of R$^8$, OR$^8$, C(O)R$^8$, C(O)OR$^8$, SO$_2$R$^8$, NHR$^8$, N(R$^8$)$_2$, NH$_2$, C(O)OH, OH, CN, NO$_2$, F, Cl, Br and I. In another embodiment of Formula (II), n is 1; and R$^2$ is independently selected from the group consisting of R$^8$ and C(O)OR$^8$. In another embodiment of Formula (II), n is 0. In another embodiment of Formula (II), n is 1; and R$^2$ is independently R$^8$. In another embodiment of Formula (II), n is 1; and R$^2$ is independently C(O)OR$^8$. In another embodiment of Formula (II), n is 1; and R$^2$ is independently R$^8$; and R$^8$ is independently C$_1$-C$_6$ alkyl. In another embodiment of Formula (II), n is 1; and R$^2$ is independently C(O)OR$^8$; and R$^8$ is independently C$_1$-C$_6$ alkyl.

In one embodiment of Formula (II), R$^3$ is selected from the group consisting of C$_1$-C$_6$ alkyl, C$_2$-C$_6$ alkenyl, C$_2$-C$_6$ alkynyl, 6-10 membered aryl, 5-11 membered heteroaryl, C$_3$-C$_{11}$ cycloalkyl, C$_4$-C$_{11}$ cycloalkenyl, and 4-12 membered heterocyclyl; wherein the R$^3$ C$_1$-C$_6$ alkyl, C$_2$-C$_6$ alkenyl, and C$_2$-C$_6$ alkynyl are optionally substituted with one or more substituents independently selected from the group consisting of C$_1$-C$_6$ alkoxy, phenyl, OH, oxo, CN, NO$_2$, F, Cl, Br and I; wherein the R$^3$ 6-10 membered aryl, 5-11 membered heteroaryl, C$_3$-C$_{11}$ cycloalkyl, C$_4$-C$_{11}$ cycloalkenyl, and 4-12 membered heterocyclyl are optionally substituted with one or more substituents independently selected from the group consisting of R$^9$, OR$^9$, SR$^9$, C(O)R$^9$, OC(O)R$^9$, C(O)OR$^9$, SO$_2$R$^9$, C(O)NH$_2$, C(O)NHR$^9$, C(O)N(R$^9$)$_2$, NHC(O)R$^9$, NHR$^9$, N(R$^9$)$_2$, NH$_2$, C(O)OH, OH, oxo, CN, NO$_2$, F, Cl, Br and I. In another embodiment of Formula (II), R$^3$ is selected from the group consisting of C$_1$-C$_6$ alkyl, 6-10 membered aryl, 5-11 membered heteroaryl, C$_3$-C$_{11}$ cycloalkyl, and 4-12 membered heterocyclyl; wherein the R$^3$ C$_1$-C$_6$ alkyl is optionally substituted with one or more substituents independently selected from the group consisting of phenyl, F, and Cl; wherein the R$^3$ 6-10 membered aryl, 5-11 membered heteroaryl, C$_3$-C$_{11}$ cycloalkyl, and 4-12 membered heterocyclyl are optionally substituted with one or more substituents independently selected from the group consisting of R$^9$, OR$^9$, C(O)R$^9$, C(O)OR$^9$, SO$_2$R$^9$, NHR$^9$, N(R$^9$)$_2$, NH$_2$, C(O)OH, OH, oxo, CN, NO$_2$, Cl, and Br.

In another embodiment of Formula (II), R$^3$ is C$_1$-C$_6$ alkyl; wherein the R$^3$ C$_1$-C$_6$ alkyl is optionally substituted with one or more substituents independently selected from the group consisting of phenyl, F, and Cl. In another embodiment of Formula (II), R$^3$ is 6-10 membered aryl; wherein the R$^3$ 6-10 membered aryl is optionally substituted with one or more substituents independently selected from the group consisting of R$^9$, OR$^9$, C(O)R$^9$, C(O)OR$^9$, SO$_2$R$^9$, NHR$^9$, N(R$^9$)$_2$, NH$_2$, C(O)OH, OH, oxo, CN, NO$_2$, Cl, and Br. In another embodiment of Formula (II), R$^3$ is 5-11 membered heteroaryl; wherein the R$^3$ 5-11 membered heteroaryl is optionally substituted with one or more substituents independently selected from the group consisting of R$^9$, OR$^9$, C(O)R$^9$, C(O)OR$^9$, SO$_2$R$^9$, NHR$^9$, N(R$^9$)$_2$, NH$_2$, C(O)OH, OH, oxo, CN, NO$_2$, Cl, and Br. In another embodiment of Formula (II), R$^3$ is C$_3$-C$_{11}$ cycloalkyl; wherein the R$^3$ C$_3$-C$_{11}$ cycloalkyl is optionally substituted with one or more substituents independently selected from the group consisting of R$^9$, OR$^9$, C(O)R$^9$, C(O)OR$^9$, SO$_2$R$^9$, NHR$^9$, N(R$^9$)$_2$, NH$_2$, C(O)OH, OH, oxo, CN, NO$_2$, Cl, and Br. In another embodiment of Formula (II), $R^3$ is 4-12 membered heterocyclyl; wherein the $R^3$ 4-12 membered heterocyclyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (II), $R^3$ is phenyl; wherein the $R^3$ phenyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (II), $R^3$ is napthyl; wherein the $R^3$ napthyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (II), $R^3$ is quinolinyl; wherein the $R^3$ quinolinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (II), $R^3$ is tetrahydroquinolinyl; wherein the $R^3$ tetrahydroquinolinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (II), $R^3$ is indazolyl; wherein the $R^3$ indazolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (II), $R^3$ is pyrazolo[1,5-a]pyridinyl; wherein the $R^3$ pyrazolo[1,5-a]pyridinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (II), $R^3$ is indolyl; wherein the $R^3$ indolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$. In another embodiment of Formula (II), $R^3$ is benzoimidazolyl; wherein the $R^3$ benzoimidazolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, $OH$, oxo, $CN$, $NO_2$, $Cl$, and $Br$.

In one embodiment of Formula (II), $R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $OR^{10}$, $F$, $Cl$, $Br$ and $I$. In another embodiment of Formula (II), $R^4$ is selected from the group consisting of hydrogen and $C_1$-$C_6$ alkyl. In another embodiment of Formula (II), $R^4$ is hydrogen. In another embodiment of Formula (II), $R^4$ is $C_1$-$C_6$ alkyl. In another embodiment of Formula (II), $R^4$ is $CH_3$.

In one embodiment of Formula (II), $R^T$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, $C_3$-$C_7$ cycloalkyl, $OH$, oxo, $CN$, $NO_2$, $F$, $Cl$, $Br$ and $I$; wherein each $R^7$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{11}$, $OR^{11}$, $SR^{11}$, $C(O)R^{11}$, $OC(O)R^{11}$, $C(O)OR^{11}$, $SO_2R^{11}$, $C(O)NH_2$, $C(O)NHR^{11}$, $C(O)N(R^{11})_2$, $NHC(O)R^{11}$, $NHR^{11}$, $N(R^{11})_2$, $NH_2$, $C(O)OH$, $OH$, oxo, $CN$, $NO_2$, $F$, $Cl$, $Br$ and $I$. In another embodiment of Formula (II), $R^T$, at each occurrence, is independently selected from the group consisting of $C_1$-$C_6$ alkyl, $C_3$-$C_{11}$ cycloalkyl, 5-11 membered heteroaryl, and 4-12 membered heterocyclyl; wherein each $R^7$ $C_1$-$C_6$ alkyl is optionally substituted with one or more substituents independently selected from the group consisting of $C_1$-$C_6$ alkoxy, $C_3$-$C_7$ cycloalkyl, $OH$ and $F$; wherein each $R^7$ $C_3$-$C_{11}$ cycloalkyl, 5-11 membered heteroaryl, and 4-12 membered heterocyclyl are optionally substituted with one or more substituents independently selected from the group consisting of $R^{11}$, $OR^{11}$, $NHR^{11}$, and $C(O)OR^{11}$.

In one embodiment of Formula (II), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{11}$, $OR^{11}$, $SR^{11}$, $C(O)R^3$, $OC(O)R^3$, $C(O)OR^3$, $SO_2R^{13}$, $C(O)NH_2$, $C(O)NHR^{13}$, $C(O)N(R^{13})_2$, $NHC(O)R^{13}$, $NHR^{11}$, $N(R^{13})_2$, $NH_2$, $C(O)OH$, $OH$, oxo, $CN$, $NO_2$, $F$, $Cl$, $Br$ and $I$; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{14}$, $OR^{14}$, $SR^{14}$, $C(O)R^{14}$, $OC(O)R^{14}$, $C(O)OR^{14}$, $SO_2R^{14}$, $C(O)NH_2$, $C(O)NHR^{14}$, $C(O)N(R^{14})_2$, $NHC(O)R^{14}$, $NHR^{11}$, $N(R^{14})_2$, $NH_2$, $C(O)OH$, $OH$, oxo, $CN$, $NO_2$, $F$, $Cl$, $Br$ and $I$. In another embodiment of Formula (II), $R^9$, at each occurrence, is independently selected from the group consisting of $C_1$-$C_6$ alkyl, 5-11 membered heteroaryl, and 4-12 membered heterocyclyl; wherein each $R^9$ $C_1$-$C_6$ alkyl is optionally substituted with one or more substituents independently selected from the group consisting of $R^{11}$, and $F$; wherein each $R^9$ 5-11 membered heteroaryl and 4-12 membered heterocyclyl is optionally substituted with one or more oxo. In another embodiment of Formula (II), $R^9$, at each occurrence, is independently selected from the group consisting of 5-11 membered heteroaryl and 4-12 membered heterocyclyl; wherein each $R^9$ 5-11 membered heteroaryl and 4-12 membered heterocyclyl is optionally substituted with one or more oxo. In another embodiment of Formula (II), $R^9$, at each occurrence, is independently $C_1$-$C_6$ alkyl; wherein each $R^9$ $C_1$-$C_6$ alkyl is optionally substituted with one or more substituents independently selected from the group consisting of $R^{11}$ and $F$. In another embodiment of Formula (II), $R^9$, at each occurrence, is independently $C_1$-$C_6$ alkyl; wherein each $R^9$ $C_1$-$C_6$ alkyl is unsubstituted.

In one embodiment of Formula (II), $R^{10}$, at each occurrence, is independently $C_1$-$C_4$ alkyl.

In one embodiment of Formula (II), $R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of $C_1$-$C_6$ alkoxy, $OH$, oxo, $CN$, $NO_2$, $F$, $Cl$, $Br$ and $I$; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I. In another embodiment of Formula (II), $R^{11}$, at each occurrence, is independently $C_1$-$C_6$ alkyl; wherein each $R^{11}$ $C_1$-$C_6$ alkyl is optionally substituted with $C_1$-$C_6$ alkoxy.

In one embodiment of Formula (II), $R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl.

In one embodiment of Formula (II), $R^{11}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, NO$_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, NO$_2$, F, Cl, Br and I. In another embodiment of Formula (II), $R^{11}$, at each occurrence, is $C_6$-$C_{10}$ membered aryl.

In one embodiment of Formula (II), $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, NO$_2$, F, Cl, Br and I.

In one embodiment of Formula (II),
$R^1$ is selected from the group consisting of 6-10 membered aryl, 5-11 membered heteroaryl, and 4-12 membered heterocyclyl; wherein the $R^1$ 6-10 membered aryl, 5-11 membered heteroaryl, and 4-12 membered heterocyclyl are substituted with two or more substituents independently selected from the group consisting of $R^T$, $OR^7$, $C(O)OR^7$, $N(R^7)_2$, NH$_2$, CN, F, Cl, and Br;
$R^2$ is independently selected from the group consisting of $R^8$ and $C(O)OR^8$;
n is 0 or 1;
$R^3$ is selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein the $R^3$ $C_1$-$C_6$ alkyl is optionally substituted with one or more substituents independently selected from the group consisting of phenyl, F, and Cl; wherein the $R^3$ 6-10 membered aryl, 5-11 membered heteroaryl, $C_3$-$C_{11}$ cycloalkyl, and 4-12 membered heterocyclyl are optionally substituted with one or more substituents independently selected from the group consisting of $R^9$, $OR^9$, $C(O)R^9$, $C(O)OR^9$, $SO_2R^9$, $NHR^9$, $N(R^9)_2$, NH$_2$, C(O)OH, OH, oxo, CN, NO$_2$, Cl, and Br;
$R^4$ is selected from the group consisting of hydrogen and $C_1$-$C_6$ alkyl;
$R^7$, at each occurrence, is independently selected from the group consisting of $C_1$-$C_6$ alkyl, 5-11 membered heteroaryl, $C_3$-$C_{11}$ cycloalkyl, and 4-12 membered heterocyclyl; wherein each $R^7$ $C_1$-$C_6$ alkyl is optionally substituted with one or more substituents independently selected from the group consisting of $C_1$-$C_6$ alkoxy, $C_3$-$C_7$ cycloalkyl, OH and F; wherein each $R^7$ 5-11 membered heteroaryl, $C_3$-$C_{11}$ cycloalkyl and 4-12 membered heterocyclyl is optionally substituted with one or more substituents independently selected from the group consisting of $R^{11}$, $OR^{11}$, $NHR^{11}$, and C(O)$OR^{11}$;
$R^8$ is independently $C_1$-$C_6$ alkyl;
$R^9$, at each occurrence, is independently selected from the group consisting of $C_1$-$C_6$ alkyl, 5-11 membered heteroaryl, and 4-12 membered heterocyclyl; wherein each $R^9$ $C_1$-$C_6$ alkyl, is optionally substituted with one or more substituents independently selected from the group consisting of $R^{11}$ and F; wherein each $R^9$ 5-11 membered heteroaryl, and 4-12 membered heterocyclyl is optionally substituted with one oxo;
$R^{11}$, at each occurrence, is independently $C_1$-$C_6$ alkyl; wherein each $R^{11}$ $C_1$-$C_6$ alkyl is optionally substituted with one $C_1$-$C_6$ alkoxy; and
$R^{13}$, at each occurrence, is independently $C_6$-$C_{10}$ membered aryl.

Exemplary compounds of Formula (II) include, but are not limited to:
1-(5-bromo-2-methoxyphenyl)-N-(naphthalene-1-sulfonyl)cyclopropane-1-carboxamide;
1-(5-cyclobutyl-2-methoxyphenyl)-N-(naphthalene-1-sulfonyl)cyclopropane-1-carboxamide;
1-(5-cyclobutyl-2-methoxypyridin-3-yl)-N-(2-methylquinoline-5-sulfonyl)cyclopropane-1-carboxamide;
1-(5-cyclobutyl-2-methoxypyridin-3-yl)-N-(quinoline-5-sulfonyl)cyclopropane-1-carboxamide;
1-(5-cyclobutyl-2-methoxypyridin-3-yl)-N-(naphthalene-1-sulfonyl)cyclopropane-1-carboxamide;
1-(5-cyclobutyl-2-methoxypyridin-3-yl)-N-(1,2,3,4-tetrahydroquinoline-5-sulfonyl)cyclopropane-1-carboxamide;
1-(2,6-dimethoxyphenyl)-N-(naphthalene-1-sulfonyl)cyclopropane-1-carboxamide;
1-[2-methoxy-5-(trifluoromethyl)pyridin-3-yl]-N-(naphthalene-1-sulfonyl)cyclopropane-1-carboxamide;
1-(5-bromo-2-methoxyphenyl)-N-(1,2,3,4-tetrahydroquinoline-5-sulfonyl)cyclopropane-1-carboxamide;
1-(5-cyclopropyl-2-methoxyphenyl)-N-(naphthalene-1-sulfonyl)cyclopropane-1-carboxamide;
1-(5-cyclopropyl-2-methoxyphenyl)-N-(quinoline-5-sulfonyl)cyclopropane-1-carboxamide;
1-{2-methoxy-5-[(propan-2-yl)oxy]phenyl}-N-(quinoline-5-sulfonyl)cyclopropane-1-carboxamide;
1-(2-methoxy-5-methylpyridin-3-yl)-N-(naphthalene-1-sulfonyl)cyclopropane-1-carboxamide;
1-(5-cyclobutyl-2-methoxyphenyl)-N-(1,2,3,4-tetrahydroquinoline-5-sulfonyl)cyclopropane-1-carboxamide;
1-(5-cyclobutyl-2-methoxyphenyl)-N-(quinoline-5-sulfonyl)cyclopropane-1-carboxamide;
1-(5-bromo-2-methoxyphenyl)-N-(quinoline-5-sulfonyl)cyclopropane-1-carboxamide;
1-(5-cyclobutyl-2-methoxypyridin-3-yl)-N-(pyrazolo[1,5-a]pyridine-4-sulfonyl)cyclopropane-1-carboxamide;
1-(5-cyclobutyl-2-methoxypyridin-3-yl)-N-(1-methyl-1H-indole-7-sulfonyl)cyclopropane-1-carboxamide;
1-(5-cyclobutyl-2-methoxypyridin-3-yl)-N-(1H-indole-4-sulfonyl)cyclopropane-1-carboxamide;
N-(1H-indole-4-sulfonyl)-1-[2-methoxy-5-(trifluoromethyl)pyridin-3-yl]cyclopropane-1-carboxamide;
1-(2,5-dimethoxyphenyl)-N-(naphthalene-1-sulfonyl)cyclopropane-1-carboxamide;

1-(2,5-dimethoxyphenyl)-N-(quinoline-5-sulfonyl)cyclopropane-1-carboxamide;
1-[2-(dimethylamino)-5-(trifluoromethyl)pyridin-3-yl]-N-(naphthalene-1-sulfonyl)cyclopropane-1-carboxamide;
1-(5-ethoxy-2-methoxyphenyl)-N-(quinoline-5-sulfonyl)cyclopropane-1-carboxamide;
1-[5-(cyclobutyloxy)-2-methoxyphenyl]-N-(quinoline-5-sulfonyl)cyclopropane-1-carboxamide;
1-(5-tert-butyl-2-methoxyphenyl)-N-(quinoline-5-sulfonyl)cyclopropane-1-carboxamide;
1-[2-methoxy-5-(propan-2-yl)phenyl]-N-(quinoline-5-sulfonyl)cyclopropane-1-carboxamide;
1-[4-fluoro-2-methoxy-5-(propan-2-yl)phenyl]-N-(quinoline-5-sulfonyl)cyclopropane-1-carboxamide;
1-[2-methoxy-5-(trifluoromethyl)phenyl]-N-(quinoline-5-sulfonyl)cyclopropane-1-carboxamide;
1-[5-(bicyclo[1.1.1]pentan-1-yl)-2-methoxyphenyl]-N-(quinoline-5-sulfonyl)cyclopropane-1-carboxamide;
1-(5-tert-butyl-2-methoxyphenyl)-N-(1,2,3,4-tetrahydroquinoline-5-sulfonyl)cyclopropane-1-carboxamide;
1-(2,6-dimethoxy-3-methylphenyl)-N-(naphthalene-1-sulfonyl)cyclopropane-1-carboxamide;
1-(2,6-dimethoxy-3-methylphenyl)-N-(quinoline-5-sulfonyl)cyclopropane-1-carboxamide;
1-(2,6-dimethoxy-3-methylphenyl)-N-(1H-indole-4-sulfonyl)cyclopropane-1-carboxamide;
1-(2,6-dimethoxy-3-methylphenyl)-N-(2-methylquinoline-5-sulfonyl)cyclopropane-1-carboxamide;
1-(2-methoxy-5-methylphenyl)-N-(quinoline-5-sulfonyl)cyclopropane-1-carboxamide;
1-(2-ethoxy-6-methoxyphenyl)-N-(quinoline-5-sulfonyl)cyclopropane-1-carboxamide;
1-[2-(cyclopropylmethoxy)-6-methoxyphenyl]-N-(quinoline-5-sulfonyl)cyclopropane-1-carboxamide;
1-(6-methoxy-2,3-dimethylphenyl)-N-(quinoline-5-sulfonyl)cyclopropane-1-carboxamide;
1-(3-cyclopropyl-6-methoxy-2-methylphenyl)-N-(quinoline-5-sulfonyl)cyclopropane-1-carboxamide;
N-(1H-indole-4-sulfonyl)-1-(2-methoxy-5-methylphenyl)cyclopropane-1-carboxamide;
1-[2-methoxy-6-(propan-2-yl)phenyl]-N-(quinoline-5-sulfonyl)cyclopropane-1-carboxamide;
1-(2-cyclobutyl-6-methoxyphenyl)-N-(quinoline-5-sulfonyl)cyclopropane-1-carboxamide;
1-[2-methoxy-5-(2-methoxypropan-2-yl)phenyl]-N-(quinoline-5-sulfonyl)cyclopropane-1-carboxamide;
N-(1H-indazole-4-sulfonyl)-1-(2-methoxy-5-methylphenyl)cyclopropane-1-carboxamide;
1-(5-cyclobutyl-2-methoxyphenyl)-N-(2,3-dihydro-1H-indole-4-sulfonyl)cyclopropane-1-carboxamide;
1-(5-cyclobutyl-2-methoxyphenyl)-N-(1H-indole-4-sulfonyl)cyclopropane-1-carboxamide;
1-(5-cyclobutyl-2-methoxyphenyl)-N-(1H-indazole-4-sulfonyl)cyclopropane-1-carboxamide;
1-[2-(dimethylamino)-5-(trifluoromethyl)pyridin-3-yl]-N-(quinoline-5-sulfonyl)cyclopropane-1-carboxamide;
1-(5-cyclobutyl-2-methoxyphenyl)-N-(1-methyl-1H-indole-4-sulfonyl)cyclopropane-1-carboxamide;
1-(5-cyclobutyl-2-methoxyphenyl)-N-(1-methyl-1H-indole-7-sulfonyl)cyclopropane-1-carboxamide;
1-(5-cyclobutyl-2-methoxyphenyl)-N-(1-methyl-1H-indazole-7-sulfonyl)cyclopropane-1-carboxamide;
1-(5-cyclobutyl-2-methoxyphenyl)-N-(pyrazolo[1,5-a]pyridine-4-sulfonyl)cyclopropane-1-carboxamide;
1-(5-cyclobutyl-2-methoxyphenyl)-N-(2-methylquinoline-8-sulfonyl)cyclopropane-1-carboxamide;
1-(5-cyclobutyl-2-methoxyphenyl)-N-(2-methylquinoline-5-sulfonyl)cyclopropane-1-carboxamide;
1-(2-methoxy-5-methylphenyl)-N-(2-methylquinoline-5-sulfonyl)cyclopropane-1-carboxamide;
1-[5-(difluoromethoxy)-2-methoxyphenyl]-N-(quinoline-5-sulfonyl)cyclopropane-1-carboxamide;
1-(2,6-diethoxyphenyl)-N-(quinoline-5-sulfonyl)cyclopropane-1-carboxamide;
N-(2-aminoquinoline-5-sulfonyl)-1-(5-cyclobutyl-2-methoxyphenyl)cyclopropane-1-carboxamide;
1-(5-cyclopropyl-2-methoxyphenyl)-N-(2-methylquinoline-5-sulfonyl)cyclopropane-1-carboxamide;
1-(5-ethoxy-2-methoxyphenyl)-N-(2-methylquinoline-5-sulfonyl)cyclopropane-1-carboxamide;
1-(5-tert-butyl-2-methoxyphenyl)-N-(2-methylquinoline-5-sulfonyl)cyclopropane-1-carboxamide;
1-[2-methoxy-5-(propan-2-yl)phenyl]-N-(2-methylquinoline-5-sulfonyl)cyclopropane-1-carboxamide;
1-[2-(dimethylamino)-5-(trifluoromethyl)pyridin-3-yl]-N-(2-methylquinoline-5-sulfonyl)cyclopropane-1-carboxamide;
1-{2-methoxy-5-[1-(methoxymethyl)cyclopropyl]phenyl}-N-(quinoline-5-sulfonyl)cyclopropane-1-carboxamide;
1-{2-methoxy-5-[1-(methoxymethyl)cyclopropyl]phenyl}-N-(2-methylquinoline-5-sulfonyl)cyclopropane-1-carboxamide;
1-{5-methyl-2-[(propan-2-yl)oxy]phenyl}-N-(quinoline-5-sulfonyl)cyclopropane-1-carboxamide;
1-{5-methyl-2-[(propan-2-yl)oxy]phenyl}-N-(2-methylquinoline-5-sulfonyl)cyclopropane-1-carboxamide;
N-(2-aminoquinoline-5-sulfonyl)-1-(2-methoxy-5-methylphenyl)cyclopropane-1-carboxamide;
1-(4-cyclobutyl-2,6-dimethoxyphenyl)-N-(quinoline-5-sulfonyl)cyclopropane-1-carboxamide;
N-(2-aminoquinoline-5-sulfonyl)-1-(2,5-dimethylphenyl)cyclopropane-1-carboxamide;
1-(2-ethoxy-5-methylphenyl)-N-(quinoline-5-sulfonyl)cyclopropane-1-carboxamide;
1-(2-ethoxy-5-methylphenyl)-N-(2-methylquinoline-5-sulfonyl)cyclopropane-1-carboxamide;
1-(5-ethyl-2-methoxyphenyl)-N-(2-methylquinoline-5-sulfonyl)cyclopropane-1-carboxamide;
1-{2-methoxy-5-[1-(methylamino)cyclopropyl]phenyl}-N-(quinoline-5-sulfonyl)cyclopropane-1-carboxamide;
1-(4-cyclobutyl-2,6-dimethoxyphenyl)-N-(1H-indole-4-sulfonyl)cyclopropane-1-carboxamide;
N-(2-aminoquinoline-5-sulfonyl)-1-{5-methyl-2-[(propan-2-yl)oxy]phenyl}cyclopropane-1-carboxamide;
1-[2-methoxy-5-(1-methoxycyclobutyl)phenyl]-N-(quinoline-5-sulfonyl)cyclopropane-1-carboxamide;
N-(2-aminoquinoline-5-sulfonyl)-1-(2-ethoxy-5-methylphenyl)cyclopropane-1-carboxamide;
1-[2-methoxy-5-(oxetan-3-yl)phenyl]-N-(quinoline-5-sulfonyl)cyclopropane-1-carboxamide;
1-(2-ethoxy-5-methylphenyl)-N-(2-methyl-1H-indole-4-sulfonyl)cyclopropane-1-carboxamide;
N-(2-aminoquinoline-5-sulfonyl)-1-[2-methoxy-5-(2-methylpropoxy)pyridin-4-yl]cyclopropane-1-carboxamide;
1-{5-methyl-2-[(oxetan-3-yl)oxy]phenyl}-N-(quinoline-5-sulfonyl)cyclopropane-1-carboxamide;
1-[5-ethyl-2-(2-methylpropoxy)pyridin-3-yl]-N-(1H-indazole-4-sulfonyl)cyclopropane-1-carboxamide;
1-(2-{[(2R)-1-methoxypropan-2-yl]oxy}-5-methylphenyl)-N-(quinoline-5-sulfonyl)cyclopropane-1-carboxamide;
N-(2-aminoquinoline-5-sulfonyl)-1-[5-methyl-2-(2-methylpropoxy)pyridin-3-yl]cyclopropane-1-carboxamide;

N-(2-aminoquinoline-5-sulfonyl)-1-{5-methyl-2-[(propan-2-yl)oxy]pyridin-3-yl}cyclopropane-1-carboxamide;
N-(2-aminoquinoline-5-sulfonyl)-1-[5-ethyl-2-(2-methylpropoxy)pyridin-3-yl]cyclopropane-1-carboxamide;
1-[2-ethoxy-5-(2-ethoxypropan-2-yl)phenyl]-N-(quinoline-5-sulfonyl)cyclopropane-1-carboxamide;
1-[2-(difluoromethoxy)-5-methylphenyl]-N-(quinoline-5-sulfonyl)cyclopropane-1-carboxamide;
1-[2-ethoxy-5-(1-methoxy-2-methylpropan-2-yl)phenyl]-N-(quinoline-5-sulfonyl)cyclopropane-1-carboxamide;
1-[2-ethoxy-5-(1-methoxycyclobutyl)phenyl]-N-(quinoline-5-sulfonyl)cyclopropane-1-carboxamide;
1-[2-ethoxy-5-(2-ethoxypropan-2-yl)phenyl]-N-(2-methylquinoline-5-sulfonyl)cyclopropane-1-carboxamide;
1-[2-ethoxy-5-(2-methoxypropan-2-yl)phenyl]-N-(2-methylquinoline-5-sulfonyl)cyclopropane-1-carboxamide;
1-[2-ethoxy-5-(1-methoxycyclobutyl)phenyl]-N-(2-methylquinoline-5-sulfonyl)cyclopropane-1-carboxamide;
1-{5-methyl-2-[(oxetan-3-yl)oxy]phenyl}-N-(2-methylquinoline-5-sulfonyl)cyclopropane-1-carboxamide;
1-(2-{[(2R)-1-methoxypropan-2-yl]oxy}-5-methylphenyl)-N-(2-methylquinoline-5-sulfonyl)cyclopropane-1-carboxamide;
1-[3-(dimethylamino)-6-(2-methylpropoxy)pyridin-2-yl]-N-(quinoline-5-sulfonyl)cyclopropane-1-carboxamide;
1-[5-(dimethylamino)-2-(2-methylpropoxy)pyridin-3-yl]-N-(2-methylquinoline-5-sulfonyl)cyclopropane-1-carboxamide;
1-[2-methoxy-5-(1-methoxy-2-methylpropan-2-yl)phenyl]-N-(quinoline-5-sulfonyl)cyclopropane-1-carboxamide;
1-(5-ethyl-2-{[(2R)-1-methoxypropan-2-yl]oxy}phenyl)-N-(quinoline-5-sulfonyl)cyclopropane-1-carboxamide;
1-(5-ethyl-2-{[(2R)-1-methoxypropan-2-yl]oxy}phenyl)-N-(2-methylquinoline-5-sulfonyl)cyclopropane-1-carboxamide;
1-{2-[(2S)-2-methoxypropoxy]-5-methylphenyl}-N-(quinoline-5-sulfonyl)cyclopropane-1-carboxamide;
1-{2-[(2S)-2-methoxypropoxy]-5-methylphenyl}-N-(2-methylquinoline-5-sulfonyl)cyclopropane-1-carboxamide;
1-{2-[(2R)-2-methoxypropoxy]-5-methylphenyl}-N-(quinoline-5-sulfonyl)cyclopropane-1-carboxamide;
1-{2-[(2R)-2-methoxypropoxy]-5-methylphenyl}-N-(2-methylquinoline-5-sulfonyl)cyclopropane-1-carboxamide;
1-(5-ethyl-2-{[(3S)-oxolan-3-yl]oxy}phenyl)-N-(quinoline-5-sulfonyl)cyclopropane-1-carboxamide;
1-(5-ethyl-2-{[(3R)-oxolan-3-yl]oxy}phenyl)-N-(quinoline-5-sulfonyl)cyclopropane-1-carboxamide;
1-(5-ethyl-2-{[(3R)-oxolan-3-yl]oxy}phenyl)-N-(2-methylquinoline-5-sulfonyl)cyclopropane-1-carboxamide;
1-(5-methyl-2-{[(3R)-oxolan-3-yl]oxy}phenyl)-N-(quinoline-5-sulfonyl)cyclopropane-1-carboxamide;
1-(5-methyl-2-{[(3R)-oxolan-3-yl]oxy}phenyl)-N-(2-methylquinoline-5-sulfonyl)cyclopropane-1-carboxamide;
1-(5-methyl-2-{[(3S)-oxolan-3-yl]oxy}phenyl)-N-(2-methylquinoline-5-sulfonyl)cyclopropane-1-carboxamide;
1-(3-methoxy-4-methylphenyl)-N-(naphthalene-1-sulfonyl)cyclopropane-1-carboxamide;
1-(1-ethyl-3-methyl-1H-pyrazol-5-yl)-N-(naphthalene-1-sulfonyl)cyclopropane-1-carboxamide;
1-(1-ethyl-5-methyl-1H-pyrazol-3-yl)-N-(naphthalene-1-sulfonyl)cyclopropane-1-carboxamide;
1-[2-methoxy-5-(trifluoromethyl)pyridin-3-yl]-N-(quinoline-5-sulfonyl)cyclopropane-1-carboxamide;
1-[2-methoxy-5-(trifluoromethyl)pyridin-3-yl]-N-(1,2,3,4-tetrahydroquinoline-5-sulfonyl)cyclopropane-1-carboxamide;
1-[2-methoxy-5-(trifluoromethyl)pyridin-3-yl]-N-(2-methylquinoline-5-sulfonyl)cyclopropane-1-carboxamide;
1-(2-methoxy-5-methylpyridin-3-yl)-N-(1,2,3,4-tetrahydroquinoline-5-sulfonyl)cyclopropane-1-carboxamide;
1-(5-cyclobutyl-2-methoxypyridin-3-yl)-N-(1-methyl-1H-benzimidazole-7-sulfonyl)cyclopropane-1-carboxamide;
1-(5-cyclobutyl-2-methoxypyridin-3-yl)-N-(1-methyl-1H-indazole-7-sulfonyl)cyclopropane-1-carboxamide;
1-(5-cyclobutyl-2-methoxypyridin-3-yl)-N-(1-methyl-1H-indole-4-sulfonyl)cyclopropane-1-carboxamide;
1-(5-cyclobutyl-2-methoxypyridin-3-yl)-N-(1H-indazole-4-sulfonyl)cyclopropane-1-carboxamide;
1-(5-cyclobutyl-2-methoxypyridin-3-yl)-N-(3-methylimidazo[1,2-a]pyridine-5-sulfonyl)cyclopropane-1-carboxamide;
1-[2-methoxy-5-(trifluoromethyl)pyridin-3-yl]-N-(1-methyl-1H-indole-7-sulfonyl)cyclopropane-1-carboxamide;
1-[2-methoxy-5-(trifluoromethyl)pyridin-3-yl]-N-(1-methyl-1H-indole-4-sulfonyl)cyclopropane-1-carboxamide;
1-[2-methoxy-5-(trifluoromethyl)pyridin-3-yl]-N-(3-methylimidazo[1,2-a]pyridine-5-sulfonyl)cyclopropane-1-carboxamide;
1-{2-methoxy-5-[(oxolan-3-yl)oxy]phenyl}-N-(quinoline-5-sulfonyl)cyclopropane-1-carboxamide;
1-[2-chloro-5-(trifluoromethoxy)phenyl]-N-(quinoline-5-sulfonyl)cyclopropane-1-carboxamide;
1-[2-chloro-5-(trifluoromethoxy)phenyl]-N-(1,2,3,4-tetrahydroquinoline-5-sulfonyl)cyclopropane-1-carboxamide;
1-[2-methoxy-5-(propan-2-yl)phenyl]-N-(1,2,3,4-tetrahydroquinoline-5-sulfonyl)cyclopropane-1-carboxamide;
1-[4-fluoro-2-methoxy-5-(propan-2-yl)phenyl]-N-(1,2,3,4-tetrahydroquinoline-5-sulfonyl)cyclopropane-1-carboxamide;
1-[2-methoxy-5-(trifluoromethyl)phenyl]-N-(1,2,3,4-tetrahydroquinoline-5-sulfonyl)cyclopropane-1-carboxamide;
methyl 1-(4-methoxy-3-{1-[(quinoline-5-sulfonyl)carbamoyl]cyclopropyl}phenyl)cyclopropane-1-carboxylate;
methyl 4-methoxy-3-{1-[(quinoline-5-sulfonyl)carbamoyl]cyclopropyl}benzoate;
methyl 4-methoxy-3-{1-[(naphthalene-1-sulfonyl)carbamoyl]cyclopropyl}benzoate;
1-(5-cyclobutyl-2-methoxy-4-methylpyridin-3-yl)-N-(2-methylquinoline-5-sulfonyl)cyclopropane-1-carboxamide;
1-(5-bromo-2-methoxyphenyl)-N-(1-methyl-2,3-dihydro-1H-indole-4-sulfonyl)cyclopropane-1-carboxamide;
1-(2-methoxy-6-methylphenyl)-N-(quinoline-5-sulfonyl)cyclopropane-1-carboxamide;
1-(6-methoxy-2,3-dimethylphenyl)-N-(1,2,3,4-tetrahydroquinoline-5-sulfonyl)cyclopropane-1-carboxamide;
1-(3-cyclopropyl-6-methoxy-2-methylphenyl)-N-(1,2,3,4-tetrahydroquinoline-5-sulfonyl)cyclopropane-1-carboxamide;
1-(5-cyclobutyl-2-methoxy-4-methylpyridin-3-yl)-N-(1,2,3,4-tetrahydroquinoline-5-sulfonyl)cyclopropane-1-carboxamide;
1-(2,6-dimethoxy-3-methylphenyl)-N-(2-methylquinoline-8-sulfonyl)cyclopropane-1-carboxamide;
1-(5-cyclobutyl-2-methoxyphenyl)-N-(1-methyl-2,3-dihydro-1H-indole-4-sulfonyl)cyclopropane-1-carboxamide;

1-(5-cyclobutyl-2-methoxy-4-methylpyridin-3-yl)-N-(1-methyl-1H-indole-4-sulfonyl)cyclopropane-1-carboxamide;
1-(5-cyclobutyl-2-methoxy-4-methylpyridin-3-yl)-N-(1-methyl-1H-indole-7-sulfonyl)cyclopropane-1-carboxamide;
1-(5-cyclobutyl-2-methoxy-4-methylpyridin-3-yl)-N-(1-methyl-1H-indazole-7-sulfonyl)cyclopropane-1-carboxamide;
1-(5-cyclobutyl-2-methoxy-4-methylpyridin-3-yl)-N-(2-methylquinoline-8-sulfonyl)cyclopropane-1-carboxamide;
1-(2-methoxy-6-methylphenyl)-N-(2-methylquinoline-8-sulfonyl)cyclopropane-1-carboxamide;
1-(2-cyclobutyl-5-methoxyphenyl)-N-(quinoline-5-sulfonyl)cyclopropane-1-carboxamide;
1-(2-cyclobutyl-5-methoxyphenyl)-N-(2-methylquinoline-5-sulfonyl)cyclopropane-1-carboxamide;
1-[5-(hydroxymethyl)-2-methoxyphenyl]-N-(quinoline-5-sulfonyl)cyclopropane-1-carboxamide;
1-[2-methoxy-5-(methoxymethyl)phenyl]-N-(quinoline-5-sulfonyl)cyclopropane-1-carboxamide;
1-(2-methoxy-6-methylphenyl)-N-(2-methylquinoline-5-sulfonyl)cyclopropane-1-carboxamide;
1-(6-methoxy-2,3-dimethylphenyl)-N-(2-methylquinoline-5-sulfonyl)cyclopropane-1-carboxamide;
1-(3-cyclopropyl-6-methoxy-2-methylphenyl)-N-(2-methylquinoline-5-sulfonyl)cyclopropane-1-carboxamide;
1-(2-methoxy-6-methylphenyl)-N-(1,2,3,4-tetrahydroquinoline-5-sulfonyl)cyclopropane-1-carboxamide;
1-(3-chloro-2,6-dimethoxyphenyl)-N-(quinoline-5-sulfonyl)cyclopropane-1-carboxamide;
1-(5-methoxy-2-methylphenyl)-N-(quinoline-5-sulfonyl)cyclopropane-1-carboxamide;
1-(2-cyclopropyl-6-methoxyphenyl)-N-(quinoline-5-sulfonyl)cyclopropane-1-carboxamide;
1-[5-methoxy-2-(propan-2-yl)phenyl]-N-(quinoline-5-sulfonyl)cyclopropane-1-carboxamide;
1-(5-methoxy-2-propylphenyl)-N-(quinoline-5-sulfonyl)cyclopropane-1-carboxamide;
1-(2-cyclopropyl-6-methoxyphenyl)-N-(2-methylquinoline-5-sulfonyl)cyclopropane-1-carboxamide;
1-(5-ethyl-2-methoxyphenyl)-N-(quinoline-5-sulfonyl)cyclopropane-1-carboxamide;
1-(2-methoxy-4-methylphenyl)-N-(quinoline-5-sulfonyl)cyclopropane-1-carboxamide;
1-(2-methoxy-3-methylphenyl)-N-(quinoline-5-sulfonyl)cyclopropane-1-carboxamide;
1-(4-cyclobutyl-2,6-dimethoxyphenyl)-N-(1-methyl-1H-indole-4-sulfonyl)cyclopropane-1-carboxamide;
1-(4-cyclobutyl-2,6-dimethoxyphenyl)-N-(1-methyl-1H-indole-7-sulfonyl)cyclopropane-1-carboxamide;
1-(4-cyclobutyl-2,6-dimethoxyphenyl)-N-(1-methyl-1H-indazole-7-sulfonyl)cyclopropane-1-carboxamide;
1-(4-cyclobutyl-2,6-dimethoxyphenyl)-N-(pyrazolo[1,5-a]pyridine-4-sulfonyl)cyclopropane-1-carboxamide;
1-(4-cyclobutyl-2,6-dimethoxyphenyl)-N-(2-methylquinoline-5-sulfonyl)cyclopropane-1-carboxamide;
N-(2-aminoquinoline-5-sulfonyl)-1-(4-cyclobutyl-2,6-dimethoxyphenyl)cyclopropane-1-carboxamide;
N-(2-aminoquinoline-5-sulfonyl)-1-(5-ethyl-2-methoxyphenyl)cyclopropane-1-carboxamide;
1-(5-ethyl-2-methoxyphenyl)-N-(1H-indazole-4-sulfonyl)cyclopropane-1-carboxamide;
1-(2-ethyl-6-methoxyphenyl)-N-(quinoline-5-sulfonyl)cyclopropane-1-carboxamide;
1-(2-ethoxy-5-methylphenyl)-N-(1H-indazole-4-sulfonyl)cyclopropane-1-carboxamide;
N-(1H-indazole-4-sulfonyl)-1-{5-methyl-2-[(propan-2-yl)oxy]phenyl}cyclopropane-1-carboxamide;
1-(4-cyclobutyl-2,6-dimethoxyphenyl)-N-(1H-indazole-4-sulfonyl)cyclopropane-1-carboxamide;
N-(1H-indazole-4-sulfonyl)-1-(6-methoxy-2,3-dimethylphenyl)cyclopropane-1-carboxamide;
1-(3-cyclopropyl-6-methoxy-2-methylphenyl)-N-(1H-indazole-4-sulfonyl)cyclopropane-1-carboxamide;
N-(1H-indole-4-sulfonyl)-1-{5-methyl-2-[(propan-2-yl)oxy]phenyl}cyclopropane-1-carboxamide;
1-(2,5-dimethylphenyl)-N-(1H-indole-4-sulfonyl)cyclopropane-1-carboxamide;
1-(2-cyclopropyl-6-methoxyphenyl)-N-(1H-indazole-4-sulfonyl)cyclopropane-1-carboxamide;
N-(2-aminoquinoline-5-sulfonyl)-1-{2-methoxy-5-[1-(methoxymethyl)cyclopropyl]phenyl}cyclopropane-1-carboxamide;
1-(2-ethoxy-5-methylphenyl)-N-(2-methoxyquinoline-5-sulfonyl)cyclopropane-1-carboxamide;
1-(2-ethoxy-5-methylphenyl)-N-[2-(methylamino)quinoline-5-sulfonyl]cyclopropane-1-carboxamide;
1-(2-ethoxy-5-methylphenyl)-N-(1H-indole-4-sulfonyl)cyclopropane-1-carboxamide;
1-[2-methoxy-5-(2,2,2-trifluoro-1-methoxyethyl)phenyl]-N-(quinoline-5-sulfonyl)cyclopropane-1-carboxamide;
1-[2-methoxy-5-(1-methoxyethyl)phenyl]-N-(quinoline-5-sulfonyl)cyclopropane-1-carboxamide;
N-(1H-indole-4-sulfonyl)-1-[2-methoxy-5-(2-methoxypropan-2-yl)phenyl]cyclopropane-1-carboxamide;
1-[2-methoxy-5-(3-methyloxetan-3-yl)phenyl]-N-(quinoline-5-sulfonyl)cyclopropane-1-carboxamide;
N-(2-aminoquinoline-5-sulfonyl)-1-{5-methyl-2-[(oxetan-3-yl)oxy]phenyl}cyclopropane-1-carboxamide;
N-(1H-indazole-4-sulfonyl)-1-[2-methoxy-5-(2-methylpropoxy)pyridin-4-yl]cyclopropane-1-carboxamide;
1-(2-{[(2S)-1-methoxypropan-2-yl]oxy}-5-methylphenyl)-N-(quinoline-5-sulfonyl)cyclopropane-1-carboxamide;
1-[5-cyclopropyl-2-(2-methylpropoxy)pyridin-3-yl]-N-(2-methoxyquinoline-5-sulfonyl)cyclopropane-1-carboxamide;
1-[5-cyclobutyl-2-(2-methylpropoxy)pyridin-3-yl]-N-(2-methoxyquinoline-5-sulfonyl)cyclopropane-1-carboxamide;
1-{5-cyclopropyl-2-[(propan-2-yl)oxy]pyridin-3-yl}-N-(2-methoxyquinoline-5-sulfonyl)cyclopropane-1-carboxamide;
1-[5-(2-ethoxypropan-2-yl)-2-methoxyphenyl]-N-(quinoline-5-sulfonyl)cyclopropane-1-carboxamide;
1-[2-ethoxy-5-(2-methoxypropan-2-yl)phenyl]-N-(quinoline-5-sulfonyl)cyclopropane-1-carboxamide;
1-[2-(difluoromethoxy)-5-ethylphenyl]-N-(quinoline-5-sulfonyl)cyclopropane-1-carboxamide;
1-[2-methoxy-5-(2-methoxypropan-2-yl)phenyl]-N-(2-methylquinoline-5-sulfonyl)cyclopropane-1-carboxamide;
1-[2-methoxy-5-(1-methoxycyclobutyl)phenyl]-N-(2-methylquinoline-5-sulfonyl)cyclopropane-1-carboxamide;
1-[2-(difluoromethoxy)-5-methylphenyl]-N-(2-methylquinoline-5-sulfonyl)cyclopropane-1-carboxamide;
1-[5-chloro-2-(difluoromethoxy)phenyl]-N-(2-methylquinoline-5-sulfonyl)cyclopropane-1-carboxamide;
1-[2-(difluoromethoxy)-5-ethylphenyl]-N-(2-methylquinoline-5-sulfonyl)cyclopropane-1-carboxamide;

1-(2-{[(2S)-1-methoxypropan-2-yl]oxy}-5-methylphenyl)-N-(2-methylquinoline-5-sulfonyl)cyclopropane-1-carboxamide;

1-[2-ethoxy-5-(1-methoxy-2-methylpropan-2-yl)phenyl]-N-(2-methylquinoline-5-sulfonyl)cyclopropane-1-carboxamide;

1-[2-(difluoromethoxy)-5-(2-ethoxypropan-2-yl)phenyl]-N-(quinoline-5-sulfonyl)cyclopropane-1-carboxamide;

1-[2-(difluoromethoxy)-5-(2-ethoxypropan-2-yl)phenyl]-N-(2-methylquinoline-5-sulfonyl)cyclopropane-1-carboxamide;

1-[2-(difluoromethoxy)-5-(2-methoxypropan-2-yl)phenyl]-N-(quinoline-5-sulfonyl)cyclopropane-1-carboxamide;

1-[2-(difluoromethoxy)-5-(2-methoxypropan-2-yl)phenyl]-N-(2-methylquinoline-5-sulfonyl)cyclopropane-1-carboxamide;

1-[5-(1-ethoxy-2-methylpropan-2-yl)-2-methoxyphenyl]-N-(quinoline-5-sulfonyl)cyclopropane-1-carboxamide;

1-[5-(1-ethoxy-2-methylpropan-2-yl)-2-methoxyphenyl]-N-(2-methylquinoline-5-sulfonyl)cyclopropane-1-carboxamide;

1-[5-(dimethylamino)-2-(2-methylpropoxy)pyridin-3-yl]-N-(quinoline-5-sulfonyl)cyclopropane-1-carboxamide;

1-[2-methoxy-5-(1-methoxy-2-methylpropan-2-yl)phenyl]-N-(2-methylquinoline-5-sulfonyl)cyclopropane-1-carboxamide;

1-(5-ethyl-2-{[(3S)-oxolan-3-yl]oxy}phenyl)-N-(2-methylquinoline-5-sulfonyl)cyclopropane-1-carboxamide;

1-(5-methyl-2-{R3S)-oxolan-3-yl]oxy}phenyl)-N-(quinoline-5-sulfonyl)cyclopropane-1-carboxamide;

N-(benzenesulfonyl)-1-(2,4-dichlorophenyl)cyclopropane-1-carboxamide;

1-(2,4-dichlorophenyl)-N-(2,3-dihydro-1H-indene-5-sulfonyl)cyclopropane-1-carboxamide;

N-(4-chlorobenzene-1-sulfonyl)-1-(2,4-dichlorophenyl)cyclopropane-1-carboxamide;

methyl 5-{[1-(2,4-dichlorophenyl)cyclopropane-1-carbonyl]sulfamoyl}-4-methoxythiophene-3-carboxylate;

1-(2,4-dichlorophenyl)-N-(3,5-dimethyl-1,2-oxazole-4-sulfonyl)cyclopropane-1-carboxamide;

1-(2,4-dichlorophenyl)-N-[2-(trifluoromethoxy)benzene-1-sulfonyl]cyclopropane-1-carboxamide;

1-(2,4-dichlorophenyl)-N-[4-(trifluoromethoxy)benzene-1-sulfonyl]cyclopropane-1-carboxamide;

1-(2,4-dichlorophenyl)-N-[3-(trifluoromethyl)benzene-1-sulfonyl]cyclopropane-1-carboxamide;

1-(2,4-dichlorophenyl)-N-[4-(2-oxopyrrolidin-1-yl)benzene-1-sulfonyl]cyclopropane-1-carboxamide;

1-(2,4-dichlorophenyl)-N-[5-(1,2-oxazol-5-yl)thiophene-2-sulfonyl]cyclopropane-1-carboxamide;

1-(2,4-dichlorophenyl)-N-[4-(pyrrolidine-1-sulfonyl)benzene-1-sulfonyl]cyclopropane-1-carboxamide;

N-(4-chlorobenzene-1-sulfonyl)-1-(2,4-dichlorophenyl)-N-methylcyclopropane-1-carboxamide;

1-(2,4-dichlorophenyl)-N-{4-[(propan-2-yl)oxy]benzene-1-sulfonyl}cyclopropane-1-carboxamide;

1-(2,4-dichlorophenyl)-N-[6-(morpholin-4-yl)pyridine-3-sulfonyl]cyclopropane-1-carboxamide;

benzyl 4-{[1-(2,4-dichlorophenyl)cyclopropane-1-carbonyl]sulfamoyl}piperidine-1-carboxylate;

1-(2,4-dichlorophenyl)-N-(4-methoxybenzene-1-sulfonyl)cyclopropane-1-carboxamide;

1-(2,4-dichlorophenyl)-N-(3,4-dimethoxybenzene-1-sulfonyl)cyclopropane-1-carboxamide;

N-(3-chlorobenzene-1-sulfonyl)-1-(2,4-dichlorophenyl)cyclopropane-1-carboxamide;

1-(2,4-dichlorophenyl)-N-(naphthalene-2-sulfonyl)cyclopropane-1-carboxamide;

N-(cyclopropanesulfonyl)-1-(2,4-dichlorophenyl)cyclopropane-1-carboxamide;

N-(benzenesulfonyl)-1-(3,4-dichlorophenyl)cyclopropane-1-carboxamide;

1-(2,4-dichlorophenyl)-N-(1,1-dioxo-1$\lambda^6$-thiolane-3-sulfonyl)cyclopropane-1-carboxamide;

1-(2,4-dichlorophenyl)-N-(4-methylbenzene-1-sulfonyl)cyclopropane-1-carboxamide;

N-(2-cyano-5-fluorobenzene-1-sulfonyl)-1-(2,4-dichlorophenyl)cyclopropane-1-carboxamide;

1-(2,4-dichlorophenyl)-N-(pyridine-3-sulfonyl)cyclopropane-1-carboxamide;

N-(6-chloropyridine-3-sulfonyl)-1-(2,4-dichlorophenyl)cyclopropane-1-carboxamide;

methyl 5-{[1-(2,4-dichlorophenyl)cyclopropane-1-carbonyl]sulfamoyl}furan-2-carboxylate;

N-(5-bromothiophene-2-sulfonyl)-1-(2,4-dichlorophenyl)cyclopropane-1-carboxamide;

1-(2,4-dichlorophenyl)-N-[3-(trifluoromethoxy)benzene-1-sulfonyl]cyclopropane-1-carboxamide;

methyl 2-{[1-(2,4-dichlorophenyl)cyclopropane-1-carbonyl]sulfamoyl}benzoate;

methyl 4-chloro-2-{[1-(2,4-dichlorophenyl)cyclopropane-1-carbonyl]sulfamoyl}benzoate;

2-{[1-(2,4-dichlorophenyl)cyclopropane-1-carbonyl]sulfamoyl}benzoic acid;

4-chloro-2-{[1-(2,4-dichlorophenyl)cyclopropane-1-carbonyl]sulfamoyl}benzoic acid;

benzyl 4-{[1-(3,4-dichlorophenyl)cyclopropane-1-carbonyl]sulfamoyl}piperidine-1-carboxylate;

1-(2,4-dichlorophenyl)-N-(piperidine-4-sulfonyl)cyclopropane-1-carboxamide;

N-(1-acetylpiperidine-4-sulfonyl)-1-(2,4-dichlorophenyl)cyclopropane-1-carboxamide;

1-(2,4-dichlorophenyl)-N-[1-(3-phenylpropanoyl)piperidine-4-sulfonyl]cyclopropane-1-carboxamide;

tert-butyl 4-{[1-(2,4-dichlorophenyl)cyclopropane-1-carbonyl]sulfamoyl}piperidine-1-carboxylate;

1-(2,4-dichlorophenyl)-N-(2-methylbenzene-1-sulfonyl)cyclopropane-1-carboxamide;

1-(2,2-difluoro-2H-1,3-benzodioxol-5-yl)-N-(naphthalene-1-sulfonyl)cyclopropane-1-carboxamide;

1-[2-methoxy-5-(trifluoromethyl)pyridin-3-yl]-N-(pyrazolo[1,5-a]pyridine-4-sulfonyl)cyclopropane-1-carboxamide;

1-[2-methoxy-5-(trifluoromethyl)pyridin-3-yl]-N-(1-methyl-1H-benzimidazole-7-sulfonyl)cyclopropane-1-carboxamide;

1-[2-methoxy-5-(trifluoromethyl)pyridin-3-yl]-N-(1-methyl-1H-indazole-7-sulfonyl)cyclopropane-1-carboxamide;

N-(1H-indazole-4-sulfonyl)-1-[2-methoxy-5-(trifluoromethyl)pyridin-3-yl]cyclopropane-1-carboxamide;

1-(5-cyano-2-methoxyphenyl)-N-(quinoline-5-sulfonyl)cyclopropane-1-carboxamide;

1-(5-cyano-2-methoxyphenyl)-N-(1,2,3,4-tetrahydroquinoline-5-sulfonyl)cyclopropane-1-carboxamide;

1-[5-(bicyclo[1.1.1]pentan-1-yl)-2-methoxyphenyl]-N-(1,2,3,4-tetrahydroquinoline-5-sulfonyl)cyclopropane-1-carboxamide;

1-(2-methoxy-6-methylphenyl)-N-(1-methyl-1H-indole-4-sulfonyl)cyclopropane-1-carboxamide;

1-(3,5-dichloro-2,6-dimethoxyphenyl)-N-(quinoline-5-sulfonyl)cyclopropane-1-carboxamide;

1-(2,4-dichlorophenyl)-N-(phenylmethanesulfonyl)cyclopropane-1-carboxamide;

1-(2,4-dichlorophenyl)-N-(trifluoromethanesulfonyl)cyclopropane-1-carboxamide;
1-(2,4-dichlorophenyl)-N-(2,2,2-trifluoroethanesulfonyl) cyclopropane-1-carboxamide;
1-(2,4-dichlorophenyl)-N-(propane-1-sulfonyl)cyclopropane-1-carboxamide;
N-(3-chloropropane-1-sulfonyl)-1-(2,4-dichlorophenyl)cyclopropane-1-carboxamide;
1-(2,4-dichlorophenyl)-N-(propane-2-sulfonyl)cyclopropane-1-carboxamide;
1-(3,4-dichlorophenyl)-N-(phenylmethanesulfonyl)cyclopropane-1-carboxamide;
N-(pentane-3-sulfonyl)-1-phenylcyclopropane-1-carboxamide; 1-[2-methoxy-6-(1-methyl-1H-pyrazol-4-yl)phenyl]-N-(quinoline-5-sulfonyl)cyclopropane-1-carboxamide;
1-(4-cyclobutyl-2,6-dimethoxyphenyl)-N-(1-methyl-1H-benzimidazole-7-sulfonyl)cyclopropane-1-carboxamide;
1-(3-methoxy-6-methylpyridin-2-yl)-N-(quinoline-5-sulfonyl)cyclopropane-1-carboxamide;
1-(3-methoxy-6-methylpyridin-2-yl)-N-(naphthalene-1-sulfonyl)cyclopropane-1-carboxamide;
1-(3-methoxy-6-methylpyridin-2-yl)-N-(2-methylquinoline-5-sulfonyl)cyclopropane-1-carboxamide;
1-(2,5-dimethylphenyl)-N-(1H-indazole-4-sulfonyl)cyclopropane-1-carboxamide;
1-[2-methoxy-5-(3-methoxyoxetan-3-yl)phenyl]-N-(quinoline-5-sulfonyl)cyclopropane-1-carboxamide;
1-{2-methoxy-5-[(3-²H)oxetan-3-yl]phenyl}-N-(quinoline-5-sulfonyl)cyclopropane-1-carboxamide;
N-(1H-indazole-4-sulfonyl)-1-[5-methyl-2-(2-methylpropoxy)pyridin-3-yl]cyclopropane-1-carboxamide;
N-(1H-indazole-4-sulfonyl)-1-{5-methyl-2-[(propan-2-yl)oxy]pyridin-3-yl}cyclopropane-1-carboxamide;
1-(2-ethyl-6-methoxyphenyl)-N-(1H-indazole-4-sulfonyl) cyclopropane-1-carboxamide;
1-(2-ethyl-6-methoxyphenyl)-N-(2-methylquinoline-5-sulfonyl)cyclopropane-1-carboxamide;
N-[2-(dimethylamino)quinoline-5-sulfonyl]-1-(2-ethoxy-5-methylphenyl)cyclopropane-1-carboxamide;
1-{5-bromo-2-[(propan-2-yl)oxy]pyridin-3-yl}-N-(quinoline-5-sulfonyl)cyclopropane-1-carboxamide 1-{5-bromo-2-[(propan-2-yl)oxy]pyridin-3-yl}-N-(1,2,3,4-tetrahydroquinoline-5-sulfonyl)cyclopropane-1-carboxamide;
1-(5-chloro-2-methoxypyridin-3-yl)-N-(naphthalene-1-sulfonyl)cyclopropane-1-carboxamide
1-[2-propyl-6-(trifluoromethyl)pyridin-3-yl]-N-(quinoline-5-sulfonyl)cyclopropane-1-carboxamide;
1-[2-cyclopropyl-6-(trifluoromethyl)pyridin-3-yl]-N-(quinoline-5-sulfonyl)cyclopropane-1-carboxamide;
1-[2-cyclopropyl-6-(trifluoromethyl)pyridin-3-yl]-N-(1,2,3,4-tetrahydroquinoline-5-sulfonyl)cyclopropane-1-carboxamide;
1-[2-(propan-2-yl)-6-(trifluoromethyl)pyridin-3-yl]-N-(quinoline-5-sulfonyl)cyclopropane-1-carboxamide;
1-[2-propyl-6-(trifluoromethyl)pyridin-3-yl]-N-(1,2,3,4-tetrahydroquinoline-5-sulfonyl)cyclopropane-1-carboxamide;
1-[2-(propan-2-yl)-6-(trifluoromethyl)pyridin-3-yl]-N-(1,2,3,4-tetrahydroquinoline-5-sulfonyl)cyclopropane-1-carboxamide;
1-[2-cyclobutyl-6-(trifluoromethyl)pyridin-3-yl]-N-(1,2,3,4-tetrahydroquinoline-5-sulfonyl)cyclopropane-1-carboxamide;
1-[2-cyclobutyl-6-(trifluoromethyl)pyridin-3-yl]-N-(naphthalene-1-sulfonyl)cyclopropane-1-carboxamide;
1-[2-cyclopropyl-5-(2-methylpropoxy)pyridin-3-yl]-N-(quinoline-5-sulfonyl)cyclopropane-1-carboxamide;
1-{5-ethyl-2-[(propan-2-yl)oxy]pyridin-3-yl}-N-(quinoline-5-sulfonyl)cyclopropane-1-carboxamide;
1-{5-ethyl-2-[(propan-2-yl)oxy]pyridin-3-yl}-N-(1,2,3,4-tetrahydroquinoline-5-sulfonyl)cyclopropane-1-carboxamide;
1-[2-(pyrrolidin-1-yl)-6-(trifluoromethyl)pyridin-3-yl]-N-(quinoline-5-sulfonyl)cyclopropane-1-carboxamide;
1-{2-methoxy-5-[(propan-2-yl)oxy]pyridin-4-yl}-N-(quinoline-5-sulfonyl)cyclopropane-1-carboxamide;
1-{6-methoxy-4-[(propan-2-yl)oxy]pyridin-3-yl}-sulfonyl) cyclopropane-1-carboxamide;
1-{6-methoxy-4-[(propan-2-yl)oxy]pyridin-3-yl}-N-(2-methylquinoline-5-sulfonyl)cyclopropane-1-carboxamide;
1-[2-methoxy-5-(2-methylpropoxy)pyridin-4-yl]-N-(quinoline-5-sulfonyl)cyclopropane-1-carboxamide;
1-[2-methoxy-5-(2-methylpropoxy)pyridin-4-yl]-N-(2-methylquinoline-5-sulfonyl)cyclopropane-1-carboxamide;
N-(1H-indole-4-sulfonyl)-1-[2-methoxy-5-(2-methylpropoxy)pyridin-4-yl]cyclopropane-1-carboxamide;
1-{5-cyclobutyl-2-[(propan-2-yl)oxy]pyridin-3-yl}-N-(quinoline-5-sulfonyl)cyclopropane-1-carboxamide;
1-{5-cyclobutyl-2-[(propan-2-yl)oxy]pyridin-3-yl}-N-(2-methylquinoline-5-sulfonyl)cyclopropane-1-carboxamide;
1-{5-cyclobutyl-2-[(propan-2-yl)oxy]pyridin-3-yl}-N-(1H-indole-4-sulfonyl)cyclopropane-1-carboxamide;
1-{2-cyclobutyl-5-[(propan-2-yl)oxy]pyridin-4-yl}-N-(quinoline-5-sulfonyl)cyclopropane-1-carboxamide;
1-{2-cyclobutyl-5-[(propan-2-yl)oxy]pyridin-4-yl}-N-(2-methylquinoline-5-sulfonyl)cyclopropane-1-carboxamide;
1-{2-cyclobutyl-5-[(propan-2-yl)oxy]pyridin-4-yl}-N-(1H-indole-4-sulfonyl)cyclopropane-1-carboxamide;
1-[5-cyclobutyl-2-(pyrrolidin-1-yl)pyridin-3-yl]-N-(quinoline-5-sulfonyl)cyclopropane-1-carboxamide;
1-[5-cyclobutyl-2-(pyrrolidin-1-yl)pyridin-3-yl]-N-(2-methylquinoline-5-sulfonyl)cyclopropane-1-carboxamide;
1-[5-cyclobutyl-2-(pyrrolidin-1-yl)pyridin-3-yl]-N-(1H-indole-4-sulfonyl)cyclopropane-1-carboxamide;
1-[5-cyclobutyl-2-(pyrrolidin-1-yl)pyridin-3-yl]-N-(1,2,3,4-tetrahydroquinoline-5-sulfonyl)cyclopropane-1-carboxamide;
1-[5-cyclopropyl-2-(pyrrolidin-1-yl)pyridin-3-yl]-N-(quinoline-5-sulfonyl)cyclopropane-1-carboxamide;
1-[5-cyclopropyl-2-(pyrrolidin-1-yl)pyridin-3-yl]-N-(2-methylquinoline-5-sulfonyl)cyclopropane-1-carboxamide;
1-[5-cyclopropyl-2-(pyrrolidin-1-yl)pyridin-3-yl]-N-(1H-indole-4-sulfonyl)cyclopropane-1-carboxamide;
1-[5-chloro-2-(pyrrolidin-1-yl)pyridin-3-yl]-N-(quinoline-5-sulfonyl)cyclopropane-1-carboxamide;
1-[5-chloro-2-(pyrrolidin-1-yl)pyridin-3-yl]-N-(2-methylquinoline-5-sulfonyl)cyclopropane-1-carboxamide;
1-[5-ethyl-2-(pyrrolidin-1-yl)pyridin-3-yl]-N-(1H-indole-4-sulfonyl)cyclopropane-1-carboxamide;
1-{6-cyclobutyl-3-[(propan-2-yl)oxy]pyridin-2-yl}-N-(1H-indole-4-sulfonyl)cyclopropane-1-carboxamide;
1-{6-cyclobutyl-3-[(propan-2-yl)oxy]pyridin-2-yl}-N-(quinoline-5-sulfonyl)cyclopropane-1-carboxamide;
1-{5-ethyl-2-[(propan-2-yl)oxy]pyridin-3-yl}-N-(2-methylquinoline-5-sulfonyl)cyclopropane-1-carboxamide;

1-{5-ethyl-2-[(propan-2-yl)oxy]pyridin-3-yl}-N-(1H-indole-4-sulfonyl)cyclopropane-1-carboxamide;
1-[5-methyl-2-(2-methylpropoxy)pyridin-3-yl]-N-(quinoline-5-sulfonyl)cyclopropane-1-carboxamide;
1-[5-methyl-2-(2-methylpropoxy)pyridin-3-yl]-N-(2-methylquinoline-5-sulfonyl)cyclopropane-1-carboxamide;
N-(1H-indole-4-sulfonyl)-1-[5-methyl-2-(2-methylpropoxy)pyridin-3-yl]cyclopropane-1-carboxamide;
1-[5-ethyl-2-(2-methylpropoxy)pyridin-3-yl]-N-(quinoline-5-sulfonyl)cyclopropane-1-carboxamide;
1-[5-ethyl-2-(2-methylpropoxy)pyridin-3-yl]-N-(2-methylquinoline-5-sulfonyl)cyclopropane-1-carboxamide;
1-[5-ethyl-2-(2-methylpropoxy)pyridin-3-yl]-N-(1H-indole-4-sulfonyl)cyclopropane-1-carboxamide;
1-[5-cyclopropyl-2-(2-methylpropoxy)pyridin-3-yl]-N-(quinoline-5-sulfonyl)cyclopropane-1-carboxamide;
1-[5-cyclopropyl-2-(2-methylpropoxy)pyridin-3-yl]-N-(2-methylquinoline-5-sulfonyl)cyclopropane-1-carboxamide;
1-[5-cyclopropyl-2-(2-methylpropoxy)pyridin-3-yl]-N-(1H-indole-4-sulfonyl)cyclopropane-1-carboxamide;
1-[5-cyclobutyl-2-(2-methylpropoxy)pyridin-3-yl]-N-(quinoline-5-sulfonyl)cyclopropane-1-carboxamide;
1-[5-cyclobutyl-2-(2-methylpropoxy)pyridin-3-yl]-N-(1H-indole-4-sulfonyl)cyclopropane-1-carboxamide;
1-[5-cyclobutyl-2-(2-methylpropoxy)pyridin-3-yl]-N-(2-methylquinoline-5-sulfonyl)cyclopropane-1-carboxamide;
1-{6-ethyl-3-[(propan-2-yl)oxy]pyridin-2-yl}-N-(2-methylquinoline-5-sulfonyl)cyclopropane-1-carboxamide;
1-{6-ethyl-3-[(propan-2-yl)oxy]pyridin-2-yl}-N-(quinoline-5-sulfonyl)cyclopropane-1-carboxamide;
1-{6-ethyl-3-[(propan-2-yl)oxy]pyridin-2-yl}-N-(1H-indole-4-sulfonyl)cyclopropane-1-carboxamide;
1-[5-cyclobutyl-2-(4-methoxypiperidin-1-yl)pyridin-3-yl]-N-(1H-indole-4-sulfonyl)cyclopropane-1-carboxamide;
1-{5-methyl-2-[(propan-2-yl)oxy]pyridin-3-yl}-N-(2-methylquinoline-5-sulfonyl)cyclopropane-1-carboxamide;
N-(1H-indole-4-sulfonyl)-1-{5-methyl-2-[(propan-2-yl)oxy]pyridin-3-yl}cyclopropane-1-carboxamide;
1-{5-cyclopropyl-2-[(propan-2-yl)oxy]pyridin-3-yl}-N-(2-methylquinoline-5-sulfonyl)cyclopropane-1-carboxamide;
1-{5-cyclopropyl-2-[(propan-2-yl)oxy]pyridin-3-yl}-N-(1H-indole-4-sulfonyl)cyclopropane-1-carboxamide;
1-{2-[(propan-2-yl)oxy]-5-(pyrrolidin-1-yl)pyridin-3-yl}-N-(quinoline-5-sulfonyl)cyclopropane-1-carboxamide;
N-(2-methylquinoline-5-sulfonyl)-1-{2-[(propan-2-yl)oxy]-5-(pyrrolidin-1-yl)pyridin-3-yl}cyclopropane-1-carboxamide;
N-(1H-indole-4-sulfonyl)-1-{2-[(propan-2-yl)oxy]-5-(pyrrolidin-1-yl)pyridin-3-yl}cyclopropane-1-carboxamide;
1-{2,5-bis[(propan-2-yl)oxy]pyridin-3-yl}-N-(quinoline-5-sulfonyl)cyclopropane-1-carboxamide;
1-{2,5-bis[(propan-2-yl)oxy]pyridin-3-yl}-N-(1H-indole-4-sulfonyl)cyclopropane-1-carboxamide;
1-{2,5-bis[(propan-2-yl)oxy]pyridin-3-yl}-N-(2-methylquinoline-5-sulfonyl)cyclopropane-1-carboxamide;
1-[2-(2-methylpropoxy)-5-(pyrrolidin-1-yl)pyridin-3-yl]-N-(quinoline-5-sulfonyl)cyclopropane-1-carboxamide;
1-[2-(2-methylpropoxy)-5-(pyrrolidin-1-yl)pyridin-3-yl]-N-(2-methylquinoline-5-sulfonyl)cyclopropane-1-carboxamide;
N-(1H-indole-4-sulfonyl)-1-[2-(2-methylpropoxy)-5-(pyrrolidin-1-yl)pyridin-3-yl]cyclopropane-1-carboxamide;
1-{5-(dimethylamino)-2-[(propan-2-yl)oxy]pyridin-3-yl}-N-(quinoline-5-sulfonyl)cyclopropane-1-carboxamide;
1-{5-(dimethylamino)-2-[(propan-2-yl)oxy]pyridin-3-yl}-N-(2-methylquinoline-5-sulfonyl)cyclopropane-1-carboxamide;
1-{5-(dimethylamino)-2-[(propan-2-yl)oxy]pyridin-3-yl}-N-(1H-indole-4-sulfonyl)cyclopropane-1-carboxamide;
1-{5-methoxy-2-[(propan-2-yl)oxy]pyridin-3-yl}-N-(quinoline-5-sulfonyl)cyclopropane-1-carboxamide;
N-(1H-indole-4-sulfonyl)-1-{5-methoxy-2-[(propan-2-yl)oxy]pyridin-3-yl}cyclopropane-1-carboxamide;
1-{5-methoxy-2-[(propan-2-yl)oxy]pyridin-3-yl}-N-(2-methylquinoline-5-sulfonyl)cyclopropane-1-carboxamide;
1-[5-methoxy-2-(2-methylpropoxy)pyridin-3-yl]-N-(quinoline-5-sulfonyl)cyclopropane-1-carboxamide;
N-(1H-indole-4-sulfonyl)-1-[5-methoxy-2-(2-methylpropoxy)pyridin-3-yl]cyclopropane-1-carboxamide;
1-[5-methoxy-2-(2-methylpropoxy)pyridin-3-yl]-N-(2-methylquinoline-5-sulfonyl)cyclopropane-1-carboxamide;
1-{6-methyl-2-[(propan-2-yl)oxy]pyridin-3-yl}-N-(quinoline-5-sulfonyl)cyclopropane-1-carboxamide;
1-{6-methyl-2-[(propan-2-yl)oxy]pyridin-3-yl}-N-(2-methylquinoline-5-sulfonyl)cyclopropane-1-carboxamide;
N-(1H-indole-4-sulfonyl)-1-{6-methyl-2-[(propan-2-yl)oxy]pyridin-3-yl}cyclopropane-1-carboxamide;
1-{5-(azetidin-1-yl)-2-[(propan-2-yl)oxy]pyridin-3-yl}-N-(quinoline-5-sulfonyl)cyclopropane-1-carboxamide;
1-{5-(azetidin-1-yl)-2-[(propan-2-yl)oxy]pyridin-3-yl}-N-(2-methylquinoline-5-sulfonyl)cyclopropane-1-carboxamide;
1-{5-(azetidin-1-yl)-2-[(propan-2-yl)oxy]pyridin-3-yl}-N-(1H-indole-4-sulfonyl)cyclopropane-1-carboxamide;
1-{6-(2-methylpropoxy)-3-[(propan-2-yl)oxy]pyridin-2-yl}-N-(quinoline-5-sulfonyl)cyclopropane-1-carboxamide;
1-[2-(cyclopropylmethoxy)-5-methoxypyridin-3-yl]-N-(quinoline-5-sulfonyl)cyclopropane-1-carboxamide;
1-[2-(cyclopropylmethoxy)-5-methoxypyridin-3-yl]-N-(1H-indole-4-sulfonyl)cyclopropane-1-carboxamide;
N-(1H-indole-4-sulfonyl)-1-{6-(2-methylpropoxy)-3-[(propan-2-yl)oxy]pyridin-2-yl}cyclopropane-1-carboxamide;
1-{6-(2-methylpropoxy)-3-[(propan-2-yl)oxy]pyridin-2-yl}-N-(2-methylquinoline-5-sulfonyl)cyclopropane-1-carboxamide;
1-[5-(cyclopropylmethoxy)-2-methoxypyridin-4-yl]-N-(quinoline-5-sulfonyl)cyclopropane-1-carboxamide;
1-[2-(cyclopropylmethoxy)-5-methoxypyridin-3-yl]-N-(2-methylquinoline-5-sulfonyl)cyclopropane-1-carboxamide;
1-[5-(cyclopropylmethoxy)-2-methoxypyridin-4-yl]-N-(2-methylquinoline-5-sulfonyl)cyclopropane-1-carboxamide;
1-[5-cyclobutyl-2-(2-methoxyethoxy)pyridin-3-yl]-N-(2-methylquinoline-5-sulfonyl)cyclopropane-1-carboxamide;
1-[5-(cyclopropylmethoxy)-2-methoxypyridin-4-yl]-N-(1H-indole-4-sulfonyl)cyclopropane-1-carboxamide;
1-[2-(cyclopropylmethoxy)-5-methylpyridin-3-yl]-N-(quinoline-5-sulfonyl)cyclopropane-1-carboxamide;
1-[2-(cyclopropylmethoxy)-5-methylpyridin-3-yl]-N-(1H-indole-4-sulfonyl)cyclopropane-1-carboxamide;
1-[5-cyclobutyl-2-(cyclopropylmethoxy)pyridin-3-yl]-N-(1H-indole-4-sulfonyl)cyclopropane-1-carboxamide;
1-[5-cyclobutyl-2-(2-methoxyethoxy)pyridin-3-yl]-N-(1H-indole-4-sulfonyl)cyclopropane-1-carboxamide;
1-[5-cyclobutyl-2-(cyclopropylmethoxy)pyridin-3-yl]-N-(quinoline-5-sulfonyl)cyclopropane-1-carboxamide;

1-[2-(cyclopropylmethoxy)-5-methylpyridin-3-yl]-N-(2-methylquinoline-5-sulfonyl)cyclopropane-1-carboxamide;
1-(5-ethyl-2-{4-[(propan-2-yl)oxy]piperidin-1-yl}pyridin-3-yl)-N-(1H-indole-4-sulfonyl)cyclopropane-1-carboxamide;
1-(5-cyclobutyl-2-{4-[(propan-2-yl)oxy]piperidin-1-yl}pyridin-3-yl)-N-(1H-indole-4-sulfonyl)cyclopropane-1-carboxamide;
1-(5-cyclobutyl-2-{4-[(propan-2-yl)oxy]piperidin-1-yl}pyridin-3-yl)-N-(quinoline-5-sulfonyl)cyclopropane-1-carboxamide;
1-[2-(cyclopropylmethoxy)-5-ethylpyridin-3-yl]-N-(quinoline-5-sulfonyl)cyclopropane-1-carboxamide;
1-[2-(cyclopropylmethoxy)-5-ethylpyridin-3-yl]-N-(2-methylquinoline-5-sulfonyl)cyclopropane-1-carboxamide;
1-[2-(cyclopropylmethoxy)-5-ethylpyridin-3-yl]-N-(1H-indole-4-sulfonyl)cyclopropane-1-carboxamide;
1-[5-ethyl-2-(2-methoxyethoxy)pyridin-3-yl]-N-(1H-indole-4-sulfonyl)cyclopropane-1-carboxamide;
1-[5-cyclobutyl-2-(cyclopropylmethoxy)pyridin-3-yl]-N-(2-methylquinoline-5-sulfonyl)cyclopropane-1-carboxamide;
1-[5-cyclobutyl-2-(2-methoxyethoxy)pyridin-3-yl]-N-(quinoline-5-sulfonyl)cyclopropane-1-carboxamide;
1-[5-ethyl-2-(2-methoxyethoxy)pyridin-3-yl]-N-(quinoline-5-sulfonyl)cyclopropane-1-carboxamide;
1-(5-cyclobutyl-2-{4-[(propan-2-yl)oxy]piperidin-1-yl}pyridin-3-yl)-N-(2-methylquinoline-5-sulfonyl)cyclopropane-1-carboxamide;
1-(5-cyclobutyl-2-ethoxypyridin-3-yl)-N-(quinoline-5-sulfonyl)cyclopropane-1-carboxamide;
1-(5-cyclobutyl-2-ethoxypyridin-3-yl)-N-(2-methylquinoline-5-sulfonyl)cyclopropane-1-carboxamide;
1-(2-ethoxy-5-ethylpyridin-3-yl)-N-(quinoline-5-sulfonyl)cyclopropane-1-carboxamide;
1-(2-ethoxy-5-ethylpyridin-3-yl)-N-(2-methylquinoline-5-sulfonyl)cyclopropane-1-carboxamide;
1-{5-cyclobutyl-2-[4-(methoxymethyl)piperidin-1-yl]pyridin-3-yl}-N-(1H-indole-4-sulfonyl)cyclopropane-1-carboxamide;
1-{5-[1-(methoxymethyl)cyclopropyl]-2-[(propan-2-yl)oxy]pyridin-3-yl}-N-(naphthalene-1-sulfonyl)cyclopropane-1-carboxamide;
1-{5-ethyl-2-[4-(methoxymethyl)piperidin-1-yl]pyridin-3-yl}-N-(1H-indole-4-sulfonyl)cyclopropane-1-carboxamide;
1-{5-cyclobutyl-2-[4-(methoxymethyl)piperidin-1-yl]pyridin-3-yl}-N-(quinoline-5-sulfonyl)cyclopropane-1-carboxamide;
1-(2,4-dimethoxypyrimidin-5-yl)-N-(naphthalene-1-sulfonyl)cyclopropane-1-carboxamide;
N-(naphthalene-1-sulfonyl)-1-{2-[(propan-2-yl)oxy]pyridin-3-yl}cyclopropane-1-carboxamide;
1-{2-[(propan-2-yl)oxy]pyridin-3-yl}-N-(quinoline-5-sulfonyl)cyclopropane-1-carboxamide;
1-{2-[(propan-2-yl)oxy]pyridin-3-yl}-N-(1,2,3,4-tetrahydroquinoline-5-sulfonyl)cyclopropane-1-carboxamide;
1-[5-chloro-2-(trifluoromethyl)pyridin-3-yl]-N-(naphthalene-1-sulfonyl)cyclopropane-1-carboxamide;
1-(5-chloro-2-methoxypyridin-4-yl)-N-(quinoline-5-sulfonyl)cyclopropane-1-carboxamide
1-(5-chloro-2-methoxypyridin-4-yl)-N-(1,2,3,4-tetrahydroquinoline-5-sulfonyl)cyclopropane-1-carboxamide;
1-[5-methyl-2-(morpholin-4-yl)pyridin-4-yl]-N-(quinoline-5-sulfonyl)cyclopropane-1-carboxamide;
1-[5-methyl-2-(pyrrolidin-1-yl)pyridin-4-yl]-N-(quinoline-5-sulfonyl)cyclopropane-1-carboxamide;
1-[2-methoxy-6-(trifluoromethyl)pyridin-3-yl]-N-(quinoline-5-sulfonyl)cyclopropane-1-carboxamide;
1-[2-(dimethylamino)-5-methylpyridin-4-yl]-N-(quinoline-5-sulfonyl)cyclopropane-1-carboxamide;
1-[2-methoxy-6-(trifluoromethyl)pyridin-3-yl]-N-(1,2,3,4-tetrahydroquinoline-5-sulfonyl)cyclopropane-1-carboxamide;
1-(2-methoxy-5-methylpyridin-4-yl)-N-(quinoline-5-sulfonyl)cyclopropane-1-carboxamide;
1-[2-cyclobutyl-6-(trifluoromethyl)pyridin-3-yl]-N-(quinoline-5-sulfonyl)cyclopropane-1-carboxamide;
1-(2-cyclopropyl-5-methoxypyridin-3-yl)-N-(quinoline-5-sulfonyl)cyclopropane-1-carboxamide;
1-{2-ethyl-5-[(propan-2-yl)oxy]pyridin-3-yl}-N-(quinoline-5-sulfonyl)cyclopropane-1-carboxamide;
1-(2-ethyl-5-methoxypyridin-3-yl)-N-(quinoline-5-sulfonyl)cyclopropane-1-carboxamide;
1-[6-(dimethylamino)-2-methoxypyridin-3-yl]-N-(quinoline-5-sulfonyl)cyclopropane-1-carboxamide;
1-(6-methoxy-2-methylpyridin-3-yl)-N-(naphthalene-1-sulfonyl)cyclopropane-1-carboxamide;
1-(4-ethylpyridin-3-yl)-N-(naphthalene-1-sulfonyl)cyclopropane-1-carboxamide;
1-(4-ethylpyridin-3-yl)-N-(1,2,3,4-tetrahydroquinoline-5-sulfonyl)cyclopropane-1-carboxamide;
1-(6-methoxy-4-methylpyridin-3-yl)-N-(naphthalene-1-sulfonyl)cyclopropane-1-carboxamide;
1-(6-methoxy-4-methylpyridin-3-yl)-N-(quinoline-5-sulfonyl)cyclopropane-1-carboxamide;
1-{6-methoxy-4-[(propan-2-yl)oxy]pyridin-3-yl}-N-(1,2,3,4-tetrahydroquinoline-5-sulfonyl)cyclopropane-1-carboxamide;
1-{5-cyclobutyl-2-[(propan-2-yl)oxy]pyridin-3-yl}-N-(1,2,3,4-tetrahydroquinoline-5-sulfonyl)cyclopropane-1-carboxamide;
1-{2-cyclobutyl-5-[(propan-2-yl)oxy]pyridin-4-yl}-N-(1,2,3,4-tetrahydroquinoline-5-sulfonyl)cyclopropane-1-carboxamide;
1-{5-cyclobutyl-3-[(propan-2-yl)oxy]pyridin-2-yl}-N-(quinoline-5-sulfonyl)cyclopropane-1-carboxamide;
1-[5-cyclobutyl-2-(morpholin-4-yl)pyridin-3-yl]-N-(quinoline-5-sulfonyl)cyclopropane-1-carboxamide;
1-[5-cyclopropyl-2-(pyrrolidin-1-yl)pyridin-3-yl]-N-(1,2,3,4-tetrahydroquinoline-5-sulfonyl)cyclopropane-1-carboxamide;
1-[5-ethyl-2-(pyrrolidin-1-yl)pyridin-3-yl]-N-(quinoline-5-sulfonyl)cyclopropane-1-carboxamide;
1-[5-ethyl-2-(pyrrolidin-1-yl)pyridin-3-yl]-N-(2-methylquinoline-5-sulfonyl)cyclopropane-1-carboxamide;
1-[5-ethyl-2-(morpholin-4-yl)pyridin-3-yl]-N-(2-methylquinoline-5-sulfonyl)cyclopropane-1-carboxamide;
1-[2-(pyrrolidin-1-yl)pyridin-3-yl]-N-(quinoline-5-sulfonyl)cyclopropane-1-carboxamide;
N-(2-methylquinoline-5-sulfonyl)-1-[2-(pyrrolidin-1-yl)pyridin-3-yl]cyclopropane-1-carboxamide;
1-[5-ethyl-2-(pyrrolidin-1-yl)pyridin-3-yl]-N-(1,2,3,4-tetrahydroquinoline-5-sulfonyl)cyclopropane-1-carboxamide;
1-[5-methyl-2-(pyrrolidin-1-yl)pyridin-3-yl]-N-(2-methylquinoline-5-sulfonyl)cyclopropane-1-carboxamide;
N-(1H-indole-4-sulfonyl)-1-[5-methyl-2-(pyrrolidin-1-yl)pyridin-3-yl]cyclopropane-1-carboxamide;
1-[5-methyl-2-(pyrrolidin-1-yl)pyridin-3-yl]-N-(quinoline-5-sulfonyl)cyclopropane-1-carboxamide;
1-(3-cyclopropyl-5-methylpyridin-2-yl)-N-(1H-indole-4-sulfonyl)cyclopropane-1-carboxamide;

1-[5-methoxy-2-(pyrrolidin-1-yl)pyridin-3-yl]-N-(quinoline-5-sulfonyl)cyclopropane-1-carboxamide;
1-[2-(dimethylamino)-5-methylpyridin-3-yl]-N-(quinoline-5-sulfonyl)cyclopropane-1-carboxamide;
1-[5-methoxy-2-(2-methoxyethoxy)pyridin-3-yl]-N-(2-methylquinoline-5-sulfonyl)cyclopropane-1-carboxamide;
N-(1H-indole-4-sulfonyl)-1-[5-methoxy-2-(2-methoxyethoxy)pyridin-3-yl]cyclopropane-1-carboxamide;
1-[5-methoxy-2-(2-methoxyethoxy)pyridin-3-yl]-N-(quinoline-5-sulfonyl)cyclopropane-1-carboxamide;
N-(1H-indole-4-sulfonyl)-1-[2-methoxy-5-(2-methoxyethoxy)pyridin-4-yl]cyclopropane-1-carboxamide;
1-[2-methoxy-5-(2-methoxyethoxy)pyridin-4-yl]-N-(2-methylquinoline-5-sulfonyl)cyclopropane-1-carboxamide;
1-[2-(dimethylamino)-5-ethylpyridin-3-yl]-N-(quinoline-5-sulfonyl)cyclopropane-1-carboxamide;
1-[2-(dimethylamino)-5-ethylpyridin-3-yl]-N-(2-methylquinoline-5-sulfonyl)cyclopropane-1-carboxamide;
1-[2-(dimethylamino)-5-ethylpyridin-3-yl]-N-(1H-indole-4-sulfonyl)cyclopropane-1-carboxamide;
1-[2-(2-methoxyethoxy)-5-methylpyridin-3-yl]-N-(2-methylquinoline-5-sulfonyl)cyclopropane-1-carboxamide;
1-{2-(dimethylamino)-6-[(propan-2-yl)oxy]pyridin-3-yl}-N-(quinoline-5-sulfonyl)cyclopropane-1-carboxamide;
1-[2-(2-methoxyethoxy)-5-methylpyridin-3-yl]-N-(quinoline-5-sulfonyl)cyclopropane-1-carboxamide;
N-(1H-indole-4-sulfonyl)-1-[2-(2-methoxyethoxy)-5-methylpyridin-3-yl]cyclopropane-1-carboxamide;
1-(5-ethyl-2-{4-[(propan-2-yl)oxy]piperidin-1-yl}pyridin-3-yl)-N-(quinoline-5-sulfonyl)cyclopropane-1-carboxamide;
1-(5-ethyl-2-{4-[(propan-2-yl)oxy]piperidin-1-yl}pyridin-3-yl)-N-(2-methylquinoline-5-sulfonyl)cyclopropane-1-carboxamide;
1-[5-ethyl-2-(2-methoxyethoxy)pyridin-3-yl]-N-(2-methylquinoline-5-sulfonyl)cyclopropane-1-carboxamide;
1-[5-ethyl-2-(4-methoxypiperidin-1-yl)pyridin-3-yl]-N-(quinoline-5-sulfonyl)cyclopropane-1-carboxamide;
1-[5-ethyl-2-(4-methoxypiperidin-1-yl)pyridin-3-yl]-N-(1H-indole-4-sulfonyl)cyclopropane-1-carboxamide;
1-{5-ethyl-2-[4-(methoxymethyl)piperidin-1-yl]pyridin-3-yl}-N-(quinoline-5-sulfonyl)cyclopropane-1-carboxamide;
1-[3-chloro-5-(trifluoromethyl)pyridin-2-yl]-N-(quinoline-5-sulfonyl)cyclopropane-1-carboxamide;
1-[5-chloro-2-(trifluoromethyl)pyridin-3-yl]-N-(quinoline-5-sulfonyl)cyclopropane-1-carboxamide;
N-(1H-indole-4-sulfonyl)-1-{6-methoxy-4-[(propan-2-yl)oxy]pyridin-3-yl}cyclopropane-1-carboxamide;
1-(3-cyclopropyl-5-methylpyridin-2-yl)-N-(quinoline-5-sulfonyl)cyclopropane-1-carboxamide;
1-[2-chloro-5-(2-methylpropoxy)pyridin-3-yl]-N-(quinoline-5-sulfonyl)cyclopropane-1-carboxamide;
1-(4-ethylpyridin-3-yl)-N-(quinoline-5-sulfonyl)cyclopropane-1-carboxamide;
1-(2-fluoro-5-methylpyridin-4-yl)-N-(1,2,3,4-tetrahydroquinoline-5-sulfonyl)cyclopropane-1-carboxamide;
1-(6-methoxy-2-methylpyridin-3-yl)-N-(quinoline-5-sulfonyl)cyclopropane-1-carboxamide;
1-[5-cyclopropyl-2-(4-methylpiperazin-1-yl)pyridin-3-yl]-N-(quinoline-5-sulfonyl)cyclopropane-1-carboxamide;
1-[5-cyclopropyl-2-(trifluoromethyl)pyridin-3-yl]-N-(quinoline-5-sulfonyl)cyclopropane-1-carboxamide;
1-[2-methoxy-5-(2-methoxyethoxy)pyridin-4-yl]-N-(quinoline-5-sulfonyl)cyclopropane-1-carboxamide;
1-(2,4-dimethoxypyrimidin-5-yl)-N-(1,2,3,4-tetrahydroquinoline-5-sulfonyl)cyclopropane-1-carboxamide;
1-{2-chloro-5-[(propan-2-yl)oxy]pyridin-3-yl}-N-(quinoline-5-sulfonyl)cyclopropane-1-carboxamide;
1-[5-(2,2-difluoroethoxy)-2-methoxypyridin-4-yl]-N-(2-methylquinoline-5-sulfonyl)cyclopropane-1-carboxamide;
1-(6-methoxy-2-methylpyridin-3-yl)-N-(1,2,3,4-tetrahydroquinoline-5-sulfonyl)cyclopropane-1-carboxamide;
1-(2-fluoro-5-methylpyridin-4-yl)-N-(quinoline-5-sulfonyl)cyclopropane-1-carboxamide;
1-(6-methoxy-4-methylpyridin-3-yl)-N-(1,2,3,4-tetrahydroquinoline-5-sulfonyl)cyclopropane-1-carboxamide;
1-[5-(2,2-difluoroethoxy)-2-methoxypyridin-4-yl]-N-(quinoline-5-sulfonyl)cyclopropane-1-carboxamide;
1-[5-(difluoromethoxy)-2-methoxypyridin-4-yl]-N-(quinoline-5-sulfonyl)cyclopropane-1-carboxamide;
1-[5-cyclopropyl-2-(morpholin-4-yl)pyridin-3-yl]-N-(2-methylquinoline-5-sulfonyl)cyclopropane-1-carboxamide;
1-[2-chloro-6-(trifluoromethyl)pyridin-3-yl]-N-(naphthalene-1-sulfonyl)cyclopropane-1-carboxamide;
1-[5-(difluoromethoxy)-2-methoxypyridin-4-yl]-N-(2-methylquinoline-5-sulfonyl)cyclopropane-1-carboxamide;
1-[5-ethyl-2-(morpholin-4-yl)pyridin-3-yl]-N-(quinoline-5-sulfonyl)cyclopropane-1-carboxamide;
1-(2,4-dimethoxypyrimidin-5-yl)-N-(quinoline-5-sulfonyl)cyclopropane-1-carboxamide;
1-[5-cyclopropyl-2-(morpholin-4-yl)pyridin-3-yl]-N-(quinoline-5-sulfonyl)cyclopropane-1-carboxamide;
1-[5-methyl-2-(4-methylpiperazin-1-yl)pyridin-3-yl]-N-(quinoline-5-sulfonyl)cyclopropane-1-carboxamide;
1-[5-cyclopropyl-2-(4-methylpiperazin-1-yl)pyridin-3-yl]-N-(2-methylquinoline-5-sulfonyl)cyclopropane-1-carboxamide;
1-[2-chloro-6-(trifluoromethyl)pyridin-3-yl]-N-(1,2,3,4-tetrahydroquinoline-5-sulfonyl)cyclopropane-1-carboxamide;
1-[2-chloro-6-(trifluoromethyl)pyridin-3-yl]-N-(quinoline-5-sulfonyl)cyclopropane-1-carboxamide;
1-(6-amino-2-methoxypyridin-3-yl)-N-(quinoline-5-sulfonyl)cyclopropane-1-carboxamide;
1-[5-cyclobutyl-2-(4-methylpiperazin-1-yl)pyridin-3-yl]-N-(quinoline-5-sulfonyl)cyclopropane-1-carboxamide;
1-[5-cyclobutyl-2-(4-methylpiperazin-1-yl)pyridin-3-yl]-N-(2-methylquinoline-5-sulfonyl)cyclopropane-1-carboxamide;
1-[5-ethyl-2-(4-methylpiperazin-1-yl)pyridin-3-yl]-N-(quinoline-5-sulfonyl)cyclopropane-1-carboxamide;
1-(5-chloro-2-fluoropyridin-3-yl)-N-(quinoline-5-sulfonyl)cyclopropane-1-carboxamide;
1-{5-(hydroxymethyl)-2-[(propan-2-yl)oxy]pyridin-3-yl}-N-(quinoline-5-sulfonyl)cyclopropane-1-carboxamide;
1-[5-cyclopropyl-2-(4-methylpiperazin-1-yl)pyridin-3-yl]-N-(1H-indole-4-sulfonyl)cyclopropane-1-carboxamide;
and pharmaceutically acceptable salts thereof.

Certain embodiments pertain to compounds of Formula (III),

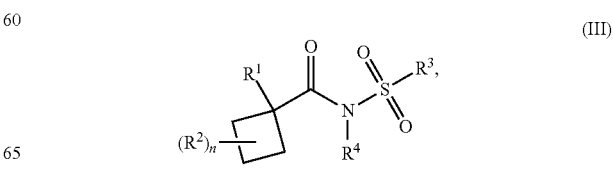

(III)

wherein
- $R^1$ is selected from the group consisting of 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are substituted with two or more substituents independently selected from the group consisting of $R^7$, $OR^7$, $C(O)R^7$, $OC(O)R^7$, $C(O)OR^7$, $SO_2R^7$, $C(O)NH_2$, $C(O)NHR^7$, $C(O)N(R^7)_2$, $NHC(O)R^7$, $NHR^7$, $N(R^7)_2$, $NH_2$, $C(O)OH$, $OH$, oxo, $CN$, $NO_2$, F, Cl, Br and I;
- $R^2$ is independently selected from the group consisting of hydrogen, $R^8$, $OR^8$, $C(O)R^8$, $C(O)OR^8$, $SO_2R^8$, $NHR^8$, $N(R^8)_2$, $NH_2$, $C(O)OH$, $OH$, $CN$, $NO_2$, F, Cl, Br and I;
- n is 0 or 1;
- $R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_1$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^9$, $OR^9$, $SR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, $OH$, oxo, $CN$, $NO_2$, F, Cl, Br and I;
- $R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $OR^{10}$, F, Cl, Br and I;
- $R^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, $C_3$-$C_7$ cycloalkyl, OH, oxo, CN, $NO_2$, F, Cl, Br and I; wherein each $R^7$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{11}$, $OR^{11}$, $SR^{11}$, $C(O)R^{11}$, $OC(O)R^{11}$, $C(O)OR^{11}$, $SO_2R^{11}$, $C(O)NH_2$, $C(O)NHR^{11}$, $C(O)N(R^{11})_2$, $NHC(O)R^{11}$, $NHR^{11}$, $N(R^{11})_2$, $NH_2$, $C(O)OH$, $OH$, oxo, $CN$, $NO_2$, F, Cl, Br and I;
- $R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $R^{12}$, $OR^{12}$, $C(O)OR^{12}$, $NHR^{12}$, $N(R^{12})_2$, $NH_2$, $C(O)OH$, $OH$, $CN$, $NO_2$, F, Cl, Br and I;
- $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $C(O)R^{13}$, $OC(O)R^{13}$, $C(O)OR^{13}$, $SO_2R^{13}$, $C(O)NH_2$, $C(O)NHR^{13}$, $C(O)N(R^{13})_2$, $NHC(O)R^{13}$, $NHR^{13}$, $N(R^{13})_2$, $NH_2$, $C(O)OH$, $OH$, oxo, $CN$, $NO_2$, F, Cl, Br and I; wherein each $R^9$ 6-10 membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $R^{14}$, $OR^{14}$, $SR^{14}$, $C(O)R^{14}$, $OC(O)R^{14}$, $C(O)OR^{14}$, $SO_2R^{14}$, $C(O)NH_2$, $C(O)NHR^{14}$, $C(O)N(R^{14})_2$, $NHC(O)R^{14}$, $NHR^{14}$, $N(R^{14})_2$, $NH_2$, $C(O)OH$, $OH$, oxo, $CN$, $NO_2$, F, Cl, Br and I;
- $R^{10}$, at each occurrence, is independently $C_1$-$C_4$ alkyl;
- $R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of $C_1$-$C_6$ alkoxy, OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I;
- $R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl;
- $R^{13}$, at each occurrence, is independently selected from the group consisting of $C_1$-$C_6$ alkyl, $C_2$, $C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I; and
- $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{11}$ $C_1$-$C_6$alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I.

In one embodiment of Formula (III), $R^1$ is selected from the group consisting of 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^1$ 6-10 membered aryl, 5-11 membered heteroaryl, $C_3$-$C_{11}$ cycloalkyl, $C_4$-$C_{11}$ cycloalkenyl, and 4-12 membered heterocyclyl are substituted with two or more substituents independently selected from the group consisting of 127, $OR^7$, $C(O)R^7$, $OC(O)R^7$, $C(O)OR^7$, $SO_2R^7$, $C(O)NH_2$, $C(O)NHR^7$, $C(O)N(R^7)_2$, $NHC(O)R^7$, $NHR^7$, $N(R^7)_2$, $NH_2$, $C(O)OH$, OH, oxo, CN, $NO_2$, F, Cl, Br and I. In another embodiment of Formula (III), $R^1$ is selected from the group consisting of 6-10 membered aryl, 5-11 membered heteroaryl, and 4-12 membered heterocyclyl; wherein the $R^1$ 6-10 membered aryl, 5-11 membered heteroaryl, and 4-12 membered heterocyclyl are substituted with two or more substituents independently selected from the group consisting of $R^T$, $OR^7$, $C(O)OR^7$, $N(R^7)_2$, CN, F, Cl, and Br. In another embodiment of Formula (III), $R^1$ is 6-10 membered aryl; wherein the $R^1$ 6-10 membered aryl is substituted with two or more substituents independently selected from the group consisting of $R^T$, $OR^7$, $C(O)OR^7$, $N(R^7)_2$, CN, F, Cl, and Br. In another embodiment of Formula (III), $R^1$ is 5-11 membered heteroaryl; wherein the $R^1$ 5-11 membered heteroaryl is substituted with two or more substituents independently selected from the group consisting of 127, $OR^7$, $C(O)OR^7$, $N(R^7)_2$, $NH_2$, CN, F, $C_1$, and Br. In another embodiment of Formula (III), $R^1$ is 4-12 membered heterocyclyl; wherein the $R^1$ 4-12 membered heterocyclyl is substituted with two or more substituents independently selected from the group consisting of 127, $OR^7$, $C(O)OR^7$, $N(R^7)_2$, $NH_2$, CN, F, Cl, and Br. In another embodiment of Formula (III), $R^1$ is phenyl; wherein the $R^1$ phenyl is substituted with two or more substituents independently selected from the group consisting of $R^7$, $OR^7$, $C(O)OR^7$, $N(R^7)_2$, $NH_2$, CN, F, Cl, and Br. In another embodiment of Formula (III), R' is selected from the group consisting of pyrazolyl, pyridinyl, quinolinyl, pyrimidinyl, and benzo[d][1,3]dioxolyl; wherein the $R^1$ pyrazolyl, pyridinyl, quinolinyl, pyrimidinyl, and benzo[d][1,3]dioxolyl are substituted with two or more substituents independently selected from the group consisting of $R^T$, $OR^7$, $C(O)OR^7$, $N(R^7)_2$, $NH_2$, CN, F, Cl, and Br.

In one embodiment of Formula (III), n is 0 or 1; and $R^2$ is independently selected from the group consisting of $R^8$, $OR^8$, $C(O)R^8$, $C(O)OR^8$, $SO_2R^8$, $NHR^8$, $N(R^8)_2$, $NH_2$, $C(O)OH$, OH, CN, $NO_2$, F, Cl, Br and I. In another embodiment of Formula (III), n is 1; and $R^2$ is independently selected from the group consisting of $R^8$ and $C(O)OR^8$. In another embodiment of Formula (III), n is 0. In another embodiment of Formula (III), n is 1; and $R^2$ is independently $R^8$. In another embodiment of Formula (III), n is 1; and $R^2$ is independently $C(O)OR^8$. In another embodiment of Formula (III), n is 1; and $R^2$ is independently $R^8$; and $R^8$ is independently $C_1$-$C_6$ alkyl. In another embodiment of Formula (III), n is 1; and $R^2$ is independently $C(O)OR^8$; and $R^8$ is independently $C_1$-$C_6$ alkyl.

In one embodiment of Formula (III), $R^3$ is selected from the group consisting of $C_1$-$C_6$ alkyl, $C_2$-$C_6$ alkenyl, $C_2$-$C_6$ alkynyl, 6-10 membered aryl, 5-11 membered heteroaryl, $C_3$-$C_{11}$ cycloalkyl, $C_4$-$C_{11}$ cycloalkenyl, and 4-12 membered heterocyclyl; wherein the $R^3$ $C_1$-$C_6$ alkyl, $C_2$-$C_6$ alkenyl, and $C_2$-$C_6$ alkynyl are optionally substituted with one or more substituents independently selected from the group consisting of $C_1$-$C_6$ alkoxy, phenyl, OH, oxo, CN, $NO_2$, F, Cl, Br and I; wherein the $R^3$ 6-10 membered aryl, 5-11 membered heteroaryl, $C_3$-$C_{11}$ cycloalkyl, $C_4$-$C_{11}$ cycloalkenyl, and 4-12 membered heterocyclyl are optionally substituted with one or more substituents independently selected from the group consisting of $R^9$, $OR^9$, $SR^9$, $C(O)R^9$, $OC(O)R^9$, $C(O)OR^9$, $SO_2R^9$, $C(O)NH_2$, $C(O)NHR^9$, $C(O)N(R^9)_2$, $NHC(O)R^9$, $NHR^9$, $N(R^9)_2$, $NH_2$, $C(O)OH$, OH, oxo, CN, $NO_2$, F, Cl, Br and I. In another embodiment of Formula (III), $R^3$ is selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein the $R^3$ $C_1$-$C_6$ alkyl is optionally substituted with one or more substituents independently selected from the group consisting of phenyl, F, and Cl; wherein the $R^3$ 6-10 membered aryl, 5-11 membered heteroaryl, $C_3$-$C_{11}$ cycloalkyl, and 4-12 membered heterocyclyl are optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br.

In another embodiment of Formula (III), $R^3$ is $C_1$-$C_6$ alkyl; wherein the $R^3$ $C_1$-$C_6$ alkyl is optionally substituted with one or more substituents independently selected from the group consisting of phenyl, F, and Cl. In another embodiment of Formula (III), $R^3$ is 6-10 membered aryl; wherein the $R^3$ 6-10 membered aryl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is 5-11 membered heteroaryl; wherein the $R^3$ 5-11 membered heteroaryl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is $C_3$-$C_{11}$ cycloalkyl; wherein the $R^3$ $C_3$-$C_{11}$ cycloalkyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is 4-12 membered heterocyclyl; wherein the $R^3$ 4-12 membered heterocyclyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is phenyl; wherein the $R^3$ phenyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is napthyl; wherein the $R^3$ napthyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is quinolinyl; wherein the $R^3$ quinolinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is tetrahydroquinolinyl; wherein the $R^3$ tetrahydroquinolinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is indazolyl; wherein the $R^3$ indazolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is pyrazolo[1,5-a]pyridinyl; wherein the $R^3$ pyrazolo[1,5-a]pyridinyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is indolyl; wherein the $R^3$ indolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br. In another embodiment of Formula (III), $R^3$ is benzoimidazolyl; wherein the $R^3$ benzoimidazolyl is optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br.

In one embodiment of Formula (III), $R^4$ is selected from the group consisting of hydrogen and $C_1$-$C_6$ alkyl; wherein the $R^4$ $C_1$-$C_6$ alkyl is optionally substituted with one or more substituents independently selected from the group consisting of $OR^{10}$, F, Cl, Br and I. In another embodiment of Formula (III), $R^4$ is selected from the group consisting of hydrogen and $C_1$-$C_6$ alkyl. In another embodiment of Formula (III), $R^4$ is hydrogen. In another embodiment of Formula (III), $R^4$ is $C_1$-$C_6$ alkyl. In another embodiment of Formula (III), $R^4$ is $CH_3$.

In one embodiment of Formula (III), $R^7$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, cycloalkyl, $C_4$-$C_{11}$ cycloalkenyl, and 4-12 membered heterocyclyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkoxy, $C_3$-$C_7$ cycloalkyl, OH, oxo, CN, $NO_2$, F, Cl, Br and I; wherein each $R^7$ 6-10 membered aryl, 5-11 membered heteroaryl, cycloalkyl, $C_4$-$C_{11}$ cycloalkenyl, and 4-12 membered heterocyclyl is optionally substituted with one or more substituents independently selected from the group consisting of $R^{11}$, $OR^{11}$, $SR^{11}$, $C(O)R^{11}$, $OC(O)R^{11}$, $C(O)OR^{11}$, $SO_2R^{11}$, $C(O)NH_2$, $C(O)NHR^{11}$, $C(O)N(R^{11})_2$, $NHC(O)R^{11}$, $NHR^{11}$, $N(R^{11})_2$, $NH_2$, $C(O)OH$, OH, oxo, CN, $NO_2$, F, Cl, Br and I. In another embodiment of Formula (III), $R^7$, at each occurrence, is independently selected from the group consisting of $C_1$-$C_6$ alkyl, $C_3$-$C_{11}$ cycloalkyl, 5-11 membered heteroaryl, and 4-12 membered heterocyclyl; wherein each $R^7$ $C_1$-$C_6$ alkyl is optionally substituted with one or more substituents independently selected from the group consisting of $C_1$-$C_6$ alkoxy, $C_3$-$C_7$ cycloalkyl, OH and F; wherein each $R^7$ $C_3$-$C_{11}$ cycloalkyl, 5-11 membered heteroaryl, and 4-12 membered heterocyclyl are optionally substituted with one or more substituents independently selected from the group consisting of $R^{11}$, $OR^{11}$, $NHR^{11}$, and $C(O)OR^{11}$.

In one embodiment of Formula (III), $R^9$, at each occurrence, is independently selected from the group consisting of $C_1$-$C_6$ alkyl, $C_2$-$C_6$ alkenyl, $C_2$-$C_6$ alkynyl, 6-10 membered aryl, 5-11 membered heteroaryl, cycloalkyl, $C_4$-$C_{11}$ cycloalkenyl, and 4-12 membered heterocyclyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $C(O)R^{13}$, $OC(O)R^{13}$, $C(O)OR^{13}$, $SO_2R^{13}$, $C(O)NH_2$, $C(O)NHR^{13}$, $C(O)N(R^{13})_2$, $NHC(O)R^{13}$, $NHR^{13}$, $N(R^{13})_2$, $NH_2$, $C(O)OH$, OH, oxo, CN, $NO_2$, F, Cl, Br and I; wherein each $R^9$ 6-10 membered aryl, 5-11 membered heteroaryl, cycloalkyl, $C_4$-$C_{11}$ cycloalkenyl, and 4-12 membered heterocyclyl is optionally substituted with one or more substituents independently selected from the group consisting of $R^{14}$, $OR^{14}$, $SR^{14}$, $C(O)R^{14}$, $OC(O)R^{14}$, $C(O)OR^{14}$, $SO_2R^{14}$, $C(O)NH_2$, $C(O)NHR^{14}$, $C(O)N(R^{14})_2$, $NHC(O)R^{14}$, $NHR^{14}$, $N(R^{14})_2$, $NH_2$, $C(O)OH$, OH, oxo, CN, $NO_2$, F, Cl, Br and I. In another embodiment of Formula (III), $R^9$, at each occurrence, is independently selected from the group consisting of $C_1$-$C_6$ alkyl, 5-11 membered heteroaryl, and 4-12 membered heterocyclyl; wherein each $R^9$ $C_1$-$C_6$ alkyl is optionally substituted with one or more substituents independently selected from the group consisting of $R^{11}$, and F; wherein each $R^9$ 5-11 membered heteroaryl and 4-12 membered heterocyclyl is optionally substituted with one or more oxo. In another embodiment of Formula (III), $R^9$, at each occurrence, is independently selected from the group consisting of 5-11 membered heteroaryl and 4-12 membered heterocyclyl; wherein each $R^9$ 5-11 membered heteroaryl and 4-12 membered heterocyclyl is optionally substituted with one or more oxo. In another embodiment of Formula (III), $R^9$, at each occurrence, is independently $C_1$-$C_6$ alkyl; wherein each $R^9$ $C_1$-$C_6$ alkyl is optionally substituted with one or more substituents independently selected from the group consisting of $R^{11}$ and F. In another embodiment of Formula (III), $R^9$, at each occurrence, is independently $C_1$-$C_6$ alkyl; wherein each $R^9$ $C_1$-$C_6$ alkyl is unsubstituted.

In one embodiment of Formula (III), $R^{10}$, at each occurrence, is independently $C_1$-$C_4$ alkyl.

In one embodiment of Formula (III), $R^{11}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl; wherein each $R^{11}$ $C_1$-$C_6$ alkyl and $C_1$-$C_6$ alkoxy is optionally substituted with one or more substituents independently selected from the group consisting of $C_1$-$C_6$ alkoxy, OH, oxo, CN, $NO_2$, F, Cl, Br and I; wherein each $R^{11}$ $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl is optionally substituted with one or more substituents independently selected from the group consisting of $C_1$-$C_6$ alkyl, $C_1$-$C_6$ alkoxy, F, Cl, Br and I. In another embodiment of Formula (III), $R^{11}$, at each occurrence, is independently $C_1$-$C_6$ alkyl; wherein each $R^{11}$ $C_1$-$C_6$ alkyl is optionally substituted with $C_1$-$C_6$ alkoxy.

In one embodiment of Formula (III), $R^{12}$, at each occurrence, is independently selected from the group consisting of $C_1$-$C_6$ alkyl, $C_1$-$C_6$ alkoxy, $C_6$-$C_{10}$ membered aryl, $C_3$-$C_{11}$ cycloalkyl, 4-12 membered heterocyclyl, $C_4$-$C_{11}$ cycloalkenyl, and 5-6 membered heteroaryl.

In one embodiment of Formula (III), $R^{11}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of OH, oxo, CN, $NO_2$, F, Cl, Br and I; wherein each $R^{13}$ $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl is optionally substituted with one or more substituents independently selected from the group consisting of $C_1$-$C_6$ alkyl, $C_1$-$C_6$ alkoxy, 5-6 membered heteroaryl, OH, oxo, CN, $NO_2$, F, Cl, Br and I. In another embodiment of Formula (III), $R^{13}$, at each occurrence, is $C_6$-$C_{10}$ membered aryl.

In one embodiment of Formula (III), $R^{14}$, at each occurrence, is independently selected from the group consisting of $C_1$-$C_6$ alkyl, $C_2$-$C_6$ alkenyl, $C_2$-$C_6$ alkynyl, $C_6$-$C_{10}$ membered aryl, 5-11 membered heteroaryl, $C_3$-$C_{11}$ cycloalkyl, $C_4$-$C_{11}$ cycloalkenyl, and 4-12 membered heterocyclyl;

wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of $C_1$-$C_6$ alkyl, $C_1$-$C_6$ alkoxy, 5-6 membered heteroaryl, 4-12 membered heterocyclyl, OH, oxo, CN, $NO_2$, F, Cl, Br and I.

In one embodiment of Formula (III),
- $R^1$ is selected from the group consisting of 6-10 membered aryl, 5-11 membered heteroaryl, and 4-12 membered heterocyclyl; wherein the $R^1$ 6-10 membered aryl, 5-11 membered heteroaryl, and 4-12 membered heterocyclyl are substituted with two or more substituents independently selected from the group consisting of $R^7$, $OR^7$, $C(O)OR^7$, $N(R^7)_2$, $NH_2$, CN, F, Cl, and Br;
- $R^2$ is independently selected from the group consisting of $R^8$ and $C(O)OR^8$;
- n is 0 or 1;
- $R^3$ is selected from the group consisting of $C_1$-$C_6$ alkyl, 6-10 membered aryl, 5-11 membered heteroaryl, $C_3$-$C_{11}$ cycloalkyl, and 4-12 membered heterocyclyl; wherein the $R^3$ $C_1$-$C_6$ alkyl is optionally substituted with one or more substituents independently selected from the group consisting of phenyl, F, and Cl; wherein the $R^3$ 6-10 membered aryl, 5-11 membered heteroaryl, $C_3$-$C_{11}$ cycloalkyl, and 4-12 membered heterocyclyl are optionally substituted with one or more substituents independently selected from the group consisting of $R^9$, $OR^9$, $C(O)R^9$, $C(O)OR^9$, $SO_2R^9$, $NHR^9$, $N(R^9)_2$, $NH_2$, $C(O)OH$, OH, oxo, CN, $NO_2$, Cl, and Br;
- $R^4$ is selected from the group consisting of hydrogen and $C_1$-$C_6$ alkyl;
- $R^7$, at each occurrence, is independently selected from the group consisting of $C_1$-$C_6$ alkyl, 5-11 membered heteroaryl, $C_3$-$C_{11}$ cycloalkyl, and 4-12 membered heterocyclyl; wherein each $R^7$ $C_1$-$C_6$ alkyl is optionally substituted with one or more substituents independently selected from the group consisting of $C_1$-$C_6$ alkoxy, $C_3$-$C_7$ cycloalkyl, OH and F; wherein each $R^7$ 5-11 membered heteroaryl, $C_3$-$C_{11}$ cycloalkyl and 4-12 membered heterocyclyl is optionally substituted with one or more substituents independently selected from the group consisting of $R^{11}$, $OR^{11}$, $NHR^{11}$, and $C(O)OR^{11}$; $R^8$ is independently $C_1$-$C_6$ alkyl;
- $R^9$, at each occurrence, is independently selected from the group consisting of $C_1$-$C_6$ alkyl, 5-11 membered heteroaryl, and 4-12 membered heterocyclyl; wherein each $R^9$ $C_1$-$C_6$ alkyl, is optionally substituted with one or more substituents independently selected from the group consisting of $R^{11}$ and F; wherein each $R^9$ 5-11 membered heteroaryl, and 4-12 membered heterocyclyl is optionally substituted with one oxo;
  - $R^{11}$, at each occurrence, is independently $C_1$-$C_6$ alkyl; wherein each $R^{11}$ $C_1$-$C_6$ alkyl is optionally substituted with one $C_1$-$C_6$ alkoxy; and
  - $R^{13}$, at each occurrence, is independently $C_6$-$C_{10}$ membered aryl.

Exemplary compounds of Formula (III) include, but are not limited to:
1-(5-bromo-2-methoxyphenyl)-N-(1,2,3,4-tetrahydroquinoline-5-sulfonyl)cyclobutane-1-carboxamide;
1-(5-cyclobutyl-2-methoxyphenyl)-N-(1,2,3,4-tetrahydroquinoline-5-sulfonyl)cyclobutane-1-carboxamide;
1-(5-cyclobutyl-2-methoxyphenyl)-N-(pyrazolo[1,5-a]pyridine-4-sulfonyl)cyclobutane-1-carboxamide;
1-(5-cyclobutyl-2-methoxyphenyl)-N-(1-methyl-1H-benzimidazole-7-sulfonyl)cyclobutane-1-carboxamide;
1-(5-cyclobutyl-2-methoxyphenyl)-N-(1-methyl-1H-indazole-7-sulfonyl)cyclobutane-1-carboxamide;
1-(5-cyclobutyl-2-methoxyphenyl)-N-(1H-indazole-4-sulfonyl)cyclobutane-1-carboxamide;
1-(5-cyclopropyl-2-methoxyphenyl)-N-(1,2,3,4-tetrahydroquinoline-5-sulfonyl)cyclobutane-1-carboxamide;
1-(5-cyclobutyl-2-methoxyphenyl)-N-(2-methylquinoline-5-sulfonyl)cyclobutane-1-carboxamide;
1-[2-methoxy-5-(propan-2-yl)phenyl]-N-(1,2,3,4-tetrahydroquinoline-5-sulfonyl)cyclobutane-1-carboxamide;
1-(5-cyclopentyl-2-methoxyphenyl)-N-(1,2,3,4-tetrahydroquinoline-5-sulfonyl)cyclobutane-1-carboxamide;
1-[5-(butan-2-yl)-2-methoxyphenyl]-N-(1,2,3,4-tetrahydroquinoline-5-sulfonyl)cyclobutane-1-carboxamide;
1-(5-bromo-2-methoxyphenyl)-N-(2-methylquinoline-5-sulfonyl)cyclobutane-1-carboxamide;
1-(3,4-dimethoxyphenyl)-N-(naphthalene-1-sulfonyl)cyclobutane-1-carboxamide; and
pharmaceutically acceptable salts thereof.

One embodiment pertains to:
1-(5-bromo-2-methoxyphenyl)-N-(naphthalene-1-sulfonyl)cyclopropane-1-carboxamide;
1-(5-cyclobutyl-2-methoxyphenyl)-N-(naphthalene-1-sulfonyl)cyclopropane-1-carboxamide;
1-(5-cyclobutyl-2-methoxypyridin-3-yl)-N-(2-methylquinoline-5-sulfonyl)cyclopropane-1-carboxamide;
1-(5-cyclobutyl-2-methoxypyridin-3-yl)-N-(quinoline-5-sulfonyl)cyclopropane-1-carboxamide;
1-(5-cyclobutyl-2-methoxypyridin-3-yl)-N-(naphthalene-1-sulfonyl)cyclopropane-1-carboxamide;
1-(5-cyclobutyl-2-methoxypyridin-3-yl)-N-(1,2,3,4-tetrahydroquinoline-5-sulfonyl)cyclopropane-1-carboxamide;
1-(2,6-dimethoxyphenyl)-N-(naphthalene-1-sulfonyl)cyclopropane-1-carboxamide;
1-[2-methoxy-5-(trifluoromethyl)pyridin-3-yl]-N-(naphthalene-1-sulfonyl)cyclopropane-1-carboxamide;
1-(5-bromo-2-methoxyphenyl)-N-(1,2,3,4-tetrahydroquinoline-5-sulfonyl)cyclobutane-1-carboxamide;
1-(5-cyclobutyl-2-methoxyphenyl)-N-(1,2,3,4-tetrahydroquinoline-5-sulfonyl)cyclobutane-1-carboxamide;
1-(5-bromo-2-methoxyphenyl)-N-(1,2,3,4-tetrahydroquinoline-5-sulfonyl)cyclopropane-1-carboxamide;
1-(5-cyclopropyl-2-methoxyphenyl)-N-(naphthalene-1-sulfonyl)cyclopropane-1-carboxamide;
1-(5-cyclopropyl-2-methoxyphenyl)-N-(quinoline-5-sulfonyl)cyclopropane-1-carboxamide;
1-{2-methoxy-5-[(propan-2-yl)oxy]phenyl}-N-(quinoline-5-sulfonyl)cyclopropane-1-carboxamide;
1-(2-methoxy-5-methylpyridin-3-yl)-N-(naphthalene-1-sulfonyl)cyclopropane-1-carboxamide;
1-(5-cyclobutyl-2-methoxyphenyl)-N-(1,2,3,4-tetrahydroquinoline-5-sulfonyl)cyclopropane-1-carboxamide;
1-(5-cyclobutyl-2-methoxyphenyl)-N-(quinoline-5-sulfonyl)cyclopropane-1-carboxamide;
1-(5-bromo-2-methoxyphenyl)-N-(quinoline-5-sulfonyl)cyclopropane-1-carboxamide;
1-(5-cyclobutyl-2-methoxypyridin-3-yl)-N-(pyrazolo[1,5-a]pyridine-4-sulfonyl)cyclopropane-1-carboxamide;
1-(5-cyclobutyl-2-methoxypyridin-3-yl)-N-(1-methyl-1H-indole-7-sulfonyl)cyclopropane-1-carboxamide;
1-(5-cyclobutyl-2-methoxypyridin-3-yl)-N-(1H-indole-4-sulfonyl)cyclopropane-1-carboxamide;
N-(1H-indole-4-sulfonyl)-1-[2-methoxy-5-(trifluoromethyl)pyridin-3-yl]cyclopropane-1-carboxamide;
1-(5-cyclobutyl-2-methoxyphenyl)-N-(pyrazolo[1,5-a]pyridine-4-sulfonyl)cyclobutane-1-carboxamide;
1-(5-cyclobutyl-2-methoxyphenyl)-N-(1-methyl-1H-benzimidazole-7-sulfonyl)cyclobutane-1-carboxamide;

1-(5-cyclobutyl-2-methoxyphenyl)-N-(1-methyl-1H-indazole-7-sulfonyl)cyclobutane-1-carboxamide;
1-(5-cyclobutyl-2-methoxyphenyl)-N-(1H-indazole-4-sulfonyl)cyclobutane-1-carboxamide;
1-(5-cyclopropyl-2-methoxyphenyl)-N-(1,2,3,4-tetrahydroquinoline-5-sulfonyl)cyclobutane-1-carboxamide;
1-(2,5-dimethoxyphenyl)-N-(naphthalene-1-sulfonyl)cyclopropane-1-carboxamide;
1-(2,5-dimethoxyphenyl)-N-(quinoline-5-sulfonyl)cyclopropane-1-carboxamide;
1-[2-(dimethylamino)-5-(trifluoromethyl)pyridin-3-yl]-N-(naphthalene-1-sulfonyl)cyclopropane-1-carboxamide;
1-(5-ethoxy-2-methoxyphenyl)-N-(quinoline-5-sulfonyl)cyclopropane-1-carboxamide;
1-[5-(cyclobutyloxy)-2-methoxyphenyl]-N-(quinoline-5-sulfonyl)cyclopropane-1-carboxamide;
1-(5-cyclobutyl-2-methoxyphenyl)-N-(2-methylquinoline-5-sulfonyl)cyclobutane-1-carboxamide;
1-(5-tert-butyl-2-methoxyphenyl)-N-(quinoline-5-sulfonyl)cyclopropane-1-carboxamide;
1-[2-methoxy-5-(propan-2-yl)phenyl]-N-(quinoline-5-sulfonyl)cyclopropane-1-carboxamide;
1-[4-fluoro-2-methoxy-5-(propan-2-yl)phenyl]-N-(quinoline-5-sulfonyl)cyclopropane-1-carboxamide;
1-[2-methoxy-5-(trifluoromethyl)phenyl]-N-(quinoline-5-sulfonyl)cyclopropane-1-carboxamide;
1-[5-(bicyclo[1.1.1]pentan-1-yl)-2-methoxyphenyl]-N-(quinoline-5-sulfonyl)cyclopropane-1-carboxamide;
1-(5-tert-butyl-2-methoxyphenyl)-N-(1,2,3,4-tetrahydroquinoline-5-sulfonyl)cyclopropane-1-carboxamide;
1-(2,6-dimethoxy-3-methylphenyl)-N-(naphthalene-1-sulfonyl)cyclopropane-1-carboxamide;
1-(2,6-dimethoxy-3-methylphenyl)-N-(quinoline-5-sulfonyl)cyclopropane-1-carboxamide;
1-(2,6-dimethoxy-3-methylphenyl)-N-(1H-indole-4-sulfonyl)cyclopropane-1-carboxamide;
1-(2,6-dimethoxy-3-methylphenyl)-N-(2-methylquinoline-5-sulfonyl)cyclopropane-1-carboxamide;
1-(2-methoxy-5-methylphenyl)-N-(quinoline-5-sulfonyl)cyclopropane-1-carboxamide;
1-(2-ethoxy-6-methoxyphenyl)-N-(quinoline-5-sulfonyl)cyclopropane-1-carboxamide;
1-[2-(cyclopropylmethoxy)-6-methoxyphenyl]-N-(quinoline-5-sulfonyl)cyclopropane-1-carboxamide;
1-(6-methoxy-2,3-dimethylphenyl)-N-(quinoline-5-sulfonyl)cyclopropane-1-carboxamide;
1-(3-cyclopropyl-6-methoxy-2-methylphenyl)-N-(quinoline-5-sulfonyl)cyclopropane-1-carboxamide;
N-(1H-indole-4-sulfonyl)-1-(2-methoxy-5-methylphenyl)cyclopropane-1-carboxamide;
1-[2-methoxy-6-(propan-2-yl)phenyl]-N-(quinoline-5-sulfonyl)cyclopropane-1-carboxamide;
1-(2-cyclobutyl-6-methoxyphenyl)-N-(quinoline-5-sulfonyl)cyclopropane-1-carboxamide;
1-[2-methoxy-5-(2-methoxypropan-2-yl)phenyl]-N-(quinoline-5-sulfonyl)cyclopropane-1-carboxamide;
N-(1H-indazole-4-sulfonyl)-1-(2-methoxy-5-methylphenyl)cyclopropane-1-carboxamide;
1-(5-cyclobutyl-2-methoxyphenyl)-N-(2,3-dihydro-1H-indole-4-sulfonyl)cyclopropane-1-carboxamide;
1-(5-cyclobutyl-2-methoxyphenyl)-N-(1H-indole-4-sulfonyl)cyclopropane-1-carboxamide;
1-(5-cyclobutyl-2-methoxyphenyl)-N-(1H-indazole-4-sulfonyl)cyclopropane-1-carboxamide;
1-[2-(dimethylamino)-5-(trifluoromethyl)pyridin-3-yl]-N-(quinoline-5-sulfonyl)cyclopropane-1-carboxamide;
1-(5-cyclobutyl-2-methoxyphenyl)-N-(1-methyl-1H-indole-4-sulfonyl)cyclopropane-1-carboxamide;
1-(5-cyclobutyl-2-methoxyphenyl)-N-(1-methyl-1H-indole-7-sulfonyl)cyclopropane-1-carboxamide;
1-(5-cyclobutyl-2-methoxyphenyl)-N-(1-methyl-1H-indazole-7-sulfonyl)cyclopropane-1-carboxamide;
1-(5-cyclobutyl-2-methoxyphenyl)-N-(pyrazolo[1,5-a]pyridine-4-sulfonyl)cyclopropane-1-carboxamide;
1-(5-cyclobutyl-2-methoxyphenyl)-N-(2-methylquinoline-8-sulfonyl)cyclopropane-1-carboxamide;
1-(5-cyclobutyl-2-methoxyphenyl)-N-(2-methylquinoline-5-sulfonyl)cyclopropane-1-carboxamide;
1-(2-methoxy-5-methylphenyl)-N-(2-methylquinoline-5-sulfonyl)cyclopropane-1-carboxamide;
1-[5-(difluoromethoxy)-2-methoxyphenyl]-N-(quinoline-5-sulfonyl)cyclopropane-1-carboxamide;
1-(2,6-diethoxyphenyl)-N-(quinoline-5-sulfonyl)cyclopropane-1-carboxamide;
N-(2-aminoquinoline-5-sulfonyl)-1-(5-cyclobutyl-2-methoxyphenyl)cyclopropane-1-carboxamide;
1-(5-cyclopropyl-2-methoxyphenyl)-N-(2-methylquinoline-5-sulfonyl)cyclopropane-1-carboxamide;
1-(5-ethoxy-2-methoxyphenyl)-N-(2-methylquinoline-5-sulfonyl)cyclopropane-1-carboxamide;
1-(5-tert-butyl-2-methoxyphenyl)-N-(2-methylquinoline-5-sulfonyl)cyclopropane-1-carboxamide;
1-[2-methoxy-5-(propan-2-yl)phenyl]-N-(2-methylquinoline-5-sulfonyl)cyclopropane-1-carboxamide;
1-[2-(dimethylamino)-5-(trifluoromethyl)pyridin-3-yl]-N-(2-methylquinoline-5-sulfonyl)cyclopropane-1-carboxamide;
1-{2-methoxy-5-[1-(methoxymethyl)cyclopropyl]phenyl}-N-(quinoline-5-sulfonyl)cyclopropane-1-carboxamide;
1-{2-methoxy-5-[1-(methoxymethyl)cyclopropyl]phenyl}-N-(2-methylquinoline-5-sulfonyl)cyclopropane-1-carboxamide;
1-(2-methoxyquinolin-3-yl)-N-(2-methylquinoline-5-sulfonyl)cyclopropane-1-carboxamide;
1-(2-methoxyquinolin-3-yl)-N-(quinoline-5-sulfonyl)cyclopropane-1-carboxamide;
1-{5-methyl-2-[(propan-2-yl)oxy]phenyl}-N-(quinoline-5-sulfonyl)cyclopropane-1-carboxamide;
1-{5-methyl-2-[(propan-2-yl)oxy]phenyl}-N-(2-methylquinoline-5-sulfonyl)cyclopropane-1-carboxamide;
N-(2-aminoquinoline-5-sulfonyl)-1-(2-methoxy-5-methylphenyl)cyclopropane-1-carboxamide;
1-(4-cyclobutyl-2,6-dimethoxyphenyl)-N-(quinoline-5-sulfonyl)cyclopropane-1-carboxamide;
N-(2-aminoquinoline-5-sulfonyl)-1-(2,5-dimethylphenyl)cyclopropane-1-carboxamide;
1-(2-ethoxy-5-methylphenyl)-N-(quinoline-5-sulfonyl)cyclopropane-1-carboxamide;
1-(2-ethoxy-5-methylphenyl)-N-(2-methylquinoline-5-sulfonyl)cyclopropane-1-carboxamide;
1-(5-ethyl-2-methoxyphenyl)-N-(2-methylquinoline-5-sulfonyl)cyclopropane-1-carboxamide;
1-{2-methoxy-5-[1-(methylamino)cyclopropyl]phenyl}-N-(quinoline-5-sulfonyl)cyclopropane-1-carboxamide;
1-(4-cyclobutyl-2,6-dimethoxyphenyl)-N-(1H-indole-4-sulfonyl)cyclopropane-1-carboxamide;
N-(2-aminoquinoline-5-sulfonyl)-1-{5-methyl-2-[(propan-2-yl)oxy]phenyl}cyclopropane-1-carboxamide;
1-[2-methoxy-5-(1-methoxycyclobutyl)phenyl]-N-(quinoline-5-sulfonyl)cyclopropane-1-carboxamide;
N-(2-aminoquinoline-5-sulfonyl)-1-(2-ethoxy-5-methylphenyl)cyclopropane-1-carboxamide;

1-[2-methoxy-5-(oxetan-3-yl)phenyl]-N-(quinoline-5-sulfonyl)cyclopropane-1-carboxamide;
1-(2-ethoxy-5-methylphenyl)-N-(2-methyl-1H-indole-4-sulfonyl)cyclopropane-1-carboxamide;
N-(2-aminoquinoline-5-sulfonyl)-1-[2-methoxy-5-(2-methylpropoxy)pyridin-4-yl]cyclopropane-1-carboxamide;
1-{5-methyl-2-[(oxetan-3-yl)oxy]phenyl}-N-(quinoline-5-sulfonyl)cyclopropane-1-carboxamide;
1-[5-ethyl-2-(2-methylpropoxy)pyridin-3-yl]-N-(1H-indazole-4-sulfonyl)cyclopropane-1-carboxamide;
1-(2-{[(2R)-1-methoxypropan-2-yl]oxy}-5-methylphenyl)-N-(quinoline-5-sulfonyl)cyclopropane-1-carboxamide;
N-(2-aminoquinoline-5-sulfonyl)-1-[5-methyl-2-(2-methylpropoxy)pyridin-3-yl]cyclopropane-1-carboxamide;
N-(2-aminoquinoline-5-sulfonyl)-1-{5-methyl-2-[(propan-2-yl)oxy]pyridin-3-yl}cyclopropane-1-carboxamide;
N-(2-aminoquinoline-5-sulfonyl)-1-[5-ethyl-2-(2-methylpropoxy)pyridin-3-yl]cyclopropane-1-carboxamide;
1-[2-ethoxy-5-(2-ethoxypropan-2-yl)phenyl]-N-(quinoline-5-sulfonyl)cyclopropane-1-carboxamide;
1-[2-(difluoromethoxy)-5-methylphenyl]-N-(quinoline-5-sulfonyl)cyclopropane-1-carboxamide;
1-[2-ethoxy-5-(1-methoxy-2-methylpropan-2-yl)phenyl]-N-(quinoline-5-sulfonyl)cyclopropane-1-carboxamide;
1-[2-ethoxy-5-(1-methoxycyclobutyl)phenyl]-N-(quinoline-5-sulfonyl)cyclopropane-1-carboxamide;
1-[2-ethoxy-5-(2-ethoxypropan-2-yl)phenyl]-N-(2-methylquinoline-5-sulfonyl)cyclopropane-1-carboxamide;
1-[2-ethoxy-5-(2-methoxypropan-2-yl)phenyl]-N-(2-methylquinoline-5-sulfonyl)cyclopropane-1-carboxamide;
1-[2-ethoxy-5-(1-methoxycyclobutyl)phenyl]-N-(2-methylquinoline-5-sulfonyl)cyclopropane-1-carboxamide;
1-{5-methyl-2-[(oxetan-3-yl)oxy]phenyl}-N-(2-methylquinoline-5-sulfonyl)cyclopropane-1-carboxamide;
1-(2-{[(2R)-1-methoxypropan-2-yl]oxy}-5-methylphenyl)-N-(2-methylquinoline-5-sulfonyl)cyclopropane-1-carboxamide;
1-[3-(dimethylamino)-6-(2-methylpropoxy)pyridin-2-yl]-N-(quinoline-5-sulfonyl)cyclopropane-1-carboxamide;
1-[5-(dimethylamino)-2-(2-methylpropoxy)pyridin-3-yl]-N-(2-methylquinoline-5-sulfonyl)cyclopropane-1-carboxamide;
1-[2-methoxy-5-(1-methoxy-2-methylpropan-2-yl)phenyl]-N-(quinoline-5-sulfonyl)cyclopropane-1-carboxamide;
1-(5-ethyl-2-{[(2R)-1-methoxypropan-2-yl]oxy}phenyl)-N-(quinoline-5-sulfonyl)cyclopropane-1-carboxamide;
1-(5-ethyl-2-{[(2R)-1-methoxypropan-2-yl]oxy}phenyl)-N-(2-methylquinoline-5-sulfonyl)cyclopropane-1-carboxamide;
1-{2-[(2S)-2-methoxypropoxy]-5-methylphenyl}-N-(quinoline-5-sulfonyl)cyclopropane-1-carboxamide;
1-{2-[(2S)-2-methoxypropoxy]-5-methylphenyl}-N-(2-methylquinoline-5-sulfonyl)cyclopropane-1-carboxamide;
1-{2-[(2R)-2-methoxypropoxy]-5-methylphenyl}-N-(quinoline-5-sulfonyl)cyclopropane-1-carboxamide;
1-{2-[(2R)-2-methoxypropoxy]-5-methylphenyl}-N-(2-methylquinoline-5-sulfonyl)cyclopropane-1-carboxamide;
1-(5-ethyl-2-{[(3S)-oxolan-3-yl]oxy}phenyl)-N-(quinoline-5-sulfonyl)cyclopropane-1-carboxamide;
1-(5-ethyl-2-{[(3R)-oxolan-3-yl]oxy}phenyl)-N-(quinoline-5-sulfonyl)cyclopropane-1-carboxamide;
1-(5-ethyl-2-{[(3R)-oxolan-3-yl]oxy}phenyl)-N-(2-methylquinoline-5-sulfonyl)cyclopropane-1-carboxamide;
1-(5-methyl-2-{[(3R)-oxolan-3-yl]oxy}phenyl)-N-(quinoline-5-sulfonyl)cyclopropane-1-carboxamide;
1-(5-methyl-2-{[(3R)-oxolan-3-yl]oxy}phenyl)-N-(2-methylquinoline-5-sulfonyl)cyclopropane-1-carboxamide;
1-(5-methyl-2-{[(3S)-oxolan-3-yl]oxy}phenyl)-N-(2-methylquinoline-5-sulfonyl)cyclopropane-1-carboxamide;
1-(3-methoxyphenyl)-N-(naphthalene-1-sulfonyl)cyclopropane-1-carboxamide;
1-(3-methoxy-4-methylphenyl)-N-(naphthalene-1-sulfonyl)cyclopropane-1-carboxamide;
N-(quinoline-5-sulfonyl)-1-[2-(trifluoromethoxy)phenyl]cyclobutane-1-carboxamide;
1-(1-ethyl-3-methyl-1H-pyrazol-5-yl)-N-(naphthalene-1-sulfonyl)cyclopropane-1-carboxamide;
1-(1-ethyl-5-methyl-1H-pyrazol-3-yl)-N-(naphthalene-1-sulfonyl)cyclopropane-1-carboxamide;
1-(2-methoxyphenyl)-N-(quinoline-5-sulfonyl)cyclobutane-1-carboxamide;
1-[2-methoxy-5-(trifluoromethyl)pyridin-3-yl]-N-(quinoline-5-sulfonyl)cyclopropane-1-carboxamide;
1-[2-methoxy-5-(trifluoromethyl)pyridin-3-yl]-N-(1,2,3,4-tetrahydroquinoline-5-sulfonyl)cyclopropane-1-carboxamide;
1-[2-methoxy-5-(trifluoromethyl)pyridin-3-yl]-N-(2-methylquinoline-5-sulfonyl)cyclopropane-1-carboxamide;
1-(2-methoxy-5-methylpyridin-3-yl)-N-(1,2,3,4-tetrahydroquinoline-5-sulfonyl)cyclopropane-1-carboxamide;
1-(2-methoxyphenyl)-N-(1,2,3,4-tetrahydroquinoline-5-sulfonyl)cyclopropane-1-carboxamide;
1-(5-cyclobutyl-2-methoxypyridin-3-yl)-N-(1-methyl-1H-benzimidazole-7-sulfonyl)cyclopropane-1-carboxamide;
1-(5-cyclobutyl-2-methoxypyridin-3-yl)-N-(1-methyl-1H-indazole-7-sulfonyl)cyclopropane-1-carboxamide;
1-(5-cyclobutyl-2-methoxypyridin-3-yl)-N-(1-methyl-1H-indole-4-sulfonyl)cyclopropane-1-carboxamide;
1-(5-cyclobutyl-2-methoxypyridin-3-yl)-N-(1H-indazole-4-sulfonyl)cyclopropane-1-carboxamide;
1-(5-cyclobutyl-2-methoxypyridin-3-yl)-N-(3-methylimidazo[1,2-a]pyridine-5-sulfonyl)cyclopropane-1-carboxamide;
1-[2-methoxy-5-(trifluoromethyl)pyridin-3-yl]-N-(1-methyl-1H-indole-7-sulfonyl)cyclopropane-1-carboxamide;
1-[2-methoxy-5-(trifluoromethyl)pyridin-3-yl]-N-(1-methyl-1H-indole-4-sulfonyl)cyclopropane-1-carboxamide;
1-[2-methoxy-5-(trifluoromethyl)pyridin-3-yl]-N-(3-methylimidazo[1,2-a]pyridine-5-sulfonyl)cyclopropane-1-carboxamide;
1-[2-methoxy-5-(propan-2-yl)phenyl]-N-(1,2,3,4-tetrahydroquinoline-5-sulfonyl)cyclobutane-1-carboxamide;
1-(5-cyclopentyl-2-methoxyphenyl)-N-(1,2,3,4-tetrahydroquinoline-5-sulfonyl)cyclobutane-1-carboxamide;
1-[5-(butan-2-yl)-2-methoxyphenyl]-N-(1,2,3,4-tetrahydroquinoline-5-sulfonyl)cyclobutane-1-carboxamide;
1-{2-methoxy-5-[(oxolan-3-yl)oxy]phenyl}-N-(quinoline-5-sulfonyl)cyclopropane-1-carboxamide;
1-[2-chloro-5-(trifluoromethoxy)phenyl]-N-(quinoline-5-sulfonyl)cyclopropane-1-carboxamide;
1-[2-chloro-5-(trifluoromethoxy)phenyl]-N-(1,2,3,4-tetrahydroquinoline-5-sulfonyl)cyclopropane-1-carboxamide;
1-[2-methoxy-5-(propan-2-yl)phenyl]-N-(1,2,3,4-tetrahydroquinoline-5-sulfonyl)cyclopropane-1-carboxamide;
1-[4-fluoro-2-methoxy-5-(propan-2-yl)phenyl]-N-(1,2,3,4-tetrahydroquinoline-5-sulfonyl)cyclopropane-1-carboxamide;
1-[2-methoxy-5-(trifluoromethyl)phenyl]-N-(1,2,3,4-tetrahydroquinoline-5-sulfonyl)cyclopropane-1-carboxamide;

1-(5-bromo-2-methoxyphenyl)-N-(2-methylquinoline-5-sulfonyl)cyclobutane-1-carboxamide;
methyl 1-(4-methoxy-3-{1[(quinoline-5-sulfonyl)carbamoyl]cyclopropyl}phenyl)cyclopropane-1-carboxylate;
methyl 4-methoxy-3-{1-[(quinoline-5-sulfonyl)carbamoyl]cyclopropyl}benzoate;
methyl 4-methoxy-3-{1-[(naphthalene-1-sulfonyl)carbamoyl]cyclopropyl}benzoate;
1-(5-cyclobutyl-2-methoxy-4-methylpyridin-3-yl)-N-(2-methylquinoline-5-sulfonyl)cyclopropane-1-carboxamide;
1-(5-bromo-2-methoxyphenyl)-N-(1-methyl-2,3-dihydro-1H-indole-4-sulfonyl)cyclopropane-1-carboxamide;
1-(2-methoxy-6-methylphenyl)-N-(quinoline-5-sulfonyl)cyclopropane-1-carboxamide;
1-(6-methoxy-2,3-dimethylphenyl)-N-(1,2,3,4-tetrahydroquinoline-5-sulfonyl)cyclopropane-1-carboxamide;
1-(3-cyclopropyl-6-methoxy-2-methylphenyl)-N-(1,2,3,4-tetrahydroquinoline-5-sulfonyl)cyclopropane-1-carboxamide;
1-(5-cyclobutyl-2-methoxy-4-methylpyridin-3-yl)-N-(1,2,3,4-tetrahydroquinoline-5-sulfonyl)cyclopropane-1-carboxamide;
1-(2,6-dimethoxy-3-methylphenyl)-N-(2-methylquinoline-8-sulfonyl)cyclopropane-1-carboxamide;
1-(5-cyclobutyl-2-methoxyphenyl)-N-(1-methyl-2,3-dihydro-1H-indole-4-sulfonyl)cyclopropane-1-carboxamide;
1-(5-cyclobutyl-2-methoxy-4-methylpyridin-3-yl)-N-(1-methyl-1H-indole-4-sulfonyl)cyclopropane-1-carboxamide;
1-(5-cyclobutyl-2-methoxy-4-methylpyridin-3-yl)-N-(1-methyl-1H-indole-7-sulfonyl)cyclopropane-1-carboxamide;
1-(5-cyclobutyl-2-methoxy-4-methylpyridin-3-yl)-N-(1-methyl-1H-indazole-7-sulfonyl)cyclopropane-1-carboxamide;
1-(5-cyclobutyl-2-methoxy-4-methylpyridin-3-yl)-N-(2-methylquinoline-8-sulfonyl)cyclopropane-1-carboxamide;
1-(2-methoxy-6-methylphenyl)-N-(2-methylquinoline-8-sulfonyl)cyclopropane-1-carboxamide;
1-(2-cyclobutyl-5-methoxyphenyl)-N-(quinoline-5-sulfonyl)cyclopropane-1-carboxamide;
1-(2-cyclobutyl-5-methoxyphenyl)-N-(2-methylquinoline-5-sulfonyl)cyclopropane-1-carboxamide;
1-[5-(hydroxymethyl)-2-methoxyphenyl]-N-(quinoline-5-sulfonyl)cyclopropane-1-carboxamide;
1-[2-methoxy-5-(methoxymethyl)phenyl]-N-(quinoline-5-sulfonyl)cyclopropane-1-carboxamide;
1-(2-methoxy-6-methylphenyl)-N-(2-methylquinoline-5-sulfonyl)cyclopropane-1-carboxamide;
1-(6-methoxy-2,3-dimethylphenyl)-N-(2-methylquinoline-5-sulfonyl)cyclopropane-1-carboxamide;
1-(3-cyclopropyl-6-methoxy-2-methylphenyl)-N-(2-methylquinoline-5-sulfonyl)cyclopropane-1-carboxamide;
1-(2-methoxy-6-methylphenyl)-N-(1,2,3,4-tetrahydroquinoline-5-sulfonyl)cyclopropane-1-carboxamide;
1-(3-chloro-2,6-dimethoxyphenyl)-N-(quinoline-5-sulfonyl)cyclopropane-1-carboxamide;
1-(5-methoxy-2-methylphenyl)-N-(quinoline-5-sulfonyl)cyclopropane-1-carboxamide;
1-(3-methoxyphenyl)-N-(quinoline-5-sulfonyl)cyclopropane-1-carboxamide;
1-(2-cyclopropyl-6-methoxyphenyl)-N-(quinoline-5-sulfonyl)cyclopropane-1-carboxamide;
1-[5-methoxy-2-(propan-2-yl)phenyl]-N-(quinoline-5-sulfonyl)cyclopropane-1-carboxamide;
1-(5-methoxy-2-propylphenyl)-N-(quinoline-5-sulfonyl)cyclopropane-1-carboxamide;
1-(2-cyclopropyl-6-methoxyphenyl)-N-(2-methylquinoline-5-sulfonyl)cyclopropane-1-carboxamide;
1-(2,5-dimethylphenyl)-N-(quinoline-5-sulfonyl)cyclopropane-1-carboxamide;
1-(5-ethyl-2-methoxyphenyl)-N-(quinoline-5-sulfonyl)cyclopropane-1-carboxamide;
1-(2-methoxy-4-methylphenyl)-N-(quinoline-5-sulfonyl)cyclopropane-1-carboxamide;
1-(2-methoxy-3-methylphenyl)-N-(quinoline-5-sulfonyl)cyclopropane-1-carboxamide;
1-(4-cyclobutyl-2,6-dimethoxyphenyl)-N-(1-methyl-1H-indole-4-sulfonyl)cyclopropane-1-carboxamide;
1-(4-cyclobutyl-2,6-dimethoxyphenyl)-N-(1-methyl-1H-indole-7-sulfonyl)cyclopropane-1-carboxamide;
1-(4-cyclobutyl-2,6-dimethoxyphenyl)-N-(1-methyl-1H-indazole-7-sulfonyl)cyclopropane-1-carboxamide;
1-(4-cyclobutyl-2,6-dimethoxyphenyl)-N-(pyrazolo[1,5-a]pyridine-4-sulfonyl)cyclopropane-1-carboxamide;
1-(4-cyclobutyl-2,6-dimethoxyphenyl)-N-(2-methylquinoline-5-sulfonyl)cyclopropane-1-carboxamide;
N-(2-aminoquinoline-5-sulfonyl)-1-(4-cyclobutyl-2,6-dimethoxyphenyl)cyclopropane-1-carboxamide;
N-(2-aminoquinoline-5-sulfonyl)-1-(5-ethyl-2-methoxyphenyl)cyclopropane-1-carboxamide;
1-(5-ethyl-2-methoxyphenyl)-N-(1H-indazole-4-sulfonyl)cyclopropane-1-carboxamide;
1-(2-ethyl-6-methoxyphenyl)-N-(quinoline-5-sulfonyl)cyclopropane-1-carboxamide;
1-(2-ethoxy-5-methylphenyl)-N-(1H-indazole-4-sulfonyl)cyclopropane-1-carboxamide;
N-(1H-indazole-4-sulfonyl)-1-{5-methyl-2-[(propan-2-yl)oxy]phenyl}cyclopropane-1-carboxamide;
1-(4-cyclobutyl-2,6-dimethoxyphenyl)-N-(1H-indazole-4-sulfonyl)cyclopropane-1-carboxamide;
N-(1H-indazole-4-sulfonyl)-1-(6-methoxy-2,3-dimethylphenyl)cyclopropane-1-carboxamide;
1-(3-cyclopropyl-6-methoxy-2-methylphenyl)-N-(1H-indazole-4-sulfonyl)cyclopropane-1-carboxamide;
N-(1H-indole-4-sulfonyl)-1-{5-methyl-2-[(propan-2-yl)oxy]phenyl}cyclopropane-1-carboxamide;
1-(2,5-dimethylphenyl)-N-(1H-indole-4-sulfonyl)cyclopropane-1-carboxamide;
1-(2-cyclopropyl-6-methoxyphenyl)-N-(1H-indazole-4-sulfonyl)cyclopropane-1-carboxamide;
N-(2-aminoquinoline-5-sulfonyl)-1-{2-methoxy-5-[1-(methoxymethyl)cyclopropyl]phenyl}cyclopropane-1-carboxamide;
1-(2-ethoxy-5-methylphenyl)-N-(2-methoxyquinoline-5-sulfonyl)cyclopropane-1-carboxamide;
1-(2-ethoxy-5-methylphenyl)-N-[2-(methylamino)quinoline-5-sulfonyl]cyclopropane-1-carboxamide;
1-(2-ethoxy-5-methylphenyl)-N-(1H-indole-4-sulfonyl)cyclopropane-1-carboxamide;
1-[2-methoxy-5-(2,2,2-trifluoro-1-methoxyethyl)phenyl]-N-(quinoline-5-sulfonyl)cyclopropane-1-carboxamide;
1-[2-methoxy-5-(1-methoxyethyl)phenyl]-N-(quinoline-5-sulfonyl)cyclopropane-1-carboxamide;
N-(1H-indole-4-sulfonyl)-1-[2-methoxy-5-(2-methoxypropan-2-yl)phenyl]cyclopropane-1-carboxamide;
1-[2-methoxy-5-(3-methyloxetan-3-yl)phenyl]-N-(quinoline-5-sulfonyl)cyclopropane-1-carboxamide;
N-(2-aminoquinoline-5-sulfonyl)-1-{5-methyl-2-[(oxetan-3-yl)oxy]phenyl}cyclopropane-1-carboxamide;

N-(1H-indazole-4-sulfonyl)-1-[2-methoxy-5-(2-methylpropoxy)pyridin-4-yl]cyclopropane-1-carboxamide;
1-(2-{[(2S)-1-methoxypropan-2-yl]oxy}-5-methylphenyl)-N-(quinoline-5-sulfonyl)cyclopropane-1-carboxamide;
1-[5-cyclopropyl-2-(2-methylpropoxy)pyridin-3-yl]-N-(2-methoxyquinoline-5-sulfonyl)cyclopropane-1-carboxamide;
1-[5-cyclobutyl-2-(2-methylpropoxy)pyridin-3-yl]-N-(2-methoxyquinoline-5-sulfonyl)cyclopropane-1-carboxamide;
1-{5-cyclopropyl-2-[(propan-2-yl)oxy]pyridin-3-yl}-N-(2-methoxyquinoline-5-sulfonyl)cyclopropane-1-carboxamide;
1-[5-(2-ethoxypropan-2-yl)-2-methoxyphenyl]-N-(quinoline-5-sulfonyl)cyclopropane-1-carboxamide;
1-[2-ethoxy-5-(2-methoxypropan-2-yl)phenyl]-N-(quinoline-5-sulfonyl)cyclopropane-1-carboxamide;
1-[2-(difluoromethoxy)-5-ethylphenyl]-N-(quinoline-5-sulfonyl)cyclopropane-1-carboxamide;
1-[2-methoxy-5-(2-methoxypropan-2-yl)phenyl]-N-(2-methylquinoline-5-sulfonyl)cyclopropane-1-carboxamide;
1-[2-methoxy-5-(1-methoxycyclobutyl)phenyl]-N-(2-methylquinoline-5-sulfonyl)cyclopropane-1-carboxamide;
1-[2-(difluoromethoxy)-5-methylphenyl]-N-(2-methylquinoline-5-sulfonyl)cyclopropane-1-carboxamide;
1-[5-chloro-2-(difluoromethoxy)phenyl]-N-(2-methylquinoline-5-sulfonyl)cyclopropane-1-carboxamide;
1-[2-(difluoromethoxy)-5-ethylphenyl]-N-(2-methylquinoline-5-sulfonyl)cyclopropane-1-carboxamide;
1-(2-{[(2S)-1-methoxypropan-2-yl]oxy}-5-methylphenyl)-N-(2-methylquinoline-5-sulfonyl)cyclopropane-1-carboxamide;
1-[2-ethoxy-5-(1-methoxy-2-methylpropan-2-yl)phenyl]-N-(2-methylquinoline-5-sulfonyl)cyclopropane-1-carboxamide;
1-[2-(difluoromethoxy)-5-(2-ethoxypropan-2-yl)phenyl]-N-(quinoline-5-sulfonyl)cyclopropane-1-carboxamide;
1-[2-(difluoromethoxy)-5-(2-ethoxypropan-2-yl)phenyl]-N-(2-methylquinoline-5-sulfonyl)cyclopropane-1-carboxamide;
1-[2-(difluoromethoxy)-5-(2-methoxypropan-2-yl)phenyl]-N-(quinoline-5-sulfonyl)cyclopropane-1-carboxamide;
1-[2-(difluoromethoxy)-5-(2-methoxypropan-2-yl)phenyl]-N-(2-methylquinoline-5-sulfonyl)cyclopropane-1-carboxamide;
1-[5-(1-ethoxy-2-methylpropan-2-yl)-2-methoxyphenyl]-N-(quinoline-5-sulfonyl)cyclopropane-1-carboxamide;
1-[5-(1-ethoxy-2-methylpropan-2-yl)-2-methoxyphenyl]-N-(2-methylquinoline-5-sulfonyl)cyclopropane-1-carboxamide;
1-[5-(dimethylamino)-2-(2-methylpropoxy)pyridin-3-yl]-N-(quinoline-5-sulfonyl)cyclopropane-1-carboxamide;
1-[2-methoxy-5-(1-methoxy-2-methylpropan-2-yl)phenyl]-N-(2-methylquinoline-5-sulfonyl)cyclopropane-1-carboxamide;
1-(5-ethyl-2-{[(3S)-oxolan-3-yl]oxy}phenyl)-N-(2-methylquinoline-5-sulfonyl)cyclopropane-1-carboxamide;
1-(5-methyl-2-{[(3S)-oxolan-3-yl]oxy}phenyl)-N-(quinoline-5-sulfonyl)cyclopropane-1-carboxamide;
N-(benzenesulfonyl)-1-(2,4-dichlorophenyl)cyclopropane-1-carboxamide;
N-(3-cyanobenzene-1-sulfonyl)-4-(3-fluorophenyl)oxane-4-carboxamide;
N-(benzenesulfonyl)-1-(4-methoxyphenyl)cyclopropane-1-carboxamide;
N-(benzenesulfonyl)-1-phenylcyclopropane-1-carboxamide;
N-(benzenesulfonyl)-1-(4-chlorophenyl)cyclobutane-1-carboxamide;
1-(2,4-dichlorophenyl)-N-(2,3-dihydro-1H-indene-5-sulfonyl)cyclopropane-1-carboxamide;
N-(4-chlorobenzene-1-sulfonyl)-1-(2,4-dichlorophenyl)cyclopropane-1-carboxamide;
N-(4-chlorobenzene-1-sulfonyl)-1-(3-chlorophenyl)cyclopropane-1-carboxamide;
methyl 5-{[1-(2,4-dichlorophenyl)cyclopropane-1-carbonyl]sulfamoyl}-4-methoxythiophene-3-carboxylate;
1-(2,4-dichlorophenyl)-N-(3,5-dimethyl-1,2-oxazole-4-sulfonyl)cyclopropane-1-carboxamide;
1-(2,4-dichlorophenyl)-N-[2-(trifluoromethoxy)benzene-1-sulfonyl]cyclopropane-1-carboxamide;
1-(2,4-dichlorophenyl)-N-[4-(trifluoromethoxy)benzene-1-sulfonyl]cyclopropane-1-carboxamide;
1-(2,4-dichlorophenyl)-N-[3-(trifluoromethyl)benzene-1-sulfonyl]cyclopropane-1-carboxamide;
1-(2,4-dichlorophenyl)-N-[4-(2-oxopyrrolidin-1-yl)benzene-1-sulfonyl]cyclopropane-1-carboxamide;
1-(2,4-dichlorophenyl)-N-[5-(1,2-oxazol-5-yl)thiophene-2-sulfonyl]cyclopropane-1-carboxamide;
1-(2,4-dichlorophenyl)-N-[4-(pyrrolidine-1-sulfonyl)benzene-1-sulfonyl]cyclopropane-1-carboxamide;
N-(4-chlorobenzene-1-sulfonyl)-1-(2,4-dichlorophenyl)-N-methylcyclopropane-1-carboxamide;
1-(2,4-dichlorophenyl)-N-{4-[(propan-2-yl)oxy]benzene-1-sulfonyl}cyclopropane-1-carboxamide;
1-(2,4-dichlorophenyl)-N-[6-(morpholin-4-yl)pyridine-3-sulfonyl]cyclopropane-1-carboxamide;
benzyl 4-{[1-(2,4-dichlorophenyl)cyclopropane-1-carbonyl]sulfamoyl}piperidine-1-carboxylate;
N-(2-chlorobenzene-1-sulfonyl)-1-(3-chlorophenyl)cyclopropane-1-carboxamide;
1-(2,4-dichlorophenyl)-N-(4-methoxybenzene-1-sulfonyl)cyclopropane-1-carboxamide;
1-(2,4-dichlorophenyl)-N-(3,4-dimethoxybenzene-1-sulfonyl)cyclopropane-1-carboxamide;
N-(3-chlorobenzene-1-sulfonyl)-1-(2,4-dichlorophenyl)cyclopropane-1-carboxamide;
1-(2,4-dichlorophenyl)-N-(naphthalene-2-sulfonyl)cyclopropane-1-carboxamide;
N-(cyclopropanesulfonyl)-1-(2,4-dichlorophenyl)cyclopropane-1-carboxamide;
N-(benzenesulfonyl)-1-(4-methylphenyl)cyclopropane-1-carboxamide;
N-(benzenesulfonyl)-1-(2-fluorophenyl)cyclopropane-1-carboxamide;
N-(benzenesulfonyl)-1-(4-fluorophenyl)cyclopropane-1-carboxamide;
N-(benzenesulfonyl)-1-(2-chlorophenyl)cyclopropane-1-carboxamide;
N-(benzenesulfonyl)-1-(4-chlorophenyl)cyclopropane-1-carboxamide;
N-(benzenesulfonyl)-1-(3,4-dichlorophenyl)cyclopropane-1-carboxamide;
1-(2-fluorophenyl)-N-(phenylmethanesulfonyl)cyclopropane-1-carboxamide;
1-(2,4-dichlorophenyl)-N-(1,1-dioxo-1$\lambda^6$-thiolane-3-sulfonyl)cyclopropane-1-carboxamide;
1-(2,4-dichlorophenyl)-N-(4-methylbenzene-1-sulfonyl)cyclopropane-1-carboxamide;
N-(2-cyano-5-fluorobenzene-1-sulfonyl)-1-(2,4-dichlorophenyl)cyclopropane-1-carboxamide;

N-(2-chloro-5-nitrobenzene-1-sulfonyl)-1-(3-chlorophenyl)
 cyclopropane-1-carboxamide;
1-(3-chlorophenyl)-N-(6-ethoxy-1,3-benzothiazole-2-sulfo-
 nyl)cyclopropane-1-carboxamide;
1-(3-chlorophenyl)-N-(5-hydroxynaphthalene-1-sulfonyl)
 cyclopropane-1-carboxamide;
1-(3-chlorophenyl)-N-[5-(dimethylamino)naphthalene-1-
 sulfonyl]cyclopropane-1-carboxamide;
1-(2,4-dichlorophenyl)-N-(pyridine-3-sulfonyl)cyclopro-
 pane-1-carboxamide;
N-(6-chloropyridine-3-sulfonyl)-1-(2,4-dichlorophenyl)cy-
 clopropane-1-carboxamide;
N-(benzenesulfonyl)-2,2-dimethyl-1-phenylcyclopropane-
 1-carboxamide;
methyl 5-{[1-(2,4-dichlorophenyl)cyclopropane-1-carbo-
 nyl]sulfamoyl}furan-2-carboxylate;
N-(5-bromothiophene-2-sulfonyl)-1-(2,4-dichlorophenyl)
 cyclopropane-1-carboxamide;
1-(2,4-dichlorophenyl)-N-[3-(trifluoromethoxy)benzene-1-
 sulfonyl]cyclopropane-1-carboxamide;
methyl 2-{[1-(2,4-dichlorophenyl)cyclopropane-1-carbo-
 nyl]sulfamoyl}benzoate;
methyl 4-chloro-2-{[1-(2,4-dichlorophenyl)cyclopropane-
 1-carbonyl]sulfamoyl}benzoate;
2-{[1-(2,4-dichlorophenyl)cyclopropane-1-carbonyl]
 sulfamoyl}benzoic acid;
4-chloro-2-{[1-(2,4-dichlorophenyl)cyclopropane-1-carbo-
 nyl]sulfamoyl}benzoic acid;
benzyl 4-{[1-(4-methylphenyl)cyclopropane-1-carbonyl]
 sulfamoyl}piperidine-1-carboxylate;
benzyl 4-{[1-(3,4-dichlorophenyl)cyclopropane-1-carbo-
 nyl]sulfamoyl}piperidine-1-carboxylate;
N-(benzenesulfonyl)-1-(3-bromophenyl)cyclopropane-1-
 carboxamide;
1-(3-chlorophenyl)-N-[2-(trifluoroacetyl)-1,2,3,4-tetrahy-
 droisoquinoline-7-sulfonyl]cyclopropane-1-carboxam-
 ide;
1-(3-chlorophenyl)-N-[4-(1H-pyrazol-1-yl)benzene-1-sul-
 fonyl]cyclopropane-1-carboxamide;
1-(3-chlorophenyl)-N-(3,4-dimethylbenzene-1-sulfonyl)cy-
 clopropane-1-carboxamide;
1-(3-chlorophenyl)-N-(2-oxo-2,3-dihydro-1H-indole-5-sul-
 fonyl)cyclopropane-1-carboxamide;
N-(1-acetyl-2,3-dihydro-1H-indole-5-sulfonyl)-1-(3-chlo-
 rophenyl)cyclopropane-1-carboxamide;
1-(2,4-dichlorophenyl)-N-(piperidine-4-sulfonyl)cyclopro-
 pane-1-carboxamide;
N-(1-acetylpiperidine-4-sulfonyl)-1-(2,4-dichlorophenyl)
 cyclopropane-1-carboxamide;
1-(2,4-dichlorophenyl)-N-[1-(3-phenylpropanoyl)piperi-
 dine-4-sulfonyl]cyclopropane-1-carboxamide;
tert-butyl 4-{[1-(2,4-dichlorophenyl)cyclopropane-1-carbo-
 nyl]sulfamoyl}piperidine-1-carboxylate;
4-(3-methoxyphenyl)-N-(2-methylbenzene-1-sulfonyl)ox-
 ane-4-carboxamide;
N-(2-methylbenzene-1-sulfonyl)-4-(3-methylphenyl)oxane-
 4-carboxamide;
1-(3-chlorophenyl)-N-(2-methylbenzene-1-sulfonyl)cyclo-
 pentane-1-carboxamide;
1-(3-chlorophenyl)-N-(5-methylpyridine-2-sulfonyl)cyclo-
 propane-1-carboxamide;
1-(2-methoxyphenyl)-N-(2-methylbenzene-1-sulfonyl)cy-
 clopropane-1-carboxamide;
1-(2H-1,3-benzodioxol-5-yl)-N-(2-methylbenzene-1-sulfo-
 nyl)cyclopropane-1-carboxamide;
1-(2,4-dichlorophenyl)-N-(2-methylbenzene-1-sulfonyl)cy-
 clopropane-1-carboxamide;
1-(4-chlorophenyl)-N-(2-methylbenzene-1-sulfonyl)cyclo-
 propane-1-carboxamide;
tert-butyl 4-(4-fluorophenyl)-4-[(naphthalene-1-sulfonyl)
 carbamoyl]piperidine-1-carboxylate;
1-(3,4-dimethoxyphenyl)-N-(naphthalene-1-sulfonyl)cyclo-
 pentane-1-carboxamide;
1-(2,2-difluoro-2H-1,3-benzodioxol-5-yl)-N-(naphthalene-
 1-sulfonyl)cyclopropane-1-carboxamide;
1-(3-bromophenyl)-N-(naphthalene-1-sulfonyl)cyclopro-
 pane-1-carboxamide;
1-(3-bromophenyl)-N-(quinoline-5-sulfonyl)cyclopropane-
 1-carboxamide;
4-(5-methoxy-2-methylphenyl)-1-methyl-N-(quinoline-5-
 sulfonyl)piperidine-4-carboxamide;
1-[2-methoxy-5-(trifluoromethyl)pyridin-3-yl]-N-(pyrazolo
 [1,5-a]pyridine-4-sulfonyl)cyclopropane-1-carboxamide;
1-[2-methoxy-5-(trifluoromethyl)pyridin-3-yl]-N-(1-
 methyl-1H-benzimidazole-7-sulfonyl)cyclopropane-1-
 carboxamide;
1-[2-methoxy-5-(trifluoromethyl)pyridin-3-yl]-N-(1-
 methyl-1H-indazole-7-sulfonyl)cyclopropane-1-carbox-
 amide;
N-(1H-indazole-4-sulfonyl)-1-[2-methoxy-5-(trifluorom-
 ethyl)pyridin-3-yl]cyclopropane-1-carboxamide;
1-(5-cyano-2-methoxyphenyl)-N-(quinoline-5-sulfonyl)cy-
 clopropane-1-carboxamide;
1-(5-cyano-2-methoxyphenyl)-N-(1,2,3,4-tetrahydroquino-
 line-5-sulfonyl)cyclopropane-1-carboxamide;
1-[5-(bicyclo[1.1.1]pentan-1-yl)-2-methoxyphenyl]-N-(1,2,
 3,4-tetrahydroquinoline-5-sulfonyl)cyclopropane-1-car-
 boxamide;
1-(2-methoxy-6-methylphenyl)-N-(1-methyl-1H-indole-4-
 sulfonyl)cyclopropane-1-carboxamide;
1-(3,5-dichloro-2,6-dimethoxyphenyl)-N-(quinoline-5-sul-
 fonyl)cyclopropane-1-carboxamide;
1-(2,4-dichlorophenyl)-N-(phenylmethanesulfonyl)cyclo-
 propane-1-carboxamide;
1-(2,4-dichlorophenyl)-N-(trifluoromethanesulfonyl)cyclo-
 propane-1-carboxamide;
1-(2,4-dichlorophenyl)-N-(2,2,2-trifluoroethanesulfonyl)
 cyclopropane-1-carboxamide;
1-(2,4-dichlorophenyl)-N-(propane-1-sulfonyl)cyclopro-
 pane-1-carboxamide;
N-(3-chloropropane-1-sulfonyl)-1-(2,4-dichlorophenyl)cy-
 clopropane-1-carboxamide;
1-(3-chlorophenyl)-N-(phenylmethanesulfonyl)cyclopro-
 pane-1-carboxamide;
1-(2,4-dichlorophenyl)-N-(propane-2-sulfonyl)cyclopro-
 pane-1-carboxamide;
1-(4-methylphenyl)-N-(phenylmethanesulfonyl)cyclopro-
 pane-1-carboxamide;
1-(4-fluorophenyl)-N-(phenylmethanesulfonyl)cyclopro-
 pane-1-carboxamide;
1-(2-chlorophenyl)-N-(phenylmethanesulfonyl)cyclopro-
 pane-1-carboxamide;
1-(4-chlorophenyl)-N-(phenylmethanesulfonyl)cyclopro-
 pane-1-carboxamide;
1-(3,4-dichlorophenyl)-N-(phenylmethanesulfonyl)cyclo-
 propane-1-carboxamide;
N-(pentane-3-sulfonyl)-1-phenylcyclopropane-1-carboxam-
 ide;
4-(3-methoxyphenyl)-N-(propane-1-sulfonyl)oxane-4-car-
 boxamide;
4-(3-methylphenyl)-N-(propane-1-sulfonyl)oxane-4-car-
 boxamide;
1-(3,4-dimethoxyphenyl)-N-(naphthalene-1-sulfonyl)cy-
 clobutane-1-carboxamide;

1-[2-methoxy-6-(1-methyl-1H-pyrazol-4-yl)phenyl]-N-(quinoline-5-sulfonyl)cyclopropane-1-carboxamide;
1-(4-cyclobutyl-2,6-dimethoxyphenyl)-N-(1-methyl-1H-benzimidazole-7-sulfonyl)cyclopropane-1-carboxamide;
1-(3-methoxy-6-methylpyridin-2-yl)-N-(quinoline-5-sulfonyl)cyclopropane-1-carboxamide;
1-(3-methoxy-6-methylpyridin-2-yl)-N-(naphthalene-1-sulfonyl)cyclopropane-1-carboxamide;
1-(3-methoxy-6-methylpyridin-2-yl)-N-(2-methylquinoline-5-sulfonyl)cyclopropane-1-carboxamide;
1-(2,5-dimethylphenyl)-N-(1H-indazole-4-sulfonyl)cyclopropane-1-carboxamide;
1-[2-methoxy-5-(3-methoxyoxetan-3-yl)phenyl]-N-(quinoline-5-sulfonyl)cyclopropane-1-carboxamide;
1-{2-methoxy-5-[(3-$^2$H)oxetan-3-yl]phenyl}-N-(quinoline-5-sulfonyl)cyclopropane-1-carboxamide;
N-(1H-indazole-4-sulfonyl)-1-[5-methyl-2-(2-methylpropoxy)pyridin-3-yl]cyclopropane-1-carboxamide;
N-(1H-indazole-4-sulfonyl)-1-{5-methyl-2-[(propan-2-yl)oxy]pyridin-3-yl}cyclopropane-1-carboxamide;
1-(2-ethyl-6-methoxyphenyl)-N-(1H-indazole-4-sulfonyl)cyclopropane-1-carboxamide;
1-(2-ethyl-6-methoxyphenyl)-N-(2-methylquinoline-5-sulfonyl)cyclopropane-1-carboxamide;
N-[2-(dimethylamino)quinoline-5-sulfonyl]-1-(2-ethoxy-5-methylphenyl)cyclopropane-1-carboxamide;
1-{5-bromo-2-[(propan-2-yl)oxy]pyridin-3-yl}-N-(quinoline-5-sulfonyl)cyclopropane-1-carboxamide 1-{5-bromo-2-[(propan-2-yl)oxy]pyridin-3-yl}-N-(1,2,3,4-tetrahydroquinoline-5-sulfonyl)cyclopropane-1-carboxamide;
1-(5-chloro-2-methoxypyridin-3-yl)-N-(naphthalene-1-sulfonyl)cyclopropane-1-carboxamide
1-[2-propyl-6-(trifluoromethyl)pyridin-3-yl]-N-(quinoline-5-sulfonyl)cyclopropane-1-carboxamide;
1-[2-cyclopropyl-6-(trifluoromethyl)pyridin-3-yl]-N-(quinoline-5-sulfonyl)cyclopropane-1-carboxamide;
1-[2-cyclopropyl-6-(trifluoromethyl)pyridin-3-yl]-N-(1,2,3,4-tetrahydroquinoline-5-sulfonyl)cyclopropane-1-carboxamide;
1-[2-(propan-2-yl)-6-(trifluoromethyl)pyridin-3-yl]-N-(quinoline-5-sulfonyl)cyclopropane-1-carboxamide;
1-[2-propyl-6-(trifluoromethyl)pyridin-3-yl]-N-(1,2,3,4-tetrahydroquinoline-5-sulfonyl)cyclopropane-1-carboxamide;
1-[2-(propan-2-yl)-6-(trifluoromethyl)pyridin-3-yl]-N-(1,2,3,4-tetrahydroquinoline-5-sulfonyl)cyclopropane-1-carboxamide;
1-[2-cyclobutyl-6-(trifluoromethyl)pyridin-3-yl]-N-(1,2,3,4-tetrahydroquinoline-5-sulfonyl)cyclopropane-1-carboxamide;
1-[2-cyclobutyl-6-(trifluoromethyl)pyridin-3-yl]-N-(naphthalene-1-sulfonyl)cyclopropane-1-carboxamide;
1-[2-cyclopropyl-5-(2-methylpropoxy)pyridin-3-yl]-N-(quinoline-5-sulfonyl)cyclopropane-1-carboxamide;
1-{5-ethyl-2-[(propan-2-yl)oxy]pyridin-3-yl}-N-(quinoline-5-sulfonyl)cyclopropane-1-carboxamide;
1-{5-ethyl-2-[(propan-2-yl)oxy]pyridin-3-yl}-N-(1,2,3,4-tetrahydroquinoline-5-sulfonyl)cyclopropane-1-carboxamide;
1-[2-(pyrrolidin-1-yl)-6-(trifluoromethyl)pyridin-3-yl]-N-(quinoline-5-sulfonyl)cyclopropane-1-carboxamide;
1-{2-methoxy-5-[(propan-2-yl)oxy]pyridin-4-yl}-N-(quinoline-5-sulfonyl)cyclopropane-1-carboxamide;
1-{6-methoxy-4-[(propan-2-yl)oxy]pyridin-3-yl}-N-(quinoline-5-sulfonyl)cyclopropane-1-carboxamide;
1-{6-methoxy-4-[(propan-2-yl)oxy]pyridin-3-yl}-N-(2-methylquinoline-5-sulfonyl)cyclopropane-1-carboxamide;
1-[2-methoxy-5-(2-methylpropoxy)pyridin-4-yl]-N-(quinoline-5-sulfonyl)cyclopropane-1-carboxamide;
1-[2-methoxy-5-(2-methylpropoxy)pyridin-4-yl]-N-(2-methylquinoline-5-sulfonyl)cyclopropane-1-carboxamide;
N-(1H-indole-4-sulfonyl)-1-[2-methoxy-5-(2-methylpropoxy)pyridin-4-yl]cyclopropane-1-carboxamide;
1-{5-cyclobutyl-2-[(propan-2-yl)oxy]pyridin-3-yl}-sulfonyl)cyclopropane-1-carboxamide;
1-{5-cyclobutyl-2-[(propan-2-yl)oxy]pyridin-3-yl}-N-(2-methylquinoline-5-sulfonyl)cyclopropane-1-carboxamide;
1-{5-cyclobutyl-2-[(propan-2-yl)oxy]pyridin-3-yl}-N-(1H-indole-4-sulfonyl)cyclopropane-1-carboxamide;
1-{2-cyclobutyl-5-[(propan-2-yl)oxy]pyridin-4-yl}-N-(quinoline-5-sulfonyl)cyclopropane-1-carboxamide;
1-{2-cyclobutyl-5-[(propan-2-yl)oxy]pyridin-4-yl}-N-(2-methylquinoline-5-sulfonyl)cyclopropane-1-carboxamide;
1-{2-cyclobutyl-5-[(propan-2-yl)oxy]pyridin-4-yl}-N-(1H-indole-4-sulfonyl)cyclopropane-1-carboxamide;
1-[5-cyclobutyl-2-(pyrrolidin-1-yl)pyridin-3-yl]-N-(quinoline-5-sulfonyl)cyclopropane-1-carboxamide;
1-[5-cyclobutyl-2-(pyrrolidin-1-yl)pyridin-3-yl]-N-(2-methylquinoline-5-sulfonyl)cyclopropane-1-carboxamide;
1-[5-cyclobutyl-2-(pyrrolidin-1-yl)pyridin-3-yl]-N-(1H-indole-4-sulfonyl)cyclopropane-1-carboxamide;
1-[5-cyclobutyl-2-(pyrrolidin-1-yl)pyridin-3-yl]-N-(1,2,3,4-tetrahydroquinoline-5-sulfonyl)cyclopropane-1-carboxamide;
1-[5-cyclopropyl-2-(pyrrolidin-1-yl)pyridin-3-yl]-N-(quinoline-5-sulfonyl)cyclopropane-1-carboxamide;
1-[5-cyclopropyl-2-(pyrrolidin-1-yl)pyridin-3-yl]-N-(2-methylquinoline-5-sulfonyl)cyclopropane-1-carboxamide.
1-[5-cyclopropyl-2-(pyrrolidin-1-yl)pyridin-3-yl]-N-(1H-indole-4-sulfonyl)cyclopropane-1-carboxamide;
1-[5-chloro-2-(pyrrolidin-1-yl)pyridin-3-yl]-N-(quinoline-5-sulfonyl)cyclopropane-1-carboxamide;
1-[5-chloro-2-(pyrrolidin-1-yl)pyridin-3-yl]-N-(2-methylquinoline-5-sulfonyl)cyclopropane-1-carboxamide;
1-[5-ethyl-2-(pyrrolidin-1-yl)pyridin-3-yl]-N-(1H-indole-4-sulfonyl)cyclopropane-1-carboxamide;
1-{6-cyclobutyl-3-[(propan-2-yl)oxy]pyridin-2-yl}-N-(1H-indole-4-sulfonyl)cyclopropane-1-carboxamide;
1-{6-cyclobutyl-3-[(propan-2-yl)oxy]pyridin-2-yl}-N-(quinoline-5-sulfonyl)cyclopropane-1-carboxamide;
1-{5-ethyl-2-[(propan-2-yl)oxy]pyridin-3-yl}-N-(2-methylquinoline-5-sulfonyl)cyclopropane-1-carboxamide;
1-{5-ethyl-2-[(propan-2-yl)oxy]pyridin-3-yl}-N-(1H-indole-4-sulfonyl)cyclopropane-1-carboxamide;
1-[5-methyl-2-(2-methylpropoxy)pyridin-3-yl]-N-(quinoline-5-sulfonyl)cyclopropane-1-carboxamide;
1-[5-methyl-2-(2-methylpropoxy)pyridin-3-yl]-N-(2-methylquinoline-5-sulfonyl)cyclopropane-1-carboxamide;
N-(1H-indole-4-sulfonyl)-1-[5-methyl-2-(2-methylpropoxy)pyridin-3-yl]cyclopropane-1-carboxamide;
1-[5-ethyl-2-(2-methylpropoxy)pyridin-3-yl]-N-(quinoline-5-sulfonyl)cyclopropane-1-carboxamide;
1-[5-ethyl-2-(2-methylpropoxy)pyridin-3-yl]-N-(2-methylquinoline-5-sulfonyl)cyclopropane-1-carboxamide;
1-[5-ethyl-2-(2-methylpropoxy)pyridin-3-yl]-N-(1H-indole-4-sulfonyl)cyclopropane-1-carboxamide;

1-[5-cyclopropyl-2-(2-methylpropoxy)pyridin-3-yl]-N-(quinoline-5-sulfonyl)cyclopropane-1-carboxamide;
1-[5-cyclopropyl-2-(2-methylpropoxy)pyridin-3-yl]-N-(2-methylquinoline-5-sulfonyl)cyclopropane-1-carboxamide;
1-[5-cyclopropyl-2-(2-methylpropoxy)pyridin-3-yl]-N-(1H-indole-4-sulfonyl)cyclopropane-1-carboxamide;
1-[5-cyclobutyl-2-(2-methylpropoxy)pyridin-3-yl]-N-(quinoline-5-sulfonyl)cyclopropane-1-carboxamide;
1-[5-cyclobutyl-2-(2-methylpropoxy)pyridin-3-yl]-N-(1H-indole-4-sulfonyl)cyclopropane-1-carboxamide;
1-[5-cyclobutyl-2-(2-methylpropoxy)pyridin-3-yl]-N-(2-methylquinoline-5-sulfonyl)cyclopropane-1-carboxamide;
1-{6-ethyl-3-[(propan-2-yl)oxy]pyridin-2-yl}-N-(2-methylquinoline-5-sulfonyl)cyclopropane-1-carboxamide;
1-{6-ethyl-3-[(propan-2-yl)oxy]pyridin-2-yl}-N-(quinoline-5-sulfonyl)cyclopropane-1-carboxamide;
1-{6-ethyl-3-[(propan-2-yl)oxy]pyridin-2-yl}-N-(1H-indole-4-sulfonyl)cyclopropane-1-carboxamide;
1-[5-cyclobutyl-2-(4-methoxypiperidin-1-yl)pyridin-3-yl]-N-(1H-indole-4-sulfonyl)cyclopropane-1-carboxamide;
1-{5-methyl-2-[(propan-2-yl)oxy]pyridin-3-yl}-N-(2-methylquinoline-5-sulfonyl)cyclopropane-1-carboxamide;
N-(1H-indole-4-sulfonyl)-1-{5-methyl-2-[(propan-2-yl)oxy]pyridin-3-yl}cyclopropane-1-carboxamide;
1-{5-cyclopropyl-2-[(propan-2-yl)oxy]pyridin-3-yl}-N-(2-methylquinoline-5-sulfonyl)cyclopropane-1-carboxamide;
1-{5-cyclopropyl-2-[(propan-2-yl)oxy]pyridin-3-yl}-N-(1H-indole-4-sulfonyl)cyclopropane-1-carboxamide;
1-{2-[(propan-2-yl)oxy]-5-(pyrrolidin-1-yl)pyridin-3-yl}-N-(quinoline-5-sulfonyl)cyclopropane-1-carboxamide;
N-(2-methylquinoline-5-sulfonyl)-1-{2-[(propan-2-yl)oxy]-5-(pyrrolidin-1-yl)pyridin-3-yl}cyclopropane-1-carboxamide;
N-(1H-indole-4-sulfonyl)-1-{2-[(propan-2-yl)oxy]-5-(pyrrolidin-1-yl)pyridin-3-yl}cyclopropane-1-carboxamide;
1-{2,5-bis[(propan-2-yl)oxy]pyridin-3-yl}-N-(quinoline-5-sulfonyl)cyclopropane-1-carboxamide;
1-{2,5-bis[(propan-2-yl)oxy]pyridin-3-yl}-N-(1H-indole-4-sulfonyl)cyclopropane-1-carboxamide;
1-{2,5-bis[(propan-2-yl)oxy]pyridin-3-yl}-N-(2-methylquinoline-5-sulfonyl)cyclopropane-1-carboxamide;
1-[2-(2-methylpropoxy)-5-(pyrrolidin-1-yl)pyridin-3-yl]-N-(quinoline-5-sulfonyl)cyclopropane-1-carboxamide;
1-[2-(2-methylpropoxy)-5-(pyrrolidin-1-yl)pyridin-3-yl]-N-(2-methylquinoline-5-sulfonyl)cyclopropane-1-carboxamide;
N-(1H-indole-4-sulfonyl)-1-[2-(2-methylpropoxy)-5-(pyrrolidin-1-yl)pyridin-3-yl]cyclopropane-1-carboxamide;
1-{5-(dimethylamino)-2-[(propan-2-yl)oxy]pyridin-3-yl}-N-(quinoline-5-sulfonyl)cyclopropane-1-carboxamide;
1-{5-(dimethylamino)-2-[(propan-2-yl)oxy]pyridin-3-yl}-N-(2-methylquinoline-5-sulfonyl)cyclopropane-1-carboxamide;
1-{5-(dimethylamino)-2-[(propan-2-yl)oxy]pyridin-3-yl}-N-(1H-indole-4-sulfonyl)cyclopropane-1-carboxamide;
1-{5-methoxy-2-[(propan-2-yl)oxy]pyridin-3-yl}-N-(quinoline-5-sulfonyl)cyclopropane-1-carboxamide;
N-(1H-indole-4-sulfonyl)-1-{5-methoxy-2-[(propan-2-yl)oxy]pyridin-3-yl}cyclopropane-1-carboxamide;
1-{5-methoxy-2-[(propan-2-yl)oxy]pyridin-3-yl}-N-(2-methylquinoline-5-sulfonyl)cyclopropane-1-carboxamide;
1-[5-methoxy-2-(2-methylpropoxy)pyridin-3-yl]-N-(quinoline-5-sulfonyl)cyclopropane-1-carboxamide;
N-(1H-indole-4-sulfonyl)-1-[5-methoxy-2-(2-methylpropoxy)pyridin-3-yl]cyclopropane-1-carboxamide;
1-[5-methoxy-2-(2-methylpropoxy)pyridin-3-yl]-N-(2-methylquinoline-5-sulfonyl)cyclopropane-1-carboxamide;
1-{6-methyl-2-[(propan-2-yl)oxy]pyridin-3-yl}-N-(quinoline-5-sulfonyl)cyclopropane-1-carboxamide;
1-{6-methyl-2-[(propan-2-yl)oxy]pyridin-3-yl}-N-(2-methylquinoline-5-sulfonyl)cyclopropane-1-carboxamide;
N-(1H-indole-4-sulfonyl)-1-{6-methyl-2-[(propan-2-yl)oxy]pyridin-3-yl}cyclopropane-1-carboxamide;
1-{5-(azetidin-1-yl)-2-[(propan-2-yl)oxy]pyridin-3-yl}-N-(quinoline-5-sulfonyl)cyclopropane-1-carboxamide;
1-{5-(azetidin-1-yl)-2-[(propan-2-yl)oxy]pyridin-3-yl}-N-(2-methylquinoline-5-sulfonyl)cyclopropane-1-carboxamide;
1-{5-(azetidin-1-yl)-2-[(propan-2-yl)oxy]pyridin-3-yl}-N-(1H-indole-4-sulfonyl)cyclopropane-1-carboxamide;
1-{6-(2-methylpropoxy)-3-[(propan-2-yl)oxy]pyridin-2-yl}-N-(quinoline-5-sulfonyl)cyclopropane-1-carboxamide;
1-[2-(cyclopropylmethoxy)-5-methoxypyridin-3-yl]-N-(quinoline-5-sulfonyl)cyclopropane-1-carboxamide;
1-[2-(cyclopropylmethoxy)-5-methoxypyridin-3-yl]-N-(1H-indole-4-sulfonyl)cyclopropane-1-carboxamide;
N-(1H-indole-4-sulfonyl)-1-{6-(2-methylpropoxy)-3-[(propan-2-yl)oxy]pyridin-2-yl}cyclopropane-1-carboxamide;
1-{6-(2-methylpropoxy)-3-[(propan-2-yl)oxy]pyridin-2-yl}-N-(2-methylquinoline-5-sulfonyl)cyclopropane-1-carboxamide;
1-[5-(cyclopropylmethoxy)-2-methoxypyridin-4-yl]-N-(quinoline-5-sulfonyl)cyclopropane-1-carboxamide;
1-[2-(cyclopropylmethoxy)-5-methoxypyridin-3-yl]-N-(2-methylquinoline-5-sulfonyl)cyclopropane-1-carboxamide;
1-[5-(cyclopropylmethoxy)-2-methoxypyridin-4-yl]-N-(2-methylquinoline-5-sulfonyl)cyclopropane-1-carboxamide;
1-[5-cyclobutyl-2-(2-methoxyethoxy)pyridin-3-yl]-N-(2-methylquinoline-5-sulfonyl)cyclopropane-1-carboxamide;
1-[5-(cyclopropylmethoxy)-2-methoxypyridin-4-yl]-N-(1H-indole-4-sulfonyl)cyclopropane-1-carboxamide;
1-[2-(cyclopropylmethoxy)-5-methylpyridin-3-yl]-N-(quinoline-5-sulfonyl)cyclopropane-1-carboxamide;
1-[2-(cyclopropylmethoxy)-5-methylpyridin-3-yl]-N-(1H-indole-4-sulfonyl)cyclopropane-1-carboxamide;
1-[5-cyclobutyl-2-(cyclopropylmethoxy)pyridin-3-yl]-N-(1H-indole-4-sulfonyl)cyclopropane-1-carboxamide;
1-[5-cyclobutyl-2-(2-methoxyethoxy)pyridin-3-yl]-N-(1H-indole-4-sulfonyl)cyclopropane-1-carboxamide;
1-[5-cyclobutyl-2-(cyclopropylmethoxy)pyridin-3-yl]-N-(quinoline-5-sulfonyl)cyclopropane-1-carboxamide;
1-[2-(cyclopropylmethoxy)-5-methylpyridin-3-yl]-N-(2-methylquinoline-5-sulfonyl)cyclopropane-1-carboxamide;
1-(5-ethyl-2-{4-[(propan-2-yl)oxy]piperidin-1-yl}pyridin-3-yl)-N-(1H-indole-4-sulfonyl)cyclopropane-1-carboxamide;
1-(5-cyclobutyl-2-{4-[(propan-2-yl)oxy]piperidin-1-yl}pyridin-3-yl)-N-(1H-indole-4-sulfonyl)cyclopropane-1-carboxamide;
1-(5-cyclobutyl-2-{4-[(propan-2-yl)oxy]piperidin-1-yl}pyridin-3-yl)-N-(quinoline-5-sulfonyl)cyclopropane-1-carboxamide;
1-[2-(cyclopropylmethoxy)-5-ethylpyridin-3-yl]-N-(quinoline-5-sulfonyl)cyclopropane-1-carboxamide;

1-[2-(cyclopropylmethoxy)-5-ethylpyridin-3-yl]-N-(2-methylquinoline-5-sulfonyl)cyclopropane-1-carboxamide;
1-[2-(cyclopropylmethoxy)-5-ethylpyridin-3-yl]-N-(1H-indole-4-sulfonyl)cyclopropane-1-carboxamide;
1-[5-ethyl-2-(2-methoxyethoxy)pyridin-3-yl]-N-(1H-indole-4-sulfonyl)cyclopropane-1-carboxamide;
1-[5-cyclobutyl-2-(cyclopropylmethoxy)pyridin-3-yl]-N-(2-methylquinoline-5-sulfonyl)cyclopropane-1-carboxamide;
1-[5-cyclobutyl-2-(2-methoxyethoxy)pyridin-3-yl]-N-(quinoline-5-sulfonyl)cyclopropane-1-carboxamide;
1-[5-ethyl-2-(2-methoxyethoxy)pyridin-3-yl]-N-(quinoline-5-sulfonyl)cyclopropane-1-carboxamide;
1-(5-cyclobutyl-2-{4-[(propan-2-yl)oxy]piperidin-1-yl}pyridin-3-yl)-N-(2-methylquinoline-5-sulfonyl)cyclopropane-1-carboxamide;
1-(5-cyclobutyl-2-ethoxypyridin-3-yl)-N-(quinoline-5-sulfonyl)cyclopropane-1-carboxamide;
1-(5-cyclobutyl-2-ethoxypyridin-3-yl)-N-(2-methylquinoline-5-sulfonyl)cyclopropane-1-carboxamide;
1-(2-ethoxy-5-ethylpyridin-3-yl)-N-(quinoline-5-sulfonyl)cyclopropane-1-carboxamide;
1-(2-ethoxy-5-ethylpyridin-3-yl)-N-(2-methylquinoline-5-sulfonyl)cyclopropane-1-carboxamide;
1-{5-cyclobutyl-2-[4-(methoxymethyl)piperidin-1-yl]pyridin-3-yl}-N-(1H-indole-4-sulfonyl)cyclopropane-1-carboxamide;
1-{5-[1-(methoxymethyl)cyclopropyl]-2-[(propan-2-yl)oxy]pyridin-3-yl}-N-(naphthalene-1-sulfonyl)cyclopropane-1-carboxamide;
1-{5-ethyl-2-[4-(methoxymethyl)piperidin-1-yl]pyridin-3-yl}-N-(1H-indole-4-sulfonyl)cyclopropane-1-carboxamide;
1-{5-cyclobutyl-2-[4-(methoxymethyl)piperidin-1-yl]pyridin-3-yl}-N-(quinoline-5-sulfonyl)cyclopropane-1-carboxamide;
1-(2,4-dimethoxypyrimidin-5-yl)-N-(naphthalene-1-sulfonyl)cyclopropane-1-carboxamide;
N-(naphthalene-1-sulfonyl)-1-{2-[(propan-2-yl)oxy]pyridin-3-yl}cyclopropane-1-carboxamide;
1-{2-[(propan-2-yl)oxy]pyridin-3-yl}-N-(quinoline-5-sulfonyl)cyclopropane-1-carboxamide;
1-{2-[(propan-2-yl)oxy]pyridin-3-yl}-N-(1,2,3,4-tetrahydroquinoline-5-sulfonyl)cyclopropane-1-carboxamide;
1-[5-chloro-2-(trifluoromethyl)pyridin-3-yl]-N-(naphthalene-1-sulfonyl)cyclopropane-1-carboxamide;
1-(5-chloro-2-methoxypyridin-4-yl)-N-(quinoline-5-sulfonyl)cyclopropane-1-carboxamide;
1-(5-chloro-2-methoxypyridin-4-yl)-N-(1,2,3,4-tetrahydroquinoline-5-sulfonyl)cyclopropane-1-carboxamide;
1-[5-methyl-2-(morpholin-4-yl)pyridin-4-yl]-N-(quinoline-5-sulfonyl)cyclopropane-1-carboxamide;
1-[5-methyl-2-(pyrrolidin-1-yl)pyridin-4-yl]-N-(quinoline-5-sulfonyl)cyclopropane-1-carboxamide;
1-[2-methoxy-6-(trifluoromethyl)pyridin-3-yl]-N-(quinoline-5-sulfonyl)cyclopropane-1-carboxamide;
1-[2-(dimethylamino)-5-methylpyridin-4-yl]-N-(quinoline-5-sulfonyl)cyclopropane-1-carboxamide;
1-[2-methoxy-6-(trifluoromethyl)pyridin-3-yl]-N-(1,2,3,4-tetrahydroquinoline-5-sulfonyl)cyclopropane-1-carboxamide;
1-(2-methoxy-5-methylpyridin-4-yl)-N-(quinoline-5-sulfonyl)cyclopropane-1-carboxamide;
1-[2-cyclobutyl-6-(trifluoromethyl)pyridin-3-yl]-N-(quinoline-5-sulfonyl)cyclopropane-1-carboxamide;
1-(2-cyclopropyl-5-methoxypyridin-3-yl)-N-(quinoline-5-sulfonyl)cyclopropane-1-carboxamide;
1-{2-ethyl-5-[(propan-2-yl)oxy]pyridin-3-yl}-N-(quinoline-5-sulfonyl)cyclopropane-1-carboxamide;
1-(2-ethyl-5-methoxypyridin-3-yl)-N-(quinoline-5-sulfonyl)cyclopropane-1-carboxamide;
1-[6-(dimethylamino)-2-methoxypyridin-3-yl]-N-(quinoline-5-sulfonyl)cyclopropane-1-carboxamide;
1-(6-methoxy-2-methylpyridin-3-yl)-N-(naphthalene-1-sulfonyl)cyclopropane-1-carboxamide;
1-(4-ethylpyridin-3-yl)-N-(naphthalene-1-sulfonyl)cyclopropane-1-carboxamide;
1-(4-ethylpyridin-3-yl)-N-(1,2,3,4-tetrahydroquinoline-5-sulfonyl)cyclopropane-1-carboxamide;
1-(6-methoxy-4-methylpyridin-3-yl)-N-(naphthalene-1-sulfonyl)cyclopropane-1-carboxamide;
1-(6-methoxy-4-methylpyridin-3-yl)-N-(quinoline-5-sulfonyl)cyclopropane-1-carboxamide;
1-{6-methoxy-4-[(propan-2-yl)oxy]pyridin-3-yl}-N-(1,2,3,4-tetrahydroquinoline-5-sulfonyl)cyclopropane-1-carboxamide;
1-{5-cyclobutyl-2-[(propan-2-yl)oxy]pyridin-3-yl}-N-(1,2,3,4-tetrahydroquinoline-5-sulfonyl)cyclopropane-1-carboxamide;
1-{2-cyclobutyl-5-[(propan-2-yl)oxy]pyridin-4-yl}-N-(1,2,3,4-tetrahydroquinoline-5-sulfonyl)cyclopropane-1-carboxamide;
1-{5-cyclobutyl-3-[(propan-2-yl)oxy]pyridin-2-yl}-N-(quinoline-5-sulfonyl)cyclopropane-1-carboxamide;
1-[5-cyclobutyl-2-(morpholin-4-yl)pyridin-3-yl]-N-(quinoline-5-sulfonyl)cyclopropane-1-carboxamide;
1-[5-cyclopropyl-2-(pyrrolidin-1-yl)pyridin-3-yl]-N-(1,2,3,4-tetrahydroquinoline-5-sulfonyl)cyclopropane-1-carboxamide;
1-[5-ethyl-2-(pyrrolidin-1-yl)pyridin-3-yl]-N-(quinoline-5-sulfonyl)cyclopropane-1-carboxamide;
1-[5-ethyl-2-(pyrrolidin-1-yl)pyridin-3-yl]-N-(2-methylquinoline-5-sulfonyl)cyclopropane-1-carboxamide;
1-[5-ethyl-2-(morpholin-4-yl)pyridin-3-yl]-N-(2-methylquinoline-5-sulfonyl)cyclopropane-1-carboxamide;
1-[2-(pyrrolidin-1-yl)pyridin-3-yl]-N-(quinoline-5-sulfonyl)cyclopropane-1-carboxamide;
N-(2-methylquinoline-5-sulfonyl)-1-[2-(pyrrolidin-1-yl)pyridin-3-yl]cyclopropane-1-carboxamide;
1-[5-ethyl-2-(pyrrolidin-1-yl)pyridin-3-yl]-N-(1,2,3,4-tetrahydroquinoline-5-sulfonyl)cyclopropane-1-carboxamide;
1-[5-methyl-2-(pyrrolidin-1-yl)pyridin-3-yl]-N-(2-methylquinoline-5-sulfonyl)cyclopropane-1-carboxamide;
N-(1H-indole-4-sulfonyl)-1-[5-methyl-2-(pyrrolidin-1-yl)pyridin-3-yl]cyclopropane-1-carboxamide;
1-[5-methyl-2-(pyrrolidin-1-yl)pyridin-3-yl]-N-(quinoline-5-sulfonyl)cyclopropane-1-carboxamide;
1-(3-cyclopropyl-5-methylpyridin-2-yl)-N-(1H-indole-4-sulfonyl)cyclopropane-1-carboxamide;
1-[5-methoxy-2-(pyrrolidin-1-yl)pyridin-3-yl]-N-(quinoline-5-sulfonyl)cyclopropane-1-carboxamide;
1-[2-(dimethylamino)-5-methylpyridin-3-yl]-N-(quinoline-5-sulfonyl)cyclopropane-1-carboxamide;
1-[5-methoxy-2-(2-methoxyethoxy)pyridin-3-yl]-N-(2-methylquinoline-5-sulfonyl)cyclopropane-1-carboxamide;
N-(1H-indole-4-sulfonyl)-1-[5-methoxy-2-(2-methoxyethoxy)pyridin-3-yl]cyclopropane-1-carboxamide;
1-[5-methoxy-2-(2-methoxyethoxy)pyridin-3-yl]-N-(quinoline-5-sulfonyl)cyclopropane-1-carboxamide;
N-(1H-indole-4-sulfonyl)-1-[2-methoxy-5-(2-methoxyethoxy)pyridin-4-yl]cyclopropane-1-carboxamide;

1-[2-methoxy-5-(2-methoxyethoxy)pyridin-4-yl]-N-(2-methylquinoline-5-sulfonyl)cyclopropane-1-carboxamide;
1-[2-(dimethylamino)-5-ethylpyridin-3-yl]-N-(quinoline-5-sulfonyl)cyclopropane-1-carboxamide;
1-[2-(dimethylamino)-5-ethylpyridin-3-yl]-N-(2-methylquinoline-5-sulfonyl)cyclopropane-1-carboxamide;
1-[2-(dimethylamino)-5-ethylpyridin-3-yl]-N-(1H-indole-4-sulfonyl)cyclopropane-1-carboxamide;
1-[2-(2-methoxyethoxy)-5-methylpyridin-3-yl]-N-(2-methylquinoline-5-sulfonyl)cyclopropane-1-carboxamide;
1-{2-(dimethylamino)-6-[(propan-2-yl)oxy]pyridin-3-yl}-N-(quinoline-5-sulfonyl)cyclopropane-1-carboxamide;
1-[2-(2-methoxyethoxy)-5-methylpyridin-3-yl]-N-(quinoline-5-sulfonyl)cyclopropane-1-carboxamide;
N-(1H-indole-4-sulfonyl)-1-[2-(2-methoxyethoxy)-5-methylpyridin-3-yl]cyclopropane-1-carboxamide;
1-(5-ethyl-2-{4-[(propan-2-yl)oxy]piperidin-1-yl}pyridin-3-yl)-N-(quinoline-5-sulfonyl)cyclopropane-1-carboxamide;
1-(5-ethyl-2-{4-[(propan-2-yl)oxy]piperidin-1-yl}pyridin-3-yl)-N-(2-methylquinoline-5-sulfonyl)cyclopropane-1-carboxamide;
1-[5-ethyl-2-(2-methoxyethoxy)pyridin-3-yl]-N-(2-methylquinoline-5-sulfonyl)cyclopropane-1-carboxamide;
1-[5-ethyl-2-(4-methoxypiperidin-1-yl)pyridin-3-yl]-5-sulfonyl)cyclopropane-1-carboxamide;
1-[5-ethyl-2-(4-methoxypiperidin-1-yl)pyridin-3-yl]-N-(1H-indole-4-sulfonyl)cyclopropane-1-carboxamide;
1-{5-ethyl-2-[4-(methoxymethyl)piperidin-1-yl]pyridin-3-yl}-N-(quinoline-5-sulfonyl)cyclopropane-1-carboxamide;
1-[3-chloro-5-(trifluoromethyl)pyridin-2-yl]-N-(quinoline-5-sulfonyl)cyclopropane-1-carboxamide;
1-[5-chloro-2-(trifluoromethyl)pyridin-3-yl]-N-(quinoline-5-sulfonyl)cyclopropane-1-carboxamide;
N-(1H-indole-4-sulfonyl)-1-{6-methoxy-4-[(propan-2-yl)oxy]pyridin-3-yl}cyclopropane-1-carboxamide;
1-(3-cyclopropyl-5-methylpyridin-2-yl)-N-(quinoline-5-sulfonyl)cyclopropane-1-carboxamide;
1-[2-chloro-5-(2-methylpropoxy)pyridin-3-yl]-N-(quinoline-5-sulfonyl)cyclopropane-1-carboxamide;
1-(4-ethylpyridin-3-yl)-N-(quinoline-5-sulfonyl)cyclopropane-1-carboxamide;
1-(2-fluoro-5-methylpyridin-4-yl)-N-(1,2,3,4-tetrahydroquinoline-5-sulfonyl)cyclopropane-1-carboxamide;
1-(6-methoxy-2-methylpyridin-3-yl)-N-(quinoline-5-sulfonyl)cyclopropane-1-carboxamide;
1-[5-cyclopropyl-2-(4-methylpiperazin-1-yl)pyridin-3-yl]-N-(quinoline-5-sulfonyl)cyclopropane-1-carboxamide;
1-[5-cyclopropyl-2-(trifluoromethyl)pyridin-3-yl]-N-(quinoline-5-sulfonyl)cyclopropane-1-carboxamide;
1-[2-methoxy-5-(2-methoxyethoxy)pyridin-4-yl]-N-(quinoline-5-sulfonyl)cyclopropane-1-carboxamide;
1-(2,4-dimethoxypyrimidin-5-yl)-N-(1,2,3,4-tetrahydroquinoline-5-sulfonyl)cyclopropane-1-carboxamide;
1-{2-chloro-5-[(propan-2-yl)oxy]pyridin-3-yl}-N-(quinoline-5-sulfonyl)cyclopropane-1-carboxamide;
1-[5-(2,2-difluoroethoxy)-2-methoxypyridin-4-yl]-N-(2-methylquinoline-5-sulfonyl)cyclopropane-1-carboxamide;
1-(6-methoxy-2-methylpyridin-3-yl)-N-(1,2,3,4-tetrahydroquinoline-5-sulfonyl)cyclopropane-1-carboxamide;
1-(2-fluoro-5-methylpyridin-4-yl)-N-(quinoline-5-sulfonyl)cyclopropane-1-carboxamide;
1-(6-methoxy-4-methylpyridin-3-yl)-N-(1,2,3,4-tetrahydroquinoline-5-sulfonyl)cyclopropane-1-carboxamide;
1-[5-(2,2-difluoroethoxy)-2-methoxypyridin-4-yl]-N-(quinoline-5-sulfonyl)cyclopropane-1-carboxamide;
1-[5-(difluoromethoxy)-2-methoxypyridin-4-yl]-N-(quinoline-5-sulfonyl)cyclopropane-1-carboxamide;
1-[5-cyclopropyl-2-(morpholin-4-yl)pyridin-3-yl]-N-(2-methylquinoline-5-sulfonyl)cyclopropane-1-carboxamide;
1-[2-chloro-6-(trifluoromethyl)pyridin-3-yl]-N-(naphthalene-1-sulfonyl)cyclopropane-1-carboxamide;
1-[5-(difluoromethoxy)-2-methoxypyridin-4-yl]-N-(2-methylquinoline-5-sulfonyl)cyclopropane-1-carboxamide;
1-[5-ethyl-2-(morpholin-4-yl)pyridin-3-yl]-N-(quinoline-5-sulfonyl)cyclopropane-1-carboxamide;
1-(2,4-dimethoxypyrimidin-5-yl)-N-(quinoline-5-sulfonyl)cyclopropane-1-carboxamide;
1-[5-cyclopropyl-2-(morpholin-4-yl)pyridin-3-yl]-N-(quinoline-5-sulfonyl)cyclopropane-1-carboxamide;
1-[5-methyl-2-(4-methylpiperazin-1-yl)pyridin-3-yl]-N-(quinoline-5-sulfonyl)cyclopropane-1-carboxamide;
1-[5-cyclopropyl-2-(4-methylpiperazin-1-yl)pyridin-3-yl]-N-(2-methylquinoline-5-sulfonyl)cyclopropane-1-carboxamide;
1-[2-chloro-6-(trifluoromethyl)pyridin-3-yl]-N-(1,2,3,4-tetrahydroquinoline-5-sulfonyl)cyclopropane-1-carboxamide;
1-[2-chloro-6-(trifluoromethyl)pyridin-3-yl]-N-(quinoline-5-sulfonyl)cyclopropane-1-carboxamide;
1-(6-amino-2-methoxypyridin-3-yl)-N-(quinoline-5-sulfonyl)cyclopropane-1-carboxamide;
1-[5-cyclobutyl-2-(4-methylpiperazin-1-yl)pyridin-3-yl]-N-(quinoline-5-sulfonyl)cyclopropane-1-carboxamide;
1-[5-cyclobutyl-2-(4-methylpiperazin-1-yl)pyridin-3-yl]-N-(2-methylquinoline-5-sulfonyl)cyclopropane-1-carboxamide;
1-[5-ethyl-2-(4-methylpiperazin-1-yl)pyridin-3-yl]-N-(quinoline-5-sulfonyl)cyclopropane-1-carboxamide;
1-(5-chloro-2-fluoropyridin-3-yl)-N-(quinoline-5-sulfonyl)cyclopropane-1-carboxamide;
1-{5-(hydroxymethyl)-2-[(propan-2-yl)oxy]pyridin-3-yl}-N-(quinoline-5-sulfonyl)cyclopropane-1-carboxamide;
1-[5-cyclopropyl-2-(4-methylpiperazin-1-yl)pyridin-3-yl]-N-(1H-indole-4-sulfonyl)cyclopropane-1-carboxamide;
and pharmaceutically acceptable salts thereof.

Various embodiments of $A^1$, $R^1$, $R^2$, $R^3$, $R^4$, and n have been discussed above. These embodiments can be combined to form various embodiments of the invention. All embodiments of present compounds, formed by combining the substituent embodiments discussed above are within the scope of Applicant's invention.

Compounds of the invention were named using Name 2016.1.1 (File Version N30E41, Build 86668, 25 May, 2016) or Name 2017.2.1 (File Version N40E41, Build 96719, 6 Sep. 2017) naming algorithm by Advanced Chemical Development, Inc., or Struct=Name naming algorithm as part of CHEMDRAW® ULTRA v. 12.0.2.1076 or Professional Version 15.0.0.106.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of Formula (I), II, and III wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula (I), II, and III for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I), II, and III may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of Formula (I), (II), and (III) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Compounds of Formula (I), (II), and (III) may contain either a basic or an acidic functionality, or both, and can be converted to a pharmaceutically acceptable salt, when desired, by using a suitable acid or base. The salts may be prepared in situ during the final isolation and purification of the compounds of the invention.

The term "pharmaceutically acceptable prodrug" or "prodrug", as used herein, refers to derivatives of the compounds of the invention which have cleavable groups. Such derivatives become, by solvolysis or under physiological conditions, the compounds of the invention which are pharmaceutically active in vivo. Prodrugs of the compounds of the invention are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of Formula (I), (II), and (III) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

When employed as a pharmaceutical, a compound of the invention is typically administered in the form of a pharmaceutical composition that comprise a therapeutically effective amount of a compound of Formula (I), (II), (III), or a pharmaceutically acceptable salt thereof, together with a pharmaceutically acceptable carrier. The phrase "pharmaceutical composition" refers to a composition suitable for administration in medical or veterinary use. The term "pharmaceutically acceptable carrier" as used herein, means a non-toxic, inert solid, semi-solid or liquid filler, diluent, encapsulating material or formulation auxiliary of any type.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject.

Compounds of the invention are useful as modulators of CFTR. Thus, the compounds and compositions are particularly useful for treating or lessening the severity or progression of a disease, disorder, or condition where hyperactivity or inactivity of CFTR is involved. Accordingly, the invention provides a method for treating cystic fibrosis in a subject, wherein the method comprises the step of administering to said subject a therapeutically effective amount of a compound of Formula (I), (II), or (III) or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

In another embodiment, the present invention provides compounds of the invention, or pharmaceutical compositions comprising a compound of the invention for use in medicine. In a particular embodiment, the present invention provides compounds of the invention, or a pharmaceutically acceptable salt thereof, or a pharmaceutical composition comprising a compound of the invention, for use in medicine. In a particular embodiment, the present invention provides compounds of the invention or pharmaceutical compositions comprising a compound of the invention, for use in the treatment of cystic fibrosis. In a more particular embodiment, the cystic fibrosis is caused by a Class I, II, III, IV, V, and/or VI mutation.

One embodiment is directed to the use of a compound according to Formula (I), (II) or (III), or a pharmaceutically acceptable salt thereof, in the preparation of a medicament. The medicament optionally can comprise one or more additional therapeutic agents. In some embodiments, the medicament is for use in the treatment of cystic fibrosis. In a more particular embodiment, the cystic fibrosis is caused by a Class I, II, III, IV, V, and/or VI mutation.

This invention also is directed to the use of a compound according to Formula (I), (II) or (III), or a pharmaceutically acceptable salt thereof, in the manufacture of a medicament for the treatment of cystic fibrosis. The medicament optionally can comprise one or more additional therapeutic agents. In a particular embodiment, the invention is directed to the use of a compound according to Formula (I), (II) or (III), or a pharmaceutically acceptable salt thereof, in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention, or a pharmaceutically acceptable salt thereof, and one or more additional therapeutic agents. In another embodiment, the present invention provides pharmaceutical compositions comprising a compound of the invention, or a pharmaceutically acceptable salt thereof, and one or more additional therapeutic agents wherein the additional therapeutic agents are selected from the group consisting of CFTR modulators and CFTR amplifiers. In another embodiment, the present invention provides pharmaceutical compositions comprising a compound of the invention, or a pharmaceutically acceptable salt thereof, and one or more additional therapeutic agents wherein the additional therapeutic agents are CFTR modulators.

The present compounds or pharmaceutically acceptable salts thereof may be administered as the sole active agent or it may be co-administered with other therapeutic agents, including other compounds or a pharmaceutically acceptable salt thereof that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers.

In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulator. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered two correctors. In one embodiment, the compounds of the invention or pharmaceutically acceptable salts thereof may be co-administered with one or more correctors, and one amplifier. In one embodiment, the compounds of the invention or pharmaceutically acceptable salts thereof may be co-administered with one corrector, and one amplifier. In one embodiment, the compounds of the invention or pharmaceutically acceptable salts thereof may be co-administered with two correctors, and one amplifier. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), GLPG2451, GLPG1837, CTP-656, NVS-QBW251, FD1860293, PTI-808, N-(3-carbamoyl-5,5,7,7-tetramethyl-5,7-dihydro-4H-thieno[2,3-c]
pyran-2-yl)-1H-pyrazole-5-carboxamide, and 3-amino-N-
[(2S)-2-hydroxypropyl]-5-{[4-(trifluoromethoxy)phenyl]
sulfonyl}pyridine-2-carboxamide. Examples of potentiators
are also disclosed in publications: WO2005120497,
WO2008147952, WO2009076593, WO2010048573,
WO2006002421, WO2008147952, WO2011072241,
WO2011113894, WO2013038373, WO2013038378,
WO2013038381, WO2013038386, WO2013038390,
WO2014/180562, WO2015018823, WO2016193812 and
WO2017208115.

In one embodiment, the potentiator can be selected from the group consisting of

Ivacaftor (VX-770, N-(2,4-di-tert-butyl-5-hydroxyphenyl)-4-oxo-1,4-dihydroquinoline-3-carboxamide);
GLPG2451;
GLPG1837,
CTP-656;
NVS-QBW251;
FD1860293;
PTI-808;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide;
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;
2-[[(2R)-2-hydroxy-3,3-dimethyl-butanoyl]amino]-5,5,7,7-tetramethyl-4H-thieno[2,3-c]pyran-3-carboxamide;
2-[(2-hydroxy-2,3,3-trimethyl-butanoyl)amino]-5,5,7,7-tetramethyl-4H-thieno[2,3-c]pyran-3-carboxamide;
[5-[(3-carbamoyl-5,5,7,7-tetramethyl-4H-thieno[2,3-c]pyran-2-yl)carbamoyl]pyrazol-1-yl]methyl dihydrogen phosphate;
[3-[(3-carbamoyl-5,5,7,7-tetramethyl-4H-thieno[2,3-c]pyran-2-yl)carbamoyl]pyrazol-1-yl]methyl dihydrogen phosphate;
N-(3-carbamoyl-5,5,7,7-tetramethyl-4H-thieno[2,3-c]pyran-2-yl)-4-(1,4-dioxan-2-yl)-1H-pyrazole-3-carboxamide;
5,5,7,7-tetramethyl-24[(2S)-3,3,3-trifluoro-2-hydroxy-2-methyl-propanoyl]aminol-4H-thieno[2,3-c]pyran-3-carboxamide;
2-[[(2S)-2-hydroxypropanoyl]aminol-5,5,7,7-tetramethyl-4H-thieno[2,3-c]pyran-3-carboxamide;
3-amino-N-(2-hydroxy-2-methylpropyl)-5-{[4-(trifluoromethoxy)phenyl]sulfonyl}pyridine-2-carboxamide;
3-amino-N4(4-hydroxy-1-methylpiperidin-4-yl)methyl]-5-{[4-(trifluoromethoxy)phenyl]sulfonyl}pyridine-2-carboxamide;
3-amino-N-(3-hydroxy-2,2-dimethylpropyl)-5-{[4-(trifluoromethoxy)phenyl]sulfonyl}pyridine-2-carboxamide;
3-amino-5-[(4-fluorophenyl)sulfonyl]-N-[(1-hydroxycyclopropyl)methyl]pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-5-[(3-fluorophenyl)sulfonyl]-N-(2-hydroxy-2-methylpropyl)pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(azetidin-1-yl)methanone;
(3-amino-5-{[4-(trifluoromethoxy)phenyl]sulfonyl}pyridin-2-yl)[3-(hydroxymethyl)azetidin-1-yl]methanone;
(3-amino-5-{[4-(trifluoromethoxy)phenyl]sulfonyl}pyridin-2-yl)(3-fluoroazetidin-1-yl)methanone;
3-amino-N-[(2R)-2-hydroxy-3-methoxypropyl]-5-{[4-(trifluoromethyl)phenyl]sulfonyl}pyridine-2-carboxamide;

(3-amino-5-{[2-fluoro-4-(trifluoromethoxy)phenyl]
  sulfonyl}pyridin-2-yl)(3-hydroxyazetidin-1-yl)metha-
  none;
(3-amino-5-{[2-(trifluoromethoxy)phenyl]
  sulfonyl}pyridin-2-yl)(3,3-difluoroazetidin-1-yl)metha-
  none;
rac-3-amino-N-[(3R,4S)-4-hydroxytetrahydro-2H-pyran-3-
  yl]-5-{[2-(trifluoromethoxy)phenyl]sulfonyl}pyridine-2-
  carboxamide;
3-amino-5-[(4,4-difluoropiperidin-1-yl)sulfonyl]-N-(3,3,3-
  trifluoro-2-hydroxypropyl)pyridine-2-carboxamide;
(3-amino-5-{[2-(trifluoromethoxy)phenyl]
  sulfonyl}pyridin-2-yl)[3-hydroxy-3-(trifluoromethyl)
  azetidin-1-yl]methanone;
3-amino-N-(2-hydroxy-4-methylpentyl)-5-{[4-(trifluo-
  romethoxy)phenyl]sulfonyl}pyridine-2-carboxamide;
(3-amino-5-{[4-(trifluoromethyl)phenyl]sulfonyl}pyridin-
  2-yl)(3-hydroxy-3-methylazetidin-1-yl)methanone;
3-amino-N-(3,3,3-trifluoro-2-hydroxypropyl)-5-{[4-(trif-
  luoromethyl)piperidin-1-yl]sulfonyl}pyridine-2-carbox-
  amide;
3-amino-N-[2-hydroxy-1-(4-methoxyphenyl)ethyl]-5-{[4-
  (trifluoromethoxy)phenyl]sulfonyl}pyridine-2-carbox-
  amide;
3-amino-5-[(3,3-difluoroazetidin-1-yl)sulfonyl]-N-(3,3,3-
  trifluoro-2-hydroxypropyl)pyridine-2-carboxamide;
3-amino-5-{[2-fluoro-4-(trifluoromethyl)phenyl]sulfonyl}-
  N-[(2S)-2-hydroxypropyl]pyridine-2-carboxamide;
3-amino-5-{[2-fluoro-4-(trifluoromethyl)phenyl]sulfonyl}-
  N-[(2R)-2-hydroxy-3-methoxypropyl]pyridine-2-carbox-
  amide;
3-amino-N-[2-oxo-2-(propan-2-ylamino)ethyl]-5-{[4-(trif-
  luoromethyl)phenyl]sulfonyl}pyridine-2-carboxamide;
(3-amino-5-{[4-(trifluoromethyl)phenyl]sulfonyl}pyridin-
  2-yl) [3-hydroxy-3-(trifluoromethyl)azetidin-1-yl]metha-
  none;
3-amino-5-{[2-fluoro-4-(trifluoromethyl)phenyl]sulfonyl}-
  N-[(3R)-tetrahydrofuran-3-ylmethyl]pyridine-2-carbox-
  amide;
(3-amino-5-{[2-fluoro-4-(trifluoromethyl)phenyl]
  sulfonyl}pyridin-2-yl)[3-hydroxy-3-(trifluoromethyl)
  azetidin-1-yl]methanone;
3-amino-5-{[2-fluoro-4-(trifluoromethyl)phenyl]sulfonyl}-
  N-[(3S)-tetrahydrofuran-3-ylmethyl]pyridine-2-carbox-
  amide;
3-amino-5-{[2-fluoro-4-(trifluoromethoxy)phenyl]sulfo-
  nyl}-N-[(3S)-tetrahydrofuran-3-ylmethyl]pyridine-2-car-
  boxamide;
3-amino-N-[2-hydroxy-3-(2,2,2-trifluoroethoxy)propyl]-5-
  {[4-(trifluoromethyl)phenyl]sulfonyl}pyridine-2-carbox-
  amide;
3-amino-N-(3-tert-butoxy-2-hydroxypropyl)-5-{[2-fluoro-
  4-(trifluoromethyl)phenyl]sulfonyl}pyridine-2-carbox-
  amide;
[3-amino-5-(phenylsulfonyl)pyridin-2-yl][3-hydroxy-3-(tri-
  fluoromethyl)azetidin-1-yl]methanone;
{3-amino-5-[(3-fluorophenyl)sulfonyl]pyridin-2-yl}[3-hy-
  droxy-3-(trifluoromethyl)azetidin-1-yl]methanone; and
3-amino-N-[(2S)-2-hydroxypropyl]-5-{[4-(trifluo-
  romethoxy)phenyl]sulfonyl}pyridine-2-carboxamide.
  Non-limiting examples of correctors include Lumacaftor
(VX-809), 1-(2,2-difluoro-1,3-benzodioxol-5-yl)-N-{1-
[(2R)-2,3-dihydroxypropyl]-6-fluoro-2-(1-hydroxy-2-meth-
ylpropan-2-yl)-1H-indol-5-yl}cyclopropanecarboxamide
(VX-661), VX-983, GLPG2222, GLPG2665, GLPG2737,
GLPG2851, GLPG3221, PTI-801, VX-152, VX-440,
VX-659, VX-445, FDL169, FDL304, FD2052160, and FD2035659. Examples of correctors are also disclosed in
U.S. application Ser. Nos. 14/925,649, 14/926,727, 15/205,
512, 15/496,094, 15/287,922, 15/287,911, 15/723,896 and
15/726,075.
  In one embodiment, the corrector(s) can be selected from
the group consisting of
  Lumacaftor (VX-809);
  1-(2,2-difluoro-1,3-benzodioxol-5-yl)-N-{1-[(2R)-2,3-dihy-
    droxypropyl]-6-fluoro-2-(1-hydroxy-2-methylpropan-2-
    yl)-1H-indol-5-yl}cyclopropanecarboxamide (VX-661);
  VX-983;
  GLPG2665;
  GLPG2737;
  GLPG3221;
  PTI-801;
  VX-152;
  VX-440;
  VX-659;
  VX-445
  FDL169
  FDL304;
  FD2052160;
  FD2035659;
  3-[(2R,4R)-4-({[1-(2,2-difluoro-1,3-benzodioxol-5-yl)cy-
    clopropyl]carbonyl}amino)-7-methoxy-3,4-dihydro-2H-
    chromen-2-yl]benzoic acid;
  3-[(2R,4R)-4-({[1-(2,2-difluoro-1,3-benzodioxol-5-yl)cy-
    clopropyl]carbonyl}amino)-3,4-dihydro-2H-chromen-2-
    yl]benzoic acid;
  3-[(2R,4R)-4-({[1-(2,2-difluoro-1,3-benzodioxol-5-yl)cy-
    clopropyl]carbonyl}amino)-6-methyl-3,4-dihydro-2H-
    chromen-2-yl]benzoic acid;
  3-[(2R,4R)-4-({[1-(2,2-difluoro-1,3-benzodioxol-5-yl)cy-
    clopropyl]carbonyl}amino)-7-methyl-3,4-dihydro-2H-
    chromen-2-yl]benzoic acid;
  3-[(2R,4R)-4-({[1-(2,2-difluoro-1,3-benzodioxol-5-yl)cy-
    clopropyl]carbonyl}amino)-6-methoxy-3,4-dihydro-2H-
    chromen-2-yl]benzoic acid;
  3-[(2R,4R)-4-({[1-(2,2-difluoro-1,3-benzodioxol-5-yl)cy-
    clopropyl]carbonyl}amino)-7-(difluoromethoxy)-3,4-di-
    hydro-2H-chromen-2-yl]cyclohexanecarboxylic acid;
  3-[(2R,4R)-4-({[1-(2,2-difluoro-1,3-benzodioxol-5-yl)cy-
    clopropyl]carbonyl}amino)-7-(difluoromethoxy)-3,4-di-
    hydro-2H-chromen-2-yl]benzoic acid;
  3-[(2R,4R)-4-({[1-(2,2-difluoro-1,3-benzodioxol-5-yl)cy-
    clopropyl]carbonyl}amino)-7-methoxy-3,4-dihydro-2H-
    chromen-2-yl]cyclohexanecarboxylic acid;
  3-[(2R,4R)-4-({[1-(2,2-difluoro-1,3-benzodioxol-5-yl)cy-
    clopropyl]carbonyl}amino)-7-fluoro-3,4-dihydro-2H-
    chromen-2-yl]benzoic acid;
  3-({3-[(2R,4R)-4-({[1-(2,2-difluoro-1,3-benzodioxol-5-yl)
    cyclopropyl]carbonyl}amino)-7-methyl-3,4-dihydro-2H-
    chromen-2-yl]benzoyl}amino)-1-methylcyclopentan-
    ecarboxylic acid;
  3-[(2R,4R)-4-({[1-(2,2-difluoro-1,3-benzodioxol-5-yl)cy-
    clopropyl]carbonyl}amino)-7-methyl-3,4-dihydro-2H-
    chromen-2-yl]-N-[(2R)-2,3-dihydroxypropyl]benzamide;
  3-[(2R,4R)-4-({[1-(2,2-difluoro-1,3-benzodioxol-5-yl)cy-
    clopropyl]carbonyl}amino)-7-(2-methoxyethoxy)-3,4-di-
    hydro-2H-chromen-2-yl]benzoic acid;
  3-[(2R,4R)-7-(benzyloxy)-4-({[1-(2,2-difluoro-1,3-benzo-
    dioxol-5-yl)cyclopropyl]carbonyl}amino)-3,4-dihydro-
    2H-chromen-2-yl]benzoic acid;
  3-[(2R,4R)-4-({[1-(2,2-difluoro-1,3-benzodioxol-5-yl)cy-
    clopropyl]carbonyl}amino)-7-(2-fluoroethoxy)-3,4-di-
    hydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl]benzoic acid;

4-[6-(4-cyanopiperidin-1-yl)pyridin-3-yl]-3-cyclobutyl-N-(methane sulfonyl)-1-phenyl-1H-pyrazolo[3,4-b]pyridine-6-carboxamide;

3-cyclobutyl-N-(methane sulfonyl)-4-[4-(methoxymethyl)piperidin-1-yl]-1-phenyl-1H-pyrazolo[3,4-b]pyridine-6-carboxamide;

4-[6-(4-cyanopiperidin-1-yl)pyridin-3-yl]-3-cyclobutyl-N-(methane sulfonyl)-1-[2-(morpholin-4-yl)pyridin-4-yl]-1H-pyrazolo[3,4-b]pyridine-6-carboxamide;

N-(methanesulfonyl)-4-[4-(methoxymethyl)piperidin-1-yl]-1-[2-(morpholin-4-yl)pyridin-4-yl]-3-(propan-2-yl)-1H-pyrazolo[3,4-b]pyridine-6-carboxamide;

3-cyclobutyl-4-[4-(methoxymethyl)piperidin-1-yl]-N-[2-(morpholin-4-yl)ethanesulfonyl]-1-phenyl-1H-pyrazolo[3,4-b]pyridine-6-carboxamide;

3-cyclobutyl-N-[2-(dimethylamino)ethane sulfonyl]-4-[4-(methoxymethyl)piperidin-1-yl]-1-phenyl-1H-pyrazolo[3,4-b]pyridine-6-carboxamide;

1-(4-fluorophenyl)-N-(methane sulfonyl)-4-(1'-methyl[4,4'-bipiperidin]-1-yl)-3-(propan-2-yl)-1H-pyrazolo[3,4-b]pyridine-6-carboxamide;

3-cyclobutyl-N-(methane sulfonyl)-4-{4-[2-(morpholin-4-yl)ethyl]piperidin-1-yl}-1-phenyl-1H-pyrazolo[3,4-b]pyridine-6-carboxamide;

3-cyclobutyl-4-[4-(methoxymethyl)piperidin-1-yl]-N-(oxolane-3-sulfonyl)-1-phenyl-1H-pyrazolo[3,4-b]pyridine-6-carboxamide;

3-cyclobutyl-N-(dimethylsulfamoyl)-1-(4-fluorophenyl)-4-(4-methoxy[1,4'-bipiperidin]-1'-yl)-1H-pyrazolo[3,4-b]pyridine-6-carboxamide;

3-cyclobutyl-N-(morpholine-4-sulfonyl)-4-[4-(morpholin-4-yl)piperidin-1-yl]-1-phenyl-1H-pyrazolo[3,4-b]pyridine-6-carboxamide;

3-cyclobutyl-N-(morpholine-4-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(methane sulfonyl)-4-[4-(morpholin-4-yl)piperidin-1-yl]-1-phenyl-1H-pyrazolo[3,4-b]pyridine-6-carboxamide;

3-cyclobutyl-4-[4-(morpholin-4-yl)piperidin-1-yl]-1-phenyl-1H-pyrazolo[3,4-b]pyridine-6-carboxylic acid;

3-cyclobutyl-1-phenyl-4-{4-[(pyrrolidin-1-yl)methyl]piperidin-1-yl}-1H-pyrazolo[3,4-b]pyridine-6-carboxylic acid;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl]

amino}-7-methoxy-3,4-dihydro-2H-1-benzopyran-2-yl]cyclohexane-1-carboxylic acid;

trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

4-{(2R,4R)-4-[2-(2,2-difluoro-2H-1,3-benzodioxol-5-yl)-2-methylpropanamido]-7-methoxy-3,4-dihydro-2H-1-benzopyran-2-yl}benzoic acid;

4-[(2R,4R)-4-{[1-(3,4-dichlorophenyl)cyclopropane-1-carbonyl]amino}-7-methoxy-3,4-dihydro-2H-1-benzopyran-2-yl]benzoic acid;

4-[(2R,4R)-4-{[1-(4-bromophenyl)cyclopropane-1-carbonyl]amino}-7-methoxy-3,4-dihydro-2H-1-benzopyran-2-yl]benzoic acid;

4-[(2R,4R)-7-methoxy-4-({1-[4-(trifluoromethyl)phenyl]cyclopropane-1-carbonyl}amino)-3,4-dihydro-2H-1-benzopyran-2-yl]benzoic acid;

4-[(2R,4R)-7-methoxy-4-{[1-(4-methylphenyl)cyclopropane-1-carbonyl]amino}-3,4-dihydro-2H-1-benzopyran-2-yl]benzoic acid;

4-{(2R,4R)-4-[(1,5-dimethyl-2,3-dihydro-1H-indene-1-carbonyl)amino]-7-methoxy-3,4-dihydro-2H-1-benzopyran-2-yl}benzoic acid;

3-[(2R,4R)-4-{[(1S)-1,5-dimethyl-2,3-dihydro-1H-indene-1-carbonyl]amino}-7-methoxy-3,4-dihydro-2H-1-benzopyran-2-yl]benzoic acid;

4-[(2R,4R)-4-{[(1S)-1,5-dimethyl-2,3-dihydro-1H-indene-1-carbonyl]amino}-7-methoxy-3,4-dihydro-2H-1-benzopyran-2-yl]benzoic acid;

trans-4-[(2R,4R)-4-{[1-(2,2-difluoro-2H-1,3-benzodioxol-5-yl)cyclopropane-1-carbonyl]amino}-7-methoxy-3,4-dihydro-2H-1-benzopyran-2-yl]cyclohexane-1-carboxylic acid;

trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylic acid; and 4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylic acid.

In one embodiment, the additional therapeutic agent is a CFTR amplifier. CFTR amplifiers enhance the effect of known CFTR modulators, such as potentiators and correctors. Examples of CFTR amplifiers include PTI130 and PTI-428. Examples of amplifiers are also disclosed in International Patent Publication Nos.: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is cavosonstat (N91115). Examples of stabilizers are also disclosed in International Patent Publication No.: WO2012048181.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in International Patent Publication Nos.: WO2009074575 and WO2013043720; and U.S. Pat. No. 8,999,976.

In one embodiment, the ENaC inhibitor is VX-371.

In one embodiment, the ENaC inhibitor is SPX-101 (S18).

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

General Synthesis

The compounds of the present disclosure can be better understood in connection with the following synthetic schemes and methods which illustrate a means by which the compounds can be prepared.

The compounds of this disclosure can be prepared by a variety of synthetic procedures. Representative procedures are shown in, but are not limited to, Schemes 1-4. In Schemes 1-4, the variables $A^1$, $R^1$, $R^2$, $R^3$, $R^4$, and n are is as described in the Summary, or they represent a moiety that can be converted to one of said groups using chemical transformations known to one of skill in the art.

Schemes

Scheme 1

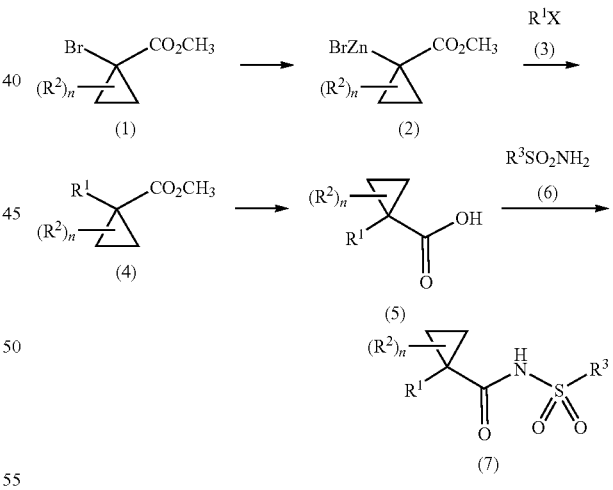

Scheme 1 describes the synthesis of compounds of formula (7) from compounds of formula (1). Compounds of formula (1), wherein $R^2$ and n are as described herein, can be treated with a zinc slurry containing a mixture of indium (III) chloride, zinc and bromine to provide organozinc compounds of formula (2). The reaction is typically performed under nitrogen at ambient temperature in a solvent such as, but not limited to tetrahydrofuran, before increasing to an elevated temperature after the addition.

Compounds of formula (4) can be prepared by reacting compounds of formula (3) wherein $R^1$ is as described herein and X is I, Br, Cl or triflate, with organozinc compounds of formula (2) under Negishi coupling conditions known to those skilled in the art and widely available in the literature. The reaction typically requires the use of a palladium or nickel catalyst, and may require the use of a ligand. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IPentCl), tetrakis(triphenylphosphine)nickel(0), tetrakis(triphenylphosphine)palladium(0), bis(triphenylphosphine) palladium(II) dichloride, [1,1'-bis(diphenylphosphino) ferrocene]dichloropalladium(II) dichloromethane, tris (dibenzylideneacetone)dipalladium(0), and palladium(II) acetate. Examples of ligands include, but are not limited to, triphenylphosphine, 1,2-bis(diphenylphosphino)ethane (dppe), 2,2'-bis(diphenylphosphino)-1,1'-binaphthyl (BINAP), Chiraphos, and 1,2,3,4,5-pentaphenyl-1'-(di-tert-butylphosphino)ferrocene. The reaction may be conducted in a solvent such as, but not limited to, water, dioxane, 1-methyl-2-pyrrolidinone, N,N-dimethylacetamide, 1,2-dimethoxyethane, N,N-dimethylformamide, toluene, ethanol, tetrahydrofuran and the like, or mixtures thereof. The reaction may be conducted at ambient or elevated temperatures, and optionally in a microwave oven.

Esters of formula (4) can be hydrolyzed in an aqueous hydroxide solution to provide compounds of formula (5). The reaction is typically performed in a solvent such as, but not limited to, methanol, tetrahydrofuran, or mixtures thereof, and may be performed at ambient temperature or an elevated temperature.

Carboxylic acids of formula (5) can be coupled with sulfonamides of formula (6), wherein $R^3$ is as described herein, to provide compounds of formula (7), which are representative of compounds of Formula (I). Examples of conditions known to generate compounds of formula (7) from a mixture of a carboxylic acid and a sulfonamide include, but are not limited to, adding a coupling reagent such as, but not limited to, N-(3-dimethylaminopropyl)-N-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-ylmethylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), 0-(benzotriazol-1-yl)-N,N,N',N'-tetramethyluronium tetrafluoroborate (TB TU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino) pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or an elevated temperature. The heating can be accomplished either conventionally or with microwave irradiation.

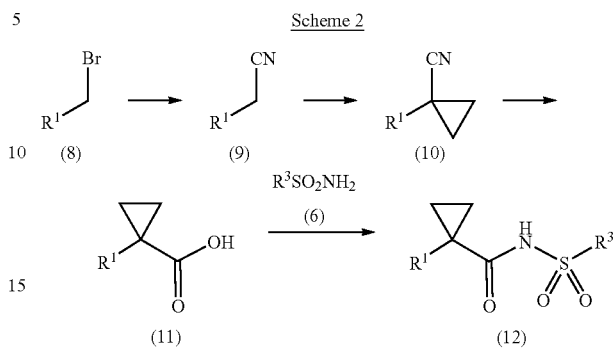

As shown in Scheme 2, compounds of formula (12) can be prepared from compounds of formula (8). Compounds of formula (8), wherein $R^1$ is as described herein, can be treated with an aqueous solution of sodium cyanide to provide compounds of formula (9). The reaction is typically performed at an elevated temperature in a solvent such as, but not limited to, ethanol.

Compounds of formula (10) can be prepared by reacting compounds of formula (9) with a strong base such as, but not limited to sodium hydride, followed by 1,2-dibromoethane. The reaction is typically performed at ambient temperature in a solvent such as, but not limited to, N,N-dimethylformamide.

Compounds of formula (10) can be treated with a strong acid or a strong base such as sodium or lithium hydroxide to provide compounds of formula (11). The reaction is typically performed at an elevated temperature in a solvent such as, but not limited to, ethanol.

Carboxylic acids of formula (11) can be coupled with sulfonamides of formula (6) as described in Scheme 1, wherein $R^3$ is as described herein, to provide compounds of formula (12), which are representative of compounds of Formula (I).

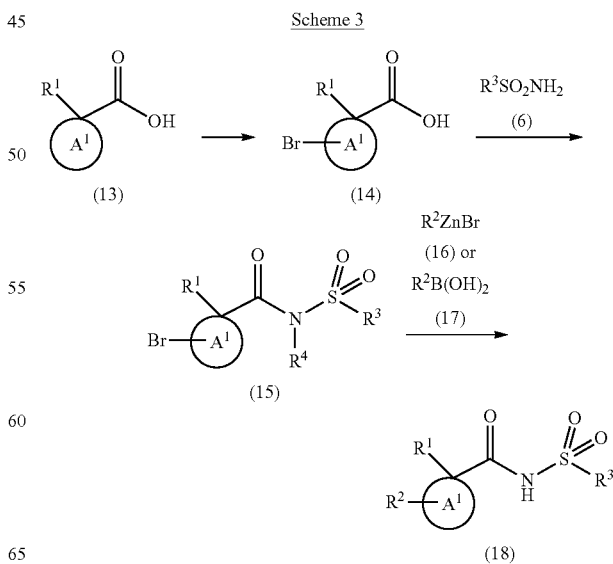

Scheme 3 describes the synthesis of compounds of formula (18) from compounds of formula (13). Compounds of formula (13), wherein R' and A' are as described herein, can be treated with N-bromosuccinimide to provide compounds of formula (14). The reaction is typically performed at ambient temperature in a solvent such as, but not limited to, dichloromethane.

Carboxylic acids of formula (14) can be coupled with sulfonamides of formula (6) as described in Scheme 1, wherein $R^3$ is as described herein, to provide compounds of formula (1S).

Compounds of formula (18), which are representative of compounds of Formula (I), can be prepared by reacting compounds of formula (1S) with organozinc compounds of formula (16), wherein $R^2$ is as described herein, under Negishi coupling conditions known to those skilled in the art and widely available in the literature. The reaction typically requires the use of a palladium or nickel catalyst, and may require the use of a ligand. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IPentCl), tetrakis(triphenylphosphine)nickel(0), tetrakis(triphenylphosphine)palladium(0), bis(triphenylphosphine)palladium(II) dichloride, [1,1'-bis(diphenylphosphino)ferrocene]dichloropalladium(II) dichloromethane, tris(dibenzylideneacetone)dipalladium(0), and palladium(II) acetate. Examples of ligands include, but are not limited to, triphenylphosphine, 1,2-bis(diphenylphosphino)ethane (dppe), 2,2'-bis(diphenylphosphino)-1,1'-binaphthyl (BINAP), Chiraphos, and 1,2,3,4,5-pentaphenyl-1-(di-tert-butylphosphino)ferrocene. The reaction may be conducted in a solvent such as, but not limited to, water, dioxane, 1-methyl-2-pyrrolidinone, N,N-dimethylacetamide, 1,2-dimethoxyethane, N,N-dimethylformamide, toluene, ethanol, tetrahydrofuran and the like, or mixtures thereof. The reaction may be conducted at ambient or elevated temperatures, and optionally in a microwave oven.

Alternatively, compounds of formula (18) can be prepared by reacting compounds of formula (1S) with boronic acid compounds of formula (17), wherein $R^2$ is as described herein (or the boronic ester equivalents), under Suzuki coupling conditions known to those skilled in the art and widely available in the literature. The reaction typically requires the use of a base and a catalyst. Examples of bases include, but are not limited to, potassium carbonate, potassium t-butoxide, sodium carbonate, cesium carbonate, and cesium fluoride. Examples of catalysts include, but are not limited to, tetrakis(triphenylphosphine)palladium(0), [1,1'-bis(diphenylphosphino)ferrocene]dichloropalladium(II) dichloromethane, bis(triphenylphosphine)palladium(II) dichloride, and tris(dibenzylideneacetone)dipalladium(0). The reaction may be conducted in a solvent such as, but not limited to, water, dioxane, 1,2-dimethoxyethane, N,N-dimethylformamide, toluene, ethanol, tetrahydrofuran and the like or mixtures thereof. The reaction may be conducted at ambient or elevated temperatures, and optionally in a microwave oven.

Scheme 4

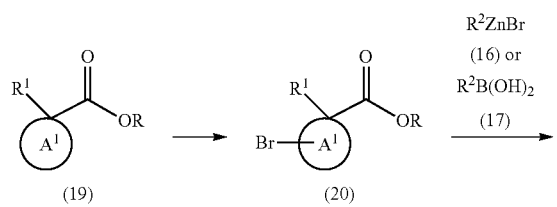

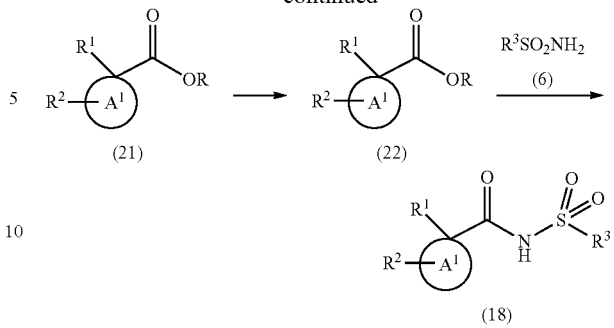

As described in Scheme 4, compounds of formula (19), wherein $A^1$ and R' are as described herein, and R is an alkyl group, can be treated with benzyltrimethylammonium tribromide to provide compounds of formula (20). The reaction is typically performed at ambient temperature in a solvent such as, but not limited to, tetrahydrofuran, water, or mixtures thereof.

Compounds of formula (21) can be prepared by reacting compounds of formula (20) with organozinc compounds of formula (16), wherein $R^2$ is as described herein, under Negishi coupling conditions known to those skilled in the art and widely available in the literature. The reaction typically requires the use of a palladium or nickel catalyst, and may require the use of a ligand. Examples of catalysts include, but are not limited to, dichloro[4,5-dichloro-1,3-bis(2,6-di-3-pentylphenyl)imidazol-2-ylidene](3-chloropyridyl)palladium(II) (PEPPSI-IPentCl), tetrakis(triphenylphosphine)nickel(0), tetrakis(triphenylphosphine)palladium(0), bis(triphenylphosphine)palladium(II) dichloride, [1,1'-bis(diphenylphosphino)ferrocene]dichloropalladium(II) dichloromethane, tris(dibenzylideneacetone)dipalladium(0), and palladium(II) acetate. Examples of ligands include, but are not limited to, triphenylphosphine, 1,2-bis(diphenylphosphino)ethane (dppe), 2,2'-bis(diphenylphosphino)-1,1'-binaphthyl (BINAP), Chiraphos, and 1,2,3,4,5-pentaphenyl-1'-(di-tert-butylphosphino)ferrocene. The reaction may be conducted in a solvent such as, but not limited to, water, dioxane, 1-methyl-2-pyrrolidinone, N,N-dimethylacetamide, 1,2-dimethoxyethane, N,N-dimethylformamide, toluene, ethanol, tetrahydrofuran and the like, or mixtures thereof. The reaction may be conducted at ambient or elevated temperatures, and optionally in a microwave oven.

Alternatively, compounds of formula (21) can be prepared by reacting compounds of formula (20) with boronic acid compounds of formula (17), wherein $R^2$ is as described herein (or the boronic ester equivalents), under Suzuki coupling conditions known to those skilled in the art and widely available in the literature. The reaction typically requires the use of a base and a catalyst. Examples of bases include, but are not limited to, potassium carbonate, potassium t-butoxide, sodium carbonate, cesium carbonate, and cesium fluoride. Examples of catalysts include, but are not limited to, tetrakis(triphenylphosphine)palladium(0), [1,1'-bis(diphenylphosphino)ferrocene]dichloropalladium(II) dichloromethane, bis(triphenylphosphine)palladium(II) dichloride, and tris(dibenzylideneacetone)dipalladium(0). The reaction may be conducted in a solvent such as, but not limited to, water, dioxane, 1,2-dimethoxyethane, N,N-dimethylformamide, toluene, ethanol, tetrahydrofuran and the like or mixtures thereof. The reaction may be conducted at ambient or elevated temperatures, and optionally in a microwave oven.

Esters of formula (21) can be hydrolyzed in an aqueous hydroxide solution to provide compounds of formula (22). The reaction is typically performed in a solvent such as, but not limited to, methanol, tetrahydrofuran, or mixtures thereof, and may be performed at ambient temperature or an elevated temperature.

Carboxylic acids of formula (22) can be coupled with sulfonamides of formula (6) as described in Scheme 1, wherein $R^3$ is as described herein, to provide compounds of formula (18), which are representative of compounds of Formula (I).

Chemical Synthetic Procedures

List of abbreviations used in the examples section: min for minute; DBU for 1,8-diazabicyclo[5.4.0]undec-7-ene; DCI for desorption chemical ionization; DMSO for dimethyl sulfoxide; EDCI for 1-(3-dimethylaminopropyl)-3-ethylcarbodiimide hydrochloride; ESI for electrospray ionization; HATU for 1-[bis(dimethylamino)methylene]-1H-1,2,3-triazolo[4,5-b]pyridinium 3-oxid hexafluorophosphate; HPLC for high performance liquid chromatography; MS for mass spectrometry; NMR for nuclear magnetic resonance; wt for weight, and UPLC for ultra performance liquid chromatography.

The compounds of the invention can be prepared from readily available starting materials using the following general methods and procedures. It will be appreciated that where typical or preferred process conditions (i.e. reaction temperatures, times, mole ratios of reactants, solvents, pressures, etc.) were given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Protective Groups in Organic Synthesis Third Edition; Greene, T W and Wuts, P G M, Eds.; Wiley-Interscience: New York, 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker Advance 300 NMR spectrometer (300 MHz), an Agilent 400 MHz NMR spectrometer, or a 500 MHz NMR. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), doublet of quartets (dq), triplet (t), quartet (q), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L, Waters Acquity UPLC BEH C18 1.7 μm, 2.1 mm ID×30 mm L, or Waters Xterra® MS 5 μm C18, 100×4.6 mm. The methods were using either CH$_3$CN/H$_2$O gradients (H$_2$O 2O contains either 0.1% CF$_3$CO$_2$H or 0.1% NH$_3$) or CH$_3$OH/H$_2$O gradients (H$_2$O contains 0.05% CF$_3$CO$_2$H). Microwave heating was performed with a Biotage® Initiator.

Reverse Phase Purification Methods

Trifluoroacetic Acid Method

Samples were purified by preparative HPLC on a Phenomenex® Luna® C8(2) 5 μm 100 Å AXIA™ column (30 mm×75 mm). A gradient of acetonitrile (A) and 0.1% trifluoroacetic acid in water (B) was used, at a flow rate of 50 mL/minute (0-1.0 minute 5% A, 1.0-8.5 minute linear gradient 5-100% A, 8.5-11.5 minute 100% A, 11.5-12.0 minute linear gradient 95-5% A).

Prep LC/MS Method TFA6

Samples were purified by reverse phase preparative HPLC on a Phenomenex® Luna® C8(2) 5 μm 100 Å AXIA™ column (50 mm×21.2 mm). A gradient of acetonitrile (A) and 0.1% trifluoroacetic acid in water (B) was used, at a flow rate of 40 mL/minute (0-0.5 minute 15% A, 0.5-8.0 minute linear gradient 15-100% A, 8.0-9.0 minute 100% A, 7.0-8.9 minute 100% A, 9.0-9.1 minute linear gradient 100-15% A, 9.1-10 minute 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Prep LC/MS Method TFA8

Samples were purified by reverse phase preparative HPLC on a Phenomenex® Luna® C8(2) 5 μm 100 Å AXIA™ column (50 mm×21.2 mm). A gradient of acetonitrile (A) and 0.1% trifluoroacetic acid in water (B) was used, at a flow rate of 40 mL/minute (0-0.5 minute 35% A, 0.5-8.0 minute linear gradient 35-100% A, 8.0-9.0 minute 100% A, 7.0-8.9 minute 100% A, 9.0-9.1 minute linear gradient 100-35% A, 9.1-10 minute 35% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Prep LC/MS Method TFA10

Samples were purified by reverse phase preparative HPLC on a Phenomenex® Luna® C8(2) 5 μm 100 Å AXIA™ column (50 mm×21.2 mm). A gradient of acetonitrile (A) and 0.1% trifluoroacetic acid in water (B) was used, at a flow rate of 30 mL/minute (0-0.2 minute 5% A, 0.2-3.0 minute linear gradient 5-100% A, 4.1-4.5 minute 100-5% A, 4.5-5.0 minute 5% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Prep LC/MS Method AA6

Samples were purified by reverse phase preparative HPLC on a Phenomenex® Luna® C8(2) 5 μm 100 Å AXIA™ column (50 mm×21.2 mm). A gradient of acetonitrile (A) and 0.1% ammonium acetate in water (B) was used, at a flow rate of 40 mL/minute (0-0.5 minute 15% A, 0.5-8.0 minute linear gradient 15-100% A, 8.0-9.0 minute 100% A, 7.0-8.9 minute 100% A, 9.0-9.1 minute linear gradient 100-15% A, 9.1-10 minute 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Prep LC/MS Method AA7

Samples were purified by reverse phase preparative HPLC on a Phenomenex® Luna® C8(2) 5 μm 100 Å AXIA™ column (50 mm×21.2 mm). A gradient of acetonitrile (A) and 0.1% ammonium acetate in water (B) was used, at a flow rate of 40 mL/minute (0-0.5 minute 25% A, 0.5-8.0 minute linear gradient 25-100% A, 8.0-9.0 minute 100% A, 7.0-8.9 minute 100% A, 9.0-9.1 minute linear gradient 100-25% A, 9.1-10 minute 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Example I-1

1-(5-bromo-2-methoxyphenyl)-N-(naphthalene-1-sulfonyl)cyclopropane-1-carboxamide Example I-1A (1-(methoxycarbonyl)cyclopropyl)zinc(II) bromide A 250-mL round bottom flask equipped with a magnetic stir bar under an atmosphere of nitrogen was treated with indium(III) chloride (0.323 g, 1.460 mmol) and acid washed zinc (7.32 g, 112 mmol) and then purged with nitrogen for several minutes. Tetrahydrofuran (70 mL) was added. Bromine (0.201 mL, 3.93 mmol) was added in a single portion resulting in a mild temperature increase. The mixture was warmed to 55° C. and stirred rapidly under a nitrogen atmosphere. In a separate flask, a solution of methyl 1-bromocyclopropanecarboxylate (6.54 mL, 56.2 mmol) in tetrahydrofuran (30 mL) was purged with nitrogen for 10 minutes. The mixture was added to the zinc slurry in a single portion via a cannula. The reaction was warmed at 55° C. for one hour. Using the titration method described in Knochel, P. Krasovskiy, A. *Synthesis* 2006-2006 (05), 0890-0891, the solution was determined to be 0.47 M and was used immediately in the next step.

Example I-1B methyl 1-(2-methoxyphenyl)cyclopropane-1-carboxylate

Into a 500 mL round bottom flask was added tris(dibenzylideneacetone)dipalladium(0) (0.086 g, 0.094 mmol), 1,2,3,4,5-pentaphenyl-1'-(di-tert-butylphosphino)ferrocene (0.133 g, 0.187 mmol) and tetrahydrofuran (144 mL) under nitrogen. 1-Bromo-2-methoxybenzene (2.313 mL, 18.71 mmol) was added and the resulting solution was treated with a 0.47 M solution of Example I-1A ((1-(methoxycarbonyl)cyclopropyl)zinc(II) bromide) (47.8 mL, 22.46 mmol) slowly over 10 minutes. The mixture was stirred at ambient temperature overnight. The reaction was quenched with saturated aqueous $NH_4Cl$ solution (50 mL) and extracted with ethyl acetate (200 mL). The organic layer was washed with saturated aqueous $NH_4Cl$ solution, dried over sodium sulfate, filtered, and concentrated. The crude residue was purified by chromatography on silica gel eluting with a gradient of 0-20% ethyl acetate in heptanes to provide the title compound. $^1$H NMR (400 MHz, $CDCl_3$) δ ppm 7.30-7.25 (m, 1H), 7.20 (dd, J=1.7, 7.5 Hz, 1H), 6.92 (dd, J=1.1, 7.5 Hz, 1H), 6.88 (d, J=8.3 Hz, 1H), 3.84 (s, 3H), 3.61 (d, J=0.8 Hz, 3H), 1.60 (q, J=3.9 Hz, 2H), 1.11 (q, J=4.1 Hz, 2H).

Example I-1C methyl 1-(5-bromo-2-methoxyphenyl)cyclopropane-1-carboxylate

A solution of Example I-1B (methyl 1-(2-methoxyphenyl)cyclopropanecarboxylate) (3.88 g, 18.81 mmol) and benzyltrimethylammonium tribromide (7.72 g, 19.80 mmol) in tetrahydrofuran (58.8 mL) and degassed water (35.3 mL) was stirred at ambient temperature for 16 hours. The mixture was concentrated in vacuo and the resulting aqueous residue was extracted with methyl tert-butyl ether (850 mL). The organic layer was dried ($Na_2SO_4$), filtered through a pad of silica gel and concentrated to give the title compound. $^1$H NMR (501 MHz, $CDCl_3$) δ ppm 7.38 (dd, J=8.7, 2.5 Hz, 1H), 7.32 (d, J=2.5 Hz, 1H), 6.77 (d, J=8.7 Hz, 1H), 3.84 (s, 3H), 3.63 (s, 3H), 1.64-1.61 (m, 2H), 1.14-1.09 (m, 2H).

Example I-1D 1-(5-bromo-2-methoxyphenyl)cyclopropane-1-carboxylic Acid

Example I-1C (48 mg, 0.17 mmol) was dissolved in tetrahydrofuran (600 μL) and methanol (600 μL), treated with 3 M aqueous NaOH (300 μL) and heated at 50° C. for three hours. The reaction mixture was allowed to cool to ambient temperature and was concentrated. The residue was partitioned between 1 M aqueous citric acid (2 mL) and methyl tert-butyl ether. The separated aqueous phase was extracted with additional methyl tert-butyl ether. The combined organic phases were washed with brine, dried (Na$_2$SO$_4$), filtered, and concentrated. The crude material was dissolved in methyl tert-butyl ether, washed twice with water and once with brine, dried (Na$_2$SO$_4$), filtered, and concentrated to provide the title compound. $^1$H NMR (500 MHz, dimethyl sulfoxide-d$_6$) δ ppm 7.40 (dd, J=8.7, 2.6 Hz, 1H), 7.31 (d, J=2.6 Hz, 1H), 6.93 (d, J=8.7 Hz, 1H), 3.77 (s, 3H), 1.41-1.38 (m, 2H), 1.06-1.03 (m, 2H). MS (ESI−) m/z 269/271 (M−H)$^-$.

Example I-1E 1-(5-bromo-2-methoxyphenyl)-N-(naphthalene-1-sulfonyl)cyclopropane-1-carboxamide To a solution of Example I-1D (1-(5-bromo-2-methoxyphenyl)cyclopropanecarboxylic acid) (43 mg, 0.16 mmol), 1-(3-dimethylaminopropyl)-3-ethylcarbodiimide hydrochloride (61 mg, 0.32 mmol) and 4-dimethylaminopyridine (22 mg, 0.18 mmol) in anhydrous dichloromethane (500 µL) was added naphthalene-1-sulfonamide (40 mg, 0.19 mmol). The mixture was stirred at ambient temperature for 16 hours and was purified by reverse-phase HPLC [Waters XBridge™ C18 5 µm OBD column, 30×100 mm, flow rate 40 mL/minute, 20 to 70% gradient of acetonitrile in 0.1% aqueous trifluoroacetic acid] to give the title compound. $^1$H NMR (501 MHz, dimethyl sulfoxide-d$_6$) δ ppm 11.67 (s, 1H), 8.54-8.50 (m, 1H), 8.28 (d, J=8.2 Hz, 1H), 8.24 (dd, J=7.4, 1.3 Hz, 1H), 8.13-8.09 (m, 1H), 7.70-7.66 (m, 3H), 7.43 (dd, J=8.7, 2.5 Hz, 1H), 7.26 (d, J=2.5 Hz, 1H), 6.81 (d, J=8.7 Hz, 1H), 3.27 (s, 3H), 1.25-1.22 (m, 2H), 0.99-0.96 (m, 2H). MS (ESI) m/z=460/462 (M+H)$^+$.

Example I-2

1-(5-cyclobutyl-2-methoxyphenyl)-N-(naphthalene-1-sulfonyl)cyclopropane-1-carboxamide Example I-1 (30 mg, 0.065 mmol, 1.0 eq) was dissolved in tetrahydrofuran (0.4 mL). PEPPSI IPentCl (dichloro[1,3-bis(2,6-di-3-pentylphenyl)imidazol-2-ylidene](3-chloropyridyl)palladium(II), 5.60 mg, 0.0065 mmol, 0.1 eq) in tetrahydrofuran (0.2 mL) was added, followed by the addition of cyclobutylzinc bromide (0.5 M in tetrahydrofuran, 0.4 mL, 0.2 mmol, 3.0 eq). The reaction was stirred for 16 hours at ambient temperature. The reaction was purified directly via preparative reverse phase HPLC/MS method trifluoroacetic acid8 to afford the title compound. $^1$H NMR (501 MHz, dimethyl sulfoxide-d$_6$) δ ppm 8.56-8.52 (m, 1H), 8.26-8.22 (m, 2H), 8.13-8.09 (m, 1H), 7.70-7.66 (m, 3H), 7.17-7.11 (m, 1H), 6.95 (d, J=2.3 Hz, 1H), 6.81 (d, J=8.5 Hz, 1H), 3.43 (p, J=8.8 Hz, 1H), 3.34 (s, 3H), 2.29-2.19 (m, 2H), 2.11-1.99 (m, 2H), 1.99-1.88 (m, 1H), 1.83-1.74 (m, 1H), 1.27-1.23 (m, 2H), 0.96-0.92 (m, 2H). MS (APCI) m/z 436.1 (M+H)$^+$.

Example I-3

1-(5-cyclobutyl-2-methoxypyridin-3-yl)-N-(2-methylquinoline-5-sulfonyl)cyclopropane-1-carboxamide Example I-3A 2-(5-cyclobutyl-2-methoxypyridin-3-yl)acetonitrile 3-(Bromomethyl)-5-cyclobutyl-2-methoxypyridine (3.6 g, 14.05 mmol) in ethanol (60 mL) was treated with a solution of sodium cyanide (0.758 g, 15.46 mmol) in water (6.00 mL). The mixture was stirred at 50° C. for one hour. The solvent was removed under reduced pressure. The residue was dissolved in dichloromethane and was washed with brine, dried over MgSO$_4$, filtered, and concentrated. The residue was purified via chromatography on a 50 g silica gel cartridge, eluting with ethyl acetate/methanol (9:1) in heptane using a 0-50% at gradient to provide the title compound. $^1$H NMR (501 MHz, chloroform-d) δ ppm 7.96 (dd, J=2.2, 0.8 Hz, 1H), 7.55 (dq, J=2.3, 0.8 Hz, 1H), 3.96 (s, 3H), 3.66 (t, J=0.8 Hz, 2H), 3.50 (dtdt, J=10.2, 9.5, 8.0, 0.8 Hz, 1H), 2.42-2.28 (m, 2H), 2.17-1.99 (m, 3H), 1.94-1.83 (m, 1H). MS (trifluoroacetic acid/APCI+) m/z 203 (M+H)$^+$.

Example I-3B 1-(5-cyclobutyl-2-methoxypyridin-3-yl)cyclopropanecarbonitrile

To 2-(5-cyclobutyl-2-methoxypyridin-3-yl)acetonitrile (2.5 g, 12.36 mmol) in N,N-dimethylformamide (25 mL) was added sodium hydride (1.483 g, 37.1 mmol) slowly and the resulting mixture was stirred at ambient temperature until the bubbling subsided. To the mixture was slowly added 1,2-dibromoethane (1.278 mL, 14.83 mmol) and stirring was continued at ambient temperature for one hour. Dichloromethane (50 mL) was added. The mixture was washed with brine, dried over MgSO$_4$, filtered, and concentrated. Purification via chromatography on a 25 g silica gel cartridge, eluting with ethyl acetate/methanol in hexane at 0-60%, provided the title compound. MS (APCI+) m/z 229 (M+H)$^+$.

Example I-3C 1-(5-cyclobutyl-2-methoxypyridin-3-yl)cyclopropanecarboxylic Acid

To 1-(5-cyclobutyl-2-methoxypyridin-3-yl)cyclopropanecarbonitrile (1.7 g, 7.45 mmol) in ethanol (10 mL) was added sodium hydroxide (2.5 g, 62.5 mmol) in water (10 mL) slowly and the resulting mixture was stirred at 90° C. for 16 hours. The solvent was removed and the residue was purified via chromatography on a 25 g cartridge, eluting with ethyl acetate/methanol (1:1) in hexane (0-60%) to provide the title compound. $^1$H NMR (501 MHz, chloroform-d) δ ppm 7.91 (dd, J=2.4, 0.8 Hz, 1H), 7.33 (dd, J=2.4, 0.6 Hz, 1H), 3.94 (s, 3H), 3.50-3.39 (m, 1H), 2.37-2.26 (m, 2H), 2.15-1.95 (m, 3H), 1.90-1.81 (m, 1H), 1.67 (q, J=4.1 Hz, 2H), 1.15 (q, J=4.2 Hz, 2H). MS (ESI+) m/z 248 (M+H)$^+$.

Example I-3D 1-(5-cyclobutyl-2-methoxypyridin-3-yl)-N-((2-methylquinolin-5-yl)sulfonyl)cyclopropanecarboxamide A mixture of Example I-3C (60 mg, 0.243 mmol), N$^1$-((ethylimino)methylene)-N$^3$,N$^3$-dimethylpropane-1,3-diamine (75 mg, 0.485 mmol) and N,N-dimethylpyridin-4-amine (59.3 mg, 0.485 mmol) in dichloromethane (2 mL) was stirred at 50° C. for 2 hours. The reaction mixture was loaded onto a 12 g silica gel cartridge, eluting with methanol in ethyl acetate at 0-10% gradient to provide the title compound. $^1$H NMR (501 MHz, dimethyl sulfoxide-d$_6$) δ ppm 8.89 (d, J=8.8 Hz, 1H), 7.93 (d, J=7.7 Hz, 2H), 7.80 (d, J=2.4 Hz, 1H), 7.66 (t, J=7.9 Hz, 1H), 7.40 (d, J=8.8 Hz, 1H), 7.27 (d, J=2.5 Hz, 1H), 3.61 (s, 3H), 3.42 (t, J=8.8 Hz, 1H), 2.66 (s, 3H), 2.24 (dtd, J=10.5, 8.1, 2.5 Hz, 2H), 2.11-2.00 (m, 2H), 2.00-1.89 (m, 1H), 1.84-1.77 (m, 1H), 1.18-1.11 (m, 2H), 0.66 (s, 2H). MS (ESI+) m/z 452 (M+H)$^+$.

Example I-4

1-(5-cyclobutyl-2-methoxypyridin-3-yl)-N-(quinoline-5-sulfonyl)cyclopropane-1-carboxamide A mixture of Example I-3C (60 mg, 0.243 mmol) and N$^1$-((ethylimino)methylene)-N$^3$,N$^3$-dimethylpropane-1,3-diamine (75 mg, 0.485 mmol) and N,N-dimethylpyridin-4-amine (59.3 mg, 0.485 mmol) in dichloromethane (2 mL) was stirred at ambient temperature for 30 minutes, and quinoline-5-sulfonamide (55.6 mg, 0.267 mmol) was added. The mixture was stirred at 50° C. for 2 hours. The solvent was removed and the residue was purified via reverse phase HPLC (C18, CH$_3$CN/H$_2$O (0.1% trifluoroacetic acid)=5-95%, 20 minutes) to provide the title compound. $^1$H NMR (400 MHz, dimethyl sulfoxide-d$_6$) δ ppm 11.81 (s, 1H), 9.06 (dd, J=4.2, 1.6 Hz, 1H), 8.95 (dt, J=8.9, 1.2 Hz, 1H), 8.41-8.28 (m, 2H), 8.02-7.91 (m, 2H), 7.71 (dd, J=8.8, 4.2 Hz, 1H), 7.43 (d, J=2.3 Hz, 1H), 3.46 (t, J=8.9 Hz, 1H), 3.41 (s, 3H), 2.26 (qt, J=8.1, 2.5 Hz, 2H), 2.12 (pd, J=9.1, 8.7, 2.5 Hz, 2H), 2.02-1.79 (m, 2H), 1.28 (q, J=4.3 Hz, 2H), 1.02 (q, J=4.4 Hz, 2H). MS (ESI+) m/z 438 (M+H)$^+$.

Example I-5

1-(5-cyclobutyl-2-methoxypyridin-3-yl)-N-(naphthalene-1-sulfonyl)cyclopropane-1-carboxamide A mixture of Example I-3C (60 mg, 0.243 mmol), N$^1$-((ethylimino)methylene)-N$^3$,N$^3$-dimethylpropane-1,3-diamine (75 mg, 0.485 mmol) and N,N-dimethylpyridin-4-amine (59.3 mg, 0.485 mmol) in dichloromethane (2 mL) was stirred at ambient temperature for 30 minutes. Naphthalene-1-sulfonamide (55.3 mg, 0.267 mmol) was added. The mixture was stirred at 50° C. for two hours. The solvent was removed, and the residue was dissolved in methanol (2 mL) and filtered through a syringe filter. The filtrate was purified via reverse phase HPLC (C18, CH$_3$CN/H$_2$O (0.1% trifluoroacetic acid), 5-95%, 20 minutes) to provide the title compound. $^1$H NMR (400 MHz, dimethyl sulfoxide-d$_6$) δ ppm 11.71 (s, 1H), 8.59-8.49 (m, 1H), 8.32-8.21 (m, 2H), 8.17-8.08 (m, 1H), 7.92 (d, J=2.3 Hz, 1H), 7.74-7.64 (m, 3H), 7.41 (d, J=2.4 Hz, 1H), 3.47 (q, J=8.8 Hz, 1H), 3.42 (s, 3H), 2.25 (dtt, J=10.9, 7.8, 2.8 Hz, 2H), 2.18-2.06 (m, 2H), 2.03-1.90 (m, 1H), 1.87-1.77 (m, 1H), 1.28 (q, J=4.3 Hz, 2H), 1.00 (q, J=4.4 Hz, 2H). MS (ESI+) m/z 437 (M+H)$^+$.

Example I-6

1-(5-cyclobutyl-2-methoxypyridin-3-yl)-N-(1,2,3,4-tetrahydroquinoline-5-sulfonyl)cyclopropane-1-carboxamide A mixture of Example I-3C (60 mg, 0.243 mmol) and N$^1$-((ethylimino)methylene)-N$^3$,N$^3$-dimethylpropane-1,3-diamine (75 mg, 0.485 mmol) and N,N-dimethylpyridin-4-amine (59.3 mg, 0.485 mmol) in dichloromethane (2 mL) was stirred at ambient temperature for 30 minutes. 1,2,3,4-Tetrahydroisoquinoline-5-sulfonamide (56.7 mg, 0.267 mmol) was added. The mixture was stirred at 50° C. for two hours. The solvent was removed and the residue was dissolved in methanol (2 mL). The mixture was filtered through a syringe filter. The filtrate was purified via reverse phase HPLC (C18, CH$_3$CN/H$_2$O (0.1% trifluoroacetic acid)=5-95%, 20 minutes) to provide the title compound. $^1$H NMR (400 MHz, dimethyl sulfoxide-d$_6$) δ ppm 11.22 (s, 1H), 7.94 (d, J=2.3 Hz, 1H), 7.47 (d, J=2.3 Hz, 1H), 7.08-6.97 (m, 2H), 6.69 (dd, J=7.4, 2.0 Hz, 1H), 6.14 (s, 1H), 3.77 (s, 3H), 3.46 (p, J=8.8 Hz, 1H), 3.18 (t, J=5.5 Hz, 2H), 2.88 (t, J=6.4 Hz, 2H), 2.26 (qt, J=8.1, 2.5 Hz, 2H), 2.18-2.06 (m, 2H), 1.96 (tq, J=10.5, 8.4 Hz, 1H), 1.88-1.79 (m, 1H), 1.75 (dt, J=11.1, 5.6 Hz, 2H), 1.38 (q, J=4.3 Hz, 2H), 1.06 (q, J=4.4 Hz, 2H). MS (ESI+) m/z 442 (M+H)$^+$.

Example I-7

1-(2,6-dimethoxyphenyl)-N-(naphthalene-1-sulfonyl)cyclopropane-1-carboxamide

Example I-7A methyl 1-(2,6-dimethoxyphenyl)cyclopropane-1-carboxylate

2-Bromo-1,3-dimethoxybenzene (80 mg, 0.369 mmol) was dissolved in dry tetrahydrofuran (4.2 mL) and Q-Phos (pentaphenyl(di-tert-butylphosphino)ferrocene, 5.24 mg, 7.37 µmol) and Pd(dba)$_2$ (tris(dibenzylideneacetone)dipalladium(0), 4.24 mg, 7.37 µmop were added. A freshly-prepared solution of 0.26 M Example I-1A ((1-(methoxycarbonyl)cyclopropyl)zinc(II) bromide) in tetrahydrofuran (2.078 mL, 0.553 mmol) was added dropwise. The reaction was stirred for three hours at ambient temperature, at which point the starting material was consumed. The reaction was quenched with saturated aqueous ammonium chloride (0.5 mL) and extracted with methyl tert-butyl ether. The organic phase was concentrated and the crude residue was chromatographed on silica (0-40% methyl tert-butyl ether/heptanes) to provide the title compound. $^1$H NMR (400 MHz, CDCl$_3$) δ ppm 7.21 (t, J=8.4 Hz, 1H), 6.54 (d, J=8.4 Hz, 2H), 3.80 (s, 6H), 3.58 (s, 3H), 1.68-1.64 (m, 2H), 1.14-1.11 (m, 2H). MS (ESI) m/z=237 (M+H)$^+$.

Example I-7B 1-(2,6-dimethoxyphenyl)cyclopropane-1-carboxylic Acid

Example I-7A (64 mg, 0.27 mmol) was added to isopropanol (1.5 mL), treated with 3 M aqueous NaOH (500 µL) and heated at 70° C. for 24 hours. Additional 3 M aqueous NaOH (200 µL) was added and the reaction mixture was heated at 70° C. another five hours. The mixture was cooled to ambient temperature, acidified with trifluoroacetic acid and extracted with methyl tert-butyl ether. The combined extracts were washed with 1 M aqueous citric acid and concentrated. The residue was dissolved in ethyl acetate and the mixture was washed twice with water, dried (Na$_2$SO$_4$), filtered, and concentrated to provide the impure title compound which was used in the next step without further purification. $^1$H NMR (400 MHz, dimethyl sulfoxide-d$_6$) δ ppm 7.19 (t, J=8.4 Hz, 1H), 6.60 (d, J=8.4 Hz, 2H), 3.75 (s, 6H), 1.50-1.43 (m, 2H), 1.00-0.93 (m, 2H). MS (DCI) m/z 240 (M+NH$_4$)$^+$.

Example I-7C 1-(2,6-dimethoxyphenyl)-N-(naphthalene-1-sulfonyl)cyclopropane-1-carboxamide To a mixture of Example I-7B (1-(2,6-dimethoxyphenyl)cyclopropanecarboxylic acid) (34 mg, 0.1 mmol), 1-(3- dimethylaminopropyl)-3-ethylcarbodiimide hydrochloride (69 mg, 0.36 mmol) and 4-dimethylaminopyridine (26 mg, 0.21 mmol) in anhydrous dichloromethane (500 µL) was added naphthalene-1-sulfonamide (44 mg, 0.21 mmol). The mixture was stirred at ambient temperature for 16 hours, concentrated and purified by reverse-phase HPLC [Waters XBridge™ C18 5 µm OBD column, 30×100 mm, flow rate 40 mL/minute, 20 to 70% gradient of acetonitrile in 0.1% aqueous trifluoroacetic acid] to provide the title compound. $^1$H NMR (400 MHz, dimethyl sulfoxide-$d_6$) δ ppm 11.07 (s, 1H), 8.57-8.52 (m, 1H), 8.28 (dd, J=8.3, 1.1 Hz, 1H), 8.23 (dd, J=7.5, 1.2 Hz, 1H), 8.14-8.08 (m, 1H), 7.73-7.64 (m, 3H), 7.25 (t, J=8.4 Hz, 1H), 6.59 (d, J=8.4 Hz, 2H), 3.58 (s, 6H), 1.40-1.36 (m, 2H), 0.92-0.88 (m, 2H). MS (ESI) m/z 412 (M+H)$^+$.

Example I-8

1-[2-methoxy-5-(trifluoromethyl)pyridin-3-yl]-N-(naphthalene-1-sulfonyl)cyclopropane-1-carboxamide Example I-8A 1-(2-methoxy-5-(trifluoromethyl)pyridin-3-yl)cyclopropanecarboxylic Acid To 3-bromo-2-methoxy-5-(trifluoromethyl)pyridine [CAS #124432-63-9](2 g, 7.81 mmol) in 20 mL of dry tetrahydrofuran was added Q-Phos (pentaphenyl(di-tert-butylphosphino)ferrocene, 0.122 g, 0.172 mmol) and Pd(dba)$_2$ (tris(dibenzylideneacetone)dipalladium(0), 0.143 g, 0.156 mmol). A solution of freshly-prepared (1-(methoxycarbonyl)cyclopropyl)zinc(II) bromide (2.86 g, 11.72 mmol) in tetrahydrofuran (0.5 mmol/mL, 30 mL) was added via a stainless steel cannula with nitrogen pressure. The mixture was stirred at ambient temperature for one hour. Dichloromethane (30 mL) and saturated aqueous NH$_4$Cl (10 mL) was added and the organic layer was washed with brine, dried over MgSO$_4$, filtered, and concentrated. The residue was purified via chromatography on a 50 g silica gel cartridge, eluting with ethyl acetate/methanol (9:1) in heptane at a 0-50% gradient to provide methyl 1-(2-methoxy-5-(trifluoromethyl)-pyridin-3-yl)cyclopropanecarboxylate, HTP-LC/MS (APCI), m/z=276 (M+H)$^+$. Methyl 1-(2-methoxy-5-(trifluoromethyl)-pyridin-3-yl)cyclopropanecarboxylate was dissolved in methanol (6 mL) and lithium hydroxide (1.096 g, 45.8 mmol) in water (1 mL). The mixture was stirred at 50° C. for 3 hours. The solvent was removed and the residue was adjusted pH to 1~2 by adding 2 N aqueous HCl. The mixture was extracted using dichloromethane and methanol (10:1). The extracts were washed with brine, dried over MgSO$_4$, filtered, concentrated to dryness, and dried in an oven to provide the title compound. HTP-LC/MS (APCI+) m/z 262.18 (M+H)$^+$.

Example I-8B 1-(2-methoxy-5-(trifluoromethyl)pyridin-3-yl)-N-(naphthalen-1-ylsulfonyl)cyclopropanecarboxamide A mixture of 1-(2-methoxy-5-(trifluoromethyl)pyridin-3-yl)cyclopropanecarboxylic acid (65 mg, 0.249 mmol), N$^1$-((ethylimino)methylene)-N$^3$,N$^3$-dimethylpropane-1,3-diamine (77 mg, 0.498 mmol) and N,N-dimethylpyridin-4-amine (60.8 mg, 0.498 mmol) in dichloromethane (2 mL) was stirred at ambient temperature for 30 minutes. Naphthalene-1-sulfonamide (56.7 mg, 0.274 mmol) was added. The mixture was stirred at 45° C. for 2 hours. The solvent was removed and the residue was dissolved in methanol (3 mL) and filtered. Purification via reverse phase HPLC (C18, CH$_3$CN/H$_2$O (0.1% trifluoroacetic acid), 5-95%, 20 minutes) provided the title compound. $^1$H NMR (400 MHz, dimethyl sulfoxide-$d_6$) δ ppm 11.86 (s, 1H), 8.51 (dd, J=2.4, 1.2 Hz, 1H), 8.49-8.44 (m, 1H), 8.30 (d, J=8.2 Hz, 1H), 8.26 (dd, J=7.5, 1.3 Hz, 1H), 8.17-8.10 (m, 1H), 7.86 (d, J=2.4 Hz, 1H), 7.75-7.63 (m, 3H), 3.44 (s, 3H), 1.30 (q, J=4.3 Hz, 2H), 1.09 (q, J=4.4 Hz, 2H). MS (ESI+) m/z 451 (M+H)$^+$.

Example I-9

1-(5-bromo-2-methoxyphenyl)-N-(1,2,3,4-tetrahydroquinoline-5-sulfonyl)cyclobutane-1-carboxamide A mixture of Example I-26A (300 mg, 1.052 mmol), N$^1$-(ethylimino)methylene)-N$^3$,N$^3$-dimethylpropane-1,3-diamine (327 mg, 2.104 mmol) and N,N-dimethylpyridin-4-amine (257 mg, 2.104 mmol) in dichloromethane (6 mL) was stirred at ambient temperature for 30 minutes. 1,2,3,4-Tetrahydroquinoline-5-sulfonamide (246 mg, 1.157 mmol) was added. The mixture was stirred at 45° C. for 3 hours. The solvent was removed and the residue was dissolved in methanol (3 mL) and filtered. Purification via reverse phase HPLC (C18, CH$_3$CN/H$_2$O (0.1% trifluoroacetic acid), 5-95%, 20 minutes) provided the title compound. $^1$H NMR (501 MHz, dimethyl sulfoxide-$d_6$) δ ppm 11.12 (s, 1H), 7.55 (d, J=2.5 Hz, 1H), 7.44 (dd, J=8.7, 2.4 Hz, 1H), 7.06 (dd, J=7.8, 1.3 Hz, 1H), 7.01 (t, J=7.9 Hz, 1H), 6.91 (d, J=8.6 Hz, 1H), 6.74-6.65 (m, 1H), 6.09 (s, 1H), 3.48 (s, 3H), 3.14-3.08 (m, 2H), 2.67-2.60 (m, 2H), 2.60-2.53 (m, 2H), 2.21 (dt, J=12.3, 8.7 Hz, 2H), 1.73 (q, J=7.8 Hz, 2H), 1.61 (p, J=6.2 Hz, 2H). MS (ESI+) m/z 481 (M+H)$^+$.

Example I-10

1-(5-cyclobutyl-2-methoxyphenyl)-N-(1,2,3,4-tetrahydroquinoline-5-sulfonyl)cyclobutane-1-carboxamide A mixture of Example I-26B (70 mg, 0.269 mmol), N$^1$-((ethylimino)methylene)-N$^3$,N$^3$-dimethylpropane-1,3-diamine (83 mg, 0.538 mmol) and N,N-dimethylpyridin-4-amine (65.7 mg, 0.538 mmol) in dichloromethane (2 mL) was stirred at ambient temperature for 30 minutes. 1,2,3,4-Tetrahydroquinoline-5-sulfonamide (62.8 mg, 0.296 mmol) was added. The mixture was stirred at 45° C. for 16 hours. The solvent was removed and the residue was dissolved in methanol (3 mL) and filtered. Purification via reverse phase HPLC (C18, CH$_3$CN/H$_2$O (0.1% trifluoroacetic acid), 5-95%, 20 minutes) provided the title compound. $^1$H NMR (400 MHz, dimethyl sulfoxide-$d_6$) δ ppm 10.85 (s, 1H), 7.23 (d, J=2.3 Hz, 1H), 7.13 (dd, J=8.4, 2.2 Hz, 1H), 7.07 (dd, J=7.8, 1.3 Hz, 1H), 7.00 (t, J=7.9 Hz, 1H), 6.87 (d, J=8.4 Hz, 1H), 6.68 (dd, J=8.0, 1.4 Hz, 1H), 3.49 (s, 4H), 3.07 (t, J=5.5 Hz, 2H), 2.61 (dddd, J=12.5, 7.9, 5.7, 2.4 Hz, 2H), 2.53 (d, J=6.4 Hz, 2H), 3.26 (s, 3H), 3.50-3.44 (ddt, J=14.9, 10.6, 6.0 Hz, 1H), 2.12 (pd, J=9.4, 8.7, 5.5 Hz, 2H), 2.02-1.90 (m, 1H), 1.87-1.67 (m, 3H), 1.55 (p, J=6.1 Hz, 2H). MS (ESI+) m/z 455 (M+H)$^+$.

Example I-11

1-(5-bromo-2-methoxyphenyl)-N-(1,2,3,4-tetrahydroquinoline-5-sulfonyl)cyclopropane-1-carboxamide In a 4 mL vial was added Example I-1D (75 mg, 0.277 mmol), N$^1$-((ethylimino)methylene)-N$^3$,N$^3$-dimethylpropane-1,3-diamine hydrochloride (106 mg, 0.553 mmol), and N,N-dimethylpyridin-4-amine (37.2 mg, 0.304 mmol) in dichloromethane (2 mL). 1,2,3,4-Tetrahydroquinoline-5-sulfonamide (64.6 mg, 0.304 mmol) was added. The reaction was stirred overnight at ambient temperature. The solvent was removed under nitrogen and the residue was dissolved in methanol and purified directly via preparative reverse phase HPLC/MS method trifluoroacetic acid8 to provide the title compound. $^1$H NMR (501 MHz, dimethyl sulfoxide-$d_6$:D2O=9:1 (v/v)) δ ppm 7.46 (dd, J=8.7, 2.5 Hz, 1H), 7.32 (d, J=2.5 Hz, 1H), 7.06-6.99 (m, 2H), 6.96 (d, J=8.8 Hz, 1H), 6.70 (dd, J=6.2, 3.1 Hz, 1H), 3.70 (s, 3H), 3.21-3.14 (m, 2H), 2.86 (t, J=6.4 Hz, 2H), 1.77 (p, J=6.3 Hz, 2H), 1.36 (q, J=4.4 Hz, 2H), 1.06-1.02 (m, 2H). MS (APCI+) m/z 464.9 (M+H)$^+$.

Example I-12

1-(5-cyclopropyl-2-methoxyphenyl)-N-(naphthalene-1-sulfonyl)cyclopropane-1-carboxamide

Example I-12A methyl 1-(5-cyclopropyl-2-methoxyphenyl)cyclopropane-1-carboxylate

A mixture of Example I-1C (methyl 1-(5-bromo-2-methoxyphenyl)cyclopropanecarboxylate) (48 mg, 0.168 mmol), potassium cyclopropyltrifluoroborate (29.9 mg, 0.202 mmol), palladium(II) acetate (3.78 mg, 0.017 mmol), butyl di-1-adamantylphosphine (9.05 mg, 0.025 mmol), and $Cs_2CO_3$ (165 mg, 0.505 mmol) was added to toluene (0.9 mL) and water (0.11 mL). The mixture was treated with a stream of nitrogen for 1 minute. The mixture was stirred at 80° C. for 23 hours, cooled and partitioned between ethyl acetate (30 mL) and 1 M aqueous HCl (10 mL). The layers were separated and the aqueous layer was extracted with ethyl acetate (15 mL). The combined ethyl acetate layers were washed with brine, dried (MgSO$_4$), filtered, concentrated and chromatographed on silica gel, eluting with a gradient of 5% to 25% ethyl acetate in heptanes to provide the title compound. $^1$H NMR (501 MHz, CDCl$_3$) δ ppm 6.97-6.93 (m, 2H), 6.77 (d, J=8.1 Hz, 1H), 3.79 (s, 3H), 3.60 (s, 3H), 1.83 (tt, J=5.1, 8.4 Hz, 1H), 1.59-1.57 (m, 2H), 1.11-1.08 (m, 2H), 0.91-0.86 (m, 2H), 0.63-0.59 (m, 2H). LC/MS (APCI+) m/z 247 (M+H)$^+$.

Example I-12B

1-(5-cyclopropyl-2-methoxyphenyl)cyclopropane-1-carboxylic Acid

A solution of Example I-12A (methyl 1-(5-cyclopropyl-2-methoxyphenyl)cyclopropanecarboxylate) (34.2 mg, 0.139 mmol) in tetrahydrofuran (~1.5 mL) was diluted with methanol (~1.5 mL), treated with 1 M aqueous NaOH (~1 mL), and stirred at ambient temperature for 30 minutes. The mixture was heated to 60° C. for 20 minutes, treated with 3 M aqueous NaOH (~1 mL), heated to 60° C. for 1 hour, cooled, and partitioned between methyl tert-butyl ether (40 mL) and 1 M aqueous HCl (15 mL). The methyl tert-butyl ether layer was washed with brine, dried (MgSO$_4$), filtered, and concentrated to provide the title compound. $^1$H NMR (400 MHz, CDCl$_3$) δ ppm 6.97-6.94 (m, 2H), 6.77 (d, J=8.9 Hz, 1H), 3.81 (s, 3H), 1.82 (tt, J=5.1, 8.4 Hz, 1H), 1.63 (q, J=4.1 Hz, 2H), 1.16 (q, J=4.1 Hz, 2H), 0.90-0.85 (m, 2H), 0.63-0.57 (m, 2H).

Example I-12C

1-(5-cyclopropyl-2-methoxyphenyl)-N-(naphthalene-1-sulfonyl)cyclopropane-1-carboxamide To a solution of Example I-12B (1-(5-cyclopropyl-2-methoxyphenyl)cyclopropanecarboxylic acid) (15 mg, 0.065 mmol), EDC (1-(3-dimethylaminopropyl)-3-ethylcarbodiimide hydrochloride) (24.76 mg, 0.129 mmol) and naphthalene-1-sulfonamide (14.72 mg, 0.071 mmol) in N,N-dimethylformamide (0.3 mL) was added 4-dimethylaminopyridine (8.68 mg, 0.071 mmol). The mixture was stirred for 2 days. The mixture was partitioned between methyl tert-butyl ether (75 mL) and 1 M aqueous HCl (15 mL). The methyl tert-butyl ether layer was washed with 0.2 M aqueous HCl (~10 mL), washed with brine, dried (MgSO$_4$), filtered, concentrated and chromatographed on silica gel, eluting with a gradient of 10% to 100% [9:1 dichloromethane: [200:1:1 ethyl acetate:HCOOH:H$_2$O]] in heptanes to provide the title compound. $^1$H NMR (400 MHz, dimethyl sulfoxide-$d_6$) δ ppm 11.41 (s, 1H), 8.58-8.53 (m, 1H), 8.30-8.21 (m, 2H), 8.13-8.08 (m, 1H), 7.70-7.65 (m, 3H), 6.93 (dd, J=2.3, 8.4 Hz, 1H), 6.83 (d, J=2.3 Hz, 1H), 6.74 (d, J=8.4 Hz, 1H), 3.31 (s, 3H), 1.84 (tt, J=5.1, 8.4 Hz, 1H), 1.25-1.21 (m, 2H), 0.93 (bs, 2H), 0.89-0.84 (m, 2H), 0.62-0.57 (m, 2H). LC/MS (APCI+) m/z 422 (M+H)$^+$.

Example I-13

1-(5-cyclopropyl-2-methoxyphenyl)-N-(quinoline-5-sulfonyl)cyclopropane-1-carboxamide To a solution of Example I-12B (1-(5-cyclopropyl-2-methoxyphenyl)cyclopropanecarboxylic acid) (15 mg, 0.065 mmol), 1-(3-dimethylaminopropyl)-3-ethylcarbodiimide hydrochloride (24.76 mg, 0.129 mmol) and quinoline-5-sulfonamide (14.79 mg, 0.071 mmol) in N,N-dimethylformamide (0.3 mL) was added 4-dimethylaminopyridine (8.68 mg, 0.071 mmol). The mixture was stirred for 2 days at ambient temperature. The mixture was treated with additional 4-dimethylaminopyridine (~5 mg) and quinoline-5-sulfonamide (~10 mg) and stirred at ambient temperature for 2 hours. The mixture was partitioned between methyl tert-butyl ether (75 mL) and 1 M aqueous HCl (15 mL). The methyl tert-butyl ether layer was washed with 0.2 M aqueous HCl (~10 mL), washed with brine, dried (MgSO$_4$), filtered, concentrated and chromatographed on silica gel, eluting with a gradient of 25% to 100% [200:1:1 ethyl acetate:HCOOH:H$_2$O] in heptanes to provide the title compound. $^1$H NMR (501 MHz, dimethyl sulfoxide-$d_6$) δ ppm 11.56 (s, 1H), 9.04 (dd, J=1.6, 4.1 Hz, 1H), 8.97 (dd, J=1.1, 8.8 Hz, 1H), 8.35-8.29 (m, 2H), 7.93 (t, J=7.9 Hz, 1H), 7.70 (dd, J=4.2, 8.8 Hz, 1H), 6.93 (dd, J=2.3, 8.4 Hz, 1H), 6.84 (d, J=2.3 Hz, 1H), 6.74 (d, J=8.5 Hz, 1H), 3.31 (s, 3H), 1.84 (tt, J=5.1, 8.5 Hz, 1H), 1.21 (q, J=4.2 Hz, 2H), 0.93 (s, 2H), 0.89-0.85 (m, 2H), 0.62-0.58 (m, 2H). LC/MS (APCI+) m/z 423 (M+H)$^+$.

Example I-14

1-{2-methoxy-5-[(propan-2-yl)oxy]phenyl}-N-(quinoline-5-sulfonyl)cyclopropane-1-carboxamide

Example I-14A methyl 1-(2-methoxy-5-(4,4,5,5-tetramethyl-1,3,2-dioxaborolan-2-yl)phenyl)cyclopropane-1-carboxylate A mixture of Example I-1C (methyl 1-(5-bromo-2-methoxyphenyl)cyclopropanecarboxylate) (0.31 g, 1.087 mmol), potassium acetate (0.534 g, 5.44 mmol) and bis(pinacolato)diboron (0.828 g, 3.26 mmol) in dioxane (15 mL) was vacuum purged with nitrogen several times, treated with [1,1'-bis(diphenylphosphino)ferrocene]dichloropalladium(II), complex with dichloromethane, (0.089 g, 0.109 mmol) and heated for 16 hours at 100° C. under nitrogen. The mixture was cooled and partitioned between methyl tert-butyl ether (~75 mL) and saturated aqueous Sodium bicarbonate solution (15 mL). The layers were separated and the aqueous layer was extracted with methyl tert-butyl ether (~25 mL). The combined methyl tert-butyl ether layers were washed with brine, dried (MgSO$_4$), filtered, and concentrated. The residue was chromatographed on silica gel, eluting with a gradient of 10% to 30% [200:1:1 ethyl acetate:HCOOH:H$_2$O] in heptanes to provide the title compound. $^1$H NMR (501 MHz, CDCl$_3$) δ ppm 7.74 (dd, J=1.7, 8.2 Hz, 1H), 7.63 (d, J=1.7 Hz, 1H), 6.86 (d, J=8.2 Hz, 1H), 3.85 (s, 3H), 3.58 (s, 3H), 1.58 (q, J=4.1 Hz, 2H), 1.32 (s, 12H), 1.14 (q, J=4.1 Hz, 2H). LC/MS (APCI+) m/z 333 (M+H)$^+$.

Example I-14B methyl 1-(5-hydroxy-2-methoxyphenyl)cyclopropane-1-carboxylate

A solution of Example I-14A (methyl 1-(2-methoxy-5-(4,4,5,5-tetramethyl-1,3,2-dioxaborolan-2-yl)phenyl)cyclopropanecarboxylate) (136 mg, 0.409 mmol) in methanol (4 mL) was treated with 30% aqueous hydrogen peroxide (418 µl, 4.09 mmol) and stirred for 2 days at ambient temperature. The mixture was partitioned between methyl tert-butyl ether (~50 mL) and water (~25 mL). The layers were separated. The methyl tert-butyl ether layer was washed with 0.75 M aqueous solution of sodium thiosulfate pentahydrate (5.1 mL, 4.09 mmol). The biphasic mixture was treated with 1 M aqueous HCl until the aqueous layer was acidic. The methyl tert-butyl ether layer was isolated, washed with brine, dried (MgSO$_4$), filtered, and concentrated to provide the title compound. $^1$H NMR (501 MHz, CDCl$_3$) δ ppm 6.74-6.70 (m, 3H), 4.97 (s, 1H), 3.77 (s, 3H), 3.61 (s, 3H), 1.59-1.57 (m, 2H), 1.10-1.08 (m, 2H).

Example I-14C methyl 1-(5-isopropoxy-2-methoxyphenyl)cyclopropane-1-carboxylate

A solution of Example I-14B (methyl 1-(5-hydroxy-2-methoxyphenyl)cyclopropanecarboxylate) (27 mg, 0.121 mmol), cesium carbonate (198 mg, 0.607 mmol) and 2-bromopropane (57.0 0.607 mmol) in N,N-dimethylformamide (0.5 mL) was stirred at ambient temperature for 1 hour, treated with sodium iodide (1.821 mg, 0.012 mmol), heated to 60° C. for 30 minutes, cooled and partitioned between methyl tert-butyl ether (30 mL) and water (15 mL). The layers were separated. The methyl tert-butyl ether layer was washed with water (10 mL), washed with brine, dried (MgSO$_4$), filtered, concentrated and chromatographed on silica gel, eluting with a gradient of 10% to 30% ethyl acetate in heptanes to provide the title compound. $^1$H NMR (400 MHz, CDCl$_3$) δ ppm 6.77 (s, 3H), 4.42 (hept, J=6.1 Hz, 1H), 3.78 (s, 3H), 3.61 (s, 3H), 1.58 (q, J=4.1 Hz, 2H), 1.31 (d, J=6.1 Hz, 6H), 1.10 (q, J=4.1 Hz, 2H).

Example I-14D 1-(5-isopropoxy-2-methoxyphenyl)cyclopropane-1-carboxylic Acid

A solution of Example I-14C (methyl 1-(5-isopropoxy-2-methoxyphenyl)cyclopropanecarboxylate) (15 mg, 0.057 mmol) in tetrahydrofuran (~1.5 mL) was diluted with methanol (~1.5 mL), treated with 3 M aqueous NaOH (~1 mL) heated to 60° C. for 2 hours, cooled and partitioned between methyl tert-butyl ether (40 mL) and 1 M aqueous HCl (10 mL). The methyl tert-butyl ether layer was washed with brine, dried (MgSO$_4$), filtered, and concentrated to provide the title compound. $^1$H NMR (400 MHz, CDCl$_3$) δ ppm 6.79-6.76 (m, 3H), 4.40 (hept, J=6.0 Hz, 1H), 3.80 (s, 3H), 1.63 (q, J=4.1 Hz, 2H), 1.29 (d, J=6.1 Hz, 6H), 1.16 (q, J=4.2 Hz, 2H).

Example I-14E

1-{2-methoxy-5-[(propan-2-yl)oxy]phenyl}-N-(quinoline-5-sulfonyl)cyclopropane-1-carboxamide To a solution of Example I-14D (1-(5-isopropoxy-2-methoxyphenyl)cyclopropanecarboxylic acid) (15 mg, 0.060 mmol), 1-(3-dimethylaminopropyl)-3-ethylcarbodiimide hydrochloride (22.98 mg, 0.120 mmol) and quinoline-5-sulfonamide (18.72 mg, 0.090 mmol) in N,N-dimethylformamide (0.3 mL) was added 4-dimethylaminopyridine (14.64 mg, 0.120 mmol). The mixture was stirred for 80 minutes. The mixture was partitioned between methyl tert-butyl ether (50 mL) and 0.2 M aqueous HCl (15 mL). The methyl tert-butyl ether layer was washed with 0.2 M aqueous HCl (~10 mL), washed with brine, dried (MgSO$_4$), filtered, concentrated and chromatographed on silica gel, eluting with a gradient of 25% to 100% [200:1:1 ethyl acetate:HCOOH:H$_2$O] in heptanes to provide the title compound. $^1$H NMR (400 MHz, dimethyl sulfoxide-d$_6$) δ ppm 11.62 (bs, 1H), 9.04 (dd, J=1.5, 4.1 Hz, 1H), 8.98 (d, J=8.7 Hz, 1H), 8.37-8.29 (m, 2H), 7.93 (t, J=7.9 Hz, 1H), 7.69 (dd, J=4.2, 8.8 Hz, 1H), 6.80 (dd, J=2.8, 8.9 Hz, 1H), 6.76 (d, J=8.8 Hz, 1H), 6.66 (d, J=2.8 Hz, 1H), 4.47 (hept, J=6.0 Hz, 1H), 3.30 (s, 3H), 1.23 (d, J=6.0 Hz, 6H), 1.22-1.19 (m, 2H), 0.97-0.91 (m, 2H). MS (APCI+) m/z 441 (M+H)$^+$.

Example I-15

1-(2-methoxy-5-methylpyridin-3-yl)-N-(naphthalene-1-sulfonyl)cyclopropane-1-carboxamide Example I-15A 1-(2-methoxy-5-methylpyridin-3-yl)cyclopropanecarboxylic Acid To 3-bromo-2-methoxy-5-methylpyridine [CAS #717843-56-6] (1.0 g, 4.95 mmol) in 20 mL of dry tetrahydrofuran was added Q-Phos (1,2,3,4,5-pentaphenyl-1'-(di-tert-butylphosphino)ferrocene) (0.077 g, 0.109 mmol) and bis(dibenzylideneacetone)palladium (0.091 g, 0.099 mmol). A solution of freshly-prepared (1-(methoxycarbonyl)cyclopropyl)zinc(II) bromide (2.419 g, 9.90 mmol) in tetrahydrofuran (0.45 mmol/mL, 17 mL) was added via a stainless steel cannula under nitrogen pressure. The mixture was stirred at ambient temperature for 40 minutes. Dichloromethane and saturated aqueous NH₄Cl were added. The organic layer was washed with brine and concentrated. The residue was purified via chromatography on a 40 g silica gel cartridge, eluting with ethyl acetate in heptane at 0-50% gradient to yield methyl 1-(2-methoxy-5-methylpyridin-3-yl)cyclopropanecarboxylate which was dissolved in methanol (10 mL) and 6M aqueous lithium hydroxide (3 mL) and stirred at 50° C. for 15 hours. The solvent was removed, and water (10 mL) was added. The aqueous layer was extracted with ethyl acetate (10 mL×2). The aqueous layer was adjusted pH 1~2 and extracted with dichloromethane (30 mL×3), and the extracts washed with brine, dried over MgSO₄ and concentrated to provide the title compound which used in next step without further purification. MS (APCI+) m/z 208 (M+H)⁺.

Example I-15B 1-(2-methoxy-5-methylpyridin-3-yl)-N-(naphthalene-1-sulfonyl)cyclopropane-1-carboxamide A mixture of 1-(2-methoxy-5-methylpyridin-3-yl)cyclopropanecarboxylic acid (50 mg, 0.241 mmol) from Example I-15A and N¹-((ethylimino)methylene)-N³,N³-dimethylpropane-1,3-diamine (74.9 mg, 0.483 mmol) and N,N-dimethylpyridin-4-amine (59.0 mg, 0.483 mmol) in dichloromethane (2 mL) was stirred at ambient temperature for 30 minutes, and then naphthalene-1-sulfonamide (55.0 mg, 0.265 mmol) was added. The mixture was stirred at 45° C. for 3 hours. The solvent was removed and the residue was dissolved in methanol (3 mL) and filtered. The filtrate was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. ¹H NMR (400 MHz, dimethyl sulfoxide-d₆) δ ppm 11.67 (s, 1H), 8.49 (dt, J=7.1, 3.6 Hz, 1H), 8.29-8.18 (m, 2H), 8.11-8.04 (m, 1H), 7.85 (d, J=2.2 Hz, 1H), 7.71-7.61 (m, 3H), 7.32 (d, J=2.3 Hz, 1H), 3.36 (s, 3H), 2.17 (s, 3H), 1.23 (q, J=4.3 Hz, 2H), 0.94 (q, J=4.4 Hz, 2H). MS(ESI+) m/z 397 (M+H)⁺.

Example I-16

1-(5-cyclobutyl-2-methoxyphenyl)-N-(1,2,3,4-tetrahydroquinoline-5-sulfonyl)cyclopropane-1-carboxamide Example I-11 (60 mg, 0.13 mmol, 1.0 eq) was dissolved in tetrahydrofuran (0.5 mL). PEPPSI IPentCl (dichloro[1,3-bis(2,6-di-3-pentylphenyl)imidazol-2-ylidene](3-chloropyridyl)palladium(II), 11.2 mg, 0.013 mmol, 0.1 eq) in tetrahydrofuran (0.2 mL) was added. Cyclobutylzinc bromide (0.5 M in tetrahydrofuran, 0.77 mL, 0.39 mmol, 3.0 eq) was added and the reaction was stirred overnight at ambient temperature. The reaction mixture was purified directly via preparative reverse phase HPLC/MS method trifluoroacetic acid7 to provide the title compound. ¹H NMR (400 MHz, dimethyl sulfoxide-d₆:D2O=9:1 (v/v)) ppm 6 ppm 7.18 (dd, J=8.5, 2.2 Hz, 1H), 7.09-6.96 (m, 3H), 6.93 (d, J=8.5 Hz, 1H), 6.72 (dd, J=6.5, 2.8 Hz, 1H), 3.70 (s, 3H), 3.43 (q, J=8.7 Hz, 1H), 3.17 (t, J=5.4 Hz, 2H), 2.84 (t, J=6.3 Hz, 2H), 2.33-2.17 (m, 2H), 2.15-1.71 (m, 6H), 1.38 (q, J=4.3 Hz, 2H), 1.03 (q, J=4.5 Hz, 2H). MS (APCI) m/z 441.1 (M+H)⁺.

Example I-17

1-(5-cyclobutyl-2-methoxyphenyl)-N-(quinoline-5-sulfonyl)cyclopropane-1-carboxamide Example I-18 (60 mg, 0.13 mmol, 1.0 eq) was dissolved in tetrahydrofuran (0.5 mL). PEPPSI IPentCl (dichloro[1,3-bis(2,6-di-3-pentylphenyl)imidazol-2-ylidene](3-chloropyridyl)palladium(II), 11.2 mg, 0.013 mmol, 0.1 eq) in tetrahydrofuran (0.2 mL) was added. Cyclobutylzinc bromide (0.5 M in tetrahydrofuran, 0.77 mL, 0.39 mmol, 3.0 eq) was added and the reaction was stirred for 16 hours at ambient temperature. The reaction mixture was purified directly via preparative reverse phase HPLC/MS method trifluoroacetic acid8 to provide the title compound. ¹H NMR (400 MHz, dimethyl sulfoxide-d₆) δ ppm 9.05 (dd, J=4.2, 1.6 Hz, 1H), 8.96 (dt, J=8.8, 1.3 Hz, 1H), 8.36 (dt, J=8.5, 1.1 Hz, 1H), 8.32 (dd, J=7.5, 1.3 Hz, 1H), 7.95 (dd, J=8.5, 7.5 Hz, 1H), 7.72 (dd, J=8.8, 4.2 Hz, 1H), 7.14 (dd, J=8.4, 2.3 Hz, 1H), 6.95 (d, J=2.2 Hz, 1H), 6.80 (d, J=8.4 Hz, 1H), 3.46-3.34 (m, 1H), 3.31 (s, 3H), 2.29-2.17 (m, 2H), 2.11-1.84 (m, 3H), 1.84-1.71 (m, 1H), 1.24 (q, J=4.4 Hz, 2H), 0.95 (q, J=4.5 Hz, 2H). MS (APCI) m/z 437.0 (M+H)⁺.

Example I-18

1-(5-bromo-2-methoxyphenyl)-N-(quinoline-5-sulfonyl)cyclopropane-1-carboxamide

Example I-18 was prepared using the general procedure described in Example I-11, substituting quinoline-5-sulfonamide for 1,2,3,4-tetrahydroquinoline-5-sulfonamide. ¹H NMR (400 MHz, dimethyl sulfoxide-d₆:D₂O=9:1 (v/v)) δ ppm 9.07 (dd, J=4.2, 1.6 Hz, 1H), 8.94 (dt, J=8.8, 1.3 Hz, 1H), 8.47-8.29 (m, 2H), 7.98 (dd, J=8.4, 7.5 Hz, 1H), 7.74 (dd, J=8.8, 4.2 Hz, 1H), 7.45 (dd, J=8.7, 2.5 Hz, 1H), 7.28 (d, J=2.5 Hz, 1H), 6.84 (d, J=8.8 Hz, 1H), 3.29 (s, 3H), 1.25 (q, J=4.4 Hz, 2H), 1.00 (q, J=4.5 Hz, 2H). MS (APCI) m/z 460.9 (M+H)⁺.

Example I-19

1-(5-cyclobutyl-2-methoxypyridin-3-yl)-N-(pyrazolo[1,5-a]pyridine-4-sulfonyl)cyclopropane-1-carboxamide Example I-19 was prepared using the general procedure described in Example I-11, substituting pyrazolo[1,5-a]pyridine-4-sulfonamide for 1,2,3,4-tetrahydroquinoline-5-sulfonamide and Example I-3C for Example I-1D. ¹H NMR (400 MHz, dimethyl sulfoxide-d₆:D₂O=9:1 (v/v)) δ ppm 8.96 (dt, J=7.0, 1.0 Hz, 1H), 8.21 (d, J=2.3 Hz, 1H), 7.93 (dd, J=2.4, 0.7 Hz, 1H), 7.86 (dd, J=7.2, 1.0 Hz, 1H), 7.42 (d, J=2.4 Hz, 1H), 7.10 (t, J=7.1 Hz, 1H), 6.92 (dd, J=2.3, 0.9 Hz, 1H), 3.53 (s, 3H), 3.46 (q, J=8.8 Hz, 1H), 2.34-2.18 (m, 2H), 2.18-2.04 (m, 2H), 2.04-1.89 (m, 1H), 1.89-1.75 (m, 1H), 1.31 (q, J=4.4 Hz, 2H), 1.05 (q, J=4.5 Hz, 2H). MS (APCI) m/z 427.1 (M+H)⁺.

Example I-20

1-(5-cyclobutyl-2-methoxypyridin-3-yl)-N-(1-methyl-1H-indole-7-sulfonyl)cyclopropane-1-carboxamide Example I-20 was prepared using the general procedure described in Example I-11, substituting 1-methyl-1H-indole-7-sulfonamide for 1,2,3,4-tetrahydroquinoline-5-sulfonamide and Example I-3C for Example I-1D. $^1$H NMR (400 MHz, dimethyl sulfoxide-d$_6$:D$_2$O=9:1 (v/v)) δ ppm 7.98-7.87 (m, 2H), 7.79 (dd, J=7.7, 1.2 Hz, 1H), 7.49 (d, J=2.2 Hz, 1H), 7.42 (d, J=3.2 Hz, 1H), 7.19 (t, J=7.8 Hz, 1H), 6.68 (d, J=3.2 Hz, 1H), 3.90 (s, 3H), 3.56-3.39 (m, 4H), 2.35-2.19 (m, 2H), 2.19-2.05 (m, 2H), 2.05-1.90 (m, 1H), 1.90-1.75 (m, 1H), 1.38 (q, J=4.4 Hz, 2H), 1.07 (q, J=4.5 Hz, 2H). MS (APCI) 440.1 m/z (M+H)$^+$.

Example I-21

1-(5-cyclobutyl-2-methoxypyridin-3-yl)-N-(1H-indole-4-sulfonyl)cyclopropane-1-carboxamide 1H-Indole-4-sulfonamide (21.8 mg, 0.11 mmol, 1.1 eq) was weighed into 4 mL vial. Example I-3C (25 mg, 0.10 mmol, 1.0 eq), 4-dimethylaminopyridine (13.6 mg, 0.11 mmol, 1.1 eq) and 1-(3-dimethylaminopropyl)-3-ethylcarbodiimide HCl (38.4 mg, 0.20 mmol, 2.0 eq) were all combined and dissolved in 0.5 mL dichloromethane. The stock solution was added to the 4 mL vial containing 1H-indole-4-sulfonamide. The reaction was stirred overnight at ambient temperature. The solvent was removed under a stream of nitrogen, and the residue was dissolved in dimethyl sulfoxide/methanol. The mixture was purified via preparative reverse phase HPLC/MS method trifluoroacetic acid7 to provide the title compound. $^1$H NMR (400 MHz, dimethyl sulfoxide-d$_6$:D$_2$O=9:1 (v/v)) δ ppm 7.90 (d, J=2.3 Hz, 1H), 7.73 (d, J=8.1 Hz, 1H), 7.62-7.54 (m, 2H), 7.39 (d, J=2.4 Hz, 1H), 7.25 (t, J=7.8 Hz, 1H), 6.79 (dd, J=3.1, 0.9 Hz, 1H), 3.56 (s, 3H), 3.44 (q, J=8.8 Hz, 1H), 2.31-2.19 (m, 2H), 2.16-1.87 (m, 3H), 1.86-1.75 (m, 1H), 1.28 (q, J=4.4 Hz, 2H), 1.02-0.97 (m, 2H). MS (APCI) m/z 426.1 (M+H)$^+$.

Example I-22

N-(1H-indole-4-sulfonyl)-1-[2-methoxy-5-(trifluoromethyl)pyridin-3-yl]cyclopropane-1-carboxamide Example I-22 was prepared using the general procedure described in Example I-21, substituting 1-(2-methoxy-5-(trifluoromethyl)pyridin-3-yl)cyclopropane-1-carboxylic acid from Example I-8A for Example I-3C. $^1$H NMR (500 MHz, dimethyl sulfoxide-d$_6$:D$_2$O=9:1 (v/v)) δ ppm 11.62 (s, 1H), 8.50-8.45 (m, 1H), 7.83-7.78 (m, 1H), 7.74 (dt, J=8.1, 1.0 Hz, 1H), 7.61-7.54 (m, 2H), 7.29-7.22 (m, 1H), 6.72 (dd, J=3.1, 0.9 Hz, 1H), 3.59 (s, 3H), 1.29 (q, J=4.4 Hz, 2H), 1.07 (q, J=4.5 Hz, 2H). MS (APCI) m/z 440.0 (M+H)$^+$.

Example I-23

1-(5-cyclobutyl-2-methoxyphenyl)-N-(pyrazolo[1,5-a]pyridine-4-sulfonyl)cyclobutane-1-carboxamide Example I-23 was prepared as described in Example I-30D, substituting Example I-26B for 1-(2-(dimethylamino)-5-(trifluoromethyl)pyridin-3-yl)cyclopropanecarboxylic acid, and pyrazolo[1,5-a]pyridine-4-sulfonamide for naphthalene-1-sulfonamide. $^1$H NMR (500 MHz, dimethyl sulfoxide-d$_6$:D$_2$O=9:1 (v/v)) δ ppm 8.19 (s, 1H), 8.00 (dd, J=8.0, 1.1 Hz, 1H), 7.92 (dd, J=7.8, 1.1 Hz, 1H), 7.42 (t, J=7.9 Hz, 1H), 7.29 (d, J=2.2 Hz, 1H), 7.14 (ddd, J=8.3, 2.2, 0.7 Hz, 1H), 6.55 (d, J=8.4 Hz, 1H), 3.62-3.45 (m, 1H), 3.42 (s, 3H), 2.74 (s, 3H), 2.61-2.48 (m, 2H), 2.37-2.07 (m, 6H), 2.06-1.90 (m, 1H), 1.90-1.69 (m, 3H). MS (APCI) m/z 440.1 (M+H)$^+$.

Example I-24

1-(5-cyclobutyl-2-methoxyphenyl)-N-(1-methyl-1H-benzimidazole-7-sulfonyl)cyclobutane-1-carboxamide Example I-24 was prepared as described in Example I-30D, substituting Example I-26B for 1-(2-(dimethylamino)-5-(trifluoromethyl)pyridin-3-yl)cyclopropanecarboxylic acid, and 1-methyl-1H-benzo[d]imidazole-7-sulfonamide for naphthalene-1-sulfonamide. $^1$H NMR (500 MHz, dimethyl sulfoxide-d$_6$:D$_2$O=9:1 (v/v)) δ ppm 8.18 (s, 1H), 8.02-7.96 (m, 1H), 7.91 (dd, J=7.8, 1.1 Hz, 1H), 7.42 (t, J=7.9 Hz, 1H), 7.32-7.23 (m, 1H), 7.19-7.07 (m, 1H), 6.55 (d, J=8.4 Hz, 1H), 3.51 (t, J=8.9 Hz, 1H), 3.42 (s, 3H), 2.74 (s, 3H), 2.59-2.49 (m, 2H), 2.35-2.26 (m, 2H), 2.22-2.11 (m, 4H), 2.05-1.90 (m, 1H), 1.90-1.69 (m, 3H). MS (APCI) m/z 454.0 (M+H)$^+$.

Example I-25

1-(5-cyclobutyl-2-methoxyphenyl)-N-(1-methyl-1H-indazole-7-sulfonyl)cyclobutane-1-carboxamide Example I-25 was prepared as described in Example I-30D, substituting Example I-26B for 1-(2-(dimethylamino)-5-(trifluoromethyl)pyridin-3-yl)cyclopropanecarboxylic acid, and 1-methyl-1H-indazole-7-sulfonamide for naphthalene-1-sulfonamide. $^1$H NMR (500 MHz, dimethyl sulfoxide-d$_6$:D$_2$O=9:1 (v/v)) δ ppm 8.26 (s, 1H), 8.21-8.13 (m, 1H), 8.10 (dd, J=7.5, 1.1 Hz, 1H), 7.34 (t, J=7.7 Hz, 1H), 7.29 (d, J=2.2 Hz, 1H), 7.16-7.07 (m, 1H), 6.57 (d, J=8.4 Hz, 1H), 3.67 (s, 3H), 3.51 (p, J=8.8 Hz, 1H), 2.72 (s, 3H), 2.59-2.49 (m, 2H), 2.35-2.08 (m, 6H), 2.05-1.91 (m, 1H), 1.87-1.70 (m, 3H). MS (APCI) m/z 454.0 (M+H)$^+$.

Example I-26

1-(5-cyclobutyl-2-methoxyphenyl)-N-(1H-indazole-4-sulfonyl)cyclobutane-1-carboxamide Example I-26A 1-(5-bromo-2-methoxyphenyl)cyclobutanecarboxylic Acid To 1-(2-methoxyphenyl)cyclobutanecarboxylic acid [CAS #74205-38-2](920 mg, 4.46 mmol) in dichloromethane (20 mL) was added N-bromosuccinimide (873 mg, 4.91 mmol). The mixture was stirred at ambient temperature for 16 hours. Saturated aqueous Na$_2$S$_2$O$_3$ was added and the organic layer was washed with brine, dried over MgSO$_4$, filtered and concentrated. The residue was purified via chromatography on a 24 g silica gel cartridge, eluting with methanol in ethyl acetate (0-10% at gradient) to provide the title compound. MS (APCI+) m/z 241 (M-COOH)$^+$.

Example I-26B 1-(5-cyclobutyl-2-methoxyphenyl)cyclobutane-1-carboxylic Acid

A mixture of Example I-26A (200 mg, 0.701 mmol) and [1,1'-bis(diphenylphosphino)ferrocene]dichloropalladium (II) (PdCl$_2$(dppf)$_2$, 57 mg) in tetrahydrofuran (5 mL) was degassed by bubbling a stream of nitrogen through the suspension. Cyclobutylzinc(II) bromide (1 mL, 0.5 M in tetrahydrofuran) was added. The mixture was stirred at ambient temperature for 16 hours. The solvent was removed and the residue was purified via chromatography, eluting with ethyl acetate/methanol (9:1) in heptane at a 0-60% gradient to provide the title compound. MS (APCI+) m/z 215 (M-COOH)+.

Example I-26C 1H-indazole-4-sulfinate

An 20 mL microwave vial was charged with 4-bromo-1H-indazole (500 mg, 2.54 mmol), 1,4-diazabicyclo[2.2.2] octane-1,4-diium-1,4-disulfinate (610 mg, 2.54 mmol), and PdCl$_2$ (AmPhos)$_2$ (bis(di-tert-butyl(4-dimethylaminophenyl)phosphine)dichloropalladium(II), 90 mg, 0.127 mmol). A mixture of N-cyclohexyl-N-methylcyclohexanamine (1.640 mL, 7.61 mmol) in anhydrous isopropyl alcohol (IPA) (10 mL) was added. The vial was sealed with a Teflon cap, sparged for 5 minutes with nitrogen and subject to microwave conditions at 110° C. for 2.5 hours. After cooling to ambient temperature, the mixture was filtered to give the crude title product solution. LC/MS (ESI+) m/z 183.1 (M+H)+.

Example I-26D 1H-indazole-4-sulfonamide

To a solution of crude 1H-indazole-4-sulfinate (1 g, 5.52 mmol) in isopropyl alcohol (20 mL), water (40 mL) was added. After sodium acetate trihydrate (2.253 g, 16.56 mmol) and (aminooxy)sulfonic acid (1.872 g, 16.56 mmol) were added, the mixture was stirred at ambient temperature for 3 hours. The organic solvent was removed under reduced pressure to provide the crude product which was purified by CombiFlash® chromatography (H$_2$O (0.01% trifluoroacetic acid) (A)/methanol (B), gradient from 5%-30% of B at 10 minutes-20 minutes to provide the title compound and it was used without further purification.

Example I-26E 1-(5-cyclobutyl-2-methoxyphenyl)-N-(1H-indazole-4-sulfonyl)cyclobutane-1-carboxamide The title compound was prepared as described in Example I-30D, substituting Example I-26B for 1-(2-(dimethylamino)-5-(trifluoromethyl)pyridin-3-yl)cyclopropanecarboxylic acid, and 1H-indazole-4-sulfonamide for naphthalene-1-sulfonamide. $^1$H NMR (500 MHz, dimethyl sulfoxide-d$_6$) δ ppm 11.58 (t, J=2.3 Hz, 1H), 7.72 (dt, J=8.1, 0.9 Hz, 1H), 7.59 (dd, J=7.5, 0.9 Hz, 1H), 7.54-7.46 (m, 1H), 7.25 (dd, J=8.1, 7.5 Hz, 1H), 7.17-7.10 (m, 2H), 6.80 (d, J=8.3 Hz, 1H), 6.74-6.67 (m, 1H), 3.45 (p, J=8.6 Hz, 1H), 3.38 (s, 3H), 2.46-2.37 (m, 2H), 2.32-2.21 (m, 2H), 2.17-2.04 (m, 4H), 2.02-1.88 (m, 1H), 1.86-1.72 (m, 1H), 1.70-1.58 (m, 1H), 1.58-1.47 (m, 1H). MS (APCI) m/z 439.1 (M+H)+

Example I-27

1-(5-cyclopropyl-2-methoxyphenyl)-N-(1,2,3,4-tetrahydroquinoline-5-sulfonyl)cyclobutane-1-carboxamide Example I-27 was prepared as described in Example I-16, substituting 1-(5-bromo-2-methoxyphenyl)-N-((1,2,3,4-tetrahydroquinolin-5-yl)sulfonyl)cyclobutane-1-carboxamide from Example 1-9 for Example 11, and cyclopropylzinc bromide for cyclobutylzinc bromide. $^1$H NMR (400 MHz, dimethyl sulfoxide-d$_6$:D$_2$O=9:1 (v/v)) δ ppm 7.14-6.98 (m, 3H), 6.95 (dd, J=8.5, 2.2 Hz, 1H), 6.85 (d, J=8.4 Hz, 1H), 6.69 (dd, J=7.9, 1.5 Hz, 1H), 3.51 (s, 3H), 3.06 (t, J=5.5 Hz, 2H), 2.64-2.48 (m, 4H), 2.43-2.01 (m, 2H), 1.98-1.83 (m, 1H), 1.83-1.67 (m, 2H), 1.67-1.50 (m, 2H), 0.99-0.82 (m, 2H), 0.74-0.56 (m, 2H). MS (APCI) m/z 441.1 (M+H)+.

Example I-28

1-(2,5-dimethoxyphenyl)-N-(naphthalene-1-sulfonyl)cyclopropane-1-carboxamide

Example I-28A methyl 1-(2,5-dimethoxyphenyl)cyclopropanecarboxylate

To a mixture of bis(dibenzylideneacetone)palladium (81 mg, 0.14 mmol) and Q-Phos (1,2,3,4,5-pentaphenyl-1'-(di-tert-butylphosphino)ferrocene) (100 mg, 0.14 mmol) in anhydrous tetrahydrofuran (30 mL) was added 2-bromo-1, 4-dimethoxybenzene (1.05 mL, 7.0 mmol) followed by ~0.4 M (1-(methoxycarbonyl)cyclopropyl)zinc(II) bromide in tetrahydrofuran (21 mL, ~8.4 mmol) and the reaction was stirred at ambient temperature for 16 hours. The reaction was quenched with 1 M aqueous citric acid (7 mL) and diluted with brine (7 mL) and heptane (15 mL). The aqueous phase was separated and extracted with methyl tert-butyl ether. The combined organic phases were dried (Na$_2$SO$_4$), concentrated and the residue was chromatographed on silica (15 to 20% methyl tert-butyl ether/heptanes) to provide the title compound. $^1$H NMR (501 MHz, CDCl$_3$) δ ppm 6.81-6.76 (m, 3H), 3.79 (s, 3H), 3.76 (s, 3H), 3.61 (s, 3H), 1.60-1.57 (m, 2H), 1.12-1.09 (m, 2H). MS (DCI) m/z 254 (M+NH$_4$)+.

Example I-28B 1-(2,5-dimethoxyphenyl)cyclopropanecarboxylic Acid

Methyl 1-(2,5-dimethoxyphenyl)cyclopropanecarboxylate (473 mg, 2.00 mmol) from example I-28A was placed in isopropanol (12 mL), treated with 3 M aqueous NaOH (4 mL) and heated at 55° C. for 15 hours. The reaction was reduced in volume and acidified with 1 M aqueous citric acid (10 mL). The resulting suspension was extracted with methyl tert-butyl ether and the combined extracts were washed twice with water, and each wash was back-extracted once with methyl tert-butyl ether. The organics were dried (Na$_2$SO$_4$) and concentrated to provide the title compound. $^1$H NMR (500 MHz, dimethyl sulfoxide-d$_6$) δ ppm 11.98 (bs, 1H), 6.87 (d, J=8.8 Hz, 1H), 6.78 (dd, J=8.8, 3.1 Hz, 1H), 6.74 (d, J=3.1 Hz, 1H), 3.71 (s, 3H), 3.69 (s, 3H), 1.40-1.37 (m, 2H), 1.04-1.00 (m, 2H). MS (ESI−) m/z 221 (M−H)−.

Example I-28C 1-(2,5-dimethoxyphenyl)-N-(naphthalen-1-ylsulfonyl)cyclopropanecarboxamide To a mixture of 1-(2,5-dimethoxyphenyl)cyclopropanecarboxylic acid (89 mg, 0.4 mmol) from Example I-28B, EDAC (1-(3-dimethylaminopropyl)-3-ethylcarbodiimide HCl, 153 mg, 0.80 mmol) and 4-dimethylaminopyridine (54 mg, 0.44 mmol) in anhydrous dichloromethane (1.5 mL) was added naphthalene-1-sulfonamide (104 mg, 0.50 mmol). The solution was stirred at ambient temperature for 16 hours, concentrated and purified by reverse-phase HPLC [Waters XBridge™ C18 5 μm OBD column, 30×100 mm, flow rate 40 mL/minute, 20 to 70% gradient of acetonitrile in 0.1% aqueous trifluoroacetic acid] to give the title compound. $^1$H NMR (400 MHz, dimethyl sulfoxide-$d_6$) δ ppm 11.46 (s, 1H), 8.58-8.53 (m, 1H), 8.30-8.22 (m, 2H), 8.13-8.08 (m, 1H), 7.71-7.65 (m, 3H), 6.82 (dd, J=8.9, 2.9 Hz, 1H), 6.77 (d, J=8.9 Hz, 1H), 6.70 (d, J=2.9 Hz, 1H), 3.70 (s, 3H), 3.28 (s, 3H), 1.25-1.20 (m, 2H), 0.98-0.92 (m, 2H). MS (ESI) m/z 412 (M+H)$^+$.

Example I-29

1-(2,5-dimethoxyphenyl)-N-(quinoline-5-sulfonyl) cyclopropane-1-carboxamide

A mixture of 1-(2,5-dimethoxyphenyl)cyclopropanecarboxylic acid (23 mg, 0.10 mmol) from Example I-28B, quinoline-5-sulfonamide (25 mg, 0.12 mmol), EDAC (1-(3-dimethylaminopropyl)-3-ethylcarbodiimide HCl, 38 mg, 0.20 mmol) and 4-dimethylaminopyridine (13 mg, 0.11 mmol) was diluted with anhydrous N,N-dimethylacetamide (400 μL), stirred at ambient temperature for 16 hours and then purified by reverse-phase HPLC [Waters XBridge™ C18 5 μm OBD column, 30×100 mm, flow rate 40 mL/minute, 10 to 50% gradient of acetonitrile in 0.1% aqueous trifluoroacetic acid] to give the title compound. $^1$H NMR (400 MHz, dimethyl sulfoxide-$d_6$) δ ppm 11.60 (bs, 1H), 9.06 (dd, J=4.2, 1.6 Hz, 1H), 9.00-8.96 (m, 1H), 8.35 (dd, J=8.5, 1.2 Hz, 1H), 8.32 (dd, J=7.5, 1.2 Hz, 1H), 7.95 (dd, J=8.5, 7.5 Hz, 1H), 7.71 (dd, J=8.8, 4.2 Hz, 1H), 6.83 (dd, J=8.8, 2.9 Hz, 1H), 6.78 (d, J=8.8 Hz, 1H), 6.71 (d, J=2.9 Hz, 1H), 3.71 (s, 3H), 3.29 (s, 3H), 1.24-1.20 (m, 2H), 0.98-0.94 (m, 2H). MS (ESI+) m/z 413 (M+H)$^+$.

Example I-30

1-[2-(dimethylamino)-5-(trifluoromethyl)pyridin-3-yl]-N-(naphthalene-1-sulfonyl)cyclopropane-1-carboxamide Example I-30A 3-bromo-N,N-dimethyl-5-(trifluoromethyl)pyridin-2-amine To a solution of 3-bromo-2-chloro-5-(trifluoromethyl) pyridine (1.575 g, 6.05 mmol) in tetrahydrofuran (3 mL) was added 3 mL of a 40% aqueous solution of dimethylamine (1.704 g, 15.12 mmol). The mixture became cloudy and initially cooled down but then warmed up slightly, to about 35° C. The reaction mixture was stirred at ambient temperature for 1 hour. The aqueous layer was extracted with hexanes (3×5 mL) and the extracts were filtered through a very small silica gel plug. The solvent was blown off under a stream of nitrogen to provide the title compound. $^1$H NMR (501 MHz, chloroform-d) δ ppm 8.40 (dq, J=2.0, 0.9 Hz, 1H), 8.01-7.81 (m, 1H), 3.14 (s, 6H). MS (APCI+) m/z 269 (M+H)$^+$.

Example I-30B methyl 1-(2-(dimethylamino)-5-(trifluoromethyl) pyridin-3-yl)cyclopropanecarboxylate In a 4 mL vial was added Pd$_2$(dba)$_3$ (tris(dibenzylideneacetone)dipalladium(0)) (6.53 mg, 7.14 μmop and Q-Phos (1,2,3,4,5-pentaphenyl-1'-(di-tert-butylphosphino)ferrocene) (1,2,3,4,5-Pentaphenyl-1'-(di-tert-butylphosphino)ferrocene) (5.07 mg, 7.14 μmop in tetrahydrofuran (tetrahydrofuran) (0.5 mL). 3-Bromo-N,N-dimethyl-5-(trifluoromethyl)pyridin-2-amine (Example I-30A, 96 mg, 0.357 mmol) in tetrahydrofuran (0.500 mL) was added. (1-(Methoxycarbonyl)cyclopropyl)zinc(II) bromide (0.741 mL, 0.392 mmol) was added and the reaction mixture was stirred at ambient temperature for 16 hours. The reaction mixture was poured into 5 mL saturated aqueous NH$_4$Cl and was extracted with 2×5 mL methyl tert-butyl ether. The organic layer was concentrated in vacuo and was carried on to the next step.

Example I-30C 1-(2-(dimethylamino)-5-(trifluoromethyl)pyridin-3-yl)cyclopropanecarboxylic Acid In a 20 mL vial, methyl 1-(2-(dimethylamino)-5-(trifluoromethyl)pyridin-3-yl)cyclopropanecarboxylate (Example I-30B, 536 mg, 1.858 mmol) was dissolved in 10 mL 3:2 tetrahydrofuran:methanol. Lithium hydroxide (5 M aqueous solution, 1.858 mL, 9.29 mmol) was added and the reaction was stirred for 16 hours at 45° C. The sample was concentrated in vacuo, and was acidified with 2 M aqueous HCl. The material was purified directly via reverse phase HPLC on a Phenomenex® Luna® C8(2) 5 μm 100 Å AXIA™ column (50 mm×21.2 mm). A gradient of acetonitrile (A) and 0.1% trifluoroacetic acid in water (B) was used, at a flow rate of 2-40 mL/minute from 0-0.5 minute with 5% A, flow rate of 40 mL/minute from 0.5-4.9 minute with a linear gradient 5-100% A, and flow rate from 40-2 mL/minute from 4.9-5.0 minutes, to obtain title compound.

Example I-30D

1-[2-(dimethylamino)-5-(trifluoromethyl)pyridin-3-yl]-N-(naphthalene-1-sulfonyl)cyclopropane-1-carboxamide Into a 4 mL vial was added 1-(2-(dimethylamino)-5-(trifluoromethyl)pyridin-3-yl)cyclopropanecarboxylic acid (Example I-30C, 64 mg, 0.233 mmol), N$^1$-((ethylimino)methylene)-N$^3$,N$^3$-dimethylpropane-1,3-diamine hydrochloride (89 mg, 0.467 mmol), and N,N-dimethylpyridin-4-amine (31.4 mg, 0.257 mmol) in dichloromethane (2 mL). Naphthalene-1-sulfonamide (53.2 mg, 0.257 mmol) was added. The reaction was stirred for 16 hours at ambient temperature. The solvent was removed under nitrogen. The residue was dissolved in methanol and the mixture was purified using preparative reverse phase HPLP/MS method trifluoroacetic acid1 to provide the title compound. $^1$H NMR (501 MHz, dimethyl sulfoxide-$d_6$) δ ppm 8.64-8.46 (m, 1H), 8.35 (dd, J=2.4, 1.1 Hz, 1H), 8.31-8.19 (m, 2H), 8.19-8.05 (m, 1H), 7.75-7.65 (m, 3H), 7.61 (d, J=2.4 Hz, 1H), 2.64 (s, 6H), 1.48 (q, J=4.4 Hz, 2H), 1.15 (q, J=4.3 Hz, 2H). MS (APCI) m/z 464.0 (M+H)$^+$.

Example I-31

1-(5-ethoxy-2-methoxyphenyl)-N-(quinoline-5-sulfonyl)cyclopropane-1-carboxamide

Example I-31A ethyl 2-(2-methoxyphenyl)acrylate

A solution of ethyl pyruvate (4.47 mL, 40.0 mmol) in tetrahydrofuran (40 mL) at 0° C. was treated dropwise with 1 M 2-methoxyphenyl magnesium bromide in tetrahydrofuran (20 mL, 20.00 mmol) at 0° C. The mixture was stirred at ambient temperature for 30 minutes and quenched with saturated aqueous NH$_4$Cl solution (20 mL). The mixture was concentrated to remove the majority of the tetrahydrofuran. The residue was extracted with methyl tert-butyl ether (2×50 mL). The combined methyl tert-butyl ether layers were washed with brine, dried (MgSO$_4$), filtered, and concentrated. The residue was taken up in toluene (50 mL), treated with p-toluenesulfonic acid monohydrate (3.80 g, 20.00 mmol), and, using a Dean-Starke trap, heated to 120° C. for 1 hour, and then further heated to 140° C. for 30 minutes. The mixture was cooled and partitioned between methyl tert-butyl ether (~50 mL) and saturated aqueous NaHCO$_3$ solution (25 mL). The organic layer was washed with brine, dried (MgSO$_4$), filtered, concentrated, and chromatographed on silica gel, eluting with a gradient of 5% to 50% ethyl acetate in heptanes to provide the title compound. $^1$H NMR (400 MHz, CDCl$_3$) δ ppm 7.33 (ddd, J=1.8, 7.5, 8.3 Hz, 1H), 7.23 (dd, J=1.7, 7.4 Hz, 1H), 6.96 (td, J=1.1, 7.4 Hz, 1H), 6.89 (dd, J=1.0, 8.3 Hz, 1H), 6.27 (d, J=1.6 Hz, 1H), 5.73 (d, J=1.6 Hz, 1H), 4.24 (q, J=7.1 Hz, 2H), 3.79 (s, 3H), 1.27 (t, J=7.1 Hz, 3H).

Example I-31B ethyl 1-(2-methoxyphenyl)cyclopropane-1-carboxylate

A solution of trimethylsulfoxonium iodide (4.05 g, 18.41 mmol) in dimethylsulfoxide (20 mL) was treated with potassium tert-butoxide (2.065 g, 18.41 mmol), and stirred at ambient temperature for 45 minutes. The mixture was treated with a solution of Example I-31A (ethyl 2-(2-methoxyphenyl)acrylate) (2.92 g, 14.16 mmol) in toluene (20 mL), stirred at ambient temperature for 50° C. for 1 hour, cooled to 0° C., and partitioned between methyl tert-butyl ether (100 mL) and 1 M aqueous HCl (50 mL). The layers were separated and the aqueous layer was extracted with methyl tert-butyl ether (50 mL). The combined organic layers were washed with water (30 mL) and washed with brine, dried (MgSO$_4$), filtered, concentrated, and chromatographed on silica gel, eluting with a gradient of 5% to 50% ethyl acetate in heptanes to provide the title compound. $^1$H NMR (400 MHz, CDCl$_3$) δ ppm 7.26 (td, J=1.8, 8.0 Hz, 1H), 7.19 (dd, J=1.7, 7.5 Hz, 1H), 6.90 (td, J=1.2, 7.5 Hz, 1H), 6.87 (dd, J=1.1, 8.2 Hz, 1H), 4.08 (q, J=7.1 Hz, 2H), 3.83 (s, 3H), 1.59 (q, J=4.1 Hz, 2H), 1.14 (t, J=7.1 Hz, 3H), 1.10 (q, J=4.1 Hz, 2H).

Example I-31C ethyl 1-(5-bromo-2-methoxyphenyl)cyclopropane-1-carboxylate

A solution of Example I-31B (ethyl 1-(2-methoxyphenyl)cyclopropanecarboxylate) (1.47 g, 6.67 mmol) in tetrahydrofuran (25 mL) and water (degassed, 14 mL) was treated with benzyltrimethylammonium tribromide (2.73 g, 7.01 mmol) and stirred for 16 hours at ambient temperature. The tetrahydrofuran was removed on a rotavap and the residue was extracted with methyl tert-butyl ether (twice). The combined methyl tert-butyl ether layers were washed with brine, dried (MgSO$_4$), filtered through a pad of silica gel, and concentrated to provide the title compound. $^1$H NMR (400 MHz, CDCl$_3$) δ ppm 7.34 (dd, J=2.5, 8.6 Hz, 1H), 7.28 (d, J=2.5 Hz, 1H), 6.73 (d, J=8.7 Hz, 1H), 4.08 (q, J=7.1 Hz, 2H), 3.80 (s, 3H), 1.58 (q, J=4.2 Hz, 2H), 1.14 (t, J=7.1 Hz, 3H), 1.08 (q, J=4.2 Hz, 2H). LC/MS (APCI+) m/z 299,301 (M+H)$^+$.

Example I-31D ethyl 1-(2-methoxy-5-(4,4,5,5-tetramethyl-1,3,2-dioxaborolan-2-yl)phenyl)cyclopropane-1-carboxylate A mixture of Example I-31C (ethyl 1-(5-bromo-2-methoxyphenyl)cyclopropanecarboxylate) (1.87 g, 6.25 mmol), potassium acetate (3.07 g, 31.3 mmol) and bis(pinacolato)diboron (4.76 g, 18.75 mmol) in dioxane (90 mL) was vacuum purged with nitrogen several times, treated with [1,1'-bis(diphenylphosphino)ferrocene]dichloropalladium(II), complex with dichloromethane, (0.510 g, 0.625 mmol) and heated for 16 hours at 100° C. under nitrogen. The mixture was cooled and partitioned between methyl tert-butyl ether (~75 mL) and 1 M aqueous HCl (15 mL). The layers were separated and the aqueous layer was extracted with methyl tert-butyl ether (~25 mL). The combined methyl tert-butyl ether layers were washed with brine, dried (MgSO$_4$), filtered, concentrated, and chromatographed on silica gel, eluting with a gradient of 5% to 30% [200:1:1 ethyl acetate:HCOOH:H$_2$O] in heptanes to provide the title compound. $^1$H NMR (400 MHz, CDCl$_3$) δ ppm 7.73 (dd, J=1.5, 8.2 Hz, 1H), 7.62 (d, J=1.6 Hz, 1H), 6.85 (d, J=8.2 Hz, 1H), 4.05 (q, J=7.0 Hz, 2H), 3.84 (s, 3H), 1.56 (q, J=4.1 Hz, 2H), 1.32 (s, 12H), 1.15-1.09 (m, 5H).

Example I-31E ethyl 1-(5-hydroxy-2-methoxyphenyl)cyclopropane-1-carboxylate

A solution of Example I-31D (ethyl 1-(2-methoxy-5-(4,4,5,5-tetramethyl-1,3,2-dioxaborolan-2-yl)phenyl)cyclopropanecarboxylate) (0.65 g, 1.877 mmol) in methanol (20 mL) was treated with 30% aqueous hydrogen peroxide solution (1.918 mL, 18.77 mmol). The mixture was stirred for 16 hours. The mixture was diluted with methyl tert-butyl ether (100 mL), washed with 0.1 M aqueous HCl (2×100 mL), washed with a solution of sodium thiosulfate pentahydrate (5.13 g, 20.65 mmol) in water (50 mL), washed with brine, dried (MgSO$_4$), filtered, and concentrated to provide title compound. $^1$H NMR (400 MHz, CDCl$_3$) δ ppm 6.73-6.67 (m, 3H), 4.97 (s, 1H), 4.09 (q, J=7.0 Hz, 2H), 3.77 (s, 3H), 1.59-1.55 (m, 2H), 1.15 (t, J=7.1 Hz, 3H), 1.10-1.06 (m, 2H).

Example I-31F ethyl 1-(5-ethoxy-2-methoxyphenyl)cyclopropane-1-carboxylate

A solution of Example I-31E (ethyl 1-(5-hydroxy-2-methoxyphenyl)cyclopropanecarboxylate) (37 mg, 0.157 mmol) and iodoethane (41.5 µl, 0.513 mmol) in N,N-dimethylformamide (0.5 mL) was treated with 60% dispersion of sodium hydride in mineral oil (18.79 mg, 0.470 mmol), stirred at ambient temperature for 15 minutes, and partitioned between methyl tert-butyl ether (50 mL) and 1 M aqueous HCl (15 mL). The layers were separated and the methyl tert-butyl ether layer was washed with 0.2 M aqueous HCl (~10 mL), washed with brine, dried (MgSO$_4$), filtered, concentrated and chromatographed on silica gel eluting with 10% ethyl acetate in heptanes to provide the title compound. $^1$H NMR (400 MHz, CDCl$_3$) δ ppm 6.78-6.74 (m, 3H), 4.08 (q, J=7.1 Hz, 2H), 3.97 (q, J=7.0 Hz, 2H), 3.78 (s, 3H), 1.58-1.55 (m, 2H), 1.38 (t, J=7.0 Hz, 3H), 1.14 (t, J=7.1 Hz, 3H), 1.09 (q, J=4.1 Hz, 2H).

Example I-31G 1-(5-ethoxy-2-methoxyphenyl)cyclopropane-1-carboxylic Acid

A solution of Example I-31F (ethyl 1-(5-ethoxy-2-methoxyphenyl)cyclopropanecarboxylate) (33 mg, 0.125 mmol) in tetrahydrofuran (~1.5 mL) was diluted with methanol (~1.5 mL), treated with 3 M aqueous NaOH (~1 mL), heated to 70° C. for 90 minutes, cooled, and partitioned between methyl tert-butyl ether (40 mL) and 1 M aqueous HCl (10 mL). The methyl tert-butyl ether layer was washed with brine, dried (MgSO$_4$), filtered, and concentrated to provide the title compound. $^1$H NMR (501 MHz, CDCl$_3$) δ ppm 6.80-6.77 (m, 3H), 3.96 (q, J=7.0 Hz, 2H), 3.79 (s, 3H), 1.63 (q, J=4.1 Hz, 2H), 1.37 (t, J=7.0 Hz, 3H), 1.16 (q, J=4.1 Hz, 2H).

Example I-31H 1-(5-ethoxy-2-methoxyphenyl)-N-(quinoline-5-sulfonyl)cyclopropane-1-carboxamide To a solution of Example I-31G (1-(5-ethoxy-2-methoxyphenyl)cyclopropanecarboxylic acid) (13 mg, 0.055 mmol), quinoline-5-sulfonamide (17.19 mg, 0.083 mmol) and 1-(3-dimethylaminopropyl)-3-ethylcarbodiimide hydrochloride (21.10 mg, 0.110 mmol) in N,N-dimethylformamide (0.3 mL) was added 4-dimethylaminopyridine (13.44 mg, 0.110 mmol). The mixture was stirred for about 72 hours. The mixture was partitioned between methyl tert-butyl ether (50 mL) and 0.2 M aqueous HCl (15 mL). The methyl tert-butyl ether layer was washed with 0.2 M aqueous HCl(~10 mL), washed with brine, dried (MgSO$_4$), filtered, concentrated and chromatographed on silica gel, eluting with a gradient of 25% to 100% [200:1:1 ethyl acetate:HCOOH:H$_2$O] in heptanes to provide the title compound. $^1$H NMR (501 MHz, dimethyl sulfoxide-d$_6$) δ ppm 11.60 (s, 1H), 9.04 (dd, J=1.6, 4.2 Hz, 1H), 8.97 (dt, J=1.2, 8.7 Hz, 1H), 8.36-8.29 (m, 2H), 7.93 (t, J=7.9 Hz, 1H), 7.69 (dd, J=4.2, 8.8 Hz, 1H), 6.81 (dd, J=2.9, 8.9 Hz, 1H), 6.77 (d, J=8.9 Hz, 1H), 6.69 (d, J=2.9 Hz, 1H), 3.96 (q, J=6.9 Hz, 2H), 3.29 (s, 3H), 1.30 (t, J=7.0 Hz, 3H), 1.20 (q, J=4.3 Hz, 2H), 0.96-0.93 (m, 2H). LC/MS (APCI+) m/z 427 (M+H)$^+$.

Example I-32

1-[5-(cyclobutyloxy)-2-methoxyphenyl]-N-(quinoline-5-sulfonyl)cyclopropane-1-carboxamide Example I-32A 1-(5-cyclobutoxy-2-methoxyphenyl)cyclopropane-1-carboxylic Acid A solution of Example I-31E (ethyl 1-(5-hydroxy-2-methoxyphenyl)cyclopropanecarboxylate) (41 mg, 0.174 mmol) and bromocyclobutane (120 mg, 0.889 mmol) in N,N-dimethylformamide (0.5 mL) was treated with 60% dispersion of sodium hydride in mineral oil (30 mg, 0.750 mmol), stirred at ambient temperature for 3 hours, heated to 45° C. for 1 hour, cooled and partitioned between methyl tert-butyl ether (50 mL) and 1 M aqueous HCl (15 mL). The methyl tert-butyl ether layer wash washed with 0.2 M aqueous HCl (10 mL), washed with brine, dried (MgSO$_4$), filtered, concentrated and chromatographed on silica gel, eluting with a gradient of 10% to 30% ethyl acetate in heptanes to provide the title compound. $^1$H NMR (500 MHz, CDCl$_3$) δ ppm 6.76 (d, J=8.8 Hz, 1H), 6.72 (d, J=2.9 Hz, 1H), 6.68 (dd, J=3.0, 8.8 Hz, 1H), 4.57-4.51 (m, 1H), 3.79 (s, 3H), 2.44-2.36 (m, 2H), 2.18-2.08 (m, 2H), 1.87-1.78 (m, 1H), 1.70-1.58 (m, 3H), 1.15 (t, J=3.6 Hz, 2H).

Example I-32B

1-[5-(cyclobutyloxy)-2-methoxyphenyl]-N-(quinoline-5-sulfonyl)cyclopropane-1-carboxamide A solution of Example I-32A (1-(5-cyclobutoxy-2-methoxyphenyl)cyclopropanecarboxylic acid) (8.6 mg, 0.033 mmol), quinoline-5-sulfonamide (10.24 mg, 0.049 mmol) and 1-(3-dimethylaminopropyl)-3-ethylcarbodiimide hydrochloride (12.57 mg, 0.066 mmol) in N,N-dimethylformamide (0.3 mL) was treated with 4-dimethylaminopyridine (8.01 mg, 0.066 mmol) and stirred at ambient temperature for 16 hours. The mixture was diluted with N,N-dimethylformamide and was directly purified by reverse-phase HPLC [Waters XBridge™ RP18 column, 5 µm, 30×100 mm, flow rate 40 mL/minute, 5-95% gradient of acetonitrile in 0.1% trifluoroacetic acid] to afford the title compound. $^1$H NMR (400 MHz, dimethyl sulfoxide-d$_6$) δ ppm 11.60 (s, 1H), 9.05 (dd, J=1.6, 4.2 Hz, 1H), 8.98 (dt, J=1.1, 8.9 Hz, 1H), 8.35 (d, J=8.5 Hz, 1H), 8.31 (dd, J=1.2, 7.5 Hz, 1H), 7.94 (dd, J=7.6, 8.3 Hz, 1H), 7.70 (dd, J=4.2, 8.8 Hz, 1H), 6.75 (d, J=8.9 Hz, 1H), 6.71 (dd, J=2.9, 8.8 Hz, 1H), 6.61 (d, J=2.8 Hz, 1H), 4.59 (p, J=7.2 Hz, 1H), 3.29 (s, 3H), 2.43-2.34 (m, 2H), 2.06-1.95 (m, 2H), 1.81-1.71 (m, 1H), 1.68-1.56 (m, 1H), 1.21 (q, J=4.3 Hz, 2H), 0.94 (q, J=4.4 Hz, 2H). LC/MS (APCI+) m/z 453 (M+H)$^+$.

Example I-33

1-(5-cyclobutyl-2-methoxyphenyl)-N-(2-methylquinoline-5-sulfonyl)cyclobutane-1-carboxamide A mixture of Example I-26B (60 mg, 0.230 mmol), N$^1$-((ethylimino)methylene)-N$^3$,N$^3$-dimethylpropane-1,3-diamine (71.6 mg, 0.461 mmol) and N,N-dimethylpyridin-4-amine (56.3 mg, 0.461 mmol) in dichloromethane (2 mL) was stirred at ambient temperature for 30 minutes. 2-Methylquinoline-5-sulfonamide (56.3 mg, 0.254 mmol) was added. The mixture was stirred at 45° C. for 3 hours. The solvent was removed and the residue was dissolved in methanol (3 mL) and filtered. Purification via HPLC with the trifluoroacetic acid method provided the title compound. $^1$H NMR (400 MHz, dimethyl sulfoxide-d$_6$) δ ppm 11.49 (s, 1H), 8.58 (d, J=8.8 Hz, 1H), 8.29-8.16 (m, 2H), 7.88 (dd, J=8.4, 7.5 Hz, 1H), 7.37 (d, J=8.9 Hz, 1H), 7.21 (d, J=2.2 Hz, 1H), 7.09 (dd, J=8.4, 2.2 Hz, 1H), 6.59 (d, J=8.3 Hz, 1H), 3.51 (q, J=8.8 Hz, 1H), 3.17 (s, 1H), 3.12 (s, 3H), 2.69 (s, 3H), 2.45-2.35 (m, 2H), 2.31 (dtt, J=10.6, 7.5, 2.5 Hz, 2H), 2.22-2.06 (m, 4H), 2.04-1.92 (m, 1H), 1.90-1.77 (m, 1H), 1.73-1.50 (m, 2H). MS (ESI+) m/z 465 (M+H)$^+$.

Example I-34

1-(5-tert-butyl-2-methoxyphenyl)-N-(quinoline-5-sulfonyl)cyclopropane-1-carboxamide

Example I-34A

1-(5-(tert-butyl)-2-methoxyphenyl)cyclopropanecarboxylic Acid

The title compound was prepared as described in Example I-30B to Example I-30C, substituting 2-bromo-4-(tert-butyl)-1-methoxybenzene for Example I-30A.

Example I-34B

1-(5-tert-butyl-2-methoxyphenyl)-N-(quinoline-5-sulfonyl)cyclopropane-1-carboxamide Quinoline-5-sulfonamide (24.9 mg, 0.10 mmol, 1.2 eq) was weighed into a 4 mL vial and dichloromethane (0.2 mL) was added. 1-(5-(tert-Butyl)-2-methoxyphenyl)cyclopropanecarboxylic acid (24.8 mg, 0.12 mmol, 1.0 eq) from Example I-34A was mixed with a solution of 1-ethyl-3-[3-(dimethylamino)propyl]-carbodiimide hydrochloride (38.0 mg, 0.2 mmol, 2.0 eq) and 4-dimethylaminopyridine (13.4 mg, 0.11 mmol, 1.1 eq) in dichloromethane (0.5 mL). The stock solution was combined with the sulfonamide and the mixture was stirred for 16 hours at ambient temperature. The solvent was removed under a stream of nitrogen. The residue was dissolved in 1:1 dimethyl sulfoxide/methanol and purified via preparative reverse phase HPLC/MS method trifluoroacetic acid7 to provide the title compound. $^1$H NMR (400 MHz, dimethyl sulfoxide-$d_6$) δ ppm 9.06 (dd, J=4.2, 1.6 Hz, 1H), 9.01-8.94 (m, 1H), 8.36 (dt, J=8.4, 1.1 Hz, 1H), 8.32 (dd, J=7.5, 1.2 Hz, 1H), 7.96 (dd, J=8.5, 7.5 Hz, 1H), 7.73 (dd, J=8.8, 4.2 Hz, 1H), 7.26 (dd, J=8.6, 2.5 Hz, 1H), 7.08 (d, J=2.5 Hz, 1H), 6.78 (d, J=8.6 Hz, 1H), 3.31 (s, 3H), 1.28 (q, J=4.4 Hz, 2H), 1.23 (s, 9H), 0.97 (q, J=4.6 Hz, 2H). MS (APCI) m/z 439.1 (M+H)$^+$.

Example I-35

1-[2-methoxy-5-(propan-2-yl)phenyl]-N-(quinoline-5-sulfonyl)cyclopropane-1-carboxamide

Example I-35A

1-(5-isopropyl-2-methoxyphenyl)cyclopropanecarboxylic Acid

The title compound was prepared as described in the procedure described from Example I-30B to Example I-30C, substituting 2-bromo-4-isopropyl-1-methoxybenzene for Example I-30A.

Example I-35B

1-[2-methoxy-5-(propan-2-yl)phenyl]-N-(quinoline-5-sulfonyl)cyclopropane-1-carboxamide Quinoline-5-sulfonamide (24.9 mg, 0.12 mmol, 1.2 eq) was weighed into a 4 mL vial and dichloromethane (0.2 mL) was added. 1-(5-(Isopropyl)-2-methoxyphenyl)cyclopropanecarboxylic acid (23.4 mg, 0.12 mmol, 1.0 eq) from Example 35A was mixed with a solution of 1-ethyl-3-[3-(dimethylamino)propyl]-carbodiimide hydrochloride (38.0 mg, 0.2 mmol, 2.0 eq) and 4-dimethylaminopyridine (13.4 mg, 0.11 mmol, 1.1 eq) in dichloromethane (0.5 mL). The stock solution was combined with the sulfonamide and the mixture was stirred for 16 hours at ambient temperature. The solvent was removed under a stream of nitrogen. The residue was dissolved in dimethyl sulfoxide/methanol (1:1) and purified via preparative reverse phase HPLC/MS method trifluoroacetic acid7 to provide the title compound. $^1$H NMR (400 MHz, dimethyl sulfoxide-$d_6$) δ ppm 9.06 (dd, J=4.2, 1.6 Hz, 1H), 8.98 (dt, J=8.8, 1.3 Hz, 1H), 8.36 (dt, J=8.5, 1.1 Hz, 1H), 8.33 (dd, J=7.5, 1.2 Hz, 1H), 7.96 (dd, J=8.4, 7.5 Hz, 1H), 7.74 (dd, J=8.8, 4.2 Hz, 1H), 7.12 (dd, J=8.4, 2.3 Hz, 1H), 6.95 (d, J=2.3 Hz, 1H), 6.78 (d, J=8.4 Hz, 1H), 3.30 (s, 3H), 2.80 (p, J=6.9 Hz, 1H), 1.26 (q, J=4.4 Hz, 2H), 1.15 (d, J=6.9 Hz, 6H), 0.96 (q, J=4.5 Hz, 2H). MS (APCI) m/z 425.1 (M+H)$^+$.

Example I-36

1-[4-fluoro-2-methoxy-5-(propan-2-yl)phenyl]-N-(quinoline-5-sulfonyl)cyclopropane-1-carboxamide Example I-36 was prepared as described in Example I-34B, substituting 1-(4-fluoro-5-isopropyl-2-methoxyphenyl)cyclopropane-1-carboxylic acid for Example I-34A. $^1$H NMR (400 MHz, dimethyl sulfoxide-$d_6$:$D_2O$=9:1 (v/v)) δ ppm 9.07 (dd, J=4.2, 1.6 Hz, 1H), 8.96 (dt, J=8.8, 1.3 Hz, 1H), 8.42-8.27 (m, 2H), 7.97 (dd, J=8.5, 7.5 Hz, 1H), 7.74 (dd, J=8.8, 4.2 Hz, 1H), 7.02 (d, J=8.8 Hz, 1H), 6.68 (d, J=12.6 Hz, 1H), 3.32 (s, 3H), 3.06 (p, J=7.0 Hz, 1H), 1.28 (q, J=4.3 Hz, 2H), 1.20 (d, J=6.9 Hz, 6H), 0.97 (q, J=4.5 Hz, 2H). MS (APCI) m/z 443.0 (M+H)$^+$.

Example I-37

1-[2-methoxy-5-(trifluoromethyl)phenyl]-N-(quinoline-5-sulfonyl)cyclopropane-1-carboxamide

Example I-37A

1-(2-methoxy-5-(trifluoromethyl)phenyl)cyclopropane-1-carboxylic Acid

The title compound was prepared as described in Example I-30B to Example I-30C, substituting 2-bromo-1-methoxy-4-(trifluoromethyl)benzene [CAS #402-10-8] for Example I-30A.

Example I-37B

1-[2-methoxy-5-(trifluoromethyl)phenyl]-N-(quinoline-5-sulfonyl)cyclopropane-1-carboxamide Example I-37B was prepared as described in Example I-34B, substituting 1-(2-methoxy-5-(trifluoromethyl)phenyl)cyclopropane-1-carboxylic acid from Example I-37A for Example I-34A. $^1$H NMR (400 MHz, dimethyl sulfoxide-$d_6$:$D_2O$=9:1 (v/v)) δ ppm 9.06 (dd, J=4.2, 1.6 Hz, 1H), 8.91 (dt, J=8.8, 1.3 Hz, 1H), 8.40-8.29 (m, 2H), 7.96 (dd, J=8.5, 7.5 Hz, 1H), 7.72 (dd, J=8.8, 4.2 Hz, 1H), 7.64 (dd, J=8.8, 2.3 Hz, 1H), 7.42 (d, J=2.3 Hz, 1H), 7.03 (d, J=8.6 Hz, 1H), 3.34 (s, 3H), 1.29 (q, J=4.5 Hz, 2H), 1.02 (q, J=4.6 Hz, 2H). MS (APCI) m/z 451.0 (M+H)$^+$.

Example I-38

1-[5-(bicyclo[1.1.1]pentan-1-yl)-2-methoxyphenyl]-N-(quinoline-5-sulfonyl)cyclopropane-1-carboxamide

Example I-38A 1-(3-bromo-4-methoxyphenyl)bicyclo[1.1.1]pentane

A solution of 4-(bicyclo[1.1.1]pentan-1-yl)phenol (0.511 g, 3.19 mmol) and benzyltrimethylammonium tribromide (1.244 g, 3.19 mmol) in tetrahydrofuran (9) and degassed water (6.00 mL) was stirred at ambient temperature overnight. The volatiles were reduced in volume and the resulting mixture was diluted with 500 mL of methyl tert-butyl ether. The organics were washed with brine, dried ($Na_2SO_4$), filtered through a pad of cotton and concentrated to give 4-(bicyclo[1.1.1]pentan-1-yl)-2-bromophenol. The 4-(bicyclo[1.1.1]pentan-1-yl)-2-bromophenol was treated with potassium carbonate (0.662 g, 4.79 mmol), and dimethyl sulfate (0.453 mL, 4.79 mmol) in acetone (15.96 mL) and stirred at ambient temperature for 3 hours. The reaction mixture was quenched with N-ethyl-N-isopropylpropan-2-amine (1.0 mL, 5.73 mmol) and the solvent was removed. The mixture was diluted with water and the organics separated, concentrated, and purified using a 10 g silica gel cartridge with a gradient of 1-100% ethyl acetate/heptanes over 20 minutes to provide the title compound. $^1$H NMR (400 MHz, chloroform-d) δ ppm 7.38 (d, J=2.1 Hz, 1H), 7.10 (dd, J=8.3, 2.1 Hz, 1H), 6.83 (d, J=8.3 Hz, 1H), 3.88 (s, 3H), 2.54 (s, 1H), 2.05 (s, 6H).

Example I-38B 1-(5-(bicyclo[1.1.1]pentan-1-yl)-2-methoxyphenyl)cyclopropanecarboxylic Acid The title compound was prepared as described in the procedure described from Example I-30B to Example I-30C, substituting 1-(3-bromo-4-methoxyphenyl)bicyclo[1.1.1]pentane from Example I-38A for Example I-30A.

Example I-38C

1-[5-(bicyclo[1.1.1]pentan-1-yl)-2-methoxyphenyl]-N-(quinoline-5-sulfonyl)cyclopropane-1-carboxamide Quinoline-5-sulfonamide (24.9 mg, 0.12 mmol, 1.2 eq) was weighed into 4 mL vials and dichloromethane (0.2 mL) was added. 1-(5-(Bicyclo[1.1.1]pentan-1-yl)-2-methoxyphenyl)cyclopropanecarboxylic acid (25.8 mg, 0.12 mmol, 1.0 eq) from Example I-38B was mixed with a solution of 1-ethyl-3-[3-(dimethylamino)propyl]-carbodiimide hydrochloride (38.0 mg, 0.2 mmol, 2.0 eq) and DMAP (4-dimethylaminopyridine, 13.4 mg, 0.11 mmol, 1.1 eq) in dichloromethane (0.5 mL). The stock solution was combined with the sulfonamide and the mixture was stirred for 16 hours at ambient temperature. The solvent was removed under a stream of nitrogen. The residue was dissolved in dimethyl sulfoxide/methanol and purified via preparative reverse phase HPLC/MS method trifluoroacetic acid7 to afford the title compound. $^1$H NMR (400 MHz, dimethyl sulfoxide-$d_6$) δ ppm 9.05 (dd, J=4.2, 1.6 Hz, 1H), 8.97 (dt, J=8.9, 1.2 Hz, 1H), 8.39-8.28 (m, 2H), 7.95 (dd, J=8.4, 7.5 Hz, 1H), 7.73 (dd, J=8.8, 4.2 Hz, 1H), 7.08 (dd, J=8.3, 2.1 Hz, 1H), 6.91 (d, J=2.1 Hz, 1H), 6.79 (d, J=8.4 Hz, 1H), 3.30 (s, 3H), 2.49 (s, 1H), 1.99 (s, 6H), 1.25 (q, J=4.4 Hz, 2H), 0.95 (q, J=4.5 Hz, 2H). MS (APCI) m/z 449.0 (M+H)$^+$.

Example I-39

1-(5-tert-butyl-2-methoxyphenyl)-N-(1,2,3,4-tetrahydroquinoline-5-sulfonyl)cyclopropane-1-carboxamide Example I-39 was prepared as described in Example I-34B, substituting 1,2,3,4-tetrahydroquinoline-5-sulfonamide acid for quinoline-5-sulfonamide. $^1$H NMR (400 MHz, dimethyl sulfoxide-$d_6$:$D_2O$=9:1 (v/v)) δ ppm 7.32 (dd, J=8.6, 2.5 Hz, 1H), 7.20 (d, J=2.5 Hz, 1H), 7.11-6.98 (m, 2H), 6.93 (d, J=8.6 Hz, 1H), 6.72 (dd, J=6.9, 2.6 Hz, 1H), 3.71 (s, 3H), 3.23-3.12 (m, 2H), 2.84 (t, J=6.4 Hz, 2H), 1.76 (p, J=6.2 Hz, 2H), 1.40 (q, J=4.3 Hz, 2H), 1.26 (s, 9H), 1.14-0.95 (m, 2H). MS (APCI) m/z 443.1 (M+H)$^+$.

Example I-40

1-(2,6-dimethoxy-3-methylphenyl)-N-(naphthalene-1-sulfonyl)cyclopropane-1-carboxamide

Example I-40A 3-bromo-2,4-dimethoxybenzaldehyde

2-Bromo-1,3-dimethoxybenzene (2.22 g, 10.2 mmol) dissolved into anhydrous dichloromethane (25 mL), chilled near −40° C. and treated over a few minutes with 1 M $TiCl_4$ in dichloromethane (15.3 mL, 15.3 mmol) followed several minutes later with dichloro(methoxy)methane (1.0 mL, 11.1 mmol). The reaction mixture and Dewer flask were covered with insulation, allowed to warm slowly to ambient temperature for 16 hours and then poured over ice. The product was extracted into dichloromethane and the combined extracts were dried ($Na_2SO_4$), concentrated and chromatographed on silica (20 to 40% methyl tert-butyl ether/heptane) to give the title compound. $^1$H NMR (501 MHz, $CDCl_3$) δ ppm 10.23 (d, J=0.8 Hz, 1H), 7.85 (d, J=8.8 Hz, 1H), 6.82 (dd, J=8.8, 0.8 Hz, 1H), 3.99 (s, 3H), 3.99 (s, 3H). MS (DCI) m/z 245/247 (M+H)$^+$.

Example I-40B 2-bromo-1,3-dimethoxy-4-methylbenzene

To trifluoroacetic acid (15 mL) stirred at −15° C. was added 3-bromo-2,4-dimethoxybenzaldehyde (980 mg, 4.0 mmol) from Example I-40A followed immediately by triethylsilane (3.2 mL, 20 mmol). The reaction mixture was stirred cold for six minutes, concentrated under vacuum, filtered through silica with chloroform/heptane, reconcentrated and chromatographed through silica (10 to 30% chloroform/heptane) to give the title compound. $^1$H NMR (501 MHz, $CDCl_3$) δ ppm 7.06 (dq, J=8.4, 0.75 Hz, 1H), 6.61 (d, J=8.4 Hz, 1H), 3.87 (s, 3H), 3.81 (s, 3H), 2.27 (d, J=0.75 Hz, 3H). MS (APCI) m/z 231/233 (M+H)$^+$.

Example I-40C methyl 1-(2,6-dimethoxy-3-methylphenyl)cyclopropanecarboxylate To bis(dibenzylideneacetone)palladium (29 mg, 0.050 mmol) and Q-Phos (1,2,3,4,5-pentaphenyl-1'-(di-tert-butylphosphino)ferrocene) (36 mg, 0.051 mmol) under nitrogen was added a solution of 2-bromo-1,3-dimethoxy-4-methylbenzene (578 mg, 2.50 mmol) from Example I-40B in anhydrous tetrahydrofuran (10 mL) followed by 0.4 M (1-(methoxycarbonyl)cyclopropyl)zinc(II) bromide in tetrahydrofuran (12.5 mL, 5 mmol) and the reaction was stirred at ambient temperature for 16 hours. The reaction was quenched with 1 M aqueous citric acid (4 mL) and diluted with brine (4 mL) and heptane (10 mL). The aqueous phase was separated and extracted with methyl tert-butyl ether and the combined organic phases were dried ($Na_2SO_4$), concentrated and chromatographed on silica (15 to 20% methyl tert-butyl ether/heptanes) to give the title compound. $^1$H NMR (400 MHz, $CDCl_3$) δ ppm 7.06 (dq, J=8.4, 0.8 Hz, 1H), 6.58 (d, J=8.4 Hz, 1H), 3.79 (s, 3H), 3.75 (s, 3H), 3.62 (s, 3H), 2.20 (d, J=0.8 Hz, 3H), 1.72-1.68 (m, 2H), 1.26-1.22 (m, 2H). MS (DCI) m/z=268 $(M+NH_4)^+$.

Example I-40D 1-(2,6-dimethoxy-3-methylphenyl)cyclopropanecarboxylic Acid

Methyl 1-(2,6-dimethoxy-3-methylphenyl)cyclopropanecarboxylate (0.57 g, 2.28 mmol) from Example I-40C was placed in isopropanol (15 mL) within a HDPE (high density polyethylene) bottle, treated with 3 M aqueous NaOH (5 mL) and heated one day at 70° C. More 3 M aqueous NaOH (2 mL) was added and the reaction mixture was heated in a glass microwave vial at 140° C. for 80 minutes, brought toward ambient temperature, partially concentrated and acidified with 1 M aqueous citric acid (15 mL). The desired product was extracted with methyl tert-butyl ether and the combined extracts were washed twice with water. The first wash was back-extracted once with methyl tert-butyl ether, dried ($Na_2SO_4$) and concentrated to give the title compound. $^1$H NMR (501 MHz, $CDCl_3$) δ ppm 7.07-7.04 (m, 1H), 6.57 (d, J=8.4 Hz, 1H), 3.80 (s, 3H), 3.77 (s, 3H), 2.19 (d, J=0.7 Hz, 3H), 1.77-1.73 (m, 2H), 1.33-1.26 (m, 2H). MS (ESI) m/z=235 (M−H)⁻.

Example I-40E 1-(2,6-dimethoxy-3-methylphenyl)-N-(naphthalene-1-sulfonyl)cyclopropane-1-carboxamide To a mixture of 1-(2,6-dimethoxy-3-methylphenyl)cyclopropanecarboxylic acid (40 mg, 0.17 mmol) from Example I-40D, EDAC (1-(3-dimethylaminopropyl)-3-ethylcarbodiimide HCl, 65 mg, 0.34 mmol) and 4-dimethylaminopyridine (23 mg, 0.19 mmol) in anhydrous dichloromethane (600 μL) was added naphthalene-1-sulfonamide (44 mg, 0.21 mmol). The solution was stirred at ambient temperature three hours, concentrated and purified by reverse-phase HPLC [Waters XBridge™ C18 5 μm OBD column, 30×100 mm, flow rate 40 mL/minute, 20 to 70% gradient of acetonitrile in 0.1% aqueous trifluoroacetic acid] to give the title compound. $^1$H NMR (400 MHz, dimethyl sulfoxide-$d_6$) δ ppm 11.43 (bs, 1H), 8.64-8.58 (m, 1H), 8.28-8.22 (m, 2H), 8.12-8.07 (m, 1H), 7.72-7.63 (m, 3H), 7.09-7.05 (m, 1H), 6.63 (d, J=8.4 Hz, 1H), 3.54 (s, 3H), 3.21 (s, 3H), 2.06 (s, 3H), 1.52-1.46 (m, 2H), 1.04-0.99 (m, 2H). MS (ESI) m/z 426 $(M+H)^+$.

Example I-41

1-(2,6-dimethoxy-3-methylphenyl)-N-(quinoline-5-sulfonyl)cyclopropane-1-carboxamide A mixture of 1-(2,6-dimethoxy-3-methylphenyl)cyclopropanecarboxylic acid (24 mg, 0.10 mmol) from Example I-40D, quinoline-5-sulfonamide (25 mg, 0.12 mmol), 1-(3-dimethylaminopropyl)-3-ethylcarbodiimide (38 mg, 0.20 mmol) and 4-dimethylaminopyridine (14 mg, 0.11 mmol) in anhydrous N,N-dimethylacetamide (600 μL) was stirred at ambient temperature for 16 hours. The mixture was purified by reverse-phase HPLC [Waters XBridge™ C18 5 μm OBD column, 30×100 mm, flow rate 40 mL/minute, 10 to 60% gradient of acetonitrile in 0.1% aqueous trifluoroacetic acid] to give the title compound. $^1$H NMR (400 MHz, dimethyl sulfoxide-$d_6$) δ ppm 11.56 (bs, 1H), 9.08-9.03 (m, 2H), 8.36-8.31 (m, 2H), 7.94 (dd, J=8.4, 7.5 Hz, 1H), 7.74 (dd, J=8.6, 4.4 Hz, 1H), 7.11-7.07 (m, 1H), 6.64 (d, J=8.4 Hz, 1H), 3.54 (s, 3H), 3.30 (s, 3H), 2.08 (s, 3H), 1.50-1.45 (m, 2H), 1.06-1.01 (m, 2H). MS (ESI) m/z 427 $(M+H)^+$.

Example I-42

1-(2,6-dimethoxy-3-methylphenyl)-N-(1H-indole-4-sulfonyl)cyclopropane-1-carboxamide A mixture of 1-(2,6-dimethoxy-3-methylphenyl)cyclopropanecarboxylic acid (24 mg, 0.10 mmol) from Example I-40D, 1H-indole-4-sulfonamide (24 mg, 0.12 mmol), 1-(3-dimethylaminopropyl)-3-ethylcarbodiimide (38 mg, 0.20 mmol) and 4-dimethylaminopyridine (14 mg, 0.11 mmol) in anhydrous N,N-dimethylacetamide (600 μL) was stirred at ambient temperature for 16 hours and was purified by reverse-phase HPLC [Waters XBridge™ C18 5 μm OBD column, 30×100 mm, flow rate 40 mL/minute, 10 to 70% gradient of acetonitrile in 0.1% aqueous trifluoroacetic acid] to give the title compound. $^1$H NMR (501 MHz, $CD_2Cl_2$/$CD_3OD$) δ ppm 9.94 (bs, 1H), 7.79 (dd, J=7.5, 0.9 Hz, 1H), 7.71-7.68 (m, 1H), 7.40-7.38 (m, 1H), 7.27 (dd, J=8.1, 7.5 Hz, 1H), 7.19-7.16 (m, 1H), 6.71-6.69 (m, 1H), 6.67 (d, J=8.4 Hz, 1H), 3.72 (s, 3H), 3.55 (s, 3H), 2.20-2.18 (m, 3H), 1.52-1.47 (m, 2H), 1.13-1.05 (m, 2H). MS (ESI) m/z 415 $(M+H)^+$.

Example I-43

1-(2,6-dimethoxy-3-methylphenyl)-N-(2-methylquinoline-5-sulfonyl)cyclopropane-1-carboxamide A mixture of 1-(2,6-dimethoxy-3-methylphenyl)cyclopropanecarboxylic acid (40 mg, 0.17 mmol) from Example I-40D, 2-methylquinoline-5-sulfonamide (47 mg, 0.21 mmol), 1-(3-dimethylaminopropyl)-3-ethylcarbodiimide (65 mg, 0.34 mmol) and 4-dimethylaminopyridine (23 mg, 0.19 mmol) in anhydrous N,N-dimethylacetamide (1.0 mL) was stirred at ambient temperature for 16 hours and then purified by reverse-phase HPLC [Waters XBridge™ C18 5 μm OBD column, 30×100 mm, flow rate 40 mL/minute, 10 to 60% gradient of acetonitrile in 0.1% aqueous trifluoroacetic acid] to give the title compound. $^1$H NMR (400 MHz, dimethyl sulfoxide-$d_6$) δ ppm 8.99 (d, J=8.9 Hz, 1H), 8.27-8.24 (m, 2H), 7.91 (dd, J=8.0 Hz, 1H), 7.68 (d, J=8.9 Hz, 1H), 7.11-7.08 (m, 1H), 6.65 (d, J=8.4 Hz, 1H), 3.56 (s, 3H), 3.31 (s, 3H), 2.75 (s, 3H), 2.09-2.08 (m, 3H), 1.50-1.45 (m, 2H), 1.06-1.01 (m, 2H). MS (ESI) m/z 441 $(M+H)^+$.

Example I-44

1-(2-methoxy-5-methylphenyl)-N-(quinoline-5-sulfonyl)cyclopropane-1-carboxamide

Example I-44A methyl 1-(2-methoxy-5-methylphenyl)cyclopropanecarboxylate

To a solution of bis(dibenzylideneacetone)palladium (0.029 g, 0.050 mmol) and Q-Phos (pentaphenyl(di-tertbutylphosphino)ferrocene, 0.035 g, 0.050 mmol) in tetrahydrofuran (10 mL) at ambient temperature was added 2-bromo-1-methoxy-4-methylbenzene (Aldrich, CAS #23002-45-5) (0.359 mL, 2.487 mmol) followed by a solution of freshly prepared (1-(methoxycarbonyl)cyclopropyl) zinc(II) bromide (12.43 mL, 4.97 mmol). The mixture was stirred at ambient temperature for 16 hours. Ethyl acetate and saturated aqueous ammonium chloride were added. The organic layer was washed with brine and concentrated. The residue was purified via chromatography on a 24 g silica gel cartridge, eluting with ethyl acetate in heptane at 0-30% gradient over a period of 15 minutes to provide the title compound. $^1$H NMR (501 MHz, chloroform-d) δ ppm 7.08-7.03 (m, 1H), 7.00 (d, J=2.2 Hz, 1H), 6.77 (d, J=8.2 Hz, 1H), 3.80 (s, 3H), 3.60 (s, 3H), 2.31 (s, 3H), 1.58 (q, J=4.0 Hz, 2H), 1.13-1.07 (m, 2H). MS (APCI+) m/z 221 (M+H)$^+$.

Example I-44B 1-(2-methoxy-5-methylphenyl)cyclopropanecarboxylic Acid

Methyl 1-(2-methoxy-5-methylphenyl)cyclopropanecarboxylate from Example I-44A (0.465 g, 2.111 mmol) was dissolved in tetrahydrofuran (5.00 mL), methanol (5.00 mL) and water (5 mL) and treated with sodium hydroxide (0.439 g, 10.98 mmol). After 4 hours at 60° C., the reaction mixture was concentrated, cooled in an ice bath and carefully quenched with 3 N aqueous HCl (about 3.5 mL) until the pH was acidic. The resulting slurry was stirred vigorously and filtered. The precipitate was washed with water and dried in a vacuum oven for 16 hours to provide the title compound. $^1$H NMR (501 MHz, dimethyl sulfoxide-d$_6$) δ ppm 11.91 (s, 1H), 7.02 (ddd, J=8.2, 2.3, 0.9 Hz, 1H), 6.99-6.93 (m, 1H), 6.83 (d, J=8.2 Hz, 1H), 3.73 (s, 3H), 2.21 (s, 3H), 1.38 (q, J=3.9 Hz, 2H), 0.99 (q, J=3.9 Hz, 2H). MS (APCI+) m/z 207 (M+H)$^+$.

Example I-44C 1-(2-methoxy-5-methylphenyl)-N-(quinoline-5-sulfonyl)cyclopropane-1-carboxamide To a solution of 1-(2-methoxy-5-methylphenyl)cyclopropanecarboxylic acid from Example I-44B (0.100 g, 0.485 mmol), N$^1$-((ethylimino)methylene)-N$^3$,N$^3$-dimethylpropane-1,3-diamine hydrochloride (0.186 g, 0.970 mmol) and N,N-dimethylpyridin-4-amine (0.065 g, 0.533 mmol) in anhydrous dichloromethane (1 mL) was added quinoline-5-sulfonamide (0.101 g, 0.485 mmol). After 5 hours, the reaction was quenched with 3.5 mL of aqueous 1 N HCl and the organic layer was concentrated in vacuo. The residue was purified via chromatography on a 24 g silica gel cartridge, eluting with ethyl acetate in heptane at a 0-50% gradient over a period of 10 minutes. The crude material was triturated with methanol and filtered to provide the title compound. $^1$H NMR (501 MHz, dimethyl sulfoxide-d$_6$) δ ppm 11.55 (s, 1H), 9.05 (dd, J=4.2, 1.6 Hz, 1H), 8.98 (dd, J=8.7, 1.1 Hz, 1H), 8.34 (d, J=8.5 Hz, 1H), 8.30 (d, J=7.4 Hz, 1H), 7.93 (t, J=7.9 Hz, 1H), 7.70 (dd, J=8.8, 4.2 Hz, 1H), 7.10-7.03 (m, 1H), 6.94 (d, J=2.2 Hz, 1H), 6.76 (d, J=8.3 Hz, 1H), 3.33 (s, 3H), 2.23 (s, 3H), 1.22 (q, J=4.3 Hz, 2H), 0.93 (q, J=4.4 Hz, 2H). MS (APCI+) m/z 397 (M+H)$^+$.

Example I-45

1-(2-ethoxy-6-methoxyphenyl)-N-(quinoline-5-sulfonyl)cyclopropane-1-carboxamide

Example I-45A methyl 1-(2-ethoxy-6-methoxyphenyl)cyclopropanecarboxylate

A solution of Example I-46A (methyl 1-(2-hydroxy-6-methoxyphenyl)cyclopropanecarboxylate) (25 mg, 0.112 mmol) and ethyl iodide (31.8 0.394 mmol) in N,N-dimethylformamide (0.5 mL) was treated with a 60% dispersion of sodium hydride in mineral oil (13.50 mg, 0.337 mmol), stirred at ambient temperature for 20 minutes, and partitioned between methyl tert-butyl ether (30 mL) and 1 M aqueous HCl (10 mL). The methyl tert-butyl ether layer was washed with water (5 mL), washed with brine, dried (MgSO$_4$), filtered, concentrated and chromatographed on silica gel, eluting with a gradient of 5% to 30% ethyl acetate in heptanes to provide the title compound. $^1$H NMR (400 MHz, CDCl$_3$) δ ppm 7.19 (t, J=8.3 Hz, 1H), 6.52 (d, J=8.4 Hz, 2H), 4.03 (q, J=7.0 Hz, 2H), 3.81 (s, 3H), 3.59 (s, 3H), 1.66 (q, J=4.3 Hz, 2H), 1.37 (t, J=7.0 Hz, 3H), 1.14 (q, J=4.4 Hz, 2H).

Example I-45B 1-(2-ethoxy-6-methoxyphenyl)cyclopropanecarboxylic Acid

A solution of Example I-45A (methyl 1-(2-ethoxy-6-methoxyphenyl)cyclopropanecarboxylate) (25 mg, 0.100 mmol) in tetrahydrofuran (1.5 mL) and methanol (1.5 mL) was treated with 3 M aqueous NaOH (1 mL) and heated to 60° C. for 30 minutes, heated to 80° C. for 8 hours, cooled and partitioned between methyl tert-butyl ether (50 mL) and 1 M aqueous HCl (15 mL). The methyl tert-butyl ether layer was washed with brine, dried (MgSO$_4$), filtered, and concentrated to provide the title compound. $^1$H NMR (501 MHz, CDCl$_3$) δ ppm 7.18 (t, J=8.3 Hz, 1H), 6.51 (d, J=8.4 Hz, 2H), 4.03 (q, J=7.0 Hz, 2H), 3.81 (s, 3H), 1.71 (q, J=4.3 Hz, 2H), 1.39 (t, J=7.0 Hz, 3H), 1.21-1.19 (m, 2H).

Example I-45C 1-(2-ethoxy-6-methoxyphenyl)-N-(quinoline-5-sulfonyl)cyclopropane-1-carboxamide A solution of Example I-45B (1-(2-ethoxy-6-methoxyphenyl)cyclopropanecarboxylic acid) (21 mg, 0.089 mmol), quinoline-5-sulfonamide (27.8 mg, 0.133 mmol) and 1-(3-dimethylaminopropyl)-3-ethylcarbodiimide hydrochloride (34.1 mg, 0.178 mmol) in N,N-dimethylformamide (0.3 mL) was treated with 4-dimethylaminopyridine (21.72 mg, 0.178 mmol) and stirred over night at ambient temperature. The mixture was partitioned between methyl tert-butyl ether (50 mL) and 1 M aqueous HCl (15 mL). The methyl tert-butyl ether layer was washed with 0.2 M aqueous HCl (15 mL), washed with brine, dried (MgSO$_4$), filtered, concentrated and chromatographed on silica gel, eluting with a gradient of 25% to 100% [200:1:1 ethyl acetate:formic acid:H$_2$O] in heptanes to provide the title compound. $^1$H NMR (400 MHz, dimethyl sulfoxide-d$_6$) δ ppm 11.25 (bs, 1H), 9.05 (dd, J=1.6, 4.1 Hz, 1H), 9.00-8.97 (m, 1H), 8.34 (d, J=8.4 Hz, 1H), 8.29 (dd, J=1.3, 7.5 Hz, 1H), 7.92 (dd, J=7.5, 8.4 Hz, 1H), 7.70 (dd, J=4.1, 8.8 Hz, 1H), 7.21 (t, J=8.3 Hz, 1H), 6.57 (d, J=8.1 Hz, 1H), 6.53 (d, J=8.2 Hz, 1H), 3.79 (q, J=7.0 Hz, 2H), 3.62 (s, 3H), 1.39 (q, J=4.3 Hz, 2H), 0.92 (q, J=4.4 Hz, 2H), 0.87 (t, J=6.9 Hz, 3H). LC/MS (APCI+) m/z 427 (M+H)+.

Example I-46

1-[2-(cyclopropylmethoxy)-6-methoxyphenyl]-N-(quinoline-5-sulfonyl)cyclopropane-1-carboxamide Example I-46A methyl 1-(2-hydroxy-6-methoxyphenyl)cyclopropane-1-carboxylate A solution of Example I-7A (methyl 1-(2,6-dimethoxyphenyl)cyclopropanecarboxylate) (0.5 g, 2.116 mmol) in dichloromethane (20 mL, anhydrous) under nitrogen at −78° C. was treated with 1 M BBr$_3$ in dichloromethane (2.96 mL, 2.96 mmol) over approximately three minutes. The mixture was stirred at −78° C. for two hours. The mixture was poured into rapidly stirred 1 M aqueous HCl (20 mL) at 0° C. over 30 seconds. The mixture was transferred to a separatory funnel, shaken, and the layers were separated. The aqueous layer was extracted with additional dichloromethane (~25 mL). The combined dichloromethane layers were dried (MgSO$_4$), filtered, concentrated, and chromatographed on silica gel, eluting with a gradient of 15% to 50% ethyl acetate in heptanes to provide the title compound. $^1$H NMR (400 MHz, CDCl$_3$) δ ppm 7.15 (t, J=8.2 Hz, 1H), 6.53 (dd, J=1.0, 8.2 Hz, 1H), 6.47 (dd, J=1.0, 8.3 Hz, 1H), 5.45 (s, 1H), 3.81 (s, 3H), 3.63 (s, 3H), 1.75 (q, J=4.0 Hz, 2H), 1.17 (q, J=3.8 Hz, 2H).

Example I-46B methyl 1-(2-(cyclopropylmethoxy)-6-methoxyphenyl)cyclopropane-1-carboxylate A solution of Example I-46A (methyl 1-(2-hydroxy-6-methoxyphenyl)cyclopropanecarboxylate) (25 mg, 0.112 mmol) and (iodomethyl)cyclopropane (102 mg, 0.562 mmol) in N,N-dimethylformamide (0.5 mL) was treated with a 60% dispersion of sodium hydride in mineral oil (13.50 mg, 0.337 mmol), stirred at ambient temperature for 15 minutes, and partitioned between methyl tert-butyl ether (30 mL) and 1 M aqueous HCl (10 mL). The methyl tert-butyl ether layer was washed with water (5 mL), washed with brine, dried (MgSO$_4$), filtered, concentrated, and chromatographed on silica gel, eluting with a gradient of 5% to 30% ethyl acetate in heptanes to provide the title compound. $^1$H NMR (400 MHz, CDCl$_3$) δ ppm 7.18 (t, J=8.3 Hz, 1H), 6.54-6.48 (m, 2H), 3.84 (d, J=6.4 Hz, 2H), 3.81 (s, 3H), 3.59 (s, 3H), 1.69-1.66 (m, 2H), 1.27-1.19 (m, 1H), 1.18-1.15 (m, 2H), 0.59-0.54 (m, 2H), 0.35-0.30 (m, 2H). LC/MS (APCI+) m/z 277 (M+H)+.

Example I-46C 1-(2-(cyclopropylmethoxy)-6-methoxyphenyl)cyclopropane-1-carboxylic Acid A solution of Example I-46B (methyl 1-(2-(cyclopropylmethoxy)-6-methoxyphenyl)cyclopropanecarboxylate) (25 mg, 0.090 mmol) in tetrahydrofuran (1.5 mL) and methanol (1.5 mL) was treated with 3 M aqueous NaOH (1 mL), heated to 60° C. for 30 minutes, heated to 80° C. for 8 hours, cooled and partitioned between methyl tert-butyl ether (50 mL) and 1 M aqueous HCl (15 mL). The methyl tert-butyl ether layer was washed with brine, dried (MgSO$_4$), filtered, and concentrated to provide the title compound. $^1$H NMR (400 MHz, CDCl$_3$) δ ppm 7.18 (t, J=8.3 Hz, 1H), 6.53-6.48 (m, 2H), 3.84 (d, J=6.6 Hz, 2H), 3.81 (s, 3H), 1.73 (q, J=4.3 Hz, 2H), 1.29-1.19 (m, 3H), 0.61-0.55 (m, 2H), 0.36-0.31 (m, 2H). LC/MS (APCI+) m/z 263 (M+H)+.

Example I-46D

1-[2-(cyclopropylmethoxy)-6-methoxyphenyl]-N-(quinoline-5-sulfonyl)cyclopropane-1-carboxamide A solution of Example I-46C (1-(2-(cyclopropylmethoxy)-6-methoxyphenyl)cyclopropanecarboxylic acid) (21.4 mg, 0.082 mmol), quinoline-5-sulfonamide (25.5 mg, 0.122 mmol) and 1-(3-dimethylaminopropyl)-3-ethylcarbodiimide hydrochloride (31.3 mg, 0.163 mmol) in N,N-dimethylformamide (0.3 mL) was treated with 4-dimethylaminopyridine (19.93 mg, 0.163 mmol) and stirred for 16 hours at ambient temperature. The mixture was partitioned between methyl tert-butyl ether (50 mL) and 1 M aqueous HCl (15 mL). The methyl tert-butyl ether layer was washed with 0.2 M aqueous HCl (15 mL), washed with brine, dried (MgSO$_4$), filtered, concentrated, and chromatographed on silica gel, eluting with a gradient of 25% to 100% [200:1:1 ethyl acetate:HCOOH:H$_2$O] in heptanes to provide the title compound. $^1$H NMR (400 MHz, dimethyl sulfoxide-d$_6$) δ ppm 11.23 (bs, 1H), 9.04 (dd, J=1.6, 4.2 Hz, 1H), 8.99 (dt, J=1.3, 8.7 Hz, 1H), 8.34 (d, J=8.4 Hz, 1H), 8.29 (dd, J=1.2, 7.4 Hz, 1H), 7.92 (dd, J=7.4, 8.5 Hz, 1H), 7.70 (dd, J=4.1, 8.8 Hz, 1H), 7.20 (t, J=8.3 Hz, 1H), 6.57 (d, J=8.2 Hz, 1H), 6.53 (d, J=8.1 Hz, 1H), 3.66 (d, J=6.3 Hz, 2H), 3.61 (s, 3H), 1.41 (q, J=4.4 Hz, 2H), 0.95 (q, J=4.5 Hz, 2H), 0.81-0.72 (m, 1H), 0.26-0.21 (m, 2H), 0.07-0.03 (m, 2H). LC/MS (APCI+) m/z 453 (M+H)+.

Example I-47

1-(6-methoxy-2,3-dimethylphenyl)-N-(quinoline-5-sulfonyl)cyclopropane-1-carboxamide Example I-47A methyl 1-(2-methoxy-6-methylphenyl)cyclopropanecarboxylate To a solution of 2-bromo-1-methoxy-3-methylbenzene (Combi-Blocks CAS #38197-43-2) (1.024 g, 5.09 mmol) in tetrahydrofuran (25.5 mL) was added bis(dibenzylideneacetone)palladium (0.059 g, 0.102 mmol) and Q-Phos (1,2,3,4,5-Pentaphenyl-1'-(di-tert-butylphosphino)ferrocene) (pentaphenyl(di-tert-butylphosphino)ferrocene, 0.072 g, 0.102 mmol). Nitrogen was bubbled through the solution for about 3 minutes, then a 0.4 M in tetrahydrofuran solution of (1-(methoxycarbonyl)cyclopropyl)zinc(II) bromide (25.5 mL, 10.19 mmol) was added dropwise over 5 minutes and the internal temperature rose from 23.5° C. to 24.8° C. The reaction was stirred for 15 hours at ambient temperature, at which point it was quenched with saturated aqueous ammonium chloride (30 mL), diluted with methyl tert-butyl ether (130 mL), and the layers were separated. The organic layer was filtered through a pad of silica gel. The filtrate was concentrated in vacuo to give a crude residue that was purified via flash chromatography, eluting on a 40 g silica gel cartridge with 1-40% ethyl acetate/heptanes over 40 minutes to provide the title compound. $^1$H NMR (400 MHz, CDCl$_3$) δ ppm 7.15 (t, J=7.9 Hz, 1H), 6.76-6.80 (m, 1H), 6.73 (d, J=8.2 Hz, 1H), 3.80 (s, 3H), 3.60 (s, 3H), 2.32 (s, 3H), 1.71-1.75 (m, 2H), 1.54 (s, 2H). MS (ESI+) m/z 221 (M+H)$^+$, 243 (M+Na)$^+$.

Example I-47B methyl 1-(3-bromo-6-methoxy-2-methylphenyl) cyclopropanecarboxylate A solution of methyl 1-(2-methoxy-6-methylphenyl)cyclopropanecarboxylate from Example I-47A (0.551 g, 2.502 mmol) and benzyltrimethylammonium tribromide (1.0656 g, 2.73 mmol) in tetrahydrofuran (7.82 mL) and degassed water (4.69 mL) was stirred at ambient temperature for 16 hours. The volatiles were removed in vacuo and the resulting crude material was diluted with 100 mL of methyl tert-butyl ether. The organics were filtered through a pad of silica gel. The filtrate was concentrated to provide the title compound. $^1$H NMR (400 MHz, chloroform-d) δ ppm 7.45 (d, J=8.8 Hz, 1H), 6.63 (d, J=8.8 Hz, 1H), 3.80 (s, 3H), 3.62 (s, 3H), 2.41 (s, 3H), 1.78 (tt, J=6.8, 3.4 Hz, 2H), 1.28-1.16 (m, 1H), 1.07-0.95 (m, 1H).

Example I-47C methyl 1-(6-methoxy-2,3-dimethylphenyl)cyclopropanecarboxylate

A solution of methyl 1-(3-bromo-6-methoxy-2-methylphenyl)cyclopropanecarboxylate from Example I-47B (233 mg, 0.779 mmol), potassium carbonate (431 mg, 3.12 mmol), trimethylboroxine (436 µl, 3.12 mmol) in 1,4-dioxane (6676 µl) and water (1113 µl) was degassed with bubbling nitrogen for 10 minutes. 1,1'-Bis(diphenylphosphino)ferrocene-palladium(II)dichloride dichloromethane complex (254 mg, 0.312 mmol) was added. The reaction was heated at 90° C. with stirring for 16 hours. The solvent was reduced in volume and the crude material was diluted with ethyl acetate and filtered through a 4 µM syringe filter. The solvent was removed and the crude material was chromatographed using a 24 g silica gel cartridge with 0-100% ethyl acetate/heptanes over a period of 20 minutes to provide the title compound. $^1$H NMR (400 MHz, chloroform-d) δ ppm 7.06 (d, J=8.3 Hz, 1H), 6.67 (d, J=8.3 Hz, 1H), 3.80 (s, 3H), 3.62 (s, 3H), 2.25 (s, 3H), 2.22 (s, 3H), 1.77 (t, J=3.3 Hz, 2H), 1.23 (d, J=10.2 Hz, 1H), 1.02 (d, J=6.0 Hz, 1H).

Example I-47D 1-(6-methoxy-2,3-dimethylphenyl)cyclopropane carboxylic Acid

Methyl 1-(6-methoxy-2,3-dimethylphenyl)cyclopropanecarboxylate from Example I-47C (0.165 g, 0.704 mmol) was dissolved in tetrahydrofuran (0.5 mL) and methanol (0.500 mL), and water (0.5 mL). The mixture was treated with sodium hydroxide (0.197 g, 4.93 mmol) and stirred at ambient temperature for 16 hours, and at 70° C. for 5 hours. The reaction mixture was concentrated, cooled in an ice bath and carefully quenched with 12 N aqueous HCl (about 1.0 mL) until the pH was acidic. The resulting slurry was stirred vigorously and filtered, and the precipitate was washed with water and dried in a vacuum oven for 16 hours to provide the title compound. $^1$H NMR (400 MHz, chloroform-d) δ ppm 11.22 (s, 1H), 7.06 (d, J=8.3 Hz, 1H), 6.66 (d, J=8.3 Hz, 1H), 3.80 (s, 3H), 2.27 (s, 3H), 2.21 (s, 3H), 1.88-1.75 (m, 2H), 1.35-1.23 (m, 1H), 1.13-1.00 (m, 1H).

Example I-47E 1-(6-methoxy-2,3-dimethylphenyl)-N-(quinoline-5-sulfonyl)cyclopropane-1-carboxamide To a solution of 1-(6-methoxy-2,3-dimethylphenyl)cyclopropanecarboxylic acid from Example I-47D (52 mg, 0.236 mmol), N$^1$-((ethylimino)methylene)-N$^3$,N$^3$-dimethylpropane-1,3-diamine hydrochloride (91 mg, 0.472 mmol) and N,N-dimethylpyridin-4-amine (28.8 mg, 0.236 mmol) in anhydrous dimethylacetamide (1 mL) was added quinoline-5-sulfonamide (54.1 mg, 0.260 mmol). After 16 hours the reaction was diluted with 1 mL of saturated aqueous ammonium chloride then quenched with 0.5 mL of 1 N aqueous HCl to give a cloudy mixture. The mixture was extracted with 3×2 mL of dichloromethane using an aqueous/organic extractor tube. The solvent was removed and the crude material was taken up in dimethylsulfoxide and methanol (1:1) and purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (400 MHz, chloroform-d) δ ppm 9.50 (d, J=8.7 Hz, 1H), 9.34 (d, J=4.9 Hz, 1H), 8.76 (d, J=8.6 Hz, 1H), 8.65 (dd, J=7.5, 1.0 Hz, 1H), 8.41 (s, 1H), 8.17-8.08 (m, 1H), 7.92 (dd, J=8.9, 4.6 Hz, 1H), 7.19 (d, J=8.3 Hz, 1H), 6.75 (d, J=8.4 Hz, 1H), 3.76 (s, 3H), 2.23 (s, 3H), 2.09 (s, 3H), 1.73 (ddd, J=10.0, 7.7, 4.0 Hz, 1H), 1.52 (ddd, J=9.9, 7.5, 4.5 Hz, 1H), 1.11 (ddd, J=9.4, 7.7, 4.4 Hz, 1H), 0.96 (ddd, J=9.4, 7.5, 4.0 Hz, 1H). MS (APCI+) m/z 411 (M+H)$^+$.

Example I-48

1-(3-cyclopropyl-6-methoxy-2-methylphenyl)-N-(quinoline-5-sulfonyl)cyclopropane-1-carboxamide Example I-48A methyl 1-(3-cyclopropyl-6-methoxy-2-methylphenyl)cyclopropanecarboxylate A mixture of methyl 1-(3-bromo-6-methoxy-2-methylphenyl)cyclopropanecarboxylate from Example I-47B (286 mg, 0.956 mmol), potassium cyclopropyltrifluoroborate (170 mg, 1.147 mmol), palladium(II) acetate (21.46 mg, 0.096 mmol), butyl di-1-adamantylphosphine (51.4 mg, 0.143 mmol), and cesium carbonate (934 mg, 2.87 mmol) was flushed with nitrogen, combined with toluene (5295 µL 49.7 mmol) and degassed with a stream of nitrogen for 15 minutes. The mixture was treated with degassed water (637 µL 35.4 mmol) and stirred at 90° C. for 18 hours. The solvent was reduced in volume and the crude organics were applied directly to a 24 g silica gel cartridge and purified using a gradient of 5-100% ethyl acetate/hexanes to provide the title compound. $^1$H NMR (400 MHz, chloroform-d) δ ppm 7.00 (d, J=8.4 Hz, 1H), 6.67 (d, J=8.5 Hz, 1H), 3.79 (s, 3H), 3.62 (s, 3H), 2.43 (s, 3H), 1.86-1.72 (m, 3H), 1.28-1.20 (m, 1H), 1.08-0.99 (m, 1H), 0.94-0.83 (m, 2H), 0.64-0.49 (m, 2H).

Example I-48B 1-(3-cyclopropyl-6-methoxy-2-methylphenyl)cyclopropanecarboxylic Acid Methyl 1-(3-cyclopropyl-6-methoxy-2-methylphenyl)cyclopropanecarboxylate from Example I-48A (0.171 g, 0.657 mmol) was dissolved in tetrahydrofuran (0.5 mL), methanol (0.500 mL), and water (0.5 mL). The mixture was treated with sodium hydroxide (0.229 g, 5.73 mmol) and stirred at ambient temperature for 16 hours, then at 70° C. for 5 hours. The reaction was concentrated, cooled in an ice bath and carefully quenched with 12 N aqueous HCl (about 1.0 mL) until the pH was acidic. The resulting slurry was stirred vigorously and filtered. The material was washed with water and dried in a vacuum oven for 16 hours to provide the title compound. $^1$H NMR (400 MHz, chloroform-d) δ ppm 6.99 (d, J=8.5 Hz, 1H), 6.65 (d, J=8.5 Hz, 1H), 3.80 (s, 3H), 2.45 (s, 3H), 1.86-1.75 (m, 3H), 1.32-1.21 (m, 1H), 1.09 (dd, J=9.5, 4.4 Hz, 1H), 0.92-0.82 (m, 2H), 0.60-0.52 (m, 2H).

Example I-48C 1-(3-cyclopropyl-6-methoxy-2-methylphenyl)-N-(quinoline-5-sulfonyl)cyclopropane-1-carboxamide To a solution of 1-(3-cyclopropyl-6-methoxy-2-methylphenyl)cyclopropanecarboxylic acid from Example I-48B (57 mg, 0.231 mmol), $N^1$-((ethylimino)methylene)-$N^3$,$N^3$-dimethylpropane-1,3-diamine hydrochloride (89 mg, 0.463 mmol) and N,N-dimethylpyridin-4-amine (28.3 mg, 0.231 mmol) in anhydrous N,N-dimethylacetamide (1 mL) was added quinoline-5-sulfonamide (53.0 mg, 0.255 mmol). After 16 hours, the reaction was diluted with 1 mL of water and quenched with 0.5 mL of 1 N aqueous HCl. A precipitate formed. The precipitate was washed with water, dried under a stream of nitrogen, added to 1 mL of methanol, heated to dissolve, cooled, filtered, diluted with 1 mL of dimethylsulfoxide and purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (400 MHz, chloroform-d) δ ppm 9.23 (d, J=5.0 Hz, 1H), 9.20 (d, J=9.0 Hz, 1H), 8.65 (d, J=8.6 Hz, 1H), 8.61 (dd, J=7.5, 1.0 Hz, 1H), 8.36 (s, 1H), 8.03 (dd, J=8.5, 7.4 Hz, 1H), 7.77 (dd, J=8.8, 4.5 Hz, 1H), 7.11 (d, J=8.5 Hz, 1H), 6.75 (d, J=8.5 Hz, 1H), 3.75 (d, J=0.9 Hz, 3H), 2.24 (s, 3H), 1.75 (tdd, J=11.6, 8.1, 4.7 Hz, 2H), 1.52 (ddd, J=10.0, 7.4, 4.4 Hz, 1H), 1.10 (ddd, J=9.7, 7.7, 4.4 Hz, 1H), 1.04-0.88 (m, 3H), 0.61 (ddt, J=13.1, 9.3, 4.8 Hz, 2H). MS (APCI+) m/z 437 (M+H)$^+$.

Example I-49

N-(1H-indole-4-sulfonyl)-1-(2-methoxy-5-methylphenyl)cyclopropane-1-carboxamide

Example I-49A methyl 1-(2-methoxy-5-methylphenyl)cyclopropanecarboxylate

To a solution of bis(dibenzylideneacetone)palladium (0.029 g, 0.050 mmol) and 1,2,3,4,5-pentaphenyl-1'-(di-tert-butylphosphino)ferrocene (0.035 g, 0.050 mmol) in tetrahydrofuran (10 mL) at ambient temperature was added 2-bromo-1-methoxy-4-methylbenzene (0.359 mL, 2.487 mmol) followed by a solution of freshly-prepared (1-(methoxycarbonyl)cyclopropyl)zinc(II) bromide (12.43 mL, 4.97 mmol). The mixture was stirred at ambient temperature for 16 hours. Ethyl acetate and saturated aqueous $NH_4Cl$ were added. The organic layer was washed with brine, dried over $MgSO_4$, filtered, and concentrated. The residue was purified via chromatography on a 24 g silica gel cartridge, eluting with ethyl acetate in heptane at 0-30% gradient to provide the title compound. $^1$H NMR (501 MHz, chloroform-d) δ ppm 7.08-7.03 (m, 1H), 7.00 (d, J=2.2 Hz, 1H), 6.77 (d, J=8.2 Hz, 1H), 3.80 (s, 3H), 3.60 (s, 3H), 2.27 (d, J=0.8 Hz, 3H), 1.58 (q, J=4.0 Hz, 2H), 1.13-1.07 (m, 2H). MS (APCI+) m/z 221 (M+H)$^+$.

Example I-49B 1-(2-methoxy-5-methylphenyl)cyclopropanecarboxylic Acid

Example I-49A (0.465 g, 2.111 mmol) in a mixture of tetrahydrofuran (5 mL), methanol (5 mL) and water (5 mL) was treated with sodium hydroxide (0.439 g, 10.98 mmol). The mixture was stirred at 60° C. for 4 hours. The solvent was removed and the pH was adjusted to 1-2 by adding 2 N aqueous HCl. The resulting slurry was vigorously stirred and the precipitated was filtered, washed with water and dried in a vacuum oven for 16 hours to provide the title compound. $^1$H NMR (501 MHz, dimethyl sulfoxide-$d_6$) δ ppm 11.91 (s, 1H), 7.02 (ddd, J=8.2, 2.3, 0.9 Hz, 1H), 6.99-6.93 (m, 1H), 6.83 (d, J=8.2 Hz, 1H), 3.73 (s, 3H), 2.21 (s, 3H), 1.38 (q, J=3.9 Hz, 2H), 0.99 (q, J=3.9 Hz, 2H). MS (APCI+) m/z 189 (M+H-H2O)$^+$.

Example I-49C tert-butyl 4-bromo-1H-indole-1-carboxylate

Di-tert-butyl dicarbonate (5.33 mL, 22.95 mmol) was added to a solution of 4-bromo-1H-indole (3.00 g, 15.30 mmol) and DMAP (4-dimethylaminopyridine) (0.187 g, 1.530 mmol)) in tetrahydrofuran (20 mL). The reaction mixture was stirred for 30 minutes. The mixture was partitioned between ether (100 mL) and water (100 mL). The ether layer was washed with (3×50 mL) of saturated aqueous sodium bicarbonate and 75 mL of brine. The ether layer was dried over magnesium sulfate, filtered and concentrated. The residue was chromatographed over silica gel eluting with 1:100 ethyl acetate: petroleum ether to afford the title compound.

Example I-49D

N-cyclohexyl-N-methylcyclohexanaminium 1-(tert-butoxycarbonyl)-1H-indole-4-sulfinate An 20 mL microwave vial was charged with tert-butyl 4-bromo-1H-indole-1-carboxylate (500 mg, 1.688 mmol), 1,4-diazabicyclo[2.2.2]octane-1,4-diium-1,4-disulfinate (406 mg, 1.688 mmol) and $PdCl_2(AmPhos)_2$ (bis(di-tert-butyl(4-dimethylaminophenyl)phosphine)dichloropalladium(II), 71.7 mg, 0.101 mmol). A solution of N-cyclohexyl-N-methylcyclohexanamine (1.091 mL, 5.06 mmol) in anhydrous isopropyl alcohol (10 mL) was added, the vial was sealed with a Teflon cap, sparged for 5 minutes with nitrogen and subjected to microwave conditions at 110° C. for 1 hour. After cooling to ambient temperature, the mixture was filtered to give the crude title compound solution which was used without further purification. MS (ESI+) m/z 282.2 (M+H)+.

Example I-49E tert-butyl 4-sulfamoyl-1H-indole-1-carboxylate

To a solution of crude 1-(tert-butoxycarbonyl)-1H-indole-4-sulfinate (940 mg, 3.35 mmol) in isopropyl alcohol (20 mL), water (40 mL) was added, followed by sodium acetate trihydrate (1369 mg, 10.06 mmol) and (aminooxy)sulfonic acid (1138 mg, 10.06 mmol). The mixture was stirred at ambient temperature for 2 hours. The mixture was concentrated under reduced pressure to provide the solution of crude product. The crude material was purified by silica gel chromatography (40% of ethyl acetate in petroleum) to give title compound. MS (ESI+) m/z 319 (M+23)+.

Example I-49F 1H-indole-4-sulfonamide

To a solution of tert-butyl 4-sulfamoyl-1H-indole-1-carboxylate (800 mg, 2.70 mmol) in dichloromethane (16 mL) cooled to 0° C., 2,2,2-trifluoroacetic acid (8 mL, 2.70 mmol) was added. The reaction mixture was stirred at 0° C. for 3 hours. After completion, the mixture was concentrated under reduced pressure to give crude title compound. The crude material was washed with water (10 mL×2), methanol (5 mL×2), and dichloromethane (5 mL×2) to provide the title compound. $^1$H NMR (400 MHz, dimethyl sulfoxide-$d_6$) δ ppm 11.54 (s, 1H), 7.63 (d, J=8.1 Hz, 1H), 7.57-7.52 (m, 1H), 7.50 (d, J=7.4 Hz, 1H), 7.25 (s, 2H), 7.20 (t, J=7.8 Hz, 1H), 6.86 (s, 1H). MS (ESI+) m/z 197.1 (M+H)+.

Example I-49G

N-(1H-indol-4-ylsulfonyl)-1-(2-methoxy-5-methylphenyl)cyclopropanecarboxamide

Example I-49B (26 mg, 0.125 mmol), $N^1$-((ethylimino)methylene)-$N^3$,$N^3$-dimethylpropane-1,3-diamine, hydrochloric acid (48.8 mg, 0.255 mmol) and N,N-dimethylpyridin-4-amine (31.1 mg, 0.255 mmol) in dichloromethane (4 mL) was stirred at ambient temperature for 30 minutes. 1H-Indole-4-sulfonamide (25 mg, 0.127 mmol) was added. The mixture was stirred at 45° C. for 2 hours. The solvent was removed and the residue was purified via HPLC with reverse phase HPLC (C18, CH$_3$CN/H$_2$O (0.1% trifluoroacetic acid)=5-95%, 20 minutes) to provide the title compound. $^1$H NMR (400 MHz, dimethyl sulfoxide-$d_6$) δ ppm 11.63 (s, 1H), 10.86 (s, 1H), 7.71 (dt, J=8.1, 1.0 Hz, 1H), 7.61-7.53 (m, 2H), 7.23 (t, J=7.8 Hz, 1H), 7.10-7.03 (m, 1H), 6.94 (d, J=2.3 Hz, 1H), 6.85-6.77 (m, 2H), 3.49 (s, 3H), 2.22 (s, 3H), 1.24 (q, J=4.2 Hz, 2H), 0.93 (q, J=4.4 Hz, 2H). MS (APCI+) m/z 385.24 (M+H)+.

Example I-50

1-[2-methoxy-6-(propan-2-yl)phenyl]-N-(quinoline-5-sulfonyl)cyclopropane-1-carboxamide Example I-50A 2-isopropyl-6-methoxyaniline To a solution of 2-bromo-6-methoxyaniline (AK-90829) (1.000 mL, 7.55 mmol) in tetrahydrofuran (10 mL) was added Pd-PEPPSI-IPent-$C_1$ (dichloro[1,3-bis(2,6-di-3-pentylphenyl)imidazol-2-ylidene](3-chloropyridyl)palladium (II), 0.208 g, 0.242 mmol). Nitrogen was bubbled through the solution for about 3 minutes, then a 0.4 M in tetrahydrofuran solution of isopropylzinc(II) bromide (52 mL, 20.80 mmol) was added dropwise over 5 minutes, with nitrogen flushing through the system and the internal temperature rising slowly from 21° C. to 32° C. The reaction mixture was stirred for 15 hours at ambient temperature, at which point it was quenched with saturated aqueous ammonium chloride (50 mL), diluted with methyl tert-butyl ether (400 mL), and the layers were separated. The organic layer was filtered through a pad of silica gel and concentrated in vacuo. The crude material was purified via flash chromatography, eluting on a 40 g silica gel cartridge with 1-40% ethyl acetate/heptanes over 40 minutes to provide the title compound. $^1$H NMR (400 MHz, chloroform-d) δ ppm 6.89-6.66 (m, 3H), 3.87 (s, 3H), 3.86 (s, 2H), 2.96 (hept, J=6.8 Hz, 1H), 1.28 (d, J=6.9 Hz, 6H).

Example I-50B methyl 1-(2-isopropyl-6-methoxyphenyl)cyclopropanecarboxylate

To a cooled (−5° C.) suspension of 2-isopropyl-6-methoxyaniline from Example I-50A (0.942 g, 5.70 mmol) in 20% aqueous sulfuric acid (10 mL) was added a solution of sodium nitrite (0.393 g, 5.70 mmol) in water (2 mL) dropwise. The starting material slowly dissolved upon the dropwise addition of the sodium nitrite, and the resulting mixture was stirred in the ice bath for 1 hour, then was added slowly to a cooled solution of copper(I) bromide (1.227 g, 8.55 mmol) in 40% aqueous HBr (6.75 mL). The mixture was warmed to 60° C. for 16 hours, then cooled to ambient temperature and extracted with 3×50 mL of ethyl acetate. The combined extracts were washed with saturated aqueous sodium bicarbonate and brine, dried over sodium sulfate, filtered, and concentrated in vacuo. The crude product was chromatographed using a 10 g silica gel cartridge with a methyl tert-butyl ether/hexanes solvent system to give 2-bromo-1-isopropyl-3-methoxybenzene. To a solution of crude 2-bromo-1-isopropyl-3-methoxybenzene (0.227 g, 0.991 mmol) in tetrahydrofuran (4.95 mL) was added bis(dibenzylideneacetone)palladium (0.011 g, 0.020 mmol) and Q-Phos (1,2,3,4,5-Pentaphenyl-1'-(di-tert-butylphosphino)ferrocene) (pentaphenyl(di-tert-butylphosphino)ferrocene, 0.014 g, 0.020 mmol). Nitrogen was bubbled through the solution for about 3 minutes, then a 0.4 M in tetrahydrofuran solution of (1-(methoxycarbonyl)cyclopropyl)zinc(II) bromide (4.95 mL, 1.982 mmol) was added dropwise over 5 minutes and the internal temperature rose from 17.2° C. to 21.0° C. The reaction was stirred for 15 hours at ambient temperature, at which point it was quenched with saturated ammonium chloride (5 mL), diluted with methyl tert-butyl ether (30 mL), and the layers were separated. The organic layer was filtered through a pad of silica gel and concentrated in vacuo. The crude material was purified via flash chromatography, eluting on a 10 g silica gel cartridge with 1-40% methyl tert-butyl ether/hexanes over 40 minutes to provide the title compound. $^1$H NMR (501 MHz, chloroform-d) δ ppm 7.32-7.26 (m, 1H), 6.93 (dd, J=7.9, 1.1 Hz, 1H), 6.73 (dd, J=8.2, 1.1 Hz, 1H), 3.83 (s, 3H), 3.63 (s, 3H), 3.46 (p, J=6.9 Hz, 1H), 1.81-1.75 (m, 2H), 1.29-1.22 (m, 5H), 1.18 (d, J=6.8 Hz, 3H). MS (ESI+) m/z 221 (M+H)+.

Example I-50C 1-(2-isopropyl-6-methoxyphenyl)cyclopropanecarboxylic Acid

Methyl 1-(2-isopropyl-6-methoxyphenyl)cyclopropanecarboxylate from Example I-50B (0.095 g, 0.383 mmol) was dissolved in tetrahydrofuran (0.5 mL) and methanol (0.500 mL), and water (0.5 mL), then treated with sodium hydroxide (0.113 g, 2.83 mmol) and warmed to 70° C. After 5 hours at 70° C., the reaction was concentrated, cooled in an ice bath and carefully quenched with 12 N aqueous HCl (about 0.2 mL) until the pH was acidic. The resulting slurry was stirred vigorously and filtered. The material was washed with water and dried in a vacuum oven for 16 hours to provide the title compound. $^1$H NMR (501 MHz, chloroform-d) δ ppm 7.32-7.25 (m, 1H), 6.93 (dd, J=7.9, 1.1 Hz, 1H), 6.73 (dd, J=8.1, 1.1 Hz, 1H), 3.84 (s, 3H), 3.49 (h, J=6.7 Hz, 1H), 1.89-1.80 (m, 2H), 1.32-1.23 (m, 4H), 1.20 (d, J=6.8 Hz, 3H), 1.15 (dd, J=9.4, 4.5 Hz, 1H).

Example I-50D

1-[2-methoxy-6-(propan-2-yl)phenyl]-N-(quinoline-5-sulfonyl)cyclopropane-1-carboxamide To a solution of 1-(2-isopropyl-6-methoxyphenyl)cyclopropanecarboxylic acid from Example I-50C (70 mg, 0.299 mmol), $N^1$-((ethylimino)methylene)-$N^3$,$N^3$-dimethylpropane-1,3-diamine hydrochloride (115 mg, 0.598 mmol) and N,N-dimethylpyridin-4-amine (36.5 mg, 0.299 mmol) in anhydrous N,N-dimethylacetamide (1.0 mL) was added quinoline-5-sulfonamide (68.4 mg, 0.329 mmol). After 16 hours, the reaction was diluted with a small piece of ice and quenched with 0.5 mL of 1 N aqueous HCl and a precipitate formed. The precipitate was washed with water, and dried under a stream of nitrogen. The crude material was taken up in a small amount of 10% methanol/dichloromethane and purified using a 10 g silica gel cartridge with a gradient of 0-10% methanol/dichloromethane to provide the title compound. $^1$H NMR (501 MHz, chloroform-d) δ ppm 9.01 (dd, J=4.2, 1.6 Hz, 1H), 8.76 (ddd, J=8.8, 1.6, 0.9 Hz, 1H), 8.52 (dd, J=7.4, 1.2 Hz, 1H), 8.41 (dt, J=8.5, 1.1 Hz, 1H), 8.38 (s, 1H), 7.86 (dd, J=8.5, 7.4 Hz, 1H), 7.46 (dd, J=8.7, 4.1 Hz, 1H), 7.39 (t, J=8.0 Hz, 1H), 6.96 (dd, J=8.0, 1.0 Hz, 1H), 6.81 (dd, J=8.2, 1.0 Hz, 1H), 3.79 (s, 3H), 3.32 (hept, J=6.9 Hz, 1H), 1.79 (ddd, J=10.2, 7.4, 3.7 Hz, 1H), 1.51 (ddd, J=9.6, 7.1, 4.2 Hz, 1H), 1.18 (d, J=6.8 Hz, 3H), 1.06 (ddd, J=9.4, 7.4, 4.2 Hz, 1H), 1.01 (dd, J=7.3, 3.9 Hz, 1H), 0.98 (d, J=6.8 Hz, 3H). MS (APCI+) m/z 425 (M+H)$^+$.

Example I-51

1-(2-cyclobutyl-6-methoxyphenyl)-N-(quinoline-5-sulfonyl)cyclopropane-1-carboxamide

Example I-51A 2-cyclobutyl-6-methoxyaniline

To a solution of 2-bromo-6-methoxyaniline (1.539 g, 7.62 mmol) in tetrahydrofuran (12 mL) was added 1,1'-bis(diphenylphosphino)ferrocene-palladium(II)dichloride dichloromethane complex (0.297 g, 0.364 mmol). Nitrogen was bubbled through the solution for about 3 minutes, then a 0.35 M in tetrahydrofuran solution of cyclobutylzinc(II) bromide (40 mL, 14.00 mmol) was added dropwise over 5 minutes. The reaction was stirred for 15 hours at ambient temperature. Additional cyclobutylzincbromide solution (24 mL) was added and the mixture was stirred at ambient temperature for 24 hours. The reaction was quenched with saturated aqueous ammonium chloride (50 mL), diluted with methyl tert-butyl ether (400 mL), and the layers were separated. The organic layer was concentrated in vacuo to give crude material that was purified via flash chromatography, eluting on a 40 g silica gel cartridge with 1-60% methyl tert-butyl ether/hexanes over 40 minutes to provide the title compound. $^1$H NMR (501 MHz, chloroform-d) δ ppm 6.81 (ddd, J=7.5, 1.7, 0.8 Hz, 1H), 6.77 (t, J=7.7 Hz, 1H), 6.74 (dd, J=7.9, 1.8 Hz, 1H), 3.88 (s, 3H), 3.75 (d, J=17.6 Hz, 2H), 3.59-3.49 (m, 1H), 2.47-2.37 (m, 2H), 2.27-2.16 (m, 2H), 2.09 (tdt, J=10.5, 9.3, 7.9 Hz, 1H), 1.95-1.86 (m, 1H). MS (ESI+) m/z 178 (M+H)$^+$.

Example I-51B methyl 1-(2-cyclobutyl-6-methoxyphenyl)cyclopropanecarboxylate To a cooled (0° C.) suspension of 2-cyclobutyl-6-methoxyaniline from Example I-51A (0.450 g, 2.54 mmol) in 40% aqueous HBr (1 mL) was added a solution of sodium nitrite (0.175 g, 2.54 mmol) in water (0.5 mL) dropwise, keeping the internal temperature below 5° C. The resulting mixture was stirred in the ice bath for 1 hour, then was added to a solution of copper(I) bromide (0.364 g, 2.54 mmol) in 40% aqueous HBr (1 mL). The mixture was warmed to 85° C. for 1 hour, then cooled to ambient temperature and extracted with 3×50 mL of methyl tert-butyl ether. The combined extracts were washed with saturated aqueous sodium bicarbonate and brine, and filtered through a pad of silica gel to give crude 2-bromo-1-cyclobutyl-3-methoxybenzene. To a solution of the crude 2-bromo-1-cyclobutyl-3-methoxybenzene (0.090 g, 0.373 mmol) in tetrahydrofuran (1.866 mL) was added bis(dibenzylideneacetone) palladium (4.29 mg, 7.47 µmol) and Q-Phos (1,2,3,4,5-pentaphenylentaphenyl-1'-(di-tert-butylphosphino) ferrocene) (pentaphenyl(di-tert-butylphosphino)ferrocene, 5.31 mg, 7.47 µmol). Nitrogen was bubbled through the solution for about 3 minutes, pentaphenyla 0.4 M in tetrahydrofuran solution of (1-(methoxycarbonyl)cyclopropyl)zinc(II) bromide (1.866 mL, 0.747 mmol) was added dropwise over 5 minutes and the internal temperature rose from 17.2° C. to 21.0° C. The reaction was stirred for 15 hours at ambient temperature, at which point it was quenched with saturated aqueous ammonium chloride (30 mL), diluted with methyl tert-butyl ether (130 mL), and the layers were separated. The organic layer was filtered through a pad of silica gel and concentrated in vacuo to give crude material that was purified via flash chromatography, eluting on a 12 g silica gel cartridge with 1-40% methyl tert-butyl ether/hexanes over 40 minutes to provide the title compound. $^1$H NMR (501 MHz, chloroform-d) δ ppm 7.32-7.27 (m, 1H), 7.02 (dt, J=7.7, 0.9 Hz, 1H), 6.77 (dd, J=8.1, 1.1 Hz, 1H), 3.95-3.85 (m, 1H), 3.83 (s, 3H), 3.61 (s, 3H), 2.39-2.30 (m, 1H), 2.29-2.19 (m, 2H), 2.13-1.97 (m, 2H), 1.90-1.81 (m, 1H), 1.81-1.69 (m, 2H), 1.19-1.07 (m, 2H). MS (ESI+) m/z 221 (M+H)$^+$.

Example I-51C 1-(2-cyclobutyl-6-methoxyphenyl)cyclopropanecarboxylic Acid

Methyl 1-(2-cyclobutyl-6-methoxyphenyl)cyclopropanecarboxylate from Example I-51B (0.028 g, 0.108 mmol)

was dissolved in tetrahydrofuran (0.5 mL) and methanol (0.500 mL), and water (0.5 mL), treated with sodium hydroxide (0.075 g, 1.875 mmol) and warmed to 70° C. After 3 hours, the reaction was concentrated, cooled in an ice bath and carefully quenched with 12 N aqueous HCl (about 0.2 mL) until the pH was acidic. The crude material was taken up in methyl tert-butyl ether and dried over magnesium sulfate, filtered, and concentrated to provide the title compound. $^1$H NMR (501 MHz, chloroform-d) δ ppm 7.33-7.25 (m, 1H), 7.02 (dd, J=7.8, 1.1 Hz, 1H), 6.76 (dd, J=8.2, 1.0 Hz, 1H), 3.95-3.85 (m, 1H), 3.84 (s, 3H), 2.39-2.27 (m, 1H), 2.27-2.10 (m, 2H), 2.09-1.94 (m, 1H), 1.92-1.76 (m, 3H), 1.24-1.15 (m, 3H). MS (DCI+) m/z 247 (M+H)$^+$.

Example I-51D 1-(2-cyclobutyl-6-methoxyphenyl)-N-(quinoline-5-sulfonyl)cyclopropane-1-carboxamide To a solution of 1-(2-cyclobutyl-6-methoxyphenyl)cyclopropanecarboxylic acid from Example I-51C (20 mg, 0.081 mmol), N$^1$-((ethylimino)methylene)-N$^3$,N$^3$-dimethylpropane-1,3-diamine hydrochloride (31.1 mg, 0.162 mmol) and N,N-dimethylpyridin-4-amine (9.92 mg, 0.081 mmol) in anhydrous N,N-dimethylacetamide (0.4 mL) was added quinoline-5-sulfonamide (18.60 mg, 0.089 mmol). After 16 hours, the reaction was diluted with a small piece of ice and quenched with 0.25 mL of 1 N aqueous HCl and a precipitate formed. The precipitate was washed with ice and was taken up in 1.5 mL of methanol/dimethylsulfoxide, filtered, and purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (400 MHz, chloroform-d) δ ppm 9.01 (dd, J=4.2, 1.6 Hz, 1H), 8.73 (dt, J=8.6, 1.3 Hz, 1H), 8.51 (dd, J=7.5, 1.2 Hz, 1H), 8.40 (dt, J=8.5, 1.1 Hz, 1H), 8.26 (s, 1H), 7.85 (dd, J=8.5, 7.5 Hz, 1H), 7.47 (dd, J=8.8, 4.2 Hz, 1H), 7.39 (t, J=8.1 Hz, 1H), 7.04 (d, J=7.8 Hz, 1H), 6.83 (dd, J=8.2, 1.1 Hz, 1H), 3.77 (s, 3H), 3.67 (p, J=8.7 Hz, 1H), 2.35-2.22 (m, 1H), 2.15-2.03 (m, 1H), 2.03-1.94 (m, 1H), 1.94-1.78 (m, 2H), 1.78-1.63 (m, 2H), 1.51-1.42 (m, 1H), 1.07-0.90 (m, 2H). MS (APCI+) m/z 437 (M+H)$^+$.

Example I-52

1-[2-methoxy-5-(2-methoxypropan-2-yl)phenyl]-N-(quinoline-5-sulfonyl)cyclopropane-1-carboxamide Example I-52A 1-methoxy-4-(2-methoxypropan-2-yl)benzene To a solution of 2-(4-methoxyphenyl)propan-2-ol (CAS #7428-99-1) (2.3 g, 13.84 mmol) in N,N-dimethylformamide (13 mL) at 0° C. was added sodium hydride (0.830 g, 20.76 mmol). After 30 minutes, iodomethane (1.298 mL, 20.76 mmol) was added and the reaction was stirred at 0° C. for 1 hour. The mixture was quenched via addition of saturated aqueous ammonium chloride (50 mL) and extracted with ethyl acetate. The crude material was purified by chromatography, eluting on 40 g silica gel cartridge with a gradient of 0-50% ethyl acetate/heptanes over a period of 20 minutes to provide the title compound. $^1$H NMR (400 MHz, chloroform-d) δ ppm 7.33 (d, J=8.9 Hz, 2H), 6.88 (d, J=8.8 Hz, 2H), 3.81 (s, 3H), 3.04 (s, 3H), 1.51 (s, 6H). MS (DCI+) m/z 149 (M+H-methanol)$^+$.

Example I-52B 2-(3-bromo-4-methoxyphenyl)propan-2-ol

A solution of 1-methoxy-4-(2-methoxypropan-2-yl)benzene from Example I-52A (1.75 g, 9.71 mmol) and benzyltrimethylammonium tribromide (4.16 g, 10.68 mmol) in tetrahydrofuran (30.3 mL) and degassed water (18.20 mL) was stirred at ambient temperature for 5 hours. The volatiles were removed in vacuo and the resulting mixture was diluted with 100 mL of methyl tert-butyl ether and the organics were concentrated. The crude material was purified by chromatography, eluting on 40 g silica gel cartridge with a gradient of 0-50% ethyl acetate/heptanes over a period of 20 minutes to provide the title compound. $^1$H NMR (501 MHz, chloroform-d) δ ppm 7.67 (d, J=2.3 Hz, 1H), 7.39 (dd, J=8.6, 2.3 Hz, 1H), 6.86 (d, J=8.5 Hz, 1H), 3.89 (s, 3H), 1.68 (s, 1H), 1.56 (s, 6H). MS (DCI+) m/z 227 (M+H-H$_2$O)$^+$.

Example I-52C 2-bromo-1-methoxy-4-(2-methoxypropan-2-yl)benzene

To a solution of 2-(3-bromo-4-methoxyphenyl)propan-2-ol from Example I-52B (0.45 g, 1.836 mmol) in N,N-dimethylformamide (4 mL) at 0° C. was added sodium hydride (0.147 g, 3.67 mmol). After 30 minutes, iodomethane (0.230 mL, 3.67 mmol) was added and the reaction was stirred at 0° C. for 3 hours. The mixture was quenched via addition of saturated aqueous ammonium chloride (20 mL) and extracted with ethyl acetate. The crude material was concentrated, and the residue was purified by chromatography, eluting on a 10 g silica gel cartridge with a gradient of 0-50% ethyl acetate/heptanes over a period of 10 minutes to provide the title compound. $^1$H NMR (400 MHz, chloroform-d) δ ppm 7.58 (d, J=2.3 Hz, 1H), 7.31 (dd, J=8.6, 2.3 Hz, 1H), 6.87 (d, J=8.6 Hz, 1H), 3.90 (s, 3H), 3.05 (s, 3H), 1.50 (s, 6H). MS (APCI+) m/z 227 (M+H-methanol)$^+$.

Example I-52D methyl 1-(2-methoxy-5-(2-methoxypropan-2-yl)phenyl)cyclopropanecarboxylate To a solution of bis(dibenzylideneacetone)palladium (0.022 g, 0.039 mmol) and Q-Phos (pentaphenyl(di-tert-butylphosphino)ferrocene, 0.028 g, 0.039 mmol) in tetrahydrofuran (10 mL) at ambient temperature was added 2-bromo-1-methoxy-4-(2-methoxypropan-2-yl)benzene from Example I-52C (0.364 mL, 1.956 mmol) in 1 mL tetrahydrofuran followed by a solution of freshly prepared (1-(methoxycarbonyl)cyclopropyl)zinc(II) bromide (9.78 mL, 3.91 mmol). The mixture was stirred at ambient temperature for 16 hours. Ethyl acetate and saturated aqueous ammonium chloride was added, and the organic layer was washed with brine and concentrated. The residue was purified via chromatography on a 24 g silica gel cartridge, eluting with ethyl acetate in heptane at a 0-50% gradient over a period of 15 minutes to provide the title compound. $^1$H NMR (400 MHz, chloroform-d) δ ppm 7.28 (d, J=2.4 Hz, OH), 7.24 (d, J=2.3 Hz, 1H), 6.82 (d, J=8.4 Hz, 1H), 3.83 (s, 3H), 3.60 (s, 3H), 3.04 (s, 3H), 1.60 (q, J=4.1 Hz, 2H), 1.51 (s, 6H), 1.11 (q, J=4.1 Hz, 2H). MS (APCI+) m/z 247 (M+H-methanol)$^+$.

Example I-52E 1-(2-methoxy-5-(2-methoxypropan-2-yl)phenyl) cyclopropanecarboxylic Acid Methyl 1-(2-methoxy-5-(2-methoxypropan-2-yl)phenyl) cyclopropanecarboxylate from Example I-52D (435 mg, 1.563 mmol) was dissolved in tetrahydrofuran (3.50 mL), methanol (3.50 mL), and water (3.5 mL) and treated with sodium hydroxide (313 mg, 7.81 mmol). The reaction mixture was warmed to 45° C. for 2 hours and at 35° C. for 16 hours. The reaction mixture was concentrated, cooled in an ice bath and carefully quenched with 1 N aqueous citric acid (about 5.5 mL) until pH~5. The resulting slurry was stirred vigorously and filtered, and the precipitate was washed with water and dried in a vacuum oven for 16 hours to provide the title compound. $^1$H NMR (400 MHz, chloroform-d) δ ppm 10.82 (bs, 1H), 7.30-7.24 (m, 2H), 6.82 (d, J=8.2 Hz, 1H), 3.84 (s, 3H), 3.02 (s, 3H), 1.65 (q, J=4.1 Hz, 2H), 1.49 (s, 6H), 1.17 (q, J=4.2 Hz, 2H). MS (APCI+) m/z 233 (M+H-methanol)$^+$.

Example I-52F 1-(2-methoxy-5-(2-methoxypropan-2-yl)phenyl)-N-(quinolin-5-ylsulfonyl)cyclopropane-1-carboxamide To a solution of 1-(2-methoxy-5-(2-methoxypropan-2-yl) phenyl)cyclopropanecarboxylic acid from Example I-52E (0.100 g, 0.378 mmol), N$^1$-((ethylimino)methylene)-N$^3$,N$^3$-dimethylpropane-1,3-diamine hydrochloride (0.145 g, 0.757 mmol) and N,N-dimethylpyridin-4-amine (0.051 g, 0.416 mmol) in anhydrous dichloromethane (1 mL) was added quinoline-5-sulfonamide (0.079 g, 0.378 mmol). After 16 hours, the reaction was quenched with 1 mL of aqueous 1 N citric acid and the organic layer was concentrated in vacuo. The residue was purified via chromatography on a 10 g silica gel cartridge, eluting with a gradient of 0-10% methanol/dichloromethane over a period of 10 minutes. The material was triturated with diethyl ether and filtered to provide the title compound. $^1$H NMR (400 MHz, dimethyl sulfoxide-d$_6$) δ ppm 11.55 (s, 1H), 9.06 (dd, J=4.2, 1.6 Hz, 1H), 8.97 (dt, J=8.8, 1.2 Hz, 1H), 8.35 (d, J=8.5 Hz, 1H), 8.31 (dd, J=7.5, 1.2 Hz, 1H), 7.94 (dd, J=8.4, 7.5 Hz, 1H), 7.71 (dd, J=8.8, 4.2 Hz, 1H), 7.24 (dd, J=8.5, 2.4 Hz, 1H), 7.07 (d, J=2.4 Hz, 1H), 6.82 (d, J=8.5 Hz, 1H), 3.35 (s, 3H), 2.95 (s, 3H), 1.41 (s, 6H), 1.31 (q, J=4.3 Hz, 2H), 0.95 (q, J=4.5 Hz, 2H). MS (ESI−) m/z 453 (M−H)$^−$.

Example I-53

N-(1H-indazole-4-sulfonyl)-1-(2-methoxy-5-methylphenyl)cyclopropane-1-carboxamide A mixture of Example I-49B (50 mg, 0.242 mmol) and N$^1$-((ethylimino)methylene)-N$^3$,N$^3$-dimethylpropane-1,3-diamine, hydrochloric acid (93 mg, 0.485 mmol) and N,N-dimethylpyridin-4-amine (59.2 mg, 0.485 mmol) in dichloromethane (4 mL) was stirred at ambient temperature for 30 minutes. 3a,7a-Dihydro-1H-indazole-4-sulfonamide (58.0 mg, 0.291 mmol) was added. The mixture was stirred at 45° C. for two hours. The solvent was removed and the residue was dissolved in methanol (3 mL) and filtered through a syringe filter. The filtrate was purified via reverse phase HPLC (C18, CH$_3$CN/H$_2$O (0.1% trifluoroacetic acid),) provided the title compound. $^1$H NMR (501 MHz, dimethyl sulfoxide-d$_6$) δ ppm 11.62 (s, 1H), 10.86 (s, 1H), 7.71 (s, 1H), 7.64-7.49 (m, 2H), 7.23 (s, 1H), 7.13 (d, J=8.2 Hz, 1H), 6.96 (d, J=2.3 Hz, 1H), 6.85 (d, J=8.4 Hz, 1H), 6.81 (s, 1H), 3.51 (s, 3H), 3.45-3.41 (m, 1H), 2.24 (qt, J=8.0, 2.4 Hz, 2H), 2.06 (pd, J=9.2, 2.7 Hz, 2H), 1.99-1.90 (m, 1H), 1.85-1.70 (m, 1H), 1.26 (q, J=4.2 Hz, 2H), 0.94 (s, 2H). MS (APCI+) m/z 386 (M+H)$^+$. Also obtained was 1-(1-(2-methoxy-5-methylphenyl)cyclopropanecarbonyl)-1H-indazole-4-sulfonamide. $^1$H NMR (400 MHz, dimethyl sulfoxide-d$_6$) δ ppm 8.50 (ddd, J=7.5, 1.6, 0.8 Hz, 1H), 8.31 (d, J=0.8 Hz, 1H), 7.81-7.73 (m, 2H), 7.64 (s, 2H), 7.13 (d, J=2.2 Hz, 1H), 6.94 (dd, J=8.2, 2.0 Hz, 1H), 6.67 (d, J=8.2 Hz, 1H), 3.36 (s, 3H), 2.27 (s, 3H), 1.70 (q, J=4.5 Hz, 2H), 1.38 (q, J=4.6 Hz, 2H). MS (APCI+) m/z 386 (M+H)$^+$.

Example I-54

1-(5-cyclobutyl-2-methoxyphenyl)-N-(2,3-dihydro-1H-indole-4-sulfonyl)cyclopropane-1-carboxamide Example I-54A methyl 1-(2-methoxyphenyl)cyclopropanecarboxylate To a mixture of tris(dibenzylideneacetone)dipalladium(0) (0.086 g, 0.094 mmol), 1,2,3,4,5-pentaphenyl-1'-(di-tert-butylphosphino)ferrocene (0.133 g, 0.187 mmol) and 1-bromo-2-methoxybenzene (2.313 mL, 18.71 mmol) in tetrahydrofuran (144 mL) under nitrogen gas, (1-(methoxycarbonyl)cyclopropyl)zinc(II) bromide (47.8 mL, 22.46 mmol) was added slowly. After the addition, the mixture stirred at ambient temperature for 16 hours. The mixture was quenched with saturated aqueous ammonium chloride (20 mL) and 200 mL of ethyl acetate was added. The combined organic layer was washed with saturated aqueous ammonium chloride and brine, dried over sodium sulfate, filtered, and concentrated. The residue was purified via chromatography on 120 g silica gel column, eluting with 0-20% ethyl acetate in heptane to provide the title compound. MS (APCI+) m/z 207 (M+H)$^+$.

Example I-54B methyl 1-(5-bromo-2-methoxyphenyl)cyclopropanecarboxylate

A solution of methyl 1-(2-methoxyphenyl)cyclopropanecarboxylate (3.8 g, 18.4 mmol) and benzyltrimethylammonium tribromide (7.72 g, 19.80 mmol) in tetrahydrofuran (58.8 mL) and water (35.3 mL) was stirred at ambient temperature overnight. The solvents were removed under vacuum and the resulting aqueous layer was diluted with 85 mL of methyl tert-butyl ether. The organics were washed with brine, dried over Na$_2$SO$_4$, filtered through a pad of silica gel and concentrated to provide the title compound. $^1$H NMR (501 MHz, chloroform-d) δ ppm 7.38 (dd, J=8.7, 2.5 Hz, 1H), 7.32 (d, J=2.5 Hz, 1H), 6.77 (d, J=8.7 Hz, 1H), 3.84 (s, 3H), 3.63 (s, 3H), 1.64-1.61 (m, 2H), 1.14-1.09 (m, 2H).

Example I-54C 1-(5-bromo-2-methoxyphenyl)cyclopropanecarboxylic Acid

A mixture of Example I-54B (4.88 g, 17.11 mmol) in tetrahydrofuran (35 mL) and methanol (35.0 mL) was treated with 3 M aqueous sodium hydroxide (28.5 mL, 86 mmol) and heated at 50° C. for 3 hours and concentrated. The residue was cooled in an ice bath and the pH was carefully adjusted to 1-2 by adding 6 N aqueous HCl. The resulting slurry was stirred vigorously and filtered. The precipitate was washed with water and dried in a vacuum oven overnight to provide the title compound. $^1$H NMR (400 MHz, dimethyl sulfoxide-$d_6$) δ ppm 12.06 (s, 1H), 7.37 (dd, J=8.7, 2.5 Hz, 1H), 7.28 (d, J=2.6 Hz, 1H), 6.90 (d, J=8.8 Hz, 1H), 3.74 (s, 3H), 1.36 (q, J=4.0 Hz, 2H), 1.01 (q, J=4.1 Hz, 2H).

Example I-54D 1-(5-cyclobutyl-2-methoxyphenyl)cyclopropanecarboxylic Acid

A mixture of Example I-54C (0.8 g, 2.95 mmol) and [1,1'-bis(diphenylphosphino)ferrocene]dichloropalladium (II) (435 mg) in tetrahydrofuran (5 mL) was degassed by bubbling a stream of nitrogen through the suspension, and cyclobutylzinc(II) bromide (0.5 M in tetrahydrofuran, 12 mL) was added through a syringe filter. The mixture was stirred at ambient temperature for 2 hours. The solvent was removed and the residue was purified via chromatography on a 25 g silica gel cartridge, eluting with ethyl acetate/methanol (9:1) in heptane at 0-40% gradient to provide the title compound. $^1$H NMR (501 MHz, chloroform-d) δ ppm 7.11 (ddd, J=8.3, 2.3, 0.7 Hz, 1H), 7.04 (d, J=2.3 Hz, 1H), 6.80 (d, J=8.3 Hz, 1H), 3.81 (s, 3H), 3.45 (p, J=8.8 Hz, 1H), 2.34-2.25 (m, 2H), 2.14-2.04 (m, 2H), 2.03-1.91 (m, 1H), 1.88-1.77 (m, 1H), 1.63 (q, J=4.0 Hz, 2H), 1.17 (q, J=4.0 Hz, 2H). MS (ESI+) m/z 246 (M+H)$^+$.

Example I-54E 1-(5-cyclobutyl-2-methoxyphenyl)-N-(indolin-4-ylsulfonyl)cyclopropanecarboxamide A mixture of Example I-54D (50 mg, 0.203 mmol) and N$^1$-((ethylimino)methylene)-N$^3$,N$^3$-dimethylpropane-1,3-diamine, hydrochloric acid (78 mg, 0.406 mmol) and N,N-dimethylpyridin-4-amine (49.6 mg, 0.406 mmol) in dichloromethane (4 mL) was stirred at ambient temperature for 30 minutes. Indoline-4-sulfonamide (40.7 mg, 0.203 mmol) was added. The mixture was stirred at 40° C. for 2 hours. The solvent was removed and the residue was dissolved in methanol (3 mL) and filtered through a syringe filter. Purification via reverse phase HPLC (C18, CH$_3$CN/H$_2$O (0.1% trifluoroacetic acid), 5-95%, 20 minutes) provided Example I-54E. $^1$H NMR (501 MHz, dimethyl sulfoxide-$d_6$) δ ppm 10.83 (s, 1H), 7.15 (d, J=8.3 Hz, 1H), 7.07 (t, J=7.9 Hz, 1H), 7.01 (d, J=2.2 Hz, 1H), 6.91 (dd, J=16.1, 8.1 Hz, 2H), 6.68 (d, J=7.7 Hz, 1H), 5.93 (s, 1H), 3.65 (s, 3H), 3.48-3.43 (m, 3H), 3.14 (t, J=8.7 Hz, 2H), 2.24 (qt, J=8.1, 2.5 Hz, 2H), 2.07 (pd, J=9.1, 2.6 Hz, 2H), 1.93 (dtd, J=11.4, 9.8, 8.9, 2.2 Hz, 1H), 1.83-1.73 (m, 1H), 1.35 (q, J=4.3 Hz, 2H), 1.00 (s, 2H). MS (trifluoroacetic acid/APCI+) m/z 427 (M+H)$^+$. Also provided was the oxidized product, Example I-55.

Example I-55

1-(5-cyclobutyl-2-methoxyphenyl)-N-(1H-indole-4-sulfonyl)cyclopropane-1-carboxamide The title compound was obtained as a by-product from Example I-54E. $^1$H NMR (501 MHz, dimethyl sulfoxide-$d_6$) δ ppm 11.62 (s, 1H), 10.86 (s, 1H), 7.71 (s, 1H), 7.64-7.49 (m, 2H), 7.23 (s, 1H), 7.13 (d, J=8.2 Hz, 1H), 6.96 (d, J=2.3 Hz, 1H), 6.85 (d, J=8.4 Hz, 1H), 6.81 (s, 1H), 3.51 (s, 3H), 3.45-3.41 (m, 1H), 2.24 (qt, J=8.0, 2.4 Hz, 2H), 2.06 (pd, J=9.2, 2.7 Hz, 2H), 1.99-1.90 (m, 1H), 1.85-1.70 (m, 1H), 1.26 (q, J=4.2 Hz, 2H), 0.94 (s, 2H). MS (APCI+) m/z 427 (M+H)$^+$.

Example I-56

1-(5-cyclobutyl-2-methoxyphenyl)-N-(1H-indazole-4-sulfonyl)cyclopropane-1-carboxamide A mixture of Example I-54D (60 mg, 0.244 mmol) and N$^1$-((ethylimino)methylene)-N$^3$,N$^3$-dimethylpropane-1,3-diamine, hydrochloric acid (93 mg, 0.487 mmol) and N,N-dimethylpyridin-4-amine (59.5 mg, 0.487 mmol) in dichloromethane (4 mL) was stirred at ambient temperature for 30 minutes. 1H-Indazole-4-sulfonamide (58.2 mg, 0.292 mmol) was added. The mixture was stirred at 45° C. for 2 hours. The solvent was removed and the residue was dissolved in methanol (3 mL). Purification via reverse phase HPLC (C18, CH$_3$CN/H$_2$O (0.1% trifluoroacetic acid), 5-95%, 20 minutes) provided the title compound. $^1$H NMR (501 MHz, dimethyl sulfoxide-$d_6$) δ ppm 13.60 (s, 1H), 11.28 (s, 1H), 8.35 (s, 1H), 7.88 (d, J=8.1 Hz, 1H), 7.68 (d, J=7.0 Hz, 1H), 7.53 (t, J=7.8 Hz, 1H), 7.15 (d, J=7.8 Hz, 1H), 6.97 (d, J=2.3 Hz, 1H), 6.85 (d, J=8.3 Hz, 1H), 3.47 (s, 3H), 3.45-3.42 (m, 3H), 2.29-2.20 (m, 2H), 2.13-2.01 (m, 2H), 1.98-1.88 (m, 1H), 1.84-1.74 (m, 1H), 1.25-1.22 (m, 2H), 0.96 (s, 2H). MS (ESI+): m/z=426 (M+H). Also provided was 1-(1-(5-cyclobutyl-2-methoxyphenyl)cyclopropanecarbonyl)-1H-indazole-4-sulfonamide. $^1$H NMR (501 MHz, dimethyl sulfoxide-$d_6$) δ ppm 8.52-8.48 (m, 1H), 8.31 (s, 1H), 7.81-7.74 (m, 2H), 7.64 (s, 2H), 7.17 (d, J=2.2 Hz, 1H), 7.03 (dd, J=8.3, 2.2 Hz, 1H), 6.71 (d, J=8.3 Hz, 1H), 3.48 (t, J=8.8 Hz, 1H), 3.40 (s, 3H), 2.28 (qq, J=7.5, 2.5 Hz, 2H), 2.09 (pd, J=9.0, 8.6, 2.6 Hz, 2H), 1.99-1.90 (m, 1H), 1.82 (tdd, J=12.3, 11.1, 6.9, 2.7 Hz, 1H), 1.71 (q, J=4.5 Hz, 2H), 1.39 (q, J=4.6 Hz, 2H). MS (ESI+) m/z 426 (M+H)$^+$.

Example I-57

1-[2-(dimethylamino)-5-(trifluoromethyl)pyridin-3-yl]-N-(quinoline-5-sulfonyl)cyclopropane-1-carboxamide In a 4 mL vial was added Example I-30C (64 mg, 0.233 mmol), N$^1$-((ethylimino)methylene)-N$^3$,N$^3$-dimethylpropane-1,3-diamine hydrochloride (89 mg, 0.467 mmol), and N,N-dimethylpyridin-4-amine (31.4 mg, 0.257 mmol) in dichloromethane (1 mL). Quinoline-5-sulfonamide (53.5 mg, 0.257 mmol) was added and the reaction was stirred overnight at ambient temperature. The solvent was removed under a stream of nitrogen and the residue was dissolved in methanol. The sample was purified via preparative reverse phase HPLC/MS method trifluoroacetic acid1, and subsequently repurified using method AA3 to afford the title compound. $^1$H NMR (400 MHz, dimethyl sulfoxide-$d_6$: D$_2$O=9:1 (v/v)) δ ppm 9.03 (dd, J=8.7, 1.7 Hz, 1H), 8.90 (dd, J=4.2, 1.7 Hz, 1H), 8.24-8.16 (m, 1H), 8.07 (s, 1H), 8.05 (s, 1H), 7.75 (t, J=7.9 Hz, 1H), 7.52 (dd, J=8.7, 4.2 Hz, 1H), 7.46 (d, J=2.5 Hz, 1H), 2.77 (s, 6H), 1.35-1.30 (m, 2H), 0.79-0.72 (m, 2H). MS (APCI) m/z 464.9 (M+H)$^+$.

Example I-58

1-(5-cyclobutyl-2-methoxyphenyl)-N-(1-methyl-1H-indole-4-sulfonyl)cyclopropane-1-carboxamide Example I-58 was prepared as described in Example I-62, substituting 1-methyl-1H-indole-4-sulfonamide for 2-methylquinoline-8-sulfonamide. $^1$H NMR (400 MHz, dimethyl sulfoxide-$d_6$:$D_2O$=9:1 (v/v)) δ ppm 7.80 (d, J=8.2 Hz, 1H), 7.62 (d, J=7.5 Hz, 1H), 7.55 (d, J=3.1 Hz, 1H), 7.31 (t, J=7.9 Hz, 1H), 7.22-7.11 (m, 1H), 6.97 (d, J=2.3 Hz, 1H), 6.88 (d, J=8.4 Hz, 1H), 6.77 (dd, J=3.0, 0.9 Hz, 1H), 3.87 (s, 3H), 3.53 (s, 3H), 3.43 (p, J=8.6 Hz, 1H), 2.25 (qt, J=7.7, 2.3 Hz, 2H), 2.14-1.71 (m, 4H), 1.26 (q, J=4.3 Hz, 2H), 1.00-0.91 (m, 2H). MS (APCI) m/z 439.0 (M+H)$^+$.

Example I-59

1-(5-cyclobutyl-2-methoxyphenyl)-N-(1-methyl-1H-indole-7-sulfonyl)cyclopropane-1-carboxamide Example I-59 was prepared as described in Example I-62, substituting 1-methyl-1H-indole-7-sulfonamide for 2-methylquinoline-8-sulfonamide. $^1$H NMR (400 MHz, dimethyl sulfoxide-$d_6$:$D_2O$=9:1 (v/v)) δ ppm 7.92 (dd, J=7.9, 1.2 Hz, 1H), 7.78 (dd, J=7.8, 1.2 Hz, 1H), 7.41 (d, J=3.2 Hz, 1H), 7.24-7.10 (m, 2H), 7.05 (d, J=2.2 Hz, 1H), 6.84 (d, J=8.4 Hz, 1H), 6.67 (d, J=3.2 Hz, 1H), 3.89 (s, 3H), 3.44 (p, J=8.6 Hz, 1H), 3.34 (s, 3H), 2.32-2.17 (m, 2H), 2.16-1.72 (m, 4H), 1.37 (q, J=4.3 Hz, 2H), 1.01 (q, J=4.5 Hz, 2H). MS (APCI) m/z 439.0 (M+H)$^+$.

Example I-60

1-(5-cyclobutyl-2-methoxyphenyl)-N-(1-methyl-1H-indazole-7-sulfonyl)cyclopropane-1-carboxamide Example I-60 was prepared as described in Example I-62, substituting 1-methyl-1H-indazole-7-sulfonamide for 2-methylquinoline-8-sulfonamide. $^1$H NMR (400 MHz, dimethyl sulfoxide-$d_6$:$D_2O$=9:1 (v/v)) δ ppm 8.29 (s, 1H), 8.13 (d, J=8.1 Hz, 1H), 8.02 (d, J=7.4 Hz, 1H), 7.31 (t, J=7.8 Hz, 1H), 7.13 (d, J=8.8 Hz, 1H), 7.02 (d, J=2.3 Hz, 1H), 6.80 (d, J=8.4 Hz, 1H), 4.12 (s, 3H), 3.50-3.37 (m, 1H), 3.24 (s, 3H), 2.31-2.17 (m, 2H), 2.13-1.88 (m, 3H), 1.85-1.74 (m, 1H), 1.38-1.27 (m, 2H), 0.96 (s, 2H). MS (APCI) m/z 440.0 (M+H)$^+$.

Example I-61

1-(5-cyclobutyl-2-methoxyphenyl)-N-(pyrazolo[1,5-a]pyridine-4-sulfonyl)cyclopropane-1-carboxamide Example I-61 was prepared as described in Example I-62, substituting pyrazolo[1,5-a]pyridine-4-sulfonamide for 2-methylquinoline-8-sulfonamide. $^1$H NMR (400 MHz, dimethyl sulfoxide-$d_6$:$D_2O$=9:1 (v/v)) δ ppm 8.93 (d, J=7.1 Hz, 1H), 8.19 (s, 1H), 7.84-7.77 (m, 1H), 7.20-7.02 (m, 2H), 6.95 (dd, J=7.1, 2.3 Hz, 2H), 6.84 (d, J=8.4 Hz, 1H), 3.50-3.37 (m, 4H), 2.40-2.17 (m, 2H), 2.12-1.86 (m, 3H), 1.86-1.73 (m, 1H), 1.27 (q, J=4.3 Hz, 2H), 1.00-0.91 (m, 2H). MS (APCI) m/z 426.0 (M+H)$^+$.

Example I-62

1-(5-cyclobutyl-2-methoxyphenyl)-N-(2-methylquinoline-8-sulfonyl)cyclopropane-1-carboxamide 2-Methylquinoline-8-sulfonamide (21.7 mg, 0.10 mmol, 1.0 eq) was weighed into 4 mL vial. 1-(5-Cyclobutyl-2-methoxyphenyl)cyclopropanecarboxylic acid (20.0 mg, 0.08 mmol, 1.0 eq) from Example I-54D, 1-ethyl-3-[3-(dimethylamino)propyl]-carbodiimide hydrochloride (30.9 mg, 0.16 mmol, 2.0 eq) and DMAP (4-dimethylaminopyridine, 10.9 mg, 0.09 mmol, 1.1 eq) dissolved dichloromethane (0.5 mL) was added and the reaction was stirred overnight at ambient temperature. The solvent was removed under a stream of nitrogen, and the residue was reconstituted in dimethylsulfoxide/methanol (1:1). The sample was purified via preparative reverse phase HPLC/MS method trifluoroacetic acid7 to provide the title compound. $^1$H NMR (400 MHz, dimethyl sulfoxide-$d_6$) δ ppm 8.43 (d, J=8.5 Hz, 1H), 8.33 (dd, J=7.4, 1.4 Hz, 1H), 8.30 (dd, J=8.2, 1.4 Hz, 1H), 7.77-7.68 (m, 1H), 7.60 (d, J=8.5 Hz, 1H), 7.20 (dd, J=8.4, 2.3 Hz, 1H), 7.01 (d, J=2.3 Hz, 1H), 6.79 (d, J=8.5 Hz, 1H), 3.47-3.40 (m, 1H), 3.34 (s, 3H), 2.57 (s, 3H), 2.31-2.20 (m, 2H), 2.12-1.89 (m, 3H), 1.85-1.76 (m, 1H), 1.32-1.21 (m, 2H), 1.02-0.94 (m, 2H). MS (APCI+) m/z 451.0 (M+H)$^+$

Example I-63

1-(5-cyclobutyl-2-methoxyphenyl)-N-(2-methylquinoline-5-sulfonyl)cyclopropane-1-carboxamide A mixture of Example I-54D (60 mg, 0.244 mmol) and $N^1$-((ethylimino)methylene)-$N^3$,$N^3$-dimethylpropane-1,3-diamine (76 mg, 0.487 mmol) and N,N-dimethylpyridin-4-amine (59.5 mg, 0.487 mmol) in dichloromethane (2 mL) was stirred at ambient temperature for 30 minutes, and 2-methylquinoline-5-sulfonamide (59.6 mg, 0.268 mmol) was added. The mixture was stirred at 45° C. for 2 hours, and stirred at 45° C. for 3 hours. The solvent was removed and the residue was dissolved in methanol (3 mL) and filtered. Purification via HPLC with trifluoroacetic acid method provided the title compound. $^1$H NMR (501 MHz, dimethyl sulfoxide-$d_6$) δ ppm 11.51 (s, 1H), 8.89 (d, J=8.8 Hz, 1H), 8.30-8.20 (m, 2H), 7.94-7.86 (m, 1H), 7.61 (d, J=8.9 Hz, 1H), 7.14 (dd, J=8.3, 2.2 Hz, 1H), 6.96 (d, J=2.3 Hz, 1H), 6.81 (d, J=8.4 Hz, 1H), 3.44 (d, J=8.9 Hz, 1H), 3.39 (s, 3H), 2.72 (s, 3H), 2.24 (qq, J=7.3, 2.5 Hz, 2H), 2.07 (pd, J=9.0, 2.5 Hz, 2H), 2.00-1.89 (m, 1H), 1.84-1.73 (m, 1H), 1.29-1.20 (m, 2H), 0.96 (q, J=4.4 Hz, 2H). MS (ESI+) m/z 451 (M+H)$^+$.

Example I-64

1-(2-methoxy-5-methylphenyl)-N-(2-methylquinoline-5-sulfonyl)cyclopropane-1-carboxamide A mixture of Example I-49B (60 mg, 0.291 mmol) and $N^1$-((ethylimino)methylene)-$N^3$,$N^3$-dimethylpropane-1,3-diamine (90 mg, 0.582 mmol) and N,N-dimethylpyridin-4-amine (71.1 mg, 0.582 mmol) in dichloromethane (2 mL) was stirred at ambient temperature for 30 minutes. 2-Methylquinoline-5-sulfonamide (71.1 mg, 0.320 mmol) was added. The mixture was stirred at 45° C. for 2 hours, and was stirred at 45° C. for 3 hours. The solvent was removed and the residue was dissolved in methanol (3 mL) and was filtered. Purification via HTP with trifluoroacetic acid method provided the title compound. $^1$H NMR (400 MHz, dimethyl sulfoxide-$d_6$) δ ppm 11.49 (s, 1H), 8.87 (d, J=8.9 Hz, 1H), 8.28-8.18 (m, 2H), 7.92-7.85 (m, 1H), 7.60 (d, J=8.9 Hz, 1H), 7.12-7.05 (m, 1H), 7.00-6.89 (m, 1H), 6.77 (d, J=8.3 Hz, 1H), 3.36 (s, 3H), 2.72 (s, 3H), 2.23 (s, 3H), 1.22 (q, J=4.3 Hz, 2H), 0.93 (q, J=4.4 Hz, 2H). MS (ESI+) m/z 411 (M+H)$^+$.

Example I-65

1-[5-(difluoromethoxy)-2-methoxyphenyl]-N-(quinoline-5-sulfonyl)cyclopropane-1-carboxamide

Example I-65A ethyl 1-(5-(difluoromethoxy)-2-methoxyphenyl)cyclopropane-1-carboxylate A solution of Example I-31E (ethyl 1-(5-hydroxy-2-methoxyphenyl)cyclopropanecarboxylate) (30 mg, 0.127 mmol) in acetonitrile (0.6 mL) at 0° C. was treated dropwise with 2 M KOH in water (635 µl, 1.270 mmol) over 2 minutes, stirred for 5 minutes, treated with diethyl (bromodifluoromethyl)phosphonate (49.6 0.279 mmol) dropwise over 2 minutes, stirred at 0° C. for 30 minutes, and partitioned between methyl tert-butyl ether (50 mL) and water (25 mL). The methyl tert-butyl ether was washed with brine, dried ($MgSO_4$), filtered, concentrated and chromatographed on silica gel, eluting with a gradient of 10% to 100% ethyl acetate in heptanes to provide the title compound. $^1$H NMR (501 MHz, $CDCl_3$) δ ppm 7.02 (dd, J=3.0, 8.8 Hz, 1H), 6.97 (d, J=2.9 Hz, 1H), 6.80 (d, J=8.8 Hz, 1H), 6.42 (t, J=74.5 Hz, 1H), 4.08 (q, J=7.1 Hz, 2H), 3.82 (s, 3H), 1.60 (q, J=4.2 Hz, 2H), 1.14 (t, J=7.1 Hz, 3H), 1.08 (q, J=4.2 Hz, 2H). LC/MS (APCI+) m/z 287 (M+H)$^+$.

Example I-65B 1-(5-(difluoromethoxy)-2-methoxyphenyl)cyclopropane-1-carboxylic Acid In a vial, a solution of Example I-65A (ethyl 1-(5-(difluoromethoxy)-2-methoxyphenyl)cyclopropanecarboxylate) (20 mg, 0.070 mmol) in tetrahydrofuran (1.5 mL) and methanol (1.5 mL) was treated with 3 M aqueous NaOH (1.5 mL), stirred at 80° C. for 12 hours, cooled and partitioned between 1 M aqueous HCl (15 mL) and methyl tert-butyl ether (50 mL). The methyl tert-butyl ether layer was washed with brine, dried ($MgSO_4$), filtered, and concentrated to provide the title compound. $^1$H NMR (400 MHz, $CDCl_3$) δ ppm 7.03 (dd, J=2.9, 8.8 Hz, 1H), 6.99 (d, J=2.9 Hz, 1H), 6.81 (d, J=8.8 Hz, 1H), 6.40 (t, J=74.4 Hz, 1H), 3.83 (s, 3H), 1.67 (q, J=4.2 Hz, 2H), 1.16 (q, J=4.2 Hz, 2H).

Example I-65C

1-[5-(difluoromethoxy)-2-methoxyphenyl]-N-(quinoline-5-sulfonyl)cyclopropane-1-carboxamide A solution of Example I-65B (1-(5-(difluoromethoxy)-2-methoxyphenyl)cyclopropanecarboxylic acid (17.2 mg, 0.067 mmol), quinoline-5-sulfonamide) (27.7 mg, 0.133 mmol), 1-(3-dimethylaminopropyl)-3-ethylcarbodiimide hydrochloride (25.5 mg, 0.133 mmol) and 4-dimethylaminopyridine (16.28 mg, 0.133 mmol) in N,N-dimethylformamide (0.3 mL) was stirred overnight at ambient temperature. The mixture was partitioned between methyl tert-butyl ether (50 mL) and 1 M aqueous HCl (15 mL). The methyl tert-butyl ether layer was washed with 0.2 M aqueous HCl (15 mL), washed with brine, dried ($MgSO_4$), filtered, concentrated and chromatographed on silica gel, eluting with a gradient of 25% to 100%[200:1:1 ethyl acetate:formic acid:$H_2O$] in heptanes to provide the title compound. $^1$H NMR (501 MHz, dimethyl sulfoxide-d$_6$) δ ppm 11.69 (s, 1H), 9.05 (dd, J=1.6, 4.2 Hz, 1H), 8.94 (dd, J=1.2, 8.7 Hz, 1H), 8.34 (d, J=8.5 Hz, 1H), 8.31 (d, J=7.4 Hz, 1H), 7.94 (t, J=7.9 Hz, 1H), 7.70 (dd, J=4.1, 8.8 Hz, 1H), 7.08 (dd, J=3.0, 8.7 Hz, 1H), 7.08 (t, J=74.7 Hz, 1H), 6.97 (d, J=3.0 Hz, 1H), 6.87 (d, J=8.9 Hz, 1H), 3.30 (s, 3H), 1.26 (q, J=4.4 Hz, 2H), 0.98 (q, J=4.5 Hz, 2H). LC/MS (APCI+) m/z 449 (M+H)$^+$.

Example I-66

1-(2,6-diethoxyphenyl)-N-(quinoline-5-sulfonyl)cyclopropane-1-carboxamide

Example I-66A methyl 1-(2,6-dihydroxyphenyl)cyclopropane-1-carboxylate

A solution of Example I-7A (methyl 1-(2,6-dimethoxyphenyl)cyclopropanecarboxylate) (1.03 g, 4.36 mmol) in $CH_2Cl_2$ (50 mL) was cooled to −78° C. under nitrogen, treated dropwise with 1 M $BBr_3$ in $CH_2Cl_2$ (4.5 mL, 4.5 mmol), stirred at −78° C. for 40 minutes, treated more 1 M $BBr_3$ in $CH_2Cl_2$ (4 mL, 4 mmol), stirred at −78° C. for 25 minutes, and treated all at once with 1 M aqueous HCl (25 mL). The mixture was stirred at ambient temperature for 5 minutes and the layers were separated. The aqueous layer was extracted with $CH_2Cl_2$ (25 mL). The combined $CH_2Cl_2$ layers were dried ($MgSO_4$), filtered, concentrated and chromatographed on silica gel, eluting with a gradient of 15% to 50% ethyl acetate in heptanes to provide the title compound. $^1$H NMR (400 MHz, dimethyl sulfoxide-d$_6$) δ ppm 9.05 (s, 2H), 6.82 (t, J=8.1 Hz, 1H), 6.24 (d, J=8.0 Hz, 2H), 3.47 (s, 3H), 1.47 (q, J=4.1 Hz, 2H), 1.05 (q, J=4.2 Hz, 2H).

Example I-66B methyl 1-(2,6-diethoxyphenyl)cyclopropane-1-carboxylate

A solution of Example I-66B (methyl 1-(2,6-dihydroxyphenyl)cyclopropanecarboxylate) (25 mg, 0.120 mmol) and ethyl iodide (34.0 0.420 mmol) in N,N-dimethylformamide (0.5 mL) was treated with 60% dispersion of sodium hydride in mineral oil (14.41 mg, 0.360 mmol), stirred at ambient temperature for 20 minutes, and partitioned between methyl tert-butyl ether (30 mL) and 1 M aqueous HCl (10 mL). The methyl tert-butyl ether layer was washed with water (5 mL), washed with brine, dried ($MgSO_4$), filtered, concentrated and chromatographed on silica gel, eluting with a gradient of 5% to 30% ethyl acetate in heptanes to provide the title compound. $^1$H NMR (400 MHz, $CDCl_3$) δ ppm 7.16 (t, J=8.3 Hz, 1H), 6.50 (d, J=8.3 Hz, 2H), 4.02 (q, J=7.0 Hz, 4H), 3.58 (s, 3H), 1.66 (q, J=4.3 Hz, 2H), 1.37 (t, J=7.0 Hz, 6H), 1.16 (q, J=4.3 Hz, 2H).

Example I-66C 1-(2,6-diethoxyphenyl)cyclopropane-1-carboxylic Acid

In a vial, a solution of Example I-66B (methyl 1-(2,6-diethoxyphenyl)cyclopropanecarboxylate) (25 mg, 0.095 mmol) in tetrahydrofuran (1.5 mL) and methanol (1.5 mL) was treated with 3 M aqueous NaOH (1.5 mL), stirred at 80° C. for 12 hours, cooled and partitioned between 1 M aqueous HCl (15 mL) and methyl tert-butyl ether (50 mL). The methyl tert-butyl ether layer was washed with brine, dried (MgSO$_4$), filtered, and concentrated to provide the title compound. $^1$H NMR (400 MHz, CDCl$_3$) δ ppm 7.15 (t, J=8.3 Hz, 1H), 6.49 (d, J=8.3 Hz, 2H), 4.03 (q, J=7.0 Hz, 4H), 1.71 (q, J=4.3 Hz, 2H), 1.39 (t, J=7.0 Hz, 6H), 1.22 (q, J=4.4 Hz, 2H).

Example I-66D 1-(2,6-diethoxyphenyl)-N-(quinoline-5-sulfonyl)cyclopropane-1-carboxamide A solution of Example I-66C, 1-(2,6-diethoxyphenyl)cyclopropanecarboxylic acid (22.8 mg, 0.091 mmol), quinoline-5-sulfonamide (37.9 mg, 0.182 mmol), 1-(3-dimethylaminopropyl)-3-ethylcarbodiimide hydrochloride (34.9 mg, 0.182 mmol) and 4-dimethylaminopyridine (22.26 mg, 0.182 mmol) in N,N-dimethylformamide (0.3 mL) was stirred overnight at ambient temperature. The mixture was partitioned between methyl tert-butyl ether (50 mL) and 1 M aqueous HCl (15 mL). The methyl tert-butyl ether layer was washed with 0.2 M aqueous HCl (15 mL), washed with brine, dried (MgSO$_4$), filtered, concentrated and chromatographed on silica gel, eluting with a gradient of 25% to 100% [200:1:1 ethyl acetate:formic acid:H$_2$O] in heptanes to provide the title compound. $^1$H NMR (501 MHz, dimethyl sulfoxide-d$_6$) δ ppm 11.21 (s, 1H), 9.04 (dd, J=1.6, 4.2 Hz, 1H), 9.00-8.97 (m, 1H), 8.34 (d, J=8.4 Hz, 1H), 8.30 (dd, J=1.3, 7.5 Hz, 1H), 7.92 (dd, J=7.4, 8.4 Hz, 1H), 7.69 (dd, J=4.1, 8.8 Hz, 1H), 7.18 (t, J=8.3 Hz, 1H), 6.52 (d, J=8.3 Hz, 2H), 3.83 (q, J=6.9 Hz, 4H), 1.41 (q, J=4.3 Hz, 2H), 0.98-0.93 (m, 8H). LC/MS (APCI+) m/z 441 (M+H)$^+$.

Example I-67

N-(2-aminoquinoline-5-sulfonyl)-1-(5-cyclobutyl-2-methoxyphenyl)cyclopropane-1-carboxamide In a 4 mL vial was added 1-(5-cyclobutyl-2-methoxyphenyl)cyclopropanecarboxylic acid (20 mg, 0.081 mmol) from Example I-54D, N$^1$-((ethylimino)methylene)-N$^3$,N$^3$-dimethylpropane-1,3-diamine hydrochloride (31.1 mg, 0.162 mmol), and N,N-dimethylpyridin-4-amine (10.91 mg, 0.089 mmol) in dichloromethane (DCM) (0.5 mL). tert-Butyl N-tert-butoxycarbonyl-N-(5-sulfamoyl-2-quinolyl)carbamate (37.8 mg, 0.089 mmol) was added. The reaction was stirred overnight at ambient temperature. The solvent was removed under a stream of nitrogen. 2,2,2-Trifluoroacetic acid (1 mL, 12.98 mmol) was added and the reaction was stirred at ambient temperature for 1 hour. The solvent was removed under a stream of nitrogen, and the residue reconstituted in dimethyl sulfoxide/methanol and purified on preparative reverse phase HPLC/MS method trifluoroacetic acid7. $^1$H NMR (400 MHz, dimethyl sulfoxide-d$_6$:D$_2$O=9:1 (v/v)) δ ppm 8.84 (d, J=9.8 Hz, 1H), 8.06-8.00 (m, 1H), 7.93-7.87 (m, 2H), 7.21-7.08 (m, 2H), 6.96 (d, J=2.2 Hz, 1H), 6.85 (d, J=8.4 Hz, 1H), 3.51 (s, 3H), 3.47-3.32 (m, 1H), 2.29-2.16 (m, 2H), 2.11-1.83 (m, 3H), 1.83-1.70 (m, 1H), 1.30-1.19 (m, 2H), 1.02-0.92 (m, 2H). MS (APCI) m/z 452.0 (M+H)$^+$.

Example I-68

1-(5-cyclopropyl-2-methoxyphenyl)-N-(2-methylquinoline-5-sulfonyl)cyclopropane-1-carboxamide A solution of Example I-12B (1-(5-cyclopropyl-2-methoxyphenyl)cyclopropanecarboxylic acid) (21.4 mg, 0.092 mmol), 2-methylquinoline-5-sulfonamide (41.0 mg, 0.184 mmol), 1-(3-dimethylaminopropyl)-3-ethylcarbodiimide hydrochloride (35.3 mg, 0.184 mmol) and 4-dimethylaminopyridine (22.51 mg, 0.184 mmol) in N,N-dimethylformamide (0.3 mL) was stirred overnight at ambient temperature. The mixture was partitioned between methyl tert-butyl ether (50 mL) and 1 M aqueous HCl (15 mL). The methyl tert-butyl ether layer was washed with 0.2 M aqueous HCl (15 mL), washed with brine, dried (MgSO$_4$), filtered, concentrated and chromatographed on silica gel, eluting with a gradient of 25% to 100% [200:1:1 ethyl acetate:formic acid:H$_2$O] in heptanes to provide the title compound. $^1$H NMR (501 MHz, dimethyl sulfoxide-d$_6$) δ ppm 11.50 (bs, 1H), 8.85 (d, J=8.8 Hz, 1H), 8.23-8.19 (m, 2H), 7.86 (t, J=7.9 Hz, 1H), 7.58 (d, J=8.9 Hz, 1H), 6.94 (dd, J=2.3, 8.4 Hz, 1H), 6.84 (d, J=2.3 Hz, 1H), 6.75 (d, J=8.4 Hz, 1H), 3.35 (s, 3H), 2.71 (s, 3H), 1.84 (tt, J=5.1, 8.4 Hz, 1H), 1.21 (q, J=4.3 Hz, 2H), 0.93 (q, J=4.4 Hz, 2H), 0.89-0.84 (m, 2H), 0.63-0.58 (m, 2H). LC/MS (APCI+) m/z 437 (M+H)$^+$.

Example I-69

1-(5-ethoxy-2-methoxyphenyl)-N-(2-methylquinoline-5-sulfonyl)cyclopropane-1-carboxamide Example I-69 was prepared as described in Example I-34B, substituting 1-(5-ethoxy-2-methoxyphenyl)cyclopropane-1-carboxylic acid from Example I-31G for Example I-34B, and 2-methylquinoline-5-sulfonamide for quinoline-5-sulfonamide. $^1$H NMR (500 MHz, dimethyl sulfoxide-d$_6$:D$_2$O=9:1 (v/v)) δ ppm 8.91-8.76 (m, 1H), 8.24 (ddd, J=7.5, 5.6, 1.1 Hz, 2H), 7.90 (dd, J=8.4, 7.5 Hz, 1H), 7.61 (d, J=8.9 Hz, 1H), 6.88-6.73 (m, 2H), 6.69 (d, J=2.9 Hz, 1H), 3.96 (q, J=6.9 Hz, 2H), 3.31 (s, 3H), 2.73 (s, 3H), 1.31 (t, J=7.0 Hz, 3H), 1.21 (q, J=2.8 Hz, 2H), 0.96 (q, J=4.5 Hz, 2H). MS (APCI) m/z 441.0 (M+H)$^+$.

Example I-70

1-(5-tert-butyl-2-methoxyphenyl)-N-(2-methylquinoline-5-sulfonyl)cyclopropane-1-carboxamide Example I-70 was prepared as described in Example I-34B, substituting 2-methylquinoline-5-sulfonamide for quinoline-5-sulfonamide. $^1$H NMR (501 MHz, dimethyl sulfoxide-d$_6$:D$_2$O=9:1 (v/v)) δ ppm 8.86 (d, J=8.9 Hz, 1H), 8.20 (t, J=7.7 Hz, 2H), 7.87 (t, J=7.9 Hz, 1H), 7.59 (d, J=8.9 Hz, 1H), 7.26 (dd, J=8.6, 2.5 Hz, 1H), 7.08 (d, J=2.5 Hz, 1H), 6.79 (d, J=8.7 Hz, 1H), 3.36 (s, 3H), 2.72 (s, 3H), 1.42-1.14 (m, 11H), 0.98-0.88 (m, 2H). MS (APCI) m/z 453.0 (M+H)$^+$.

Example I-71

1-[2-methoxy-5-(propan-2-yl)phenyl]-N-(2-methylquinoline-5-sulfonyl)cyclopropane-1-carboxamide Example I-71 was prepared as described in Example I-35B, substituting 2-methylquinoline-5-sulfonamide for quinoline-5-sulfonamide. $^1$H NMR (400 MHz, dimethyl sulfoxide-d$_6$:D$_2$O=9:1 (v/v)) δ ppm 8.93 (d, J=9.0 Hz, 1H), 8.34-8.18 (m, 2H), 7.94 (t, J=8.0 Hz, 1H), 7.68 (d, J=9.0 Hz, 1H), 7.13 (dd, J=8.4, 2.3 Hz, 1H), 6.95 (d, J=2.3 Hz, 1H), 6.80 (d, J=8.4 Hz, 1H), 3.35 (s, 3H), 2.86-2.67 (m, 4H), 1.25

(q, J=2.8 Hz, 2H), 1.16 (d, J=6.9 Hz, 6H), 0.96 (q, J=4.5 Hz, 2H). MS (APCI) m/z 439.0 (M+H)⁺.

Example I-72

1-[2-(dimethylamino)-5-(trifluoromethyl)pyridin-3-yl]-N-(2-methylquinoline-5-sulfonyl)cyclopropane-1-carboxamide Example I-72 was prepared as described in Example I-57, substituting 2-methylquinoline-5-sulfonamide for quinoline-5-sulfonamide. ¹H NMR (501 MHz, dimethyl sulfoxide-$d_6$:$D_2O$=9:1 (v/v)) δ ppm 7.21 (dd, J=8.3, 7.5 Hz, 1H), 7.10-6.99 (m, 2H), 6.91-6.85 (m, 1H), 6.84-6.78 (m, 1H), 6.73 (dd, J=7.4, 1.9 Hz, 1H), 3.77 (s, 3H), 3.18 (t, J=5.5 Hz, 2H), 2.85 (t, J=6.4 Hz, 2H), 2.19 (s, 3H), 1.78 (p, J=6.1 Hz, 2H), 1.66-1.47 (m, 2H), 1.17-0.95 (m, 2H). MS (APCI) m/z 478.9 (M+H)⁺.

Example I-73

1-{2-methoxy-5-[1-(methoxymethyl)cyclopropyl]phenyl}-N-(quinoline-5-sulfonyl)cyclopropane-1-carboxamide Example I-73A methyl 1-(4-methoxyphenyl)cyclopropanecarboxylate To a solution of Q-Phos (pentaphenyl(di-tert-butylphosphino)ferrocene, 0.076 g, 0.107 mmol) and bis(dibenzylideneacetone)palladium (0.061 g, 0.107 mmol) in tetrahydrofuran (25 mL) at ambient temperature was added 1-bromo-4-methoxybenzene (0.669 mL, 5.35 mmol) followed by a solution of freshly-prepared (1-(methoxycarbonyl)cyclopropyl)zinc(II) bromide (24.87 mL, 10.69 mmol). The mixture was stirred at ambient temperature for 16 hours. Ethyl acetate and saturated aqueous ammonium chloride were added. The organic layer was washed with brine and was concentrated. The residue was purified via chromatography on a 24 g silica gel cartridge, eluting with ethyl acetate in heptane at 0-30% gradient in a period of 15 minutes to provide the title compound. ¹H NMR (400 MHz, chloroform-d) δ ppm 7.29-7.22 (m, 2H), 6.88-6.81 (m, 2H), 3.80 (s, 3H), 3.62 (s, 3H), 1.57 (q, J=3.9 Hz, 2H), 1.15 (q, J=3.9 Hz, 2H). MS (APCI+) m/z 207 (M+H)⁺.

Example I-73B methyl 1-(3-bromo-4-methoxyphenyl)cyclopropanecarboxylate

A solution of methyl 1-(4-methoxyphenyl)cyclopropanecarboxylate from Example I-73A (0.702 g, 3.40 mmol) and benzyltrimethylammonium tribromide (2.65 g, 6.81 mmol) in tetrahydrofuran (10 mL) and degassed water (6.00 mL) was stirred at ambient temperature for 40 hours. The mixture was diluted with 100 mL of diethyl ether, and filtered. The organic layer was separated and concentrated in vacuo. The crude residue was purified by chromatography, eluting on a 24 g silica gel cartridge with 100% dichloromethane to provide crude product which was purified further on a 10 g silica gel cartridge with a gradient of 0-4% methanol/dichloromethane over a period of 15 minutes to provide the title compound. ¹H NMR (400 MHz, chloroform-d) δ ppm 7.52 (d, J=2.2 Hz, 1H), 7.24 (dd, J=8.4, 2.2 Hz, 1H), 6.84 (d, J=8.4 Hz, 1H), 3.89 (s, 3H), 3.63 (s, 3H), 1.59 (q, J=4.0 Hz, 2H), 1.15 (q, J=4.0 Hz, 2H). MS (ESI+) m/z 285 (M+H)⁺.

Example I-73C (1-(3-bromo-4-methoxyphenyl)cyclopropyl)methanol

To a solution of methyl 1-(3-bromo-4-methoxyphenyl)cyclopropanecarboxylate from Example I-73B (0.7 g, 2.455 mmol) in dichloromethane (7.0 mL) at 0° C. was added diisobutylaluminium hydride in dichloromethane (7.36 mL, 7.36 mmol). The reaction was stirred at 0° C. for 30 minutes and was quenched with 20 mL 1 N aqueous citric acid. The organic layer was separated and concentrated in vacuo. The residue was purified on a 10 g silica gel cartridge with a gradient of 0-4% methanol/dichloromethane over a period of 15 minutes to provide the title compound. ¹H NMR (501 MHz, chloroform-d) δ ppm 7.55 (d, J=2.2 Hz, 1H), 7.28 (dd, J=8.4, 2.2 Hz, 1H), 6.84 (d, J=8.4 Hz, 1H), 3.88 (s, 3H), 3.62 (d, J=5.6 Hz, 2H), 1.39 (t, J=6.1 Hz, 1H), 0.86-0.79 (m, 4H). MS (ESI+) m/z 239 (M+H-$H_2O$)⁺.

Example I-73D 2-bromo-1-methoxy-4-(1-(methoxymethyl)cyclopropyl)benzene

To a solution of (1-(3-bromo-4-methoxyphenyl)cyclopropyl)methanol from Example I-73C (525 mg, 2.042 mmol) in N,N-dimethylformamide (4 mL) at 0° C. was added sodium hydride (163 mg, 4.08 mmol). After 30 minutes, iodomethane (0.255 mL, 4.08 mmol) was added and the reaction was stirred at 0° C. for 2 hours. The mixture was quenched via addition of saturated aqueous ammonium chloride (50 mL) and extracted with ethyl acetate. The organic layer was concentrated, and the crude material was purified by chromatography, eluting on a 10 g silica gel cartridge with a gradient of 0-50% ethyl acetate/heptanes over a period of 10 minutes to provide the title compound. ¹H NMR (400 MHz, chloroform-d) δ ppm 7.51 (d, J=2.2 Hz, 1H), 7.24 (dd, J=8.4, 2.2 Hz, 1H), 6.82 (d, J=8.5 Hz, 1H), 3.87 (s, 3H), 3.42 (s, 2H), 3.30 (s, 3H), 0.83 (s, 4H). MS (APCI+) m/z 239 (M+H-methanol)⁺.

Example I-73E methyl 1-(2-methoxy-5-(1-(methoxymethyl)cyclopropyl)phenyl)cyclopropanecarboxylate To a solution of Q-Phos (pentaphenyl(di-tert-butylphosphino)ferrocene, 0.028 g, 0.039 mmol) and bis(dibenzylideneacetone)palladium (0.022 g, 0.039 mmol) in tetrahydrofuran (10 mL) at ambient temperature was added 2-bromo-1-methoxy-4-(1-(methoxymethyl)cyclopropyl)benzene from Example I-73D (0.53 g, 1.955 mmol) followed by a solution of freshly prepared (1-(methoxycarbonyl)cyclopropyl)zinc(II) bromide (9.09 mL, 3.91 mmol). The mixture was stirred at ambient temperature for 3 days. Ethyl acetate and saturated aqueous ammonium chloride was added, and the organic layer was washed with brine and concentrated. The residue was purified via chromatography on a 24 g silica gel cartridge, eluting with an ethyl acetate in heptane at 0-60% gradient for a period of 15 minutes to provide the title compound. ¹H NMR (501 MHz, chloroform-d) δ ppm 7.23 (dd, J=8.4, 2.4 Hz, 1H), 7.15 (d, J=2.4 Hz, 1H), 6.78 (d, J=8.4 Hz, 1H), 3.80 (s, 3H), 3.59 (s, 3H), 3.43 (s, 2H), 3.30

(s, 3H), 1.58 (q, J=4.1 Hz, 2H), 1.10 (q, J=4.1 Hz, 2H), 0.86-0.79 (m, 4H). MS (APCI+) m/z 259 (M+H-methanol)$^+$.

Example I-73F 1-(2-methoxy-5-(1-(methoxymethyl)cyclopropyl)phenyl)cyclopropanecarboxylic Acid Methyl 1-(2-methoxy-5-(1-(methoxymethyl)cyclopropyl)phenyl)cyclopropanecarboxylate from Example I-73E (340 mg, 1.171 mmol) was dissolved in tetrahydrofuran (2.6 mL), methanol (2.60 mL) and water (2.60 mL) and then treated with sodium hydroxide (234 mg, 5.85 mmol). The reaction mixture was stirred at 35° C. overnight. The reaction was concentrated, cooled in an ice bath and carefully quenched with 1 N aqueous citric acid (about 6 mL) until pH~5. The resulting slurry was stirred vigorously and filtered. The material was washed with water and dried in a vacuum oven overnight to provide the title compound. $^1$H NMR (501 MHz, chloroform-d) δ ppm 7.23 (dd, J=8.4, 2.3 Hz, 1H), 7.17 (d, J=2.4 Hz, 1H), 6.78 (d, J=8.4 Hz, 1H), 3.81 (s, 3H), 3.42 (s, 2H), 3.29 (s, 3H), 1.63 (q, J=4.0 Hz, 2H), 1.16 (q, J=4.1 Hz, 2H), 0.83-0.80 (m, 4H). MS (ESI-) m/z 275 (M-H).

Example I-73G

1-{2-methoxy-5-[1-(methoxymethyl)cyclopropyl]phenyl}-N-(quinoline-5-sulfonyl)cyclopropane-1-carboxamide To a solution of 1-(2-methoxy-5-(1-(methoxymethyl)cyclopropyl)phenyl)cyclopropanecarboxylic acid from Example I-73F (80 mg, 0.290 mmol), N$^1$-((ethylimino)methylene)-N$^3$,N$^3$-dimethylpropane-1,3-diamine hydrochloride (111 mg, 0.579 mmol) and N,N-dimethylpyridin-4-amine (38.9 mg, 0.318 mmol) in anhydrous dichloromethane (1 mL) was added quinoline-5-sulfonamide (60.3 mg, 0.290 mmol). After 16 hours, the reaction was quenched with 1 mL of aqueous 1 N citric acid and the organic layer was concentrated in vacuo. The residue was purified via chromatography on a 10 g silica gel cartridge, eluting with a gradient of 0-10% methanol/dichloromethane over a period of 10 minutes. The material was triturated with diethyl ether and filtered to provide the title compound. $^1$H NMR (501 MHz, dimethyl sulfoxide-d$_6$) δ ppm 11.52 (s, 1H), 9.05 (dd, J=4.2, 1.6 Hz, 1H), 9.01-8.95 (m, 1H), 8.34 (d, J=8.5 Hz, 1H), 8.30 (d, J=7.4 Hz, 1H), 7.93 (t, J=7.9 Hz, 1H), 7.70 (dd, J=8.8, 4.2 Hz, 1H), 7.17 (dd, J=8.4, 2.3 Hz, 1H), 6.97 (d, J=2.3 Hz, 1H), 6.75 (d, J=8.5 Hz, 1H), 3.40 (s, 2H), 3.32 (s, 3H), 3.21 (s, 3H), 1.27 (q, J=4.3 Hz, 2H), 0.93 (s, 2H), 0.80-0.76 (m, 4H). MS (APCI+) m/z 467 (M+H)$^+$.

Example I-74

1-{2-methoxy-5-[1-(methoxymethyl)cyclopropyl]phenyl}-N-(2-methylquinoline-5-sulfonyl)cyclopropane-1-carboxamide To a solution of 1-(2-methoxy-5-(1-(methoxymethyl)cyclopropyl)phenyl)cyclopropanecarboxylic acid from Example I-73F (80 mg, 0.290 mmol), N$^1$-((ethylimino)methylene)-N$^3$,N$^3$-dimethylpropane-1,3-diamine hydrochloride (111 mg, 0.579 mmol) and N,N-dimethylpyridin-4-amine (38.9 mg, 0.318 mmol) in anhydrous dichloromethane (1 mL) was added 2-methylquinoline-5-sulfonamide (64.3 mg, 0.290 mmol). After 16 hours, the reaction was quenched with 1 mL of aqueous 1 N citric acid and the organic layer was concentrated in vacuo. The residue was purified via chromatography on a 10 g silica gel cartridge, eluting with a gradient of 0-10% methanol/dichloromethane over a period of 10 minutes. The material was triturated with diethyl ether and filtered to provide the title compound. $^1$H NMR (400 MHz, dimethyl sulfoxide-d$_6$) δ ppm 11.47 (s, 1H), 8.85 (d, J=8.9 Hz, 1H), 8.21 (t, J=8.5 Hz, 2H), 7.86 (t, J=8.0 Hz, 1H), 7.58 (d, J=8.9 Hz, 1H), 7.17 (dd, J=8.5, 2.3 Hz, 1H), 6.96 (d, J=2.3 Hz, 1H), 6.75 (d, J=8.5 Hz, 1H), 3.40 (s, 2H), 3.33 (s, 3H), 3.21 (s, 3H), 2.71 (s, 3H), 1.27 (q, J=4.3 Hz, 2H), 0.92 (s, 2H), 0.84-0.72 (m, 4H). MS (APCI+) m/z 481 (M+H)$^+$.

Example I-75

1-(2-methoxyquinolin-3-yl)-N-(2-methylquinoline-5-sulfonyl)cyclopropane-1-carboxamide Example I-75A 1-(2-methoxyquinolin-3-yl)cyclopropanecarboxylic Acid The title compound was prepared as described in the procedures described in Example I-3A to Example I-3D, substituting 3-(bromomethyl)-2-methoxyquinoline for 3-(bromomethyl)-5-cyclobutyl-2-methoxypyridine.

Example I-75B 1-(2-methoxyquinolin-3-yl)-N-(2-methylquinoline-5-sulfonyl)cyclopropane-1-carboxamide A mixture of Example I-75A (45 mg, 0.185 mmol), N$^1$-((ethylimino)methylene)-N$^3$,N$^3$-dimethylpropane-1,3-diamine (57.4 mg, 0.370 mmol) and N,N-dimethylpyridin-4-amine (45.2 mg, 0.370 mmol) in dichloromethane (2 mL) was stirred at ambient temperature for 30 minutes. 2-Methylquinoline-5-sulfonamide (41.1 mg, 0.185 mmol) was added. The mixture was stirred at 45° C. for 2 hours, and concentrated. The residue was dissolved in methanol (3 mL) and filtered. Purification via reverse phase HPLC (C18, CH$_3$CN/H$_2$O (0.1% trifluoroacetic acid), 5-95%, 20 minutes) provided the title compound. $^1$H NMR (400 MHz, dimethyl sulfoxide-d$_6$) δ ppm 11.86 (s, 1H), 8.82 (d, J=8.9 Hz, 1H), 8.27 (dd, J=7.9, 4.2 Hz, 2H), 8.11 (s, 1H), 7.96-7.89 (m, 1H), 7.87 (dd, J=8.1, 1.4 Hz, 1H), 7.79 (d, J=8.3 Hz, 1H), 7.67 (ddd, J=8.4, 6.8, 1.4 Hz, 1H), 7.61 (d, J=8.9 Hz, 1H), 7.45 (t, J=7.4 Hz, 1H), 3.62 (s, 3H), 2.74 (s, 3H), 1.33 (q, J=4.2 Hz, 2H), 1.13 (q, J=4.3 Hz, 2H). MS (ESI+) m/z 448.2 (M+H)$^+$.

Example I-76

1-(2-methoxyquinolin-3-yl)-N-(quinoline-5-sulfonyl)cyclopropane-1-carboxamide

A mixture of 1-(2-methoxyquinolin-3-yl)cyclopropanecarboxylic acid (Example I-75A, 30 mg, 0.123 mmol) and N$^1$-((ethylimino)methylene)-N$^3$,N$^3$-dimethylpropane-1,3-diamine (38.3 mg, 0.247 mmol) and N,N-dimethylpyridin-4-amine (30.1 mg, 0.247 mmol) in dichloromethane (2 mL) was stirred at ambient temperature for 30 minutes. Quinoline-5-sulfonamide (25.7 mg, 0.123 mmol) was added. The mixture was stirred at 45° C. for 3 hours, and concentrated. The residue was dissolved in methanol (3 mL) and filtered.

Purification via reverse phase HPLC (C18, CH$_3$CN/H$_2$O (0.1% trifluoroacetic acid), 5-95%, 20 minutes), followed by purification through a 4 g silica gel cartridge provided the title compound. $^1$H NMR (400 MHz, dimethyl sulfoxide-d$_6$) δ ppm 11.90 (d, J=58.4 Hz, 1H), 9.07 (dd, J=4.2, 1.5 Hz, 1H), 8.91 (dd, J=8.9, 1.4 Hz, 1H), 8.36 (dd, J=11.8, 7.8 Hz, 2H), 8.11 (s, 1H), 8.00-7.94 (m, 1H), 7.87 (dd, J=8.1, 1.4 Hz, 1H), 7.79 (d, J=8.2 Hz, 1H), 7.73-7.63 (m, 2H), 7.45 (t, J=7.4 Hz, 1H), 3.58 (s, 3H), 1.34 (q, J=4.2 Hz, 2H), 1.13 (q, J=4.3 Hz, 2H). MS (ESI+) m/z 434 (M+H)$^+$.

Example I-77

1-{5-methyl-2-[(propan-2-yl)oxy]phenyl}-N-(quinoline-5-sulfonyl)cyclopropane-1-carboxamide Example I-77A 2-bromo-1-isopropoxy-4-methylbenzene To 2-bromo-4-methylphenol [CAS #6627-56-0] (2 g, 10.69 mmol) in N,N-dimethylformamide (10 mL) was added potassium carbonate (2.96 g, 21.39 mmol) at ambient temperature. The mixture was stirred at ambient temperature for 10 minutes. 2-Iodopropane (2.135 mL, 21.39 mmol) was added dropwise, and the mixture stirred at 50° C. for overnight. To the reaction mixture was added ethyl acetate (20 mL). The mixture was filtered, and the material was washed with ethyl acetate (10 mL×2). The combined organics were washed with water and brine, dried over MgSO$_4$, filtered, and concentrated. The residue was purified via chromatography on a 24 g silica gel cartridge, eluting with ethyl acetate in heptane at 0-40% gradient to provide 2-bromo-1-isopropoxy-4-methylbenzene. $^1$H NMR (400 MHz, chloroform-d) δ ppm 7.35 (dd, J=2.1, 0.8 Hz, 1H), 7.01 (ddd, J=8.3, 2.1, 0.8 Hz, 1H), 6.81 (d, J=8.3 Hz, 1H), 4.47 (hept, J=6.1 Hz, 1H), 2.26 (s, 3H), 1.35 (d, J=6.1 Hz, 6H). MS (APCI+) m/z 229 (M+H)$^+$.

Example I-77B methyl 1-(2-isopropoxy-5-methylphenyl)cyclopropane-1-carboxylate

To Example I-77A (2.10 g, 9.17 mmol) in 10 mL of dry tetrahydrofuran was added Q-Phos (pentaphenyl(di-tert-butylphosphino)ferrocene, 0.130 g, 0.183 mmol) and tris(dibenzylideneacetone)dipalladium(0) (0.168 g, 0.183 mmol). A solution of freshly-prepared (1-(methoxycarbonyl)cyclopropyl)zinc(II) bromide (45.8 mL, 18.33 mmol) in tetrahydrofuran (0.40 mmol/mL, 46 mL) was added via a stainless steel cannula under nitrogen pressure. The mixture was stirred at ambient temperature for 20 minutes. Ethyl acetate and saturated aqueous NH$_4$Cl were added. The organic layer was washed with brine and was concentrated. The residue was purified via chromatography on a 40 g silica gel cartridge, eluting with ethyl acetate in heptane using 0-50% gradient to provide the title compound. MS (APCI+) m/z 249 (M+H)$^+$.

Example I-77C 1-(2-isopropoxy-5-methylphenyl)cyclopropanecarboxylic Acid

Example I-77B (2.0 g, 8.05 mmol) and lithium hydroxide (1.93 g, 81 mmol) were added to methanol (10 mL) and water (3 mL). The mixture was stirred at 45° C. overnight. The mixture was concentrated to half its volume and the pH was adjusted to between 0~1 by adding 2 M aqueous HCl. The mixture was extracted with dichloromethane (20 mL×3) and the combined organics were washed with brine, dried over MgSO$_4$, filtered, and concentrated to provide the title compound. $^1$H NMR (500 MHz, chloroform-d) δ ppm 7.09-6.96 (m, 2H), 6.79-6.68 (m, 1H), 4.53 (pd, J=6.1, 0.6 Hz, 1H), 2.25 (t, J=0.7 Hz, 3H), 1.60 (q, J=4.1 Hz, 2H), 1.30 (d, J=6.0 Hz, 6H), 1.13 (q, J=4.1 Hz, 2H). MS (APCI+) m/z 235 (M+H)$^+$.

Example I-77D 1-(2-isopropoxy-5-methylphenyl)-N-(quinolin-5-ylsulfonyl)cyclopropanecarboxamide A mixture of Example I-77C (100 mg, 0.427 mmol), N$^1$-((ethylimino)methylene)-N$^3$,N$^3$-dimethylpropane-1,3-diamine (133 mg, 0.854 mmol) and N,N-dimethylpyridin-4-amine (104 mg, 0.854 mmol) in dichloromethane (2 mL) was stirred at ambient temperature for 30 minutes. Quinoline-5-sulfonamide (89 mg, 0.427 mmol) was added. The mixture was stirred at 45° C. for 3 hours, and concentrated. The residue was dissolved in methanol (3 mL) and filtered. Purification via reverse phase HPLC (C18, CH$_3$CN/H$_2$O (0.1% trifluoroacetic acid), 5-95%, 20 minutes), followed by purification through a 4 g silica gel cartridge, eluting with methanol in ethyl acetate at 0-10% gradient to get rid of salts, provided the title compound. $^1$H NMR (400 MHz, dimethyl sulfoxide-d$_6$) δ ppm 11.48 (s, 1H), 9.10-8.96 (m, 2H), 8.32 (ddd, J=7.3, 6.1, 1.1 Hz, 2H), 7.92 (dd, J=8.4, 7.5 Hz, 1H), 7.70 (dd, J=8.7, 4.2 Hz, 1H), 7.02 (dd, J=8.3, 2.2 Hz, 1H), 6.92 (d, J=2.2 Hz, 1H), 6.76 (d, J=8.3 Hz, 1H), 4.33 (hept, J=6.1 Hz, 1H), 2.21 (s, 3H), 1.24 (q, J=4.4 Hz, 2H), 0.92 (q, J=4.4 Hz, 2H), 0.89 (d, J=6.0 Hz, 6H). MS (ESI+) m/z 425 (M+H)$^+$.

Example I-78

1-{5-methyl-2-[(propan-2-yl)oxy]phenyl}-N-(2-methylquinoline-5-sulfonyl)cyclopropane-1-carboxamide A mixture of Example I-77C (100 mg, 0.427 mmol), N$^1$-((ethylimino)methylene)-N$^3$,N$^3$-dimethylpropane-1,3-diamine (133 mg, 0.854 mmol) and N,N-dimethylpyridin-4-amine (104 mg, 0.854 mmol) in dichloromethane (2 mL) was stirred at ambient temperature for 30 minutes. 2-Methylquinoline-5-sulfonamide (95 mg, 0.427 mmol) was added. The mixture was stirred at 45° C. for 2 hours, and was concentrated. The residue was dissolved in methanol (2 mL) and the mixture was filtered. Purification via reverse phase HPLC (C18, CH$_3$CN/H$_2$O (0.1% trifluoroacetic acid), 5-95%, 20 minutes), followed by purification through a 4 g silica gel cartridge, eluting with methanol in ethyl acetate at 0-10% gradient to get rid of salts, provided the title compound. $^1$H NMR (400 MHz, dimethyl sulfoxide-d$_6$) δ ppm 11.45 (s, 1H), 8.95 (d, J=8.9 Hz, 1H), 8.32-8.17 (m, 2H), 7.88 (dd, J=8.5, 7.4 Hz, 1H), 7.63 (d, J=8.9 Hz, 1H), 7.03 (dd, J=8.5, 2.2 Hz, 1H), 6.92 (d, J=2.3 Hz, 1H), 6.77 (d, J=8.3 Hz, 1H), 4.36 (hept, J=6.0 Hz, 1H), 2.72 (s, 3H), 2.56

(s, 3H), 2.21 (s, 3H), 1.23 (q, J=4.3 Hz, 2H), 0.98-0.83 (m, 8H). MS (ESI+) m/z 439 (M+H)$^+$.

Example I-79

N-(2-aminoquinoline-5-sulfonyl)-1-(2-methoxy-5-methylphenyl)cyclopropane-1-carboxamide Example I-79 was prepared as described in Example I-67, substituting 1-(2-methoxy-5-methylphenyl)cyclopropane-1-carboxylic acid from Example I-44B for 1-(5-cyclobutyl-2-methoxyphenyl)cyclopropanecarboxylic acid. $^1$H NMR (501 MHz, dimethyl sulfoxide-d$_6$:D$_2$O=9:1 (v/v)) δ ppm 8.83 (d, J=9.8 Hz, 1H), 8.02 (dd, J=6.4, 2.4 Hz, 1H), 7.92-7.84 (m, 2H), 7.15 (d, J=9.7 Hz, 1H), 7.12-7.06 (m, 1H), 6.96 (d, J=2.2 Hz, 1H), 6.82 (d, J=8.2 Hz, 1H), 3.51 (s, 3H), 2.24 (s, 3H), 1.24 (q, J=4.2 Hz, 2H), 0.95 (q, J=4.4 Hz, 2H). MS (APCI) m/z 412.0 (M+H)$^+$.

Example I-80

1-(4-cyclobutyl-2,6-dimethoxyphenyl)-N-(quinoline-5-sulfonyl)cyclopropane-1-carboxamide Quinoline-5-sulfonamide (22.6 mg, 0.11 mmol, 1.2 eq) was weighed into 4 mL vial. 1-(4-Cyclobutyl-2,6-dimethoxyphenyl)cyclopropanecarboxylic acid (Example I-86D, 25 mg, 0.09 mmol, 1.0 eq), 4-dimethylaminopyridine (12.2 mg, 0.10 mmol, 1.1 eq) and EDC HCl (1-(3-dimethylaminopropyl)-3-ethylcarbodiimide HCl, 34.4 mg, 0.18 mmol, 2.0 eq) were all combined and dissolved in 0.4 mL dichloromethane. This stock solution was added to the 4 mL vial containing quinoline-5-sulfonamide. The reaction was stirred overnight at ambient temperature. The solvent was removed under a stream of nitrogen, and the residue was dissolved in dimethyl sulfoxide/methanol. The mixture was purified via preparative reverse phase HPLC/MS method trifluoroacetic acid8 to provide the title compound. $^1$H NMR (501 MHz, dimethyl sulfoxide-d$_6$:D$_2$O=9:1 (v/v)) δ ppm 9.10-8.99 (m, 2H), 8.40-8.28 (m, 2H), 7.95 (dd, J=8.4, 7.4 Hz, 1H), 7.76 (dd, J=8.8, 4.2 Hz, 1H), 6.41-6.33 (m, 2H), 3.77 (s, 3H), 3.63 (s, 3H), 3.41 (p, J=8.9 Hz, 1H), 2.17-2.06 (m, 1H), 2.06-1.92 (m, 1H), 1.69-1.31 (m, 6H), 0.94-0.86 (m, 2H). MS (APCI) m/z 467.0 (M+H)$^+$.

Example I-81

N-(2-aminoquinoline-5-sulfonyl)-1-(2,5-dimethylphenyl)cyclopropane-1-carboxamide Example I-81 was prepared as described in Example I-67, substituting 1-(2,5-dimethylphenyl)cyclopropane-1-carboxylic acid [CAS #1260676-68-3] for 1-(5-cyclobutyl-2-methoxyphenyl)cyclopropanecarboxylic acid. $^1$H NMR (400 MHz, dimethyl sulfoxide-d$_6$:D$_2$O=9:1 (v/v)) δ ppm 8.84 (d, J=9.8 Hz, 1H), 8.01 (q, J=4.6 Hz, 1H), 7.93-7.83 (m, 2H), 7.14 (d, J=9.8 Hz, 1H), 7.04-6.94 (m, 3H), 2.26 (s, 3H), 1.93 (s, 3H), 1.37 (q, J=3.6 Hz, 2H), 1.00 (q, J=3.9 Hz, 2H). MS (APCI) m/z 396.1 (M+H)$^+$.

Example I-82

1-(2-ethoxy-5-methylphenyl)-N-(quinoline-5-sulfonyl)cyclopropane-1-carboxamide

To a solution of 1-(2-ethoxy-5-methylphenyl)cyclopropanecarboxylic acid (50 mg, 0.227 mmol) from Example I-89B, N$^1$-((ethylimino)methylene)-N$^3$,N$^3$-dimethylpropane-1,3-diamine hydrochloride (87 mg, 0.454 mmol) and N,N-dimethylpyridin-4-amine (30.5 mg, 0.250 mmol) in anhydrous dichloromethane (0.75 mL) was added quinoline-5-sulfonamide (47.3 mg, 0.227 mmol). After 16 hours, the reaction was quenched with 1 mL of aqueous IN citric acid and the organic layer was concentrated in vacuo. The residue was purified via chromatography on a 10 g silica gel cartridge, eluting with a gradient of 0-10% methanol/dichloromethane over a period of 10 minutes. The crude material was triturated with methanol (0.75 mL), filtered to provide the title compound. $^1$H NMR (400 MHz, dimethyl sulfoxide-d$_6$) δ ppm 11.51 (s, 1H), 9.04 (dd, J=4.2, 1.6 Hz, 1H), 8.96 (dt, J=8.8, 1.2 Hz, 1H), 8.32 (t, J=8.2 Hz, 2H), 7.92 (d, J=8.0 Hz, 1H), 7.68 (dd, J=8.8, 4.2 Hz, 1H), 7.08-7.01 (m, 1H), 6.94 (d, J=2.2 Hz, 1H), 6.73 (d, J=8.2 Hz, 1H), 3.61 (q, J=6.9 Hz, 2H), 2.23 (s, 3H), 1.22 (q, J=4.3 Hz, 2H), 0.92 (q, J=4.4 Hz, 2H), 0.76 (t, J=6.9 Hz, 3H). MS (APCI+) m/z 411 (M+H)$^+$.

Example I-83

1-(2-ethoxy-5-methylphenyl)-N-(2-methylquinoline-5-sulfonyl)cyclopropane-1-carboxamide To a solution of 1-(2-ethoxy-5-methylphenyl)cyclopropanecarboxylic acid (50 mg, 0.227 mmol) from Example I-89B, N$^1$-((ethylimino)methylene)-N$^3$,N$^3$-dimethylpropane-1,3-diamine hydrochloride (87 mg, 0.454 mmol) and N,N-dimethylpyridin-4-amine (30.5 mg, 0.250 mmol) in anhydrous dichloromethane (0.75 mL) was added 2-methylquinoline-5-sulfonamide (50.5 mg, 0.227 mmol). After 16 hours, the reaction was quenched with 1 mL of aqueous IN citric acid and the organic layer was concentrated in vacuo. The residue was purified via chromatography on a 10 g silica gel cartridge, eluting with a gradient of 0-10% methanol/dichloromethane over a period of 10 minutes to yield crude product. The crude material was triturated with methanol (1 mL) and filtered to provide the title compound. $^1$H NMR (500 MHz, dimethyl sulfoxide-d$_6$) δ ppm 11.47 (s, 1H), 8.84 (d, J=8.8 Hz, 1H), 8.20 (d, J=7.5 Hz, 2H), 7.85 (t, J=7.9 Hz, 1H), 7.56 (d, J=8.9 Hz, 1H), 7.16-6.98 (m, 1H), 6.93 (d, J=2.2 Hz, 1H), 6.73 (d, J=8.3 Hz, 1H), 3.64 (q, J=6.9 Hz, 2H), 2.70 (s, 3H), 2.22 (s, 3H), 1.21 (q, J=4.2 Hz, 2H), 0.90 (bs, 2H), 0.79 (t, J=6.9 Hz, 3H). MS (APCI+) m/z 425 (M+H)$^+$.

Example I-84

1-(5-ethyl-2-methoxyphenyl)-N-(2-methylquinoline-5-sulfonyl)cyclopropane-1-carboxamide Example I-84A 2-bromo-4-ethyl-1-methoxybenzene To a solution of 1-ethyl-4-methoxybenzene (2 mL, 14.10 mmol) in acetonitrile (30 mL) was added 1-bromopyrrolidine-2,5-dione (2.76 g, 15.51 mmol) and the reaction was stirred under nitrogen at ambient temperature for 16 hours. The solvent was removed in vacuo and the crude material taken up in water (50 mL) and hexanes (100 mL). The organics were separated and dried over anhydrous magnesium sulfate to provide the title compound. $^1$H NMR (400 MHz, chloroform-d) δ ppm 7.39 (d, J=2.3 Hz, 1H), 7.10 (dd, J=8.4, 2.2 Hz, 1H), 6.83 (d, J=8.4 Hz, 1H), 3.88 (s, 3H), 2.59 (q, J=7.6 Hz, 2H), 1.22 (t, J=7.6 Hz, 3H).

Example I-84B 1-(5-ethyl-2-methoxyphenyl)cyclopropanecarbonitrile

To a 100 mL round bottomed flask under nitrogen was added BINAP (2,2'-bis(diphenylphosphino)-1,1'-binaphthyl, 0.463 g, 0.744 mmol) and Pd$_2$(dba)$_3$ (tris(dibenzylideneacetone)dipalladium(0), 0.341 g, 0.372 mmol) and degassed tetrahydrofuran (7.59 mL) and the mixture was degassed and was stirred under nitrogen for 30 minutes. Then a degassed solution of 2-bromo-4-ethyl-1-methoxybenzene (1.497 mL, 9.30 mmol) from Example I-84A and cyclopropanecarbonitrile (1.345 mL, 13.95 mmol) in cyclopentyl methyl ether (18.98 mL) was added to the catalyst suspension. To the mixture was added 1 M LiHMDS (lithium bis(trimethylsilyl)amide, 27.9 mL, 27.9 mmol) in tetrahydrofuran slowly within 30 minutes at ambient temperature. The reaction was heated at 80° C. overnight. The reaction was cooled to ambient temperature and diluted with ethyl acetate (200 mL) and saturated aqueous ammonium chloride (500 mL). The organic layer was separated and the aqueous layer was back extracted twice with 100 mL of ethyl acetate. The combined organic layers were dried over sodium sulfate, filtered and concentrated under reduced pressure. The residue was purified using an 80 g silica gel cartridge with a gradient of 5-100% ethyl acetate/hexanes over 40 minutes to provide the title compound. $^1$H NMR (400 MHz, chloroform-d) δ ppm 7.14 (ddd, J=8.4, 2.3, 0.8 Hz, 1H), 7.05 (d, J=2.2 Hz, 1H), 6.83 (d, J=8.4 Hz, 1H), 3.92 (d, J=0.8 Hz, 3H), 2.58 (q, J=7.6 Hz, 2H), 1.63-1.59 (m, 2H), 1.30-1.24 (m, 2H), 1.21 (td, J=7.6, 0.8 Hz, 3H).

Example I-84C 1-(5-ethyl-2-methoxyphenyl)cyclopropanecarboxylic Acid 1-(5-Ethyl-2-methoxyphenyl)cyclopropanecarbonitrile (0.681 g, 3.38 mmol) from Example I-84B was dissolved in ethanol (5 mL). A solution of sodium hydroxide (1.320 g, 33.0 mmol) in water (2.500 mL) was added, and the resulting mixture was heated at 90° C. for 16 hours. The solvent was reduced in volume and the residue was cooled in an ice bath and acidified with 6M aqueous HCl (6 mL). The resulting precipitate was filtered and washed with water. The crude material was resubjected to the reaction conditions overnight to provide the title compound. $^1$H NMR (501 MHz, dimethyl sulfoxide-d$_6$) δ ppm 7.01 (dd, J=8.3, 2.3 Hz, 1H), 6.96 (d, J=2.3 Hz, 1H), 6.81 (d, J=8.3 Hz, 1H), 3.70 (s, 3H), 2.54-2.49 (m, 2H), 1.33 (q, J=3.8 Hz, 2H), 1.12 (t, J=7.5 Hz, 3H), 0.91 (q, J=3.8 Hz, 2H). MS (APCI+) m/z 221 (M+H)$^+$.

Example I-84D 1-(5-ethyl-2-methoxyphenyl)-N-(2-methylquinoline-5-sulfonyl)cyclopropane-1-carboxamide To a solution of 1-(5-ethyl-2-methoxyphenyl)cyclopropanecarboxylic acid (55 mg, 0.250 mmol) from Example I-84C, N$^1$-((ethylimino)methylene)-N$^3$,N$^3$-dimethylpropane-1,3-diamine hydrochloride (96 mg, 0.499 mmol) and N,N-dimethylpyridin-4-amine (30.5 mg, 0.250 mmol) in anhydrous N,N-dimethylformamide (1 mL) was added 2-methylquinoline-5-sulfonamide (60 mg, 0.270 mmol). The solution was stirred at ambient temperature overnight. The reaction was quenched with 1.0 mL of aqueous 1N HCl and the reaction was filtered through a syringe filter and diluted with dimethyl sulfoxide and purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (400 MHz, chloroform-d) δ ppm 9.15 (d, J=8.9 Hz, 1H), 8.62 (dt, J=8.6, 1.0 Hz, 1H), 8.49 (dd, J=7.6, 1.2 Hz, 1H), 8.27 (s, 1H), 7.95 (dd, J=8.5, 7.6 Hz, 1H), 7.57 (d, J=8.9 Hz, 1H), 7.22 (dd, J=8.4, 2.3 Hz, 1H), 7.03 (d, J=2.3 Hz, 1H), 6.87 (d, J=8.4 Hz, 1H), 3.68 (s, 3H), 2.96 (s, 3H), 2.62 (q, J=7.6 Hz, 2H), 1.49 (q, J=4.1 Hz, 2H), 1.24 (t, J=7.6 Hz, 3H), 1.05 (q, J=4.2 Hz, 2H). MS (APCI+) m/z 425 (M+H)$^+$.

Example I-85

1-{2-methoxy-5-[1-(methylamino)cyclopropyl]phenyl}-N-(quinoline-5-sulfonyl)cyclopropane-1-carboxamide Example I-85A 1-(3-bromo-4-methoxyphenyl)cyclopropanecarboxylic Acid Methyl 1-(3-bromo-4-methoxyphenyl)cyclopropanecarboxylate (0.5 g, 1.754 mmol, Example I-I-73B) was dissolved in tetrahydrofuran (3 mL), methanol (3 mL), and water (3 mL) and was treated with sodium hydroxide (0.351 g, 8.77 mmol). The reaction mixture was stirred at 35° C. overnight, concentrated in vacuo, and quenched with 1N aqueous citric acid (about 10 mL) until the pH~5. The resulting slurry was stirred vigorously and filtered. The precipitate was washed with water and hexanes, and dried in a vacuum oven overnight to provide the title compound. $^1$H NMR (400 MHz, chloroform-d) δ ppm 7.53 (d, J=2.2 Hz, 1H), 7.25 (dd, J=2.2 Hz, 8.5 Hz, 1H), 6.83 (d, J=8.5 Hz, 1H), 3.88 (s, 3H), 1.65 (q, J=4.0 Hz, 2H), 1.23 (q, J=4.0 Hz, 2H). MS (ESI+) m/z 271 (M+H)$^+$.

Example I-85B tert-butyl (1-(3-bromo-4-methoxyphenyl)cyclopropyl)carbamate

To a solution of 1-(3-bromo-4-methoxyphenyl)cyclopropanecarboxylic acid (100 mg, 0.369 mmol) from Example I-85A, 2-methylpropan-2-ol (0.141 mL, 1.475 mmol) in toluene (1 mL) at ambient temperature under nitrogen in a dried 20 mL vial, was added triethylamine (0.072 mL, 0.516 mmol) followed by 4 Å molecular sieves (0.13 g). The mixture was stirred for 5 minutes, and diphenyl phosphorazidate (0.087 mL, 0.406 mmol) was added. The mixture was stirred another 15 minutes at ambient temperature, and for 2 hours at 77° C. The mixture was filtered and the filtrate was concentrated in vacuo. The crude material was purified on a 12 g cartridge with 0-100% ethyl acetate/heptanes in 12 minutes to provide the title compound. $^1$H NMR (400 MHz, chloroform-d) δ ppm 7.43 (d, J=2.3 Hz, 1H), 7.20 (d, J=8.5

Hz, 1H), 6.82 (d, J=8.6 Hz, 1H), 5.21 (bs, 1H), 3.87 (s, 3H), 1.43 (s, 9H), 1.22 (bs, 2H), 1.14 (bs, 2H). MS (APCI+) m/z 243 (M+H-Boc)+.

Example I-85C tert-butyl (1-(3-bromo-4-methoxyphenyl)cyclopropyl)(methyl)carbamate A suspension of NaH (25.9 mg, 0.649 mmol) in N,N-dimethylformamide (1.5 mL) was cooled down to 0° C. tert-Butyl (1-(3-bromo-4-methoxyphenyl)cyclopropyl)carbamate from Example I-85B (148 mg, 0.432 mmol) was added. The mixture was stirred at 0° C. for 10 minutes, warmed up to ambient temperature and stirred for 20 minutes. Iodomethane (0.035 mL, 0.562 mmol) was added neat dropwise. The mixture was stirred at ambient temperature for 2 hours, quenched with 1 N aqueous ammonium chloride and extracted with ethyl acetate. The organic layer was separated, dried over $Na_2SO_4$, filtered, and concentrated to dryness. The crude material was purified on a 10 g silica gel cartridge with a gradient of 0-100% ethyl acetate/heptanes in 12 minutes to provide the title compound. $^1$H NMR (400 MHz, chloroform-d) δ ppm 7.38 (d, J=2.3 Hz, 1H), 7.10 (d, J=8.4 Hz, 1H), 6.83 (d, J=8.6 Hz, 1H), 3.89 (s, 3H), 2.91 (s, 3H), 1.47 (s, 9H), 1.29 (s, 2H), 1.17 (s, 2H). MS (ESI+) m/z=256 (M+H-Boc)+.

Example I-85D tert-butyl (1-(3-(1-cyanocyclopropyl)-4-methoxyphenyl)cyclopropyl)(methyl)carbamate To a 100 mL round bottomed flask under nitrogen was added BINAP (2,2'-bis(diphenylphosphino)-1,1'-binaphthyl, 19.58 mg, 0.031 mmol) and $Pd_2(dba)_3$ (tris(dibenzylideneacetone)dipalladium(0), 14.39 mg, 0.016 mmol) and degassed tetrahydrofuran (321 µl). The mixture was degassed and was stirred under nitrogen for 30 minutes. A degassed solution of tert-butyl (1-(3-bromo-4-methoxyphenyl)cyclopropyl)(methyl)carbamate (140 mg, 0.393 mmol) from Example I-85C and cyclopropanecarbonitrile (56.8 0.589 mmol) in cyclopentyl methyl ether (802 µl) was added to the catalyst suspension. To the mixture was then added 1M LiHMDS (lithium bis(trimethylsilyl)amide, 1179 µl, 1.179 mmol) in tetrahydrofuran slowly within 20 minutes at ambient temperature. The reaction was heated at 80° C. for 16 hours. The reaction was cooled to ambient temperature and diluted with ethyl acetate (7 mL) and saturated aqueous ammonium chloride (16 mL). The organic layer was separated and the aqueous layer was back extracted twice with 10 mL of ethyl acetate. The combined organic layers were dried over sodium sulfate, filtered and concentrated under reduced pressure. The residue was purified using a 12 g silica gel cartridge with a gradient of 0-50% ethyl acetate/hexanes over 12 minutes to provide the title compound. $^1$H NMR (400 MHz, chloroform-d) δ ppm 7.12 (dd, J=8.6, 2.3 Hz, 1H), 7.06 (bs, 1H), 6.81 (d, J=8.5 Hz, 1H), 3.91 (s, 3H), 2.89 (s, 3H), 1.60 (bs, 2H), 1.46 (s, 9H), 1.26 (bs, 2H), 1.25-1.19 (m, 2H), 1.14 (bs, 2H). MS (ESI+) m/z 243 (M+H-Boc)+.

Example I-85E 1-(5-(1-((tert-butoxycarbonyl)(methyl)amino)cyclopropyl)-2-methoxyphenyl)cyclopropanecarboxylic Acid tert-Butyl (1-(3-(1-cyanocyclopropyl)-4-methoxyphenyl)cyclopropyl)(methyl)carbamate (75 mg, 0.219 mmol) from Example I-85D was dissolved in ethanol (0.5 mL). A solution of sodium hydroxide (85 mg, 2.135 mmol) in water (0.250 mL) was added, and the resulting mixture was heated at 90° C. for 5 days. The solvent was reduced in volume and the residue was acidified with 1 M aqueous citric acid (2 mL). The resulting precipitate was extracted with dichloromethane. The organics were concentrated and purified on a 12 g silica gel cartridge with a gradient of 20-100% ethyl acetate/heptanes over a period of 10 minutes to provide the title compound. $^1$H NMR (400 MHz, chloroform-d) δ ppm 7.11-7.06 (m, 1H), 7.06-7.02 (bs, 1H), 6.78 (d, J=8.4 Hz, 1H), 3.81 (s, 3H), 2.88 (s, 3H), 1.63 (s, 2H), 1.44 (s, 9H), 1.25 (m, 2H), 1.13 (bs, 4H). MS (APCI+) m/z 262 (M+H-Boc)+.

Example I-85F

1-{2-methoxy-5-[1-(methylamino)cyclopropyl]phenyl}-N-(quinoline-5-sulfonyl)cyclopropane-1-carboxamide To a solution of 1-(5-(1-((tert-butoxycarbonyl)(methyl)amino)cyclopropyl)-2-methoxyphenyl)cyclopropanecarboxylic acid (31 mg, 0.086 mmol) from Example I-85E, $N^1$-((ethylimino)methylene)-$N^3$,$N^3$-dimethylpropane-1,3-diamine hydrochloride (32.9 mg, 0.172 mmol) and N,N-dimethylpyridin-4-amine (11.53 mg, 0.094 mmol) in anhydrous dichloromethane (0.5 mL) was added quinoline-5-sulfonamide (17.86 mg, 0.086 mmol). After 16 hours, the reaction was quenched with 1 mL of aqueous 1N citric acid and the organic layer was concentrated in vacuo. The residue was purified via chromatography on a 10 g silica gel cartridge, eluting with a gradient of 0-10% methanol/dichloromethane over a period of 10 minutes to yield the Boc-intermediate. The intermediate was treated with 0.2 mL dichloromethane and trifluoroacetic acid (0.4 mL, 5.19 mmol), and stirred for 1 hour at ambient temperature. The solvent was evaporated in vacuo, and the residue was triturated with 4 mL diethyl ether. The resulting precipitate was filtered to provide the title compound as the trifluoroacetic acid salt. $^1$H NMR (400 MHz, dimethyl sulfoxide-$d_6$) δ ppm 11.57 (s, 1H), 9.05 (d, J=3.0 Hz, 1H), 8.94 (d, J=8.8 Hz, 2H), 8.33 (d, J=8.4 Hz, 1H), 8.28 (d, J=7.3 Hz, 1H), 7.93 (t, J=8.0 Hz, 1H), 7.70 (dd, J=8.8, 4.2 Hz, 1H), 7.39 (dd, J=8.4, 2.3 Hz, 1H), 7.27 (d, J=2.3 Hz, 1H), 6.92 (d, J=8.6 Hz, 1H), 3.39 (s, 3H), 2.44 (s, 3H), 1.37-1.26 (m, 4H), 1.14 (d, J=6.4 Hz, 2H), 0.98 (s, 2H). MS (APCI+) m/z 452 (M+H)+.

Example I-86

1-(4-cyclobutyl-2,6-dimethoxyphenyl)-N-(1H-indole-4-sulfonyl)cyclopropane-1-carboxamide Example I-86A 1-cyclobutyl-3,5-dimethoxybenzene In a 250 mL flask, 1-bromo-3,5-dimethoxybenzene (2 g, 9.21 mmol) [CAS #20469-65-2] was dissolved in tetrahydrofuran (120 mL) and treated with palladium(II) acetate (0.207 g, 0.921 mmol) and dicyclohexyl(2',6'-dimethoxy-[1,1'-biphenyl]-2-yl)phosphine (0.378 g, 0.921 mmol), followed by dropwise addition over a few minutes of 0.5 M cyclobutylzinc(II) bromide (23.96 mL, 11.98 mmol) in tetrahydrofuran via addition funnel at ambient temperature. After 16 hours, the mixture was poured into 80 mL of saturated aqueous ammonium chloride and extracted with ethyl acetate (2×100 mL). The combined organics were dried over sodium sulfate, filtered, and concentrated to provide the title compound. MS (ESI+) m/z 193 (M+H)+.

Example I-86B 2-bromo-5-cyclobutyl-1,3-dimethoxybenzene

In a 250 mL round bottom flask, 1-cyclobutyl-3,5-dimethoxybenzene (1.7 g, 8.84 mmol) from Example I-86A was dissolved in dichloromethane (25 mL), and cooled to 0° C. in an ice bath. N-Bromosuccinimide (1.574 g, 8.84 mmol) was added to the reaction. The reaction was stirred at 0° C. for 1 hour. The mixture was poured into 50 mL of saturated aqueous sodium bicarbonate and was extracted with dichloromethane (2×100 mL). The combined organics were dried over sodium sulfate, filtered, and concentrated. The crude material was purified by silica gel chromatography (ethyl acetate/petroleum ether=1/10) to provide the title compound. $^1$H NMR: (400 MHz, CDCl$_3$) δ ppm 6.52 (d, J=2.4 Hz, 1H), 6.36 (d, J=2.4 Hz, 1H), 3.86 (s, 3H), 3.83 (s, 3H), 3.81-3.72 (m 1H), 2.46-2.39 (m, 2H), 2.12-1.96 (m, 3H), 1.84-1.77 (m, 1H).

Example I-86C methyl 1-(4-cyclobutyl-2,6-dimethoxyphenyl)cyclopropanecarboxylate The title compound was prepared as described in Example I-1B, substituting 2-bromo-5-cyclobutyl-1,3-dimethoxybenzene from Example I-86B for 1-bromo-2-methoxybenzene. MS (ESI+) m/z 291 (M+H)+.

Example I-86D 1-(4-cyclobutyl-2,6-dimethoxyphenyl)cyclopropanecarboxylic Acid

In a 250 mL round bottom flask, methyl 1-(4-cyclobutyl-2,6-dimethoxyphenyl)cyclopropanecarboxylate (3.8 g, 13.09 mmol) from Example I-86C was dissolved in methanol (20 mL) and tetrahydrofuran (40 mL), and 10 M aqueous sodium hydroxide (42.3 mL, 423 mmol) was added. The reaction mixture was stirred at 70° C. for 32 hours, cooled in an ice bath and acidified with 6 N aqueous hydrogen chloride to pH=2. The reaction mixture was extracted with ethyl acetate (2×100 mL) and the organic extracts were washed with brine (100 mL), dried over sodium sulfate, filtered, and concentrated. The residue was triturated with tert-butyl methyl ether (20 mL). The material was filtered and dried to provide the title compound. $^1$H NMR: (400 MHz, CDCl$_3$) δ ppm 6.52 (d, J=2.0 Hz, 1H), 6.32 (d, J=2.0 Hz, 1H), 3.90-3.83 (m, 1H), 3.82 (s, 3H), 3.79 (s, 3H), 2.35-2.22 (m 2H), 2.22-2.08 (m, 2H), 2.04-1.95 (m, 1H), 1.86-1.70 (m, 3H), 1.17-1.08 (m, 2H). MS (ESI+) m/z 277 (M+H)+.

Example I-86E

To a solution of 1-(4-cyclobutyl-2,6-dimethoxyphenyl) cyclopropanecarboxylic acid (87 mg, 0.315 mmol) from Example I-86D, N$^1$-((ethylimino)methylene)-N$^3$,N$^3$-dimethylpropane-1,3-diamine hydrochloride (121 mg, 0.630 mmol) and N,N-dimethylpyridin-4-amine (38.5 mg, 0.315 mmol) in anhydrous dichloromethane (1 mL) was added 1H-indole-4-sulfonamide (61.8 mg, 0.315 mmol). The solution was stirred at ambient temperature overnight. The reaction was quenched with 0.5 mL of aqueous 1N HCl and the crude organics were purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The material was washed with ethyl acetate, ether and methanol to provide the title compound. $^1$H NMR (400 MHz, dimethyl sulfoxide-d$_6$) δ ppm 11.59 (s, 1H), 10.40 (s, 1H), 7.67 (d, J=8.1 Hz, 1H), 7.60-7.50 (m, 2H), 7.17 (t, J=7.8 Hz, 1H), 6.82-6.71 (m, 1H), 6.43-6.31 (m, 2H), 3.73 (s, 3H), 3.65 (s, 3H), 3.49-3.38 (m, 1H), 2.19-2.05 (m, 1H), 2.03-1.90 (m, 1H), 1.79-1.60 (m, 3H), 1.58-1.49 (m, 2H), 1.36-1.25 (m, 1H), 0.91-0.76 (m, 2H). MS (ESI+) m/z 455 (M+H)+.

Example I-87

N-(2-aminoquinoline-5-sulfonyl)-1-{5-methyl-2-[(propan-2-yl)oxy]phenyl}cyclopropane-1-carboxamide Example I-87A 2-bromo-1-isopropoxy-4-methylbenzene To 2-bromo-4-methylphenol (2 g, 10.69 mmol) in N,N-dimethylformamide (10 mL) was added potassium carbonate (2.96 g, 21.39 mmol) at ambient temperature. The mixture was stirred for 10 minutes and then 2-iodopropane (2.135 mL, 21.39 mmol) was added dropwise, and the mixture was heated to 50° C. for 16 hours with stirring. Ethyl acetate (20 mL) was added, the reaction was filtered, and the material was rinsed with ethyl acetate (2×20 mL). The combined organics were washed with water and brine, dried over MgSO$_4$, filtered, and concentrated. The residue was purified via chromatography on a 24 g silica gel cartridge, eluting with ethyl acetate in heptane at 0-40% gradient to provide the title compound. $^1$H NMR (400 MHz, chloroform-d) δ ppm 7.35 (dd, J=2.1, 0.8 Hz, 1H), 7.01 (ddd, J=8.3, 2.1, 0.8 Hz, 1H), 6.81 (d, J=8.3 Hz, 1H), 4.47 (hept, J=6.1 Hz, 1H), 2.26 (s, 3H), 1.35 (d, J=6.1 Hz, 6H). MS (APCI+) m/z 229 (M+H)+.

Example I-87B methyl 1-(2-isopropoxy-5-methylphenyl)cyclopropanecarboxylate

To 2-Bromo-1-isopropoxy-4-methylbenzene (2.10 g, 9.17 mmol) from Example I-87A in 10 mL of dry tetrahydrofuran was added Q-Phos (1,2,3,4,5-pentaphenyl-1'-(di-tert-butylphosphino)ferrocene) (0.130 g, 0.183 mmol) and tris(dibenzylideneacetone)dipalladium(0) (0.168 g, 0.183 mmol). A solution of freshly-prepared (1-(methoxycarbonyl)cyclopropyl)zinc(II) bromide (45.8 mL, 18.33 mmol) in tetrahydrofuran (0.40 mmol/mL, 46 mL) was added via a stainless steel cannula under nitrogen pressure. The mixture was stirred at ambient temperature for 20 minutes. Ethyl acetate and saturated aqueous ammonium chloride were added. The organic layer was washed with brine and was concentrated. The residue was purified via chromatography on a 40 g silica gel cartridge, eluting with ethyl acetate in heptane at 0-50% gradient to provide the title compound. MS (APCI+) m/z 249 (M+H)±.

Example I-87C

1-(2-isopropoxy-5-methylphenyl)cyclopropanecarboxylic Acid

A mixture of methyl 1-(2-isopropoxy-5-methylphenyl) cyclopropanecarboxylate (2.0 g, 8.05 mmol) from Example I-87B and lithium hydroxide (1.929 g, 81 mmol) in methanol (10 mL) and water (3 mL) were stirred at 40° C. for 16 hours. The solvent was reduced to half and was adjusted to pH~1 by adding 6M aqueous HCl. The mixture was extracted with dichloromethane (20 mL×3), washed with brine, dried over $MgSO_4$, filtered, and concentrated to provide the title compound. $^1$H NMR (500 MHz, chloroform-d) δ ppm 7.09-6.96 (m, 2H), 6.79-6.68 (m, 1H), 4.53 (pd, J=6.1, 0.6 Hz, 1H), 2.25 (t, J=0.7 Hz, 3H), 1.60 (q, J=4.1 Hz, 2H), 1.30 (d, J=6.0 Hz, 6H), 1.13 (q, J=4.1 Hz, 2H). MS(APCI+) m/z 235 (M+H)$^+$.

Example I-87D

2-(diallylamino)quinoline-5-sulfonamide

5-Bromo-2-chloroquinoline (8 g, 33.0 mmol) was dissolved in 1-methyl-2-pyrrolidinone (33.0 mL). Diallylamine (12.22 mL, 99 mmol) was added, and the resulting solution was heated at 100° C. for 30 hours, adding more (3×8 mL) portions of allylamine spread over that time. The reaction was reduced in volume, diluted with water (100 mL), and extracted with methyl tert-butyl ether (3×100 mL). The combined extracts were washed with water (50 mL) and brine (50 mL) and dried over sodium sulfate. After filtration, the solvent was removed in vacuo and the crude material was purified via silica gel chromatography, eluting with 0-5% ethyl acetate in hexanes to give N,N-diallyl-5-bromoquinolin-2-amine (10 g, 33.0 mmol). The N,N-diallyl-5-bromoquinolin-2-amine was dissolved in tetrahydrofuran (165 mL) and the solution was cooled to <–70° C. before addition of n-butyllithium (2.5M in hexane, 14.45 mL, 36.3 mmol) dropwise over approximately 5 minutes, maintaining an internal temperature below –68° C. The resulting mixture was stirred for 2 minutes at the same temperature and quenched by $SO_2$ (g) addition. The mixture was concentrated in vacuo to provide lithium 2-(diallylamino)quinoline-5-sulfinate (9.71 g, 33.0 mmol). The lithium 2-(diallylamino)quinoline-5-sulfinate was then dissolved in water (66.0 mL) and sodium acetate trihydrate (6.29 g, 46.2 mmol) and (aminooxy)sulfonic acid (5.22 g, 46.2 mmol) were added in one portion. The reaction mixture was stirred at ambient temperature for 1 hour, 2 mL of tetrahydrofuran was added, and stirring was continued for another 30 minutes at ambient temperature. After 90 minutes the reaction was filtered, and the material was washed with water and heptanes. The crude material was dissolved in 300 mL of ethyl acetate, washed with water and brine, dried over sodium sulfate, filtered, and concentrated in vacuo. The crude material was purified by silica gel chromatography, eluting with ethyl acetate in heptanes (0 to 40%) to provide the title compound. $^1$H NMR (400 MHz, chloroform-d) δ ppm 8.64 (dd, J=9.6, 0.8 Hz, 1H), 8.00-7.85 (m, 2H), 7.53 (dd, J=8.5, 7.4 Hz, 1H), 6.95 (d, J=9.6 Hz, 1H), 5.91 (ddt, J=17.2, 10.5, 5.2 Hz, 2H), 5.25-5.15 (m, 4H), 4.89 (s, 2H), 4.27 (dt, J=5.5, 1.7 Hz, 4H).

Example I-87E

N-42-(diallylamino)quinolin-5-yl)sulfonyl)-1-(2-isopropoxy-5-methylphenyl)cyclopropanecarboxamide To a solution of 1-(2-isopropoxy-5-methylphenyl)cyclopropanecarboxylic acid (50 mg, 0.213 mmol) from Example I-87C, N,N-dimethylpyridin-4-amine (26.1 mg, 0.213 mmol) and $N^1$-((ethylimino)methylene)-$N^3$,$N^3$-dimethylpropane-1,3-diamine hydrochloride (82 mg, 0.427 mmol) in dichloromethane (1 mL) was added 2-(diallylamino)quinoline-5-sulfonamide (78 mg, 0.257 mmol) from Example I-87D. The reaction mixture was stirred at ambient temperature for 5 hours, and quenched with 0.5 mL of IN aqueous HCl. The organics were purified using a 12 g silica gel cartridge with a gradient of 0-100% ethyl acetate/hexanes over 20 minutes to provide the title compound. $^1$H NMR (501 MHz, chloroform-d) δ ppm 8.47-8.39 (m, 2H), 8.07 (dd, J=7.5, 1.2 Hz, 1H), 7.93 (dt, J=8.4, 1.0 Hz, 1H), 7.60 (dd, J=8.5, 7.5 Hz, 1H), 7.14 (ddd, J=8.4, 2.3, 0.8 Hz, 1H), 7.06-7.00 (m, 1H), 6.85 (d, J=9.6 Hz, 1H), 6.82 (d, J=8.4 Hz, 1H), 6.00-5.89 (m, 2H), 5.24 (dq, J=7.2, 1.6 Hz, 2H), 5.23-5.19 (m, 2H), 4.50 (hept, J=6.1 Hz, 1H), 4.29 (dt, J=5.5, 1.6 Hz, 4H), 2.30 (s, 3H), 1.51 (t, J=3.2 Hz, 2H), 1.22 (d, J=6.0 Hz, 6H), 1.00 (q, J=3.9 Hz, 2H). MS (ESI+) m/z 520 (M+H)$^+$.

Example I-87F

N-(2-aminoquinoline-5-sulfonyl)-1-{5-methyl-2-[(propan-2-yl)oxy]phenyl}cyclopropane-1-carboxamide N-((2-(diallylamino)quinolin-5-yl)sulfonyl)-1-(2-isopropoxy-5-methylphenyl)cyclopropanecarboxamide (30 mg, 0.058 mmol) was dissolved in ethanol (0.5 mL) and water (0.5 mL), degassed with a stream of nitrogen bubbling through, and treated with RhCl(PPh$_3$)$_3$ (Wilkinson's catalyst, chloridotris(triphenylphosphane)rhodium(I), 2.67 mg, 2.89 μmol). The reaction mixture was stirred at 100° C. After 5 hours, the solvent was reduced in volume and the reaction was filtered. The precipitate was washed with ether to give crude material which was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (400 MHz, dimethyl sulfoxide-d$_6$) δ ppm 11.64 (s, 1H), 8.87 (d, J=9.8 Hz, 1H), 8.61 (s, 2H), 7.99 (dd, J=7.0, 1.8 Hz, 1H), 7.92-7.75 (m, 2H), 7.11 (d, J=9.8 Hz, 1H), 7.00 (dd, J=8.4, 2.2 Hz, 1H), 6.90 (d, J=2.2 Hz, 1H), 6.76 (d, J=8.4 Hz, 1H), 4.40 (p, J=6.0 Hz, 1H), 2.19 (s, 3H), 1.22 (q, J=4.2 Hz, 2H), 1.00 (d, J=6.0 Hz, 6H), 0.91 (q, J=4.3 Hz, 2H). MS (ESI+) m/z 440 (M+H)$^+$.

Example I-88

1-[2-methoxy-5-(1-methoxycyclobutyl)phenyl]-N-(quinoline-5-sulfonyl)cyclopropane-1-carboxamide

Example I-88A

1-(4-methoxyphenyl)cyclobutanol (4-Methoxyphenyl)magnesium bromide (121 mL, 60.5 mmol) solution was cooled to –78° C. before dropwise addition of cyclobutanone (4.76 mL, 63.7 mmol). After the addition was complete, the reaction was warmed to ambient temperature and quenched with saturated aqueous ammonium chloride. The mixture was diluted with methyl tert-butyl ether. The organic layer was washed with saturated aqueous ammonium chloride and brine, dried over sodium sulfate, filtered and concentrated to provide the title compound. $^1$H NMR (400 MHz, chloroform-d) δ ppm 7.50-7.40 (m, 2H), 6.97-6.89 (m, 2H), 3.84 (s, 3H), 2.65-2.53 (m, 2H), 2.45-2.31 (m, 2H), 2.17-2.07 (m, 1H), 2.07-1.94 (m, 1H), 1.74-1.60 (m, 1H).

Example I-88B 1-methoxy-4-(1-methoxycyclobutyl)benzene

To a cooled (ice bath) solution of 1-(4-methoxyphenyl) cyclobutanol (7.10 g, 39.8 mmol) from Example I-88A in N,N-dimethylformamide (66.4 mL) was added sodium hydride (2.390 g, 59.8 mmol) and the reaction was stirred at 5° C. for one hour. Iodomethane (4.96 mL, 80 mmol) was added and the reaction was allowed to warm to ambient temperature and was stirred for 16 hours. Water was added and the solution was diluted with methyl tert-butyl ether (400 mL). The organic layer was separated and dried over sodium sulfate, filtered and concentrated under reduced pressure to provide the title compound. $^1$H NMR (400 MHz, chloroform-d) δ ppm 7.39-7.30 (m, 2H), 6.95-6.75 (m, 2H), 3.82 (s, 3H), 2.91 (s, 3H), 2.44-2.27 (m, 4H), 1.91 (dtt, J=11.1, 9.3, 4.9 Hz, 1H), 1.64 (dp, J=11.0, 8.5 Hz, 1H).

Example I-88C 2-bromo-1-methoxy-4-(1-methoxycyclobutyl)benzene

A solution of 1-methoxy-4-(1-methoxycyclobutyl)benzene (8 g, 41.6 mmol) from Example I-88B and N-bromosuccinimide (8.15 g, 45.8 mmol) in acetonitrile (41.6 mL) was stirred at ambient temperature for 3 hours. The solvent was evaporated in vacuo. The crude material was triturated with dichloromethane, and filtered. The filtrate was purified by chromatography, eluting on 40 g silica gel cartridge with a gradient of 0-20% ethyl acetate/heptanes over a period of 12 minutes to provide the title compound. $^1$H NMR (501 MHz, chloroform-d) δ ppm 7.60 (d, J=2.2 Hz, 1H), 7.33 (dd, J=8.5, 2.2 Hz, 1H), 6.90 (d, J=8.5 Hz, 1H), 3.91 (s, 3H), 2.92 (s, 3H), 2.35 (d, J=7.1 Hz, 2H), 2.34 (d, J=7.0 Hz, 2H), 2.01-1.87 (m, 1H), 1.65 (dq, J=11.2, 8.4 Hz, 1H). MS (APCI+) m/z 239 (M+H-methanol)$^+$.

Example I-88D methyl 1-(2-methoxy-5-(1-methoxycyclobutyl)phenyl)cyclopropanecarboxylate To a solution of Q-Phos (1,2,3,4,5-pentaphenyl-1'-(di-tert-butylphosphino)ferrocene, 0.052 g, 0.074 mmol) and bis(dibenzylideneacetone)palladium (0.042 g, 0.074 mmol) in tetrahydrofuran (12 mL) at ambient temperature was added 2-bromo-1-methoxy-4-(1-methoxycyclobutyl)benzene (1 g, 3.69 mmol) from Example I-88C followed by a solution of freshly-prepared (1-(methoxycarbonyl)cyclopropyl)zinc(II) bromide (16.39 mL, 7.38 mmol). The mixture was stirred at ambient temperature for 16 hours. Dichloromethane and saturated aqueous ammonium chloride were added. The organic layer was separated, washed with brine and concentrated. The residue was purified via chromatography on a 40 g silica gel cartridge, eluting with ethyl acetate in heptane at 0-50% gradient in a period of 15 minutes to provide the title compound. $^1$H NMR (501 MHz, chloroform-d) δ ppm 7.30 (dd, J=8.4, 2.4 Hz, 1H), 7.24 (d, J=2.3 Hz, 1H), 6.85 (d, J=8.4 Hz, 1H), 3.84 (s, 3H), 3.60 (s, 3H), 2.91 (s, 3H), 2.42-2.28 (m, 4H), 1.92 (dtt, J=11.1, 9.3, 4.9 Hz, 1H), 1.66 (dq, J=11.1, 8.4 Hz, 1H), 1.60 (q, J=4.1 Hz, 2H), 1.12 (q, J=4.1 Hz, 2H). MS (APCI+) m/z 259 (M+H-methanol)$^+$.

Example I-88E 1-(2-methoxy-5-(1-methoxycyclobutyl)phenyl)cyclopropanecarboxylic Acid Methyl 1-(2-methoxy-5-(1-methoxycyclobutyl)phenyl) cyclopropanecarboxylate (0.29 g, 0.999 mmol) from Example I-88D was dissolved in tetrahydrofuran (1.5 mL) and methanol (1.500 mL), and water (1.500 mL) and treated with sodium hydroxide (0.200 g, 4.99 mmol). The reaction mixture was stirred at 35° C. overnight, and the reaction was concentrated, cooled in an ice bath and carefully quenched with 1N citric acid (about 2.5 mL) until the pH~5. The resulting slurry was stirred vigorously and filtered. The precipitate was washed with water and dried in a vacuum oven overnight to provide the title compound. $^1$H NMR (501 MHz, chloroform-d) δ ppm 7.30 (dd, J=8.4, 2.3 Hz, 1H), 7.25 (d, J=2.3 Hz, 1H), 6.85 (d, J=8.4 Hz, 1H), 3.85 (s, 3H), 2.89 (s, 3H), 2.41-2.28 (m, 4H), 1.91 (dtd, J=11.2, 9.2, 4.6 Hz, 1H), 1.70-1.57 (m, 3H), 1.18 (q, J=4.1 Hz, 2H). MS (APCI+) m/z 245 (M+H-methanol)$^+$.

Example I-88F

1-[2-methoxy-5-(1-methoxycyclobutyl)phenyl]-N-(quinoline-5-sulfonyl)cyclopropane-1-carboxamide To a solution of 1-(2-methoxy-5-(1-methoxycyclobutyl) phenyl)cyclopropanecarboxylic acid (60 mg, 0.217 mmol) from Example I-88E, $N^1$-((ethylimino)methylene)-$N^3$,$N^3$-dimethylpropane-1,3-diamine hydrochloride (83 mg, 0.434 mmol) and N,N-dimethylpyridin-4-amine (29.2 mg, 0.239 mmol) in anhydrous dichloromethane (1 mL) was added quinoline-5-sulfonamide (45.2 mg, 0.217 mmol). After 16 hours, the reaction was quenched with 1 mL of aqueous 1N citric acid and the organic layer was concentrated in vacuo. The residue was purified via chromatography on a 10 g silica gel cartridge, eluting with a gradient of 0-10% methanol/dichloromethane over a period of 10 minutes. The material was triturated with diethyl ether (3 mL) and filtered to provide the title compound. $^1$H NMR (501 MHz, dimethyl sulfoxide-d$_6$) δ ppm 11.58 (s, 1H), 9.06 (dd, J=4.2, 1.5 Hz, 1H), 8.97 (d, J=8.7 Hz, 1H), 8.34 (d, J=8.6 Hz, 1H), 8.31 (d, J=7.4 Hz, 1H), 7.94 (t, J=7.9 Hz, 1H), 7.70 (dd, J=8.8, 4.1 Hz, 1H), 7.28 (dd, J=8.5, 2.3 Hz, 1H), 7.07 (d, J=2.3 Hz, 1H), 6.86 (d, J=8.5 Hz, 1H), 3.38 (s, 3H), 2.82 (s, 3H), 2.32 (ddd, J=12.9, 8.6, 4.7 Hz, 2H), 2.24 (ddd, J=12.2, 9.5, 7.9 Hz, 2H), 1.84 (ddq, J=10.9, 9.3, 4.8 Hz, 1H), 1.58 (dp, J=10.9, 8.4 Hz, 1H), 1.31 (q, J=4.3 Hz, 2H), 0.95 (s, 2H). MS (APCI+) m/z 467 (M+H)$^+$.

Example I-89

N-(2-aminoquinoline-5-sulfonyl)-1-(2-ethoxy-5-methylphenyl)cyclopropane-1-carboxamide

Example I-89A

1-(2-ethoxy-5-methylphenyl)cyclopropanecarbonitrile

To a 250 mL round bottomed flask under nitrogen was added BINAP (2,2'-bis(diphenylphosphino)-1,1'-binaphthyl, 1.033 g, 1.658 mmol) and Pd$_2$(dba)$_3$ (tris(dibenzylideneacetone)dipalladium(0), 0.759 g, 0.829 mmol) and degassed tetrahydrofuran (16.92 mL). The mixture was degassed and was stirred under nitrogen for 30 minutes. A degassed solution of 2-bromo-1-ethoxy-4-methylbenzene (4.459 g, 20.73 mmol) [CAS #103260-55-5] and cyclopropanecarbonitrile (3.00 mL, 31.1 mmol) in cyclopentyl methyl ether (42.3 mL) was added to the catalyst suspension. To this mixture was added 1 M lithium bis(trimethylsilyl)amide (62.2 mL, 62.2 mmol) in tetrahydrofuran slowly within 30 minutes at ambient temperature. The reaction was heated at 80° C. overnight. The reaction was cooled to ambient temperature and was diluted with methyl tert-butyl ether (200 mL) and saturated aqueous ammonium chloride (140 mL). The organic layer was separated and the aqueous layer was back extracted twice with 250 mL of methyl tert-butyl ether. The combined organic layers were dried over sodium sulfate, filtered through a plug of silica gel and concentrated under reduced pressure. The residue was purified using a 120 g silica gel cartridge with a gradient of 0-100% ethyl acetate/hexanes over 60 minutes to provide the title compound. $^1$H NMR (400 MHz, chloroform-d) δ ppm 7.08 (dd, J=8.3, 2.2 Hz, 1H), 7.02 (d, J=2.3 Hz, 1H), 6.78 (d, J=8.2 Hz, 1H), 4.12 (q, J=6.9 Hz, 2H), 2.27 (s, 3H), 1.63-1.57 (m, 2H), 1.50 (t, J=6.9 Hz, 3H), 1.30-1.22 (m, 2H). MS (ESI+) m/z 202 (M+H)$^+$.

Example I-89B

1-(2-ethoxy-5-methylphenyl)cyclopropanecarboxylic Acid 1-(2-Ethoxy-5-methylphenyl)cyclopropanecarbonitrile (2.865 g, 14.24 mmol) from Example I-89A was dissolved in ethanol (10 mL). A solution of sodium hydroxide (5.392 g, 135 mmol) in water (5.00 mL) was added, and the resulting mixture was heated at 90° C. After 1 hour, additional ethanol (10 mL) was added and the reaction continued heating at 90° C. for 72 hours. The reaction was poured into an ice cooled solution of 6 N aqueous hydrogen chloride (23.13 mL, 139 mmol) to acidic pH. The resulting precipitate was filtered and washed with water to provide the title compound. $^1$H NMR (400 MHz, dimethyl sulfoxide-d$_6$) δ ppm 11.85 (s, 1H), 6.98-6.90 (m, 2H), 6.78 (d, J=8.1 Hz, 1H), 3.95 (q, J=7.0 Hz, 2H), 2.17 (s, 3H), 1.34 (q, J=3.9 Hz, 2H), 1.23 (t, J=6.9 Hz, 3H), 0.95 (q, J=3.9 Hz, 2H). MS (ESI−) m/z 218 (M−H)

Example I-89C

N-(2-aminoquinoline-5-sulfonyl)-1-(2-ethoxy-5-methylphenyl)cyclopropane-1-carboxamide To a solution of 1-(2-ethoxy-5-methylphenyl)cyclopropanecarboxylic acid (0.1 g, 0.454 mmol) from Example I-89B, N$^1$-((ethylimino)methylene)-N$^3$,N$^3$-dimethylpropane-1,3-diamine hydrochloride (0.174 g, 0.908 mmol) and N,N-dimethylpyridin-4-amine (0.061 g, 0.499 mmol) in anhydrous dichloromethane (2 mL) was added 2-(diallylamino)quinoline-5-sulfonamide (0.138 g, 0.454 mmol) from Example I-87D. After 1 hour, the reaction was quenched with 1 mL of aqueous 1N HCl and put through an aqueous/organic extractor tube with dichloromethane. The solvent was removed to give crude N-((2-(diallylamino)quinolin-5-yl)sulfonyl)-1-(2-ethoxy-5-methylphenyl)cyclopropanecarboxamide. The crude N-((2-(diallylamino)quinolin-5-yl)sulfonyl)-1-(2-ethoxy-5-methylphenyl)cyclopropanecarboxamide was deprotected by diluting with 0.5 mL of ethanol and 0.5 mL of water, degassing with nitrogen, and adding RhCl(PPh$_3$)$_3$ (Wilkinson's catalyst, chloridotris(triphenylphosphane)rhodium(I), 3.4 mg, 3.67 μmol). The reaction was heated at 100° C. for 3 hours. Additional RhCl(PPh$_3$)$_3$ (10 mg) was added and the mixture was stirred at 100° C. for another 3 hours. The mixture was concentrated and the residue was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). The material was triturated with methanol to provide the title compound as the trifluoroacetic acid salt. $^1$H NMR (501 MHz, dimethyl sulfoxide-d$_6$) δ ppm 8.83 (d, J=9.7 Hz, 1H), 8.58 (s, 2H), 8.00 (dd, J=7.2, 1.6 Hz, 1H), 7.91-7.81 (m, 2H), 7.11 (d, J=9.7 Hz, 1H), 7.04 (dd, J=8.3, 2.1 Hz, 1H), 6.93 (d, J=2.2 Hz, 1H), 6.76 (d, J=8.2 Hz, 1H), 3.77 (q, J=6.9 Hz, 2H), 2.21 (s, 3H), 1.22 (q, J=4.2 Hz, 2H), 0.97 (t, J=6.9 Hz, 3H), 0.93 (q, J=4.3 Hz, 2H). MS (ESI−) m/z 424 (M−H)$^-$.

Example I-90

1-[2-methoxy-5-(oxetan-3-yl)phenyl]-N-(quinoline-5-sulfonyl)cyclopropane-1-carboxamide

Example I-90A

3-(4-methoxyphenyl)oxetan-3-ol

To a cooled (ice/brine bath) solution of 0.5 M (4-methoxyphenyl)magnesium bromide (102 mL, 51.0 mmol) in tetrahydrofuran (5 mL) was added oxetan-3-one (3.061 g, 42.5 mmol) dropwise, keeping the internal temperature below 0° C. The reaction was allowed to slowly warm to ambient temperature and was stirred for 16 hours. The reaction was cooled in an ice bath, quenched with saturated aqueous ammonium chloride (100 mL) and diluted with methyl tert-butyl ether (500 mL). The organic layer was separated, dried over sodium sulfate, filtered and concentrated under reduced pressure. The material was triturated with diethyl ether. The residue was purified using an 80 g silica gel cartridge with a gradient of 5-50% ethyl acetate/hexanes over 40 minutes to provide the title compound. $^1$H NMR (400 MHz, chloroform-d) δ ppm 7.51-7.46 (m, 2H), 6.97-6.92 (m, 2H), 4.92-4.85 (m, 4H), 3.83 (s, 3H), 3.14 (s, 1H). MS (ESI+) m/z 378 (2M+NH$_4$)$^+$, 383 (2M+Na)$^+$.

Example I-90B

3-(4-methoxyphenyl)oxetane

To a cooled (ice bath) solution of 3-(4-methoxyphenyl)oxetan-3-ol (1.679 g, 9.32 mmol) from Example I-90A and triethylsilane (1.651 mL, 10.34 mmol) in dichloromethane (24 mL) was added 2,2,2-trifluoroacetic acid (7.90 mL, 102 mmol) and the reaction was allowed to warm to ambient temperature. After about 4 hours, the reaction was quenched by slowly pouring it into a rapidly stirring solution of saturated aqueous sodium bicarbonate (100 mL) and when the bubbling had subsided (pH mildly basic) the solution was diluted with methyl tert-butyl ether (500 mL). The organic layer was separated and dried over sodium sulfate, filtered and concentrated under reduced pressure to provide the title compound. $^1$H NMR (400 MHz, chloroform-d) δ ppm 7.38-7.31 (m, 2H), 6.96-6.89 (m, 2H), 5.06 (dd, J=8.4, 6.0 Hz, 2H), 4.76 (dd, J=6.9, 6.0 Hz, 2H), 4.20 (tt, J=8.4, 6.9 Hz, 1H), 3.83 (s, 3H). MS (ESI+) m/z 189 (M+H)$^+$.

Example I-90C 3-(3-bromo-4-methoxyphenyl)oxetane

To a solution of 3-(4-methoxyphenyl)oxetane (1.45 g, 8.83 mmol) from Example I-90B in acetonitrile (25 mL) was added 1-bromopyrrolidine-2,5-dione (1.729 g, 9.71 mmol) and the reaction was stirred under nitrogen at ambient temperature for 15 hours. Additional 1-bromopyrrolidine-2,5-dione (0.891 g) was added and stirring was continued for 30 minutes. The solvent was removed in vacuo and the crude material taken up in water (50 mL) and hexanes (100 mL). The organics were removed, dried over anhydrous sodium sulfate, filtered, and concentrated. The crude material was purified using an 80 g silica gel cartridge with a gradient of 0-50% ethyl acetate/hexanes over 40 minutes to provide the title compound. $^1$H NMR (400 MHz, chloroform-d) δ ppm 7.60 (d, J=2.2 Hz, 1H), 7.33-7.30 (m, 1H), 6.91 (d, J=8.4 Hz, 1H), 5.06 (dd, J=8.3, 6.1 Hz, 2H), 4.72 (dd, J=6.7, 6.1 Hz, 2H), 4.16 (tt, J=8.4, 6.7 Hz, 1H), 3.91 (s, 3H).

Example I-90D methyl 1-(2-methoxy-5-(oxetan-3-yl)phenyl)cyclopropanecarboxylate

To a solution of 3-(3-bromo-4-methoxyphenyl)oxetane (1.100, 4.52 mmol) from Example I-90C in tetrahydrofuran (5 mL) was added bis(dibenzylideneacetone)palladium (0.052 g, 0.090 mmol) and Q-Phos (1,2,3,4,5-pentaphenyl-1'-(di-tert-butylphosphino)ferrocene) (0.064 g, 0.090 mmol). Nitrogen was bubbled through the solution for about 3 minutes, and a 0.4 M in tetrahydrofuran solution of (1-(methoxycarbonyl)cyclopropyl)zinc(II) bromide (20.11 mL, 9.05 mmol) was added dropwise over 5 minutes. The reaction mixture was stirred for 15 hours at ambient temperature, at which point it was quenched with saturated aqueous ammonium chloride (50 mL), diluted with methyl tert-butyl ether (400 mL), and the layers were separated. The organic layer was filtered and concentrated in vacuo. The residue was purified on a 80 g silica gel cartridge with 0-50% ethyl acetate/hexanes over 40 minutes to provide the title compound. $^1$H NMR (400 MHz, chloroform-d) δ ppm 7.37-7.31 (m, 1H), 7.22 (d, J=2.4 Hz, 1H), 6.89 (d, J=8.4 Hz, 1H), 5.05 (dd, J=8.4, 6.0 Hz, 2H), 4.76 (dd, J=6.9, 6.0 Hz, 2H), 4.18 (tt, J=8.4, 6.9 Hz, 1H), 3.85 (s, 3H), 3.62 (s, 3H), 1.63 (q, J=4.1 Hz, 2H), 1.13 (q, J=4.1 Hz, 2H). MS (APCI+) m/z 263 (M+H)$^+$.

Example I-90E 1-(2-methoxy-5-(oxetan-3-yl)phenyl)cyclopropanecarboxylic Acid

Methyl 1-(2-methoxy-5-(oxetan-3-yl)phenyl)cyclopropanecarboxylate (1.141 g, 4.35 mmol) from Example I-90D was dissolved in tetrahydrofuran (3.0 mL), methanol (3.0 mL) and water (3.0 mL), treated with sodium hydroxide (1.218 g, 30.4 mmol), and stirred at 70° C. for 3 hours. The reaction was reduced in volume, cooled in an ice bath and carefully quenched with concentrated aqueous HCl (about 2.5 mL) until the pH was acidic. The resulting slurry was stirred vigorously, and filtered. The precipitate was washed with water and dried in a vacuum oven overnight to provide the title compound. $^1$H NMR (400 MHz, chloroform-d) δ ppm 7.33 (dd, J=8.4, 2.4 Hz, 1H), 7.23 (d, J=2.3 Hz, 1H), 6.88 (d, J=8.4 Hz, 1H), 5.04 (dd, J=8.4, 6.0 Hz, 2H), 4.75 (dd, J=6.9, 6.0 Hz, 2H), 4.21-4.12 (m, 1H), 3.85 (s, 3H), 1.68 (q, J=4.1 Hz, 2H), 1.19 (q, J=4.1 Hz, 2H). MS (ESI-) m/z 247 (M-H)$^-$.

Example I-90F

1-[2-methoxy-5-(oxetan-3-yl)phenyl]-N-(quinoline-5-sulfonyl)cyclopropane-1-carboxamide To a solution of 1-(2-methoxy-5-(oxetan-3-yl)phenyl)cyclopropanecarboxylic acid (53 mg, 0.213 mmol) from Example I-90E, N$^1$-((ethylimino)methylene)-N$^3$,N$^3$-dimethylpropane-1,3-diamine hydrochloride (82 mg, 0.427 mmol) and N,N-dimethylpyridin-4-amine (28.7 mg, 0.235 mmol) in anhydrous dichloromethane (1 mL) was added quinoline-5-sulfonamide (50 mg, 0.240 mmol). The reaction was stirred at ambient temperature for 16 hours. The reaction was quenched with 0.5 mL of 1N aqueous HCl and the reaction was put through an aqueous/organic extractor tube with dichloromethane. The organic layer was concentrated and purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (400 MHz, chloroform-d) δ ppm 9.23-9.08 (m, 2H), 8.66-8.44 (m, 2H), 8.40-8.06 (m, 1H), 7.98 (t, J=8.0 Hz, 1H), 7.72 (dd, J=8.8, 4.5 Hz, 1H), 7.47 (dd, J=8.5, 2.3 Hz, 1H), 7.23 (d, J=2.3 Hz, 1H), 6.94 (d, J=8.5 Hz, 1H), 5.11 (dd, J=8.3, 6.1 Hz, 2H), 4.96-4.88 (m, OH), 4.73 (t, J=6.4 Hz, 2H), 4.67-4.61 (m, OH), 4.24-4.12 (m, 1H), 4.08 (t, J=10.4 Hz, OH), 3.65 (s, 3H), 1.51 (q, J=4.2 Hz, 2H), 1.04 (q, J=4.3 Hz, 2H). MS (ESI-) m/z 437(M-H)$^-$.

Example I-91

1-(2-ethoxy-5-methylphenyl)-N-(2-methyl-1H-indole-4-sulfonyl)cyclopropane-1-carboxamide Example I-91A 1-(2-bromophenyl)propan-2-one oxime A solution of 2-bromophenylacetone (5.00 g, 23.47 mmol), hydroxylamine hydrochloride (1.680 g, 24.17 mmol) and sodium acetate (1.981 g, 24.15 mmol) in methanol (160 mL) and water (8 mL) was stirred at ambient temperature for 15 hours. The solvent was removed in vacuo and the crude material was added to 500 mL of methyl tert-butyl ether and washed with 50 mL each of water, saturated aqueous sodium bicarbonate, and brine. The organics were dried over sodium sulfate, filtered, and concentrated to provide the title compound. MS (ESI+) m/z 228, 230 Br doublet (M+H)+.

Example I-91B 2-(2-bromophenyl)-3-methyl-2H-azirine

To a solution of 1-(2-bromophenyl)propan-2-one oxime (5.17 g, 22.67 mmol) from Example I-91A and N-ethyl-N-isopropylpropan-2-amine (7.92 mL, 45.3 mmol) in anhydrous tetrahydrofuran (227 mL) at ambient temperature was added dropwise a solution of methanesulfonyl chloride (3.53 mL, 45.3 mmol) in 20 mL of anhydrous tetrahydrofuran via cannula. After stirring at ambient temperature for 1 hour, 1,8-diazabicyclo[5.4.0]undec-7-ene (13.67 mL, 91 mmol) was added dropwise. Stirring was continued at ambient temperature for 1 hour. The reaction mixture was passed through a pad of silica gel, concentrated in vacuo and purified using an 120 g silica gel cartridge with 10% ethyl acetate/hexanes to provide the title compound. $^1$H NMR (400 MHz, chloroform-d) δ ppm 7.54 (dd, J=8.0, 1.2 Hz, 1H), 7.23 (td, J=7.6, 1.2 Hz, 1H), 7.13-7.06 (m, 1H), 6.73 (dd, J=7.8, 1.7 Hz, 1H), 3.25 (s, 1H), 2.54 (s, 3H). MS (ESI+) m/z (M+H)+.

Example I-91C 4-bromo-2-methyl-1H-indole

A solution of 2-(2-bromophenyl)-3-methyl-2H-azirine (1.73 g, 8.24 mmol) from Example I-91B in o-xylene (27.5 mL) was heated at 170° C. overnight. The reaction mixture was purified using an 80 g silica gel cartridge with 0-100% ethyl acetate/hexanes to provide the title compound. $^1$H NMR (501 MHz, chloroform-d) δ ppm 8.01 (s, 1H), 7.29-7.22 (m, 2H), 6.99 (t, J=7.8 Hz, 1H), 6.32 (dq, J=2.2, 1.0 Hz, 1H), 2.48 (d, J=0.9 Hz, 3H). MS (ESI-) m/z 208 (M-H)-.

Example I-91D 2-methyl-1H-indole-4-sulfonamide

A solution of 4-bromo-2-methyl-1H-indole (0.978 g, 4.66 mmol) from Example I-91C, 1,4-diazabicyclo[2.2.2]octane-1,4-diium-1,4-disulfinate (0.671 g, 2.79 mmol), PdCl$_2$(AmPhos)$_2$ (bis(di-tert-butyl(4-dimethylaminophenyl)phosphine)dichloropalladium(II), 0.165 g, 0.233 mmol) in 2-propanol (23.28 mL) and N-ethyl-N-isopropylpropan-2-amine (2.439 mL, 13.97 mmol) was sparged with nitrogen and heated at 75° C. overnight. The reaction mixture was cooled to ambient temperature and filtered to give crude 1-(tert-butoxycarbonyl)-1H-indazole-4-sulfinate. To the solution was added 40 mL of water, followed by sodium acetate (0.458 g, 5.59 mmol) and (aminooxy)sulfonic acid (0.632 g, 5.59 mmol). The mixture was stirred at ambient temperature for 72 hours. Additional sodium acetate (0.458 g, 5.59 mmol) and (aminooxy)sulfonic acid (0.632 g, 5.59 mmol) were added. After 4 hours, Hunig's base (2 mL) was added to make the reaction mixture more basic, and additional (aminooxy)sulfonic acid (0.632 g, 5.59 mmol) was added. An hour later, the solvent was reduced in volume and the mixture was extracted with 2×200 mL ethyl acetate. The combined organics were dried over sodium sulfate, filtered, and the solvent removed in vacuo. The crude material was purified using a 40 g silica gel cartridge with an ethyl acetate/hexanes solvent system to provide the title compound. $^1$H NMR (400 MHz, dimethyl sulfoxide-d$_6$) δ ppm 11.32 (s, 1H), 7.45 (dt, J=8.1, 0.9 Hz, 1H), 7.39 (dd, J=7.5, 0.9 Hz, 1H), 7.12 (s, 2H), 7.06 (t, J=7.8 Hz, 1H), 6.52 (dt, J=2.0, 1.0 Hz, 1H), 2.39 (d, J=0.8 Hz, 3H). MS (ESI-) m/z 208 (M-H)-.

Example I-91E 1-(2-ethoxy-5-methylphenyl)-N-(2-methyl-1H-indole-4-sulfonyl)cyclopropane-1-carboxamide To a solution of 1-(2-ethoxy-5-methylphenyl)cyclopropanecarboxylic acid (60 mg, 0.272 mmol) from Example I-89B, N$^1$-((ethylimino)methylene)-N$^3$,N$^3$-dimethylpropane-1,3-diamine hydrochloride (104 mg, 0.545 mmol) and N,N-dimethylpyridin-4-amine (36.6 mg, 0.300 mmol) in anhydrous dichloromethane (1 mL) was added 2-methyl-1H-indole-4-sulfonamide (57.3 mg, 0.272 mmol) from Example I-91D. The reaction was stirred at ambient temperature for 15 hours and quenched with 0.5 mL of 1N aqueous HCl. The crude material was purified using a 1 2 g silica gel cartridge with a gradient of 0-10% methanol/dichloromethane and the resulting product was triturated with methanol to provide the title compound. $^1$H NMR (400 MHz, dimethyl sulfoxide-d$_6$) δ ppm 11.42 (s, 1H), 10.52 (s, 1H), 7.52 (d, J=8.0 Hz, 1H), 7.48 (dd, J=7.7, 0.9 Hz, 1H), 7.08 (t, J=7.8 Hz, 1H), 7.04-7.00 (m, 1H), 6.92 (d, J=2.2 Hz, 1H), 6.76 (d, J=8.3 Hz, 1H), 6.42 (dt, J=2.0, 0.9 Hz, 1H), 3.75 (q, J=7.0 Hz, 2H), 2.39 (d, J=1.0 Hz, 3H), 2.19 (s, 3H), 1.21 (q, J=4.2 Hz, 2H), 0.94 (t, J=6.9 Hz, 3H), 0.89 (q, J=4.4 Hz, 2H). MS (APCI+) m/z 413 (M+H)+.

Example I-92

N-(2-aminoquinoline-5-sulfonyl)-1-[2-methoxy-5-(2-methylpropoxy)pyridin-4-yl]cyclopropane-1-carboxamide To a solution of 1-(5-isobutoxy-2-methoxy-4-pyridyl)cyclopropanecarboxylic acid (33 mg, 0.124 mmol), N$^1$-((ethylimino)methylene)-N$^3$,N$^3$-dimethylpropane-1,3-diamine hydrochloride (47.7 mg, 0.249 mmol) and N,N-dimethylpyridin-4-amine (24 mg, 0.196 mmol) in anhydrous dichloromethane (1 mL) was added 2-(diallylamino)quinoline-5-sulfonamide (47 mg, 0.155 mmol) from Example I-87D. The reaction was stirred at ambient temperature overnight. The reaction was quenched with 0.2 mL of aqueous 1N HCl and purified using a 12 g silica gel cartridge with a gradient of 5-100% ethyl acetate/hexanes over 20 minutes to provide N-42-(diallylamino)quinolin-5-yl)sulfonyl)-1-(5-isobutoxy-2-methoxypyridin-4-yl)cyclopropanecarboxamide. The N-((2-(diallylamino)quinolin-5-yl)sulfonyl)-1-(5-isobutoxy-2-methoxypyridin-4-yl)cyclopropanecarboxamide was dissolved in ethanol (0.5 mL) and water (0.5 mL), degassed with a stream of nitrogen bubbling through, and treated with RhCl(PPh$_3$)$_3$ (Wilkinson's catalyst, chloridotris(triphenylphosphane)rhodium(I), 3.2 mg, 3.46 μmop. The reaction was stirred at 100° C. After 4 hours, RhCl(PPh$_3$)$_3$ (1 mg) was added and stirring was continued with heating overnight. The reaction was cooled and the resulting precipitate was triturated with ether. The precipitate was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10%

A) to provide the title compound as a trifluoroacetic acid salt. $^1$H NMR (400 MHz, dimethyl sulfoxide-d$_6$) δ ppm 8.78 (d, J=9.8 Hz, 1H), 8.01 (dd, J=7.0, 1.8 Hz, 1H), 7.94-7.82 (m, 2H), 7.65 (s, 1H), 7.14 (d, J=9.8 Hz, 1H), 6.61 (s, 1H), 3.76 (s, 3H), 3.44 (d, J=6.4 Hz, 2H), 1.36 (dt, J=13.2, 6.6 Hz, 1H), 1.29 (q, J=4.4 Hz, 2H), 1.02 (q, J=4.5 Hz, 2H), 0.68 (d, J=6.7 Hz, 6H). MS (ESI+) m/z 471 (M+H)$^+$.

Example I-93

1-{5-methyl-2-[(oxetan-3-yl)oxy]phenyl}-N-(quinoline-5-sulfonyl)cyclopropane-1-carboxamide Example I-93A 3-(2-bromo-4-methylphenoxy)oxetane To 2-bromo-4-methylphenol (1.3 mL, 10.63 mmol) in N,N-dimethylformamide (10 mL) was added potassium carbonate (2.94 g, 21.25 mmol) at ambient temperature. The mixture was stirred at ambient temperature for 10 minutes before adding 3-bromooxetane (2.91 g, 21.25 mmol) dropwise. The reaction was heated at 50° C. for 72 hours with stirring. Ethyl acetate (100 mL) was added and the reaction was filtered. The material was washed with ethyl acetate (50 mL) two times. The combined organics were washed with water and brine, dried over MgSO$_4$, filtered, and concentrated. The residue was purified via chromatography on a 80 g silica gel cartridge, eluting with ethyl acetate in heptane at 0-40% gradient to provide the title compound. $^1$H NMR (400 MHz, chloroform-d) δ ppm 7.40 (d, J=2.1 Hz, 1H), 7.01 (dd, J=8.3, 2.1 Hz, 1H), 6.37 (d, J=8.2 Hz, 1H), 5.21 (p, J=5.7 Hz, 1H), 4.97 (dd, J=7.4, 6.2 Hz, 2H), 4.87-4.81 (m, 2H), 2.28 (s, 3H).

Example I-93B methyl 1-(5-methyl-2-(oxetan-3-yloxy)phenyl)cyclopropanecarboxylate To a solution of 3-(2-bromo-4-methylphenoxy)oxetane (1.724 g, 7.09 mmol) from Example I-93A in tetrahydrofuran (6 mL) was added bis(dibenzylideneacetone)palladium (0.082 g, 0.142 mmol) and Q-Phos (1,2,3,4,5-pentaphenyl-1'-(di-tert-butylphosphino)ferrocene) (0.101 g, 0.142 mmol). Nitrogen was bubbled through the solution for about 3 minutes, then a 0.54M in tetrahydrofuran solution of (1-(methoxycarbonyl)cyclopropyl)zinc(II) bromide (26.3 mL, 14.18 mmol) was added dropwise over 5 minutes. The reaction was stirred for 3 hours at ambient temperature. The reaction was quenched with saturated aqueous ammonium chloride (50 mL), diluted with methyl tert-butyl ether (400 mL), and the layers were separated. The organic layer was filtered and concentrated in vacuo. The residue was purified via flash chromatography, eluting on an 80 g silica gel cartridge with 0-50% ethyl acetate/hexanes over 40 minutes to provide the title compound. $^1$H NMR (400 MHz, chloroform-d) δ ppm 7.05 (d, J=2.2 Hz, 1H), 7.00 (ddt, J=8.2, 2.3, 0.8 Hz, 1H), 6.32 (d, J=8.1 Hz, 1H), 5.28-5.20 (m, 1H), 4.95 (ddt, J=6.9, 6.1, 0.8 Hz, 2H), 4.70 (ddt, J=6.9, 5.2, 0.8 Hz, 2H), 3.65 (d, J=0.7 Hz, 3H), 2.28 (d, J=0.7 Hz, 3H), 1.63 (qd, J=4.0, 0.6 Hz, 2H), 1.18-1.11 (m, 2H). MS (APCI+) m/z 263 (M+H)$^+$.

Example I-93C 1-(5-methyl-2-(oxetan-3-yloxy)phenyl)cyclopropanecarboxylic Acid

Methyl 1-(5-methyl-2-(oxetan-3-yloxy)phenyl)cyclopropanecarboxylate (1.84 g, 7.01 mmol) from Example I-93B was dissolved in tetrahydrofuran (5 mL) and methanol (5 mL) and water (5 mL) water. The mixture was treated with sodium hydroxide (1.922 g, 48.1 mmol) and stirred at 50° C. for 16 hours. The reaction was reduced in volume, cooled in an ice bath and carefully quenched with concentrated aqueous HCl (~4 mL, diluted with ice) until the pH was acidic. The resulting slurry was stirred vigorously and filtered. The material was washed with water and dried in a vacuum oven overnight to provide the title compound. $^1$H NMR (400 MHz, chloroform-d) δ ppm 9.66 (s, 1H), 7.06 (d, J=2.2 Hz, 1H), 7.00 (dd, J=8.3, 2.2 Hz, 1H), 6.31 (d, J=8.2 Hz, 1H), 5.22 (p, J=5.7 Hz, 1H), 4.95 (t, J=6.6 Hz, 2H), 4.74 (dd, J=7.2, 5.3 Hz, 2H), 2.27 (s, 3H), 1.68 (q, J=4.1 Hz, 2H), 1.21 (q, J=4.1 Hz, 2H). MS (ESI−) m/z 247 (M−H)$^-$.

Example I-93D

1-{5-methyl-2-[(oxetan-3-yl)oxy]phenyl}-N-(quinoline-5-sulfonyl)cyclopropane-1-carboxamide To a solution of 1-(5-methyl-2-(oxetan-3-yloxy)phenyl)cyclopropanecarboxylic acid (66 mg, 0.266 mmol) from Example I-93C, N$^1$-((ethylimino)methylene)-N$^3$,N$^3$-dimethylpropane-1,3-diamine hydrochloride (114 mg, 0.595 mmol) and N,N-dimethylpyridin-4-amine (33 mg, 0.270 mmol) in anhydrous dichloromethane (1 mL) was added quinoline-5-sulfonamide (55.4 mg, 0.266 mmol). The reaction was stirred at ambient temperature for 15 hours and was quenched with 0.3 mL of 1N aqueous HCl. The crude material was purified using a 12 g silica gel cartridge with a gradient of 0-10% methanol/dichloromethane and the resulting product triturated with ether then methanol to provide the title compound. $^1$H NMR (400 MHz, chloroform-d) δ ppm 9.05 (dd, J=4.1, 1.6 Hz, 1H), 8.83 (dt, J=8.9, 1.2 Hz, 1H), 8.52 (dd, J=7.5, 1.2 Hz, 1H), 8.41 (d, J=8.4 Hz, 1H), 8.14 (s, 1H), 7.87 (t, J=8.0 Hz, 1H), 7.55 (dd, J=8.8, 4.2 Hz, 1H), 7.12 (dd, J=8.2, 2.2 Hz, 1H), 7.06 (d, J=2.2 Hz, 1H), 6.33 (d, J=8.3 Hz, 1H), 4.96 (p, J=5.5 Hz, 1H), 4.80-4.69 (m, 2H), 4.41 (dd, J=7.4, 5.1 Hz, 2H), 2.31 (s, 3H), 1.54 (q, J=4.0 Hz, 2H), 1.05 (q, J=4.0 Hz, 2H). MS (ESI−) m/z 437 (M−H)$^-$.

Example I-94

1-[5-ethyl-2-(2-methylpropoxy)pyridin-3-yl]-N-(1H-indazole-4-sulfonyl)cyclopropane-1-carboxamide Example I-94 was prepared as described in Example I-26, substituting 1-(5-ethyl-2-isobutoxypyridin-3-yl)cyclopropane-1-carboxylic acid for Example I-26B. $^1$H NMR (400 MHz, dimethyl sulfoxide-d$_6$:D$_2$O=9:1 (v/v)) δ ppm 8.35 (d, J=1.0 Hz, 1H), 7.98-7.92 (m, 1H), 7.90 (d, J=2.3 Hz, 1H), 7.74 (d, J=7.1 Hz, 1H), 7.58 (dd, J=8.4, 7.3 Hz, 1H), 7.43 (d, J=2.3 Hz, 1H), 3.74 (d, J=6.4 Hz, 2H), 2.61-2.53 (m, 2H), 1.52-1.40 (m, 1H), 1.37 (q, J=4.4 Hz, 2H), 1.20 (t, J=7.6 Hz, 3H), 1.06 (q, J=4.5 Hz, 2H), 0.71 (d, J=6.7 Hz, 6H). MS (APCI) m/z 443.0 (M+H)$^+$.

Example I-95

1-(2-{[(2R)-1-methoxypropan-2-yl]oxy}-5-methylphenyl)-N-(quinoline-5-sulfonyl)cyclopropane-1-carboxamide

Example I-95A (R)-2-bromo-1-((1-methoxypropan-2-yl)oxy)-4-methylbenzene

In a 100 mL flask was added 2-bromo-4-methylphenol (0.897 g, 4.60 mmol) and triphenylphosphine (1.932 g, 7.37 mmol) in tetrahydrofuran (23.02 mL). The mixture was stirred briefly at ambient temperature, under nitrogen, and DIAD (diisopropyl azodicarboxylate, 1.433 mL, 7.37 mmol) was added to the mixture. The mixture was stirred briefly under nitrogen at ambient temperature. (S)-1-Methoxypropan-2-ol (0.415 g, 4.60 mmol) was added dropwise to the solution. The reaction mixture was stirred for 16 hours at ambient temperature. The solvent was removed under reduced pressure and the crude material was purified by silica gel chromatography eluting with ethyl acetate in heptanes (0 to 30%) to provide the title compound. $^1$H NMR (400 MHz, chloroform-d) δ ppm 7.34 (dt, J=1.6, 0.8 Hz, 1H), 7.06-6.97 (m, 1H), 6.89 (dd, J=8.3, 5.5 Hz, 1H), 4.46 (pd, J=6.2, 4.8 Hz, 1H), 3.63 (dd, J=10.4, 5.9 Hz, 1H), 3.51 (dd, J=10.3, 4.7 Hz, 1H), 3.42 (d, J=0.6 Hz, 3H), 2.26 (d, J=0.8 Hz, 3H), 1.36-1.30 (m, 3H).

Example I-95B (R)-methyl 1-(2-((1-methoxypropan-2-yl)oxy)-5-methylphenyl)cyclopropanecarboxylate To a solution of (R)-2-bromo-1-((1-methoxypropan-2-yl)oxy)-4-methylbenzene (0.350 g, 1.351 mmol) from Example I-95A in tetrahydrofuran (4 mL) was added bis(dibenzylideneacetone)palladium (0.016 g, 0.027 mmol) and Q-Phos (1,2,3,4,5-pentaphenyl-1'-(di-tert-butylphosphino)ferrocene) (0.019 g, 0.027 mmol). Nitrogen was bubbled through the solution for about 3 minutes, then a 0.54 M in tetrahydrofuran solution of (1-(methoxycarbonyl)cyclopropyl)zinc (II) bromide (5.00 mL, 2.70 mmol) was added dropwise over 5 minutes. The reaction was stirred for 5 hours at ambient temperature and 3 mL additional ZnBr reagent was added and the reaction was stirred at ambient temperature for 16 hours. The reaction was quenched with saturated aqueous ammonium chloride (25 mL), diluted with methyl tert-butyl ether (200 mL), and the layers were separated. The organic layer was dried over sodium sulfate, filtered and concentrated in vacuo. The crude material was purified via flash chromatography, eluting on a 24 g silica gel cartridge with 0-50% ethyl acetate/hexanes over 20 minutes to provide the title compound. $^1$H NMR (501 MHz, chloroform-d) δ ppm 7.08-6.99 (m, 2H), 6.82 (d, J=8.2 Hz, 1H), 4.56 (h, J=5.9 Hz, 1H), 3.62 (s, 3H), 3.59 (dd, J=10.2, 5.7 Hz, 1H), 3.45 (dd, J=10.2, 5.1 Hz, 1H), 3.42 (s, 3H), 2.30 (s, 3H), 1.61-1.57 (m, 2H), 1.29 (d, J=6.2 Hz, 3H), 1.16-1.09 (m, 2H).

Example I-95C (R)-1-(2-((1-methoxypropan-2-yl)oxy)-5-methylphenyl)cyclopropanecarboxylic Acid (R)-Methyl 1-(2-((1-methoxypropan-2-yl)oxy)-5-methylphenyl)cyclopropanecarboxylate (0.251 g, 0.902 mmol) from Example I-95B was dissolved in tetrahydrofuran (1 mL), methanol (1 mL), and water (1 mL). The mixture was treated with sodium hydroxide (0.185 g, 4.63 mmol) and stirred at 70° C. for 45 minutes. The reaction was reduced in volume, cooled in an ice bath and carefully quenched with concentrated aqueous HCl (about 4 mL, diluted with ice) until the pH was acidic. The resulting material was stirred vigorously and the water was decanted. The material was washed with water and azeotroped with toluene to provide the title compound. $^1$H NMR (500 MHz, chloroform-d) δ ppm 8.13 (s, 1H), 7.03 (d, J=7.2 Hz, 2H), 6.84-6.74 (m, 1H), 4.55 (td, J=6.3, 4.8 Hz, 1H), 3.59 (dd, J=10.2, 6.1 Hz, 1H), 3.43 (dd, J=10.2, 4.7 Hz, 1H), 3.36 (s, 3H), 2.28 (s, 3H), 1.67-1.56 (m, 2H), 1.26 (d, J=6.2 Hz, 3H), 1.18 (dt, J=8.5, 2.5 Hz, 1H), 1.11-1.02 (m, 1H). MS (ESI–) m/z 263 (M–H)$^-$.

Example I-95D 1-(2-{[(2R)-1-methoxypropan-2-yl]oxy}-5-methylphenyl)-N-(quinoline-5-sulfonyl)cyclopropane-1-carboxamide To a solution of (R)-1-(2-((1-methoxypropan-2-yl)oxy)-5-methylphenyl)cyclopropanecarboxylic acid (59 mg, 0.223 mmol) from Example I-95C, N$^1$-((ethylimino)methylene)-N$^3$,N$^3$-dimethylpropane-1,3-diamine hydrochloride (96 mg, 0.501 mmol) and N,N-dimethylpyridin-4-amine (28 mg, 0.229 mmol) in anhydrous dichloromethane (1 mL) was added quinoline-5-sulfonamide (46.5 mg, 0.223 mmol). The reaction was stirred at ambient temperature for 16 hours and was quenched with 0.3 mL of 1N aqueous HCl. The crude material was purified using a 12 g silica gel cartridge with a gradient of 0-10% methanol/dichloromethane and the resulting product triturated with ether then a scant amount of methanol to provide the title compound. $^1$H NMR (400 MHz, chloroform-d) δ ppm 8.99 (dd, J=4.2, 1.6 Hz, 1H), 8.76 (ddd, J=8.7, 1.7, 0.9 Hz, 1H), 8.70 (s, 1H), 8.49 (dd, J=7.5, 1.2 Hz, 1H), 8.38 (dt, J=8.5, 1.1 Hz, 1H), 7.83 (dd, J=8.5, 7.5 Hz, 1H), 7.44 (dd, J=8.8, 4.2 Hz, 1H), 7.14 (ddd, J=8.4, 2.3, 0.8 Hz, 1H), 6.94-6.92 (m, 1H), 6.89 (d, J=8.4 Hz, 1H), 4.56 (pd, J=6.2, 4.5 Hz, 1H), 3.46 (dd, J=10.1, 6.1 Hz, 1H), 3.40-3.36 (m, 1H), 3.36 (s, 3H), 2.26 (s, 3H), 1.53-1.45 (m, 1H), 1.45-1.36 (m, 1H), 1.24 (d, J=6.2 Hz, 3H), 1.00 (td, J=3.7, 2.2 Hz, 2H). MS (ESI–) m/z 437 (M–H)$^-$.

Example I-96

N-(2-aminoquinoline-5-sulfonyl)-1-[5-methyl-2-(2-methylpropoxy)pyridin-3-yl]cyclopropane-1-carboxamide

Example I-96A

N-((2-(diallylamino)quinolin-5-yl)sulfonyl)-1-(2-isobutoxy-5-methylpyridin-3-yl)cyclopropanecarboxamide To a solution of 1-(2-isobutoxy-5-methylpyridin-3-yl)cyclopropanecarboxylic acid (35 mg, 0.140 mmol), N$^1$-((ethylimino)methylene)-N$^3$,N$^3$-dimethylpropane-1,3-diamine hydrochloride (65 mg, 0.339 mmol) and N,N-dimethylpyridin-4-amine (20 mg, 0.164 mmol) in anhydrous dichloromethane (1 mL) was added 2-(diallylamino)quinoline-5-sulfonamide (52 mg, 0.171 mmol) from Example I-87D. The reaction was stirred at ambient temperature for 16 hours.

The reaction was quenched with 0.3 mL of aqueous 1N HCl and purified using a 12 g silica gel cartridge with a gradient of 5-100% ethyl acetate/hexanes over 20 minutes to provide the title compound. MS (APCI+) m/z 535 (M+H)$^+$.

Example I-96B

N-(2-aminoquinoline-5-sulfonyl)-1-[5-methyl-2-(2-methylpropoxy)pyridin-3-yl]cyclopropane-1-carboxamide A solution of ethanol (0.5 mL) and water (0.5 mL) was degassed by bubbling nitrogen through for 15 minutes. The mixture was added to a mixture of N-42-(diallylamino)quinolin-5-yl)sulfonyl)-1-(2-isobutoxy-5-methylpyridin-3-yl)cyclopropanecarboxamide (73 mg, 0.137 mmol) from Example I-96A and RhCl(PPh$_3$)$_3$ (Wilkinson's catalyst, chloridotris(triphenylphosphane)rhodium(I), 4.3 mg, 4.65 µmol) under nitrogen. The reaction was heated at 100° C. for 4 hours. The reaction was cooled and filtered and the resulting material was purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (400 MHz, dimethyl sulfoxide-d$_6$) δ ppm 11.75 (s, 1H), 8.84 (s, 2H), 8.79 (d, J=9.9 Hz, 1H), 8.01 (dd, J=6.9, 1.8 Hz, 1H), 7.93-7.84 (m, 2H), 7.82 (dd, J=2.3, 1.0 Hz, 1H), 7.36 (d, J=2.3 Hz, 1H), 7.12 (d, J=9.8 Hz, 1H), 3.66 (d, J=6.5 Hz, 2H), 2.17 (s, 3H), 1.41 (hept, J=6.6 Hz, 1H), 1.31 (q, J=4.3 Hz, 2H), 0.97 (q, J=4.4 Hz, 2H), 0.67 (d, J=6.7 Hz, 6H). MS (APCI+) m/z 455 (M+H)$^+$.

Example I-97

N-(2-aminoquinoline-5-sulfonyl)-1-{5-methyl-2-[(propan-2-yl)oxy]pyridin-3-yl}cyclopropane-1-carboxamide To a solution of 1-(2-isopropoxy-5-methylpyridin-3-yl)cyclopropanecarboxylic acid (35 mg, 0.149 mmol), N$^1$-((ethylimino)methylene)-N$^3$,N$^3$-dimethylpropane-1,3-diamine hydrochloride (65 mg, 0.339 mmol) and N,N-dimethylpyridin-4-amine (25 mg, 0.205 mmol) in anhydrous dichloromethane (1 mL) was added 2-(diallylamino)quinoline-5-sulfonamide (47 mg, 0.155 mmol) from Example I-87D. The reaction was stirred at ambient temperature for 15 hours. The reaction was quenched with 0.3 mL of aqueous 1N HCl and was purified using a 12 g silica gel cartridge with a gradient of 5-100% ethyl acetate/hexanes over 20 minutes to provide N-42-(diallylamino)quinolin-5-yl)sulfonyl)-1-(2-isopropoxy-5-methylpyridin-3-yl)cyclopropanecarboxamide. The N-((2-(diallylamino)quinolin-5-yl)sulfonyl)-1-(2-isopropoxy-5-methylpyridin-3-yl)cyclopropanecarboxamide was combined with RhCl(PPh$_3$)$_3$ (Wilkinson's catalyst, chloridotris(triphenylphosphane)rhodium(I), 3.2 mg, 3.46 µmol) in a degassed solution of ethanol (0.5 mL) and water (0.5 mL) under nitrogen. The reaction was heated at 100° C. for 4 hours. The reaction was cooled and filtered and the resulting material was purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. 1H NMR (501 MHz, dimethyl sulfoxide-d$_6$) δ ppm 11.73 (s, 1H), 9.07 (s, 2H), 8.91 (d, J=9.8 Hz, 1H), 8.05 (dd, J=6.9, 1.9 Hz, 1H), 7.95-7.88 (m, 2H), 7.87 (dd, J=2.3, 1.0 Hz, 1H), 7.34 (d, J=2.3 Hz, 1H), 7.18 (d, J=9.8 Hz, 1H), 5.06 (hept, J=6.1 Hz, 1H), 2.18 (s, 3H), 1.27 (q, J=4.3 Hz, 2H), 1.07 (d, J=6.1 Hz, 6H), 0.99 (q, J=4.4 Hz, 2H). MS (APCI+) m/z 441 (M+H)$^+$.

Example I-98

N-(2-aminoquinoline-5-sulfonyl)-1-[5-ethyl-2-(2-methylpropoxy)pyridin-3-yl]cyclopropane-1-carboxamide To a solution of 1-(5-ethyl-2-isobutoxypyridin-3-yl)cyclopropanecarboxylic acid (35 mg, 0.133 mmol), N$^1$-((ethylimino)methylene)-N$^3$,N$^3$-dimethylpropane-1,3-diamine hydrochloride (58 mg, 0.303 mmol) and N,N-dimethylpyridin-4-amine (25 mg, 0.205 mmol) in anhydrous dichloromethane (1 mL) was added 2-(diallylamino)quinoline-5-sulfonamide (46 mg, 0.152 mmol) from Example I-87D. The reaction was stirred at ambient temperature for 15 hours. The reaction was quenched with 0.2 mL of aqueous 1N HCl and purified using a 12 g silica gel cartridge with a gradient of 5-100% ethyl acetate/hexanes over 20 minutes to provide N-((2-(diallylamino)quinolin-5-yl)sulfonyl)-1-(5-ethyl-2-isobutoxypyridin-3-yl)cyclopropanecarboxamide. The N-((2-(diallylamino)quinolin-5-yl)sulfonyl)-1-(5-ethyl-2-isobutoxypyridin-3-yl)cyclopropanecarboxamide was combined with RhCl(PPh$_3$)$_3$ (Wilkinson's catalyst, chloridotris(triphenylphosphane)rhodium(I), 3.2 mg, 3.46 µmol) in a degassed solution of ethanol (0.5 mL) and water (0.5 mL) under nitrogen. The reaction was heated to 100° C. for 4 hours. The reaction was cooled and filtered and the resulting material was purified by reverse-phase preparative HPLC on a Phenomenex® Luna® C8(2) 5 µm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (501 MHz, dimethyl sulfoxide-d$_6$) δ ppm 11.49 (s, 1H), 8.84 (s, 2H), 8.80 (d, J=9.7 Hz, 1H), 8.01 (dd, J=7.2, 1.7 Hz, 1H), 7.93-7.86 (m, 2H), 7.85 (d, J=2.3 Hz, 1H), 7.39 (d, J=2.4 Hz, 1H), 7.13 (d, J=9.8 Hz, 1H), 3.68 (d, J=6.5 Hz, 2H), 2.55-2.50 (m, 2H), 1.42 (hept, J=6.6 Hz, 1H), 1.35 (q, J=4.3 Hz, 2H), 1.16 (t, J=7.6 Hz, 3H), 1.01 (q, J=4.4 Hz, 2H), 0.68 (d, J=6.7 Hz, 6H). MS (APCI+) m/z 469 (M+H)$^+$.

Example I-99

1-[2-ethoxy-5-(2-ethoxypropan-2-yl)phenyl]-N-(quinoline-5-sulfonyl)cyclopropane-1-carboxamide To a solution of 1-(2-ethoxy-5-(2-ethoxypropan-2-yl)phenyl)cyclopropanecarboxylic acid (60 mg, 0.205 mmol) from Example I-103E, N$^1$-((ethylimino)methylene)-N$^3$,N$^3$-dimethylpropane-1,3-diamine hydrochloride (79 mg, 0.410 mmol) and N,N-dimethylpyridin-4-amine (27.6 mg, 0.226 mmol) in anhydrous dichloromethane (1 mL) was added quinoline-5-sulfonamide (42.7 mg, 0.205 mmol). After 16 hours, the reaction was quenched with 1 mL of 1N aqueous citric acid and the organic layer was concentrated in vacuo.

The residue was purified via chromatography on a 10 g silica gel cartridge, eluting with a gradient of 0-10% methanol/dichloromethane over a period of 10 minutes. The crude material was triturated with methanol (0.5 mL) and filtered to provide the title compound. $^1$H NMR (400 MHz, dimethyl sulfoxide-$d_6$) δ ppm 11.48 (s, 1H), 9.05 (dd, J=4.2, 1.6 Hz, 1H), 8.95 (d, J=8.7 Hz, 1H), 8.34 (d, J=8.6 Hz, 1H), 8.31 (d, J=7.6 Hz, 1H), 7.93 (t, J=7.9 Hz, 1H), 7.68 (dd, J=8.8, 4.1 Hz, 1H), 7.22 (dd, J=8.5, 2.3 Hz, 1H), 7.08 (d, J=2.4 Hz, 1H), 6.77 (d, J=8.5 Hz, 1H), 3.64 (q, J=6.9 Hz, 2H), 3.12 (q, J=7.0 Hz, 2H), 1.42 (s, 6H), 1.33 (q, J=4.4 Hz, 2H), 1.03 (t, J=6.9 Hz, 3H), 0.94 (q, J=4.6 Hz, 2H), 0.74 (t, J=6.9 Hz, 3H). MS (ESI–) m/z 481 (M–H)$^-$.

Example I-100

1-[2-(difluoromethoxy)-5-methylphenyl]-N-(quinoline-5-sulfonyl)cyclopropane-1-carboxamide Example I-100A 2-bromo-4-chloro-1-(difluoromethoxy)benzene 2-Bromo-4-chlorophenol (3.82 g, 18.4 mmol) was dissolved in acetonitrile (92 mL). The resulting suspension was cooled to <–25° C. in an acetone-dry ice bath and diethyl (bromodifluoromethyl)phosphonate (4.91 mL, 27.6 mmol) was added, followed by dropwise addition of potassium hydroxide (20.66 g, 368 mmol) at such a rate that the temperature was maintained below –15° C. After the addition was complete (<5 minutes), the reaction was stirred for an additional 15 minutes and warmed to ambient temperature. The reaction was diluted with methyl tert-butyl ether, washed three times with water, once with brine, and concentrated. The crude material was purified silica gel chromatography, eluting with 0-10% ethyl acetate/heptanes over 20 minutes to provide the title compound. $^1$H NMR (500 MHz, chloroform-d) δ ppm 7.67 (d, J=2.5 Hz, 1H), 7.34 (dd, J=8.7, 2.5 Hz, 1H), 7.21 (dt, J=8.7, 0.9 Hz, 1H), 6.55 (t, J=73.0 Hz, 1H).

Example I-100B methyl 1-(5-chloro-2-(difluoromethoxy)phenyl)cyclopropanecarboxylate To a solution of 2-bromo-4-chloro-1-(difluoromethoxy)benzene (0.887 g, 3.45 mmol) from Example I-100A in tetrahydrofuran (10 mL) was added bis(dibenzylideneacetone)palladium (0.040 g, 0.069 mmol) and Q-Phos (1,2,3,4,5-pentaphenyl-1'-(di-tert-butylphosphino)ferrocene) (0.049 g, 0.069 mmol). Nitrogen was bubbled through the solution for about 3 minutes, and a 0.54 M in tetrahydrofuran solution of (1-(methoxycarbonyl)cyclopropyl)zinc(II) bromide (12.76 mL, 6.89 mmol) was added dropwise over 5 minutes. The reaction was stirred for 15 hours at ambient temperature. The reaction was quenched with saturated aqueous ammonium chloride (25 mL), diluted with methyl tert-butyl ether (200 mL), and the layers were separated. The organic layer was dried over sodium sulfate, filtered and concentrated in vacuo to give a crude material that was purified via flash chromatography, eluting on a 24 g silica gel cartridge with 0-50% ethyl acetate/hexanes over 20 minutes to provide the title compound. $^1$H NMR (400 MHz, chloroform-d) δ ppm 7.29-7.25 (m, 2H), 7.12-7.04 (m, 1H), 6.45 (t, J=73.8 Hz, 1H), 3.64 (s, 3H), 1.72-1.65 (m, 2H), 1.22-1.13 (m, 2H).

Example I-100C methyl 1-(2-(difluoromethoxy)-5-methylphenyl)cyclopropanecarboxylate A solution of methyl 1-(5-chloro-2-(difluoromethoxy)phenyl)cyclopropanecarboxylate (260 mg, 0.940 mmol) from Example I-100B and PEPPSI IPentCl (17 mg, 0.020 mmol) in tetrahydrofuran (1 mL) was purged with nitrogen for 5 minutes. Dimethylzinc (1.880 mL, 1.880 mmol), 1M in tetrahydrofuran, was added dropwise. After 30 minutes, additional dimethylzinc solution was added (1 mL, 1 mmol). The reaction was stirred overnight at ambient temperature. The reaction was warmed to 50° C. After 4 hours, the reaction was cooled, quenched with 15 mL of saturated aqueous ammonium chloride, and diluted with 150 mL of methyl tert-butyl ether. The organics were separated, washed with brine, dried over sodium sulfate, filtered, and concentrated in vacuo. The crude material was purified using a 12 g silica gel cartridge with a gradient of 5-50% ethyl acetate/hexanes over 20 minutes to provide the title compound. $^1$H NMR (400 MHz, Chloroform-d) δ ppm 7.10 (dd, J=6.4, 2.2 Hz, 2H), 7.02 (dt, J=8.8, 1.0 Hz, 1H), 6.44 (td, J=74.5, 0.8 Hz, 1H), 3.63 (s, 3H), 2.33 (s, 3H), 1.71-1.64 (m, 2H), 1.18 (q, J=4.3 Hz, 2H).

Example I-100D

1-[2-(difluoromethoxy)-5-methylphenyl]-N-(quinoline-5-sulfonyl)cyclopropane-1-carboxamide To a solution of 1-(2-(difluoromethoxy)-5-methylphenyl)cyclopropanecarboxylic acid (58 mg, 0.239 mmol) from Example I-100C, N$^1$-((ethylimino)methylene)-N$^3$,N$^3$-dimethylpropane-1,3-diamine hydrochloride (92 mg, 0.479 mmol) and N,N-dimethylpyridin-4-amine (29.3 mg, 0.239 mmol) in anhydrous dichloromethane (1 mL) was added quinoline-5-sulfonamide (70 mg, 0.336 mmol). The reaction was stirred at ambient temperature for 15 hours. The reaction was quenched with 0.3 mL of 1 N aqueous HCl and extracted with dichloromethane (3×1 mL). The extracts were concentrated and the crude material was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (400 MHz, dimethyl sulfoxide-$d_6$) δ ppm 11.64 (s, 1H), 9.03 (dd, J=4.2, 1.6 Hz, 1H), 8.98 (dt, J=8.8, 1.2 Hz, 1H), 8.31 (dt, J=8.4, 1.0 Hz, 1H), 8.28 (dd, J=7.5, 1.2 Hz, 1H), 7.89 (dd, J=8.4, 7.5 Hz, 1H), 7.70 (dd, J=8.8, 4.2 Hz, 1H), 7.14-7.09 (m, 1H), 7.06 (d, J=2.1 Hz, 1H), 6.91 (d, J=8.2 Hz, 1H), 6.71 (t, J=74.4 Hz, 1H), 2.23 (s, 3H), 1.34 (q, J=4.5 Hz, 2H), 1.03 (q, J=4.6 Hz, 2H). MS (ESI–) m/z 431 (M–H)$^-$.

Example I-101

1-[2-ethoxy-5-(1-methoxy-2-methylpropan-2-yl)phenyl]-N-(quinoline-5-sulfonyl)cyclopropane-1-carboxamide Example I-101A methyl 2-(4-ethoxyphenyl)-2-methylpropanoate A solution of freshly-prepared (1-methoxy-2-methyl-1-oxopropan-2-yl)zinc(II) bromide (146 mL, 21.93 mmol)

was made by treating a suspension of zinc (5.42 g, 83 mmol) in tetrahydrofuran (153 mL) with bromine (0.569 mL, 11.05 mmol) and treating the ambient temperature solution with dropwise addition of methyl 2-bromo-2-methylpropanoate (10.0 g, 55.2 mmol) with stirring at ambient temperature for 2 hours. 1-Bromo-4-ethoxybenzene (2.132 mL, 14.62 mmol) was dissolved in tetrahydrofuran (58.5 mL), and Q-Phos (1,2,3,4,5-pentaphenyl-1'-(di-tert-butylphosphino) ferrocene) (0.208 g, 0.292 mmol) and bis(dibenzylideneacetone)palladium (0.168 g, 0.292 mmol) were added. The solution of freshly prepared (1-methoxy-2-methyl-1-oxopropan-2-yl)zinc(II) bromide (146 mL, 21.93 mmol) was added dropwise maintaining a slight exotherm of ~3° C. The reaction was stirred for 60 minutes at ambient temperature, quenched with saturated aqueous ammonium chloride (0.5 mL), and diluted with methyl tert-butyl ether. The organic layer was concentrated in vacuo. The residue was loaded directly onto a 120 g silica gel column and was eluted with 0-20% ethyl acetate/heptanes to provide the title compound. $^1$H NMR (400 MHz, chloroform-d) δ ppm 7.26 (d, J=8.8 Hz, 2H), 6.85 (d, J=8.9 Hz, 2H), 4.03 (q, J=7.0 Hz, 2H), 3.65 (s, 3H), 1.43-1.38 (m, 9H). MS (ESI+) m/z 222 (M+H)$^+$.

Example I-101B methyl 2-(3-bromo-4-ethoxyphenyl)-2-methylpropanoate

A solution of methyl 2-(4-ethoxyphenyl)-2-methylpropanoate (1.35 g, 6.07 mmol) from Example I-101A in acetonitrile (20.24 mL) was treated with N-bromosuccinimide (1.135 g, 6.38 mmol) and stirred at ambient temperature for 2 hours. The reaction was diluted with 200 mL of methyl tert-butyl ether, and quenched with 100 mL of 5% aqueous NaOH solution. The organic layer was separated, washed with saturated aqueous sodium bicarbonate and brine, dried over sodium sulfate, filtered, concentrated to ~20 mL, and filtered again. The filtrate was concentrated and purified by silica gel chromatography, eluting with ethyl acetate in heptanes (0 to 30%) to provide the title compound. $^1$H NMR (400 MHz, chloroform-d) δ ppm 7.51 (dd, J=2.4, 0.6 Hz, 1H), 7.29-7.17 (m, 1H), 6.83 (d, J=8.6 Hz, 1H), 4.08 (q, J=7.0 Hz, 2H), 3.65 (d, J=0.6 Hz, 3H), 1.55 (s, 6H), 1.45 (td, J=7.0, 0.6 Hz, 3H).

Example I-101C 2-(3-bromo-4-ethoxyphenyl)-2-methylpropan-1-ol

To a cooled (<5° C.) solution of methyl 2-(3-bromo-4-ethoxyphenyl)-2-methylpropanoate (1.25 g, 4.15 mmol) from Example I-101B in tetrahydrofuran (8.30 mL) was added a solution of 1 M lithium aluminum hydride (2.91 mL, 2.91 mmol) in tetrahydrofuran over 10 minutes, maintaining an internal temperature <10° C. After 1 hour, and the reaction was quenched by the addition of 1.5 mL of acetone, diluted with ethyl acetate and stirred with 50 mL of saturated aqueous Rochelle's salt until two clear layers were present. The aqueous layer was extracted with ethyl acetate and the combined extracts were washed with brine, dried over sodium sulfate, filtered and concentrated to provide the title compound. $^1$H NMR (400 MHz, chloroform-d) δ ppm 7.54 (d, J=2.4 Hz, 1H), 7.25 (dd, J=8.6, 2.4 Hz, 1H), 6.85 (d, J=8.6 Hz, 1H), 4.09 (q, J=7.0 Hz, 2H), 3.57 (s, 2H), 1.46 (t, J=7.0 Hz, 3H), 1.30 (s, 6H), 1.04-0.85 (m, 1H).

Example I-101D 2-bromo-1-ethoxy-4-(1-methoxy-2-methylpropan-2-yl)benzene

To a cooled (ice bath) solution of 2-(3-bromo-4-ethoxyphenyl)-2-methylpropan-1-ol (1.1 g, 4.03 mmol) from Example I-101C in tetrahydrofuran (8.05 mL) was added sodium hydride (0.242 g, 6.04 mmol) and the reaction was stirred at 5° C. for one hour. Iodomethane (0.501 mL, 8.05 mmol) was added and the reaction was allowed to warm to ambient temperature and stir for 16 hours. Water was added slowly to quench the reaction and the solution was diluted with methyl tert-butyl ether (30 mL). The organic layer was separated, dried over sodium sulfate, filtered and concentrated. The residue was purified by silica gel chromatography eluting with ethyl acetate in heptanes (0 to 20%) to provide the title compound. $^1$H NMR (500 MHz, chloroform-d) δ ppm 7.55 (d, J=2.4 Hz, 1H), 7.27 (dd, J=8.6, 2.4 Hz, 1H), 6.85 (d, J=8.6 Hz, 1H), 4.11 (q, J=7.0 Hz, 2H), 3.36 (s, 2H), 3.33 (s, 3H), 1.48 (t, J=7.0 Hz, 3H), 1.31 (s, 6H).

Example I-101E methyl 1-(2-ethoxy-5-(1-methoxy-2-methylpropan-2-yl)phenyl)cyclopropanecarboxylate To a solution of 2-bromo-1-ethoxy-4-(1-methoxy-2-methylpropan-2-yl)benzene (0.80 g, 2.79 mmol) from Example I-101D in tetrahydrofuran (4 mL) was added bis(dibenzylideneacetone)palladium (0.032 g, 0.056 mmol) and Q-Phos (1,2,3,4,5-pentaphenyl-1'-(di-tert-butylphosphino) ferrocene) (0.040 g, 0.056 mmol). Nitrogen was bubbled through the solution for about 10 minutes. A tetrahydrofuran solution of (1-(methoxycarbonyl)cyclopropyl)zinc(II) bromide (0.45M, 12.38 mL, 5.57 mmol) was added dropwise over 5 minutes and the temperature slowly increased from 19-23° C. The reaction was stirred for 3 hours at ambient temperature, and additional (1-(methoxycarbonyl)cyclopropyl)zinc(II) bromide (12.38 mL, 5.57 mmol) was added and the reaction was stirred at ambient temperature for 16 hours. The reaction was quenched with saturated aqueous ammonium chloride (50 mL) and diluted with methyl tert-butyl ether (400 mL). The organics were separated, washed with brine, dried over sodium sulfate, and filtered. The solvent was removed in vacuo and the crude material was purified, eluting on a 40 g silica gel cartridge with 0-50% ethyl acetate/hexanes over 20 minutes to provide the title compound. $^1$H NMR (400 MHz, chloroform-d) δ ppm 7.24 (dd, J=8.5, 2.6 Hz, 1H), 7.20 (d, J=2.5 Hz, 1H), 6.79 (d, J=8.5 Hz, 1H), 4.04 (q, J=7.0 Hz, 2H), 3.61 (s, 3H), 3.36 (s, 2H), 3.32 (s, 3H), 1.60 (q, J=4.1 Hz, 2H), 1.37 (t, J=6.9 Hz, 3H), 1.31 (s, 6H), 1.12 (q, J=4.1 Hz, 2H). MS (ESI+) m/z 307 (M+H)$^+$.

Example I-101F 1-(2-ethoxy-5-(1-methoxy-2-methylpropan-2-yl) phenyl)cyclopropanecarboxylic Acid Methyl 1-(2-ethoxy-5-(1-methoxy-2-methylpropan-2-yl) phenyl)cyclopropanecarboxylate (0.843 g, 2.75 mmol) from Example I-101E was dissolved in tetrahydrofuran (4 mL), methanol (4 mL), and water (4 mL). The mixture was treated with sodium hydroxide (0.569 g, 14.23 mmol) and stirred at 50° C. for 15 hours. The reaction was concentrated, cooled in an ice bath and carefully quenched with 2N aqueous citric acid (about 8 mL) until the pH~5. The resulting emulsion was stirred vigorously, the aqueous layer was removed, and the organic layer was washed with water (2×0.3 mL). The mixture was dried via azeotrope with toluene to provide the title compound. $^1$H NMR (400 MHz, chloroform-d) δ ppm 7.24 (dd, J=8.5, 2.5 Hz, 1H), 7.21 (d, J=2.5 Hz, 1H), 6.79 (d, J=8.5 Hz, 1H), 4.05 (q, J=7.0 Hz, 2H), 3.34 (s, 3H), 3.30 (s, 2H), 1.64 (q, J=4.0 Hz, 2H), 1.38 (t, J=7.0 Hz, 3H), 1.30 (s, 6H), 1.17 (q, J=4.1 Hz, 2H). MS (ESI–) m/z 290.9 (M–H)$^-$.

Example I-101G

1-[2-ethoxy-5-(1-methoxy-2-methylpropan-2-yl) phenyl]-N-(quinoline-5-sulfonyl)cyclopropane-1-carboxamide To a solution of 1-(2-ethoxy-5-(1-methoxy-2-methylpropan-2-yl)phenyl)cyclopropanecarboxylic acid (72 mg, 0.246 mmol) from Example I-101F, $N^1$-((ethylimino)methylene)-$N^3,N^3$-dimethylpropane-1,3-diamine hydrochloride (94 mg, 0.493 mmol) and N,N-dimethylpyridin-4-amine (30.1 mg, 0.246 mmol) in anhydrous dichloromethane (1 mL) was added quinoline-5-sulfonamide (56 mg, 0.269 mmol). The reaction was stirred at ambient temperature for 16 hours. The reaction was quenched with 0.2 mL of aqueous 2N citric acid and the residue was purified via chromatography on a 12 g silica gel cartridge, eluting with a gradient of 0-10% methanol/dichloromethane over a period of 20 minutes. The crude material was triturated with diethyl ether and filtered to provide the title compound. $^1$H NMR (501 MHz, dimethyl sulfoxide-d$_6$) δ ppm 11.42 (s, 1H), 9.03 (dd, J=4.1, 1.6 Hz, 1H), 8.94 (dt, J=8.7, 1.1 Hz, 1H), 8.32 (d, J=8.5 Hz, 1H), 8.29 (d, J=7.4 Hz, 1H), 7.91 (t, J=7.9 Hz, 1H), 7.67 (dd, J=8.8, 4.2 Hz, 1H), 7.18 (dd, J=8.6, 2.5 Hz, 1H), 7.05 (d, J=2.5 Hz, 1H), 6.71 (d, J=8.6 Hz, 1H), 3.60 (q, J=6.9 Hz, 2H), 3.28 (s, 2H), 3.20 (s, 3H), 1.30 (q, J=4.4 Hz, 2H), 1.20 (s, 6H), 0.93 (q, J=4.4 Hz, 2H), 0.69 (t, J=6.9 Hz, 3H). MS (ESI–) m/z 481 (M–H)$^-$.

Example I-102

1-[2-ethoxy-5-(1-methoxycyclobutyl)phenyl]-N-(quinoline-5-sulfonyl)cyclopropane-1-carboxamide Example I-102A 1-(4-ethoxyphenyl)cyclobutanol To a cooled (ice/NaCl bath) solution of 1M (4-ethoxyphenyl)magnesium bromide (50 mL, 50.0 mmol) was added cyclobutanone (3.25 g, 45.5 mmol) dropwise, keeping the internal temperature below 0° C. The reaction was allowed to slowly warm to ambient temperature and was stirred for 5 hours. The reaction was cooled in an ice bath and was quenched with saturated aqueous ammonium chloride (100 mL) and diluted with methyl tert-butyl ether (200 mL). The organic layer was separated, dried over sodium sulfate, filtered and concentrated in vacuo. The crude material was purified by silica gel chromatography, eluting with ethyl acetate in heptanes (0 to 20%) to provide the title compound. $^1$H NMR (501 MHz, chloroform-d) δ ppm 7.44-7.37 (m, 2H), 6.92-6.85 (m, 2H), 3.80 (s, 3H), 2.57-2.47 (m, 2H), 2.34 (tdd, J=9.5, 7.7, 3.0 Hz, 2H), 2.19 (s, 1H), 2.05-1.90 (m, 1H), 1.63 (dddd, J=16.4, 11.2, 8.7, 7.7 Hz, 1H).

Example I-102B 1-ethoxy-4-(1-methoxycyclobutyl)benzene

To a cooled (ice bath) solution of 1-(4-ethoxyphenyl) cyclobutanol (8.74 g, 45.5 mmol) from Example I-102A in tetrahydrofuran (91 mL) was added sodium hydride (3.09 g, 77 mmol) and the reaction was stirred at 5° C. for one hour. Iodomethane (6.23 mL, 100 mmol) was added and the reaction was allowed to warm to ambient temperature and stir for 18 hours. Water was added slowly to quench the reaction and the solution was diluted with methyl tert-butyl ether (300 mL). The organic layer was separated, dried over sodium sulfate, filtered and concentrated under reduced pressure. The residue was purified by silica gel chromatography, eluting with ethyl acetate in heptanes (0 to 20%) to provide the title compound. $^1$H NMR (400 MHz, chloroform-d) δ ppm 7.37-7.29 (m, 2H), 6.93-6.85 (m, 2H), 4.04 (q, J=7.0 Hz, 2H), 2.91 (s, 3H), 2.44-2.26 (m, 4H), 1.92 (dtd, J=11.1, 9.1, 4.6 Hz, 1H), 1.72-1.55 (m, 1H), 1.42 (t, J=7.0 Hz, 3H).

Example I-102C 2-bromo-1-ethoxy-4-(1-methoxycyclobutyl)benzene

A solution of 1-ethoxy-4-(1-methoxycyclobutyl)benzene (0.47 g, 2.278 mmol) from Example I-102B in acetonitrile (7.59 mL) was treated with NBS (N-bromosuccinimide, 0.426 g, 2.392 mmol), stirred at ambient temperature for 18 hours, and heated to 40° C. for 3 hours. The reaction was cooled to ambient temperature, diluted with 20 mL of methyl tert-butyl ether, and quenched with 10 mL of 5% aqueous NaOH. The organic layer was washed with saturated aqueous sodium bicarbonate and brine, dried over sodium sulfate, filtered, concentrated to ~20 mL, and filtered again. The filtrate was concentrated and purified by silica gel chromatography, eluting with ethyl acetate in heptanes (0 to 30%) to provide the title compound. $^1$H NMR (400 MHz, chloroform-d) δ ppm 7.60 (d, J=2.2 Hz, 1H), 7.31 (dd, J=8.5, 2.2 Hz, 1H), 6.89 (d, J=8.4 Hz, 1H), 4.13 (q, J=7.0 Hz, 2H), 2.93 (s, 3H), 2.43-2.29 (m, 2H), 2.01-1.86 (m, 1H), 1.73-1.58 (m, 2H), 1.49 (t, J=7.0 Hz, 3H), 1.44 (td, J=6.9, 3.9 Hz, 1H).

Example I-102D methyl 1-(2-ethoxy-5-(1-methoxycyclobutyl)phenyl) cyclopropanecarboxylate To a solution of 2-bromo-1-ethoxy-4-(1-methoxycyclobutyl)benzene (230 mg, 0.807 mmol) from Example I-102C in tetrahydrofuran (2 mL) was added bis(dibenzylideneacetone)palladium (9.28 mg, 0.016 mmol) and Q-Phos (1,2,3,4,5-pentaphenyl-1'-(di-tert-butylphosphino)ferrocene) (11.46 mg, 0.016 mmol). Nitrogen was bubbled through the solution for about 10 minutes. A tetrahydrofuran solution of (1-(methoxycarbonyl)cyclopropyl)zinc(II) bromide (0.45 M, 4 mL, 1.800 mmol) was added dropwise over 5 minutes and the temperature slowly increased from 19-23° C. The reaction was stirred for 4 hours at ambient temperature. Additional (1-(methoxycarbonyl)cyclopropyl)zinc(II) bromide (2 mL, 0.90 mmol) was added and the reaction was stirred at ambient temperature for 72 hours. The reaction was quenched with saturated aqueous ammonium chloride (15 mL) and diluted with methyl tert-butyl ether (100 mL). The organics were separated, washed with brine, dried over sodium sulfate and filtered. The solvent was removed in vacuo and the crude material was purified on a 24 g silica gel cartridge with 0-50% ethyl acetate/hexanes over 20 minutes to provide the title compound. $^1$H NMR (400 MHz, chloroform-d) δ ppm 7.31-7.22 (m, 2H), 6.83 (d, J=8.3 Hz, 1H), 4.07 (q, J=7.0 Hz, 2H), 3.61 (s, 3H), 2.92 (s, 3H), 2.44-2.29 (m, 4H), 1.94 (dtd, J=11.1, 9.1, 4.7 Hz, 1H), 1.74-1.64 (m, 1H), 1.61 (q, J=4.1 Hz, 2H), 1.39 (t, J=7.0 Hz, 3H), 1.13 (q, J=4.1 Hz, 2H).

Example I-102E 1-(2-ethoxy-5-(1-methoxycyclobutyl)phenyl)cyclopropanecarboxylic Acid Methyl 1-(2-ethoxy-5-(1-methoxycyclobutyl)phenyl)cyclopropanecarboxylate (0.160 g, 0.526 mmol) from Example I-102D was dissolved in tetrahydrofuran (1 mL), methanol (1 mL) and water (1 mL) and treated with sodium hydroxide (0.122 g, 3.05 mmol) and stirred at 70° C. for 2 hours. The reaction mixture was concentrated, cooled in an ice bath and carefully quenched with 2N aqueous citric acid (about 1.5 mL) until the pH~5. The water was removed by filtration and the material was washed with water and dried under a stream of nitrogen to provide the title compound. $^1$H NMR (501 MHz, chloroform-d) δ ppm 11.40 (s, 1H), 7.33-7.25 (m, 2H), 6.85 (d, J=8.4 Hz, 1H), 4.09 (q, J=7.0 Hz, 2H), 2.92 (s, 3H), 2.44-2.30 (m, 4H), 1.94 (dtt, J=11.1, 9.4, 4.9 Hz, 1H), 1.76-1.58 (m, 3H), 1.42 (t, J=6.9 Hz, 3H), 1.21 (q, J=4.1 Hz, 2H). MS (ESI-) m/z 288.9 (M-H)$^-$.

Example I-102F

1-[2-ethoxy-5-(1-methoxycyclobutyl)phenyl]-N-(quinoline-5-sulfonyl)cyclopropane-1-carboxamide To a solution of 1-(2-ethoxy-5-(1-methoxycyclobutyl)phenyl)cyclopropanecarboxylic acid (72 mg, 0.248 mmol) from Example I-102E, $N^1$-((ethylimino)methylene)-$N^3,N^3$-dimethylpropane-1,3-diamine hydrochloride (95 mg, 0.496 mmol) and N,N-dimethylpyridin-4-amine (30.3 mg, 0.248 mmol) in anhydrous dichloromethane (1 mL) was added quinoline-5-sulfonamide (55 mg, 0.264 mmol). The reaction was stirred at ambient temperature for 16 hours. The reaction was quenched with 0.2 mL of 2N aqueous citric acid and the residue was purified via chromatography on a 12 g silica gel cartridge, eluting with a gradient of 0-10% methanol/dichloromethane over a period of 20 minutes. The crude material was triturated with diethyl ether and filtered to provide the title compound. $^1$H NMR (400 MHz, dimethyl sulfoxide-d$_6$) δ ppm 11.49 (s, 1H), 9.01 (dd, J=4.2, 1.6 Hz, 1H), 8.91 (dt, J=8.8, 1.2 Hz, 1H), 8.35-8.23 (m, 2H), 7.90 (dd, J=8.4, 7.5 Hz, 1H), 7.64 (dd, J=8.8, 4.2 Hz, 1H), 7.21 (dd, J=8.4, 2.3 Hz, 1H), 7.04 (d, J=2.3 Hz, 1H), 6.78 (d, J=8.5 Hz, 1H), 3.62 (q, J=7.0 Hz, 2H), 2.78 (s, 3H), 2.34-2.11 (m, 4H), 1.81 (ddq, J=11.0, 9.3, 4.8 Hz, 1H), 1.54 (dp, J=10.9, 8.3 Hz, 1H), 1.29 (q, J=4.4 Hz, 2H), 0.92 (q, J=4.5 Hz, 2H), 0.71 (t, J=6.9 Hz, 3H). MS (ESI-) m/z 479 (M-H)$^-$.

Example I-103

1-[2-ethoxy-5-(2-ethoxypropan-2-yl)phenyl]-N-(2-methylquinoline-5-sulfonyl)cyclopropane-1-carboxamide Example I-103A 1-(3-bromo-4-ethoxyphenyl)ethanone To a solution of 1-(4-ethoxyphenyl)ethanone (10 g, 60.9 mmol) in methanol (70 mL) and water (7 mL) was added dibromine (3.28 mL, 63.9 mmol) dropwise and the mixture was stirred at ambient temperature for 16 hours. The solvent was removed and the reaction was diluted with water (20 mL), and extracted with dichloromethane. The organic layer was concentrated in vacuo. The mixture was purified on 40 g silica gel cartridge with 100% dichloromethane over a period of 10 minutes to provide the title compound. $^1$H NMR (501 MHz, chloroform-d) δ ppm 8.19 (d, J=2.2 Hz, 1H), 7.92 (dd, J=8.6, 2.2 Hz, 1H), 6.94 (d, J=8.6 Hz, 1H), 4.21 (q, J=7.0 Hz, 2H), 2.58 (s, 3H), 1.54 (t, J=7.0 Hz, 3H). MS (APCI+) m/z 243 (M+H)$^+$.

Example I-103B 2-(3-bromo-4-ethoxyphenyl)propan-2-ol

To a solution of methylmagnesium bromide in diethyl ether (2.98 mL, 8.93 mmol) and tetrahydrofuran (3 mL) at −30° C. was added dropwise 1-(3-bromo-4-ethoxyphenyl)ethanone (1.55 g, 6.38 mmol) from Example I-103A in dichloromethane (6 mL). The reaction mixture was stirred for 90 minutes at −15° C., and 1 hour at −5° C. The mixture was quenched with acetic acid (0.548 mL, 9.56 mmol), diluted with 30 mL of water and extracted with dichloromethane. The solvent was evaporated in vacuo and the resulting residue was purified on a 40 g silica gel cartridge eluting with a gradient 0-100% ethyl acetate/heptanes over a period of 10 minutes to provide the title compound. $^1$H NMR (400 MHz, chloroform-d) δ ppm 7.67 (d, J=2.4 Hz, 1H), 7.35 (dd, J=8.5, 2.4 Hz, 1H), 6.85 (d, J=8.6 Hz, 1H), 4.10 (q, J=7.0 Hz, 2H), 1.67 (s, 1H), 1.55 (s, 6H), 1.46 (t, J=7.0 Hz, 3H). MS (APCI+) m/z 241 (M+H-H$_2$O)$^+$.

Example I-103C 2-bromo-1-ethoxy-4-(2-ethoxypropan-2-yl)benzene

To a solution of 2-(3-bromo-4-ethoxyphenyl)propan-2-ol (400 mg, 1.544 mmol) from Example I-103B in N,N-dimethylformamide (3 mL) at 0° C. was added sodium hydride (154 mg, 3.86 mmol). After 30 minutes, iodoethane (481 mg, 3.09 mmol) was added and the reaction was stirred at 20° C. for 16 hours. The mixture was quenched via addition of saturated aqueous ammonium chloride (80 mL) and extracted with dichloromethane. The crude material was purified on 12 g silica gel cartridge with a gradient of 0-60% ethyl acetate/heptanes over a period of 10 minutes to provide the title compound. $^1$H NMR (501 MHz, chloroform-d) δ ppm 7.57 (d, J=2.3 Hz, 1H), 7.28 (dd, J=8.5, 2.3 Hz, 1H), 6.85 (d, J=8.5 Hz, 1H), 4.10 (q, J=7.0 Hz, 2H), 3.19 (q, J=7.0 Hz, 2H), 1.49 (s, 6H), 1.47 (t, J=7.0 Hz, 3H), 1.14 (t, J=7.0 Hz, 3H). MS (APCI+) m/z 241 (M+H-CH$_3$CH$_2$OH)$^+$.

Example I-103D methyl 1-(2-ethoxy-5-(2-ethoxypropan-2-yl)phenyl)cyclopropanecarboxylate To a solution of bis(dibenzylideneacetone)palladium (0.015 g, 0.027 mmol) and Q-Phos (1,2,3,4,5-pentaphenyl-1'-(di-tert-butylphosphino)ferrocene, 0.019 g, 0.027 mmol) in tetrahydrofuran (8 mL) was added 2-bromo-1-ethoxy-4-(2-ethoxypropan-2-yl)benzene (0.385 g, 1.341 mmol) from Example I-103C in 1 mL of tetrahydrofuran followed by a solution of freshly-prepared (1-(methoxycarbonyl)cyclopropyl)zinc(II) bromide (5.96 mL, 2.68 mmol). The reaction was stirred at ambient temperature for 3 hours, another equivalent of Zn reagent (3 mL) was added and the reaction was stirred at ambient temperature for 16 hours. Another equivalent Zn reagent (3 mL) was added and the reaction was stirred a total of 4 days at ambient temperature. The reaction was heated at 50° C. for 16 hours and heated at 70° C. for 3 hours. The reaction was cooled to ambient temperature and was diluted with ethyl acetate and saturated aqueous ammonium chloride. The organic layer was separated, and washed with brine and concentrated. The residue was purified via chromatography on a 24 g silica gel cartridge, eluting with ethyl acetate in heptanes at 0-100% gradient over a period of 12 minutes to provide the crude product. The crude material was rechromatographed on a 24 g silica gel cartridge, eluting with 100% dichloromethane for 7 minutes followed by 100% ethyl acetate for 2 minutes to provide the title compound. $^1$H NMR (400 MHz, chloroform-d) δ ppm 7.25 (m, 1H), 7.24 (d, J=0.8 Hz, 1H), 6.78 (m, 1H), 4.04 (q, J=6.9 Hz, 2H), 3.60 (s, 3H), 3.18 (q, J=7.0 Hz, 2H), 1.59 (q, J=4.1 Hz, 2H), 1.51 (s, 6H), 1.36 (t, J=7.0 Hz, 3H), 1.13 (t, J=7.0 Hz, 3H), 1.10 (q, J=4.1 Hz, 2H). MS (APCI+) m/z 261 (M+H-CH$_3$CH$_2$OH)$^+$.

Example I-103E 1-(2-ethoxy-5-(2-ethoxypropan-2-yl)phenyl)cyclopropanecarboxylic Acid Methyl 1-(2-ethoxy-5-(2-ethoxypropan-2-yl)phenyl)cyclopropanecarboxylate (0.295 g, 0.963 mmol) from Example I-103D was dissolved in tetrahydrofuran (1.5 mL), methanol (1.500 mL), and water (1.500 mL). The mixture was treated with sodium hydroxide (0.193 g, 4.81 mmol, stirred at 35° C. for 16 hours, concentrated, cooled in an ice bath, and carefully quenched with 1N aqueous citric acid (about 2.5 mL) until the pH~5. The resulting slurry was stirred vigorously and filtered. The precipitate was washed with water and dried in a vacuum oven overnight to provide the title compound. $^1$H NMR (400 MHz, chloroform-d) δ ppm 10.48 (bs, 1H), 7.25 (m, 2H), 6.79 (d, J=9.1 Hz, 1H), 4.06 (q, J=6.9 Hz, 2H), 3.17 (q, J=7.0 Hz, 2H), 1.65 (q, J=4.1 Hz, 2H), 1.49 (s, 6H), 1.38 (t, J=6.9 Hz, 3H), 1.16 (q, J=4.1 Hz, 2H), 1.12 (t, J=7.0 Hz, 3H). MS (ESI-) m/z 291 (M-H)$^-$.

Example I-103F

1-[2-ethoxy-5-(2-ethoxypropan-2-yl)phenyl]-N-(2-methylquinoline-5-sulfonyl)cyclopropane-1-carboxamide To a solution of 1-(2-ethoxy-5-(2-ethoxypropan-2-yl)phenyl)cyclopropanecarboxylic acid (50 mg, 0.171 mmol) from Example I-103E, N$^1$-((ethylimino)methylene)-N$^3$,N$^3$-dimethylpropane-1,3-diamine hydrochloride (65.6 mg, 0.342 mmol) and N,N-dimethylpyridin-4-amine (20.89 mg, 0.171 mmol) in anhydrous dichloromethane (1 mL) was added 2-methylquinoline-5-sulfonamide (40 mg, 0.180 mmol). The reaction was stirred at ambient temperature for 15 hours. The reaction was quenched with aqueous 2 N citric acid (0.2 mL) and the residue was purified via chromatography on a 12 g silica gel cartridge, eluting with a gradient of 0-10% methanol/dichloromethane over a period of 20 minutes to provide the crude material. The crude material was triturated with diethyl ether and filtered to provide the title compound. $^1$H NMR (400 MHz, dimethyl sulfoxide-d$_6$) δ ppm 11.38 (s, 1H), 8.79 (d, J=8.9 Hz, 1H), 8.18 (ddd, J=7.4, 5.2, 1.1 Hz, 2H), 7.83 (dd, J=8.4, 7.5 Hz, 1H), 7.53 (d, J=8.9 Hz, 1H), 7.19 (dd, J=8.5, 2.3 Hz, 1H), 7.04 (d, J=2.3 Hz, 1H), 6.74 (d, J=8.5 Hz, 1H), 3.63 (q, J=7.0 Hz, 2H), 3.09 (q, J=6.9 Hz, 2H), 2.67 (s, 3H), 1.38 (s, 6H), 1.30 (q, J=4.4 Hz, 2H), 0.99 (t, J=6.9 Hz, 3H), 0.91 (q, J=4.5 Hz, 2H), 0.72 (t, J=6.9 Hz, 3H). MS (ESI-) m/z 495 (M-H)$^-$.

Example I-104

1-[2-ethoxy-5-(2-methoxypropan-2-yl)phenyl]-N-(2-methylquinoline-5-sulfonyl)cyclopropane-1-carboxamide Example I-104A 2-bromo-1-ethoxy-4-(2-methoxypropan-2-yl)benzene To a solution of 2-(3-bromo-4-ethoxyphenyl)propan-2-ol (400 mg, 1.544 mmol) Example I-103B in N,N-dimethylformamide (3 mL) at 0° C. was added sodium hydride (123 mg, 3.09 mmol), 60% by weight in mineral oil. After 30 minutes, iodomethane (0.193 mL, 3.09 mmol) was added and the reaction was stirred at 20° C. for 6 hours. The mixture was quenched via addition of saturated aqueous ammonium chloride (70 mL) and extracted with dichloromethane. The crude material was purified by chromatography, eluting on 12 g silica gel cartridge with a gradient of 0-60% ethyl acetate/heptanes over a period of 10 minutes to provide the title compound. $^1$H NMR (400 MHz, chloroform-d) δ ppm 7.57 (d, J=2.3 Hz, 1H), 7.27 (d, J=8.5, 2.3 Hz, 1H), 6.85 (d, J=8.5 Hz, 1H), 4.10 (q, J=7.0 Hz, 2H), 3.05 (s, 3H), 1.49 (s, 6H), 1.47 (t, J=7.0 Hz, 3H). MS (DCI+) m/z 241 (M+H-methanol)$^+$.

Example I-104B methyl 1-(2-ethoxy-5-(2-methoxypropan-2-yl)phenyl)cyclopropanecarboxylate To a solution of bis(dibenzylideneacetone)palladium (0.016 g, 0.028 mmol) and Q-Phos (1,2,3,4,5-pentaphenyl-1'-(di-tert-butylphosphino)ferrocene) (0.020 g, 0.028 mmol) in tetrahydrofuran (8 mL) at ambient temperature was added 2-bromo-1-ethoxy-4-(2-methoxypropan-2-yl)benzene (0.385 g, 1.409 mmol) from Example I-104A in 1 mL tetrahydrofuran followed by a solution of freshly-prepared (1-(methoxycarbonyl)cyclopropyl)zinc(II) bromide (6.26 mL, 2.82 mmol). After 3 hours, additional Zn reagent (3 mL) was added, the reaction stirred at ambient temperature for 16 hours, additional Zn reagent (3 mL) was added and the reaction was stirred a total of 4 days at ambient temperature, and heated at 50° C. for 6 hours. The reaction mixture was cooled to ambient temperature and diluted with ethyl acetate and saturated aqueous ammonium chloride. The organic layer was washed with brine and concentrated. The residue was purified via chromatography on a 24 g silica gel cartridge, eluting with ethyl acetate in heptane at 0-100% gradient over a period of 12 minutes to provide the title compound. $^1$H NMR (501 MHz, chloroform-d) δ ppm 7.24 (dd, J=7.9, 2.4 Hz, 1H), 7.23 (s, 1H), 6.79 (dd, J=7.9, 0.9 Hz, 1H), 4.05 (q, J=7.0 Hz, 2H), 3.60 (s, 3H), 3.04 (s, 3H), 1.59 (q, J=4.1 Hz, 2H), 1.51 (s, 6H), 1.37 (t, J=7.0 Hz, 3H), 1.11 (q, J=4.1 Hz, 2H). MS (ESI+) m/z 261 (M+H-methanol)$^+$.

Example I-104C 1-(2-ethoxy-5-(2-methoxypropan-2-yl)phenyl)cyclopropanecarboxylic Acid Methyl 1-(2-ethoxy-5-(2-methoxypropan-2-yl)phenyl)cyclopropanecarboxylate (0.345 g, 1.180 mmol) from Example I-104B was dissolved in tetrahydrofuran (1.5 mL), methanol (1.500 mL), and water (1.500 mL), and treated with sodium hydroxide (0.236 g, 5.90 mmol). The reaction mixture was stirred at 35° C. for 16 hours, concentrated, cooled in an ice bath, and carefully quenched with 1N aqueous citric acid (about 3 mL) until the pH~5. The resulting slurry was stirred vigorously and the aqueous layer was decanted off. The crude material was washed with water and decanted. The material was washed with water and dried by azeotroping with toluene (3×2 mL) to provide the title compound. $^1$H NMR (501 MHz, chloroform-d) δ ppm 10.56 (bs, 1H), 7.24 (m, 2H), 6.80 (d, J=9.1 Hz, 1H), 4.06 (q, J=7.0 Hz, 2H), 3.02 (s, 3H), 1.65 (q, J=4.1 Hz, 2H), 1.49 (s, 6H), 1.39 (t, J=6.9 Hz, 3H), 1.17 (q, J=4.1 Hz, 2H). MS (ESI−) m/z 277 (M−H)$^-$.

Example I-104D

1-[2-ethoxy-5-(2-methoxypropan-2-yl)phenyl]-N-(2-methylquinoline-5-sulfonyl)cyclopropane-1-carboxamide To a solution of 1-(2-ethoxy-5-(2-methoxypropan-2-yl)phenyl)cyclopropanecarboxylic acid (50 mg, 0.180 mmol) from Example I-104C, $N^1$-((ethylimino)methylene)-$N^3$,$N^3$-dimethylpropane-1,3-diamine hydrochloride (68.9 mg, 0.359 mmol) and N,N-dimethylpyridin-4-amine (21.95 mg, 0.180 mmol) in anhydrous dichloromethane (1 mL) was added 2-methylquinoline-5-sulfonamide (40 mg, 0.180 mmol). The reaction was stirred at ambient temperature for 15 hours. The reaction was quenched with 0.2 mL of 2N aqueous citric acid and the residue was purified via chromatography on a 12 g silica gel cartridge, eluting with a gradient of 0-10% methanol/dichloromethane over a period of 20 minutes to provide the crude title compound. The crude material was triturated with diethyl ether and filtered to provide the title compound. $^1$H NMR (501 MHz, dimethyl sulfoxide-$d_6$) δ ppm 11.40 (s, 1H), 8.80 (d, J=8.8 Hz, 1H), 8.23-8.17 (m, 2H), 7.85 (dd, J=8.3, 7.5 Hz, 1H), 7.55 (d, J=8.9 Hz, 1H), 7.20 (dd, J=8.5, 2.4 Hz, 1H), 7.05 (d, J=2.3 Hz, 1H), 6.76 (d, J=8.5 Hz, 1H), 3.64 (q, J=6.9 Hz, 2H), 2.93 (s, 3H), 2.69 (s, 3H), 1.39 (s, 6H), 1.31 (q, J=4.4 Hz, 2H), 0.93 (q, J=4.4 Hz, 2H), 0.74 (t, J=6.9 Hz, 3H). MS (ESI−) m/z 481 (M−H)$^-$.

Example I-105

1-[2-ethoxy-5-(1-methoxycyclobutyl)phenyl]-N-(2-methylquinoline-5-sulfonyl)cyclopropane-1-carboxamide To a solution of 1-(2-ethoxy-5-(1-methoxycyclobutyl)phenyl)cyclopropanecarboxylic acid (55 mg, 0.189 mmol) from Example I-102E, $N^1$-((ethylimino)methylene)-$N^3$,$N^3$-dimethylpropane-1,3-diamine hydrochloride (72.6 mg, 0.379 mmol) and N,N-dimethylpyridin-4-amine (23.14 mg, 0.189 mmol) in anhydrous dichloromethane (1 mL) was added 2-methylquinoline-5-sulfonamide (40 mg, 0.180 mmol). The reaction was stirred at ambient temperature for 15 hours. The reaction mixture was quenched with 0.2 mL of aqueous 2N citric acid and the residue was purified via chromatography on a 12 g silica gel cartridge, eluting with a gradient of 0-10% methanol/dichloromethane over a period of 20 minutes to yield the product, which was triturated with diethyl ether and filtered to provide the title compound. $^1$H NMR (400 MHz, dimethyl sulfoxide-$d_6$) δ ppm 11.43 (s, 1H), 8.79 (d, J=8.9 Hz, 1H), 8.23-8.14 (m, 2H), 7.83 (t, J=7.9 Hz, 1H), 7.53 (d, J=8.9 Hz, 1H), 7.21 (dd, J=8.4, 2.3 Hz, 1H), 7.04 (d, J=2.3 Hz, 1H), 6.79 (d, J=8.4 Hz, 1H), 3.65 (q, J=7.0 Hz, 2H), 2.78 (s, 3H), 2.67 (s, 3H), 2.35-2.13 (m, 4H), 1.81 (dtd, J=15.6, 9.6, 4.7 Hz, 1H), 1.56 (dq, J=10.6, 8.2 Hz, 1H), 1.29 (q, J=4.4 Hz, 2H), 0.92 (q, J=4.5 Hz, 2H), 0.74 (t, J=6.9 Hz, 3H). MS (ESI−) m/z 493 (M−H)$^-$.

Example I-106

1-{5-methyl-2-[(oxetan-3-yl)oxy]phenyl}-N-(2-methylquinoline-5-sulfonyl)cyclopropane-1-carboxamide Example I-93C (49.2 mg, 0.20 mmol, 1.1 eq) was weighed into a 4 mL vial. 1-(3-Dimethylaminopropyl)-3-ethylcarbodiimide HCl (68.4 mg, 0.36 mmol, 2.0 eq) and 4-dimethylaminopyridine (24.2 mg, 0.20 mmol, 1.1 eq) in dichloromethane (0.4 mL) was added to the vial containing the carboxylic acid. A slurry of 2-methylquinoline-5-sulfonamide in dichloromethane (0.8 mL) was added and the reaction was stirred overnight at ambient temperature. The solvent was removed under a stream of nitrogen, and the residue was dissolved in dimethyl sulfoxide/methanol. The mixture was purified via preparative reverse phase HPLC/MS method trifluoroacetic acid6 to provide the title compound. $^1$H NMR (400 MHz, dimethyl sulfoxide-$d_6$:$D_2O$=9:1 (v/v)) δ ppm 8.90 (dd, J=8.9, 0.9 Hz, 1H), 8.29-8.21 (m, 2H), 7.91 (dd, J=8.5, 7.5 Hz, 1H), 7.63 (d, J=8.9 Hz, 1H), 7.06-6.99 (m, 1H), 6.98 (d, J=2.3 Hz, 1H), 6.41 (d, J=8.2 Hz, 1H), 4.94 (p, J=5.5 Hz, 1H), 4.61 (dd, J=7.2, 6.0 Hz, 2H), 4.12 (dd, J=7.2, 5.1 Hz, 2H), 2.73 (s, 3H), 2.22 (s, 3H), 1.25 (q, J=4.3 Hz, 2H), 0.99 (q, J=4.4 Hz, 2H). MS (APCI) m/z 453.2 (M+H)$^+$.

Example I-107

1-(2-{[(2R)-1-methoxypropan-2-yl]oxy}-5-methylphenyl)-N-(2-methylquinoline-5-sulfonyl)cyclopropane-1-carboxamide Example I-107 was prepared as described in Example I-106, substituting Example I-95C for Example I-93C. $^1$H NMR (501 MHz, dimethyl sulfoxide-$d_6$:$D_2O$=9:1 (v/v)) δ ppm 8.94 (d, J=8.9 Hz, 1H), 8.26 (d, J=7.9 Hz, 2H), 7.92 (t, J=8.0 Hz, 1H), 7.66 (d, J=8.9 Hz, 1H), 7.08-7.02 (m, 1H), 6.92 (d, J=2.3 Hz, 1H), 6.82 (d, J=8.4 Hz, 1H), 4.36 (h, J=5.8 Hz, 1H), 3.16 (s, 3H), 3.11-3.00 (m, 2H), 2.74 (s, 3H), 2.21 (s, 3H), 1.37-1.30 (m, 1H), 1.23-1.15 (m, 1H), 1.07-0.99 (m, 1H), 0.93-0.84 (m, 4H). MS (APCI) m/z 469.2 (M+H)$^+$.

Example I-108

1-[3-(dimethylamino)-6-(2-methylpropoxy)pyridin-2-yl]-N-(quinoline-5-sulfonyl)cyclopropane-1-carboxamide Example I-108A 6-isobutoxy-N,N-dimethylpyridin-3-amine 5-Bromo-2-isobutoxypyridine (0.507 g, 2.203 mmol) [CAS #1251385-87-1] was combined with a 40% by weight solution of dimethylamine (3.65 g, 32.4 mmol) in water and the mixture was degassed with a stream of nitrogen for five minutes. 3 HPMC catalyst capsules (each containing 1.2 mg allyl palladium, 4.5 mg cBRIDP (di-tert-butyl(2,2-diphenyl- 1-methyl-1-cyclopropyl)phosphine), and 110 mg potassium tert-butoxide) were added and the reaction was warmed to 50° C. for 3 hours. The reaction was warmed at 50° C. for 24 hours, and 40% aqueous dimethylamine (3.65 g, 32.4 mmol) and 2 more HPMC catalyst capsules were added. The mixture was heated at 50° C. for 16 hours. The reaction was cooled and taken up in ethyl acetate and brine. The organics were separated and the solvent removed in vacuo. The residue was purified using a 40 g silica gel cartridge with a gradient of 0-100% ethyl acetate/hexanes to provide the title compound. $^1$H NMR (400 MHz, chloroform-d) δ ppm 7.67 (d, J=3.2 Hz, 1H), 7.16 (ddd, J=9.0, 3.2, 0.9 Hz, 1H), 6.70-6.63 (m, 1H), 3.99 (dd, J=6.8, 1.1 Hz, 2H), 2.86 (d, J=0.8 Hz, 6H), 2.07 (dtd, J=13.6, 6.8, 1.0 Hz, 1H), 1.01 (dd, J=6.7, 1.0 Hz, 6H). MS (ESI+) m/z 195 (M+H)$^+$.

Example I-108B 2-bromo-6-isobutoxy-N,N-dimethylpyridin-3-amine

6-Isobutoxy-N,N-dimethylpyridin-3-amine (0.152 g, 0.782 mmol) from Example I-108A was combined with 1-bromopyrrolidine-2,5-dione (0.167 g, 0.939 mmol) in acetonitrile (2 mL) and the reaction was stirred at ambient temperature for 1 hour. The solvent was reduced in volume, and the reaction was quenched with water (20 mL) and extracted with methyl tert-butyl ether (100 mL). The organics were separated and the solvent removed in vacuo. The residue was purified using a 12 g silica gel cartridge with a gradient of 0-100% ethyl acetate/hexanes to provide the title compound. $^1$H NMR (400 MHz, chloroform-d) δ ppm 7.38 (d, J=8.5 Hz, 1H), 6.68 (d, J=8.5 Hz, 1H), 4.03 (d, J=6.6 Hz, 2H), 2.74 (s, 6H), 2.07 (dt, J=13.4, 6.7 Hz, 1H), 1.01 (d, J=6.7 Hz, 6H).

Example I-108C methyl 1-(3-(dimethylamino)-6-isobutoxypyridin-2-yl)cyclopropanecarboxylate To a solution of 2-bromo-6-isobutoxy-N,N-dimethylpyridin-3-amine (62 mg, 0.227 mmol) from Example I-108B in tetrahydrofuran (6 mL) was added bis(dibenzylideneacetone)palladium (2.61 mg, 4.54 μmol) and Q-Phos (1,2,3,4,5-pentaphenyl-1'-(di-tert-butylphosphino)ferrocene) (3.23 mg, 4.54 μmol). Nitrogen was bubbled through the solution for about 10 minutes, and a 0.45 M in tetrahydrofuran solution of (1-(methoxycarbonyl)cyclopropyl)zinc(II) bromide (0.926 mL, 0.454 mmol) was added dropwise. The reaction was stirred for 16 hours at ambient temperature. The reaction was quenched with saturated aqueous ammonium chloride (1 mL) and the organics were separated and the crude material was purified via flash chromatography, eluting on a 12 g silica gel cartridge with 0-50% ethyl acetate/hexanes over 20 minutes to provide the title compound. $^1$H NMR (400 MHz, chloroform-d) δ ppm 7.46 (dd, J=8.6, 0.6 Hz, 1H), 6.62 (dd, J=8.5, 0.6 Hz, 1H), 4.01 (dd, J=6.7, 0.6 Hz, 2H), 3.66 (d, J=0.6 Hz, 3H), 2.58 (d, J=0.6 Hz, 6H), 2.05 (dp, J=13.4, 6.7 Hz, 1H), 1.49 (t, J=2.8 Hz, 2H), 1.45 (t, J=2.9 Hz, 2H), 1.00 (dd, J=6.7, 0.6 Hz, 6H).

Example I-108D 1-(3-(dimethylamino)-6-isobutoxypyridin-2-yl)cyclopropane carboxylic Acid To a solution of methyl 1-(3-(dimethylamino)-6-isobutoxypyridin-2-yl)cyclopropanecarboxylate (53 mg, 0.181 mmol) from Example I-108C in tetrahydrofuran (0.5 mL), methanol (0.5 mL) and water (0.5 mL) was added sodium hydroxide (43 mg, 1.075 mmol). The reaction was warmed at 50° C. for 16 hours. The solvent was reduced under a stream of nitrogen and the reaction was quenched with 0.55 mL of 2 N aqueous citric acid. The aqueous layer was removed by pipette and the resulting material was washed with water (2×1 mL) and dried under vacuum to provide the title compound. $^1$H NMR (400 MHz, chloroform-d) δ ppm 7.53 (d, J=8.7 Hz, 1H), 6.69 (d, J=8.6 Hz, 1H), 4.03 (d, J=6.6 Hz, 2H), 2.80 (s, 6H), 2.06 (dp, J=13.4, 6.7 Hz, 1H), 1.72 (q, J=3.8, 3.3 Hz, 2H), 1.64-1.55 (m, 2H), 1.01 (d, J=6.7 Hz, 6H). MS (ESII+) m/z 279 (M+H)$^+$.

Example I-108E

1-[3-(dimethylamino)-6-(2-methylpropoxy)pyridin-2-yl]-N-(quinoline-5-sulfonyl)cyclopropane-1-carboxamide To a solution of 1-(3-(dimethylamino)-6-isobutoxypyridin-2-yl)cyclopropanecarboxylic acid (48 mg, 0.172 mmol) from Example I-108D, N$^1$-((ethylimino)methylene)-N$^3$,N$^3$-dimethylpropane-1,3-diamine hydrochloride (66.1 mg, 0.345 mmol) and N,N-dimethylpyridin-4-amine (21.07 mg, 0.172 mmol) in anhydrous dichloromethane (1 mL) was added quinoline-5-sulfonamide (35.9 mg, 0.172 mmol). The reaction was stirred at ambient temperature for 16 hours. The reaction was quenched with 0.2 mL of 2 N aqueous citric acid and the residue was purified via chromatography on a 12 g silica gel cartridge, eluting with a gradient of 0-10% methanol/dichloromethane over a period of 20 minutes. The crude material was triturated with methanol and filtered to provide the title compound. $^1$H NMR (400 MHz, dimethyl sulfoxide) δ ppm 12.06 (s, 1H), 8.97-9.05 (m, 2H), 8.23-8.34 (m, 2H), 7.89 (dd, J=8.5, 7.4 Hz, 1H), 7.67 (dd, J=8.6, 4.3 Hz, 1H), 7.56 (d, J=8.6 Hz, 1H), 6.66 (d, J=8.6 Hz, 1H), 3.88 (d, J=6.6 Hz, 2H), 2.28 (s, 6H), 1.94 (hept, J=6.7, 6.7 Hz, 1H), 1.20 (q, J=4.1 Hz, 2H), 0.99 (q, J=3.9 Hz, 2H), 0.90 (d, J=6.7 Hz, 6H). MS (ESI−) m/z 467 (M−H)$^−$.

Example I-109

1-[5-(dimethylamino)-2-(2-methylpropoxy)pyridin-3-yl]-N-(2-methylquinoline-5-sulfonyl)cyclopropane-1-carboxamide Example I-109A 3-bromo-2-isobutoxypyridine 3-Bromo-2-fluoropyridine (1.06 g, 6.02 mmol) and 2-methylpropan-1-ol (0.577 mL, 6.25 mmol) were combined and a 1M solution of potassium 2-methylpropan-2-olate (7.23 mL, 7.23 mmol) in tetrahydrofuran was added, dropwise, and the temperature increased form 20-35° C. The reaction was allowed to cool to ambient temperature and was stirred for 1 hour. The mixture was quenched with water (50 mL) and extracted with methyl tert-butyl ether (500 mL). The organics were washed with brine (50 mL), dried over sodium sulfate, filtered, and concentrated. The crude material was chromatographed using a 40 g silica gel cartridge with a gradient of 5-100% ethyl acetate/hexanes to provide the title compound. $^1$H NMR (400 MHz, chloroform-d) δ ppm 8.08 (dd, J=4.9, 1.8 Hz, 1H), 7.80 (dd, J=7.6, 1.7 Hz, 1H), 6.76 (dd, J=7.6, 4.9 Hz, 1H), 4.14 (d, J=6.6 Hz, 2H), 2.15 (dp, J=13.4, 6.7 Hz, 1H), 1.06 (d, J=6.7 Hz, 6H).

Example I-109B methyl 1-(2-isobutoxypyridin-3-yl)cyclopropanecarboxylate

To a solution of 3-bromo-2-isobutoxypyridine (1.287 g, 5.59 mmol) from Example I-109A in tetrahydrofuran (6 mL) was added bis(dibenzylideneacetone)palladium (0.064 g, 0.112 mmol) and Q-Phos (1,2,3,4,5-pentaphenyl-1'-(di-tert-butylphosphino)ferrocene) (0.080 g, 0.112 mmol). Nitrogen was bubbled through the solution for about 10 minutes. A 0.45 M in tetrahydrofuran solution of (1-(methoxycarbonyl)cyclopropyl)zinc(II) bromide (12 mL, 5.88 mmol) was added dropwise over 5 minutes and the temperature slowly increased from 24.4-34.2° C. The reaction was stirred for 1 hour at ambient temperature. Additional (1-(methoxycarbonyl)cyclopropyl)zinc(II) bromide (5 mL, 2.45 mmol) was added and the reaction was stirred at ambient temperature for 16 hours. The reaction was quenched with saturated aqueous ammonium chloride (30 mL) and diluted with methyl tert-butyl ether (200 mL). The organics were washed with brine, dried over sodium sulfate and filtered. The solvent was removed in vacuo and the crude material was purified via flash chromatography, eluting on a 40 g silica gel cartridge with 0-50% ethyl acetate/hexanes over 20 minutes to provide the title compound. $^1$H NMR (400 MHz, chloroform-d) δ ppm 8.07 (dd, J=5.1, 1.9 Hz, 1H), 7.44 (dd, J=7.2, 1.9 Hz, 1H), 6.82 (dd, J=7.2, 5.1 Hz, 1H), 4.10 (d, J=6.3 Hz, 2H), 3.60 (s, 3H), 2.07 (dp, J=13.2, 6.6 Hz, 1H), 1.67-1.57 (m, 2H), 1.13-1.07 (m, 2H), 1.01 (d, J=6.7 Hz, 6H). MS (APCI+) m/z 249.9 (M+H)$^+$.

Example I-109C

Methyl 1-(5-bromo-2-isobutoxypyridin-3-yl)cyclopropanecarboxylate

Methyl 1-(2-isobutoxypyridin-3-yl)cyclopropanecarboxylate (1.17 g, 4.69 mmol) from Example I-109B was combined with 1-bromopyrrolidine-2,5-dione (0.971 g, 5.46 mmol) in N,N-dimethylformamide (10 mL). The reaction was stirred at 50° C. for 19 hours. The reaction was cooled, quenched with water (30 mL) and extracted with methyl tert-butyl ether (200 mL). The organics were separated, washed with water and brine, dried over sodium sulfate, and filtered. The solvent removed in vacuo. The residue was purified using a 40 g silica gel cartridge with a gradient of 0-50% ethyl acetate/hexanes over 40 minutes to provide the title compound. $^1$H NMR (400 MHz, chloroform-d) δ ppm 8.10 (d, J=2.4 Hz, 1H), 7.53 (d, J=2.4 Hz, 1H), 4.07 (d, J=6.3 Hz, 2H), 3.61 (s, 3H), 2.06 (dp, J=13.2, 6.6 Hz, 1H), 1.64 (q, J=4.3 Hz, 2H), 1.10 (q, J=4.3 Hz, 2H), 1.00 (d, J=6.7 Hz, 6H). MS (APCI+) m/z 330 (Br doublet) (M+H)$^+$.

Example I-109D methyl 1-(5-(dimethylamino)-2-isobutoxypyridin-3-yl)cyclopropanecarboxylate Methyl 1-(5-bromo-2-isobutoxypyridin-3-yl)cyclopropanecarboxylate (0.449 g, 1.368 mmol) from Example I-109C was combined with potassium phosphate (0.926 g, 4.36 mmol), and DAVEPHOS-PD-G3 (methanesulfonato 2-dicyclohexylphosphino-2-(N,N-dimethylamino)biphenyl (2'-amino-1,1'-biphenyl-2-yl) palladium(II), 0.104 g, 0.137 mmol) and put under nitrogen. Dimethylamine (6 mL, 12.00 mmol) 2M in tetrahydrofuran was added and the mixture was degassed with a stream of nitrogen for 3 minutes. The reaction was sealed and warmed to 80° C. for 72 hours. The reaction was cooled and the solvent was reduced under a stream of nitrogen. The organics were filtered and purified using a 40 g silica gel cartridge with a gradient of 0-100% ethyl acetate/hexanes to provide the title compound. $^1$H NMR (400 MHz, chloroform-d) δ ppm 7.58 (d, J=3.0 Hz, 1H), 7.06 (d, J=3.0 Hz, 1H), 4.02 (d, J=6.4 Hz, 2H), 3.61 (s, 3H), 2.87 (s, 6H), 2.04 (dp, J=13.2, 6.6 Hz, 1H), 1.62 (q, J=4.2 Hz, 2H), 1.11 (q, J=4.2 Hz, 2H), 1.00 (d, J=6.7 Hz, 6H). MS (ESI+) m/z 293 (M+H)$^+$.

Example I-109E 1-(5-(dimethylamino)-2-isobutoxypyridin-3-yl)cyclopropanecarboxylic Acid To a solution of methyl 1-(5-(dimethylamino)-2-isobutoxypyridin-3-yl)cyclopropanecarboxylate (350 mg, 1.197 mmol) from Example I-109D in tetrahydrofuran (3 mL), methanol (3 mL) and water (3 mL) was added sodium hydroxide (403 mg, 10.08 mmol). The reaction was warmed at 50° C. for 2 hours. The solvent was reduced under a stream of nitrogen and the reaction was quenched with 4.3 of 2N aqueous citric acid. The aqueous layer was removed by pipette and the resulting material was washed with water (2×1 mL) and azeotroped with toluene to provide the title compound. $^1$H NMR (400 MHz, chloroform-d) δ ppm 7.59 (d, J=3.0 Hz, 1H), 7.06 (d, J=3.1 Hz, 1H), 4.02 (d, J=6.4 Hz, 2H), 2.85 (s, 6H), 2.05 (dp, J=13.2, 6.6 Hz, 1H), 1.63 (q, J=4.1 Hz, 2H), 1.14 (q, J=4.2 Hz, 2H), 1.00 (d, J=6.7 Hz, 6H). MS (ESI+) m/z 279 (M+H)$^+$.

Example I-109F

1-[5-(dimethylamino)-2-(2-methylpropoxy)pyridin-3-yl]-N-(2-methylquinoline-5-sulfonyl)cyclopropane-1-carboxamide To a solution of 1-(5-(dimethylamino)-2-isobutoxypyridin-3-yl)cyclopropanecarboxylic acid (58 mg, 0.208 mmol) from Example I-109E, N$^1$-((ethylimino)methylene)-N$^3$,N$^3$-dimethylpropane-1,3-diamine hydrochloride (80 mg, 0.417 mmol) and N,N-dimethylpyridin-4-amine (25.5 mg, 0.208 mmol) in anhydrous dichloromethane (1 mL) was added 2-methylquinoline-5-sulfonamide (49 mg, 0.220 mmol). The reaction was stirred at ambient temperature overnight. The reaction was quenched with 0.2 mL of 2N aqueous citric acid and the residue was purified via chromatography on a 12 g silica gel cartridge, eluting with a gradient of 0-10% methanol/dichloromethane over a period of 20 minutes. The material was further purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (400 MHz, dimethyl sulfoxide-d$_6$) δ ppm 11.57 (s, 1H), 8.82 (d, J=8.9 Hz, 1H), 8.26-8.18 (m, 2H), 7.87 (t, J=8.0 Hz, 1H), 7.80 (d, J=2.9 Hz, 1H), 7.60 (d, J=8.9 Hz, 1H), 7.40 (d, J=2.9 Hz, 1H), 3.54 (d, J=6.5 Hz, 2H), 2.94 (s, 6H), 2.70 (s, 3H), 1.33 (q, J=4.4 Hz, 2H), 1.22 (dp, J=13.3, 6.7 Hz, 1H), 1.01 (q, J=4.5 Hz, 2H), 0.55 (d, J=6.7 Hz, 6H). MS (APCI+) m/z 483 (M+H)$^+$.

Example I-110

1-[2-methoxy-5-(1-methoxy-2-methylpropan-2-yl) phenyl]-N-(quinoline-5-sulfonyl)cyclopropane-1-carboxamide

Example I-110A methyl 2-(3-bromo-4-methoxyphenyl)-2-methylpropanoate

A solution of methyl 2-(4-methoxyphenyl)-2-methylpropanoate (2 g, 9.60 mmol) [CAS #6274-50-6] and N-bromosuccinimide (1.880 g, 10.56 mmol) in acetonitrile (12.00 mL) was stirred at 38° C. for 16 hours. The solvent evaporated in vacuo. The crude material was triturated with dichloromethane, and filtered. The filtrate was purified by chromatography, eluting on 24 g silica gel cartridge with a gradient of 0-50% ethyl acetate/heptanes over a period of 12 minutes to provide the title compound. $^1$H NMR (400 MHz, chloroform-d) δ ppm 7.52 (d, J=2.4 Hz, 1H), 7.24 (dd, J=8.6, 2.4 Hz, 1H), 6.85 (d, J=8.7 Hz, 1H), 3.88 (s, 3H), 3.65 (s, 3H), 1.55 (s, 6H). MS (APCI+) m/z 287 (M+H)$^+$.

Example I-110B 2-(3-bromo-4-methoxyphenyl)-2-methylpropan-1-ol

To a solution of methyl 2-(3-bromo-4-methoxyphenyl)-2-methylpropanoate (2.1 g, 7.31 mmol) from Example I-110A in dichloromethane (20 mL) at 0° C. was added a solution of 1M diisobutylaluminium hydride in dichloromethane (14.63 mL, 14.63 mmol). The reaction was stirred at 0° C. for 2 hours and quenched with 30 mL 1 N aqueous citric acid. The organic layer was separated and the solvent was evaporated in vacuo. The resulting residue was chromatographed using a 24 g silica gel cartridge with gradient of 0-100% ethyl acetate/heptanes over a period of 10 minutes to provide the title compound. $^1$H NMR (500 MHz, chloroform-d) δ ppm 7.55 (d, J=2.4 Hz, 1H), 7.28 (dd, J=8.6, 2.4 Hz, 1H), 6.87 (d, J=8.6 Hz, 1H), 3.88 (s, 3H), 3.58 (d, J=6.3 Hz, 2H), 1.30 (s, 6H), 1.22 (t, J=6.5 Hz, 1H). MS (ESI+) m/z 241 (M+H-H$_2$O)$^+$.

Example I-110C 2-bromo-1-methoxy-4-(1-methoxy-2-methylpropan-2-yl)benzene

To a solution of 2-(3-bromo-4-methoxyphenyl)-2-methylpropan-1-ol (700 mg, 2.70 mmol) from Example I-110B in N,N-dimethylformamide (5 mL) at 0° C. was added sodium hydride (216 mg, 5.40 mmol) as a 60% by weight dispersion in mineral oil. After 30 minutes, iodomethane (0.338 mL, 5.40 mmol) was added and the reaction was stirred 1 hour at 0° C. and for 2 hours at ambient temperature. The mixture was quenched via addition of saturated aqueous ammonium chloride (80 mL) and extracted with ethyl acetate. The crude material was purified by chromatography, eluting on 12 g silica gel cartridge with a gradient of 0-50% ethyl acetate/heptanes over a period of 10 minutes to provide the title compound. $^1$H NMR (400 MHz, chloroform-d) δ ppm 7.53 (d, J=2.4 Hz, 1H), 7.30-7.26 (d, J=8.6, 2.4 Hz, 2H), 6.84 (d, J=8.6 Hz, 1H), 3.87 (s, 3H), 3.34 (s, 2H), 3.31 (s, 3H), 1.29 (s, 6H). MS (APCI+) m/z 241 (M+H-methanol)$^+$.

Example I-110D methyl 1-(2-methoxy-5-(1-methoxy-2-methylpropan-2-yl)phenyl)cyclopropanecarboxylate To a solution of 2-bromo-1-methoxy-4-(1-methoxy-2-methylpropan-2-yl)benzene (0.665 g, 2.434 mmol) from Example I-110C in tetrahydrofuran (8 mL) was added bis(dibenzylideneacetone)palladium (0.028 g, 0.049 mmol) and Q-Phos (1,2,3,4,5-pentaphenyl-1'-(di-tert-butylphosphino)ferrocene) (0.035 g, 0.049 mmol). Nitrogen was bubbled through the solution for about 3 minutes, and a 0.49 M in tetrahydrofuran solution of (1-(methoxycarbonyl)cyclopropyl)zinc(II) bromide (9.94 mL, 4.87 mmol) was added dropwise over 5 minutes. The reaction was stirred for 30 minutes at ambient temperature and for 3 hours at 67° C. The reaction was cooled to ambient temperature, quenched with saturated aqueous ammonium chloride (40 mL), diluted with ethyl acetate (40 mL), and the layers were separated. The organic layer was dried over sodium sulfate, filtered and concentrated in vacuo. The crude material was purified via chromatography on a 24 g silica gel cartridge, eluting with 100% dichloromethane for 13 minutes to provide the title compound. $^1$H NMR (501 MHz, chloroform-d) δ ppm 7.25 (dd, J=8.6, 2.5 Hz, 1H), 7.20 (d, J=2.5 Hz, 1H), 6.80 (d, J=8.6 Hz, 1H), 3.80 (s, 3H), 3.60 (s, 3H), 3.35 (s, 2H), 3.31 (s, 3H), 1.59 (q, J=4.0 Hz, 2H), 1.30 (s, 6H), 1.11 (q, J=4.1 Hz, 2H). MS (APCI+) m/z 261 (M+H-methanol)$^+$.

Example I-110E 1-(2-methoxy-5-(1-methoxy-2-methylpropan-2-yl) phenyl)cyclopropanecarboxylic Acid Methyl 1-(2-methoxy-5-(1-methoxy-2-methylpropan-2-yl)phenyl)cyclopropanecarboxylate (0.4 g, 1.368 mmol) from Example I-110D was dissolved in tetrahydrofuran (1.8 mL) and methanol (1.8 mL), and water (1.8 mL) and treated with sodium hydroxide (0.274 g, 6.84 mmol). The reaction mixture was stirred at 35° C. overnight, concentrated, cooled in an ice bath and carefully quenched with IN aqueous citric acid (about 3.4 mL) until the pH~5. The resulting slurry was stirred vigorously and the aqueous layer was decanted. The crude material was dissolved in ether. The mixture was concentrated, azeotroped with toluene (3×10 mL) to provide the title compound. $^1$H NMR (400 MHz, chloroform-d) δ ppm 7.25 (d, J=8.5, 2.5 Hz, 1H), 7.20 (d, J=2.5 Hz, 1H), 6.80 (d, J=8.5 Hz, 1H), 3.82 (s, 3H), 3.33 (s, 2H), 3.29 (s, 3H), 1.64 (q, J=4.0 Hz, 2H), 1.29 (s, 6H), 1.17 (q, J=4.1 Hz, 2H). MS (ESI−) m/z 277 (M−H)$^-$.

Example I-110F

1-[2-methoxy-5-(1-methoxy-2-methylpropan-2-yl) phenyl]-N-(quinoline-5-sulfonyl)cyclopropane-1-carboxamide To a solution of 1-(2-methoxy-5-(1-methoxy-2-methylpropan-2-yl)phenyl)cyclopropanecarboxylic acid (60 mg, 0.216 mmol) from Example I-110E, N$^1$-((ethylimino)methylene)-N$^3$,N$^3$-dimethylpropane-1,3-diamine hydrochloride (83 mg, 0.431 mmol) and N,N-dimethylpyridin-4-amine (29.0 mg, 0.237 mmol) in anhydrous dichloromethane (1 mL) was added quinoline-5-sulfonamide (44.9 mg, 0.216 mmol). After 16 hours, the reaction was quenched with 1 mL of 1N aqueous citric acid and the organic layer was concentrated in vacuo. The residue was purified via chromatography on a 12 g silica gel cartridge, eluting with a gradient of 0-10% methanol/dichloromethane over a period of 10 minutes. The material was triturated with diethyl ether (1.5 mL) and filtered to provide the title compound. $^1$H NMR (400 MHz, dimethyl sulfoxide-$d_6$) δ ppm 11.50 (s, 1H), 9.06 (dd, J=4.1, 1.6 Hz, 1H), 8.99 (d, J=8.7 Hz, OH), 8.35 (d, J=8.4 Hz, 1H), 8.31 (dd, J=7.5, 1.3 Hz, 1H), 7.94 (dd, J=8.4, 7.5 Hz, 1H), 7.72 (dd, J=8.8, 4.2 Hz, 1H), 7.23 (dd, J=8.6, 2.5 Hz, 1H), 7.07 (d, J=2.5 Hz, 1H), 6.77 (d, J=8.6 Hz, 1H), 3.33 (s, 3H), 3.30 (s, 2H), 3.21 (s, 3H), 1.30 (q, J=4.4 Hz, 2H), 1.22 (s, 6H), 0.96 (q, J=4.4 Hz, 2H). MS (ESI+) m/z 469 (M+H)$^+$.

Example I-111

1-(5-ethyl-2-{[(2R)-1-methoxypropan-2-yl]oxy}phenyl)-N-(quinoline-5-sulfonyl)cyclopropane-1-carboxamide Example I-111A 2-bromo-4-ethylphenol To a cooled 0° C. solution of 4-ethylphenol (12.94 g, 106 mmol) in dichloromethane (212 mL) was added dibromine (5.70 mL, 111 mmol) slowly. After the addition was complete, the reaction mixture was stirred for 5 minutes and quenched with 1N aqueous NaOH. The reaction mixture was diluted with water and the organic layer was separated, concentrated and purified on a 220 g silica gel cartridge eluting with a gradient 0-20% methyl tert-butyl ether/heptanes to provide the title compound. $^1$H NMR (400 MHz, chloroform-d) δ ppm 7.28 (d, J=2.1 Hz, 1H), 7.03 (dd, J=8.3, 2.1 Hz, 1H), 6.93 (d, J=8.3 Hz, 1H), 5.34 (s, 1H), 2.56 (q, J=7.6 Hz, 2H), 1.32-1.15 (t, 3H).

Example I-111B (R)-2-bromo-4-ethyl-1-((1-methoxypropan-2-yl)oxy)benzene

Into a 100 mL flask was added 2-bromo-4-ethylphenol (0.669 g, 3.33 mmol) from Example I-111A and triphenylphosphine (1.397 g, 5.33 mmol) in tetrahydrofuran (16 mL). The mixture was stirred briefly at ambient temperature under nitrogen, and (E)-diisopropyl diazene-1,2-dicarboxylate (1.049 mL, 5.33 mmol) was added. The mixture was stirred briefly under nitrogen at ambient temperature, (S)-1-methoxypropan-2-ol (0.326 mL, 3.33 mmol) was added dropwise and the reaction was stirred overnight at ambient temperature. The solvent was removed under reduced pressure, and the crude material was purified by chromatography, eluting on a 24 g silica gel cartridge with a gradient of 0-30% ethyl acetate/heptanes over a period of 10 minutes to provide the title compound. $^1$H NMR (400 MHz, chloroform-d) δ ppm 7.36 (d, J=2.2 Hz, 1H), 7.05 (dd, J=8.3, 2.2 Hz, 1H), 6.91 (d, J=8.4 Hz, 1H), 4.55-4.36 (m, 1H), 3.63 (dd, J=10.3, 5.8 Hz, 1H), 3.51 (dd, J=10.3, 4.7 Hz, 1H), 3.43 (s, 3H), 2.57 (q, J=7.6 Hz, 2H), 1.34 (d, J=6.2 Hz, 3H), 1.20 (t, J=7.6 Hz, 3H). MS (APCI+) m/z 273 (M+H)$^+$.

Example I-111C (R)-methyl 1-(5-ethyl-2-((1-methoxypropan-2-yl)oxy)phenyl)cyclopropanecarboxylate To a solution of (R)-2-bromo-4-ethyl-1-((1-methoxypropan-2-yl)oxy)benzene (0.48 g, 1.757 mmol) from Example I-111B in tetrahydrofuran (7 mL) was added bis(dibenzylideneacetone)palladium (0.020 g, 0.035 mmol) and Q-Phos (1,2,3,4,5-pentaphenyl-1'-(di-tert-butylphosphino)ferrocene) (0.025 g, 0.035 mmol). Nitrogen was bubbled through the solution for about 3 minutes, then a 0.54 M in tetrahydrofuran solution of (1-(methoxycarbonyl)cyclopropyl)zinc(II) bromide (7.81 mL, 3.51 mmol) was added dropwise over 5 minutes. The reaction was stirred for 16 hours at 35° C. The reaction mixture was quenched with saturated aqueous ammonium chloride (40 mL), diluted with ethyl acetate (40 mL), and the layers were separated. The organic layer was dried over sodium sulfate, filtered and concentrated in vacuo. The crude material was purified via chromatography on a 24 g silica gel cartridge, eluting with ethyl acetate in heptane at 0-100% gradient over a period of 12 minutes. The material was chromatographed again on a 12 g silica gel cartridge, eluting with 100% dichloromethane for 8 mins to provide the title compound. $^1$H NMR (501 MHz, chloroform-d) δ ppm 7.05 (dd, J=8.3, 2.3 Hz, 1H), 7.01 (d, J=2.3 Hz, 1H), 6.81 (d, J=8.3 Hz, 1H), 4.53 (h, J=5.9 Hz, 1H), 3.59 (s, 3H), 3.57 (dd, J=10.2, 5.7 Hz, 1H), 3.42 (dd, J=10.1, 5.1 Hz, 1H), 3.39 (s, 3H), 2.58 (q, J=7.6 Hz, 2H), 1.58-1.55 (m, 2H), 1.27 (d, J=6.2 Hz, 3H), 1.21 (t, J=7.6 Hz, 3H), 1.11 (t, J=3.8 Hz, 2H). MS (APCI+) m/z 293 (M+H)$^+$.

Example I-111D (R)-1-(5-ethyl-2-((1-methoxypropan-2-yl)oxy)phenyl)cyclopropanecarboxylic Acid (R)-Methyl 1-(5-ethyl-2-((1-methoxypropan-2-yl)oxy)phenyl)cyclopropanecarboxylate (0.44 g, 1.505 mmol) from Example I-111C was dissolved in tetrahydrofuran (2 mL), methanol (2 mL), and water (2 mL), and treated with sodium hydroxide (0.301 g, 7.52 mmol). The reaction mixture was stirred at 35° C. overnight, concentrated, cooled in an ice bath, and carefully quenched with 1N aqueous citric acid (about 3.6 mL) until the pH 5. The resulting slurry was extracted with dichloromethane, and concentrated. The crude material was azeotroped with toluene (3×10 mL) to provide the title compound. $^1$H NMR (501 MHz, chloroform-d) δ ppm 7.09-7.02 (m, 2H), 6.82 (d, J=8.1 Hz, 1H), 4.55 (h, J=6.0 Hz, 1H), 3.58 (dd, J=10.2, 5.6 Hz, 1H), 3.44 (dd, J=10.2, 5.0 Hz, 1H), 3.38 (s, 3H), 2.56 (q, J=7.6 Hz, 2H), 1.66-1.56 (m, 2H), 1.30 (d, J=6.2 Hz, 3H), 1.19 (t, J=7.6 Hz, 3H), 1.17-1.11 (m, 2H). MS (ESI−) m/z 279 (M+H)$^+$.

Example I-111E 1-(5-ethyl-2-{[(2R)-1-methoxypropan-2-yl]oxy}phenyl)-N-(quinoline-5-sulfonyl)cyclopropane-1-carboxamide To a solution of (R)-1-(5-ethyl-2-((1-methoxypropan-2-yl)oxy)phenyl)cyclopropanecarboxylic acid (60 mg, 0.216 mmol) from Example I-111D, N$^1$-((ethylimino)methylene)-N$^3$,N$^3$-dimethylpropane-1,3-diamine hydrochloride (83 mg, 0.431 mmol) and N,N-dimethylpyridin-4-amine (29.0 mg, 0.237 mmol) in anhydrous dichloromethane (1 mL) was added quinoline-5-sulfonamide (44.9 mg, 0.216 mmol). After 16 hours, the reaction was quenched with 1 mL of 1N aqueous citric acid and the organic layer was concentrated in vacuo. The residue was purified via chromatography on a 12 g silica gel cartridge, eluting with a gradient of 0-10% methanol/dichloromethane over a period of 10 minutes. The crude material was triturated with diethyl ether (1.5 mL) and filtered to provide the title compound. $^1$H NMR (400 MHz, dimethyl sulfoxide-$d_6$) δ ppm 11.46 (s, 1H), 9.10-8.98 (m, 2H), 8.43-8.24 (m, 2H), 7.92 (t, J=7.9 Hz, 1H), 7.71 (dd, J=8.7, 4.3 Hz, 1H), 7.04 (dd, J=8.4, 2.2 Hz, 1H), 6.93 (d, J=2.3 Hz, 1H), 6.82 (d, J=8.4 Hz, 1H), 4.35 (p, J=5.9 Hz, 1H), 3.15 (s, 3H), 3.06 (dd, J=10.3, 5.6 Hz, 1H), 2.99 (dd, J=10.3, 5.1 Hz, 1H), 2.51 (q, J=7.6 Hz, 2H), 1.36 (ddd, J=10.8, 6.8, 4.3 Hz, 1H), 1.22 (ddd, J=9.5, 6.8, 4.3 Hz, 1H), 1.14 (t, J=7.6 Hz, 3H), 1.02 (bs, 1H), 0.88 (bs, 1H), 0.83 (d, J=6.2 Hz, 3H). MS (APCI+) m/z 469 (M+H)$^+$.

Example I-112

1-(5-ethyl-2-{[(2R)-1-methoxypropan-2-yl]oxy}phenyl)-N-(2-methylquinoline-5-sulfonyl)cyclopropane-1-carboxamide To a solution of (R)-1-(5-ethyl-2-((1-methoxypropan-2-yl)oxy)phenyl)cyclopropanecarboxylic acid (60 mg, 0.216 mmol) from Example I-111D, N$^1$-((ethylimino)methylene)-N$^3$,N$^3$-dimethylpropane-1,3-diamine hydrochloride (83 mg, 0.431 mmol) and N,N-dimethylpyridin-4-amine (29.0 mg, 0.237 mmol) in anhydrous dichloromethane (1 mL) was added 2-methylquinoline-5-sulfonamide (47.9 mg, 0.216 mmol). After 16 hours, the reaction was quenched with 1 mL of 1N aqueous citric acid and the organic layer was concentrated in vacuo. The residue was purified via chromatography on a 12 g silica gel cartridge, eluting with a gradient of 0-10% methanol/dichloromethane over a period of 10 minutes. The crude material was triturated with diethyl ether (0.5 mL) and filtered to provide the title compound. $^1$H NMR (400 MHz, dimethyl sulfoxide-$d_6$) δ ppm 11.40 (s, 1H), 8.90 (d, J=8.9 Hz, 1H), 8.21 (dd, J=7.8, 4.6 Hz, 2H), 7.85 (t, J=8.0 Hz, 1H), 7.60 (d, J=8.9 Hz, 1H), 7.04 (dd, J=8.4, 2.2 Hz, 1H), 6.93 (d, J=2.3 Hz, 1H), 6.82 (d, J=8.4 Hz, 1H), 4.36 (p, J=5.9 Hz, 1H), 3.15 (s, 3H), 3.06 (dd, J=10.3, 5.6 Hz, 1H), 3.00 (dd, J=10.3, 5.1 Hz, 1H), 2.70 (s, 3H), 2.50 (q, J=7.6 Hz, 2H), 1.36 (ddd, J=11.1, 6.7, 4.4 Hz, 1H), 1.22 (ddd, J=9.6, 7.0, 4.3 Hz, 1H), 1.14 (t, J=7.6 Hz, 3H), 1.02 (bs, 1H), 0.88 (bs, 1H), 0.85 (d, J=6.2 Hz, 3H). MS (APCI+) m/z 483 (M+H)$^+$.

Example I-113

1-{2-[(2S)-2-methoxypropoxy]-5-methylphenyl}-N-(quinoline-5-sulfonyl)cyclopropane-1-carboxamide Example I-113A (S)-2-bromo-1-(2-methoxypropoxy)-4-methylbenzene To a cooled (−30° C.) solution of (2S)-2-methoxy-1-propanol (0.637 mL, 6.13 mmol) in dichloromethane (6 mL) was added methanesulfonyl chloride (0.717 mL, 9.20 mmol) followed by dropwise addition of N-ethyl-N-isopropylpropan-2-amine (1.713 mL, 9.81 mmol). The mixture was stirred at −20° C. for 45 minutes, quenched with cold 1N aqueous HCl and brine and diluted with dichloromethane. The organics were separated, dried over sodium sulfate, filtered, and concentrated to provide the crude mesylate. The crude mesylate was combined with 2-bromo-4-methylphenol (0.5 mL, 4.09 mmol) and cesium carbonate (4.00 g, 12.26 mmol) in anhydrous N,N-dimethylformamide and the reaction was heated at 50° C. for 16 hours. The reaction was cooled to ambient temperature, diluted with water (40 mL) and ethyl acetate (200 mL), and the layers were separated. The organics were washed with water and brine, dried over anhydrous sodium sulfate, filtered through silica gel, and concentrated. The residue was purified via chromatography on a 40 g silica gel cartridge, eluting with ethyl acetate in hexanes at 0-40% gradient over 20 minutes. The material was chromatographed again using a 40 g silica gel cartridge with a gradient of 0-50% methyl tert-butyl ether/hexanes over 40 minutes to provide the title compound. $^1$H NMR (400 MHz, chloroform-d) δ ppm 7.37 (d, J=2.2 Hz, 1H), 7.04 (dq, J=8.3, 0.9 Hz, 1H), 6.80 (d, J=8.2 Hz, 1H), 4.03 (dd, J=9.5, 5.9 Hz, 1H), 3.89 (dd, J=9.5, 4.8 Hz, 1H), 3.82-3.74 (m, 1H), 3.50 (d, J=0.5 Hz, 3H), 2.31-2.23 (m, 3H), 1.31 (d, J=6.3 Hz, 3H). MS (ESI+) m/z 259 (M+H)$^+$ bromine doublet.

Example I-113B (S)-methyl 1-(2-(2-methoxypropoxy)-5-methylphenyl)cyclopropanecarboxylate To a solution of (S)-2-bromo-1-(2-methoxypropoxy)-4-methylbenzene (0.545 g, 2.103 mmol) from Example I-113A in tetrahydrofuran (4 mL) was added bis(dibenzylideneacetone)palladium (0.024 g, 0.042 mmol) and Q-Phos (1,2,3,4,5-pentaphenyl-1'-(di-tert-butylphosphino)ferrocene) (0.030 g, 0.042 mmol). Nitrogen was bubbled through the solution for about 3 minutes, and a 0.45 M in tetrahydrofuran solution of (1-(methoxycarbonyl)cyclopropyl)zinc(II) bromide (9.35 mL, 4.21 mmol) was added dropwise over 5 minutes. The reaction mixture was stirred at ambient temperature for 15 hours. The reaction was quenched with saturated aqueous ammonium chloride (20 mL) and diluted with ethyl acetate (200 mL). Pyrrolidine-1-carbodithioic acid, ammonia salt (6.91 mg, 0.042 mmol) was added to sequester the Pd and the mixture was stirred for 30 minutes. Decolorizing charcoal was added and the layers were filtered and separated. The organic layer was dried over sodium sulfate, filtered and concentrated in vacuo. The residue was purified via flash chromatography, eluting on a 40 g silica gel cartridge with 0-50% ethyl acetate/hexanes over 20 minutes to provide the title compound. $^1$H NMR (501 MHz, chloroform-d) δ ppm 7.06 (ddd, J=8.2, 2.3, 0.9 Hz, 1H), 7.03 (d, J=2.2 Hz, 1H), 6.77 (d, J=8.2 Hz, 1H), 4.03 (dd, J=9.3, 5.6 Hz, 1H), 3.83 (dd, J=9.3, 5.3 Hz, 1H), 3.70 (dtd, J=11.7, 6.3, 5.4 Hz, 1H), 3.62 (s, 3H), 3.46 (s, 3H), 2.30 (d, J=0.7 Hz, 3H), 1.65-1.59 (m, 2H), 1.27 (d, J=6.3 Hz, 3H), 1.17-1.11 (m, 2H). MS (ESI+) m/z 279 (M+H)$^+$.

Example I-113C (S)-1-(2-(2-methoxypropoxy)-5-methylphenyl)cyclopropanecarboxylic Acid (S)-Methyl 1-(2-(2-methoxypropoxy)-5-methylphenyl)cyclopropanecarboxylate (0.574 g, 2.062 mmol) from Example I-113B was dissolved in tetrahydrofuran (2 mL), methanol (2 mL) and water (2 mL). The mixture was treated with sodium hydroxide (0.577 g, 14.44 mmol) and stirred at 70° C. for 45 minutes. The reaction mixture was reduced in volume, cooled in an ice bath and carefully quenched with 3N aqueous HCl (about 5 mL, diluted with ice) until the pH was acidic. The resulting material was stirred vigorously and the water was decanted. The material was washed with water and dried under a stream of nitrogen to provide the title compound. $^1$H NMR (400 MHz, chloroform-d) δ ppm 7.08-6.96 (m, 2H), 6.75 (d, J=8.2 Hz, 1H), 4.01 (dd, J=9.3, 5.7 Hz, 1H), 3.83 (dd, J=9.4, 5.1 Hz, 1H), 3.70 (hept, J=6.0, 5.6 Hz, 1H), 3.44 (s, 3H), 2.27 (s, 3H), 1.63 (q, J=2.9 Hz, 2H), 1.26 (d, J=6.3 Hz, 3H), 1.21-1.11 (m, 2H). MS (ESI−) m/z 263 (M−H)$^-$. X-ray analysis to confirmed absolute sterochemistry (S).

Example I-113D

1-{2-[(2S)-2-methoxypropoxy]-5-methylphenyl}-N-(quinoline-5-sulfonyl)cyclopropane-1-carboxamide To a solution of (S)-1-(2-(2-methoxypropoxy)-5-methylphenyl)cyclopropanecarboxylic acid (62 mg, 0.235 mmol) from Example I-113C, N$^1$-((ethylimino)methylene)-N$^3$,N$^3$-dimethylpropane-1,3-diamine hydrochloride (90 mg, 0.469 mmol) and N,N-dimethylpyridin-4-amine (28.7 mg, 0.235 mmol) in anhydrous dichloromethane (1 mL) was added quinoline-5-sulfonamide (59 mg, 0.283 mmol). The reaction was stirred at ambient temperature for 15 hours. The reaction was quenched with 0.2 mL of aqueous 2N citric acid and the residue was purified via chromatography on a 12 g silica gel cartridge, eluting with a gradient of 0-10% methanol/dichloromethane over a period of 20 minutes. The material was dissolved in methanol/dimethyl sulfoxide and purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (400 MHz, dimethyl sulfoxide-d$_6$) δ ppm 11.45 (s, 1H), 9.02 (dd, J=4.2, 1.6 Hz, 1H), 8.92-8.88 (m, 1H), 8.34-8.27 (m, 2H), 7.90 (dd, J=8.4, 7.5 Hz, 1H), 7.65 (dd, J=8.8, 4.2 Hz, 1H), 7.01 (dd, J=8.3, 2.1 Hz, 1H), 6.93 (d, J=2.2 Hz, 1H), 6.70 (d, J=8.3 Hz, 1H), 3.56 (dd, J=9.6, 5.9 Hz, 1H), 3.31 (dd, J=9.5, 5.2 Hz, 1H), 3.05 (s, 3H), 2.89-2.75 (m, 1H), 2.19 (s, 3H), 1.23 (tq, J=9.4, 3.4 Hz, 2H), 1.00-0.92 (m, 1H), 0.88 (ddd, J=7.9, 5.6, 2.7 Hz, 1H), 0.75 (d, J=6.3 Hz, 3H). MS (ESI+) m/z 455 (M+H)$^+$.

Example I-114

1-{2-[(2S)-2-methoxypropoxy]-5-methylphenyl}-N-(2-methylquinoline-5-sulfonyl)cyclopropane-1-carboxamide To a solution of (S)-1-(2-(2-methoxypropoxy)-5-methylphenyl)cyclopropanecarboxylic acid (62 mg, 0.235 mmol) from Example I-113C, N$^1$-((ethylimino)methylene)-N$^3$,N$^3$-dimethylpropane-1,3-diamine hydrochloride (90 mg, 0.469 mmol) and N,N-dimethylpyridin-4-amine (28.7 mg, 0.235 mmol) in anhydrous dichloromethane (1 mL) was added 2-methylquinoline-5-sulfonamide (53 mg, 0.238 mmol). The reaction was stirred at ambient temperature for 16 hours. The reaction was quenched with 0.2 mL of 2N aqueous citric acid and the residue was purified via chromatography on a 12 g silica gel cartridge, eluting with a gradient of 0-10% methanol/dichloromethane over a period of 20 minutes. The crude material was dissolved in methanol/dimethyl sulfoxide and was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (400 MHz, dimethyl sulfoxide-d$_6$) δ ppm 11.43 (s, 1H), 8.90 (d, J=8.9 Hz, 1H), 8.24 (d, J=7.7 Hz, 2H), 7.89 (t, J=8.0 Hz, 1H), 7.63 (d, J=9.0 Hz, 1H), 7.06-6.97 (m, 1H), 6.92 (d, J=2.3 Hz, 1H), 6.72 (d, J=8.2 Hz, 1H), 3.60 (dd, J=9.5, 6.0 Hz, 1H), 3.37 (dd, J=9.6, 5.2 Hz, 1H), 3.06 (s, 3H), 2.90 (h, J=6.2 Hz, 1H), 2.72 (s, 3H), 2.19 (s, 3H), 1.30-1.15 (m, 2H), 0.95 (ddd, J=9.1, 5.3, 2.5 Hz, 1H), 0.89 (ddd, J=8.0, 5.4, 2.2 Hz, 1H), 0.79 (d, J=6.3 Hz, 3H). MS (ESI+) m/z 469 (M+H)$^+$.

Example I-115

1-{2-[(2R)-2-methoxypropoxy]-5-methylphenyl}-N-(quinoline-5-sulfonyl)cyclopropane-1-carboxamide Example I-115A (R)-2-bromo-1-(2-methoxypropoxy)-4-methylbenzene To a cooled (−30° C.) solution of (R)-2-methoxypropan-1-ol (0.553 g, 6.13 mmol) in dichloromethane (6 mL) was added methanesulfonyl chloride (0.717 mL, 9.20 mmol) followed by dropwise addition of N-ethyl-N-isopropylpropan-2-amine (1.713 mL, 9.81 mmol). The mixture was stirred at −20° C. for 45 minutes, quenched with cold 1N aqueous HCl and brine, and diluted with dichloromethane. The organics were separated and dried over sodium sulfate and the solvent removed in vacuo to give crude mesylate. The crude mesylate was combined with 2-bromo-4-methylphenol (0.5 mL, 4.09 mmol) and cesium carbonate (4.08 g, 12.52 mmol) in anhydrous N,N-dimethylformamide and the reaction was heated at 70° C. for 15 hours. The reaction was diluted with ethyl acetate and filtered. The material was washed with 200 mL of ethyl acetate. The organics were sequentially washed with 1N aqueous sodium hydroxide (40 mL), water (40 mL) and brine (40 mL). The organics were dried over anhydrous sodium sulfate, filtered, and concentrated. The residue was purified via chromatography on a 80 g silica gel cartridge, eluting with 0-50% methyl tert-butyl ether/hexanes over 40 minutes to provide the title compound. $^1$H NMR (501 MHz, chloroform-d) δ ppm 7.38 (dd, J=2.2, 0.8 Hz, 1H), 7.06 (ddt, J=8.3, 2.2, 0.7 Hz, 1H), 6.82 (d, J=8.3 Hz, 1H), 4.04 (dd, J=9.5, 5.9 Hz, 1H), 3.90 (dd, J=9.5, 4.8 Hz, 1H), 3.79 (pd, J=6.2, 4.9 Hz, 1H), 3.52 (d, J=0.6 Hz, 3H), 2.29 (d, J=0.8 Hz, 3H), 1.35-1.29 (m, 3H).

Example I-115B (R)-methyl 1-(2-(2-methoxypropoxy)-5-methylphenyl)cyclopropanecarboxylate To a solution of (R)-2-bromo-1-(2-methoxypropoxy)-4-methylbenzene (0.595 g, 2.296 mmol) from Example I-115A in tetrahydrofuran (4 mL) was added bis(dibenzylideneacetone)palladium (0.026 g, 0.046 mmol) and Q-Phos (1,2,3,4,5-pentaphenyl-1'-(di-tert-butylphosphino)ferrocene) (0.033 g, 0.046 mmol). Nitrogen was bubbled through the solution for about 3 minutes. A tetrahydrofuran solution (0.45M) of (1-(methoxycarbonyl)cyclopropyl)zinc (II) bromide (10.20 mL, 4.59 mmol) was added dropwise over 5 minutes. The reaction was stirred at ambient temperature for 15 hours. The reaction was quenched with saturated aqueous ammonium chloride (20 mL) and diluted with methyl tert-butyl ether (200 mL). The layers were separated. The organic layer was dried over sodium sulfate, filtered and concentrated in vacuo. The crude material was purified via flash chromatography, eluting on a 40 g silica gel cartridge with 0-100% methyl tert-butyl ether/hexanes over 40 minutes to provide the title compound. $^1$H NMR (400 MHz, chloroform-d) δ ppm 7.07-7.00 (m, 2H), 6.75 (d, J=8.2 Hz, 1H), 4.01 (dd, J=9.3, 5.6 Hz, 1H), 3.82 (dd, J=9.3, 5.3 Hz, 1H), 3.72-3.64 (m, 1H), 3.61 (s, 3H), 3.45 (s, 3H), 2.29 (s, 3H), 1.60 (q, J=3.2 Hz, 2H), 1.26 (d, J=6.3 Hz, 3H), 1.13 (dt, J=4.2, 2.5 Hz, 2H). MS (ESI+) m/z 279 (M+H)$^+$.

Example I-115C (R)-1-(2-(2-methoxypropoxy)-5-methylphenyl)cyclopropanecarboxylic Acid (R)-Methyl 1-(2-(2-methoxypropoxy)-5-methylphenyl) cyclopropanecarboxylate (0.634 g, 2.278 mmol) from Example I-115B was dissolved in tetrahydrofuran (2 mL), methanol (2 mL), and water (2 mL), treated with sodium hydroxide (0.787 g, 19.68 mmol), and stirred at 50° C. After 2 hours, the reaction mixture was reduced in volume, cooled in an ice bath and carefully quenched with 3N aqueous HCl (about 7 mL, diluted with ice) until the pH was acidic. The resulting material was stirred vigorously and the water was decanted. The material was washed with water and dried under a stream of nitrogen to provide the title compound. $^1$H NMR (501 MHz, chloroform-d) δ ppm 7.08-7.01 (m, 2H), 6.76 (d, J=8.2 Hz, 1H), 4.04 (dd, J=9.3, 5.6 Hz, 1H), 3.84 (dd, J=9.3, 5.2 Hz, 1H), 3.72 (ddd, J=11.9, 6.5, 5.5 Hz, 1H), 3.46 (s, 3H), 2.29 (s, 3H), 1.67-1.62 (m, 2H), 1.28 (d, J=6.3 Hz, 3H), 1.23-1.17 (m, 2H). MS (ESI–) m/z 263 (M–H)$^-$.

Example I-115D

1-{2-[(2R)-2-methoxypropoxy]-5-methylphenyl}-N-(quinoline-5-sulfonyl)cyclopropane-1-carboxamide To a solution of (R)-1-(2-(2-methoxypropoxy)-5-methylphenyl)cyclopropanecarboxylic acid (71 mg, 0.269 mmol) from Example I-115C, N$^1$-((ethylimino)methylene)-N$^3$,N$^3$-dimethylpropane-1,3-diamine hydrochloride (103 mg, 0.537 mmol) and N,N-dimethylpyridin-4-amine (32.8 mg, 0.269 mmol) in anhydrous dichloromethane (1 mL) was added quinoline-5-sulfonamide (55.9 mg, 0.269 mmol). The reaction was stirred at ambient temperature for 16 hours. The reaction mixture was quenched with 0.2 mL of 2N aqueous citric acid and the residue was purified via chromatography on a 12 g silica gel cartridge, eluting with a gradient of 0-10% methanol/dichloromethane over a period of 20 minutes. The material was dissolved in methanol/dimethyl sulfoxide and was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes linear gradient 95-10% A) to provide the title compound as a trifluoroacetic acid salt. $^1$H NMR (400 MHz, dimethyl sulfoxide-d$_6$) δ ppm 11.45 (s, 1H), 9.02 (dd, J=4.2, 1.6 Hz, 1H), 8.91 (dt, J=8.7, 1.2 Hz, 1H), 8.34-8.26 (m, 2H), 7.90 (dd, J=8.4, 7.5 Hz, 1H), 7.65 (dd, J=8.8, 4.2 Hz, 1H), 7.04-6.99 (m, 1H), 6.93 (d, J=2.1 Hz, 1H), 6.70 (d, J=8.3 Hz, 1H), 3.56 (dd, J=9.5, 5.9 Hz, 1H), 3.31 (dd, J=9.5, 5.2 Hz, 1H), 3.05 (s, 3H), 2.85 (p, J=6.0 Hz, 1H), 2.19 (s, 3H), 1.23 (tq, J=9.5, 3.4 Hz, 2H), 1.00-0.92 (m, 1H), 0.88 (ddd, J=7.8, 5.5, 2.8 Hz, 1H), 0.75 (d, J=6.3 Hz, 3H). MS (ESI+) m/z 455 (M+H)$^+$.

Example I-116

1-{2-[(2R)-2-methoxypropoxy]-5-methylphenyl}-N-(2-methylquinoline-5-sulfonyl)cyclopropane-1-carboxamide To a solution of (R)-1-(2-(2-methoxypropoxy)-5-methylphenyl)cyclopropanecarboxylic acid (83 mg, 0.314 mmol) from Example I-115C, N$^1$-((ethylimino)methylene)-N$^3$,N$^3$-dimethylpropane-1,3-diamine hydrochloride (120 mg, 0.628 mmol) and N,N-dimethylpyridin-4-amine (38.4 mg, 0.314 mmol) in anhydrous dichloromethane (1 mL) was added 2-methylquinoline-5-sulfonamide (74 mg, 0.333 mmol). The reaction was stirred at ambient temperature for 15 hours. The reaction was quenched with 0.2 mL of aqueous 2N citric acid and the residue was purified via chromatography on a 12 g silica gel cartridge, eluting with a gradient of 0-10% methanol/dichloromethane over a period of 20 minutes. The material was dissolved in methanol/dimethyl sulfoxide and was purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (501 MHz, dimethyl sulfoxide-d$_6$) δ ppm 11.43 (s, 1H), 8.87 (d, J=8.9 Hz, 1H), 8.24 (ddt, J=7.4, 2.6, 1.1 Hz, 2H), 7.89 (dd, J=8.3, 7.6 Hz, 1H), 7.61 (d, J=8.9 Hz, 1H), 7.03 (ddd, J=8.2, 2.3, 0.8 Hz, 1H), 6.94 (d, J=2.1 Hz, 1H), 6.73 (d, J=8.3 Hz, 1H), 3.60 (dd, J=9.5, 6.0 Hz, 1H), 3.37 (dd, J=9.4, 5.2 Hz, 1H), 3.07 (s, 3H), 2.90 (dt, J=11.8, 6.0 Hz, 1H), 2.72 (s, 3H), 2.21 (s, 3H), 1.31-1.20 (m, 2H), 0.97 (ddd, J=10.1, 5.9, 3.2 Hz, 1H), 0.90 (ddd, J=8.2, 5.8, 3.0 Hz, 1H), 0.79 (d, J=6.3 Hz, 3H). MS (ESI+) m/z 469 (M+H)$^+$. (R) absolute stereochemistry confirmed by X-ray analysis.

Example I-117

1-(5-ethyl-2-{[(3S)-oxolan-3-yl]oxy}phenyl)-N-(quinoline-5-sulfonyl)cyclopropane-1-carboxamide Example I-117A (S)-3-(2-bromo-4-ethylphenoxy)tetrahydrofuran In a 100 mL flask was added 2-bromo-4-ethylphenol (0.685 g, 3.41 mmol) from Example I-111A and triphenylphosphine (1.429 g, 5.45 mmol) in tetrahydrofuran (16 mL). The mixture was stirred briefly at ambient temperature, under nitrogen, and (E)-diisopropyl diazene-1,2-dicarboxylate (1.073 mL, 5.45 mmol) was added. The mixture was stirred briefly under nitrogen at ambient temperature and (R)-tetrahydrofuran-3-ol (0.3 g, 3.41 mmol) was added dropwise. The reaction mixture was stirred overnight at ambient temperature. The solvent was removed under reduced pressurerude material was purified by chromatography, eluting on 24 g silica gel cartridge with a gradient of 0-30% ethyl acetate/heptanes over a period of 10 minutes to provide the title compound. $^1$H NMR (501 MHz, chloroform-d) δ ppm 7.39 (d, J=2.1 Hz, 1H), 7.05 (dd, J=8.3, 2.2 Hz, 1H), 6.76 (d, J=8.3 Hz, 1H), 4.92 (ddt, J=6.8, 4.8, 2.4 Hz, 1H), 4.07-3.98 (m, 3H), 3.93 (td, J=8.1, 4.2 Hz, 1H), 2.57 (q, J=7.6 Hz, 2H), 2.26-2.11 (m, 2H), 1.20 (t, J=7.6 Hz, 3H). MS (APCI+) m/z 271 (M+H)$^+$.

Example I-117B (S)-methyl 1-(5-ethyl-2-((tetrahydrofuran-3-yl)oxy)phenyl)cyclopropanecarboxylate To a solution of (5)-3-(2-bromo-4-ethylphenoxy)tetrahydrofuran (0.39 g, 1.438 mmol) from Example I-117A in tetrahydrofuran (6 mL) was added bis(dibenzylideneacetone)palladium (0.017 g, 0.029 mmol) and Q-Phos (1,2,3,4,5-pentaphenyl-1'-(di-tert-butylphosphino)ferrocene) (0.020 g, 0.029 mmol). Nitrogen was bubbled through the solution for about 3 minutes, and a 0.45 M in tetrahydrofuran solution of (1-(methoxycarbonyl)cyclopropyl)zinc(II) bromide (6.39 mL, 2.88 mmol) was added dropwise over 2 minutes. The reaction was stirred for 4 hours at 50° C. The reaction was quenched with saturated ammonium chloride (60 mL), diluted with ethyl acetate (40 mL) and the layers were separated. The organic layer was dried over sodium sulfate, filtered and concentrated in vacuo. The crude material was purified via chromatography on a 24 g silica gel cartridge, eluting with ethyl acetate in heptane at 0-100% gradient over a period of 12 minutes to provide the title compound. $^1$H NMR (501 MHz, chloroform-d) δ ppm 7.05 (dd, J=8.2, 2.3 Hz, 1H), 7.03 (d, J=2.2 Hz, 1H), 6.68 (d, J=8.2 Hz, 1H), 4.96 (tt, J=5.0, 2.1 Hz, 1H), 4.02 (dd, J=10.0, 4.8 Hz, 1H), 3.94-3.84 (m, 3H), 3.59 (s, 3H), 2.58 (q, J=7.6 Hz, 2H), 2.19-2.09 (m, 2H), 1.62-1.53 (m, 2H), 1.21 (t, J=7.6 Hz, 3H), 1.14-1.05 (m, 2H). MS (APCI+) m/z 291 (M+H)$^+$.

Example I-117C (S)-1-(5-ethyl-2-((tetrahydrofuran-3-yl)oxy)phenyl)cyclopropanecarboxylic Acid (S)-Methyl 1-(5-ethyl-2-((tetrahydrofuran-3-yl)oxy)phenyl)cyclopropanecarboxylate (0.375 g, 1.292 mmol) from Example I-117B was dissolved in tetrahydrofuran (1.5 mL), methanol (1.5 mL), and water (1.5 mL) and treated with sodium hydroxide (0.258 g, 6.46 mmol). The reaction was stirred at 35° C. for 15 hours, concentrated, cooled in an ice bath and carefully quenched with IN aqueous citric acid (about 3.6 mL) until the pH~5. The resulting slurry was extracted with dichloromethane. The dichloromethane layer was concentrated and azeotroped with toluene 3×10 mL to provide the title compound. $^1$H NMR (501 MHz, chloroform-d) δ ppm 7.09-7.01 (m, 2H), 6.69 (d, J=9.0 Hz, 1H), 4.98-4.93 (m, 1H), 4.03 (dd, J=10.0, 4.8 Hz, 1H), 3.95-3.87 (m, 3H), 2.57 (q, J=7.6 Hz, 2H), 2.18-2.10 (m, 2H), 1.63 (q, J=3.9 Hz, 2H), 1.20 (t, J=7.6 Hz, 2H), 1.17-1.12 (m, 2H). MS (APCI+) m/z 277 (M+H)$^+$.

Example I-117D 1-(5-ethyl-2-{[(3S)-oxolan-3-yl]oxy}phenyl)-N-(quinoline-5-sulfonyl)cyclopropane-1-carboxamide To a solution of (S)-1-(5-ethyl-2-((tetrahydrofuran-3-yl)oxy)phenyl)cyclopropanecarboxylic acid (70 mg, 0.253 mmol) from Example I-117C, N$^1$-((ethylimino)methylene)-N$^3$,N$^3$-dimethylpropane-1,3-diamine hydrochloride (97 mg, 0.507 mmol) and N,N-dimethylpyridin-4-amine (34.0 mg, 0.279 mmol) in anhydrous dichloromethane (1 mL) was added quinoline-5-sulfonamide (52.8 mg, 0.253 mmol). After 16 hours, the reaction was quenched with 1 mL of IN aqueous citric acid and the organic layer was concentrated in vacuo. The residue was purified via chromatography on a 12 g silica gel cartridge, eluting with a gradient of 0-10% methanol/dichloromethane over a period of 10 minutes, The crude material was triturated with diethyl ether (1.5 mL) and filtered to provide the title compound. $^1$H NMR (400 MHz, dimethyl sulfoxide-d$_6$) δ ppm 11.52 (s, 1H), 9.04 (dd, J=4.3, 1.6 Hz, 1H), 8.95 (d, J=8.6 Hz, 1H), 8.32 (dd, J=13.3, 8.0 Hz, 2H), 7.92 (t, J=8.0 Hz, 1H), 7.68 (dd, J=8.8, 4.2 Hz, 1H), 7.10-7.03 (m, 1H), 6.98 (d, J=2.2 Hz, 1H), 6.73 (d, J=8.3 Hz, 1H), 4.64 (t, J=5.6 Hz, 1H), 3.63 (dd, J=9.9, 4.9 Hz, 1H), 3.55 (td, J=8.1, 3.5 Hz, 1H), 3.43 (td, J=8.6, 6.3 Hz, 1H), 3.19 (dd, J=9.8, 2.0 Hz, 1H), 2.53 (q, J=7.6 Hz, 1H), 1.78 (dtd, J=17.5, 8.6, 6.1 Hz, 1H), 1.39 (m, 1H), 1.26 (ddd, J=9.2, 6.3, 3.6 Hz, 1H), 1.16 (t, J=7.6 Hz, 3H), 0.93 (d, J=21.4 Hz, 2H). MS (APCI+) m/z 467 (M+H)$^+$.

Example I-118

1-(5-ethyl-2-{[(3R)-oxolan-3-yl]oxy}phenyl)-N-(quinoline-5-sulfonyl)cyclopropane-1-carboxamide Example I-118A 2-bromo-4-ethyl-1-(methoxymethoxy)benzene 2-Bromo-4-ethylphenol (3.3 g, 16.41 mmol) from Example I-111A was dissolved in dichloromethane (41.0 mL). The mixture was cooled to 0° C. (ice/water bath) and chloro(methoxy)methane (6.23 mL, 82 mmol) was added via syringe in one portion. N,N-Diisopropylethylamine (14.29 mL, 82 mmol) was added dropwise over 15 minutes. The resulting mixture was stirred at 0° C. for 10 minutes, allowed to warm to room-temperature and stirred under argon for 18 hours. The reaction mixture was quenched with saturated aqueous sodium bicarbonate (100 mL) and extracted with dichloromethane (2×100 mL). The organic extracts were combined, washed with water (1×100 mL) and brine (1×100 mL), dried over anhydrous magnesium sulfate and filtered. The solvent was removed in vacuo and the residue was purified on a 80 g silica gel cartridge eluting with a gradient of 0-20% ethyl acetate/heptanes to provide the title compound. $^1$H NMR (501 MHz, chloroform-d) δ ppm 7.38 (dd, J=1.4, 0.8 Hz, 1H), 7.06 (d, J=1.1 Hz, 2H), 5.21 (s, 2H), 3.52 (s, 3H), 2.57 (qd, J=7.7, 0.6 Hz, 2H), 1.20 (t, J=7.6 Hz, 3H).

Example I-118B methyl 1-(5-ethyl-2-(methoxymethoxy)phenyl)cyclopropanecarboxylate 2-Bromo-4-ethyl-1-(methoxymethoxy)benzene (2.02 g, 8.24 mmol) from Example I-118A was dissolved in tetrahydrofuran (33.0 mL), and Q-Phos (1,2,3,4,5-pentaphenyl-1'-(di-tert-butylphosphino)ferrocene) (0.117 g, 0.165 mmol) and bis(dibenzylideneacetone)palladium (0.095 g, 0.165 mmol) were added. Nitrogen was bubbled through the solution for 10 minutes. A solution of freshly-prepared (1-(methoxycarbonyl)cyclopropyl)zinc(II) bromide (36.6 mL, 16.48 mmol) in tetrahydrofuran was added dropwise.

The reaction was stirred at 50° C. for 2 hours and at 45° C. for 15 hours. The reaction was cooled and quenched with saturated aqueous ammonium chloride (40 mL), and diluted with methyl tert-butyl ether (100 mL). The aqueous layer was extracted once more with methyl tert-butyl ether (100 mL). The combined organic layer was washed with brine, dried over anhydrous sodium sulfate, filtered and concentrated. The residue was purified by silica gel chromatography, eluting with 0-20% ethyl acetate/heptanes to provide the title compound. $^1$H NMR (400 MHz, chloroform-d) δ ppm 7.10-6.96 (m, 3H), 5.17 (s, 2H), 3.60 (s, 3H), 3.45 (s, 3H), 2.58 (q, J=7.6 Hz, 2H), 1.60 (q, J=4.1 Hz, 2H), 1.29-1.19 (m, 3H), 1.16-1.12 (m, 2H).

Example I-118C methyl 1-(5-ethyl-2-hydroxyphenyl)cyclopropanecarboxylate

To a cooled 0° C. solution of methyl 1-(5-ethyl-2-(methoxymethoxy)phenyl)cyclopropanecarboxylate (2.16 g, 8.17 mmol) from Example I-118B in methanol (82 mL) was added 4 N aqueous hydrogen chloride (8.17 mL, 32.7 mmol) in dioxane and the reaction was stirred at ambient temperature for 4 hours. The reaction was concentrated and purified by silica gel chromatography, eluting with 0-20% ethyl acetate/heptanes to provide the title compound. $^1$H NMR (501 MHz, chloroform-d) δ ppm 7.09-7.02 (m, 2H), 6.84 (d, J=8.0 Hz, 1H), 5.63 (s, 1H), 3.69 (d, J=0.5 Hz, 3H), 2.60 (q, J=7.6 Hz, 2H), 1.72-1.66 (m, 2H), 1.29-1.20 (m, 5H).

Example I-118D (R)-methyl 1-(5-ethyl-2-((tetrahydrofuran-3-yl)oxy)phenyl)cyclopropanecarboxylate In a 100 mL flask was added methyl 1-(5-ethyl-2-hydroxyphenyl)cyclopropanecarboxylate (0.5 g, 2.270 mmol) from Example I-118C and triphenylphosphine (0.953 g, 3.63 mmol) in tetrahydrofuran (10 mL). The mixture was stirred briefly at ambient temperature under nitrogen, and (E)-diisopropyl diazene-1,2-dicarboxylate (0.715 mL, 3.63 mmol) was added. The mixture was stirred briefly under nitrogen at ambient temperature and (S)-tetrahydrofuran-3-ol (0.181 mL, 2.270 mmol) was added dropwise. The reaction mixture was stirred for 16 hours at ambient temperature. The solvent was removed under reduced pressure. The residue was purified by chromatography, eluting on a 24 g silica gel cartridge with a gradient of 0-100% ethyl acetate/heptanes over a period of 10 minutes to provide the title compound. $^1$H NMR (400 MHz, chloroform-d) δ ppm 7.05 (dd, J=8.1, 2.2 Hz, 1H), 7.03 (d, J=2.2 Hz, 1H), 6.68 (d, J=8.1 Hz, 1H), 4.95 (tt, J=5.0, 2.2 Hz, 1H), 4.02 (dd, J=10.0, 4.8 Hz, 1H), 3.96-3.83 (m, 3H), 3.59 (s, 3H), 2.58 (q, J=7.6 Hz, 2H), 2.22-2.08 (m, 2H), 1.62-1.51 (m, 3H), 1.21 (t, J=7.6 Hz, 3H), 1.15-1.04 (m, 2H). MS (APCI+) m/z 291 (M+H)$^+$.

Example I-118E (R)-1-(5-ethyl-2-((tetrahydrofuran-3-yl)oxy)phenyl)cyclopropanecarboxylic Acid (R)-Methyl 1-(5-ethyl-2-((tetrahydrofuran-3-yl)oxy)phenyl)cyclopropanecarboxylate (0.44 g, 1.515 mmol) from Example I-118D was dissolved in tetrahydrofuran (2 mL), methanol (2 mL), and water (2 mL) and treated with sodium hydroxide (0.303 g, 7.58 mmol). The reaction was stirred at 35° C. overnight, concentrated, cooled in an ice bath and carefully quenched with 1N aqueous citric acid (about 4 mL) until the pH~5. The resulting slurry was extracted with dichloromethane. The dichloromethane layer was concentrated and azeotroped with toluene 3×10 mL to provide the title compound. $^1$H NMR (501 MHz, chloroform-d) δ ppm 7.07-7.02 (m, 2H), 6.68 (d, J=9.0 Hz, 1H), 4.95 (td, J=6.2, 5.8, 4.0 Hz, 1H), 4.03 (dd, J=10.0, 4.8 Hz, 1H), 3.94-3.86 (m, 3H), 2.57 (q, J=7.6 Hz, 2H), 2.14 (td, J=7.3, 6.8, 4.4 Hz, 2H), 1.64-1.59 (m, 2H), 1.20 (t, J=7.6 Hz, 3H), 1.15 (m, 2H). MS (APCI+) m/z 277 (M+H)$^+$.

Example I-118F 1-(5-ethyl-2-{[(3R)-oxolan-3-yl]oxy}phenyl)-N-(quinoline-5-sulfonyl)cyclopropane-1-carboxamide To a solution of (R)-1-(5-ethyl-2-((tetrahydrofuran-3-yl)oxy)phenyl)cyclopropanecarboxylic acid (70 mg, 0.253 mmol) from Example I-118E, $N^1$-((ethylimino)methylene)-$N^3,N^3$-dimethylpropane-1,3-diamine hydrochloride (97 mg, 0.507 mmol) and N,N-dimethylpyridin-4-amine (34.0 mg, 0.279 mmol) in anhydrous dichloromethane (1 mL) was added quinoline-5-sulfonamide (52.8 mg, 0.253 mmol). After 16 hours, the reaction was quenched with 1 mL of 1N aqueous citric acid and the organic layer was concentrated in vacuo. The residue was purified via chromatography on a 12 g silica gel cartridge, eluting with a gradient of 0-10% methanol/dichloromethane over a period of 10 minutes. The material was triturated with diethyl ether (1.5 mL) and filtered to provide the title compound. $^1$H NMR (400 MHz, dimethyl sulfoxide-$d_6$) δ ppm 11.52 (s, 1H), 9.04 (dd, J=4.3, 1.6 Hz, 1H), 8.95 (d, J=8.6 Hz, 1H), 8.32 (dd, J=13.3, 8.0 Hz, 2H), 7.92 (t, J=8.0 Hz, 1H), 7.68 (dd, J=8.8, 4.2 Hz, 1H), 7.10-7.03 (m, 1H), 6.98 (d, J=2.2 Hz, 1H), 6.73 (d, J=8.3 Hz, 1H), 4.64 (t, J=5.6 Hz, 1H), 3.63 (dd, J=9.9, 4.9 Hz, 1H), 3.55 (td, J=8.1, 3.5 Hz, 1H), 3.43 (td, J=8.6, 6.3 Hz, 1H), 3.19 (dd, J=9.8, 2.0 Hz, 1H), 2.53 (q, J=7.6 Hz, 1H), 1.78 (dtd, J=17.5, 8.6, 6.1 Hz, 1H), 1.39 (m, 1H), 1.26 (ddd, J=9.2, 6.3, 3.6 Hz, 1H), 1.16 (t, J=7.6 Hz, 3H), 0.93 (d, J=21.4 Hz, 2H). MS (APCI+) m/z 467 (M+H)$^+$.

Example I-119

1-(5-ethyl-2-{[(3R)-oxolan-3-yl]oxy}phenyl)-N-(2-methylquinoline-5-sulfonyl)cyclopropane-1-carboxamide To a solution of (R)-1-(5-ethyl-2-((tetrahydrofuran-3-yl)oxy)phenyl)cyclopropanecarboxylic acid (70 mg, 0.253 mmol) from Example I-118E, $N^1$-((ethylimino)methylene)-$N^3,N^3$-dimethylpropane-1,3-diamine hydrochloride (97 mg, 0.507 mmol) and N,N-dimethylpyridin-4-amine (34.0 mg, 0.279 mmol) in anhydrous dichloromethane (1 mL) was added 2-methylquinoline-5-sulfonamide (56.3 mg, 0.253 mmol). After 16 hours, the reaction was quenched with 1 mL of 1N aqueous citric acid and the organic layer was concentrated in vacuo. The residue was purified via chromatography on a 12 g silica gel cartridge, eluting with a gradient of 0-10% methanol/dichloromethane over a period of 10 minutes. The material was triturated with diethyl ether (0.5 mL) and filtered to provide the title compound. $^1$H NMR (400 MHz, dimethyl sulfoxide-$d_6$) δ ppm 11.45 (s, 1H), 8.83 (d, J=8.9 Hz, 1H), 8.21 (t, J=7.2 Hz, 2H), 7.86 (t, J=7.9 Hz, 1H), 7.56 (d, J=8.9 Hz, 1H), 7.06 (dd, J=8.4, 2.2 Hz, 1H), 6.98 (d, J=2.2 Hz, 1H), 6.73 (d, J=8.3 Hz, 1H), 4.66 (td, J=4.7, 2.4 Hz, 1H), 3.65 (dd, J=9.9, 4.9 Hz, 1H), 3.56 (td, J=8.1, 3.5 Hz, 1H), 3.44 (td, J=8.6, 6.4 Hz, 1H), 3.21 (dd, J=9.8, 2.0 Hz, 1H), 2.71 (s, 3H), 2.53 (q, J=7.6 Hz, 1H), 1.86-1.72 (m, 1H), 1.40 (m, 1H), 1.26 (m, 2H), 1.16 (t, J=7.6 Hz, 3H), 0.92 (dd, J=24.2, 8.0 Hz, 2H). MS (APCI+) m/z 481 (M+H)$^+$.

Example I-122

1-(5-methyl-2-{[(3R)-oxolan-3-yl]oxy}phenyl)-N-(quinoline-5-sulfonyl)cyclopropane-1-carboxamide

Example I-122A 2-bromo-1-(methoxymethoxy)-4-methylbenzene

To a cooled (ice/water bath) solution of 2-bromo-4-methylphenol (5.27 g, 27.6 mmol) in dichloromethane (69.0 mL) was added chloro(methoxy)methane (10.49 mL, 138 mmol) via syringe in one portion. N,N-Diisopropylethylamine (24.05 mL, 138 mmol) was added dropwise over 15 minutes. The resulting mixture was stirred at 0° C. for 10 minutes, allowed to warm to room-temperature and stirred under argon for 40 minutes. The reaction mixture was quenched with saturated aqueous sodium bicarbonate (100 mL) and extracted with dichloromethane (2×100 mL). The organic extracts were combined, washed with water (1×100 mL) and brine (1×100 mL), dried over anhydrous magnesium sulfate and filtered. The solvent was removed in vacuo. The crude material was purified on an 80 g silica gel cartridge eluting with a gradient 0-20% ethyl acetate/heptanes to provide the title compound. $^1$H NMR (400 MHz, chloroform-d) δ ppm 7.36 (d, J=1.1 Hz, 1H), 7.03 (d, J=1.1 Hz, 2H), 5.20 (s, 2H), 3.51 (s, 3H), 2.27 (s, 3H).

Example I-122B methyl 1-(2-(methoxymethoxy)-5-methylphenyl)cyclopropanecarboxylate 2-Bromo-1-(methoxymethoxy)-4-methylbenzene (2.3 g, 9.95 mmol) from Example I-122A was dissolved in tetrahydrofuran (39.8 mL), and Q-Phos (1,2,3,4,5-pentaphenyl-1'-(di-tert-butylphosphino)ferrocene) (0.141 g, 0.199 mmol) and bis(dibenzylideneacetone)palladium (0.114 g, 0.199 mmol) were added. The reaction was sparged with nitrogen 10 minutes. A solution of freshly-prepared (1-(methoxycarbonyl)cyclopropyl)zinc(II) bromide (45.2 mL, 19.91 mmol) in tetrahydrofuran was added dropwise. The reaction mixture was stirred at 50° C. for 30 minutes and at 45° C. for 15 hours. The reaction was cooled to ambient temperature and quenched with saturated aqueous ammonium chloride (40 mL). The mixture was diluted with methyl tert-butyl ether. The aqueous layer was extracted once with methyl tert-butyl ether. The combined organic layers were washed with brine, dried over sodium sulfate, filtered and concentrated. The crude material was purified by flash column chromatography, eluting with 0-20% ethyl acetate/heptanes to provide the title compound. $^1$H NMR (501 MHz, chloroform-d) δ ppm 7.06-6.99 (m, 2H), 6.97 (d, J=8.1 Hz, 1H), 5.16 (s, 2H), 3.60 (s, 3H), 3.45 (s, 3H), 2.28 (s, 3H), 1.63-1.57 (m, 2H), 1.12 (q, J=4.1 Hz, 2H).

Example I-122C methyl 1-(2-hydroxy-5-methylphenyl)cyclopropanecarboxylate

Into a 200 mL flask was added methyl 1-(2-(methoxymethoxy)-5-methylphenyl)cyclopropanecarboxylate (2.5 g, 9.99 mmol) from Example I-122B and methanol (100 mL). The reaction was cooled to 0° C. and 4N hydrogen chloride (9.99 mL, 40.0 mmol) in dioxane was added. The reaction was stirred at ambient temperature for 15 hours and concentrated. The residue was purified by silica gel chromatography, eluting with 0-20% ethyl acetate/heptanes to provide the title compound. $^1$H NMR (501 MHz, chloroform-d) δ ppm 7.02-6.96 (m, 2H), 6.80-6.75 (m, 1H), 5.58 (s, 1H), 3.65 (s, 3H), 2.25 (s, 3H), 1.71-1.60 (m, 2H), 1.26-1.18 (m, 2H).

Example I-122D (R)-methyl 1-(5-methyl-2-((tetrahydrofuran-3-yl)oxy)phenyl)cyclopropanecarboxylate In a 20 mL vial was added methyl 1-(2-hydroxy-5-methylphenyl)cyclopropanecarboxylate (0.2 g, 0.970 mmol) from Example I-122C and triphenylphosphine (0.407 g, 1.552 mmol) in tetrahydrofuran (4.85 mL). The mixture was stirred briefly at ambient temperature under nitrogen, and (E)-diisopropyl diazene-1,2-dicarboxylate (0.305 mL, 1.552 mmol) was added. The mixture was stirred briefly under nitrogen at ambient temperature and (S)-tetrahydrofuran-3-ol (0.093 mL, 1.164 mmol) was added dropwise. The reaction mixture was stirred at ambient temperature for 15 hours. The solvent was removed under reduced pressure. The crude material was purified by chromatography, eluting on 24 g silica gel cartridge with a gradient of 0-30% ethyl acetate/heptanes to provide the title compound. $^1$H NMR (501 MHz, chloroform-d) δ ppm 7.07-7.03 (m, 2H), 6.69 (d, J=8.0 Hz, 1H), 4.98 (tt, J=4.9, 2.1 Hz, 1H), 4.04 (dd, J=10.0, 4.8 Hz, 1H), 3.98-3.87 (m, 3H), 3.62 (s, 3H), 2.30 (s, 3H), 2.20-2.11 (m, 2H), 1.64-1.55 (m, 2H), 1.18-1.05 (m, 2H). MS (ESI+) m/z 277 (M+H)$^+$.

Example I-122E (R)-1-(5-methyl-2-((tetrahydrofuran-3-yl)oxy)phenyl)cyclopropanecarboxylic Acid (R)-methyl 1-(5-methyl-2-((tetrahydrofuran-3-yl)oxy)phenyl)cyclopropanecarboxylate (0.245 g, 0.887 mmol) from Example I-122D was dissolved in tetrahydrofuran (2 mL), methanol (2 mL), and water (2 mL), treated with sodium hydroxide (0.177 g, 4.43 mmol) and stirred at ambient temperature for 72 hours. The reaction was reduced in volume, cooled in an ice bath and carefully quenched with 2N aqueous citric acid (about 3 mL, diluted with ice) until the pH was acidic. The resulting mixture was stirred vigorously, the water was decanted, and the material was washed with water and dried under a stream of nitrogen to provide the title compound. $^1$H NMR (400 MHz, chloroform-d) δ ppm 7.10-6.96 (m, 2H), 6.67 (d, J=8.8 Hz, 1H), 5.06-4.89 (m, 1H), 4.10-3.99 (m, 1H), 3.99-3.84 (m, 3H), 2.28 (s, 3H), 2.23-2.07 (m, 2H), 1.69-1.57 (m, 2H), 1.35-1.19 (m, 1H), 1.19-1.07 (m, 2H). MS (ESI−) m/z 260 (M−H)$^-$.

Example I-122F 1-(5-methyl-2-{[(3R)-oxolan-3-yl]oxy}phenyl)-N-(quinoline-5-sulfonyl)cyclopropane-1-carboxamide To a solution of (R)-1-(5-methyl-2-((tetrahydrofuran-3-yl)oxy)phenyl)cyclopropanecarboxylic acid (50 mg, 0.191 mmol) from Example I-122E, $N^1$-((ethylimino)methylene)-$N^3$,$N^3$-dimethylpropane-1,3-diamine hydrochloride (73.1 mg, 0.381 mmol) and N,N-dimethylpyridin-4-amine (23.29 mg, 0.191 mmol) in anhydrous N,N-dimethylformamide (1 mL) was added quinoline-5-sulfonamide (43 mg, 0.206 mmol). The reaction was stirred at ambient temperature overnight, dissolved in methanol/dimethyl sulfoxide and purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (400 MHz, dimethyl sulfoxide-d$_6$) δ ppm 11.50 (s, 1H), 9.02 (dd, J=4.2, 1.6 Hz, 1H), 8.92 (dt, J=8.8, 1.2 Hz, 1H), 8.35-8.26 (m, 2H), 7.91 (dd, J=8.4, 7.5 Hz, 1H), 7.66 (dd, J=8.8, 4.2 Hz, 1H), 7.01 (dd, J=8.4, 2.2 Hz, 1H), 6.94 (d, J=2.1 Hz, 1H), 6.68 (d, J=8.2 Hz, 1H), 4.59 (ddd, J=6.5, 4.3, 2.0 Hz, 1H), 3.59 (dd, J=9.9, 4.8 Hz, 1H), 3.52 (td, J=8.1, 3.5 Hz, 1H), 3.41 (td, J=8.6, 6.3 Hz, 1H), 3.15 (dd, J=9.9, 2.0 Hz, 1H), 2.20 (s, 3H), 1.83-1.68 (m, 1H), 1.37 (dddd, J=12.9, 5.6, 3.4, 1.6 Hz, 1H), 1.20 (qdd, J=9.2, 5.7, 3.0 Hz, 2H), 0.92 (ddd, J=9.6, 5.7, 3.1 Hz, 1H), 0.85 (ddd, J=8.5, 5.7, 2.9 Hz, 1H). MS (ESI+) m/z 453 (M+H)$^+$.

Example I-123

1-(5-methyl-2-{[(3R)-oxolan-3-yl]oxy}phenyl)-N-(2-methylquinoline-5-sulfonyl)cyclopropane-1-carboxamide To a solution of (R)-1-(5-methyl-2-((tetrahydrofuran-3-yl)oxy)phenyl)cyclopropanecarboxylic acid (50 mg, 0.191 mmol) from Example I-122E, N$^1$-((ethylimino)methylene)-N$^3$,N$^3$-dimethylpropane-1,3-diamine hydrochloride (73.1 mg, 0.381 mmol) and N,N-dimethylpyridin-4-amine (23.29 mg, 0.191 mmol) in anhydrous N,N-dimethylformamide (1 mL) was added 2-methylquinoline-5-sulfonamide (42.4 mg, 0.191 mmol). The reaction mixture was stirred at ambient temperature for 16 hours, dissolved in methanol/dimethyl sulfoxide, and purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound. $^1$H NMR (400 MHz, dimethyl sulfoxide-d$_6$) δ ppm 11.48 (s, 1H), 8.91 (d, J=8.9 Hz, 1H), 8.28-8.20 (m, 2H), 7.90 (t, J=8.0 Hz, 1H), 7.64 (d, J=9.0 Hz, 1H), 7.04-6.99 (m, 1H), 6.93 (d, J=2.2 Hz, 1H), 6.70 (d, J=8.3 Hz, 1H), 4.65 (ddt, J=6.5, 4.2, 1.9 Hz, 1H), 3.64 (dd, J=9.8, 4.8 Hz, 1H), 3.54 (td, J=8.1, 3.5 Hz, 1H), 3.46-3.38 (m, 1H), 3.19 (dd, J=9.9, 2.0 Hz, 1H), 2.73 (s, 3H), 2.20 (s, 3H), 1.79 (dddd, J=13.1, 9.3, 8.2, 6.1 Hz, 1H), 1.42 (dddd, J=12.7, 5.5, 3.5, 1.6 Hz, 1H), 1.20 (th, J=9.0, 2.8 Hz, 2H), 0.92 (ddd, J=9.5, 5.7, 3.1 Hz, 1H), 0.86 (ddd, J=8.5, 5.6, 2.8 Hz, 1H). MS (ESI+) m/z 467 (M+H)$^+$.

Example I-124

1-(5-methyl-2-{[(3S)-oxolan-3-yl]oxy}phenyl)-N-(2-methylquinoline-5-sulfonyl)cyclopropane-1-carboxamide Example I-124A (S)-methyl 1-(5-methyl-2-((tetrahydrofuran-3-yl)oxy)phenyl)cyclopropanecarboxylate Into a 20 mL vial was added methyl 1-(2-hydroxy-5-methylphenyl)cyclopropanecarboxylate (0.2 g, 0.970 mmol) from Example I-122C and triphenylphosphine (0.407 g, 1.552 mmol) in tetrahydrofuran. The mixture was stirred briefly at ambient temperature under nitrogen, and (E)-diisopropyl diazene-1,2-dicarboxylate (0.305 mL, 1.552 mmol) was added. The mixture was stirred briefly under nitrogen at ambient temperature and (R)-tetrahydrofuran-3-ol (0.093 mL, 1.164 mmol) was added dropwise. The reaction mixture was stirred for 16 hours at ambient temperature. The solvent was removed under reduced pressure. The crude material was purified by chromatography, eluting on 24 g silica gel cartridge with a gradient of 0-30% ethyl acetate/heptanes to provide the title compound. $^1$H NMR (400 MHz, chloroform-d) δ ppm 7.08-6.97 (m, 2H), 6.70-6.63 (m, 1H), 5.02-4.93 (m, 1H), 4.03 (dd, J=9.9, 4.7 Hz, 1H), 3.97-3.83 (m, 3H), 3.61 (s, 3H), 2.29 (s, 3H), 2.20-2.11 (m, 2H), 1.63-1.53 (m, 2H), 1.16-1.03 (m, 2H). MS (ESI+) m/z 277 (M+H)$^+$.

Example I-124B (S)-1-(5-methyl-2-((tetrahydrofuran-3-yl)oxy)phenyl)cyclopropanecarboxylic Acid (S)-Methyl 1-(5-methyl-2-((tetrahydrofuran-3-yl)oxy)phenyl)cyclopropanecarboxylate (0.265 g, 0.96 mmol) from Example I-124A was dissolved in tetrahydrofuran (2 mL), methanol (2 mL), and water (2 mL) and treated with sodium hydroxide (0.192 g, 4.80 mmol) and stirred at 70° C. for 45 minutes. The reaction was reduced in volume, cooled in an ice bath and carefully quenched with 2N aqueous citric acid (about 3 mL, diluted with ice) until the pH was acidic. The resulting material was stirred vigorously and the water was decanted. The material was washed with water and dried under a stream of nitrogen to provide the title compound. $^1$H NMR (500 MHz, chloroform-d) δ ppm 7.07-7.03 (m, 2H), 6.72-6.65 (m, 1H), 5.02-4.93 (m, 1H), 4.04 (dd, J=10.0, 4.8 Hz, 1H), 3.98-3.89 (m, 3H), 2.29 (s, 3H), 2.22-2.11 (m, 2H), 1.67-1.60 (m, 2H), 1.20-1.14 (m, 2H).

Example I-124C 1-(5-methyl-2-{[(3S)-oxolan-3-yl]oxy}phenyl)-N-(2-methylquinoline-5-sulfonyl)cyclopropane-1-carboxamide To a solution of (S)-1-(5-methyl-2-((tetrahydrofuran-3-yl)oxy)phenyl)cyclopropanecarboxylic acid (50 mg, 0.191 mmol) from Example I-124B, N$^1$-((ethylimino)methylene)-N$^3$,N$^3$-dimethylpropane-1,3-diamine hydrochloride (73.1 mg, 0.381 mmol) and N,N-dimethylpyridin-4-amine (23.29 mg, 0.191 mmol) in anhydrous N,N-dimethylformamide (1 mL) was added 2-methylquinoline-5-sulfonamide (45 mg, 0.202 mmol). The reaction was stirred at ambient temperature for 15 hours, dissolved in methanol/dimethyl sulfoxide and purified by reverse-phase preparative HPLC on a Phenomenex® Luna® C8(2) 5 μm 100 Å AXIA™ column (30 mm×150 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to provide the title compound as a trifluoroacetic acid salt. $^1$H NMR (400 MHz, dimethyl sulfoxide-d$_6$) δ ppm 11.48 (s, 1H), 8.88 (d, J=8.9 Hz, 1H), 8.27-8.17 (m, 2H), 7.88 (t, J=8.0 Hz, 1H), 7.61 (d, J=8.9 Hz, 1H), 7.02 (dd, J=8.3, 2.1 Hz, 1H), 6.93 (d, J=2.2 Hz, 1H), 6.70 (d, J=8.3 Hz, 1H), 4.64 (ddt, J=6.5, 4.2, 1.9 Hz, 1H), 3.63 (dd, J=9.9, 4.9 Hz, 1H), 3.54 (td, J=8.1, 3.5 Hz, 1H), 3.42 (td, J=8.6, 6.4 Hz, 1H), 3.18 (dd, J=9.8, 2.0 Hz, 1H), 2.71 (s, 3H), 2.20 (s, 3H), 1.87-1.69 (m, 1H), 1.41 (ddt, J=12.3, 5.4, 2.7 Hz, 1H), 1.20 (qdd, J=9.1, 5.7, 3.0 Hz, 2H), 0.92 (ddd, J=9.5, 5.7, 3.1 Hz, 1H), 0.85 (ddd, J=8.6, 5.7, 2.9 Hz, 1H). MS (ESI+) m/z 467 (M+H)$^+$.

TABLE 1

| Example | Name | NMR | MS |
|---|---|---|---|
| Example II-1 | 1-(3-methoxyphenyl)-N-(naphthalene-1-sulfonyl)cyclopropane-1-carboxamide | $^1$H NMR (400 MHz, DMSO-$d_6$:$D_2O$ = 9:1 (v/v)) δ ppm 8.57-8.45 (m, 1H), 8.35-8.22 (m, 2H), 8.18-8.06 (m, 1H), 7.76-7.63 (m, 3H), 7.15 (dd, J = 8.4, 7.3 Hz, 1H), 6.81 (ddd, J = 8.3, 2.5, 1.0 Hz, 1H), 6.71-6.59 (m, 2H), 3.67 (s, 3H), 1.27-1.15 (m, 2H), 1.15-0.96 (m, 2H). | MS (APCI+) m/z 382.1 (M + H)$^+$. |
| Example II-2 | 1-(3-methoxy-4-methylphenyl)-N-(naphthalene-1-sulfonyl)cyclopropane-1-carboxamide | $^1$H NMR (400 MHz, DMSO-$d_6$:$D_2O$ = 9:1 (v/v)) δ ppm 8.55-8.42 (m, 1H), 8.34-8.21 (m, 2H), 8.18-8.05 (m, 1H), 7.76-7.60 (m, 3H), 6.98 (dd, J = 7.5, 0.9 Hz, 1H), 6.62 (d, J = 1.7 Hz, 1H), 6.59 (dd, J = 7.6, 1.7 Hz, 1H), 3.72 (s, 3H), 2.10 (s, 3H), 1.23-1.12 (m, 2H), 1.10-0.95 (m, 2H). | MS (APCI+) m/z 396.1 (M + H)$^+$. |
| Example II-3 | N-(quinoline-5-sulfonyl)-1-[2-(trifluoromethoxy)phenyl]cyclobutane-1-carboxamide | $^1$H NMR (400 MHz, DMSO-$d_6$) δ ppm 11.99 (s, 1H), 8.99 (dd, J = 4.2, 1.6 Hz, 1H), 8.70 (dd, J = 8.7, 1.5 Hz, 1H), 8.35 (t, J = 8.2 Hz, 2H), 7.98-7.88 (m, 1H), 7.68 (dd, J = 7.6, 1.9 Hz, 1H), 7.51 (dd, J = 8.8, 4.2 Hz, 1H), 7.39 (dtd, J = 19.5, 7.5, 1.6 Hz, 2H), 7.00-6.90 (m, 1H), 2.46 (ddd, J = 10.8, 5.8, 3.4 Hz, 2H), 2.30-2.20 (m, 2H), 1.76-1.52 (m, 2H). | MS (ESI+) m/z 451 (M + H)$^+$. |
| Example II-4 | 1-(1-ethyl-3-methyl-1H-pyrazol-5-yl)-N-(naphthalene-1-sulfonyl)cyclopropane-1-carboxamide | $^1$H NMR (500 MHz, DMSO-$d_6$) δ ppm 8.60-8.57 (m, 1H), 8.30-8.27 (m, 1H), 8.26 (dd, J = 7.4, 1.2 Hz, 1H), 8.13-8.10 (m, 1H), 7.74-7.66 (m, 3H), 5.87 (s, 1H), 3.52 (q, J = 7.2 Hz, 2H), 2.07 (s, 3H), 1.45-1.42 (m, 2H), 1.10-1.07 (m, 2H), 0.94 (t, J = 7.2 Hz, 3H). | MS (ESI) m/z 384 (M + H)$^+$. |
| Example II-5 | 1-(1-ethyl-5-methyl-1H-pyrazol-3-yl)-N-(naphthalene-1-sulfonyl)cyclopropane-1-carboxamide | $^1$H NMR (500 MHz, DMSO-$d_6$) δ ppm 8.59-8.55 (m, 1H), 8.35-8.31 (m, 2H), 8.15-8.12 (m, 1H), 7.74-7.66 (m, 3H), 5.73 (s, 1H), 4.06 (q, J = 7.2 Hz, 2H), 2.20 (s, 3H), 1.41 (t, J = 7.2 Hz, 3H), 1.29-1.25 (m, 2H), 1.11-1.08 (m, 2H). | MS (ESI) m/z 384 (M + H)$^+$. |
| Example II-6 | 1-(2-methoxyphenyl)-N-(quinoline-5-sulfonyl)cyclobutane-1-carboxamide | $^1$H NMR (501 MHz, DMSO-$d_6$) δ ppm 11.72-11.43 (m, 1H), 8.99 (dd, J = 4.2, 1.6 Hz, 1H), 8.73 (d, J = 8.7 Hz, 1H), 8.33 (dd, J = 8.2, 3.7 Hz, 2H), 7.94 (t, J = 7.9 Hz, 1H), 7.52 (dd, J = 8.7, 4.1 Hz, 1H), 7.39 (d, J = 7.6 Hz, 1H), 7.30-7.13 (m, 1H), 6.96 (td, J = 7.4, 1.1 Hz, 1H), 6.67 (dd, J = 8.2, 1.1 Hz, 1H), 3.09 (s, 3H), 2.37 (ddd, J = 12.1, 8.8, 5.8 Hz, 2H), 2.11 (tdd, J = 9.1, 7.0, 2.3 Hz, 2H), 1.70-1.48 (m, 2H). | MS (ESI+) m/z 397 (M + H)$^+$. |
| Example II-7 | 1-[2-methoxy-5-(trifluoromethyl)pyridin-3-yl]-N-(quinoline-5-sulfonyl)cyclopropane-1-carboxamide | $^1$H NMR (500 MHz, DMSO-$d_6$) δ ppm 11.96 (s, 1H), 9.08 (dd, J = 4.2, 1.6 Hz, 1H), 8.93-8.86 (m, 1H), 8.53 (dt, J = 2.4, 1.2 Hz, 1H), 8.39 (dt, J = 8.5, 1.1 Hz, 1H), 8.35 (dd, J = 7.4, 1.2 Hz, 1H), 7.98 (dd, J = 8.5, 7.4 Hz, 1H), 7.89 (d, J = 2.4 Hz, 1H), 7.74 (dd, J = 8.8, 4.2 Hz, 1H), 3.46 (s, 3H), 1.31 (q, J = 4.4 Hz, 2H), 1.17-1.06 (m, 2H). | MS (ESI+) m/z 452 (M + H)$^+$. |
| Example II-8 | 1-[2-methoxy-5-(trifluoromethyl)pyridin-3-yl]-N-(1,2,3,4-tetrahydroquinoline-5-sulfonyl)cyclopropane-1-carboxamide | $^1$H NMR (500 MHz, DMSO-$d_6$) δ ppm 11.44 (s, 1H), 8.53 (dt, J = 2.4, 1.2 Hz, 1H), 7.91 (d, J = 2.4 Hz, 1H), 7.08-6.96 (m, 2H), 6.71 (dd, J = 7.3, 2.1 Hz, 1H), 3.89 (s, 3H), 3.19 (t, J = 5.5 Hz, 2H), 2.86 (t, J = 6.4 Hz, 2H), 1.87-1.68 (m, 2H), 1.40 (q, J = 4.3 Hz, 2H), 1.16 (q, J = 4.4 Hz, 2H). | MS (ESI+) m/z 456 (M + H)$^+$. |
| Example II-9 | 1-[2-methoxy-5-(trifluoromethyl)pyridin-3-yl]-N-(2-methylquinoline-5-sulfonyl)cyclopropane-1-carboxamide | $^1$H NMR (500 MHz, DMSO-$d_6$) δ ppm 11.91 (s, 1H), 8.79 (d, J = 8.9 Hz, 1H), 8.53 (dt, J = 2.3, 1.1 Hz, 1H), 8.30-8.22 (m, 2H), 7.95-7.87 (m, 2H), 7.64 (d, J = 8.9 Hz, 1H), 3.50 (s, 3H), 2.74 (s, 3H), 1.30 (q, J = 4.4 Hz, 2H), 1.11 (q, J = 4.4 Hz, 2H). | MS (ESI+) m/z 466 (M + H)$^+$. |
| Example II-10 | 1-(2-methoxy-5-methylpyridin-3-yl)-N-(1,2,3,4-tetrahydroquinoline-5-sulfonyl)cyclopropane-1-carboxamide | $^1$H NMR (501 MHz, DMSO-$d_6$) δ ppm 11.24 (s, 1H), 7.90 (dd, J =2.3, 1.0 Hz, 1H), 7.41 (d, J = 2.3 Hz, 1H), 7.12-6.95 (m, 2H), 6.73 (dd, J = 7.9, 1.4 Hz, 1H), 3.77 (s, 3H), 3.28-3.17 (m, 2H), 2.89 (t, J = 6.4 Hz, 2H), 2.21 (s, 3H), 1.83-1.71 (m, 2H), 1.37 (q, J = 4.3 Hz, 2H), 1.10-0.96 (m, 2H. | MS (ESI+) m/z 402 (M + H)$^+$. |
| Example II-11 | 1-(2-methoxyphenyl)-N-(1,2,3,4-tetrahydroquinoline-5-sulfonyl)cyclopropane-1-carboxamide | $^1$H NMR (400 MHz, DMSO-$d_6$:$D_2O$ = 9:1 (v/v)) δ ppm 7.38-7.26 (m, 1H), 7.21 (dd, J = 7.5, 1.7 Hz, 1H), 7.15-6.96 (m, 3H), 6.93 (td, J = 7.5, 1.1 Hz, 1H), 6.71 (dd, J = 6.5, 2.8 Hz, 1H), 3.72 (s, 3H), 3.17 (t, J = 5.5 Hz, 2H), 2.85 (t, J = 6.4 Hz, 2H), 1.84-1.69 (m, 2H), 1.48-1.26 (m, 2H), 1.12-0.92 (m, 2H). | MS (APCI+) m/z 441.1 (M + H)$^+$. |

TABLE 1-continued

| Example | Name | NMR | MS |
|---|---|---|---|
| Example II-12 | 1-(5-cyclobutyl-2-methoxypyridin-3-yl)-N-(1-methyl-1H-benzimidazole-7-sulfonyl)cyclopropane-1-carboxamide | $^1$H NMR (400 MHz, DMSO-$d_6$:$D_2O$ = 9:1 (v/v)) δ ppm 8.44 (s, 1H), 8.03 (dd, J = 8.1, 1.1 Hz, 1H), 7.97-7.85 (m, 2H), 7.53-7.40 (m, 2H), 3.92 (s, 3H), 3.48 (p, J = 8.7 Hz, 1H), 3.41 (s, 3H), 2.33-2.21 (m, 2H), 2.21-2.04 (m, 2H), 2.04-1.89 (m, 1H), 1.89-1.75 (m, 1H), 1.36 (q, J = 4.3 Hz, 2H), 1.06 (q, J = 4.5 Hz, 2H). | MS (APCI+) m/z 441.0 (M + H)$^+$. |
| Example II-13 | 1-(5-cyclobutyl-2-methoxypyridin-3-yl)-N-(1-methyl-1H-indazole-7-sulfonyl)cyclopropane-1-carboxamide | $^1$H NMR (400 MHz, DMSO-$d_6$:$D_2O$ = 9:1 (v/v)) δ ppm 8.32 (s, 1H), 8.18 (dd, J = 8.0, 1.1 Hz, 1H), 8.06 (dd, J = 7.5, 1.1 Hz, 1H), 7.92 (d, J = 2.3 Hz, 1H), 7.48 (d, J = 2.3 Hz, 1H), 7.35 (t, J = 7.8 Hz, 1H), 4.11 (s, 3H), 3.47 (p, J = 8.7 Hz, 1H), 3.33 (s, 3H), 2.27 (qt, J = 8.0, 2.5 Hz, 2H), 2.20-2.04 (m, 2H), 2.04-1.89 (m, 1H), 1.89-1.74 (m, 1H), 1.36 (q, J = 4.3 Hz, 2H), 1.27-0.98 (m, 2H). | MS (APCI+) m/z 441.0 (M + H)$^+$. |
| Example II-14 | 1-(5-cyclobutyl-2-methoxypyridin-3-yl)-N-(1-methyl-1H-indole-4-sulfonyl)cyclopropane-1-carboxamide | $^1$H NMR (400 MHz, DMSO-$d_6$:$D_2O$ = 9:1 (v/v)) δ ppm 7.92 (d, J = 2.3 Hz, 1H), 7.85-7.75 (m, 1H), 7.62 (d, J = 7.5 Hz, 1H), 7.55 (d, J = 3.1 Hz, 1H), 7.41 (d, J = 2.4 Hz, 1H), 7.32 (t, J = 7.9 Hz, 1H), 6.78 (dd, J = 3.0, 0.8 Hz, 1H), 3.87 (s, 3H), 3.60 (s, 3H), 3.46 (p, J = 8.8 Hz, 1H), 2.34-2.18 (m, 2H), 2.18-1.89 (m, 3H), 1.89-1.74 (m, 1H), 1.28 (q, J = 4.4 Hz, 2H), 1.02 (q, J = 4.5 Hz, 2H). | MS (APCI+) m/z 440.1 (M + H)$^+$. |
| Example II-15 | 1-(5-cyclobutyl-2-methoxypyridin-3-yl)-N-(1H-indazole-4-sulfonyl)cyclopropane-1-carboxamide | $^1$H NMR (400 MHz, DMSO-$d_6$:$D_2O$ = 9:1 (v/v)) δ ppm 8.33 (d, J = 1.0 Hz, 1H), 7.99-7.88 (m, 2H), 7.71 (dd, J = 7.3, 0.8 Hz, 1H), 7.57 (dd, J = 8.4, 7.3 Hz, 1H), 7.42 (d, J = 2.4 Hz, 1H), 3.53 (s, 3H), 3.46 (q, J = 8.8 Hz, 1H), 2.33-2.20 (m, 2H), 2.20-2.03 (m, 2H), 2.03-1.89 (m, 1H), 1.88-1.74 (m, 1H), 1.29 (q, J = 4.3 Hz, 2H), 1.04 (q, J = 4.5 Hz, 2H). | MS (APCI+) m/z 427.1 (M + H)$^+$. |
| Example II-16 | 1-(5-cyclobutyl-2-methoxypyridin-3-yl)-N-(3-methylimidazo[1,2-a]pyridine-5-sulfonyl)cyclopropane-1-carboxamide | $^1$H NMR (400 MHz, DMSO-$d_6$:$D_2O$ = 9:1 (v/v)) δ ppm 8.09-7.86 (m, 4H), 7.82 (d, J = 2.4 Hz, 1H), 7.38 (d, J = 2.4 Hz, 1H), 3.65 (s, 3H), 3.45 (p, J = 8.5 Hz, 1H), 2.79 (s, 3H), 2.34-2.16 (m, 2H), 2.16-1.88 (m, 3H), 1.88-1.72 (m, 1H), 1.22 (q, J = 3.7 Hz, 2H), 0.82 (q, J = 3.8 Hz, 2H). | MS (APCI+) m/z 441.1 (M + H)$^+$. |
| Example II-17 | 1-[2-methoxy-5-(trifluoromethyl)pyridin-3-yl]-N-(1-methyl-1H-indole-7-sulfonyl)cyclopropane-1-carboxamide | $^1$H NMR (500 MHz, DMSO-$d_6$:$D_2O$ = 9:1 (v/v)) δ ppm 8.50 (dd, J = 2.4, 1.1 Hz, 1H), 7.94 (dd, J = 7.8, 1.2 Hz, 1H), 7.92-7.87 (m, 1H), 7.81 (dd, J = 7.7, 1.2 Hz, 1H), 7.44 (d, J = 3.2 Hz, 1H), 7.20 (t, J = 7.8 Hz, 1H), 6.69 (d, J = 3.2 Hz, 1H), 3.89 (s, 3H), 3.53 (s, 3H), 1.40 (q, J = 4.4 Hz, 2H), 1.15 (q, J = 4.5 Hz, 2H). | MS (APCI+) m/z 454.0 (M + H)$^+$. |
| Example II-18 | 1-[2-methoxy-5-(trifluoromethyl)pyridin-3-yl]-N-(1-methyl-1H-indole-4-sulfonyl)cyclopropane-1-carboxamide | $^1$H NMR (500 MHz, DMSO-$d_6$:$D_2O$ = 9:1 (v/v)) δ ppm 8.55-8.47 (m, 1H), 7.83 (ddt, J = 2.8, 1.8, 0.8 Hz, 1H), 7.81 (t, J = 0.8 Hz, 1H), 7.63 (dd, J = 7.5, 0.9 Hz, 1H), 7.56 (d, J = 3.1 Hz, 1H), 7.34 (dd, J = 8.2, 7.5 Hz, 1H), 6.72 (dd, J = 3.1, 0.9 Hz, 1H), 3.87 (s, 3H), 3.65 (s, 3H), 1.31 (q, J = 4.4 Hz, 2H), 1.18-0.98 (m, 2H). | MS (APCI+) m/z 454.0 (M + H)$^+$. |
| Example II-19 | 1-[2-methoxy-5-(trifluoromethyl)pyridin-3-yl]-N-(3-methylimidazo[1,2-a]pyridine-5-sulfonyl)cyclopropane-1-carboxamide | $^1$H NMR (500 MHz, DMSO-$d_6$:$D_2O$ = 9:1 (v/v)) δ ppm 8.39 (dt, J = 2.4, 1.1 Hz, 1H), 8.07-7.97 (m, 3H), 7.97-7.89 (m, 1H), 7.73 (d, J = 2.5 Hz, 1H), 3.75 (s, 3H), 2.79 (d, J = 1.1 Hz, 3H), 1.23 (q, J = 3.7 Hz, 2H), 0.87 (q, J = 3.8 Hz, 2H). | MS (APCI+) m/z 455.0 (M + H)$^+$. |
| Example II-20 | 1-[2-methoxy-5-(propan-2-yl)phenyl]-N-(1,2,3,4-tetrahydroquinoline-5-sulfonyl)cyclobutane-1-carboxamide | $^1$H NMR (400 MHz, DMSO-$d_6$:$D_2O$ = 9:1 (v/v)) δ ppm 7.20 (d, J = 2.2 Hz, 1H), 7.14 (dd, J = 8.4, 2.2 Hz, 1H), 7.08 (dd, J = 7.8, 1.4 Hz, 1H), 7.02 (t, J = 7.9 Hz, 1H), 6.89 (d, J = 8.4 Hz, 1H), 6.69 (dd, J = 7.9, 1.4 Hz, 1H), 3.52 (s, 3H), 3.05 (t, J = 5.5 Hz, 2H), 2.87 (hept, J = 6.8 Hz, 1H), 2.67-2.57 (m, 2H), 2.46 (t, J = 6.3 Hz, 2H), 2.43-2.20 (m, 2H), 1.87-1.66 (m, 2H), 1.66-1.47 (m, 2H), 1.21 (d, J = 6.9 Hz, 6H). | MS (APCI+) m/z 443.1 (M + H)$^+$. |
| Example II-21 | 1-(5-cyclopentyl-2-methoxyphenyl)-N-(1,2,3,4-tetrahydroquinoline-5-sulfonyl)cyclobutane-1-carboxamide | $^1$H NMR (400 MHz, DMSO-$d_6$:$D_2O$ = 9:1 (v/v)) δ ppm 7.21 (d, J = 2.2 Hz, 1H), 7.14 (dd, J = 8.4, 2.2 Hz, 1H), 7.08 (dd, J = 7.8, 1.4 Hz, 1H), 7.02 (t, J = 7.9 Hz, 1H), 6.88 (d, J = 8.4 Hz, 1H), 6.70 (dd, J = 7.9, 1.4 Hz, 1H), 3.52 (s, 3H), 3.05 (t, J = 5.5 Hz, 2H), 3.01-2.85 (m, 1H), 2.67-2.57 (m, 2H), 2.47 (t, J = 6.4 Hz, 2H), 2.27 (dt, J = 12.4, | MS (APCI+) 469.1 m/z (M + H)$^+$. |

TABLE 1-continued

| Example | Name | NMR | MS |
|---|---|---|---|
| | | 8.7 Hz, 2H), 2.10-1.94 (m, 2H), 1.94-1.30 (m, 10H). | |
| Example II-22 | 1-[5-(butan-2-yl)-2-methoxyphenyl]-N-(1,2,3,4-tetrahydroquinoline-5-sulfonyl)cyclobutane-1-carboxamide | $^1$H NMR (400 MHz, DMSO-$d_6$:$D_2O$ = 9:1 (v/v)) δ ppm 7.18-6.95 (m, 4H), 6.89 (d, J = 8.4 Hz, 1H), 6.68 (dd, J = 7.9, 1.5 Hz, 1H), 3.52 (s, 3H), 3.04 (t, J = 5.6 Hz, 2H), 2.75-2.54 (m, 4H), 2.45 (t, J = 6.8 Hz, 2H), 2.40-2.18 (m, 2H), 1.85-1.67 (m, 2H), 1.63-1.47 (m, 4H), 1.19 (d, J = 6.9 Hz, 3H), 0.79 (t, J = 7.3 Hz, 3H). | MS (APCI+) m/z 457.1 (M + H)$^+$ |
| Example II-23 | 1-{2-methoxy-5-[(oxolan-3-yl)oxy]phenyl}-N-(quinoline-5-sulfonyl)cyclopropane-1-carboxamide | $^1$H NMR (400 MHz, CDCl$_3$) δ ppm 9.28 (d, J = 8.8 Hz, 1H), 9.22 (bs, 1H), 8.63 (d, J = 8.6 Hz, 1H), 8.59 (d, J = 7.4 Hz, 1H), 8.32 (bs, 1H), 8.01 (t, J = 7.9 Hz, 1H), 7.80 (dd, J = 3.8, 8.8 Hz, 1H), 6.86-6.85 (m, 2H), 6.75 (t, J = 1.7 Hz, 1H), 4.88-4.83 (m, 1H), 4.05-3.97 (m, 3H), 3.93 (td, J = 4.3, 8.3 Hz, 1H), 3.65 (s, 3H), 2.27-2.10 (m, 2H), 1.48 (q, J = 4.0 Hz, 2H), 1.02 (q, J = 3.9 Hz, 2H). | MS (APCI+) m/z 469 (M + H)$^+$ |
| Example II-24 | 1-[2-chloro-5-(trifluoromethoxy)phenyl]-N-(quinoline-5-sulfonyl)cyclopropane-1-carboxamide | $^1$H NMR (400 MHz, DMSO-$d_6$:$D_2O$ = 9:1 (v/v)) δ ppm 9.07 (dd, J = 4.3, 1.6 Hz, 1H), 8.98 (dt, J = 8.8, 1.3 Hz, 1H), 8.42-8.28 (m, 2H), 7.97 (dd, J = 8.5, 7.5 Hz, 1H), 7.75 (dd, J = 8.8, 4.2 Hz, 1H), 7.46 (d, J = 8.4 Hz, 1H), 7.39-7.29 (m, 2H), 1.62-1.43 (m, 2H), 1.23-1.06 (m, 2H). | MS (APCI+) m/z 470.9 (M + H)$^+$ |
| Example II-25 | 1-[2-chloro-5-(trifluoromethoxy)phenyl]-N-(1,2,3,4-tetrahydroquinoline-5-sulfonyl)cyclopropane-1-carboxamide | $^1$H NMR (400 MHz, DMSO-$d_6$:$D_2O$ = 9:1 (v/v)) δ ppm 7.57 (d, J = 8.5 Hz, 1H), 7.43-7.30 (m, 2H), 7.12-6.96 (m, 2H), 6.73 (dd, J = 7.7, 1.7 Hz, 1H), 3.18 (t, J = 5.5 Hz, 2H), 2.90 (t, J = 6.3 Hz, 2H), 1.79 (p, J = 6.3 Hz, 2H), 1.61 (q, J = 4.6 Hz, 2H), 1.22 (q, J = 4.7 Hz, 2H). | MS (APCI+) m/z 474.9 (M + H)$^+$ |
| Example II-26 | 1-[2-methoxy-5-(propan-2-yl)phenyl]-N-(1,2,3,4-tetrahydroquinoline-5-sulfonyl)cyclopropane-1-carboxamide | $^1$H NMR (400 MHz, DMSO-$d_6$:$D_2O$ = 9:1 (v/v)) δ ppm 7.17 (dd, J = 8.5, 2.3 Hz, 1H), 7.14-6.96 (m, 3H), 6.93 (d, J = 8.5 Hz, 1H), 6.71 (dd, J = 6.3, 3.0 Hz, 1H), 3.70 (s, 3H), 3.23-3.12 (m, 2H), 2.91-2.75 (m, 3H), 1.76 (p, J = 6.2 Hz, 2H), 1.39 (q, J = 4.4 Hz, 2H), 1.18 (d, J = 6.9 Hz, 6H), 1.10-0.94 (m, 2H). | MS (APCI+) m/z 429.1 (M + H)$^+$ |
| Example II-27 | 1-[4-fluoro-2-methoxy-5-(propan-2-yl)phenyl]-N-(1,2,3,4-tetrahydroquinoline-5-sulfonyl)cyclopropane-1-carboxamide | $^1$H NMR (400 MHz, DMSO-$d_6$:$D_2O$ = 9:1 (v/v)) δ ppm 7.10 (d, J = 8.8 Hz, 1H), 7.07-6.96 (m, 2H), 6.80 (d, J = 12.6 Hz, 1H), 6.71 (dd, J = 5.9, 3.4 Hz, 1H), 3.70 (s, 3H), 3.24-3.13 (m, 2H), 3.13-2.98 (m, 1H), 2.85 (t, J = 6.3 Hz, 2H), 1.77 (p, J = 6.2 Hz, 2H), 1.38 (q, J = 4.3 Hz, 2H), 1.20 (d, J = 6.9 Hz, 6H), 1.03 (q, J = 4.6 Hz, 2H). | MS (APCI+) m/z 447.0 (M + H)$^+$ |
| Example II-28 | 1-[2-methoxy-5-(trifluoromethyl)phenyl]-N-(1,2,3,4-tetrahydroquinoline-5-sulfonyl)cyclopropane-1-carboxamide | $^1$H NMR (400 MHz, DMSO-$d_6$:$D_2O$ = 9:1 (v/v)) δ ppm 7.72-7.61 (m, 1H), 7.49 (d, J = 2.3 Hz, 1H), 7.17 (d, J = 8.6 Hz, 1H), 7.11-6.97 (m, 2H), 6.73 (dd, J = 6.4, 2.9 Hz, 1H), 3.78 (s, 3H), 3.18 (t, J = 5.5 Hz, 2H), 2.86 (t, J = 6.4 Hz, 2H), 1.77 (p, J = 6.3 Hz, 2H), 1.42 (q, J = 4.5 Hz, 2H), 1.18-0.99 (m, 2H). | MS (APCI+) m/z 455.0 (M + H)$^+$ |
| Example II-29 | 1-(5-bromo-2-methoxyphenyl)-N-(2-methylquinoline-5-sulfonyl)cyclobutane-1-carboxamide | $^1$H NMR (400 MHz, DMSO-$d_6$) δ ppm 11.49 (s, 1H), 8.58 (d, J = 8.8 Hz, 1H), 8.29-8.16 (m, 2H), 7.88 (dd, J = 8.4, 7.5 Hz, 1H), 7.37 (d, J = 8.9 Hz, 1H), 7.21 (d, J = 2.2 Hz, 1H), 7.09 (dd, J = 8.4, 2.2 Hz, 1H), 6.59 (d, J = 8.3 Hz, 1H), 3.51 (q, J = 8.8 Hz, 1H), 3.17 (s, 1H), 3.12 (s, 3H), 2.69 (s, 3H), 2.45-2.35 (m, 2H), 2.31 (dtt, J = 10.6, 7.5, 2.5 Hz, 2H), 2.22-2.06 (m, 4H), 2.04-1.92 (m, 1H), 1.90-1.77 (m, 1H), 1.73-1.50 (m, 2H). | MS (ESI+) m/z 465 (M + H)$^+$ |
| Example II-30 | methyl 1-(4-methoxy-3-{1-[(quinoline-5-sulfonyl)carbamoyl]cyclopropyl}phenyl)cyclopropane-1-carboxylate | $^1$H NMR (400 MHz, DMSO-$d_6$) δ ppm 11.51 (s, 1H), 9.06 (dd, J = 4.1, 1.6 Hz, 1H), 8.97 (dd, J = 9.0, 1.4 Hz, 1H), 8.35 (d, J = 8.5 Hz, 1H), 8.31 (d, J = 7.3 Hz, 1H), 7.99-7.86 (m, 2H), 7.72 (dd, J = 8.8, 4.2 Hz, 1H), 7.22 (dd, J = 8.4, 2.3 Hz, 1H), 7.04 (d, J = 2.4 Hz, 1H), 6.78 (d, J = 8.5 Hz, 1H), 3.53 (s, 3H), 3.33 (s, 3H), 1.44 (q, J = 3.9 Hz, 2H), 1.28 (q, J = 4.4 Hz, 2H), 1.18 (q, J = 4.0 Hz, 2H), 0.96 (q, J = 4.5 Hz, 2H). | MS (ESI+) m/z 481 (M + H)$^+$ |
| Example II-31 | methyl 4-methoxy-3-{1-[(quinoline-5-sulfonyl)carbamoyl]cyclopropyl}benzoate | $^1$H NMR (400 MHz, DMSO-$d_6$) δ ppm 11.74 (s, 1H), 9.06 (dd, J = 4.2, 1.6 Hz, 1H), 8.91 (dt, J = 8.7, 1.2 Hz, 1H), 8.35 (d, J = 8.5 Hz, 1H), 8.31 (d, J = 7.4 Hz, 1H), 7.99-7.88 (m, 2H), 7.70 (dd, J = 8.2, 3.3 Hz, 2H), 6.99 (d, J = 8.7 Hz, 1H), | MS (APCI+) m/z 441 (M + H)$^+$ |

TABLE 1-continued

| Example | Name | NMR | MS |
|---|---|---|---|
| | | 3.83 (s, 2H), 3.40 (s, 3H), 1.29 (q, J = 4.4 Hz, 2H), 0.96 (q, J = 4.4 Hz, 2H). | |
| Example II-32 | methyl 4-methoxy-3-{1-[(naphthalene-1-sulfonyl)carbamoyl]cyclopropyl}benzoate | $^1$H NMR (501 MHz, DMSO-d$_6$) δ ppm 11.64 (s, 1H), 8.60-8.45 (m, 1H), 8.28 (d, J = 8.2 Hz, 1H), 8.24 (d, J = 7.4 Hz, 1H), 8.18-8.04 (m, 1H), 7.92 (dd, J = 8.6, 2.2 Hz, 1H), 7.75-7.59 (m, 4H), 6.97 (d, J = 8.6 Hz, 1H), 3.82 (s, 3H), 3.17 (s, 3H), 1.29 (q, J = 4.3 Hz, 2H), 0.95 (m, 2H). | MS (APCI+) m/z 440 (M + H)$^+$ |
| Example II-33 | 1-(5-cyclobutyl-2-methoxy-4-methylpyridin-3-yl)-N-(2-methylquinoline-5-sulfonyl)cyclopropane-1-carboxamide | $^1$H NMR (400 MHz, DMSO-d$_6$) δ ppm 11.64 (s, 1H), 8.87 (d, J = 8.8 Hz, 1H), 8.28-8.19 (m, 2H), 7.91 (s, 1H), 7.89-7.84 (m, 1H), 7.62 (d, J = 8.9 Hz, 1H), 3.72 (s, 3H), 3.52-3.47 (m, 1H), 2.73 (s, 3H), 2.31 (d, J = 14.4 Hz, 2H), 2.16 (s, 1H), 2.05-1.95 (m, 2H), 1.89 (s, 3H), 1.84-1.73 (m, 1H), 1.45 (s, 2H), 0.95 (s, 2H). | MS (ESI+) m/z 466 (M + H)$^+$ |
| Example II-34 | 1-(5-bromo-2-methoxyphenyl)-N-(1-methyl-2,3-dihydro-1H-indole-4-sulfonyl)cyclopropane-1-carboxamide | $^1$H NMR (501 MHz, chloroform-d) δ ppm 7.96 (s, 1H), 7.50 (dd, J = 8.7, 2.5 Hz, 1H), 7.40-7.30 (m, 3H), 6.92 (d, J = 7.7 Hz, 1H), 6.86 (d, J = 8.7 Hz, 1H), 3.85 (s, 3H), 3.58 (t, J = 8.2 Hz, 2H), 3.40 (t, J = 8.2 Hz, 2H), 2.93 (s, 3H), 1.62 (q, J = 4.3 Hz, 2H), 1.08 (q, J = 4.3 Hz, 2H). | MS (APCI+) m/z 465 (M + H)$^+$ |
| Example II-35 | 1-(2-methoxy-6-methylphenyl)-N-(quinoline-5-sulfonyl)cyclopropane-1-carboxamide | $^1$H NMR (501 MHz, chloroform-d) δ ppm 9.31-9.25 (m, 2H), 8.69 (d, J = 8.5 Hz, 1H), 8.63 (dd, J = 7.5, 0.9 Hz, 1H), 8.32 (s, 1H), 8.06 (dd, J = 8.5, 7.5 Hz, 1H), 7.83 (dd, J = 8.7, 4.5 Hz, 1H), 7.33 (t, J = 8.0 Hz, 1H), 6.87 (t, J = 8.4 Hz, 2H), 3.81 (s, 3H), 2.16 (s, 3H), 1.77-1.67 (m, 1H), 1.58-1.50 (m, 1H), 1.21-1.12 (m, 1H), 1.01-0.93 (m, 1H). | MS (APCI+) m/z 397 (M + H)$^+$ |
| Example II-36 | 1-(6-methoxy-2,3-dimethylphenyl)-N-(1,2,3,4-tetrahydroquinoline-5-sulfonyl)cyclopropane-1-carboxamide | $^1$H NMR (400 MHz, chloroform-d) δ ppm 8.07 (s, 1H), 7.57 (dd, J = 7.9, 1.2 Hz, 1H), 7.15 (dd, J = 8.3, 6.1 Hz, 2H), 6.84 (d, J = 8.1 Hz, 2H), 6.74 (d, J = 8.4 Hz, 1H), 3.85 (s, 3H), 3.34 (t, J = 5.6 Hz, 2H), 3.04-2.74 (m, 3H), 2.26 (s, 3H), 2.24 (s, 3H), 1.95 (hept, J = 5.8 Hz, 2H), 1.85 (ddd, J = 10.0, 7.7, 3.9 Hz, 1H), 1.65 (ddd, J = 10.0, 7.5, 4.4 Hz, 1H), 1.17 (ddd, J = 9.5, 7.7, 4.4 Hz, 1H), 0.96 (ddd, J = 9.5, 7.5, 3.9 Hz, 1H). | MS (APCI+) m/z 415 (M + H)$^+$ |
| Example II-37 | 1-(3-cyclopropyl-6-methoxy-2-methylphenyl)-N-(1,2,3,4-tetrahydroquinoline-5-sulfonyl)cyclopropane-1-carboxamide | $^1$H NMR (501 MHz, chloroform-d) δ ppm 8.09 (s, 1H), 7.60 (dd, J = 7.9, 1.1 Hz, 1H), 7.18 (t, J = 8.0 Hz, 1H), 7.11 (dd, J = 8.6, 0.8 Hz, 1H), 6.86 (dd, J = 8.1, 1.2 Hz, 1H), 6.75 (d, J = 8.5 Hz, 1H), 3.87 (s, 3H), 3.36 (t, J = 5.6 Hz, 2H), 3.01-2.87 (m, 3H), 2.45 (s, 3H), 1.97 (h, J = 5.8 Hz, 2H), 1.88 (ddd, J = 10.1, 7.7, 4.0 Hz, 1H), 1.85-1.78 (m, 1H), 1.67 (ddd, J = 9.9, 7.6, 4.4 Hz, 1H), 1.19 (ddd, J = 9.4, 7.7, 4.4 Hz, 1H), 1.04-0.87 (m, 3H), 0.66-0.57 (m, 2H). | MS (APCI+) m/z 441 (M + H)$^+$ |
| Example II-38 | 1-(5-cyclobutyl-2-methoxy-4-methylpyridin-3-yl)-N-(1,2,3,4-tetrahydroquinoline-5-sulfonyl)cyclopropane-1-carboxamide | $^1$H NMR (501 MHz, DMSO-d$_6$) δ ppm 11.12 (s, 1H), 7.89 (s, 1H), 7.00 (s, 2H), 6.68 (s, 1H), 6.14 (s, 1H), 3.81 (s, 3H), 3.52 (q, J = 8.7 Hz, 1H), 3.17 (s, 2H), 2.89 (s, 2H), 2.29 (d, J = 8.6 Hz, 2H), 2.09 (s, 3H), 2.05-1.91 (m, 2H), 1.84-1.70 (m, 3H), 1.55 (s, 2H), 1.24 (s, 1H), 0.91-0.72 (m, 2H). | MS (ESI+) m/z 456.2 (M + H)$^+$ |
| Example II-39 | 1-(2,6-dimethoxy-3-methylphenyl)-N-(2-methylquinoline-8-sulfonyl)cyclopropane-1-carboxamide | $^1$H NMR (400 MHz, DMSO-d$_6$) δ 8.41 (d, J = 8.5 Hz, 1H), 8.32 (dd, J = 7.4, 1.5 Hz, 1H), 8.25 (dd, J = 8.1, 1.5 Hz, 1H), 7.68 (dd, J = 8.1, 7.4 Hz, 1H), 7.61 (d, J = 8.5 Hz, 1H), 7.09-7.05 (m, 1H), 6.61 (d, J = 8.5 Hz, 1H), 3.50 (s, 3H), 3.01 (s, 3H), 2.67 (s, 3H), 2.04 (s, 3H), 1.67-1.63 (m, 2H), 1.07-1.02 (m, 2H). | MS (ESI) m/z 441 (M + H)$^+$ |
| Example II-40 | 1-(5-cyclobutyl-2-methoxyphenyl)-N-(1-methyl-2,3-dihydro-1H-indole-4-sulfonyl)cyclopropane-1-carboxamide | $^1$H NMR (501 MHz, DMSO-d$_6$:D$_2$O = 9:1 (v/v)) δ ppm 7.24-7.15 (m, 2H), 7.08-6.97 (m, 2H), 6.92 (d, J = 8.5 Hz, 1H), 6.71 (d, J = 8.0 Hz, 1H), 3.65 (s, 3H), 3.44 (p, J = 8.6 Hz, 1H), 3.36 (t, J = 8.4 Hz, 2H), 3.11 (t, J = 8.4 Hz, 2H), 2.75 (s, 3H), 2.30-2.20 (m, 2H), 2.12-2.00 (m, 2H), 2.00-1.87 (m, 1H), 1.86-1.73 (m, 1H), 1.37-1.31 (m, 2H), 1.05-0.98 (m, 2H). | MS (APCI+) m/z 441.0 (M + H)$^+$ |
| Example II-41 | 1-(5-cyclobutyl-2-methoxy-4-methylpyridin-3-yl)-N-(1-methyl-1H-indole-4-sulfonyl- | $^1$H NMR (400 MHz, DMSO-d$_6$:D$_2$O = 9:1 (v/v)) δ ppm 7.88 (d, J = 1.0 Hz, 1H), 7.80 (dd, J = 8.2, 0.9 Hz, 1H), 7.61 (dd, J = 7.5, 0.8 Hz, 1H), 7.55 (d, J = 3.1 Hz, 1H), 7.31 (t, J = 7.9 Hz, 1H), 6.78 (dd, J = 3.1, 0.9 Hz, 1H), 3.87 (s, 3H), 3.78 (s, | MS (APCI+) m/z 454.0 (M + H)$^+$ |

TABLE 1-continued

| Example | Name | NMR | MS |
|---|---|---|---|
| | sulfonyl)cyclopropane-1-carboxamide | 3H), 3.49 (q, J = 8.8 Hz, 1H), 2.34-2.25 (m, 2H), 2.19-1.90 (m, 6H), 1.87-1.75 (m, 1H), 1.57-1.40 (m, 2H), 1.09-0.81 (m, 2H). | |
| Example II-42 | 1-(5-cyclobutyl-2-methoxy-4-methylpyridin-3-yl)-N-(1-methyl-1H-indole-7-sulfonyl)cyclopropane-1-carboxamide | $^1$H NMR (400 MHz, DMSO-$d_6$:$D_2O$ = 9:1 (v/v)) δ ppm 7.96-7.84 (m, 2H), 7.78 (dd, J = 7.8, 1.2 Hz, 1H), 7.43 (d, J = 3.2 Hz, 1H), 7.17 (t, J = 7.7 Hz, 1H), 6.67 (d, J = 3.2 Hz, 1H), 3.99 (s, 3H), 3.78 (s, 3H), 3.60-3.43 (m, 1H), 2.40-2.26 (m, 2H), 2.24-1.90 (m, 6H), 1.85-1.74 (m, 1H), 1.64-1.42 (m, 2H), 1.08-0.88 (m, 2H). | MS (APCI+) m/z 454.0 (M + H)$^+$. |
| Example II-43 | 1-(5-cyclobutyl-2-methoxy-4-methylpyridin-3-yl)-N-(1-methyl-1H-indazole-7-sulfonyl)cyclopropane-1-carboxamide | $^1$H NMR (400 MHz, DMSO-$d_6$:$D_2O$ = 9:1 (v/v)) δ ppm 8.31 (s, 1H), 8.15 (dd, J = 7.9, 1.1 Hz, 1H), 8.04 (dd, J = 7.5, 1.1 Hz, 1H), 7.88 (d, J = 0.9 Hz, 1H), 7.32 (t, J = 7.8 Hz, 1H), 4.22 (s, 3H), 3.74 (s, 3H), 3.62-3.43 (m, 1H), 2.43-2.26 (m, 2H), 2.26-1.91 (m, 6H), 1.91-1.71 (m, 1H), 1.66-1.40 (m, 2H), 1.10-0.80 (m, 2H). | MS (APCI+) m/z 455.0 (M + H)$^+$. |
| Example II-44 | 1-(5-cyclobutyl-2-methoxy-4-methylpyridin-3-yl)-N-(2-methylquinoline-8-sulfonyl)cyclopropane-1-carboxamide | $^1$H NMR (400 MHz, DMSO-$d_6$:$D_2O$ = 9:1 (v/v)) δ ppm 8.42 (d, J = 8.5 Hz, 1H), 8.30 (ddd, J = 15.4, 7.8, 1.5 Hz, 2H), 7.85 (d, J = 1.0 Hz, 1H), 7.77-7.65 (m, 1H), 7.62 (d, J = 8.5 Hz, 1H), 3.63 (s, 3H), 3.48-3.31 (m, 1H), 2.66 (s, 3H), 2.29-2.17 (m, 2H), 2.12-1.83 (m, 3H), 1.80-1.60 (m, 6H), 1.16-0.86 (m, 2H). | MS (APCI+) m/z 466.0 (M + H)$^+$. |
| Example II-45 | 1-(2-methoxy-6-methylphenyl)-N-(2-methylquinoline-8-sulfonyl)cyclopropane-1-carboxamide | $^1$H NMR (400 MHz, DMSO-$d_6$:$D_2O$ = 9:1 (v/v)) δ ppm 8.41 (d, J = 8.5 Hz, 1H), 8.35-8.25 (m, 2H), 7.70 (t, J = 7.8 Hz, 1H), 7.60 (d, J = 8.5 Hz, 1H), 7.22 (t, J = 7.9 Hz, 1H), 6.85 (d, J = 8.3 Hz, 1H), 6.76 (d, J = 7.6 Hz, 1H), 3.61 (s, 3H), 2.59 (s, 3H), 1.82 (s, 3H), 1.57-1.53 (m, 2H), 1.15-0.81 (m, 2H). | MS (APCI+) m/z 411.1 (M + H)$^+$. |
| Example II-46 | 1-(2-cyclobutyl-5-methoxyphenyl)-N-(quinoline-5-sulfonyl)cyclopropane-1-carboxamide | $^1$H NMR (501 MHz, DMSO-$d_6$:$D_2O$ = 9:1 (v/v)) δ ppm 9.05 (dd, J = 4.2, 1.6 Hz, 1H), 8.98 (dt, J = 8.8, 1.3 Hz, 1H), 8.40-8.29 (m, 2H), 7.94 (dd, J = 8.4, 7.4 Hz, 1H), 7.72 (dd, J = 8.8, 4.2 Hz, 1H), 7.16 (d, J = 8.5 Hz, 1H), 6.84 (dd, J = 8.5, 2.8 Hz, 1H), 6.72 (d, J = 2.8 Hz, 1H), 3.73 (s, 3H), 3.20-3.06 (m, 1H), 1.75-1.57 (m, 4H), 1.53-1.33 (m, 4H), 1.09-1.00 (m, 2H). | MS (APCI+) m/z 437.0 (M + H)$^+$. |
| Example II-47 | 1-(2-cyclobutyl-5-methoxyphenyl)-N-(2-methylquinoline-5-sulfonyl)cyclopropane-1-carboxamide | $^1$H NMR (400 MHz, DMSO-$d_6$:$D_2O$ = 9:1 (v/v)) δ ppm 8.86 (d, J = 8.9 Hz, 1H), 8.28-8.18 (m, 2H), 7.88 (t, J = 7.9 Hz, 1H), 7.60 (d, J = 8.9 Hz, 1H), 7.15 (d, J = 8.5 Hz, 1H), 6.84 (dd, J = 8.5, 2.7 Hz, 1H), 6.72 (d, J = 2.8 Hz, 1H), 3.73 (s, 3H), 3.14 (p, J = 8.8 Hz, 1H), 2.72 (s, 3H), 1.77-1.59 (m, 4H), 1.56-1.33 (m, 4H), 1.07-0.95 (m, 2H). | MS (APCI+) m/z 451.0 (M + H)$^+$. |
| Example II-48 | 1-[5-(hydroxymethyl)-2-methoxyphenyl]-N-(quinoline-5-sulfonyl)cyclopropane-1-carboxamide | $^1$H NMR (501 MHz, DMSO-$d_6$) δ ppm 11.57 (bs, 1H), 9.05 (dd, J = 4.2, 1.6 Hz, 1H), 8.98 (dt, J = 8.9, 1.1 Hz, 1H), 8.34 (d, J = 8.4 Hz, 1H), 8.31 (d, J = 7.4 Hz, 1H), 7.97-7.90 (m, 1H), 7.71 (dd, J = 8.8, 4.1 Hz, 1H), 7.21 (dd, J = 8.4, 2.1 Hz, 1H), 7.07 (d, J = 2.2 Hz, 1H), 6.82 (d, J = 8.4 Hz, 1H), 5.03 (bs, 1H), 4.42 (s, 2H), 3.35 (s, 3H), 1.26 (q, J = 4.3 Hz, 2H), 0.93 (q, J = 4.4 Hz, 2H). | MS (ESI+) m/z 413 (M + H)$^+$. |
| Example II-49 | 1-[2-methoxy-5-(methoxymethyl)phenyl]-N-(quinoline-5-sulfonyl)cyclopropane-1-carboxamide | $^1$H NMR (400 MHz, DMSO-$d_6$) δ ppm 11.63 (s, 1H), 9.05 (dd, J = 4.2, 1.6 Hz, 1H), 8.97 (dd, J = 8.7, 1.1 Hz, 1H), 8.32 (dd, J = 14.2, 7.9 Hz, 2H), 7.93 (t, J = 8.0 Hz, 1H), 7.70 (dd, J = 8.8, 4.2 Hz, 1H), 7.21 (dd, J = 8.3, 2.1 Hz, 1H), 7.06 (d, J = 2.2 Hz, 1H), 6.84 (d, J = 8.4 Hz, 1H), 4.31 (s, 2H), 3.36 (s, 3H), 3.28 (s, 3H), 1.28-1.25 (m, 2H), 0.94 (m, 2H). | MS (ESI+) m/z 427 (M + H)$^+$. |
| Example II-50 | 1-(2-methoxy-6-methylphenyl)-N-(2-methylquinoline-5-sulfonyl)cyclopropane-1-carboxamide | $^1$H NMR (501 MHz, DMSO-$d_6$:$D_2O$ = 9:1 (v/v)) δ ppm 8.86 (dd, J = 8.9, 0.9 Hz, 1H), 8.28-8.18 (m, 2H), 7.89 (dd, J = 8.4, 7.4 Hz, 1H), 7.63 (d, J = 8.9 Hz, 1H), 7.24-7.09 (m, 1H), 6.85-6.71 (m, 2H), 3.62 (s, 3H), 2.73 (s, 3H), 1.97 (s, 3H), 1.52-1.45 (m, 2H), 1.01-0.90 (m, 2H). | MS (APCI+) m/z 411.1 (M + H)$^+$. |
| Example II-51 | 1-(6-methoxy-2,3-dimethylphenyl)-N-(2-methylquinoline-5-sulfonyl)cyclopropane-1-carboxamide | $^1$H NMR (501 MHz, DMSO-$d_6$:$D_2O$ = 9:1 (v/v)) δ ppm 8.88 (dd, J = 8.9, 0.9 Hz, 1H), 8.26 (td, J = 7.7, 1.1 Hz, 2H), 7.92 (dd, J = 8.4, 7.5 Hz, 1H), 7.66 (d, J = 8.9 Hz, 1H), 7.09 (d, J = 8.4 Hz, 1H), 6.72 (d, J = 8.3 Hz, 1H), 3.59 (s, 4H), 2.75 (s, 3H), 2.13 (s, 3H), 1.89 (s, 3H), 1.52-1.45 (m, 2H), 1.02-0.83 (m, 2H). | MS (APCI+) m/z 425.0 (M + H)$^+$. |

TABLE 1-continued

| Example | Name | NMR | MS |
|---|---|---|---|
| Example II-52 | 1-(3-cyclopropyl-6-methoxy-2-methylphenyl)-N-(2-methylquinoline-5-sulfonyl)cyclopropane-1-carboxamide | $^1$H NMR (501 MHz, DMSO-$d_6$:$D_2O$ = 9:1 (v/v)) δ ppm 8.86 (dd, J = 8.8, 0.9 Hz, 1H), 8.30-8.20 (m, 2H), 7.90 (dd, J = 8.4, 7.5 Hz, 1H), 7.63 (d, J = 8.9 Hz, 1H), 6.97 (d, J = 8.4 Hz, 1H), 6.72 (d, J = 8.5 Hz, 1H), 3.59 (s, 3H), 2.73 (s, 3H), 2.06 (s, 3H), 1.82-1.70 (m, 1H), 1.56-1.42 (m, 2H), 1.04-0.78 (m, 4H), 0.55-0.47 (m, 2H). | MS (APCI+) m/z 451.0 (M + H)$^+$. |
| Example II-53 | 1-(2-methoxy-6-methylphenyl)-N-(1,2,3,4-tetrahydroquinoline-5-sulfonyl)cyclopropane-1-carboxamide | $^1$H NMR (501 MHz, DMSO-$d_6$:$D_2O$ = 9:1 (v/v)) δ ppm 7.21 (dd, J = 8.3, 7.5 Hz, 1H), 7.10-6.99 (m, 2H), 6.91-6.85 (m, 1H), 6.84-6.78 (m, 1H), 6.73 (d, J = 7.4, 1.9 Hz, 1H), 3.77 (s, 3H), 3.18 (t, J = 5.5 Hz, 2H), 2.85 (t, J = 6.4 Hz, 2H), 2.19 (s, 3H), 1.78 (p, J = 6.1 Hz, 2H), 1.66-1.47 (m, 2H), 1.17-0.95 (m, 2H). | MS (APCI+) m/z 401.1 (M + H)$^+$. |
| Example II-54 | 1-(3-chloro-2,6-dimethoxyphenyl)-N-(quinoline-5-sulfonyl)cyclopropane-1-carboxamide | $^1$H NMR (501 MHz, DMSO-$d_6$) δ ppm 9.06 (dd, J = 4.2, 1.6 Hz, 1H), 9.01 (ddd, J = 8.7, 1.6, 1.0 Hz, 1H), 8.35 (ddd, J = 8.4, 1.2, 1.0 Hz, 1H), 8.32 (dd, J = 7.5, 1.2 Hz, 1H), 7.94 (dd, J = 8.4, 7.5 Hz, 1H), 7.74 (dd, J = 8.7, 4.2 Hz, 1H), 7.39 (d, J = 9.0 Hz, 1H), 6.78 (d, J = 9.0 Hz, 1H), 3.57 (s, 3H), 3.45 (s, 3H), 1.49-1.46 (m, 2H), 1.07-1.03 (m, 2H). | MS (ESI) m/z 447 (M + H)$^+$. |
| Example II-55 | 1-(5-methoxy-2-methylphenyl)-N-(quinoline-5-sulfonyl)cyclopropane-1-carboxamide | $^1$H NMR (400 MHz, DMSO-$d_6$:$D_2O$ = 9:1 (v/v)) δ ppm 9.02 (dd, J = 4.2, 1.6 Hz, 1H), 8.93-8.88 (m, 1H), 8.38-8.27 (m, 2H), 7.94 (dd, J = 8.5, 7.4 Hz, 1H), 7.66 (dd, J = 8.7, 4.2 Hz, 1H), 7.12 (t, J = 7.9 Hz, 1H), 6.82-6.74 (m, 1H), 6.66-6.61 (m, 1H), 6.61-6.55 (m, 1H), 3.65 (s, 3H), 1.19-1.14 (m, 2H), 1.07-0.99 (m, 2H). | MS (APCI+) m/z 397.0 (M + H)$^+$. |
| Example II-56 | 1-(3-methoxyphenyl)-N-(quinoline-5-sulfonyl)cyclopropane-1-carboxamide | $^1$H NMR (400 MHz, DMSO-$d_6$:$D_2O$ = 9:1 (v/v)) δ ppm 9.06 (dd, J = 4.2, 1.6 Hz, 1H), 8.99-8.91 (m, 1H), 8.41-8.30 (m, 2H), 7.96 (dd, J = 8.4, 7.5 Hz, 1H), 7.72 (dd, J = 8.8, 4.2 Hz, 1H), 7.03-6.95 (m, 1H), 6.81-6.74 (m, 2H), 1.75 (s, 3H), 1.39-1.33 (m, 2H), 1.07-1.01 (m, 2H). | MS (APCI+) m/z 383.0 (M + H)$^+$. |
| Example II-57 | 1-(2-cyclopropyl-6-methoxyphenyl)-N-(quinoline-5-sulfonyl)cyclopropane-1-carboxamide | $^1$H NMR (501 MHz, chloroform-d) δ ppm 9.05 (dd, J = 4.2, 1.6 Hz, 1H), 8.78 (dt, J = 8.6, 1.2 Hz, 1H), 8.53 (dd, J = 7.5, 1.2 Hz, 1H), 8.42 (d, J = 8.4 Hz, 1H), 8.25 (s, 1H), 7.87 (t, J = 8.0 Hz, 1H), 7.53 (dd, J = 8.8, 4.2 Hz, 1H), 7.09 (dd, J = 8.4, 2.4 Hz, 1H), 6.95 (d, J = 2.4 Hz, 1H), 6.82 (d, J = 8.4 Hz, 1H), 3.58 (s, 3H), 1.87 (tt, J = 8.5, 5.1 Hz, 1H), 1.49 (q, J = 4.1 Hz, 2H), 1.05-0.95 (m, 4H), 0.65 (dt, J = 6.5, 4.8 Hz, 2H). | MS (APCI+) m/z 423 (M + H)$^+$. |
| Example II-58 | 1-[5-methoxy-2-(propan-2-yl)phenyl]-N-(quinoline-5-sulfonyl)cyclopropane-1-carboxamide | $^1$H NMR (501 MHz, DMSO-$d_6$:$D_2O$ = 9:1 (v/v)) δ ppm 9.11-8.96 (m, 2H), 8.36-8.20 (m, 2H), 7.89 (t, J = 8.0 Hz, 1H), 7.69 (dd, J = 8.7, 4.2 Hz, 1H), 7.05 (d, J = 8.5 Hz, 1H), 6.79 (dd, J = 8.5, 2.7 Hz, 1H), 6.70 (d, J = 2.7 Hz, 1H), 3.71 (s, 3H), 2.74 (p, J = 6.8 Hz, 1H), 1.46-1.35 (m, 2H), 1.07-0.93 (m, 2H), 0.78-0.59 (m, 6H). | MS (APCI+) m/z 417.0 (M + H)$^+$. |
| Example II-59 | 1-(5-methoxy-2-propylphenyl)-N-(quinoline-5-sulfonyl)cyclopropane-1-carboxamide | $^1$H NMR (400 MHz, DMSO-$d_6$:$D_2O$ = 9:1 (v/v)) δ ppm 9.04-8.93 (m, 2H), 8.34-8.24 (m, 2H), 7.87 (t, J = 7.9 Hz, 1H), 7.61 (dd, J = 8.7, 4.2 Hz, 1H), 7.02-6.94 (m, 1H), 6.81-6.74 (m, 2H), 3.74 (s, 3H), 2.18-2.10 (m, 2H), 1.38 (q, J = 4.2 Hz, 2H), 1.32-1.14 (m, 2H), 0.98 (q, J = 4.2 Hz, 2H), 0.59 (t, J = 7.3 Hz, 3H). | MS (APCI+) m/z 417.0 (M + H)$^+$. |
| Example II-60 | 1-(2-cyclopropyl-6-methoxyphenyl)-N-(2-methylquinoline-5-sulfonyl)cyclopropane-1-carboxamide | $^1$H NMR (501 MHz, chloroform-d) δ ppm 8.66 (dd, J = 8.8, 0.8 Hz, 1H), 8.44 (dd, J = 7.5, 1.2 Hz, 1H), 8.32 (dt, J = 8.4, 1.1 Hz, 1H), 8.23 (s, 1H), 7.82 (dd, J = 8.5, 7.4 Hz, 1H), 7.40 (d, J = 8.9 Hz, 1H), 7.10 (dd, J = 8.5, 2.3 Hz, 1H), 6.94 (d, J = 2.4 Hz, 1H), 6.83 (d, J = 8.4 Hz, 1H), 3.62 (s, 3H), 2.81 (s, 3H), 1.87 (tt, J = 8.4, 5.1 Hz, 1H), 1.51-1.45 (m, 2H), 1.07-0.94 (m, 4H), 0.69-0.61 (m, 2H). | MS (APCI+) m/z 437 (M + H)$^+$. |
| Example II-61 | 1-(2,5-dimethylphenyl)-N-(quinoline-5-sulfonyl)cyclopropane-1-carboxamide | $^1$H NMR (400 MHz, DMSO-$d_6$) δ ppm 11.66 (bs, 1H), 9.06 (dd, J = 4.2, 1.6 Hz, 1H), 9.00-8.96 (m, 1H), 8.37-8.33 (m, 1H), 8.32 (dd, J = 7.5, 1.2 Hz, 1H), 7.93 (dd, J = 8.4, 7.5 Hz, 1H), 7.71 (dd, J = 8.8, 4.2 Hz, 1H), 7.02-6.97 (m, 2H), 6.95 (d, J = 7.6 Hz, 1H), 2.24 (s, 3H), 1.81 (s, 3H), 1.39-1.35 (m, 2H), 1.04-0.99 (m, 2H). | MS (ESI) m/z 381 (M + H)$^+$. |
| Example II-62 | 1-(5-ethyl-2-methoxyphenyl)-N-(quinoline-5-sulfonyl)cyclopropane-1-carboxamide | $^1$H NMR (400 MHz, DMSO-$d_6$) δ ppm 11.54 (s, 1H), 9.05-9.02 (m, 1H), 8.99 (d, J = 8.8 Hz, 1H), 8.36-8.24 (m, 2H), 7.95-7.88 (m, 1H), 7.70 (s, 1H), 7.07 (d, J = 8.2 Hz, 1H), 6.94 (d, J = | MS (APCI+) m/z 423 (M + H)$^+$. |

TABLE 1-continued

| Example | Name | NMR | MS |
|---|---|---|---|
| | carboxamide | 2.0 Hz, 1H), 6.77 (d, J = 8.3 Hz, 1H), 3.36 (s, 3H), 2.56-2.49 (m, 2H), 1.25-1.21 (m, 2H), 1.15 (t, J = 7.6 Hz, 3H), 0.94-0.89 (m, 2H). | |
| Example II-63 | 1-(2-methoxy-4-methylphenyl)-N-(quinoline-5-sulfonyl)cyclopropane-1-carboxamide | $^1$H NMR (400 MHz, DMSO-$d_6$) δ ppm 11.52 (s, 1H), 9.05 (dd, J = 4.1, 1.6 Hz, 1H), 8.98 (dt, J = 8.7, 1.2 Hz, 1H), 8.39-8.22 (m, 2H), 8.01-7.84 (m, 1H), 7.70 (dd, J = 8.8, 4.2 Hz, 1H), 7.00 (d, J = 8.0 Hz, 1H), 6.73-6.65 (m, 2H), 3.37 (s, 3H), 2.30 (s, 3H), 1.22 (q, J = 4.2 Hz, 2H), 0.90 (q, J = 4.3 Hz, 2H). | MS (APCI+) m/z 397 (M + H)+. |
| Example II-64 | 1-(2-methoxy-3-methylphenyl)-N-(quinoline-5-sulfonyl)cyclopropane-1-carboxamide | $^1$H NMR (400 MHz, DMSO-$d_6$) δ ppm 11.76 (s, 1H), 9.04 (dd, J = 4.2, 1.6 Hz, 1H), 9.02-8.97 (m, 1H), 8.32 (t, J = 6.8 Hz, 2H), 7.92 (t, J = 8.0 Hz, 1H), 7.68 (dd, J = 8.8, 4.2 Hz, 1H), 7.10 (dd, J = 7.2, 2.1 Hz, 1H), 7.01-6.88 (m, 2H), 3.20 (s, 3H), 2.09 (s, 3H), 1.27 (q, J = 4.4 Hz, 2H), 1.05-0.96 (m, 2H). | MS (APCI+) m/z 397 (M + H)+. |
| Example II-65 | 1-(4-cyclobutyl-2,6-dimethoxyphenyl)-N-(1-methyl-1H-indole-4-sulfonyl)cyclopropane-1-carboxamide | $^1$H NMR (501 MHz, DMSO-$d_6$:D$_2$O = 9:1 (v/v)) δ ppm 7.79 (d, J = 8.2 Hz, 1H), 7.59 (dd, J = 18.1, 5.3 Hz, 2H), 7.30 (t, J = 7.9 Hz, 1H), 6.80-6.73 (m, 1H), 6.46-6.36 (m, 2H), 3.86 (s, 3H), 3.77 (s, 3H), 3.69 (s, 3H), 3.66-3.29 (m, 1H), 2.25-1.87 (m, 2H), 1.87-1.13 (m, 6H), 0.89 (s, 2H). | MS (APCI+) m/z 468.9 (M + H)+. |
| Example II-66 | 1-(4-cyclobutyl-2,6-dimethoxyphenyl)-N-(1-methyl-1H-indole-7-sulfonyl)cyclopropane-1-carboxamide | $^1$H NMR (501 MHz, DMSO-$d_6$:D$_2$O = 9:1 (v/v)) δ ppm 7.93-7.87 (m, 1H), 7.81-7.72 (m, 2H), 7.45-7.38 (m, 1H), 7.18-7.12 (m, 1H), 6.69-6.62 (m, 1H), 6.47 (d, J = 2.5 Hz, 2H), 6.45-6.37 (m, 2H), 4.00 (s, 3H), 3.78 (s, 3H), 3.67-3.58 (m, 1H), 2.25-2.19 (m, 1H), 2.09-2.00 (m, 1H), 1.92-1.77 (m, 3H), 1.71-1.57 (m, 2H), 1.46-1.31 (m, 1H), 0.98-0.87 (m, 2H). | MS (APCI+) m/z 469.0 (M + H)+. |
| Example II-67 | 1-(4-cyclobutyl-2,6-dimethoxyphenyl)-N-(1-methyl-1H-indazole-7-sulfonyl)cyclopropane-1-carboxamide | $^1$H NMR (501 MHz, DMSO-$d_6$:D$_2$O = 9:1 (v/v)) δ ppm 8.30 (s, 1H), 8.16 (dd, J = 8.0, 1.1 Hz, 1H), 8.04 (dd, J = 7.6, 1.1 Hz, 1H), 7.32 (t, J = 7.8 Hz, 1H), 6.47-6.36 (m, 2H), 4.25 (s, 3H), 3.78 (s, 3H), 3.69 (s, 3H), 3.66-3.50 (m, 1H), 2.26-2.13 (m, 1H), 2.13-1.89 (m, 1H), 1.89-1.69 (m, 3H), 1.65-1.56 (m, 2H), 1.47-1.34 (m, 1H), 1.02-0.91 (m, 2H). | MS (APCI+) m/z 470.0 (M + H)+. |
| Example II-68 | 1-(4-cyclobutyl-2,6-dimethoxyphenyl)-N-(pyrazolo[1,5-a]pyridine-4-sulfonyl)cyclopropane-1-carboxamide | $^1$H NMR (501 MHz, DMSO-$d_6$:D$_2$O = 9:1 (v/v)) δ ppm 8.93 (d, J = 6.8 Hz, 1H), 8.21 (s, 1H), 7.82-7.77 (m, 1H), 7.06 (t, J = 7.1 Hz, 1H), 6.99 (s, 1H), 6.43-6.33 (m, 2H), 3.77 (s, 3H), 3.67 (s, 3H), 3.53-3.42 (m, 1H), 2.17-1.95 (m, 2H), 1.76-1.52 (m, 5H), 1.42-1.36 (m, 1H), 0.91 (s, 2H). | MS (APCI+) m/z 456.0 (M + H)+. |
| Example II-69 | 1-(4-cyclobutyl-2,6-dimethoxyphenyl)-N-(2-methylquinoline-5-sulfonyl)cyclopropane-1-carboxamide | $^1$H NMR (501 MHz, DMSO-$d_6$:D$_2$O = 9:1 (v/v)) δ ppm 8.97-8.88 (m, 1H), 8.29-8.19 (m, 2H), 7.95-7.85 (m, 1H), 7.66 (d, J = 8.9 Hz, 1H), 6.42-6.32 (m, 2H), 3.77 (s, 3H), 3.64 (s, 3H), 3.41 (p, J = 8.8 Hz, 1H), 2.73 (s, 3H), 2.31-1.87 (m, 2H), 1.70-1.43 (m, 5H), 1.40-1.30 (m, 1H), 0.98-0.84 (m, 2H). | MS (APCI+) m/z 481.0 (M + H)+. |
| Example II-70 | N-(2-aminoquinoline-5-sulfonyl)-1-(4-cyclobutyl-2,6-dimethoxyphenyl)cyclopropane-1-carboxamide | $^1$H NMR (501 MHz, DMSO-$d_6$:D$_2$O = 9:1 (v/v)) δ ppm 8.93 (d, J = 9.8 Hz, 1H), 8.09-8.00 (m, 1H), 7.96-7.85 (m, 2H), 7.22 (d, J = 9.8 Hz, 1H), 6.39 (s, 2H), 3.78 (s, 3H), 3.68 (s, 3H), 3.57-3.45 (m, 1H), 2.23-1.95 (m, 2H), 1.84-1.50 (m, 5H), 1.45-1.28 (m, 1H), 1.00-0.85 (m, 2H). | MS (APCI+) m/z 481.9 (M + H)+. |
| Example II-71 | N-(2-aminoquinoline-5-sulfonyl)-1-(5-ethyl-2-methoxyphenyl)cyclopropane-1-carboxamide | $^1$H NMR (400 MHz, DMSO-$d_6$) δ ppm 8.80 (d, J = 9.7 Hz, 1H), 8.38 (s, 1H), 7.95 (dd, J = 7.0, 1.8 Hz, 1H), 7.88-7.76 (m, 2H), 7.07 (dd, J = 8.8, 5.8 Hz, 2H), 6.93 (d, J = 2.3 Hz, 1H), 6.79 (d, J = 8.3 Hz, 1H), 3.48 (s, 3H), 2.55-2.49 (m, 2H), 1.22 (q, J = 4.2 Hz, 2H), 1.13 (t, J = 7.6 Hz, 3H), 0.92 (q, J = 4.3 Hz, 2H). | MS (ESI+) m/z 426 (M + H)+. |
| Example II-72 | 1-(5-ethyl-2-methoxyphenyl)-N-(1H-indazole-4-sulfonyl)cyclopropane-1-carboxamide | $^1$H NMR (400 MHz, DMSO-$d_6$) δ ppm 13.56 (s, 1H), 11.22 (s, 1H), 8.32 (s, 1H), 7.85 (d, J = 8.4 Hz, 1H), 7.64 (d, J = 7.3 Hz, 1H), 7.49 (t, J = 7.8 Hz, 1H), 7.07 (dd, J = 8.3, 2.2 Hz, 1H), 6.93 (d, J = 2.2 Hz, 1H), 6.79 (d, J = 8.4 Hz, 1H), 3.43 (s, 3H), 2.55-2.48 (m, 2H), 1.24-1.18 (m, 2H), 1.13 (t, J = 7.6 Hz, 3H), 0.96-0.88 (m, 2H). | MS (APCI+) m/z 399.9 (M + H)+. |
| Example II-73 | 1-(2-ethyl-6-methoxyphenyl)-N-(quinoline-5- | $^1$H NMR (400 MHz, chloroform-d) δ ppm 9.03 (dd, J = 4.2, 1.6 Hz, 1H), 8.76 (ddd, J = 8.8, 1.6, 0.9 Hz, 1H), 8.52 (dd, J = 7.4, 1.3 Hz, 1H), 8.41 | MS (APCI+) m/z 423 (M + H)+. |

TABLE 1-continued

| Example | Name | NMR | MS |
|---|---|---|---|
| | sulfonyl)cyclopropane-1-carboxamide | (dt, J = 8.5, 1.1 Hz, 1H), 8.24 (s, 1H), 7.86 (dd, J = 8.5, 7.5 Hz, 1H), 7.51 (dd, J = 8.8, 4.2 Hz, 1H), 7.22 (dd, J = 8.4, 2.3 Hz, 1H), 7.03 (s, 1H), 6.84 (d, J = 8.4 Hz, 1H), 3.58 (s, 3H), 2.62 (q, J = 7.6 Hz, 2H), 1.52-1.45 (m, 2H), 1.28-1.21 (m, 3H), 1.01 (q, J = 4.1 Hz, 2H). | |
| Example II-74 | 1-(2-ethoxy-5-methylphenyl)-N-(1H-indazole-4-sulfonyl)cyclopropane-1-carboxamide | $^1$H NMR (400 MHz, DMSO-$d_6$) δ ppm 13.66-13.50 (m, 1H), 11.22 (s, 1H), 8.34 (s, 1H), 7.88 (d, J = 8.3 Hz, 1H), 7.68 (d, J = 7.2 Hz, 1H), 7.52 (t, J = 7.9 Hz, 1H), 7.12-7.02 (m, 1H), 6.95 (d, J = 2.1 Hz, 1H), 6.79 (d, J = 8.2 Hz, 1H), 3.78 (q, J = 6.9 Hz, 2H), 2.23 (s, 3H), 1.21 (q, J = 4.2 Hz, 2H), 0.94 (bt, J = 6.7 Hz, 5H). | MS (APCI+) m/z 400 (M + H)$^+$. |
| Example II-75 | N-(1H-indazole-4-sulfonyl)-1-{5-methyl-2-[(propan-2-yl)oxy]phenyl}cyclopropane-1-carboxamide | $^1$H NMR (400 MHz, DMSO-$d_6$) δ ppm 13.55 (s, 1H), 11.17 (s, 1H), 8.36 (d, J= 1.0 Hz, 1H), 7.84 (d, J = 8.4 Hz, 1H), 7.65 (d, J = 7.2 Hz, 1H), 7.47 (dd, J = 8.4, 7.3 Hz, 1H), 7.00 (dd, J = 8.3, 2.1 Hz, 1H), 6.90 (d, J = 2.2 Hz, 1H), 6.77 (d, J = 8.3 Hz, 1H), 4.41 (hept, J = 6.0 Hz, 1H), 2.18 (s, 3H), 1.18 (q, J = 4.3 Hz, 2H), 0.99 (d, J = 6.0 Hz, 6H), 0.89 (q, J = 4.4 Hz, 2H). | MS (ESI+) m/z 414 (M + H)$^+$. MS (ESI−) m/z 412 (M − H)$^-$. |
| Example II-76 | 1-(4-cyclobutyl-2,6-dimethoxyphenyl)-N-(1H-indazole-4-sulfonyl)cyclopropane-1-carboxamide | $^1$H NMR (400 MHz, DMSO-$d_6$) δ ppm 13.53 (s, 1H), 10.93 (s, 1H), 8.35 (s, 1H), 7.84 (d, J = 8.4 Hz, 1H), 7.63 (d, J = 7.3 Hz, 1H), 7.50-7.44 (m, 1H), 6.39-6.32 (m, 2H), 3.74 (s, 3H), 3.64 (s, 3H), 3.37-3.27 (m, 1H), 2.18-2.06 (m, 1H), 2.06-1.91 (m, 1H), 1.81-1.58 (m, 3H), 1.59-1.46 (m, 2H), 1.36-1.25 (m, 1H), 0.92-0.77 (m, 2H). | MS (APCI+) m/z 456 (M + H)$^+$. |
| Example II-77 | N-(1H-indazole-4-sulfonyl)-1-(6-methoxy-2,3-dimethylphenyl)cyclopropane-1-carboxamide | $^1$H NMR (400 MHz, DMSO-$d_6$) δ ppm 13.00 (s, 1H), 8.12 (s, 1H), 7.50 (s, 1H), 7.33 (d, J = 7.1 Hz, 1H), 7.29-7.22 (m, 1H), 7.18-7.02 (m, 1H), 6.86 (d, J = 8.3 Hz, 1H), 6.56 (d, J = 8.3 Hz, 1H), 3.61 (s, 3H), 2.08 (s, 3H), 2.00 (s, 3H), 1.29 (d, J = 3.7 Hz, 2H), 0.73 (dd, J = 9.6, 3.5 Hz, 1H), 0.46-0.35 (m, 1H). | MS (APCI+) m/z 400 (M + H)$^+$. |
| Example II-78 | 1-(3-cyclopropyl-6-methoxy-2-methylphenyl)-N-(1H-indazole-4-sulfonyl)cyclopropane-1-carboxamide | $^1$H NMR (501 MHz, DMSO-$d_6$) δ ppm 13.58 (s, 1H), 11.06 (s, 1H), 8.33 (s, 1H), 7.87 (s, 1H), 7.65 (s, 1H), 7.50 (d, J = 7.1 Hz, 1H), 6.93 (d, J = 8.5 Hz, 1H), 6.69 (d, J = 8.5 Hz, 1H), 3.62 (s, 3H), 2.11 (s, 3H), 1.74 (tt, J = 8.4, 5.4 Hz, 1H), 1.49 (d, J = 27.2 Hz, 2H), 0.97 (s, 1H), 0.82 (s, 3H), 0.49 (dd, J = 5.4, 2.5 Hz, 2H). | MS (APCI+) m/z 426 (M + H)$^+$. |
| Example II-79 | N-(1H-indole-4-sulfonyl)-1-{5-methyl-2-[(propan-2-yl)oxy]phenyl}cyclopropane-1-carboxamide | $^1$H NMR (400 MHz, DMSO-$d_6$) δ ppm 11.57 (s, 1H), 10.77 (s, 1H), 7.66 (d, J = 8.1 Hz, 1H), 7.59-7.50 (m, 2H), 7.18 (t, J = 7.8 Hz, 1H), 7.03-6.96 (m, 1H), 6.89 (d, J = 2.2 Hz, 1H), 6.81 (ddd, J = 3.0, 1.9, 0.9 Hz, 1H), 6.77 (d, J = 8.3 Hz, 1H), 4.42 (hept, J = 6.0 Hz, 1H), 2.17 (s, 3H), 1.19 (q, J = 4.4 Hz, 2H), 1.02 (d, J = 6.0 Hz, 6H), 0.86 (q, J = 4.4 Hz, 2H). | MS (APCI+) m/z 413 (M + H)$^+$. |
| Example II-80 | 1-(2,5-dimethylphenyl)-N-(1H-indole-4-sulfonyl)cyclopropane-1-carboxamide | $^1$H NMR (400 MHz, DMSO-$d_6$) δ ppm 11.60 (s, 1H), 11.02 (s, 1H), 7.67 (d, J = 8.1 Hz, 1H), 7.58-7.52 (m, 2H), 7.18 (t, J = 7.8 Hz, 1H), 7.03-6.91 (m, 3H), 6.79 (d, J = 2.6 Hz, 1H), 2.20 (s, 3H), 1.89 (s, 3H), 1.41-1.31 (m, 2H), 1.05-0.89 (m, 2H). | MS (APCI+) m/z 369 (M + H)$^+$. |
| Example II-81 | 1-(2-cyclopropyl-6-methoxyphenyl)-N-(1H-indazole-4-sulfonyl)cyclopropane-1-carboxamide | $^1$H NMR (400 MHz, DMSO-$d_6$) δ ppm 13.56 (s, 1H), 11.25 (s, 1H), 8.31 (s, 1H), 7.85 (d, J = 8.3 Hz, 1H), 7.64 (d, J = 7.3 Hz, 1H), 7.49 (dd, J = 8.4, 7.3 Hz, 1H), 6.92 (dd, J = 8.4, 2.3 Hz, 1H), 6.82 (d, J = 2.3 Hz, 1H), 6.76 (d, J = 8.4 Hz, 1H), 3.41 (s, 3H), 1.81 (tt, J = 8.4, 5.1 Hz, 1H), 1.19 (q, J = 4.3 Hz, 2H), 0.92 (q, J = 4.4 Hz, 2H), 0.88-0.79 (m, 2H), 0.62-0.53 (m, 2H). | MS (APCI+) m/z 425 (M + H)$^+$. |
| Example II-82 | N-(2-aminoquinoline-5-sulfonyl)-1-{2-methoxy-5-[1-(methoxymethyl)cyclopropyl]phenyl}cyclopropane-1-carboxamide | $^1$H NMR (400 MHz, DMSO-$d_6$) δ ppm 11.55 (s, 1H), 8.80 (d, J = 9.7 Hz, 1H), 8.31 (s, 2H), 7.95 (dd, J = 7.2, 1.6 Hz, 1H), 7.88-7.78 (m, 2H), 7.15 (dd, J = 8.5, 2.3 Hz, 1H), 7.08 (d, J = 9.7 Hz, 1H), 6.95 (d, J = 2.3 Hz, 1H), 6.78 (d, J = 8.5 Hz, 1H), 3.48 (s, 3H), 3.37 (s, 2H), 3.18 (s, 3H), 1.25 (q, J = 4.2 Hz, 2H), 0.92 (q, J = 4.4 Hz, 2H), 0.75 (dt, J = 6.1, 1.8 Hz, 4H). | (ESI+) m/z 482 (M + H)$^+$. |
| Example II-83 | 1-(2-ethoxy-5-methylphenyl)-N-(2-methoxyquinoline-5- | $^1$H NMR (400 MHz, DMSO-$d_6$) δ ppm 11.40 (s, 1H), 8.81 (d, J = 9.3 Hz, 1H), 8.12-7.99 (m, 2H), 7.79 (dd, J = 8.4, 7.5 Hz, 1H), 7.14 (d, J = | MS (ESI+) m/z 441 (M + H)$^+$. |

TABLE 1-continued

| Example | Name | NMR | MS |
|---|---|---|---|
|  | sulfonyl)cyclopropane-1-carboxamide | 9.3 Hz, 1H), 7.01 (dd, J = 8.4, 2.2 Hz, 1H), 6.91 (d, J = 2.2 Hz, 1H), 6.71 (d, J = 8.3 Hz, 1H), 3.99 (s, 3H), 3.65 (q, J = 6.9 Hz, 2H), 2.19 (s, 3H), 1.19 (q, J = 4.3 Hz, 2H), 0.90 (t, J = 3.5 Hz, 2H), 0.81 (t, J = 6.9 Hz, 3H). |  |
| Example II-84 | 1-(2-ethoxy-5-methylphenyl)-N-[2-(methylamino)quinoline-5-sulfonyl]cyclopropane-1-carboxamide | : $^1$H NMR (501 MHz, DMSO-$d_6$) δ ppm 9.17 (s, 1H), 8.71 (d, J = 9.8 Hz, 1H), 8.07 (d, J = 8.4 Hz, 1H), 7.97 (d, J = 7.6 Hz, 1H), 7.82 (t, J = 8.0 Hz, 1H), 7.09 (d, J = 9.8 Hz, 1H), 7.04 (dd, J = 8.3, 2.2 Hz, 1H), 6.93 (d, J = 2.2 Hz, 1H), 6.77 (d, J = 8.3 Hz, 1H), 3.78 (q, J = 7.0 Hz, 2H), 3.07 (s, 3H), 2.21 (s, 3H), 1.21 (q, J = 4.2 Hz, 2H), 0.98 (t, J = 6.9 Hz, 3H), 0.94 (q, J = 4.3 Hz, 2H). | MS (ESI+) m/z 440 (M + H)$^+$ |
| Example II-85 | 1-(2-ethoxy-5-methylphenyl)-N-(1H-indole-4-sulfonyl)cyclopropane-1-carboxamide | $^1$H NMR (501 MHz, DMSO-$d_6$) δ ppm 11.59 (t, J = 2.2 Hz, 1H), 10.79 (s, 1H), 7.68 (dd, J = 8.1, 1.0 Hz, 1H), 7.57 (dd, J = 7.5, 0.9 Hz, 1H), 7.54 (t, J = 2.8 Hz, 1H), 7.20 (t, J = 7.8 Hz, 1H), 7.03 (dd, J = 8.3, 2.2 Hz, 1H), 6.92 (d, J = 2.2 Hz, 1H), 6.80-6.76 (m, 2H), 3.78 (q, J = 6.9 Hz, 2H), 2.20 (s, 3H), 1.21 (q, J = 4.3 Hz, 2H), 0.96 (t, J = 6.9 Hz, 3H), 0.90 (q, J = 4.4 Hz, 2H). | MS (ESI−) m/z 397 (M − H)$^−$ |
| Example II-86 | 1-[2-methoxy-5-(2,2,2-trifluoro-1-methoxyethyl)phenyl]-N-(quinoline-5-yl)oxy]phenyl}cyclopropane-1-carboxamide | $^1$H NMR (400 MHz, DMSO-$d_6$) δ ppm 11.69 (s, 1H), 9.06 (dd, J = 4.2, 1.6 Hz, 1H), 8.98 (d, J = 8.7 Hz, 1H), 8.34 (d, J = 8.5 Hz, 1H), 8.30 (d, J = 7.4 Hz, 1H), 7.93 (t, J = 7.9 Hz, 1H), 7.72 (dd, J = 8.8, 4.2 Hz, 1H), 7.33 (dd, J = 8.5, 2.1 Hz, 1H), 4.72 (td, J = 6.3, 1.0 Hz, 2H), 4.26-4.19 (m, 2H), 2.24 (s, 3H), 1.30 (q, J = 4.2 Hz, 2H), 1.02 (q, J = 4.3 Hz, 2H). | MS (APCI+) m/z 495 (M + H)$^+$ |
| Example II-87 | 1-[2-methoxy-5-(1-methoxyethyl)phenyl]-N-(quinoline-5-sulfonyl)cyclopropane-1-carboxamide | $^1$H NMR (501 MHz, DMSO-$d_6$) δ ppm 11.58 (s, 1H), 9.06 (dd, J = 4.1, 1.6 Hz, 1H), 8.98 (d, J = 8.7 Hz, 1H), 8.34 (d, J = 8.5 Hz, 1H), 8.30 (d, J = 7.4 Hz, 1H), 7.94 (t, J = 8.0 Hz, 1H), 7.71 (dd, J = 8.7, 4.2 Hz, 1H), 7.18 (dd, J = 8.4, 2.2 Hz, 1H), 7.02 (td, J = 2.2, 1.0 Hz, 1H), 6.84 (d, J = 8.4 Hz, 1H), 4.23 (q, J = 6.4 Hz, 1H), 3.35 (s, 3H), 3.11 (s, 3H), 1.31 (d, J = 6.4 Hz, 3H), 1.29 (m, 2H), 0.95 (bs, 2H). | MS (APCI+) m/z 441 (M + H)$^+$ |
| Example II-88 | N-(1H-indole-4-sulfonyl)-1-[2-methoxy-5-(2-methoxypropan-2-yl)phenyl]cyclopropane-1-carboxamide | $^1$H NMR (400 MHz, DMSO-$d_6$) δ ppm 11.60 (s, 1H), 10.78 (s, 1H), 7.67 (d, J = 8.1 Hz, 1H), 7.56-7.52 (m, 2 H), 7.25-7.15 (m, 2H), 7.05 (d, J = 2.3 Hz, 1H), 6.85 (d, J = 8.6 Hz, 1H), 6.79-6.74 (m, 1H), 3.50 (s, 3H), 2.91 (s, 3H), 1.38 (s, 6H), 1.28 (q, J = 4.3 Hz, 2H), 0.91 (q, J = 4.4 Hz, 2H). | MS (ESI−) m/z 441 (M − H)$^−$ |
| Example II-89 | 1-[2-methoxy-5-(3-methyloxetan-3-yl)phenyl]-N-(quinoline-5-sulfonyl)cyclopropane-1-carboxamide | $^1$H NMR (400 MHz, chloroform-d) δ ppm 9.03 (dd, J = 4.1, 1.6 Hz, 1H), 8.79 (ddd, J = 8.7, 1.6, 0.9 Hz, 1H), 8.57-8.48 (m, 1H), 8.41 (d, J = 8.5 Hz, 1H), 8.26 (s, 1H), 7.86 (t, J = 8.0 Hz, 1H), 7.52 (dd, J = 8.8, 4.2 Hz, 1H), 7.31-7.23 (m, 1H), 7.07 (d, J = 2.4 Hz, 1H), 6.90 (d, J = 8.5 Hz, 1H), 4.89 (d, J = 5.6 Hz, 2H), 4.65 (d, J = 5.6 Hz, 2H), 3.62 (s, 3H), 1.72 (s, 3H), 1.51 (q, J = 4.2 Hz, 2H), 1.01 (q, J = 4.2 Hz, 2H). | MS (ESI−) m/z 451 (M − H)$^−$ |
| Example II-90 | N-(2-aminoquinoline-5-sulfonyl)-1-{5-methyl-2-[(oxetan-3-yl)oxy]phenyl}cyclopropane-1-carboxamide | $^1$H NMR (500 MHz, DMSO-$d_6$) δ ppm 11.84 (s, 1H), 8.91 (d, J = 9.7 Hz, 1H), 8.63 (s, 2H), 8.03 (dd, J = 7.1, 1.7 Hz, 1H), 7.92-7.84 (m, 2H), 7.15 (d, J = 9.8 Hz, 1H), 7.06-6.97 (m, 2H), 6.45 (d, J = 8.1 Hz, 1H), 5.14-5.07 (m, 1H), 4.72 (td, J = 6.3, 1.0 Hz, 2H), 4.26-4.19 (m, 2H), 2.24 (s, 3H), 1.30 (q, J = 4.2 Hz, 2H), 1.02 (q, J = 4.3 Hz, 2H). | MS (ESI−) m/z 452 (M − H)$^−$ |
| Example II-91 | N-(1H-indazole-4-sulfonyl)-1-[2-methoxy-5-(2-methylpropoxy)pyridin-4-yl]cyclopropane-1-carboxamide | $^1$H NMR (400 MHz, DMSO-$d_6$:D$_2$O = 9:1 (v/v)) δ ppm 8.28 (d, J = 1.0 Hz, 1H), 7.90 (dt, J = 8.4, 1.0 Hz, 1H), 7.77-7.63 (m, 2H), 7.53 (dd, J = 8.4, 7.2 Hz, 1H), 6.63 (s, 1H), 3.78 (s, 3H), 3.41 (d, J = 6.4 Hz, 2H), 1.40-1.22 (m, 3H), 1.02 (q, J = 4.5 Hz, 2H), 0.65 (d, J = 6.7 Hz, 6H). | MS (APCI+) m/z 445.1 (M + H)$^+$ |
| Example II-92 | 1-(2-{[(2S)-1-methoxypropan-2-yl]oxy}-5-methylphenyl)-N-(quinoline-5-sulfonyl)cyclopropane-1-carboxamide | $^1$H NMR (501 MHz, chloroform-d) δ ppm 9.01 (dd, J = 4.2, 1.6 Hz, 1H), 8.78 (ddd, J = 8.8, 1.6, 0.8 Hz, 1H), 8.72 (s, 1H), 8.51 (dd, J = 7.5, 1.2 Hz, 1H), 8.40 (dt, J = 8.4, 1.1 Hz, 1H), 7.85 (dd, J = 8.4, 7.4 Hz, 1H), 7.46 (dd, J = 8.7, 4.1 Hz, 1H), 7.15 (ddd, J = 8.4, 2.2, 0.9 Hz, 1H), 6.98-6.93 (m, 1H), 6.91 (d, J = 8.4 Hz, 1H), 4.58 (td, J = 6.3, 4.6 Hz, 1H), 3.48 (dd, J = 10.1, 6.1 Hz, 1H), 3.42-3.35 (m, 4H), 2.28 (s, 3H), | MS (ESI−) m/z 453 (M − H)$^−$ |

TABLE 1-continued

| Example | Name | NMR | MS |
|---|---|---|---|
| | | 1.54-1.49 (m, 1H), 1.46-1.41 (m, 1H), 1.26 (d, J = 6.3 Hz, 3H), 1.06-0.98 (m, 2H). | |
| Example II-93 | 1-[5-cyclopropyl-2-(2-methylpropoxy)pyridin-3-yl]-N-(2-methoxyquinoline-5-sulfonyl)cyclopropane-1-carboxamide | $^1$H NMR (501 MHz, DMSO-$d_6$) δ ppm 11.63 (s, 1H), 8.75 (d, J = 9.3 Hz, 1H), 8.11-8.01 (m, 2H), 7.85-7.75 (m, 2H), 7.14 (dd, J = 5.9, 3.4 Hz, 2H), 4.01 (s, 3H), 3.54 (d, J = 6.6 Hz, 2H), 1.84 (tt, J = 8.4, 5.1 Hz, 1H), 1.29 (q, J = 4.3 Hz, 2H), 1.20 (hept, J = 6.7 Hz, 1H), 0.98 (q, J = 4.4 Hz, 2H), 0.93-0.84 (m, 2H), 0.70-0.63 (m, 2H), 0.58 (d, J = 6.6 Hz, 6H). | MS (ESI+) m/z 496 (M + H)$^+$. |
| Example II-94 | 1-[5-cyclobutyl-2-(2-methylpropoxy)pyridin-3-yl]-N-(2-methoxyquinoline-5-sulfonyl)cyclopropane-1-carboxamide | $^1$H NMR (400 MHz, DMSO-$d_6$) δ ppm 11.62 (s, 1H), 8.76 (dd, J = 9.3, 0.8 Hz, 1H), 8.10-8.00 (m, 2H), 7.84 (d, J = 2.3 Hz, 1H), 7.78 (dd, J = 8.4, 7.5 Hz, 1H), 7.39 (d, J = 2.4 Hz, 1H), 7.13 (d, J = 9.3 Hz, 1H), 4.00 (s, 3H), 3.55 (d, J = 6.5 Hz, 2H), 3.41 (p, J = 8.8 Hz, 1H), 2.22 (qt, J = 8.0, 2.4 Hz, 2H), 2.14-2.02 (m, 2H), 1.98-1.88 (m, 1H), 1.83-1.71 (m, 1H), 1.31 (q, J = 4.4 Hz, 2H), 1.20 (dt, J = 13.3, 6.6 Hz, 1H), 0.99 (q, J = 4.5 Hz, 2H), 0.57 (d, J = 6.7 Hz, 6H). | MS (ESI+) m/z 510 (M + H)$^+$. |
| Example II-95 | 1-{5-cyclopropyl-2-[(propan-2-yl)oxy]pyridin-3-yl}-N-(2-methoxyquinoline-5-sulfonyl)cyclopropane-1-carboxamide | $^1$H NMR (400 MHz, DMSO-$d_6$) δ ppm 11.60 (s, 1H), 8.83 (d, J = 9.4 Hz, 1H), 8.11-7.98 (m, 2H), 7.80 (d, J = 2.6 Hz, 1H), 7.77 (d, J = 8.3 Hz, 1H), 7.17 (d, J = 9.3 Hz, 1H), 7.09 (d, J = 2.4 Hz, 1H), 4.95 (p, J = 6.1 Hz, 1H), 3.99 (s, 3H), 1.81 (tt, J = 8.5, 5.2 Hz, 1H), 1.23 (q, J = 4.4 Hz, 2H), 0.98-0.94 (m, 2H), 0.93 (d, J = 6.2 Hz, 6H), 0.88-0.81 (m, 2H), 0.65-0.59 (m, 2H). | MS (ESI+) m/z 482 (M + H)$^+$. |
| Example II-96 | 1-[5-(2-ethoxypropan-2-yl)-2-methoxyphenyl]-N-(quinoline-5-sulfonyl)cyclopropane-1-carboxamide | $^1$H NMR (500 MHz, DMSO-$d_6$) δ ppm 11.56 (s, 1H), 9.06 (dd, J = 4.2, 1.6 Hz, 1H), 8.98 (dt, J = 8.7, 1.2 Hz, 1H), 8.35 (d, J = 8.4 Hz, 1H), 8.31 (dd, J = 7.4, 1.2 Hz, 1H), 7.94 (dd, J = 8.4, 7.5 Hz, 1H), 7.72 (dd, J = 8.7, 4.2 Hz, 1H), 7.25 (dd, J = 8.5, 2.3 Hz, 1H), 7.07 (d, J = 2.4 Hz, 1H), 6.82 (d, J = 8.6 Hz, 1H), 3.35 (s, 3H), 3.12 (q, J = 7.0 Hz, 2H), 1.42 (s, 6H), 1.32 (q, J = 4.3 Hz, 2H), 1.02 (t, J = 7.0 Hz, 3H), 0.95 (q, J = 4.5 Hz, 2H). | MS (ESI−) m/z 467 (M − H)$^−$. |
| Example II-97 | 1-[2-ethoxy-5-(2-methoxypropan-2-yl)phenyl]-N-(quinoline-5-sulfonyl)cyclopropane-1-carboxamide | $^1$H NMR (501 MHz, DMSO-$d_6$) δ ppm 11.49 (s, 1H), 9.05 (dd, J = 4.1, 1.6 Hz, 1H), 8.97-8.92 (m, 1H), 8.34 (d, J = 8.6 Hz, 1H), 8.31 (d, J = 7.4 Hz, 1H), 7.93 (t, J = 7.9 Hz, 1H), 7.68 (dd, J = 8.7, 4.2 Hz, 1H), 7.24-7.18 (m, 1H), 7.07 (d, J = 2.3 Hz, 1H), 6.78 (d, J = 8.5 Hz, 1H), 3.64 (q, J = 7.0 Hz, 2H), 2.95 (s, 3H), 1.42 (s, 6H), 1.33 (q, J = 4.4 Hz, 2H), 1.00-0.91 (bs, 2H), 0.73 (t, J = 6.9 Hz, 3H). | MS (ESI−) m/z 467 (M − H)$^−$. |
| Example II-98 | 1-[2-(difluoromethoxy)-5-ethylphenyl]-N-(quinoline-5-sulfonyl)cyclopropane-1-carboxamide | $^1$H NMR (400 MHz, DMSO-$d_6$) δ ppm 11.59 (s, 1H), 9.03 (dd, J = 4.2, 1.6 Hz, 1H), 8.98 (dt, J = 8.8, 1.3 Hz, 1H), 8.31 (dt, J = 8.6, 1.0 Hz, 1H), 8.28 (dd, J = 7.4, 1.2 Hz, 1H), 7.89 (dd, J = 8.5, 7.4 Hz, 1H), 7.70 (dd, J = 8.8, 4.2 Hz, 1H), 7.14 (dd, J = 8.3, 2.2 Hz, 1H), 7.07 (d, J = 2.2 Hz, 1H), 6.93 (d, J = 8.3 Hz, 1H), 6.70 (t, J = 74.4 Hz, 1H), 2.53 (q, J = 7.6 Hz, 2H), 1.36 (q, J = 4.5 Hz, 2H), 1.12 (t, J = 7.6 Hz, 3H), 1.05 (q, J = 4.6 Hz, 2H). | MS (ESI−) m/z 445 (M − H)$^−$. |
| Example II-99 | 1-[2-methoxy-5-(2-methoxypropan-2-yl)phenyl]-N-(2-methylquinoline-5-sulfonyl)cyclopropane-1-carboxamide | $^1$H NMR (501 MHz, DMSO-$d_6$) δ ppm 11.47 (s, 1H), 8.83 (d, J = 8.9 Hz, 1H), 8.26-8.15 (m, 2H), 7.90-7.79 (m, 1H), 7.57 (d, J = 8.9 Hz, 1H), 7.23 (dd, J = 8.5, 2.3 Hz, 1H), 7.05 (d, J = 2.4 Hz, 1H), 6.81 (d, J = 8.6 Hz, 1H), 3.36 (s, 3H), 2.93 (s, 3H), 2.70 (s, 3H), 1.39 (s, 6H), 1.29 (q, J = 4.3 Hz, 2H), 0.93 (q, J = 4.4 Hz, 2H). | MS (ESI−) m/z 467 (M − H)$^−$. |
| Example II-100 | 1-[2-methoxy-5-(1-methoxycyclobutyl)phenyl]-N-(2-methylquinoline-5-sulfonyl)cyclopropane-1-carboxamide | $^1$H NMR (400 MHz, DMSO-$d_6$) δ ppm 11.49 (s, 1H), 8.81 (d, J = 8.8 Hz, 1H), 8.19 (td, J = 7.6, 1.1 Hz, 2H), 7.84 (dd, J = 8.4, 7.5 Hz, 1H), 7.55 (d, J = 8.9 Hz, 1H), 7.24 (dd, J = 8.4, 2.3 Hz, 1H), 7.04 (d, J = 2.3 Hz, 1H), 6.83 (d, J = 8.5 Hz, 1H), 3.36 (s, 3H), 2.78 (s, 3H), 2.68 (s, 3H), 2.35-2.16 (m, 4H), 1.81 (ddq, J = 10.9, 9.2, 4.8 Hz, 1H), 1.54 (dp, J = 11.0, 8.4 Hz, 1H), 1.28 (q, J = 4.4 Hz, 2H), 0.92 (q, J = 4.5 Hz, 2H). | MS (ESI−) m/z 479 (M − H)$^−$. |
| Example II-101 | 1-[2-(difluoromethoxy)-5-methylphenyl]-N-(2-methylquinoline-5-sulfonyl)- | $^1$H NMR (400 MHz, DMSO-$d_6$:D$_2$O = 9:1 (v/v)) δ ppm 8.92 (d, J = 8.9 Hz, 1H), 8.28-8.20 (m, 2H), 7.94-7.86 (m, 1H), 7.66 (d, J = 9.0 Hz, 1H), 7.14 (dd, J = 8.4, 2.2 Hz, 1H), 7.07 (d, J = 2.4 Hz, 1H), 6.94 (d, J = 8.2 Hz, 1H), 6.69 (t, J = | MS (APCI+) 447.2 m/z (M + H)$^+$. |

TABLE 1-continued

| Example | Name | NMR | MS |
|---|---|---|---|
| | sulfonyl)cyclopropane-1-carboxamide | 74.5 Hz, 1H), 2.73 (s, 3H), 2.25 (s, 3H), 1.35 (q, J = 4.5 Hz, 2H), 1.05 (q, J = 4.6 Hz, 2H). | |
| Example II-102 | 1-[5-chloro-2-(difluoromethoxy)phenyl]-N-(2-methylquinoline-5-sulfonyl)cyclopropane-1-carboxamide | $^1$H NMR (501 MHz, DMSO-$d_6$:$D_2O$ = 9:1 (v/v)) δ ppm 8.92 (d, J = 8.9 Hz, 1H), 8.29-8.22 (m, 2H), 7.96-7.89 (m, 1H), 7.68 (d, J = 8.9 Hz, 1H), 7.43 (dd, J = 8.7, 2.7 Hz, 1H), 7.34 (d, J = 2.7 Hz, 1H), 7.10 (d, J = 8.7 Hz, 1H), 6.79 (t, J = 73.8 Hz, 1H), 2.75 (s, 3H), 1.35 (q, J = 4.5 Hz, 2H), 1.10 (q, J = 4.6 Hz, 2H). | MS (APCI+) 467.1 m/z (M + H)$^+$. |
| Example II-103 | 1-[2-(difluoromethoxy)-5-ethylphenyl]-N-(2-methylquinoline-5-sulfonyl)cyclopropane-1-carboxamide | $^1$H NMR (400 MHz, DMSO-$d_6$:$D_2O$ = 9:1 (v/v)) δ ppm 8.89 (d, J = 8.9 Hz, 1H), 8.26-8.18 (m, 2H), 7.92-7.84 (m, 1H), 7.63 (d, J = 9.0 Hz, 1H), 7.17 (dd, J = 8.4, 2.3 Hz, 1H), 7.08 (d, J = 2.2 Hz, 1H), 6.96 (d, J = 8.3 Hz, 1H), 6.68 (t, J = 74.5 Hz, 1H), 2.72 (s, 3H), 2.61-2.52 (m, 2H), 1.37 (q, J = 4.5 Hz, 2H), 1.14 (t, J = 7.6 Hz, 3H), 1.06 (q, J = 4.6 Hz, 2H). | MS (APCI+) 453.2 m/z (M + H)$^+$. |
| Example II-104 | 1-(2-{[(2S)-1-methoxypropan-2-yl]oxy}-5-methylphenyl)-N-(2-methylquinoline-5-sulfonyl)cyclopropane-1-carboxamide | $^1$H NMR (501 MHz, DMSO-$d_6$:$D_2O$ = 9:1 (v/v)) δ ppm 9.02 (d, J = 8.9 Hz, 1H), 8.32-8.26 (m, 2H), 7.96 (dd, J = 8.5, 7.4 Hz, 1H), 7.73 (d, J = 9.0 Hz, 1H), 7.05 (dd, J = 8.4, 2.2 Hz, 1H), 6.92 (d, J = 2.2 Hz, 1H), 6.83 (d, J = 8.4 Hz, 1H), 4.37 (h, J = 6.0 Hz, 1H), 3.16 (s, 3H), 3.13-3.03 (m, 2H), 2.77 (s, 3H), 2.21 (s, 3H), 1.37-1.29 (m, 1H), 1.22-1.14 (m, 1H), 1.07-1.00 (m, 1H), 0.93-0.85 (m, 4H). | MS (APCI+) 469.2 m/z (M + H)$^+$. |
| Example II-105 | 1-[2-ethoxy-5-(1-methoxy-2-methylpropan-2-yl)phenyl]-N-(2-methylquinoline-5-sulfonyl)cyclopropane-1-carboxamide | $^1$H NMR (400 MHz, DMSO-$d_6$:$D_2O$ = 9:1 (v/v)) δ ppm 8.78 (d, J = 8.9 Hz, 1H), 8.26-8.19 (m, 2H), 7.88 (dd, J = 8.3, 7.5 Hz, 1H), 7.57 (d, J = 8.9 Hz, 1H), 7.22 (dd, J = 8.6, 2.5 Hz, 1H), 7.06 (d, J = 2.4 Hz, 1H), 6.75 (d, J = 8.7 Hz, 1H), 3.59 (q, J = 6.9 Hz, 2H), 3.31 (s, 2H), 3.20 (s, 3H), 2.70 (s, 3H), 1.29 (q, J = 4.5 Hz, 2H), 1.21 (s, 6H), 0.94 (q, J = 4.4 Hz, 2H), 0.68 (t, J = 6.9 Hz, 3H). | MS (APCI+) m/z 497.2 (M + H)$^+$. |
| Example II-106 | 1-[2-(difluoromethoxy)-5-(2-ethoxypropan-2-yl)phenyl]-N-(quinoline-5-sulfonyl)cyclopropane-1-carboxamide | $^1$H NMR (400 MHz, DMSO-$d_6$) δ ppm 11.71 (s, 1H), 9.05 (dd, J = 4.2, 1.6 Hz, 1H), 8.99 (d, J = 8.5 Hz, 1H), 8.33 (d, J = 8.4 Hz, 1H), 8.29 (dd, J = 7.5, 1.3 Hz, 1H), 7.91 (dd, J = 8.5, 7.5 Hz, 1H), 7.71 (dd, J = 8.8, 4.2 Hz, 1H), 7.34 (dd, J = 8.5, 2.4 Hz, 1H), 7.21 (d, J = 2.3 Hz, 1H), 7.01 (d, J = 8.7 Hz, 1H), 6.79 (t, J = 74.3 Hz, 1H), 3.14 (q, J = 7.1 Hz, 2H), 1.46 (q, J = 4.5 Hz, 2H), 1.42 (s, 6H), 1.08 (q, J = 4.6 Hz, 2H), 1.03 (t, J = 7.0 Hz, 3H). | MS (ESI+) m/z 505 (M + H)$^+$. |
| Example II-107 | 1-[2-(difluoromethoxy)-5-(2-ethoxypropan-2-yl)phenyl]-N-(2-methylquinoline-5-sulfonyl)cyclopropane-1-carboxamide | $^1$H NMR (400 MHz, DMSO-$d_6$) δ ppm 11.70 (s, 1H), 8.88 (d, J = 8.9 Hz, 1H), 8.24-8.18 (m, 2H), 7.85 (dd, J = 8.4, 7.5 Hz, 1H), 7.61 (d, J = 8.9 Hz, 1H), 7.34 (dd, J = 8.5, 2.4 Hz, 1H), 7.21 (d, J = 2.4 Hz, 1H), 7.01 (d, J = 8.6 Hz, 1H), 6.81 (t, J = 74.5 Hz, 1H), 3.14 (q, J = 7.0 Hz, 2H), 2.71 (s, 3H), 1.46 (q, J = 4.5 Hz, 2H), 1.42 (s, 6H), 1.07 (q, J = 4.8 Hz, 2H), 1.03 (t, J = 7.0 Hz, 3H). | MS (ESI+) m/z 519 (M + H)$^+$. |
| Example II-108 | 1-[2-(difluoromethoxy)-5-(2-methoxypropan-2-yl)phenyl]-N-(quinoline-5-sulfonyl)cyclopropane-1-carboxamide | $^1$H NMR (400 MHz, DMSO-$d_6$) δ ppm 11.67 (s, 1H), 9.01 (dd, J = 4.1, 1.6 Hz, 1H), 8.95 (dt, J = 8.8, 1.2 Hz, 1H), 8.32-8.27 (m, 1H), 8.25 (dd, J = 7.5, 1.3 Hz, 1H), 7.87 (dd, J = 8.4, 7.4 Hz, 1H), 7.67 (dd, J = 8.8, 4.2 Hz, 1H), 7.29 (dd, J = 8.5, 2.4 Hz, 1H), 7.18 (d, J = 2.3 Hz, 1H), 6.98 (d, J = 8.5 Hz, 1H), 6.76 (t, J = 74.4 Hz, 1H), 2.94 (s, 3H), 1.42 (q, J = 4.6 Hz, 2H), 1.38 (s, 6H), 1.05 (q, J = 4.7 Hz, 2H). | MS (ESI−) m/z 489 (M − H)$^−$. |
| Example II-109 | 1-[2-(difluoromethoxy)-5-(2-methoxypropan-2-yl)phenyl]-N-(2-methylquinoline-5-sulfonyl)cyclopropane-1-carboxamide | $^1$H NMR (400 MHz, DMSO-$d_6$) δ ppm 11.65 (s, 1H), 8.84 (d, J = 8.9 Hz, 1H), 8.17 (ddd, J = 10.2, 7.4, 1.1 Hz, 2H), 7.82 (dd, J = 8.4, 7.5 Hz, 1H), 7.57 (d, J = 8.9 Hz, 1H), 7.29 (dd, J = 8.5, 2.3 Hz, 1H), 7.17 (d, J = 2.3 Hz, 1H), 6.98 (d, J = 8.5 Hz, 1H), 6.78 (t, J = 74.3 Hz, 1H), 2.94 (s, 3H), 2.68 (s, 3H), 1.41 (q, J = 4.7 Hz, 2H), 1.38 (s, 6H), 1.14-0.91 (m, 2H). | MS (ESI−) m/z 479 (M − H)$^−$. |
| Example II-110 | 1-[5-(1-ethoxy-2-methylpropan-2-yl)-2-methoxyphenyl]-N-(quinoline-5-sulfonyl)cyclopropane-1-carboxamide | $^1$H NMR (400 MHz, DMSO-$d_6$) δ ppm 11.49 (s, 1H), 9.06 (dd, J = 4.1, 1.6 Hz, 1H), 9.02-8.94 (m, 1H), 8.35 (d, J = 8.4 Hz, 1H), 8.31 (dd, J = 7.5, 1.2 Hz, 1H), 7.94 (dd, J = 8.4, 7.5 Hz, 1H), 7.71 (dd, J = 8.8, 4.1 Hz, 1H), 7.24 (dd, J = 8.6, 2.5 Hz, 1H), 7.08 (d, J = 2.4 Hz, 1H), 6.77 (d, J = 8.7 Hz, 1H), 3.40 (q, J = 7.0 Hz, 2H), 3.33 (s, | MS (APCI+) m/z 483 (M + H)$^+$. |

TABLE 1-continued

| Example | Name | NMR | MS |
|---|---|---|---|
| | | 3H), 1.31 (q, J = 4.3 Hz, 2H), 1.23 (s, 6H), 1.06 (t, J = 7.0 Hz, 3H), 0.95 (q, J = 4.5 Hz, 2H). | |
| Example II-111 | 1-[5-(1-ethoxy-2-methylpropan-2-yl)-2-methoxyphenyl]-N-(2-methylquinoline-5-sulfonyl)cyclopropane-1-carboxamide | $^1$H NMR (400 MHz, DMSO-d$_6$) δ ppm 11.43 (s, 1H), 8.86 (d, J = 8.9 Hz, 1H), 8.26-8.18 (m, 2H), 7.91-7.84 (m, 1H), 7.59 (d, J = 8.9 Hz, 1H), 7.24 (dd, J = 8.6, 2.5 Hz, 1H), 7.08 (d, J = 2.4 Hz, 1H), 6.77 (d, J = 8.7 Hz, 1H), 3.39 (q, J = 7.0 Hz, 2H), 3.36 (s, 3H), 2.72 (s, 3H), 1.30 (q, J = 4.3 Hz, 2H), 1.22 (s, 6H), 1.06 (t, J = 7.0 Hz, 3H), 0.95 (q, J = 4.4 Hz, 2H). | MS (APCI+) m/z 497 (M + H)$^+$. |
| Example II-112 | 1-[5-(dimethylamino)-2-(2-methylpropoxy)pyridin-3-yl]-N-(quinoline-5-sulfonyl)cyclopropane-1-carboxamide | $^1$H NMR (400 MHz, DMSO-d$_6$) δ ppm 11.70 (s, 1H), 9.02 (dd, J = 4.2, 1.6 Hz, 1H), 8.91-8.86 (m, 1H), 8.34-8.27 (m, 2H), 7.91 (d, J = 8.0 Hz, 1H), 7.73 (d, J = 2.8 Hz, 1H), 7.65 (dd, J = 8.8, 4.2 Hz, 1H), 7.33 (d, J = 2.9 Hz, 1H), 3.49 (d, J = 6.4 Hz, 2H), 2.91 (s, 6H), 1.32 (q, J = 4.4 Hz, 2H), 1.19 (hept, J = 6.6 Hz, 1H), 1.01 (q, J = 4.5 Hz, 2H), 0.52 (d, J = 6.6 Hz, 6H). | MS (APCI+) m/z 469 (M + H)$^+$. |
| Example II-113 | 1-[2-methoxy-5-(1-methoxy-2-methylpropan-2-yl)phenyl]-N-(2-methylquinoline-5-sulfonyl)cyclopropane-1-carboxamide | $^1$H NMR (400 MHz, chloroform-d) δ ppm 8.69-8.63 (m, 1H), 8.42 (dd, J = 7.5, 1.2 Hz, 1H), 8.39 (bs, 1H), 8.29 (d, J = 8.4 Hz, 1H), 7.79 (dd, J = 8.5, 7.4 Hz, 1H), 7.38 (dd, J = 8.8, 2.2 Hz, 2H), 7.20 (d, J = 2.5 Hz, 1H), 6.85 (d, J = 8.6 Hz, 1H), 3.62 (s, 3H), 3.37 (s, 2H), 3.33 (s, 3H), 2.78 (s, 3H), 1.48 (q, J = 4.1 Hz, 2H), 1.31 (s, 6H), 1.00 (q, J = 4.1 Hz, 2H). | MS (APCI+) m/z 483 (M + H)$^+$. |
| Example II-115 | 1-(5-ethyl-2-{[(3S)-oxolan-3-yl]oxy}phenyl)-N-(2-methylquinoline-5-sulfonyl)cyclopropane-1-carboxamide | $^1$H NMR (400 MHz, DMSO-d$_6$) δ ppm 11.45 (s, 1H), 8.83 (d, J = 8.9 Hz, 1H), 8.21 (t, J = 7.2 Hz, 2H), 7.86 (t, J = 7.9 Hz, 1H), 7.56 (d, J = 8.9 Hz, 1H), 7.06 (dd, J = 8.4, 2.2 Hz, 1H), 6.98 (d, J = 2.2 Hz, 1H), 6.73 (d, J = 8.3 Hz, 1H), 4.66 (td, J = 4.7, 2.4 Hz, 1H), 3.65 (dd, J = 9.9, 4.9 Hz, 1H), 3.56 (td, J = 8.1, 3.5 Hz, 1H), 3.44 (td, J = 8.6, 6.4 Hz, 1H), 3.21 (dd, J = 9.8, 2.0 Hz, 1H), 2.71 (s, 3H), 2.53 (q, J = 7.6 Hz, 1H), 1.86-1.72 (m, 1H), 1.40 (m, 1H), 1.26 (m, 2H), 1.16 (t, J = 7.6 Hz, 3H), 0.92 (dd, J = 24.2, 8.0 Hz, 2H). | MS (APCI+) m/z 481 (M + H)$^+$. |
| Example II-117 | 1-(5-methyl-2-{[(3S)-oxolan-3-yl]oxy}phenyl)-N-(quinoline-5-sulfonyl)cyclopropane-1-carboxamide | $^1$H NMR (400 MHz, DMSO-d$_6$) δ ppm 11.50 (s, 1H), 9.02 (dd, J = 4.2, 1.6 Hz, 1H), 8.93 (dt, J = 8.8, 1.2 Hz, 1H), 8.35-8.26 (m, 2H), 7.91 (dd, J = 8.4, 7.5 Hz, 1H), 7.66 (dd, J = 8.8, 4.2 Hz, 1H), 7.01 (dd, J = 8.4, 2.1 Hz, 1H), 6.93 (d, J = 2.2 Hz, 1H), 6.68 (d, J = 8.3 Hz, 1H), 4.59 (ddt, J = 6.7, 4.3, 1.9 Hz, 1H), 3.59 (dd, J = 9.9, 4.9 Hz, 1H), 3.52 (td, J = 8.2, 3.5 Hz, 1H), 3.41 (td, J = 8.6, 6.3 Hz, 1H), 3.15 (dd, J = 9.9, 2.0 Hz, 1H), 2.20 (s, 3H), 1.83-1.68 (m, 1H), 1.43-1.32 (m, 1H), 1.20 (qdd, J = 9.1, 5.7, 3.0 Hz, 2H), 0.92 (ddd, J = 9.6, 5.7, 3.0 Hz, 1H), 0.85 (ddd, J = 8.4, 5.7, 2.8 Hz, 1H). | MS (ESI+) m/z 453 (M + H)$^+$. |

TABLE 2

| Example | Name | MS |
|---|---|---|
| Example III-3 | N-(benzenesulfonyl)-1-(2,4-dichlorophenyl)cyclopropane-1-carboxamide | |
| Example III-4 | N-(3-cyanobenzene-1-sulfonyl)-4-(3-fluorophenyl)oxane-4-carboxamide | |
| Example III-5 | N-(benzenesulfonyl)-1-(4-methoxyphenyl)cyclopropane-1-carboxamide | |
| Example III-6 | N-(benzenesulfonyl)-1-phenylcyclopropane-1-carboxamide | |
| Example III-7 | N-(benzenesulfonyl)-1-(4-chlorophenyl)cyclobutane-1-carboxamide | |
| Example III-8 | 1-(2,4-dichlorophenyl)-N-(2,3-dihydro-1H-indene-5-sulfonyl)cyclopropane-1-carboxamide | |
| Example III-9 | N-(4-chlorobenzene-1-sulfonyl)-1-(2,4-dichlorophenyl)cyclopropane-1-carboxamide | |
| Example III-10 | N-(4-chlorobenzene-1-sulfonyl)-1-(3-chlorophenyl)cyclopropane-1-carboxamide | |
| Example III-11 | methyl 5-{[1-(2,4-dichlorophenyl)cyclopropane-1-carbonyl]sulfamoyl}-4-methoxythiophene-3-carboxylate | |

TABLE 2-continued

| Example | Name | MS |
|---|---|---|
| Example III-12 | 1-(2,4-dichlorophenyl)-N-(3,5-dimethyl-1,2-oxazole-4-sulfonyl)cyclopropane-1-carboxamide | |
| Example III-13 | 1-(2,4-dichlorophenyl)-N-[2-(trifluoromethoxy)benzene-1-sulfonyl]cyclopropane-1-carboxamide | |
| Example III-14 | 1-(2,4-dichlorophenyl)-N-[4-(trifluoromethoxy)benzene-1-sulfonyl]cyclopropane-1-carboxamide | |
| Example III-15 | 1-(2,4-dichlorophenyl)-N-[3-(trifluoromethyl)benzene-1-sulfonyl]cyclopropane-1-carboxamide | |
| Example III-16 | 1-(2,4-dichlorophenyl)-N-[4-(2-oxopyrrolidin-1-yl)benzene-1-sulfonyl]cyclopropane-1-carboxamide | |
| Example III-17 | 1-(2,4-dichlorophenyl)-N-[5-(1,2-oxazol-5-yl)thiophene-2-sulfonyl]cyclopropane-1-carboxamide | |
| Example III-18 | 1-(2,4-dichlorophenyl)-N-[4-(pyrrolidine-1-sulfonyl)benzene-1-sulfonyl]cyclopropane-1-carboxamide | |
| Example III-19 | N-(4-chlorobenzene-1-sulfonyl)-1-(2,4-dichlorophenyl)-N-methylcyclopropane-1-carboxamide | |
| Example III-20 | 1-(2,4-dichlorophenyl)-N-{4-[(propan-2-yl)oxy]benzene-1-sulfonyl}cyclopropane-1-carboxamide | |
| Example III-21 | 1-(2,4-dichlorophenyl)-N-[6-(morpholin-4-yl)pyridine-3-sulfonyl]cyclopropane-1-carboxamide | |
| Example III-22 | benzyl 4-{[1-(2,4-dichlorophenyl)cyclopropane-1-carbonyl]sulfamoyl}piperidine-1-carboxylate | |
| Example III-23 | N-(2-chlorobenzene-1-sulfonyl)-1-(3-chlorophenyl)cyclopropane-1-carboxamide | |
| Example III-24 | 1-(2,4-dichlorophenyl)-N-(4-methoxybenzene-1-sulfonyl)cyclopropane-1-carboxamide | |
| Example III-25 | 1-(2,4-dichlorophenyl)-N-(3,4-dimethoxybenzene-1-sulfonyl)cyclopropane-1-carboxamide | |
| Example III-26 | N-(3-chlorobenzene-1-sulfonyl)-1-(2,4-dichlorophenyl)cyclopropane-1-carboxamide | |
| Example III-27 | 1-(2,4-dichlorophenyl)-N-(naphthalene-2-sulfonyl)cyclopropane-1-carboxamide | |
| Example III-28 | N-(cyclopropanesulfonyl)-1-(2,4-dichlorophenyl)cyclopropane-1-carboxamide | |
| Example III-29 | N-(benzenesulfonyl)-1-(4-methylphenyl)cyclopropane-1-carboxamide | |
| Example III-30 | N-(benzenesulfonyl)-1-(2-fluorophenyl)cyclopropane-1-carboxamide | |
| Example III-31 | N-(benzenesulfonyl)-1-(4-fluorophenyl)cyclopropane-1-carboxamide | |
| Example III-32 | N-(benzenesulfonyl)-1-(2-chlorophenyl)cyclopropane-1-carboxamide | |
| Example III-33 | N-(benzenesulfonyl)-1-(4-chlorophenyl)cyclopropane-1-carboxamide | |
| Example III-34 | N-(benzenesulfonyl)-1-(3,4-dichlorophenyl)cyclopropane-1-carboxamide | |
| Example III-35 | 1-(2-fluorophenyl)-N-(phenylmethanesulfonyl)cyclopropane-1-carboxamide | |
| Example III-36 | 1-(2,4-dichlorophenyl)-N-(1,1-dioxo-1λ$^6$-thiolane-3-sulfonyl)cyclopropane-1-carboxamide | |
| Example III-37 | 1-(2,4-dichlorophenyl)-N-(4-methylbenzene-1-sulfonyl)cyclopropane-1-carboxamide | |
| Example III-38 | N-(2-cyano-5-fluorobenzene-1-sulfonyl)-1-(2,4-dichlorophenyl)cyclopropane-1-carboxamide | |
| Example III-55 | N-(2-chloro-5-nitrobenzene-1-sulfonyl)-1-(3-chlorophenyl)cyclopropane-1-carboxamide | |
| Example III-56 | 1-(3-chlorophenyl)-N-(6-ethoxy-1,3-benzothiazole-2-sulfonyl)cyclopropane-1-carboxamide | |
| Example III-57 | 1-(3-chlorophenyl)-N-(5-hydroxynaphthalene-1-sulfonyl)cyclopropane-1-carboxamide | |
| Example III-58 | 1-(3-chlorophenyl)-N-[5-(dimethylamino)naphthalene-1-sulfonyl]cyclopropane-1-carboxamide | |

TABLE 2-continued

| Example | Name | MS |
|---|---|---|
| Example III-59 | 1-(2,4-dichlorophenyl)-N-(pyridine-3-sulfonyl)cyclopropane-1-carboxamide | |
| Example III-60 | N-(6-chloropyridine-3-sulfonyl)-1-(2,4-dichlorophenyl)cyclopropane-1-carboxamide | |
| Example III-61 | N-(benzenesulfonyl)-2,2-dimethyl-1-phenylcyclopropane-1-carboxamide | |
| Example III-62 | methyl 5-{[1-(2,4-dichlorophenyl)cyclopropane-1-carbonyl]ulfamoyl}furan-2-carboxylate | |
| Example III-63 | N-(5-bromothiophene-2-sulfonyl)-1-(2,4-dichlorophenyl)cyclopropane-1-carboxamide | |
| Example III-64 | 1-(2,4-dichlorophenyl)-N-[3-(trifluoromethoxy)benzene-1-sulfonyl]cyclopropane-1-carboxamide | |
| Example III-65 | methyl 2-{[1-(2,4-dichlorophenyl)cyclopropane-1-carbonyl]sulfamoyl}benzoate | |
| Example III-66 | methyl 4-chloro-2-{[l-(2,4-dichlorophenyl)cyclopropane-1-carbonyl]sulfamoyl}benzoate | |
| Example III-67 | 2-{[1-(2,4-dichlorophenyl)cyclopropane-1-carbonyl]sulfamoyl(benzoic acid | |
| Example III-68 | 4-chloro-2-{[l-(2,4-dichlorophenyl)cyclopropane-1-carbonyl]sulfamoyl}benzoic acid | |
| Example III-69 | benzyl 4-{[1-(4-methylphenyl)cyclopropane-1-carbonyl]sulfamoyl}piperidine-1-carboxylate | |
| Example III-70 | benzyl 4-{[1-(3,4-dichlorophenyl)cyclopropane-1-carbonyl]sulfamoyl}piperidine-1-carboxylate | |
| Example III-71 | N-(benzenesulfonyl)-1-(3-bromophenyl)cyclopropane-1-carboxamide | |
| Example III-72 | 1-(3-chlorophenyl)-N-[2-(trifluoroacetyl)-1,2,3,4-tetrahydroisoquinoline-7-sulfonyl]cyclopropane-1-carboxamide | |
| Example III-73 | 1-(3-chlorophenyl )-N-[4-(1H-pyrazol-1-yl)benzene-1-sulfonyl]cyclopropane-1-carboxamide | |
| Example III-74 | 1-(3-chlorophenyl)-N-(3,4-dimethylbenzene-1-sulfonyl)cyclopropane-1-carboxamide | |
| Example III-75 | 1-(3-chlorophenyl)-N-(2-oxo-2,3-dihydro-1H-indole-5-sulfonyl)cyclopropane-1-carboxamide | |
| Example III-76 | N-(1-acetyl-2,3-dihydro-1H-indole-5-sulfonyl)-1-(3-chlorophenyl)cyclopropane-1-carboxamide | |
| Example III-77 | 1-(2,4-dichlorophcnyl)-N-(piperidine-4-sulfonyl)cyclopropane-1-carboxamide | |
| Example III-78 | N-(1-acetylpiperidine-4-sulfonyl)-1-(2,4-dichlorophenyl)cyclopropane-1-carboxamide | |
| Example III-79 | 1-(2,4-dichlorophenyl)-N-[1-(3-phenylpropanoyl)piperidine-4-sulfonyl]cyclopropane-1-carboxamide | |
| Example III-80 | tert-butyl 4-{[1-(2,4-dichlorophenyl)cyclopropane-1-carbonyl]sulfamoyl}piperidine-1-carboxylate | |
| Example III-81 | 4-(3-methoxyphenyl)-N-(2-methylbenzene-1-sulfonyl)oxane-4-carboxamide | |
| Example III-82 | N-(2-methylbenzene-1-sulfonyl)-4-(3-methylphenyl)oxane-4-carboxamide | |
| Example III-83 | 1-(3-chlorophenyl)-N-(2-methylbenzene-1-sulfonyl)cyclopentane-1-carboxamide | |
| Example III-84 | 1-(3-chlorophenyl)-N-(5-methylpyridine-2-sulfonyl)cyclopropane-1-carboxamide | |
| Example III-85 | 1-(2-methoxyphenyl)-N-(2-methylbenzene-1-sulfonyl)cyclopropane-1-carboxamide | |
| Example III-86 | 1-(2H-1,3-benzodioxol-5-yl)-N-(2-methylbenzene-1-sulfonyl)cyclopropane-1-carboxamide | |
| Example III-87 | 1-(2,4-dichlorophenyl)-N-(2-methylbenzene-1-sulfonyl)cyclopropane-1-carboxamide | |
| Example III-88 | 1-(4-chlorophenyl)-N-(2-methylbenzene-1-sulfonyl)cyclopropane-1-carboxamide | |
| Example III-89 | tert-butyl 4-(4-fluorophenyl)-4-[(naphthalene-1-sulfonyl)carbamoyl]piperidine-1-carboxylate | MS (APCI+) m/z 413.0 (M + H − Boc)+. |
| Example III-90 | 1-(3,4-dimethoxyphenyl)-N-(naphthalene-1-sulfonyl)cyclopentane-1-carboxamide | MS (APCI+) m/z 440.0 (M + H)+. |

TABLE 2-continued

| Example | Name | MS |
|---|---|---|
| Example III-91 | 1-(2,2-difluoro-2H-1,3-benzodioxol-5-yl)-N-(naphthalene-1-sulfonyl)cyclopropane-1-carboxamide | MS (APCI+) m/z 431.9 (M + H)+. |
| Example III-92 | 1-(3-bromophenyl)-N-(naphthalene-1-sulfonyl)cyclopropane-1-carboxamide | MS (ESI) m/z 430/432 (M + H)+. |
| Example III-93 | 1-(3-bromophenyl)-N-(quinoline-5-sulfonyl)cyclopropane-1-carboxamide | MS (ESI) m/z 431/433 (M + H)+. |
| Example III-94 | 4-(5-methoxy-2-methylphenyl)-1-methyl-N-(quinoline-5-sulfonyl)piperidine-4-carboxamide | MS (ESI+) m/z 454 (M + H)+. |
| Example III-95 | 1-[2-methoxy-5-(trifluoromethyl)pyridin-3-yl]-N-(pyrazolo[1,5-a]pyridine-4-sulfonyl)cyclopropane-1-carboxamide | MS (APCI+) m/z 441.0 (M + H)+. |
| Example III-96 | 1-[2-methoxy-5-(trifluoromethyl)pyridin-3-yl]-N-(1-methyl-1H-benzimidazole-7-sulfonyl)cyclopropane-1-carboxamide | MS (APCI+) m/z 455.0 (M + H)+. |
| Example III-97 | 1-[2-methoxy-5-(trifluoromethyl)pyridin-3-yl]-N-(1-methyl-1H-indazole-7-sulfonyl)cyclopropane-1-carboxamide | MS (APCI+) m/z 455.0 (M + H)+. |
| Example III-98 | N-(1H-indazole-4-sulfonyl)-1-[2-methoxy-5-(trifluoromethyl)pyridin-3-yl]cyclopropane-1-carboxamide | MS (APCI+) m/z 441.0 (M + H)+. |
| Example III-99 | 1-(5-cyano-2-methoxyphenyl)-N-(quinoline-5-sulfonyl)cyclopropane-1-carboxamide | MS (APCI+) m/z 408.1 (M + H)+. |
| Example III-100 | 1-(5-cyano-2-methoxyphenyl)-N-(1,2,3,4-tetrahydroquinoline-5-sulfonyl)cyclopropane-1-carboxamide | MS (APCI+) m/z 412.1 (M + H)+. |
| Example III-101 | 1-[5-(bicyclo[1.1.1]pentan-1-yl)-2-methoxyphenyl]-N-(1,2,3,4-tetrahydroquinoline-5-sulfonyl)cyclopropane-1-carboxamide | MS (APCI+) m/z 453.0 (M + H)+. |
| Example III-102 | 1-(2-methoxy-6-methylphenyl)-N-(1-methyl-1H-indole-4-sulfonyl[cyclopropane-1-carboxamide | MS (APCI+) m/z 399.1 (M + H)+. |
| Example III-103 | 1-(3,5-dichloro-2,6-dimethoxyphenyl)-N-(quinoline-5-sulfonyl)cyclopropane-1-carboxamide | MS (ESI) m/z 481/483 (M + H)+. |
| Example III-104 | 1-(2,4-dichlorophenyl)-N-(phenylmethanesulfonyl)cyclopropane-1-carboxamide | |
| Example III-105 | 1-(2,4-dichlorophenyl)-N-(trifluoromethanesulfonyl)cyclopropane-1-carboxamide | |
| Example III-106 | 1-(2,4-dichlorophenyl)-N-(2,2,2-trifluoroethanesulfonyl)cyclopropane-1-carboxamide | |
| Example III-107 | 1-(2,4-dichlorophenyl)-N-(propane-1-sulfonyl)cyclopropane-1-carboxamide | |
| Example III-108 | N-(3-chloropropane-1-sulfonyl)-1-(2,4-dichlorophenyl)cyclopropane-1-carboxamide | |
| Example III-109 | 1-(3-chlorophenyl)-N-(phenylmethanesulfonyl)cyclopropane-1-carboxamide | |
| Example III-110 | 1-(2,4-dichlorophenyl)-N-(propane-2-sulfonyl)cyclopropane-1-carboxamide | |
| Example III-111 | 1-(4-methylphenyl)-N-(phenylmethanesulfonyl)cyclopropane-1-carboxamide | |
| Example III-112 | 1-(4-fluorophenyl)-N-(phenylmethanesulfonyl)cyclopropane-1-carboxamide | |
| Example III-113 | 1-(2-chlorophenyl)-N-(phenylmethanesulfonyl)cyclopropane-1-carboxamide | |
| Example III-114 | 1-(4-chlorophenyl)-N-(phenylmethanesulfonyl)cyclopropane-1-carboxamide | |

TABLE 2-continued

| Example | Name | MS |
|---|---|---|
| Example III-115 | 1-(3,4-dichlorophenyl)-N-(phenylmethanesulfonyl)cyclopropane-1-carboxamide | |
| Example III-116 | N-(pentane-3-sulfonyl)-1-phenylcyclopropane-1-carboxamide | |
| Example III-119 | 4-(3-methoxyphenyl)-N-(propane-1-sulfonyl)oxane-4-carboxamide | |
| Example III-120 | 4-(3-methylphenyl)-N-(propane-1-sulfonyl)oxane-4-carboxamide | |
| Example III-121 | 1-(3,4-dimethoxyphenyl)-N-(naphthalene-1-sulfonyl)cyclobutane-1-carboxamide | MS (APCI+) m/z 426.0 (M + H)$^+$. |
| Example III-122 | 1-[2-methoxy-6-(1-methyl-1H-pyrazol-4-yl)phenyl]-N-(quinoline-5-sulfonyl)cyclopropane-1-carboxamide | MS (APCI+) m/z 463 (M + H)$^+$. |
| Example III-123 | 1-(4-cyclobutyl-2,6-dimethoxyphenyl)-N-(1-methyl-1H-benzimidazole-7-sulfonyl)cyclopropane-1-carboxamide | MS (APCI+) m/z 470.0 (M + H)$^+$. |
| Example III-124 | 1-(3-methoxy-6-methylpyridin-2-yl)-N-(quinoline-5-sulfonyl)cyclopropane-1-carboxamide | MS (APCI+) m/z 398 (M + H)$^+$. |
| Example III-125 | 1-(3-methoxy-6-methylpyridin-2-yl)-N-(naphthalene-1-sulfonyl)cyclopropane-1-carboxamide | MS (APCI+) m/z 397 (M + H)$^+$. |
| Example III-126 | 1-(3-methoxy-6-methylpyridin-2-yl)-N-(2-methylquinoline-5-sulfonyl)cyclopropane-1-carboxamide | MS (APCI+) m/z 412 (M + H)$^+$. |
| Example III-127 | 1-(2,5-dimethylphenyl)-N-(1H-indazole-4-sulfonyl)cyclopropane-1-carboxamide | MS (APCI+) m/z 370 (M + H)$^+$. |
| Example III-128 | 1-[2-methoxy-5-(3-methoxyoxetan-3-yl)phenyl]-N-(quinoline-5-sulfonyl)cyclopropane-1-carboxamide | MS (APCI+) m/z 469 (M + H)$^+$. |
| Example III-129 | 1-{2-methoxy-5-[(3-$^2$H)oxetan-3-yl]phenyl}-N-(quinoline-5-sulfonyl)cyclopropane-1-carboxamide | MS (ESI−) m/z 438 (M − H)$^−$. |
| Example III-130 | N-(1H-indazole-4-sulfonyl)-1-[5-methyl-2-(2-methylpropoxy)pyridin-3-yl]cyclopropane-1-carboxamide | MS (APCI+) m/z 429.1 (M + H)$^+$. |
| Example III-131 | N-(1H-indazole-4-sulfonyl)-1-{5-methyl-2-[(propan-2-yl)oxy]pyridin-3-yl}cyclopropane-1-carboxamide | MS (APCI+) m/z 415.1 (M + H)$^+$. |
| Example III-132 | 1-(2-ethyl-6-methoxyphenyl)-N-(1H-indazole-4-sulfonyl)cyclopropane-1-carboxamide | MS (ESI+) m/z 400 (M + H)$^+$. |
| Example III-133 | 1-(2-ethyl-6-methoxyphenyl)-N-(2-methylquinoline-5-sulfonyl)cyclopropane-1-carboxamide | MS (APCI+) m/z 425 (M + H)$^+$. |
| Example III-134 | N-[2-(dimethylamino)quinoline-5-sulfonyl]-1-(2-ethoxy-5-methylphenyl)cyclopropane-1-carboxamide | MS (ESI+) m/z 454 (M + H)$^+$. |

Example GI-1

1-{5-bromo-2-[(propan-2-yl)oxy]pyridin-3-yl}-N-(quinoline-5-sulfonyl)cyclopropane-1-carboxamide Into a vial, a solution of 1-(5-bromo-2-isopropoxy-3-pyridyl)cyclopropanecarboxylic acid (30 mg, 0.10 mmol) in anhydrous dichloromethane (1 mL), 1-(3-dimethylaminopropyl)-3-ethylcarbodiimide hydrochloride (CAS #25952-53-8) (43 mg, 0.20 mmol) and 4-dimethylaminopyridine (CAS #1122-58-3) (15 mg, 0.12 mmol) were added and the mixture was stirred at ambient temperature for 30 minutes. Quinoline-5-sulfonamide (CAS #415913-05-2) (23 mg, 0.11 mmol) was added and the reaction mixture was stirred at ambient temperature for 2.5 hours. The reaction mixture was treated with water. The organic layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.19-9.12 (m, 1H), 8.88 (dd, J=4.2, 1.7 Hz, 1H), 8.29 (dd, J=7.3, 1.2 Hz, 1H), 8.12 (dt, J=8.5, 1.1 Hz, 1H), 7.95 (d, J=2.6 Hz, 1H), 7.78 (dd, J=8.5, 7.3 Hz, 1H), 7.58 (dd, J=8.8, 4.3 Hz, 1H), 7.55 (d, J=2.6 Hz, 1H), 4.97-4.87 (m, 2H), 1.44 (q, J=4.0 Hz, 2H), 0.91 (d, J=6.2 Hz, 6H), 0.81 (q, J=4.0 Hz, 2H). MS (ESI+) m/z 492 (M+2H)$^+$.

Example GI-2

1-{5-bromo-2-[(propan-2-yl)oxy]pyridin-3-yl}-N-(1,2,3,4-tetrahydroquinoline-5-sulfonyl)cyclopropane-1-carboxamide Into a vial, a solution of 1-(5-bromo-2-isopropoxy-3-pyridyl)cyclopropanecarboxylic acid (30 mg, 0.10 mmol) in anhydrous dichloromethane (1 mL), 1-(3-dimethylaminopropyl)-3-ethylcarbodiimide hydrochloride (CAS #25952-53-8) (43 mg, 0.20 mmol) and 4-dimethylaminopyridine (CAS #1122-58-3) (15 mg, 0.12 mmol) were added and the mixture was stirred at ambient temperature for 30 minutes. 1,2,3,4-Tetrahydroquinoline-5-sulfonamide (CAS #1155515-51-7) (23 mg, 0.11 mmol) was added and the reaction mixture was stirred at ambient temperature for 2.5 hours. The reaction mixture was treated with water. The organic layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.98 (s, 1H), 7.60 (s, 1H), 7.24 (dd, J=7.8, 1.2 Hz, 1H), 6.90 (t, J=8.0 Hz, 1H), 6.58 (d, J=7.9 Hz, 1H), 5.17 (p, J=6.1 Hz, 1H), 3.27-3.19 (m, 2H), 3.11-2.98 (q, J=7.2 Hz, 6H), 1.86 (p, J=6.3 Hz, 2H), 1.49 (q, J=4.0 Hz, 2H), 1.26 (d, J=6.1 Hz, 6H), 0.92-0.80 (m, 2H). MS (ESI+) m/z 496 (M+2H)$^+$.

Example GI-3

1-(5-chloro-2-methoxypyridin-3-yl)-N-(naphthalene-1-sulfonyl)cyclopropane-1-carboxamide Into a vial, to a solution of 1-(5-chloro-2-methoxy-4-pyridyl)cyclopropanecarboxylic acid (90 mg, 0.395 mmol) in anhydrous dichloromethane (8 mL), 1-(3-dimethylaminopropyl)-3-ethylcarbodiimide hydrochloride (CAS #25952-53-8) (151 mg, 0.79 mmol) and 4-dimethylaminopyridine (CAS #1122-58-3) (48 mg, 0.395 mmol) were added, followed by naphthalene-1-sulfonamide (CAS #606-25-7)(74 mg, 0.356 mmol). The reaction mixture was stirred at ambient temperature for 4 hours. The reaction mixture was quenched with saturated aqueous NaHCO$_3$ solution, and the organic layer was separated on a phase separator and concentrated. The crude material was purified by reverse-phase HPLC Waters XBridge™ C18 5 µm OBD column, 30×100 mm, flow rate 50 mL/minute, H$_2$O+0.1% formic acid/acetonitrile+0.1% formic acid to give the compound. $^1$H NMR (400 MHz, chloroform-d) δ ppm 8.49 (dd, J=7.5, 1.3 Hz, 1H), 8.39-8.33 (m, 1H), 8.15 (d, J=8.2 Hz, 1H), 8.12 (s, 1H), 7.97 (dd, J=6.9, 2.4 Hz, 1H), 7.69-7.57 (m, 3H), 6.71 (s, 1H), 3.96 (s, 3H), 1.60 (q, J=4.3 Hz, 2H), 1.06 (q, J=4.3 Hz, 2H). MS (ESI+) m/z 417 (M+H)$^+$.

Example GI-4

1-[2-propyl-6-(trifluoromethyl)pyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (92 mg, 0.48 mmol) and 4-dimethylaminopyridine (CAS #1122-58-3) (32 mg, 0.26 mmol) in anhydrous dichloromethane (2 mL), a mixture of 1-[2-isopropyl-6-(trifluoromethyl)-3-pyridyl]cyclopropanecarboxylic acid and 1-[2-propyl-6-(trifluoromethyl)-3-pyridyl]cyclopropanecarboxylic acid (66 mg, 0.24 mmol) was added and the mixture was stirred at ambient temperature for 10 minutes. Quinoline-5-sulfonamide (CAS #415913-05-2) (50 mg, 0.24 mmol) was added and the reaction mixture was stirred at reflux for 2 hours. The reaction mixture was quenched with water and the organic layer was separated on phase separator and concentrated. The crude material was purified by reverse-phase HPLC Waters XBridge™ C18 5 µm OBD column, 30×100 mm, flow rate 50 mL/minute, H$_2$O+0.1% formic acid/acetonitrile+0.1% formic acid to give the title compound. $^1$H NMR (400 MHz, methanol-d$_4$) δ ppm 9.05-8.97 (m, 2H), 8.49 (dd, J=7.5, 1.2 Hz, 1H), 8.37 (dt, J=8.5, 1.1 Hz, 1H), 7.95 (dd, J=8.5, 7.4 Hz, 1H), 7.83 (d, J=8.0 Hz, 1H), 7.72-7.62 (m, 1H), 7.61-7.51 (m, 1H), 2.41-2.33 (m, 2H), 1.61-1.54 (m, 2H), 1.54-1.40 (m, 2H), 1.18 (q, J=4.4 Hz, 2H), 0.66 (t, J=7.4 Hz, 3H). MS (ESI+) m/z 464 (M+H)$^+$.

Example GI-5

1-[2-cyclopropyl-6-(trifluoromethyl)pyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (32 mg, 0.16 mmol) and 4-dimethylaminopyridine (CAS #1122-58-3) (11 mg, 0.09 mmol) in anhydrous dichloromethane (1 mL), 1-[2-cyclopropyl-6-(trifluoromethyl)-3-pyridyl]cyclopropanecarboxylic acid (22 mg, 0.08 mmol) was added and the mixture was stirred at ambient temperature for 10 minutes. Quinoline-5-sulfonamide (CAS #415913-05-2) (17 mg, 0.08 mmol) was added and the reaction mixture was stirred at reflux for 2 hours. The reaction mixture was quenched with water and the organic layer was separated on phase separator and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.10 (ddd, J=8.7, 1.7, 0.9 Hz, 1H), 8.87 (dd, J=4.2, 1.7 Hz, 1H), 8.29 (dd, J=7.3, 1.2 Hz, 1H), 8.13 (dt, J=8.5, 1.1 Hz, 1H), 7.79 (dd, J=8.5, 7.3 Hz, 1H), 7.67-7.60 (m, 1H), 7.51 (dd, J=8.7, 4.3 Hz, 1H), 7.34 (d, J=7.9 Hz, 1H), 5.50 (s, 1H), 2.01 (tt, J=8.1, 4.9 Hz, 1H), 1.58 (d, J=3.4 Hz, 2H), 0.97 (d, J=3.3 Hz, 2H), 0.79 (dd, J=4.8, 3.2 Hz, 2H), 0.50 (dq, J=6.6, 3.2 Hz, 2H). MS (ESI+) m/z 462 (M+H)$^+$.

Example GI-6

1-[2-cyclopropyl-6-(trifluoromethyl)pyridin-3-yl]-N-(1,2,3,4-tetrahydroquinoline-5-sulfonyl)cyclopropane-1-carboxamide Into a vial, to a solution of 1-(3-dimethylaminopropyl)-3-ethylcarbodiimide hydrochloride (CAS #25952-53-8) (32 mg, 0.16 mmol) and 4-dimethylaminopyridine (CAS #1122-58-3) (11 mg, 0.09 mmol) in anhydrous dichloromethane (1 mL), 1-[2-cyclopropyl-6-(trifluoromethyl)-3-pyridyl]cyclopropanecarboxylic acid (22 mg, 0.08 mmol) was added and the mixture was stirred at ambient temperature for 10 minutes. 1,2,3,4-Tetrahydroquinoline-5-sulfonamide (CAS #1155515-51-7) (17 mg, 0.08 mmol) was added and the reaction mixture was stirred at reflux for 2 hours. The reaction mixture was quenched with water and the organic layer was separated on phase separator and concentrated. The crude material was purified by reverse-phase HPLC Waters XBridge™ C18 5 μm OBD column, 30×100 mm, flow rate 50 mL/minute, H$_2$O+0.1% formic acid/acetonitrile+0.1% formic acid to give the title compound. $^1$H NMR (400 MHz, methanol-d$_4$) δ ppm 7.83 (dd, J=8.0, 0.8 Hz, 1H), 7.47 (d, J=7.9 Hz, 1H), 7.23 (dd, J=7.8, 1.2 Hz, 1H), 7.01 (t, J=8.0 Hz, 1H), 6.72 (dd, J=8.1, 1.2 Hz, 1H), 3.25-3.18 (m, 2H), 2.85 (t, J=6.4 Hz, 2H), 2.18 (tt, J=8.0, 4.7 Hz, 1H), 2.03 (s, 2H), 1.83-1.74 (m, 2H), 1.74-1.60 (m, 2H), 1.26 (q, J=4.3 Hz, 2H), 1.06 (dt, J=4.7, 3.1 Hz, 2H), 0.97-0.85 (m, 2H). MS (ESI+) m/z 466 (M+H)$^+$.

Example GI-7

1-[2-(propan-2-yl)-6-(trifluoromethyl)pyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (92 mg, 0.48 mmol) and 4-dimethylaminopyridine (CAS #1122-58-3) (32 mg, 0.26 mmol) in anhydrous dichloromethane (2 mL), a mixture of 1-[2-isopropyl-6-(trifluoromethyl)-3-pyridyl]cyclopropanecarboxylic acid and 1-[2-propyl-6-(trifluoromethyl)-3-pyridyl]cyclopropanecarboxylic acid (66 mg, 0.24 mmol) was added and the mixture was stirred at ambient temperature for 10 minutes. Quinoline-5-sulfonamide (CAS #415913-05-2) (50 mg, 0.24 mmol) was added and the reaction mixture was stirred at reflux for 2 hours. The reaction mixture was quenched with water and the organic layer was separated on phase separator and concentrated. The crude material was purified by reverse-phase HPLC Waters XBridge™ C18 5 μm OBD column, 30×100 mm, flow rate 50 mL/minute, H$_2$O+0.1% formic acid/acetonitrile+0.1% formic acid to give the title compound NMR (400 MHz, methanol-d$_4$) δ ppm 9.10 (dt, J=8.7, 1.3 Hz, 1H), 9.00 (dd, J=4.3, 1.6 Hz, 1H), 8.47 (dd, J=7.5, 1.2 Hz, 1H), 8.34 (dt, J=8.5, 1.1 Hz, 1H), 7.93 (dd, J=8.5, 7.4 Hz, 1H), 7.84-7.74 (m, 1H), 7.68 (dd, J=8.8, 4.3 Hz, 1H), 7.52 (d, J=8.0 Hz, 1H), 3.36 (s, 1H), 3.08 (h, J=6.7 Hz, 1H), 1.59 (q, J=4.4 Hz, 2H), 1.20 (q, J=4.4 Hz, 2H), 0.95 (d, J=6.6 Hz, 6H). MS (ESI+) m/z 464 (M+H)$^+$.

Example GI-8

1-[2-propyl-6-(trifluoromethyl)pyridin-3-yl]-N-(1,2,3,4-tetrahydroquinoline-5-sulfonyl)cyclopropane-1-carboxamide Into a vial, to a solution of 1-(3-dimethylaminopropyl)-3-ethylcarbodiimide hydrochloride (CAS #25952-53-8) (92 mg, 0.48 mmol) and 4-dimethylaminopyridine (CAS #1122-58-3) (32 mg, 0.26 mmol) in anhydrous dichloromethane (2 mL), a mixture of 1-[2-isopropyl-6-(trifluoromethyl)-3-pyridyl]cyclopropanecarboxylic acid and 1-[2-propyl-6-(trifluoromethyl)-3-pyridyl]cyclopropanecarboxylic acid (66 mg, 0.24 mmol) was added and the mixture was stirred at ambient temperature for 10 minutes. 1,2,3,4-Tetrahydroquinoline-5-sulfonamide (CAS #1155515-51-7) (51 mg, 0.24 mmol) was added and the reaction mixture was stirred at reflux for 2 hours. The reaction mixture was quenched with water and the organic layer was separated on phase separator and concentrated. The crude material was purified by reverse-phase HPLC Waters XBridge™ C18 5 μm OBD column, 30×100 mm, flow rate 50 mL/minute, H$_2$O+0.1% formic acid/acetonitrile+0.1% formic acid to give the title compound. $^1$H NMR (400 MHz, methanol-d$_4$) δ ppm 7.94-7.88 (m, 1H), 7.58 (d, J=8.0 Hz, 1H), 7.24 (dd, J=7.8, 1.2 Hz, 1H), 7.02 (t, J=8.0 Hz, 1H), 6.76-6.70 (m, 1H), 3.25-3.19 (m, 2H), 2.82 (t, J=6.4 Hz, 2H), 2.71-2.59 (m, 2H), 1.84-1.74 (m, 2H), 1.73-1.61 (m, 4H), 1.22 (q, J=4.5 Hz, 2H), 0.88 (t, J=7.4 Hz, 3H). MS (ESI+) m/z 468 (M+H)$^+$.

Example GI-9

1-[2-(propan-2-yl)-6-(trifluoromethyl)pyridin-3-yl]-N-(1,2,3,4-tetrahydroquinoline-5-sulfonyl)cyclopropane-1-carboxamide Into a vial, to a solution of 1-(3-dimethylaminopropyl)-3-ethylcarbodiimide hydrochloride (CAS #25952-53-8) (92 mg, 0.48 mmol) and 4-dimethylaminopyridine (CAS #1122-58-3) (32 mg, 0.26 mmol) in anhydrous dichloromethane (2 mL), and a mixture of 1-[2-isopropyl-6-(trifluoromethyl)-3-pyridyl]cyclopropanecarboxylic acid and 1-[2-propyl-6-(trifluoromethyl)-3-pyridyl]cyclopropanecarboxylic acid (66 mg, 0.24 mmol) was added and the mixture was stirred at ambient temperature for 10 minutes. 1,2,3,4-Tetrahydroquinoline-5-sulfonamide (CAS #1155515-51-7)) (51 mg, 0.24 mmol) was added and the reaction mixture was stirred at reflux for 2 hours. The reaction mixture was quenched with water and the organic layer was separated on a phase separator and concentrated. The crude material was purified by reverse-phase HPLC Waters XBridge™ C18 5 μm OBD column, 30×100 mm, flow rate 50 mL/minute, H$_2$O+0.1% formic acid/acetonitrile+0.1% formic acid to give the title compound. $^1$H NMR (400 MHz, methanol-d$_4$) δ ppm 7.88-7.83 (m, 1H), 7.53 (d, J=8.0 Hz, 1H), 7.21 (dd, J=7.8, 1.2 Hz, 1H), 6.99 (t, J=8.0 Hz, 1H), 6.69 (dd, J=8.1, 1.2 Hz, 1H), 3.40-3.31 (m, 1H), 3.25-3.18 (m, 2H), 2.88 (t, J=6.3 Hz, 2H), 1.83-1.75 (m, 2H), 1.67-1.61 (m, 2H), 1.27-1.22 (m, 2H), 1.10 (d, J=6.7 Hz, 6H). MS (ESI+) m/z 468 (M+H)$^+$.

Example GI-10

1-[2-cyclobutyl-6-(trifluoromethyl)pyridin-3-yl]-N-(1,2,3,4-tetrahydroquinoline-5-sulfonyl)cyclopropane-1-carboxamide Into a vial, to a solution of 1-(3-dimethylaminopropyl)-3-ethylcarbodiimide hydrochloride (CAS #25952-53-8) (50 mg, 0.26 mmol) and 4-dimethylaminopyridine (CAS #1122-58-3) (18 mg, 0.14 mmol) in anhydrous dichloromethane (1 mL), and 1-[2-cyclobutyl-6-(trifluoromethyl)-3-pyridyl]cyclopropanecarboxylic acid (38 mg, 0.13 mmol) was added and the mixture was stirred at ambient temperature for 10 minutes. 1,2,3,4-Tetrahydroquinoline-5-sulfonamide (CAS #1155515-51-7) (27 mg, 0.13 mmol) was added and the reaction mixture was stirred at reflux for 2 hours. The reaction mixture was quenched with water and the organic layer was separated on phase separator and concentrated. The crude material was purified by reverse-phase HPLC Waters XBridge™ C18 5 μm OBD column, 30×100 mm, flow rate 50 mL/minute, H$_2$O+0.1% formic acid/acetonitrile+0.1% formic acid to give the title compound. $^1$H NMR (400 MHz, methanol-d$_4$) δ ppm 7.88-7.81 (m, 1H), 7.57 (d, J=7.9 Hz, 1H), 7.24 (dd, J=7.8, 1.2 Hz, 1H), 7.03 (t, J=8.0 Hz, 1H), 6.73 (dd, J=8.1, 1.2 Hz, 1H), 3.89-3.76 (m, 1H), 3.29-3.22 (m, 2H), 2.86 (t, J=6.4 Hz, 2H), 2.41 (dq, J=11.0, 9.1 Hz, 2H), 2.14-2.04 (m, 3H), 2.04-1.92 (m, 1H), 1.84-1.77 (m, 2H), 1.65 (t, J=3.4 Hz, 2H), 1.20 (q, J=4.4 Hz, 2H). MS (ESI+) m/z 480 (M+H)$^+$.

Example GI-11

1-[2-cyclobutyl-6-(trifluoromethyl)pyridin-3-yl]-N-(naphthalene-1-sulfonyl)cyclopropane-1-carboxamide Into a vial, to a solution of 1-(3-dimethylaminopropyl)-3-ethylcarbodiimide hydrochloride (CAS #25952-53-8) (50 mg, 0.26 mmol) and 4-dimethylaminopyridine (CAS #1122-58-3) (18 mg, 0.14 mmol) in anhydrous dichloromethane (1 mL), and 1-[2-cyclobutyl-6-(trifluoromethyl)-3-pyridyl]cyclopropanecarboxylic acid (38 mg, 0.13 mmol) was added and the mixture was stirred at ambient temperature for 10 minutes. Naphthalene-1-sulfonamide (CAS #606-25-7) (27 mg, 0.13 mmol) was added and the reaction mixture was stirred at reflux for 2 hours. The reaction mixture was quenched with water and the organic layer was separated on phase separator and concentrated. The crude material was purified by reverse-phase HPLC Waters XBridge™ C18 5 μm OBD column, 30×100 mm, flow rate 50 mL/minute, $H_2O$+0.1% formic acid/acetonitrile+0.1% formic acid to give the title compound. $^1$H NMR (400 MHz, methanol-$d_4$) δ ppm 8.57-8.47 (m, 1H), 8.38 (dd, J=7.4, 1.3 Hz, 1H), 8.22 (dt, J=8.3, 1.2 Hz, 1H), 8.11-8.02 (m, 1H), 7.75 (dd, J=7.9, 0.8 Hz, 1H), 7.70-7.59 (m, 3H), 7.53 (d, J=7.9 Hz, 1H), 3.56-3.43 (m, 1H), 2.26-2.11 (m, 2H), 1.82-1.59 (m, 4H), 1.59-1.54 (m, 2H), 1.12 (q, J=4.4 Hz, 2H). MS (ESI+) m/z 475 (M+H)$^+$.

Example GI-12

1-[2-cyclopropyl-5-(2-methylpropoxy)pyridin-3-yl]-N-(quinoline-5-sulfonyl)cyclopropane-1-carboxamide Into a vial, to a solution of 1-(2-cyclopropyl-5-isobutoxy-3-pyridyl)cyclopropanecarboxylic acid (47 mg, 0.20 mmol) in anhydrous dichloromethane (2 mL), 1-(3-dimethylaminopropyl)-3-ethylcarbodiimide hydrochloride (CAS #25952-53-8) (58 mg, 0.30 mmol) and 4-dimethylaminopyridine (CAS #1122-58-3) (22 mg, 0.18 mmol) were added and the mixture was stirred at ambient temperature for 5 minutes. Quinoline-5-sulfonamide (CAS #415913-05-2) (34 mg, 0.165 mmol) was added and the reaction mixture was stirred at ambient temperature for 2 hours. The reaction mixture was treated with water. The aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% formic acid/acetonitrile+0.1% formic acid to give the title compound. $^1$H NMR (400 MHz, methanol-$d_4$) δ ppm 9.05 (dt, J=8.8, 1.3 Hz, 1H), 8.96 (dd, J=4.3, 1.6 Hz, 1H), 8.41 (dd, J=7.4, 1.2 Hz, 1H), 8.28 (d, J=8.4 Hz, 1H), 8.09 (s, 1H), 7.96 (d, J=2.8 Hz, 1H), 7.89 (dd, J=8.5, 7.4 Hz, 1H), 7.61 (dd, J=8.8, 4.2 Hz, 1H), 7.44 (s, 1H), 3.85 (d, J=6.4 Hz, 2H), 2.10 (dp, J=13.4, 6.7 Hz, 1H), 1.88 (d, J=5.3 Hz, 1H), 1.57 (d, J=3.1 Hz, 2H), 1.15 (d, J=3.1 Hz, 2H), 1.07 (d, J=6.8 Hz, 6H), 0.76 (dd, J=5.2, 2.5 Hz, 2H), 0.63 (d, J=7.1 Hz, 2H). MS (ESI+) m/z 466 (M+H)$^+$.

Example GI-13

1-{5-ethyl-2-[(propan-2-yl)oxy]pyridin-3-yl}-N-(quinoline-5-sulfonyl)cyclopropane-1-carboxamide Into a vial, a solution of 1-(5-ethyl-2-isopropoxy-3-pyridyl)cyclopropanecarboxylic acid (30 mg, 0.12 mmol), 1-(3-dimethylaminopropyl)-3-ethylcarbodiimide hydrochloride (CAS #25952-53-8) (46 mg, 0.24 mmol) and 4-dimethylaminopyridine (CAS #1122-58-3) (18 mg, 0.144 mmol) in anhydrous dichloromethane (1 mL) was added to quinoline-5-sulfonamide (CAS #415913-05-2) (27 mg, 0.132 mmol). The reaction mixture was stirred at ambient temperature for 2 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.18 (ddd, J=8.7, 1.7, 0.9 Hz, 1H), 8.89 (dd, J=4.3, 1.7 Hz, 1H), 8.26 (dd, J=7.3, 1.2 Hz, 1H), 8.12 (dt, J=8.5, 1.1 Hz, 1H), 7.77 (dd, J=8.5, 7.3 Hz, 1H), 7.73-7.68 (m, 1H), 7.57 (dd, J=8.7, 4.3 Hz, 1H), 7.34 (d, J=2.4 Hz, 1H), 4.96-4.84 (m, 1H), 2.53 (q, J=7.6 Hz, 2H), 1.47 (q, J=3.9 Hz, 2H), 1.19 (t, J=7.6 Hz, 3H), 0.91 (d, J=6.2 Hz, 6H), 0.83 (q, J=3.9 Hz, 2H). MS (ESI+) m/z 440 (M+H)$^+$.

Example GI-14

1-{5-ethyl-2-[(propan-2-yl)oxy]pyridin-3-yl}-N-(1,2,3,4-tetrahydroquinoline-5-sulfonyl)cyclopropane-1-carboxamide Into a vial, a solution of 1-(5-ethyl-2-isopropoxy-3-pyridyl)cyclopropanecarboxylic acid (30 mg, 0.12 mmol), 1-(3-dimethylaminopropyl)-3-ethylcarbodiimide hydrochloride (CAS #25952-53-8) (46 mg, 0.24 mmol) and 4-dimethylaminopyridine (CAS #1122-58-3) (18 mg, 0.144 mmol) in anhydrous dichloromethane (1 mL) was added to 1,2,3,4-tetrahydroquinoline-5-sulfonamide (CAS #1155515-51-7) (CAS #415913-05-2) (28 mg, 0.132 mmol). The reaction mixture was stirred at ambient temperature for 2 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 7.73 (d, J=2.4 Hz, 1H), 7.40 (d, J=2.4 Hz, 1H), 7.24 (dd, J=7.7, 1.2 Hz, 1H), 6.89 (t, J=7.9 Hz, 1H), 6.57 (dd, J=8.0, 1.2 Hz, 1H), 5.13 (hept, J=6.1 Hz, 1H), 3.26-3.19 (m, 2H), 3.08 (t, J=6.5 Hz, 2H), 2.55 (q, J=7.6 Hz, 2H), 1.85 (dt, J=11.0, 6.4 Hz, 2H), 1.50 (q, J=3.9 Hz, 2H), 1.27-1.24 (m, 6H), 1.21 (t, J=7.6 Hz, 3H), 0.85 (q, J=3.9 Hz, 2H). MS (ESI+) m/z 444 (M+H)$^+$.

Example GI-15

1-[2-(pyrrolidin-1-yl)-6-(trifluoromethyl)pyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (38 mg, 0.20 mmol) and 4-dimethylaminopyridine (CAS #1122-58-3) (14 mg, 0.11 mmol) in anhydrous dichloromethane (1 mL), and 1-[2-pyrrolidin-1-yl-6-(trifluoromethyl)-3-pyridyl]cyclopropanecarboxylic acid (30 mg, 0.10 mmol) was added and the mixture was stirred at ambient temperature for 10 minutes. Quinoline-5-sulfonamide (CAS #415913-05-2) (21 mg, 0.10 mmol) was added and the reaction mixture was stirred at reflux for 1 hour. The reaction mixture was quenched with water and the organic layer was separated on a phase separator and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.18 ddd, J=8.7, 1.7, 0.8 Hz, 1H), 8.88 (dd, J=4.3, 1.7 Hz, 1H), 8.28 (dd, J=7.3, 1.2 Hz, 1H), 8.12 (dt, J=8.5, 1.1 Hz, 1H), 7.78 (dd, J=8.5, 7.3 Hz, 1H), 7.57 (dd, J=8.7, 4.3 Hz, 1H), 7.50 (dd, J=7.6, 0.9 Hz, 1H), 6.84 (d, J=7.5 Hz, 1H), 3.33-3.16 (m, 4H), 1.55 (d, J=4.3 Hz, 2H, 1.46-1.30 (m, 4H), 0.97 (d, J=4.5 Hz, 2H). MS (ESI+) m/z 491 (M+H)$^+$.

Example GI-16

1-{2-methoxy-5-[(propan-2-yl)oxy]pyridin-4-yl}-N-(quinoline-5-sulfonyl)cyclopropane-1-carboxamide Into a vial, to a solution of 1-(5-isopropoxy-2-methoxy-4-pyridyl)cyclopropanecarboxylic acid (29 mg, 0.115 mmol) in anhydrous dichloromethane (1 mL), 1-(3-dimethylaminopropyl)-3-ethylcarbodiimide hydrochloride (CAS #25952-53-8) (44 mg, 0.23 mmol) and 4-dimethylaminopyridine (CAS #1122-58-3) (17 mg, 0.138 mmol) were added and the mixture was stirred at ambient temperature for 5 minutes. Quinoline-5-sulfonamide (CAS #415913-05-2) (26 mg, 0.126 mmol) was added and the reaction mixture was stirred at ambient temperature for 2.5 hours. The reaction mixture was treated with water and aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.16 (ddd, J=8.8, 1.7, 0.9 Hz, 1H), 8.88 (dd, J=4.3, 1.7 Hz, 1H), 8.26 (dd, J=7.3, 1.3 Hz, 1H), 8.12 (dt, J=8.5, 1.1 Hz, 1H), 7.77 (dd, J=8.5, 7.3 Hz, 1H), 7.57 (dd, J=8.7, 4.3 Hz, 1H), 7.50 (s, 1H), 6.61 (s, 1H), 4.17 (hept, J=6.0 Hz, 1H), 3.82 (s, 3H), 1.43 (q, J=3.9 Hz, 2H), 0.90-0.82 (m, 8H). MS (ESI+) m/z 442 (M+H)$^+$.

Example GI-17

1-{6-methoxy-4-[(propan-2-yl)oxy]pyridin-3-yl}-N-(quinoline-5-sulfonyl)cyclopropane-1-carboxamide Into a vial, to a solution of 1-(4-isopropoxy-6-methoxy-3-pyridyl)cyclopropanecarboxylic acid (40 mg, 0.159 mmol) in anhydrous dichloromethane (1 mL), 1-(3-dimethylaminopropyl)-3-ethylcarbodiimide hydrochloride (CAS #25952-53-8) (61 mg, 0.318 mmol) and 4-dimethylaminopyridine (CAS #1122-58-3) (23 mg, 0.191 mmol) were added and the mixture was stirred at ambient temperature for 5 minutes. Quinoline-5-sulfonamide (CAS #415913-05-2) (36 mg, 0.175 mmol) was added and the reaction mixture was stirred at ambient temperature for 2.5 hours. The reaction mixture was treated with water. The aqueous layer was extracted with dichloromethane, and the organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.19 (ddd, J=8.8, 1.7, 0.9 Hz, 1H), 8.88 (dd, J=4.3, 1.7 Hz, 1H), 8.24 (dd, J=7.3, 1.2 Hz, 1H), 8.11 (dt, J=8.5, 1.1 Hz, 1H), 7.77 (dd, J=8.5, 7.3 Hz, 1H), 7.69 (s, 1H), 7.58 (dd, J=8.8, 4.3 Hz, 1H), 6.11 (s, 1H), 4.34 (hept, J=6.0 Hz, 1H), 3.83 (s, 3H), 1.44 (q, J=3.8 Hz, 2H), 0.90 (d, J=6.0 Hz, 6H), 0.80 (q, J=3.8 Hz, 2H). MS (ESI+) m/z 442 (M+H)$^+$.

Example GI-18

1-{6-methoxy-4-[(propan-2-yl)oxy]pyridin-3-yl}-N-(2-methylquinoline-5-sulfonyl)cyclopropane-1-carboxamide Into a vial, to a solution of 1-(4-isopropoxy-6-methoxy-3-pyridyl)cyclopropanecarboxylic acid (25 mg, 0.10 mmol) in anhydrous dichloromethane (1 mL), 1-(3-dimethylaminopropyl)-3-ethylcarbodiimide hydrochloride (CAS #25952-53-8) (38 mg, 0.20 mmol) and 4-dimethylaminopyridine (CAS #1122-58-3) (15 mg, 0.12 mmol) were added and the mixture was stirred at ambient temperature for 5 minutes. 2-Methylquinoline-5-sulfonamide (24 mg, 0.11 mmol) was added and the reaction mixture was stirred at ambient temperature for 2.5 hours. The reaction mixture was treated with water. The aqueous layer was extracted with dichloromethane, and the organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.04 (dd, J=8.9, 0.8 Hz, 1H), 8.17 (dd, J=7.3, 1.2 Hz, 1H), 8.02 (dt, J=8.5, 1.1 Hz, 1H), 7.71 (dd, J=8.5, 7.3 Hz, 1H), 7.68 (s, 1H), 7.46 (d, J=8.9 Hz, 1H), 6.10 (s, 1H), 4.34 (hept, J=6.0 Hz, 1H), 3.83 (s, 3H), 2.73 (s, 3H), 1.43 (q, J=3.8 Hz, 2H), 0.91 (d, J=6.0 Hz, 6H), 0.79 (q, J=3.8 Hz, 2H). MS (ESI+) m/z 456 (M+H)$^+$.

Example GI-19

1-[2-methoxy-5-(2-methylpropoxy)pyridin-4-yl]-N-(quinoline-5-sulfonyl)cyclopropane-1-carboxamide Into a vial, to a solution of 1-(5-isobutoxy-2-methoxy-4-pyridyl)cyclopropanecarboxylic acid (40 mg, 0.15 mmol) in anhydrous dichloromethane (3 mL), 1-(3-dimethylaminopropyl)-3-ethylcarbodiimide hydrochloride (CAS #25952-53-8) (61 mg, 0.30 mmol) and 4-dimethylaminopyridine (CAS #1122-58-3) (19 mg, 0.15 mmol) were added, followed by quinoline-5-sulfonamide (CAS #415913-05-2) (28 mg, 0.135 mmol). The reaction mixture was stirred at ambient temperature for 1 hour. The reaction mixture was quenched with saturated aqueous $NaHCO_3$ solution, and the organic layer was separated on phase separator and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the compound with N,N-dimethylaminopyridine. The residue was washed with saturated aqueous $NH_4Cl$ solution and extracted with ethylacetate. The organic layer was separated, dried over $Na_2SO_4$, filtered and concentrated to give the title compound. $^1$H NMR (400 MHz, chloroform-d) δ ppm 8.99 (dd, J=4.2, 1.6 Hz, 1H), 8.86 (ddd, J=8.7, 1.6, 0.9 Hz, 1H), 8.42 (dd, J=7.4, 1.2 Hz, 1H), 8.32 (dt, J=8.5, 1.1 Hz, 1H), 7.78

(dd, J=8.5, 7.4 Hz, 1H), 7.65 (s, 1H), 7.49 (dd, J=8.8, 4.2 Hz, 1H), 6.58 (s, 1H), 3.89 (s, 3H), 3.44 (d, J=6.4 Hz, 2H), 1.59-1.44 (m, 3H), 0.97 (q, J=4.2 Hz, 2H), 0.74 (d, J=6.7 Hz, 6H). MS (ESI+) m/z 456 (M+H)+.

Example GI-20

1-[2-methoxy-5-(2-methylpropoxy)pyridin-4-yl]-N-(2-methylquinoline-5-sulfonyl)cyclopropane-1-carboxamide Into a vial, to a solution of 1-(5-isobutoxy-2-methoxy-4-pyridyl)cyclopropanecarboxylic acid (40 mg, 0.15 mmol) in anhydrous dichloromethane (3 mL), 1-(3-dimethylaminopropyl)-3-ethylcarbodiimide hydrochloride (CAS #25952-53-8) (61 mg, 0.30 mmol) and 4-dimethylaminopyridine (CAS #1122-58-3) (19 mg, 0.15 mmol) were added, followed by 2-methylquinoline-5-sulfonamide (30 mg, 0.135 mmol). The reaction mixture was stirred at ambient temperature for 2 hours. The reaction mixture was quenched with saturated aqueous NaHCO$_3$ solution, and the organic layer was separated on phase separator and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the compound with N,N-dimethylaminopyridine. The residue was washed with saturated aqueous NH$_4$Cl solution and extracted with ethyl acetate. The organic layer was separated, dried over Na$_2$SO$_4$, filtered and concentrated to give the title compound. MS (ESI+) m/z 470 (M+H)+.

Example GI-21

N-(1H-indole-4-sulfonyl)-1-[2-methoxy-5-(2-methylpropoxy)pyridin-4-yl]cyclopropane-1-carboxamide Into a vial, to a solution of 1-(5-isobutoxy-2-methoxy-4-pyridyl)cyclopropanecarboxylic acid (201 mg, 0.76 mmol) in anhydrous dichloromethane (7.6 mL), 1-(3-dimethylaminopropyl)-3-ethylcarbodiimide hydrochloride (CAS #25952-53-8) (291 mg, 1.52 mmol) and 4-dimethylaminopyridine (CAS #1122-58-3) (93 mg, 0.76 mmol) were added, followed by 1H-indole-4-sulfonamide (149 mg, 0.76 mmol). The reaction mixture was stirred at ambient temperature for 2 hours and heated at 55° C. for 1.5 hours. The solvent was removed and the residue was acidified with NaH$_2$PO$_4$ 0.2M aqueous solution (5 mL) to protonate 4-dimethylaminopyridine (CAS #1122-58-3). The mixture was partitioned between water and ethyl acetate and the aqueous layer was extracted with ethyl acetate. The organic layer was washed with water, dried over MgSO$_4$, filtered and concentrated. The crude material was washed with aqueous HCl (1N, 1 mL), and triturated in water. Diethyl ether and the precipitate was filtered to give the title compound. $^1$H NMR (400 MHz, methanol-d$_4$) δ ppm 11.98 (s, 1H), 8.47-8.39 (m, 2H), 8.33 (s, 1H), 8.19 (t, J=2.8 Hz, 1H), 7.96 (t, J=7.9 Hz, 1H), 7.48 (t, J=2.5 Hz, 1H), 7.40 (s, 1H), 4.57 (s, 3H), 4.10 (d, J=6.5 Hz, 2H), 2.10 (q, J=4.4 Hz, 2H), 2.07-1.97 (m, 1H), 1.75 (q, J=4.5 Hz, 2H), 1.44 (d, J=6.7 Hz, 6H). MS (ESI+) m/z 444 (M+H)+.

Example GI-22

1-{5-cyclobutyl-2-[(propan-2-yl)oxy]pyridin-3-yl}-N-(quinoline-5-sulfonyl)cyclopropane-1-carboxamide Into a vial, to a solution of 1-(5-cyclobutyl-2-isopropoxy-3-pyridyl)cyclopropanecarboxylic acid (65 mg, 0.236 mmol) in anhydrous dimethyl sulfoxide (1 mL), 1-(3-dimethylaminopropyl)-3-ethylcarbodiimide hydrochloride (CAS #25952-53-8) (90 mg, 0.472 mmol) and 4-dimethylaminopyridine (CAS #1122-58-3) (29 mg, 0.191 mmol) were added and the mixture was stirred at ambient temperature for 5 minutes. Quinoline-5-sulfonamide (CAS #415913-05-2) (54 mg, 0.26 mmol) was added and the reaction mixture was stirred at ambient temperature overnight. The mixture was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.14 (ddd, J=8.7, 1.7, 0.8 Hz, 1H), 8.85 (dd, J=4.3, 1.7 Hz, 1H), 8.22 (dd, J=7.3, 1.2 Hz, 1H), 8.09 (dt, J=8.5, 1.1 Hz, 1H), 7.74 (dd, J=8.5, 7.3 Hz, 1H), 7.68 (dd, J=2.4, 0.7 Hz, 1H), 7.53 (dd, J=8.7, 4.3 Hz, 1H), 7.34 (d, J=2.4 Hz, 1H), 4.92-4.80 (m, 1H), 3.48-3.35 (m, 1H), 2.31-2.19 (m, 2H), 2.16-1.93 (m, 3H), 1.88-1.79 (m, 1H), 1.43 (q, J=3.9 Hz, 2H), 0.88 (d, J=6.1 Hz, 6H), 0.80 (q, J=3.9 Hz, 2H). MS (ESI+) m/z 466 (M+H)+.

Example GI-23

1-{5-cyclobutyl-2-[(propan-2-yl)oxy]pyridin-3-yl}-N-(2-methylquinoline-5-sulfonyl)cyclopropane-1-carboxamide Into a vial, to a solution of 1-(5-cyclobutyl-2-isopropoxy-3-pyridyl)cyclopropanecarboxylic acid (65 mg, 0.236 mmol) in anhydrous dimethyl sulfoxide (1 mL), 1-(3-dimethylaminopropyl)-3-ethylcarbodiimide hydrochloride (CAS #25952-53-8) (90 mg, 0.472 mmol) and 4-dimethylaminopyridine (CAS #1122-58-3) (29 mg, 0.191 mmol) were added and the mixture was stirred at ambient temperature for 5 minutes. 2-Methylquinoline-5-sulfonamide (58 mg, 0.26 mmol) was added and the reaction mixture was stirred at ambient temperature overnight. The mixture was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.02 (d, J=8.6 Hz, 1H), 8.18 (dd, J=7.3, 1.2 Hz, 1H), 8.03 (dt, J=8.5, 1.1 Hz, 1H), 7.79-7.64 (m, 2H), 7.44 (d, J=8.9 Hz, 1H), 7.37 (d, J=2.4 Hz, 1H), 4.95-4.81 (m, 1H), 3.45 (p, J=8.6 Hz, 1H), 2.74 (s, 3H), 2.32-2.23 (m, 2H), 2.18-1.98 (m, 3H), 1.90-1.80 (m, 2H), 1.46 (q, J=3.9 Hz, 2H), 0.90 (d, J=6.1 Hz, 6H), 0.82 (q, J=3.9 Hz, 2H). MS (ESI+) m/z 481 (M+H)+.

Example GI-24

1-{5-cyclobutyl-2-[(propan-2-yl)oxy]pyridin-3-yl}-N-(1H-indole-4-sulfonyl)cyclopropane-1-carboxamide Into a vial, to a solution of 1-(5-cyclobutyl-2-isopropoxy-3-pyridyl)cyclopropanecarboxylic acid (65 mg, 0.236 mmol) in anhydrous dimethyl sulfoxide (1 mL), 1-(3-dimethylaminopropyl)-3-ethylcarbodiimide hydrochloride (CAS #25952-53-8) (90 mg, 0.472 mmol) and 4-dimethylaminopyridine (CAS #1122-58-3) (29 mg, 0.191 mmol) were added and the mixture was stirred at ambient temperature for 5 minutes. 1H-Indole-4-sulfonamide (51 mg, 0.26 mmol) was added and the reaction mixture was stirred at ambient temperature overnight. The mixture was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^{1}$H NMR (400 MHz, methanol-d$_{4}$) δ ppm 7.74 (dd, J=2.4, 0.8 Hz, 1H), 7.62 (dd, J=7.5, 0.9 Hz, 1H), 7.52 (dt, J=8.1, 0.9 Hz, 1H), 7.43 (d, J=2.4 Hz, 1H), 7.32 (d, J=3.2 Hz, 1H), 7.13 (t, J=7.8 Hz, 1H), 6.88 (dd, J=3.1, 0.9 Hz, 1H), 5.07 (hept, J=6.1 Hz, 1H), 3.47 (p, J=8.5 Hz, 1H), 2.35-2.27 (m, 3H), 2.21-1.98 (m, 3H), 1.94-1.83 (m, 1H), 1.50 (q, J=3.9 Hz, 2H), 1.14 (d, J=6.1 Hz, 6H), 0.86 (q, J=3.9 Hz, 2H). MS (ESI+) m/z 454 (M+H)$^{+}$.

Example GI-25

1-{2-cyclobutyl-5-[(propan-2-yl)oxy]pyridin-4-yl}-N-(quinoline-5-sulfonyl)cyclopropane-1-carboxamide Into a vial, 1-(3-dimethylaminopropyl)-3-ethylcarbodiimide hydrochloride (CAS #25952-53-8) (50 mg, 0.262 mmol), 4-dimethylaminopyridine (CAS #1122-58-3) (32 mg, 0.262 mmol) and 2-methylquinoline-5-sulfonamide (50 mg, 0.24 mmol) were charged. A solution of 1-(2-cyclobutyl-5-isopropoxypyridin-4-yl)cyclopropanecarboxylic acid (60 mg, 0.218 mmol) in anhydrous dichloromethane (1 mL) was added and the mixture was stirred at reflux overnight. Quinoline-5-sulfonamide (CAS #41591-05-2) (50 mg, 0.24 mmol) was added and the reaction mixture was stirred at ambient temperature overnight. The reaction mixture was quenched with saturated aqueous NH$_{4}$Cl solution. The aqueous layer was extracted with dichloromethane. The organic layers were combined, dried over MgSO$_{4}$, filtered and concentrated. The crude material was purified by reverse-phase HPLC Waters XBridge™ C18 5 μm OBD column, 30×100 mm, flow rate 50 mL/minute, H$_{2}$O+0.1% diethylamine/acetonitrile+0.1% diethylamine to give the title compound. $^{1}$H NMR (400 MHz, methanol-d$_{4}$) δ ppm 9.16 (ddd, J=8.7, 1.7, 0.8 Hz, 1H), 8.89 (dd, J=4.3, 1.7 Hz, 1H), 8.26 (dd, J=7.3, 1.2 Hz, 1H), 8.12 (dt, J=8.4, 1.1 Hz, 1H), 7.88 (s, 1H), 7.77 (dd, J=8.5, 7.3 Hz, 1H), 7.57 (dd, J=8.7, 4.3 Hz, 1H), 7.09 (s, 1H), 4.34 (hept, J=6.0 Hz, 1H), 3.65-3.51 (m, 1H), 2.36-2.16 (m, 4H), 2.12-1.96 (m, 1H), 1.93-1.80 (m, 1H), 1.48 (q, J=3.9 Hz, 2H), 0.94 (d, J=6.0 Hz, 6H), 0.88 (q, J=4.0 Hz, 2H). MS (ESI+) m/z 466 (M+H)$^{+}$.

Example GI-26

1-{2-cyclobutyl-5-[(propan-2-yl)oxy]pyridin-4-yl}-N-(2-methylquinoline-5-sulfonyl)cyclopropane-1-carboxamide Into a vial, 1-(3-dimethylaminopropyl)-3-ethylcarbodiimide hydrochloride (CAS #25952-53-8) (50 mg, 0.262 mmol), 4-dimethylaminopyridine (CAS #1122-58-3) (32 mg, 0.262 mmol) and 2-methylquinoline-5-sulfonamide (53 mg, 0.24 mmol) were charged. A solution of 1-(2-cyclobutyl-5-isopropoxypyridin-4-yl)cyclopropanecarboxylic acid (60 mg, 0.218 mmol) in anhydrous dichloromethane (1 mL) was added and the mixture was stirred at reflux overnight. Naphthalene-1-sulfonamide (CAS #606-25-7) (50 mg, 0.24 mmol) was added and the reaction mixture was stirred at ambient temperature overnight. The reaction mixture was quenched with saturated aqueous NH$_{4}$Cl solution. The aqueous layer was extracted with dichloromethane. The organic layers were combined, dried over MgSO$_{4}$, filtered and concentrated. The crude material was purified by reverse-phase HPLC Waters XBridge™ C18 5 μm OBD column, 30×100 mm, flow rate 50 mL/minute, H$_{2}$O+0.1% diethylamine/acetonitrile+0.1% diethylamine to give the title compound. $^{1}$H NMR (400 MHz, methanol-d$_{4}$) δ ppm 9.02 (dd, J=8.8, 0.8 Hz, 1H), 8.18 (dd, J=7.3, 1.2 Hz, 1H), 8.04 (dt, J=8.5, 1.1 Hz, 1H), 7.88 (s, 1H), 7.72 (dd, J=8.5, 7.3 Hz, 1H), 7.45 (d, J=8.8 Hz, 1H), 7.09 (s, 1H), 4.34 (hept, J=6.0 Hz, 1H), 3.58 (dddd, J=17.6, 9.3, 8.2, 1.0 Hz, 1H), 2.75 (s, 3H), 2.37-2.16 (m, 4H), 2.13-1.97 (m, 1H), 1.93-1.81 (m, 1H), 1.48 (q, J=3.9 Hz, 2H), 0.94 (d, J=6.0 Hz, 6H), 0.87 (q, J=4.0 Hz, 2H). MS (ESI+) m/z 480 (M+H)$^{+}$.

Example GI-27

1-{2-cyclobutyl-5-[(propan-2-yl)oxy]pyridin-4-yl}-N-(1H-indole-4-sulfonyl)cyclopropane-1-carboxamide Into a vial, 1-(3-dimethylaminopropyl)-3-ethylcarbodiimide hydrochloride (CAS #25952-53-8) (50 mg, 0.262 mmol), 4-dimethylaminopyridine (CAS #1122-58-3) (32 mg, 0.262 mmol) and 1H-indole-4-sulfonamide (47 mg, 0.24 mmol) were charged. A solution of 1-(2-cyclobutyl-5-isopropoxypyridin-4-yl)cyclopropanecarboxylic acid (60 mg, 0.218 mmol) in anhydrous dichloromethane (1 mL) was added and the mixture was stirred at reflux overnight. Naphthalene-1-sulfonamide (CAS #606-25-7) (CAS #41591-05-2) (50 mg, 0.24 mmol) was added and the reaction mixture was stirred at ambient temperature overnight. The reaction mixture was quenched with saturated aqueous NH$_{4}$Cl solution. The aqueous layer was extracted with dichloromethane. The organic layers were combined, dried over MgSO$_{4}$, filtered and concentrated. The crude material was purified by reverse-phase HPLC Waters XBridge™ C18 5 μm OBD column, 30×100 mm, flow rate 50 mL/minute, H$_{2}$O+0.1% diethylamine/acetonitrile+0.1% diethylamine to give the title compound. $^{1}$H NMR (400 MHz, methanol-d$_{4}$) δ ppm 8.15 (s, 1H), 8.05 (s, 1H), 7.76 (dd, J=7.6, 0.9 Hz, 1H), 7.70 (dt, J=8.2, 1.0 Hz, 1H), 7.44 (d, J=3.2 Hz, 1H), 7.23 (t, J=7.8 Hz, 1H), 7.17 (s, 1H), 6.81 (dd, J=3.2, 0.9 Hz, 1H), 4.54 (hept, J=6.0 Hz, 1H), 3.63 (dddd, J=17.6, 9.3, 8.2, 1.0 Hz, 1H), 2.39-2.20 (m, 4H), 2.14-1.98 (m, 1H), 1.95-1.82 (m, 1H), 1.47-1.35 (m, 2H), 1.09 (d, J=6.0 Hz, 6H), 1.08-1.04 (m, 2H). MS (ESI+) m/z 454 (M+H)$^{+}$.

Example GI-28

1-[5-cyclobutyl-2-(pyrrolidin-1-yl)pyridin-3-yl]-N-(quinoline-5-sulfonyl)cyclopropane-1-carboxamide In a microwave vial, to a solution of 1-(5-cyclobutyl-2-pyrrolidin-1-yl-3-pyridyl)cyclopropanecarboxylic acid (50 mg, 0.174 mmol) in anhydrous N,N-dimethylformamide (1 mL) under N2, quinoline-5-sulfonamide (CAS #415913-05-2) (40 mg, 0.191 mmol) and N,N-diisopropylethylamine (62 μL, 0.348 mmol) were added and the mixture was stirred at ambient temperature for 5 minutes. Propylphosphonic anhydride solution ~50% in N,N-dimethylformamide (CAS #68957-94-8) (179 μL, 0.209 mmol) was added and the reaction mixture was heated at 60° C. for 2 hours. The reaction mixture was cooled down at ambient temperature and the solvent was removed. The mixture was quenched with saturated aqueous NaHCO$_{3}$ solution, and the aqueous layer was extracted with dichloromethane. The organic layers were combined, dried over MgSO$_{4}$, filtered and concentrated. The crude material was purified by reverse-phase HPLC Waters XBridge™ C18 5 μm OBD column, 30×100 mm, flow rate 50 mL/minute, H$_{2}$O+0.1% diethylamine/acetonitrile+0.1% diethylamine to give the title compound. ¹H NMR (400 MHz, methanol-d₄) δ ppm 9.21 (ddd, J=8.8, 1.6, 0.8 Hz, 1H), 8.90 (dd, J=4.3, 1.7 Hz, 1H), 8.28 (dd, J=7.3, 1.2 Hz, 1H), 8.13 (dt, J=8.4, 1.1 Hz, 1H), 7.78 (dd, J=8.5, 7.3 Hz, 1H), 7.63-7.55 (m, 2H), 7.42 (d, J=2.4 Hz, 1H), 3.44-3.31 (m, 1H), 3.21 (d, J=6.3 Hz, 4H), 2.25 (dddd, J=8.6, 6.8, 4.9, 3.5 Hz, 2H), 2.12-1.91 (m, 3H), 1.90-1.77 (m, 1H), 1.57 (q, J=3.6 Hz, 2H), 1.49-1.38 (m, 4H), 0.98 (q, J=3.5 Hz, 2H). MS (ESI+) m/z 477 (M+H)⁺.

Example GI-29

1-[5-cyclobutyl-2-(pyrrolidin-1-yl)pyridin-3-yl]-N-(2-methylquinoline-5-sulfonyl)cyclopropane-1-carboxamide To a solution of 1-(5-cyclobutyl-2-pyrrolidin-1-yl-3-pyridyl)cyclopropanecarboxylic acid (60 mg, 0.209 mmol) in anhydrous dichloromethane (1 mL), 1-(3-dimethylaminopropyl)-3-ethylcarbodiimide hydrochloride (CAS #25952-53-8) (48 mg, 0.251 mmol), 4-dimethylaminopyridine (CAS #1122-58-3) (31 mg, 0.251 mmol) and 2-methylquinoline-5-sulfonamide (51 mg, 0.23 mmol) were added and the mixture was stirred at reflux overnight. 2-Methylquinoline-5-sulfonamide (23 mg, 0.104 mmol), 1-(3-dimethylaminopropyl)-3-ethylcarbodiimide hydrochloride (CAS #25952-53-8) (20 mg, 0.104 mmol) and anhydrous tetrahydrofuran (1 mL) were added and the reaction mixture was stirred and heated at 65° C. overnight. The reaction mixture was cooled down at ambient temperature and concentrated. The residue was quenched with saturated aqueous NH₄Cl solution and the aqueous layer was extracted with dichloromethane. The organic layers were combined, dried over MgSO₄, filtered and concentrated. The crude material was purified by reverse-phase HPLC Waters XBridge™ C18 5 μm OBD column, 30×100 mm, flow rate 50 mL/minute, H₂O+0.1% diethylamine/acetonitrile+0.1% diethylamine to give the title compound. ¹H NMR (400 MHz, methanol-d₄) δ ppm 9.10 (dd, J=8.9, 0.9 Hz, 1H), 8.23 (dd, J=7.3, 1.2 Hz, 1H), 8.05 (dt, J=8.5, 1.1 Hz, 1H), 7.74 (dd, J=8.5, 7.3 Hz, 1H), 7.65 (dd, J=2.4, 0.7 Hz, 1H), 7.47 (d, J=8.9 Hz, 1H), 7.41 (d, J=2.4 Hz, 1H), 3.47-3.34 (m, 1H), 3.20 (d, J=6.3 Hz, 4H), 2.75 (s, 3H), 2.34-2.22 (m, 2H), 2.15-1.94 (m, 3H), 1.92-1.80 (m, 1H), 1.57 (q, J=3.6 Hz, 2H), 1.51-1.41 (m, 4H), 0.96 (q, J=3.5 Hz, 2H). MS (ESI+) m/z 491 (M+H)⁺.

Example GI-30

1-[5-cyclobutyl-2-(pyrrolidin-1-yl)pyridin-3-yl]-N-(1H-indole-4-sulfonyl)cyclopropane-1-carboxamide In a microwave vial, to a solution of 1-(5-cyclobutyl-2-pyrrolidin-1-yl-3-pyridyl)cyclopropanecarboxylic acid (55 mg, 0.192 mmol) in anhydrous N,N-dimethylformamide (1 mL) under N2, 1H-indole-4-sulfonamide (41 mg, 0.211 mmol) and N,N-diisopropylethylamine (67 μL, 0.384 mmol) were added, The mixture was stirred at ambient temperature for 5 minutes. Propylphosphonic anhydride solution ~50% in N,N-dimethylformamide (CAS #68957-94-8) (198 μL, 0.23 mmol) was added and the reaction mixture was heated at 60° C. for 2 hours. The reaction mixture was cooled down at ambient temperature and the solvent was removed. The mixture was quenched with saturated aqueous NaHCO₃ solution, and the aqueous layer was extracted with dichloromethane. The organic layers were combined, dried over MgSO₄, filtered and concentrated. The crude material was purified by reverse-phase HPLC Waters XBridge™ C18 5 μm OBD column, 30×100 mm, flow rate 50 mL/minute, H₂O+0.1% diethylamine/acetonitrile+0.1% diethylamine to give the title compound. ¹H NMR (400 MHz, methanol-d₄) δ ppm 7.63 (dd, J=2.4, 0.7 Hz, 1H), 7.60 (dd, J=7.5, 0.9 Hz, 1H), 7.49 (dt, J=8.1, 1.0 Hz, 1H), 7.42 (d, J=2.4 Hz, 1H), 7.31 (d, J=3.2 Hz, 1H), 7.10 (t, J=7.8 Hz, 1H), 6.88 (dd, J=3.1, 0.9 Hz, 1H), 3.44-3.34 (m, 1H), 3.33-3.27 (m, 4H), 2.31-2.19 (m, 2H), 2.15-1.94 (m, 3H), 1.89-1.77 (m, 1H), 1.62 (q, J=3.6 Hz, 2H), 1.58-1.48 (m, 4H), 0.96 (q, J=3.5 Hz, 2H). MS (ESI+) m/z 465 (M+H)⁺.

Example GI-31

1-[5-cyclobutyl-2-(pyrrolidin-1-yl)pyridin-3-yl]-N-(1,2,3,4-tetrahydroquinoline-5-sulfonyl)cyclopropane-1-carboxamide In a microwave vial, to a solution of 1-(5-cyclobutyl-2-pyrrolidin-1-yl-3-pyridyl)cyclopropanecarboxylic acid (55 mg, 0.192 mmol) in anhydrous N,N-dimethylformamide (1 mL) under N₂, 1,2,3,4-tetrahydroquinoline-5-sulfonamide (CAS #1155515-51-7) (45 mg, 0.211 mmol) and N,N-diisopropylethylamine (67 μL, 0.384 mmol) were added. The mixture was stirred at ambient temperature for 5 minutes. Propylphosphonic anhydride solution ~50% in N,N-dimethylformamide (CAS #68957-94-8) (198 μL, 0.23 mmol) was added and the reaction mixture was heated at 60° C. for 2 hours. The reaction mixture was cooled down at ambient temperature and the solvent was removed. The mixture was quenched with saturated aqueous NaHCO₃ solution, and the aqueous layer was extracted with dichloromethane. The organic layers were combined, dried over MgSO₄, filtered and concentrated. The crude material was purified by reverse-phase HPLC Waters XBridge™ C18 5 μm OBD column, 30×100 mm, flow rate 50 mL/minute, H₂O+0.1% diethylamine/acetonitrile+0.1% diethylamine to give the title compound. ¹H NMR (400 MHz, DMSO-d₆) δ ppm 7.84 (s, 1H), 7.41 (s, 1H), 7.03 (dd, J=7.8, 1.3 Hz, 1H), 6.96 (t, J=7.9 Hz, 1H), 6.65 (d, J=8.0 Hz, 1H), 3.54-3.26 (m, 4H), 3.17 (dd, J=6.5, 4.6 Hz, 2H), 2.92 (t, J=6.4 Hz, 2H), 2.29-2.18 (m, 2H), 2.16-1.86 (m, 4H), 1.86-1.70 (m, 6H), 1.55 (d, J=3.2 Hz, 2H), 1.16 (q, J=4.0 Hz, 2H). MS (ESI+) m/z 481 (M+H)⁺.

Example GI-32

1-[5-cyclopropyl-2-(pyrrolidin-1-yl)pyridin-3-yl]-N-(quinoline-5-sulfonyl)cyclopropane-1-carboxamide To a solution of 1-(5-cyclopropyl-2-pyrrolidin-1-yl-3-pyridyl)cyclopropanecarboxylic acid (72 mg, 0.264 mmol) in anhydrous dichloromethane (1 mL), 1-(3-dimethylaminopropyl)-3-ethylcarbodiimide hydrochloride (CAS #25952-53-8) (60 mg, 0.317 mmol), 4-dimethylaminopyridine (CAS #1122-58-3) (39 mg, 0.317 mmol) and quinoline-5-sulfonamide (CAS #415913-05-2) (64 mg, 0.29 mmol) were added and the mixture was stirred at reflux overnight. Quinoline-5-sulfonamide (CAS #415913-05-2) (27 mg, 0.132 mmol), 1-(3-dimethylaminopropyl)-3-ethylcarbodiimide hydrochloride (CAS #25952-53-8) (25 mg, 0.132 mmol) and anhydrous tetrahydrofuran (1 mL) were added and the reaction mixture was stirred and heated at 65° C. overnight. The reaction mixture was cooled down at ambient temperature and the solvent was concentrated. The residue was quenched with saturated aqueous NH₄Cl solution and the aqueous layer was extracted with dichloromethane. The organic layers were combined, dried over MgSO₄, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.22 (ddd, J=8.7, 1.7, 0.9 Hz, 1H), 8.89 (dd, J=4.3, 1.7 Hz, 1H), 8.29 (dd, J=7.3, 1.3 Hz, 1H), 8.11 (dt, J=8.5, 1.1 Hz, 1H), 7.77 (dd, J=8.5, 7.3 Hz, 1H), 7.64-7.55 (m, 2H), 7.15 (d, J=2.4 Hz, 1H), 3.17 (d, J=6.3 Hz, 4H), 1.73 (tt, J=8.4, 5.1 Hz, 1H), 1.54 (q, J=3.6 Hz, 2H), 1.48-1.38 (m, 4H), 0.93 (q, J=3.5 Hz, 2H), 0.89-0.78 (m, 2H), 0.57-0.48 (m, 2H). MS (ESI+) m/z 463 (M+H)$^+$.

Example GI-33

1-[5-cyclopropyl-2-(pyrrolidin-1-yl)pyridin-3-yl]-N-(2-methylquinoline-5-sulfonyl)cyclopropane-1-carboxamide To a solution of 1-(5-cyclopropyl-2-pyrrolidin-1-yl-3-pyridyl)cyclopropanecarboxylic acid (72 mg, 0.264 mmol) in anhydrous dichloromethane (1 mL), 1-(3-dimethylaminopropyl)-3-ethylcarbodiimide hydrochloride (CAS #25952-53-8) (61 mg, 0.317 mmol), 4-dimethylaminopyridine (CAS #1122-58-3) (39 mg, 0.317 mmol) and 2-methylquinoline-5-sulfonamide (64 mg, 0.29 mmol) were added and the mixture was stirred at reflux overnight. 2-Methylquinoline-5-sulfonamide (29 mg, 0.132 mmol), 1-(3-dimethylaminopropyl)-3-ethylcarbodiimide hydrochloride (CAS #25952-53-8) (25 mg, 0.132 mmol) and anhydrous tetrahydrofuran (1 mL) were added and the reaction mixture was stirred and heated at 65° C. overnight. The reaction mixture was cooled down at ambient temperature and solvent was concentrated. The residue was quenched with saturated aqueous NH$_4$Cl solution and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.07 (dd, J=8.9, 0.9 Hz, 1H), 8.20 (dd, J=7.3, 1.2 Hz, 1H), 8.07-7.99 (m, 1H), 7.72 (dd, J=8.5, 7.3 Hz, 1H), 7.62 (d, J=2.4 Hz, 1H), 7.47 (d, J=8.9 Hz, 1H), 7.16 (d, J=2.4 Hz, 1H), 3.16 (d, J=6.2 Hz, 4H), 2.74 (s, 3H), 1.74 (tt, J=8.5, 5.1 Hz, 1H), 1.53 (q, J=3.6 Hz, 2H), 1.47-1.39 (m, 4H), 0.92 (q, J=3.5 Hz, 2H), 0.89-0.79 (m, 2H), 0.58-0.50 (m, 2H). MS (ESI+) m/z 477 (M+H)$^+$.

Example GI-34

1-[5-cyclopropyl-2-(pyrrolidin-1-yl)pyridin-3-yl]-N-(1H-indole-4-sulfonyl)cyclopropane-1-carboxamide To a solution of 1-(5-cyclopropyl-2-pyrrolidin-1-yl-3-pyridyl)cyclopropanecarboxylic acid (72 mg, 0.264 mmol) in anhydrous dichloromethane (1 mL), 1-(3-dimethylaminopropyl)-3-ethylcarbodiimide hydrochloride (CAS #25952-53-8) (61 mg, 0.317 mmol), 4-dimethylaminopyridine (CAS #1122-58-3) (39 mg, 0.317 mmol) and 1H-indole-4-sulfonamide (57 mg, 0.29 mmol) were added and the mixture was stirred at reflux overnight. 1H-Indole-4-sulfonamide (26 mg, 0.132 mmol), 1-(3-dimethylaminopropyl)-3-ethylcarbodiimide hydrochloride (CAS #25952-53-8) (25 mg, 0.132 mmol) and anhydrous tetrahydrofuran (1 mL) were added and the reaction mixture was stirred and heated at 65° C. overnight. The reaction mixture was cooled down at ambient temperature and solvent was concentrated. The residue was quenched with saturated aqueous NH$_4$Cl solution and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.62 (dd, J=7.4, 0.9 Hz, 1H), 7.57 (d, J=2.4 Hz, 1H), 7.48 (dt, J=8.1, 1.0 Hz, 1H), 7.31 (d, J=3.1 Hz, 1H), 7.22 (d, J=2.4 Hz, 1H), 7.10 (t, J=7.8 Hz, 1H), 6.85 (dd, J=3.1, 0.9 Hz, 1H), 3.27 (d, J=6.3 Hz, 4H), 1.73 (tt, J=8.4, 5.1 Hz, 1H), 1.58 (q, J=3.7 Hz, 2H), 1.56-1.49 (m, 4H), 0.93 (q, J=3.6 Hz, 2H), 0.88-0.80 (m, 2H), 0.60-0.49 (m, 2H). MS (ESI+) m/z 451 (M+H)$^+$.

Example GI-35

1-[5-chloro-2-(pyrrolidin-1-yl)pyridin-3-yl]-N-(quinoline-5-sulfonyl)cyclopropane-1-carboxamide In a microwave vial, to a mixture with 1-(5-ethyl-2-pyrrolidin-1-yl-3-pyridyl)cyclopropanecarboxylic acid and 1-(5-chloro-2-pyrrolidin-1-yl-3-pyridyl)cyclopropanecarboxylic acid (70 mg, 0.27 mmol) in anhydrous N,N-dimethylformamide (1 mL) under N$_2$, quinoline-5-sulfonamide (CAS #415913-05-2) (62 mg, 0.297 mmol) and N,N-diisopropylethylamine (94 μL, 0.54 mmol) were added and the mixture was stirred at ambient temperature for 5 minutes. Propylphosphonic anhydride solution ~50% in N,N-dimethylformamide (CAS #68957-94-8) (306 μL, 0.356 mmol) was added and the reaction mixture was heated at 60° C. for 2 hours. The reaction mixture was cooled down at ambient temperature and the solvent was removed. The mixture was quenched with saturated aqueous NaHCO$_3$ solution, and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.12 (dt, J=8.7, 1.3 Hz, 1H), 8.97 (dd, J=4.3, 1.6 Hz, 1H), 8.42 (dd, J=7.4, 1.2 Hz, 1H), 8.28 (dt, J=8.5, 1.1 Hz, 1H), 7.89-7.86 (m, 1H), 7.66 (dd, J=8.8, 4.3 Hz, 1H), 7.58 (d, J=2.5 Hz, 1H), 7.56 (d, J=2.5 Hz, 1H), 3.28-3.20 (m, 4H), 1.97-1.89 (m, 4H), 1.69 (q, J=4.1 Hz, 2H), 1.18 (q, J=4.1 Hz, 2H). MS (ESI−) m/z 455 & 457 (M−H)$^-$.

Example GI-36

1-[5-chloro-2-(pyrrolidin-1-yl)pyridin-3-yl]-N-(2-methylquinoline-5-sulfonyl)cyclopropane-1-carboxamide In a microwave vial, to a mixture of 1-(5-ethyl-2-pyrrolidin-1-yl-3-pyridyl)cyclopropanecarboxylic acid and 1-(5-chloro-2-pyrrolidin-1-yl-3-pyridyl)cyclopropanecarboxylic acid (70 mg, 0.27 mmol) in anhydrous N,N-dimethylformamide (1 mL) under N$_2$, 2-methylquinoline-5-sulfonamide (66 mg, 0.297 mmol) and N,N-diisopropylethylamine (94 μL, 0.54 mmol) were added. The mixture was stirred at ambient temperature for 5 minutes. Propylphosphonic anhydride solution ~50% in N,N-dimethylformamide (CAS #68957-94-8) (306 μL, 0.356 mmol) was added and the reaction mixture was heated at 60° C. for 2 hours. The reaction mixture was cooled down at ambient temperature and the solvent was removed. The mixture was quenched with saturated aqueous NaHCO$_3$ solution, and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.01 (d, J=8.9 Hz, 1H), 8.33 (dd, J=7.4, 1.2 Hz, 1H), 8.20-8.14 (m, 1H), 8.07 (s, 1H), 7.87 (d, J=2.5 Hz, 1H), 7.84 (dd, J=8.5, 7.4 Hz, 1H), 7.56-7.54 (m, 1H), 3.27-3.18 (m, 4H), 1.96-1.87 (m, 2H), 1.52 (dq, J=6.7, 4.2, 3.1 Hz, 4H), 1.16 (q, J=4.0 Hz, 2H). MS (ESI−) m/z 469 & 471 (M−H)$^-$.

Example GI-37

1-[5-ethyl-2-(pyrrolidin-1-yl)pyridin-3-yl]-N-(1H-indole-4-sulfonyl)cyclopropane-1-carboxamide In a microwave vial, to a solution of 1-(5-ethyl-2-pyrrolidin-1-yl-3-pyridyl)cyclopropanecarboxylic acid (68 mg, 0.26 mmol) in anhydrous N,N-dimethylformamide (1.5 mL) under N2, 1H-indole-4-sulfonamide (56 mg, 0.286 mmol) and N,N-diisopropylethylamine (91 μL, 0.52 mmol) were added and the mixture was stirred at ambient temperature for 5 minutes. Propylphosphonic anhydride solution ~50% in N,N-dimethylformamide (CAS #68957-94-8) (267 μL, 0.312 mmol) was added and the reaction mixture was heated at 60° C. for 1.5 hours. The reaction mixture was cooled down at ambient temperature and the solvent was removed. The mixture was quenched with saturated aqueous NaHCO$_3$ solution, and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.64-7.60 (m, 1H), 7.58 (d, J=2.4 Hz, 1H), 7.49 (dt, J=8.2, 0.9 Hz, 1H), 7.41 (dd, J=5.4, 2.7 Hz, 1H), 7.31 (d, J=3.1 Hz, 1H), 7.11 (t, J=7.8 Hz, 1H), 6.88-6.81 (m, 1H), 3.29-3.25 (m, 4H), 2.47 (q, J=7.6 Hz, 2H), 1.60 (q, J=3.6 Hz, 2H), 1.56-1.51 (m, 4H), 1.16 (t, J=7.6 Hz, 3H), 0.97 (q, J=3.6 Hz, 2H). MS (ESI+) m/z 439 (M+H)$^+$.

Example GI-38

1-{6-cyclobutyl-3-[(propan-2-yl)oxy]pyridin-2-yl}-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (77 mg, 0.40 mmol) and 4-dimethylaminopyridine (CAS #1122-58-3) (27 mg, 0.22 mmol) in anhydrous dichloromethane (2 mL), 1-(6-cyclobutyl-3-isopropoxy-2-pyridyl)cyclopropanecarboxylic acid (55 mg, 0.20 mmol) was added and the mixture was stirred at ambient temperature for 10 minutes. 1H-Indole-4-sulfonamide (39 mg, 0.20 mmol) was added and the reaction mixture was stirred at reflux for 1 hour. The reaction mixture was treated with water and organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.60 (dd, J=7.4, 0.9 Hz, 1H), 7.47 (dt, J=8.1, 0.9 Hz, 1H), 7.28 (d, J=3.1 Hz, 1H), 7.15 (d, J=8.5 Hz, 1H), 7.08 (dt, J=7.8, 3.6 Hz, 2H), 6.89 (dd, J=3.1, 0.9 Hz, 1H), 4.44 (hept, J=6.0 Hz, 1H), 3.62-3.49 (m, 1H), 2.33-2.12 (m, 4H), 2.06-1.90 (m, 1H), 1.89-1.77 (m, 1H), 1.53 (q, J=3.9 Hz, 2H, 1.03 (q, J=3.9 Hz, 2H). MS (ESI+) m/z 454 (M+H)$^+$.

Example GI-39

1-{6-cyclobutyl-3-[(propan-2-yl)oxy]pyridin-2-yl}-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (77 mg, 0.40 mmol) and 4-dimethylaminopyridine (CAS #1122-58-3) (27 mg, 0.22 mmol) in anhydrous dichloromethane (2 mL), 1-(6-cyclobutyl-3-isopropoxy-2-pyridyl)cyclopropanecarboxylic acid (55 mg, 0.20 mmol) was added and the mixture was stirred at ambient temperature for 10 minutes. Quinoline-5-sulfonamide (CAS #415913-05-2) (41 mg, 0.20 mmol) was added and the reaction mixture was stirred at reflux for 1 hour. The reaction mixture was treated with water and organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.23 (ddd, J=8.7, 1.7, 0.8 Hz, 1H), 8.90 (dd, J=4.3, 1.7 Hz, 1H), 8.27 (dd, J=7.3, 1.2 Hz, 1H), 8.13 (dt, J=8.5, 1.1 Hz, 1H), 7.78 (dd, J=8.5, 7.3 Hz, 1H), 7.59 (dd, J=8.7, 4.3 Hz, 1H), 7.10 (q, J=8.4 Hz, 2H), 4.31 (hept, J=6.0 Hz, 1H), 3.62-3.49 (m, 1H), 2.32-2.12 (m, 4H), 2.08-1.92 (m, 1H), 1.90-1.76 (m, 1H), 1.52 (q, J=3.8 Hz, 2H), 1.05 (q, J=3.9 Hz, 2H), 0.93 (d, J=6.0 Hz, 6H). MS (ESI+) m/z 466 (M+H)$^+$.

Example GI-40

1-{5-ethyl-2-[(propan-2-yl)oxy]pyridin-3-yl}-N-(2-methylquinoline-5-sulfonyl)cyclopropane-1-carboxamide Into a vial, a solution of 1-(5-ethyl-2-isopropoxy-3-pyridyl)cyclopropanecarboxylic acid (69 mg, 0.277 mmol), 1-(3-dimethylaminopropyl)-3-ethylcarbodiimide hydrochloride (CAS #25952-53-8) (64 mg, 0.332 mmol) and 4-dimethylaminopyridine (CAS #1122-58-3) (40 mg, 0.332 mmol) in anhydrous dichloromethane (2 mL) was added to 2-methylquinoline-5-sulfonamide (51 mg, 0.228 mmol). The reaction mixture was stirred at reflux for 24 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.02 (dd, J=8.9, 0.8 Hz, 1H), 8.15 (dd, J=7.3, 1.2 Hz, 1H), 8.03 (dt, J=8.5, 1.1 Hz, 1H), 7.75-7.66 (m, 2H), 7.44 (d, J=8.9 Hz, 1H), 7.32 (d, J=2.4 Hz, 1H), 4.96-4.84 (m, 1H), 2.73 (s, 3H), 2.52 (q, J=7.6 Hz, 2H), 1.46 (q, J=3.8 Hz, 2H), 0.90 (d, J=6.1 Hz, 6H), 0.82 (q, J=3.9 Hz, 2H). MS (ESI+) m/z 454 (M+H)$^+$.

Example GI-41

1-{5-ethyl-2-[(propan-2-yl)oxy]pyridin-3-yl}-N-(1H-indole-4-sulfonyl)cyclopropane-1-carboxamide Into a vial, a solution of 1-(5-ethyl-2-isopropoxy-3-pyridyl)cyclopropanecarboxylic acid (69 mg, 0.277 mmol), 1-(3-dimethylaminopropyl)-3-ethylcarbodiimide hydrochloride (CAS #25952-53-8) (64 mg, 0.332 mmol) and 4-dimethylaminopyridine (CAS #1122-58-3) (40 mg, 0.332 mmol) in anhydrous dichloromethane (2 mL) was added to 1H-indole-4-sulfonamide (54 mg, 0.277 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 7.76-7.70 (m, 1H), 7.58 (dd, J=7.4, 0.9 Hz, 1H), 7.48 (dt, J=8.2, 0.9 Hz, 1H), 7.37 (d, J=2.5 Hz, 1H), 7.29 (d, J=3.1 Hz, 1H), 7.09 (dd, J=8.1, 7.4 Hz, 1H), 6.89 (dd, J=3.1, 0.9 Hz, 1H), 5.09 (hept, J=6.1 Hz, 1H), 2.52 (q, J=7.6 Hz, 2H), 1.53 (q, J=3.8 Hz, 2H), 1.23-1.14 (m, 9H), 0.86 (q, J=3.9 Hz, 2H). MS (ESI+) m/z 428 (M+H)$^+$.

Example GI-42

1-[5-methyl-2-(2-methylpropoxy)pyridin-3-yl]-N-(quinoline-5-sulfonyl)cyclopropane-1-carboxamide Into a vial, a solution of 1-(2-isobutoxy-5-methyl-3-pyridyl)cyclopropanecarboxylic acid (60 mg, 0.24 mmol), 1-(3-dimethylaminopropyl)-3-ethylcarbodiimide hydrochloride (CAS #25952-53-8) (55 mg, 0.288 mmol) and 4-dimethylaminopyridine (CAS #1122-58-3) (35 mg, 0.288 mmol) in anhydrous dichloromethane (2 mL) was added to quinoline-5-sulfonamide (CAS #415913-05-2) (50 mg, 0.24 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.10 (ddd, J=8.8, 1.7, 0.9 Hz, 1H), 8.90 (dd, J=4.3, 1.7 Hz, 1H), 8.26 (dd, J=7.3, 1.2 Hz, 1H), 8.13 (dt, J=8.5, 1.1 Hz, 1H), 7.78 (dd, J=8.5, 7.3 Hz, 1H), 7.70 (dd, J=2.4, 0.9 Hz, 1H), 7.55 (dd, J=8.7, 4.3 Hz, 1H), 7.37-7.32 (m, 1H), 3.56 (d, J=6.5 Hz, 2H), 2.23-2.18 (m, 3H), 1.46 (q, J=3.8 Hz, 2H), 1.37 (dp, J=13.3, 6.6 Hz, 1H), 0.84 (q, J=3.8 Hz, 2H), 0.69 (d, J=6.7 Hz, 6H). MS (ESI+) m/z 440 (M+H)$^+$.

Example GI-43

1-[5-methyl-2-(2-methylpropoxy)pyridin-3-yl]-N-(2-methylquinoline-5-sulfonyl)cyclopropane-1-carboxamide Into a vial, a solution of 1-(2-isobutoxy-5-methyl-3-pyridyl)cyclopropanecarboxylic acid (60 mg, 0.24 mmol), 1-(3-dimethylaminopropyl)-3-ethylcarbodiimide hydrochloride (CAS #25952-53-8) (55 mg, 0.288 mmol) and 4-dimethylaminopyridine (CAS #1122-58-3) (35 mg, 0.288 mmol) in anhydrous dichloromethane (2 mL) was added to 2-methylquinoline-5-sulfonamide (53 mg, 0.24 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 8.94 (dd, J=8.8, 0.9 Hz, 1H), 8.17 (dd, J=7.3, 1.3 Hz, 1H), 8.04 (dt, J=8.5, 1.0 Hz, 1H), 7.75-7.70 (m, 1H), 7.70-7.67 (m, 1H), 7.41 (d, J=8.9 Hz, 1H), 7.37-7.31 (m, 1H), 3.53 (d, J=6.6 Hz, 2H), 2.75 (s, 3H), 2.20 (s, 3H), 1.44 (q, J=3.8 Hz, 2H), 1.33 (hept, J=6.7 Hz, 1H), 0.82 (q, J=3.9 Hz, 2H), 0.67 (d, J=6.7 Hz, 6H). MS (ESI+) m/z 454 (M+H)$^+$.

Example GI-44

N-(1H-indole-4-sulfonyl)-1-[5-methyl-2-(2-methylpropoxy)pyridin-3-yl]cyclopropane-1-carboxamide Into a vial, a solution of 1-(2-isobutoxy-5-methyl-3-pyridyl)cyclopropanecarboxylic acid (60 mg, 0.24 mmol), 1-(3-dimethylaminopropyl)-3-ethylcarbodiimide hydrochloride (CAS #25952-53-8) (55 mg, 0.288 mmol) and 4-dimethylaminopyridine (CAS #1122-58-3) (35 mg, 0.288 mmol) in anhydrous dichloromethane (2 mL) was added to 1H-indole-4-sulfonamide (47 mg, 0.24 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 7.71 (dd, J=2.4, 1.0 Hz, 1H), 7.59 (dd, J=7.5, 0.9 Hz, 1H), 7.51 (dt, J=8.0, 0.9 Hz, 1H), 7.40-7.35 (m, 1H), 7.31 (d, J=3.2 Hz, 1H), 7.11 (dd, J=8.1, 7.4 Hz, 1H), 6.84 (dd, J=3.1, 0.9 Hz, 1H), 3.81 (d, J=6.6 Hz, 2H), 2.22-2.17 (m, 3H), 1.82-1.67 (m, J=6.7 Hz, 1H), 1.54 (q, J=3.8 Hz, 2H), 0.92-0.84 (m, 8H). MS (ESI+) m/z 428 (M+H)$^+$.

Example GI-45

1-[5-ethyl-2-(2-methylpropoxy)pyridin-3-yl]-N-(quinoline-5-sulfonyl)cyclopropane-1-carboxamide Into a vial, a solution of 1-(5-ethyl-2-isobutoxy-3-pyridyl) cyclopropanecarboxylic acid (60 mg, 0.228 mmol), 1-(3-dimethylaminopropyl)-3-ethylcarbodiimide hydrochloride (CAS #25952-53-8) (52 mg, 0.273 mmol) and 4-dimethylaminopyridine (CAS #1122-58-3) (33 mg, 0.273 mmol) in anhydrous dichloromethane (2 mL) was added to quinoline-5-sulfonamide (CAS #415913-05-2) (47 mg, 0.228 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18

5 µm OBD column, 30×100 mm, flow rate 50 mL/minute, H₂O+0.1% diethylamine/acetonitrile+0.1% diethylamine to give the title compound. ¹H NMR (400 MHz, methanol-d₄) δ ppm 9.11 (ddd, J=8.7, 1.7, 0.8 Hz, 1H), 8.90 (dd, J=4.3, 1.7 Hz, 1H), 8.26 (dd, J=7.3, 1.2 Hz, 1H), 8.14 (dt, J=8.5, 1.1 Hz, 1H), 7.78 (dd, J=8.5, 7.3 Hz, 1H), 7.75-7.69 (m, 1H), 7.55 (dd, J=8.7, 4.3 Hz, 1H), 7.38 (d, J=2.4 Hz, 1H), 3.58 (d, J=6.5 Hz, 2H), 2.55 (q, J=7.6 Hz, 2H), 1.47 (q, J=3.8 Hz, 2H), 1.38 (dp, J=13.3, 6.6 Hz, 1H), 1.19 (d, J=7.6 Hz, 3H), 0.85 (q, J=3.8 Hz, 2H), 0.69 (d, J=6.7 Hz, 6H). MS (ESI+) m/z 454 (M+H)⁺.

Example GI-46

1-[5-ethyl-2-(2-methylpropoxy)pyridin-3-yl]-N-(2-methylquinoline-5-sulfonyl)cyclopropane-1-carboxamide Into a vial, a solution of 1-(5-ethyl-2-isobutoxy-3-pyridyl)cyclopropanecarboxylic acid (60 mg, 0.228 mmol), 1-(3-dimethylaminopropyl)-3-ethylcarbodiimide hydrochloride (CAS #25952-53-8) (52 mg, 0.273 mmol) and 4-dimethylaminopyridine (CAS #1122-58-3) (33 mg, 0.273 mmol) in anhydrous dichloromethane (2 mL) was added to 2-methylquinoline-5-sulfonamide (51 mg, 0.228 mmol). The reaction mixture was stirred at reflux for 24 hours. The reaction mixture was quenched with saturated aqueous NH₄Cl solution, and the aqueous layer was extracted with dichloromethane. The organic layers were combined, dried over MgSO₄, filtered and concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. ¹H NMR (400 MHz, methanol-d₄) δ ppm 8.95 (dd, J=8.8, 0.8 Hz, 1H), 8.18 (dd, J=7.3, 1.2 Hz, 1H), 8.05 (dt, J=8.5, 1.1 Hz, 1H), 7.73 (d, J=7.3 Hz, 1H), 7.72-7.69 (m, 1H), 7.42 (d, J=8.9 Hz, 1H), 7.37 (d, J=2.4 Hz, 1H), 3.56 (d, J=6.5 Hz, 2H), 2.75 (s, 3H), 2.55 (q, J=7.6 Hz, 2H), 1.46 (q, J=3.8 Hz, 2H), 1.34 (dp, J=13.5, 6.7 Hz, 1H), 1.20 (t, J=7.6 Hz, 3H), 0.83 (q, J=3.9 Hz, 2H), 0.68 (d, J=6.7 Hz, 6H). MS (ESI+) m/z 468 (M+H)⁺.

Example GI-47

1-[5-ethyl-2-(2-methylpropoxy)pyridin-3-yl]-N-(1H-indole-4-sulfonyl)cyclopropane-1-carboxamide Into a vial, a solution of 1-(5-ethyl-2-isobutoxy-3-pyridyl)cyclopropanecarboxylic acid (60 mg, 0.228 mmol), 1-(3-dimethylaminopropyl)-3-ethylcarbodiimide hydrochloride (CAS #25952-53-8) (52 mg, 0.273 mmol) and 4-dimethylaminopyridine (CAS #1122-58-3) (33 mg, 0.273 mmol) in anhydrous dichloromethane (2 mL) was added to 1H-indole-4-sulfonamide (45 mg, 0.228 mmol). The reaction mixture was stirred at reflux for 24 hours. The reaction mixture was quenched with saturated aqueous NH₄Cl solution, and the aqueous layer was extracted with dichloromethane. The organic layers were combined, dried over MgSO₄, filtered and concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. ¹H NMR (400 MHz, methanol-d₄) δ ppm 7.71 (d, J=2.3 Hz, 1H), 7.56 (dd, J=7.4, 0.9 Hz, 1H), 7.48 (dt, J=8.1, 0.9 Hz, 1H), 7.38 (d, J=2.4 Hz, 1H), 7.28 (d, J=3.1 Hz, 1H), 7.08 (dd, J=8.1, 7.5 Hz, 1H), 6.82 (dd, J=3.2, 0.9 Hz, 1H), 3.81 (d, J=6.6 Hz, 2H), 2.52 (q, J=7.6 Hz, 2H), 1.81-1.66 (m, J=6.7 Hz, 1H), 1.53 (q, J=3.8 Hz, 2H), 1.18 (t, J=7.6 Hz, 3H), 0.90-0.83 (m, 8H). MS (ESI+) m/z 442 (M+H)⁺.

Example GI-48

1-[5-cyclopropyl-2-(2-methylpropoxy)pyridin-3-yl]-N-(quinoline-5-sulfonyl)cyclopropane-1-carboxamide Into a vial, a solution of 1-(5-cyclopropyl-2-isobutoxy-3-pyridyl)cyclopropanecarboxylic acid (60 mg, 0.218 mmol), 1-(3-dimethylaminopropyl)-3-ethylcarbodiimide hydrochloride (CAS #25952-53-8) (50 mg, 0.26 mmol) and 4-dimethylaminopyridine (CAS #1122-58-3) (32 mg, 0.26 mmol) in anhydrous dichloromethane (2 mL) was added to quinoline-5-sulfonamide (CAS #415913-05-2) (45 mg, 0.218 mmol). The reaction mixture was stirred at reflux for 24 hours. The reaction mixture was quenched with saturated aqueous NH₄Cl solution, and the aqueous layer was extracted with dichloromethane. The organic layers were combined, dried over MgSO₄, filtered and concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. ¹H NMR (400 MHz, methanol-d₄) δ ppm 9.08 (ddd, J=8.7, 1.7, 0.8 Hz, 1H), 8.89 (dd, J=4.3, 1.7 Hz, 1H), 8.25 (dd, J=7.3, 1.2 Hz, 1H), 8.13 (dt, J=8.5, 1.1 Hz, 1H), 7.77 (dd, J=8.5, 7.3 Hz, 1H), 7.69 (dd, J=2.4, 0.5 Hz, 1H), 7.54 (dd, J=8.7, 4.3 Hz, 1H), 7.17 (d, J=2.4 Hz, 1H), 3.55 (d, J=6.6 Hz, 2H), 1.82 (tt, J=8.4, 5.1 Hz, 1H), 1.44 (q, J=3.8 Hz, 2H), 1.35 (hept, J=6.7 Hz, 1H), 0.94-0.86 (m, 2H), 0.82 (q, J=3.9 Hz, 2H), 0.67 (d, J=6.7 Hz, 6H), 0.64-0.58 (m, 2H). MS (ESI+) m/z 466 (M+H)⁺.

Example GI-49

1-[5-cyclopropyl-2-(2-methylpropoxy)pyridin-3-yl]-N-(2-methylquinoline-5-sulfonyl)cyclopropane-1-carboxamide Into a vial, a solution of 1-(5-cyclopropyl-2-isobutoxy-3-pyridyl)cyclopropanecarboxylic acid (60 mg, 0.218 mmol), 1-(3-dimethylaminopropyl)-3-ethylcarbodiimide hydrochloride (CAS #25952-53-8) (50 mg, 0.26 mmol) and 4-dimethylaminopyridine (CAS #1122-58-3) (32 mg, 0.26 mmol) in anhydrous dichloromethane (2 mL) was added to 2-methylquinoline-5-sulfonamide (48 mg, 0.218 mmol). The reaction mixture was stirred at reflux for 24 hours. The reaction mixture was quenched with saturated aqueous NH₄Cl solution, and the aqueous layer was extracted with dichloromethane. The organic layers were combined, dried over MgSO₄, filtered and concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. ¹H NMR (400 MHz, methanol-d₄) δ ppm 8.95 (dd, J=8.8, 0.9 Hz, 1H), 8.19 (dd, J=7.3, 1.2 Hz, 1H), 8.06 (dt, J=8.5, 1.1 Hz, 1H), 7.74 (dd, J=8.5, 7.3 Hz, 1H), 7.71 (d, J=2.4 Hz, 1H), 7.44 (d, J=8.9 Hz, 1H), 7.19 (d, J=2.4 Hz, 1H), 3.56 (d, J=6.6 Hz, 2H), 2.77 (s, 3H), 1.85 (tt, J=8.4, 5.1 Hz, 1H), 1.46 (q, J=3.8 Hz, 2H), 1.35 (dp, J=13.3, 6.5 Hz, 1H), 0.96-0.89 (m, 2H), 0.83 (q, J=3.9 Hz, 2H), 0.69 (d, J=6.7 Hz, 6H), 0.66-0.60 (m, 2H). MS (ESI+) m/z 480 (M+H)⁺.

Example GI-50

1-[5-cyclopropyl-2-(2-methylpropoxy)pyridin-3-yl]-N-(1H-indole-4-sulfonyl)cyclopropane-1-carboxamide Into a vial, a solution of 1-(5-cyclopropyl-2-isobutoxy-3-pyridyl)cyclopropanecarboxylic acid (60 mg, 0.218 mmol), 1-(3-dimethylaminopropyl)-3-ethylcarbodiimide hydrochloride (CAS #25952-53-8) (50 mg, 0.26 mmol) and 4-dimethylaminopyridine (CAS #1122-58-3) (32 mg, 0.26 mmol) in anhydrous dichloromethane (2 mL) was added to 1H-indole-4-sulfonamide (43 mg, 0.218 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 7.70 (dd, J=2.5, 0.5 Hz, 1H), 7.57 (dd, J=7.4, 0.9 Hz, 1H), 7.50 (dt, J=8.1, 0.9 Hz, 1H), 7.30 (d, J=3.2 Hz, 1H), 7.20 (d, J=2.4 Hz, 1H), 7.10 (dd, J=8.1, 7.4 Hz, 1H), 6.81 (dd, J=3.1, 0.9 Hz, 1H), 3.78 (d, J=6.6 Hz, 2H), 1.82 (tt, J=8.4, 5.1 Hz, 1H), 1.76-1.63 (m, J=6.6 Hz, 1H), 1.51 (q, J=3.8 Hz, 2H), 0.93-0.81 (m, 10H), 0.66-0.55 (m, 2H). MS (ESI+) m/z 454 (M+H)$^+$.

Example GI-51

1-[5-cyclobutyl-2-(2-methylpropoxy)pyridin-3-yl]-N-(quinoline-5-sulfonyl)cyclopropane-1-carboxamide Into a vial, a solution of 1-(5-cyclobutyl-2-isobutoxy-3-pyridyl)cyclopropanecarboxylic acid (60 mg, 0.207 mmol), 1-(3-dimethylaminopropyl)-3-ethylcarbodiimide hydrochloride (CAS #25952-53-8) (48 mg, 0.248 mmol) and 4-dimethylaminopyridine (CAS #1122-58-3) (30 mg, 0.248 mmol) in anhydrous dichloromethane (2 mL) was added to quinoline-5-sulfonamide (CAS #415913-05-2) (43 mg, 0.207 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.09 (dt, J=8.8, 1.2 Hz, 1H), 8.89 (dt, J=4.3, 1.5 Hz, 1H), 8.27 (dt, J=7.3, 1.3 Hz, 1H), 8.13 (dd, J=8.5, 1.2 Hz, 1H), 7.78 (ddd, J=8.5, 7.2, 1.1 Hz, 1H), 7.74-7.69 (m, 1H), 7.54 (ddd, J=8.7, 4.3, 1.1 Hz, 1H), 7.45-7.40 (m, 1H), 3.57 (dd, J=6.5, 1.1 Hz, 2H), 3.48 (p, J=8.7 Hz, 1H), 2.37-2.24 (m, 2H), 2.19-1.96 (m, 3H), 1.93-1.81 (m, 1H), 1.47 (qd, J=3.8, 1.1 Hz, 2H), 1.41-1.29 (m, 2H), 0.84 (qd, J=3.9, 1.0 Hz, 2H), 0.68 (dd, J=6.8, 1.1 Hz, 6H). MS (ESI+) m/z 480 (M+H)$^+$.

Example GI-52

1-[5-cyclobutyl-2-(2-methylpropoxy)pyridin-3-yl]-N-(1H-indole-4-sulfonyl)cyclopropane-1-carboxamide Into a vial, a solution of 1-(5-cyclobutyl-2-isobutoxy-3-pyridyl)cyclopropanecarboxylic acid (60 mg, 0.207 mmol), 1-(3-dimethylaminopropyl)-3-ethylcarbodiimide hydrochloride (CAS #25952-53-8) (48 mg, 0.248 mmol) and 4-dimethylaminopyridine (CAS #1122-58-3) (30 mg, 0.248 mmol) in anhydrous dichloromethane (2 mL) was added on 1H-indole-4-sulfonamide (41 mg, 0.207 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 7.72 (dd, J=2.4, 0.8 Hz, 1H), 7.60 (dd, J=7.5, 0.9 Hz, 1H), 7.51 (dt, J=8.1, 0.9 Hz, 1H), 7.45 (dd, J=2.4, 0.5 Hz, 1H), 7.30 (d, J=3.1 Hz, 1H), 7.12 (dd, J=8.1, 7.4 Hz, 1H), 6.82 (dd, J=3.1, 0.9 Hz, 1H), 3.78 (d, J=6.6 Hz, 2H), 3.54-3.41 (m, 1H), 2.37-2.25 (m, 2H), 2.21-1.96 (m, 3H), 1.94-1.82 (m, 1H), 1.73-1.60 (m, J=6.7 Hz, 1H), 1.52 (q, J=3.9 Hz, 2H), 0.90-0.83 (m, 8H). MS (ESI+) m/z 468 (M+H)$^+$.

Example GI-53

1-[5-cyclobutyl-2-(2-methylpropoxy)pyridin-3-yl]-N-(2-methylquinoline-5-sulfonyl)cyclopropane-1-carboxamide Into a vial, a solution of 1-(5-cyclobutyl-2-isobutoxy-3-pyridyl)cyclopropanecarboxylic acid (60 mg, 0.207 mmol), 1-(3-dimethylaminopropyl)-3-ethylcarbodiimide hydrochloride (CAS #25952-53-8) (48 mg, 0.248 mmol) and 4-dimethylaminopyridine (CAS #1122-58-3) (30 mg, 0.248 mmol) in anhydrous dichloromethane (2 mL) was added to 2-methylquinoline-5-sulfonamide (46 mg, 0.207 mmol). The reaction mixture was stirred at reflux for 24 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% formic acid/acetonitrile+0.1% formic acid to give the title compound. $^1$H NMR (400 MHz, methanol-$d_4$) δ ppm 8.80 (d, J=8.9 Hz, 1H), 8.37 (d, J=7.4 Hz, 1H), 8.24 (d, J=8.4 Hz, 1H), 7.90-7.82 (m, 2H), 7.50 (d, J=8.8 Hz, 1H), 7.48 (d, J=2.3 Hz, 1H), 3.52 (q, J=8.5 Hz, 1H), 3.47 (d, J=6.6 Hz, 2H), 2.77 (s, 3H), 2.33 (dtd, J=10.5, 8.0, 2.5 Hz, 2H), 2.23-2.04 (m, 3H), 1.95-1.83 (m, 1H), 1.42 (q, J=4.5 Hz, 2H), 1.13 (hept, J=6.7 Hz, 1H), 1.06-0.98 (m, 2H), 0.62 (d, J=6.7 Hz, 6H). MS (ESI+) m/z 494 (M+H)$^+$.

Example GI-54

1-{6-ethyl-3-[(propan-2-yl)oxy]pyridin-2-yl}-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (103 mg, 0.56 mmol) and 4-dimethylaminopyridine (CAS #1122-58-3) (38 mg, 0.31 mmol) in anhydrous dichloromethane (2 mL), and 1-(6-ethyl-3-isopropoxy-2-pyridyl)cyclopropanecarboxylic acid (70 mg, 0.28 mmol) was added and the mixture was stirred at ambient temperature for 10 minutes. 2-Methylquinoline-5-sulfonamide (65 mg, 0.28 mmol) was added and the reaction mixture was stirred at reflux overnight. The reaction mixture was treated with water and organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.05 (d, J=8.8 Hz, 1H), 8.18 (dd, J=7.3, 1.2 Hz, 1H), 8.01 (d, J=8.4 Hz, 1H), 7.70 (dd, J=8.5, 7.3 Hz, 1H), 7.46 (d, J=8.9 Hz, 1H), 7.15 (d, J=8.4 Hz, 1H), 7.03 (d, J=8.4 Hz, 1H), 4.32 (p, J=6.0 Hz, 1H), 2.73 (s, 3H), 2.66 (q, J=7.6 Hz, 2H), 1.51 (q, J=3.9 Hz, 2H), 1.19 (t, J=7.6 Hz, 3H), 0.99 (q, J=3.9 Hz, 2H), 0.93 (d, J=6.0 Hz, 6H). MS (ESI+) m/z 454 (M+H)$^+$.

Example GI-55

1-{6-ethyl-3-[(propan-2-yl)oxy]pyridin-2-yl}-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (103 mg, 0.56 mmol) and 4-dimethylaminopyridine (CAS #1122-58-3) (38 mg, 0.31 mmol) in anhydrous dichloromethane (2 mL), 1-(6-ethyl-3-isopropoxy-2-pyridyl)cyclopropanecarboxylic acid (70 mg, 0.28 mmol) was added and the mixture was stirred at ambient temperature for 10 minutes. Quinoline-5-sulfonamide (CAS #415913-05-2) (58 mg, 0.28 mmol) was added and the reaction mixture was stirred at reflux overnight. The reaction mixture was treated with water and organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.20 (ddd, J=8.7, 1.7, 0.8 Hz, 1H), 8.87 (dd, J=4.3, 1.7 Hz, 1H), 8.25 (dd, J=7.3, 1.2 Hz, 1H), 8.09 (dt, J=8.5, 1.1 Hz, 1H), 7.74 (dd, J=8.5, 7.3 Hz, 1H), 7.57 (dd, J=8.7, 4.3 Hz, 1H), 7.10 (d, J=8.5 Hz, 1H), 6.98 (d, J=8.4 Hz, 1H), 4.29 (hept, J=6.0 Hz, 1H), 2.63 (q, J=7.6 Hz, 2H), 1.52 (q, J=3.8 Hz, 2H), 1.21-1.10 (m, 3H), 1.01 (q, J=3.8 Hz, 2H), 0.92 (d, J=6.0 Hz, 6H). MS (ESI+) m/z 440 (M+H)$^+$.

Example GI-56

1-{6-ethyl-3-[(propan-2-yl)oxy]pyridin-2-yl}-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (103 mg, 0.56 mmol) and 4-dimethylaminopyridine (CAS #1122-58-3) (38 mg, 0.31 mmol) in anhydrous dichloromethane (2 mL), 1-(6-ethyl-3-isopropoxy-2-pyridyl)cyclopropanecarboxylic acid (70 mg, 0.28 mmol) was added and the mixture was stirred at ambient temperature for 10 minutes. 1H-Indole-4-sulfonamide (55 mg, 0.28 mmol) was added and the reaction mixture was stirred at reflux overnight. The reaction mixture was treated with water and organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.59 (dd, J=7.5, 0.9 Hz, 1H), 7.47 (dt, J=8.2, 1.0 Hz, 1H), 7.28 (d, J=3.2 Hz, 1H), 7.14 (d, J=8.4 Hz, 1H), 7.11-7.03 (m, 1H), 6.99 (d, J=8.4 Hz, 1H), 6.89 (dd, J=3.2, 0.9 Hz, 1H), 4.44 (hept, J=6.0 Hz, 1H), 2.65 (q, J=7.6 Hz, 2H), 1.58 (q, J=3.9 Hz, 2H), 1.14 (d, J=6.0 Hz, 6H), 1.08-1.01 (m, 5H). MS (ESI+) m/z 428 (M+H)$^+$.

Example GI-57

1-[5-cyclobutyl-2-(4-methoxypiperidin-1-yl)pyridin-3-yl]-N-(1H-indole-4-sulfonyl)cyclopropane-1-carboxamide To a suspension of 1-[5-cyclobutyl-2-(4-methoxy-1-piperidyl)-3-pyridyl]cyclopropanecarboxylic acid (58 mg, 0.18 mmol) in anhydrous dichloromethane (0.7 mL), were added 1-(3-dimethylaminopropyl)-3-ethylcarbodiimide hydrochloride (CAS #25952-53-8) (44 mg, 0.26 mmol), 4-dimethylaminopyridine (CAS #1122-58-3) (32 mg, 0.23 mmol) and 1H-indole-4-sulfonamide (35 mg, 0.18 mmol). The reaction mixture was stirred at reflux overnight. 1-(3-Dimethylaminopropyl)-3-ethylcarbodiimide hydrochloride (CAS #25952-53-8) (44 mg, 0.26 mmol) and dimethyl sulfoxide (0.1 mL) were added and the reaction mixture was heated at reflux for 4 hours more. The reaction mixture was quenched with water (5 mL), and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.80 (dd, J=2.4, 0.7 Hz, 1H), 7.59 (dd, J=7.4, 0.9 Hz, 1H), 7.52 (dd, J=2.4, 0.6 Hz, 1H), 7.49 (dt, J=8.2, 0.9 Hz, 1H), 7.30 (d, J=3.1 Hz, 1H), 7.10 (dd, J=8.1, 7.5 Hz, 1H), 6.86 (dd, J=3.1, 0.9 Hz, 1H), 3.43 (td, J=8.9, 7.4 Hz, 1H), 3.35 (dd, J=12.8, 4.1 Hz, 2H), 3.31 (s, 3H), 3.20 (tt, J=8.6, 4.0 Hz, 1H), 2.71 (ddd, J=12.8, 9.9, 2.9 Hz, 2H), 2.34-2.22 (m, 2H), 2.17-1.97 (m, 3H), 1.91-1.79 (m, 1H), 1.73-1.62 (m, 2H), 1.56 (q, J=3.6 Hz, 2H), 1.39 (dtd, J=12.8, 9.4, 3.6 Hz, 2H), 0.97 (q, J=3.7 Hz, 2H). MS (ESI+) m/z 509 (M+H)$^+$.

Example GI-58

1-{5-methyl-2-[(propan-2-yl)oxy]pyridin-3-yl}-N-(2-methylquinoline-5-sulfonyl)cyclopropane-1-carboxamide Into a vial, a solution of 1-(2-isopropoxy-5-methyl-3-pyridyl)cyclopropanecarboxylic acid (60 mg, 0.255 mmol), 1-(3-dimethylaminopropyl)-3-ethylcarbodiimide hydrochloride (CAS #25952-53-8) (59 mg, 0.306 mmol) and 4-dimethylaminopyridine (CAS #1122-58-3) (37 mg, 0.306 mmol) in anhydrous dichloromethane (2 mL) was added to 2-methylquinoline-5-sulfonamide (56 mg, 0.255 mmol). The reaction mixture was stirred at reflux for 4 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.02 (dd, J=8.9, 0.9 Hz, 1H), 8.16 (dd, J=7.3, 1.2 Hz, 1H), 8.01 (dt, J=8.5, 1.1 Hz, 1H), 7.73-7.68 (m, 1H), 7.67 (dd, J=2.4, 0.8 Hz, 1H), 7.44 (d, J=8.9 Hz, 1H), 7.29 (dd, J=2.4, 0.7 Hz, 1H), 4.86 (h, J=6.1 Hz, 5H), 2.72 (s, 3H), 2.17

(d, J=0.7 Hz, 3H), 1.44 (q, J=3.9 Hz, 2H), 0.90 (d, J=6.1 Hz, 6H), 0.80 (q, J=3.9 Hz, 2H). MS (ESI+) m/z 440 (M+H)$^+$.

Example GI-59

N-(1H-indole-4-sulfonyl)-1-{5-methyl-2-[(propan-2-yl)oxy]pyridin-3-yl}cyclopropane-1-carboxamide Into a vial, a solution of 1-(2-isopropoxy-5-methyl-3-pyridyl)cyclopropanecarboxylic acid (60 mg, 0.255 mmol), 1-(3-dimethylaminopropyl)-3-ethylcarbodiimide hydrochloride (CAS #25952-53-8) (59 mg, 0.306 mmol) and 4-dimethylaminopyridine (CAS #1122-58-3) (37 mg, 0.306 mmol) in anhydrous dichloromethane (2 mL) was added to 1H-indole-4-sulfonamide (56 mg, 0.255 mmol). The reaction mixture was stirred at reflux for 4 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.68 (dd, J=2.5, 1.0 Hz, 1H), 7.59 (dd, J=7.4, 0.9 Hz, 1H), 7.45 (dt, J=8.2, 0.9 Hz, 1H), 7.35-7.24 (m, 2H), 7.07 (dd, J=8.1, 7.4 Hz, 1H), 6.88 (dd, J=3.2, 0.9 Hz, 1H), 5.06 (hept, J=6.1 Hz, 1H), 2.17-2.13 (m, 3H), 1.15 (d, J=6.1 Hz, 6H), 1.07 (t, J=7.3 Hz, 2H), 0.85 (q, J=3.9 Hz, 2H). MS (ESI+) m/z 414 (M+H)$^+$.

Example GI-60

1-{5-cyclopropyl-2-[(propan-2-yl)oxy]pyridin-3-yl}-N-(2-methylquinoline-5-sulfonyl)cyclopropane-1-carboxamide Into a vial, a solution of 1-(5-cyclopropyl-2-isopropoxy-3-pyridyl)cyclopropanecarboxylic acid (60 mg, 0.23 mmol), 1-(3-dimethylaminopropyl)-3-ethylcarbodiimide hydrochloride (CAS #25952-53-8) (53 mg, 0.276 mmol) and 4-dimethylaminopyridine (CAS #1122-58-3) (34 mg, 0.276 mmol) in anhydrous dichloromethane (2 mL) was added to 2-methylquinoline-5-sulfonamide (51 mg, 0.23 mmol). The reaction mixture was stirred at reflux for 4 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.00 (dd, J=8.8, 0.9 Hz, 1H), 8.15 (dd, J=7.3, 1.2 Hz, 1H), 8.02 (dt, J=8.5, 1.1 Hz, 1H), 7.75-7.65 (m, 2H), 7.44 (d, J=8.8 Hz, 1H), 7.13 (d, J=2.5 Hz, 1H), 4.92-4.82 (m, 1H), 2.73 (s, 3H), 1.80 (tt, J=8.4, 5.1 Hz, 1H), 1.44 (q, J=3.9 Hz, 2H), 0.98-0.84 (m, 8H), 0.79 (q, J=3.9 Hz, 2H), 0.62-0.52 (m, 2H). MS (ESI+) m/z 466 (M+H)$^+$.

Example GI-61

1-{5-cyclopropyl-2-[(propan-2-yl)oxy]pyridin-3-yl}-N-(1H-indole-4-sulfonyl)cyclopropane-1-carboxamide Into a vial, a solution of 1-(5-cyclopropyl-2-isopropoxy-3-pyridyl)cyclopropanecarboxylic acid (60 mg, 0.23 mmol), 1-(3-dimethylaminopropyl)-3-ethylcarbodiimide hydrochloride (CAS #25952-53-8) (53 mg, 0.276 mmol) and 4-dimethylaminopyridine (CAS #1122-58-3) (34 mg, 0.276 mmol) in anhydrous dichloromethane (2 mL) was added to 1H-indole-4-sulfonamide (51 mg, 0.23 mmol). The reaction mixture was stirred at reflux for 4 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.72 (dd, J=2.4, 0.5 Hz, 1H), 7.59 (dd, J=7.5, 0.9 Hz, 1H), 7.50 (dt, J=8.1, 0.9 Hz, 1H), 7.31 (d, J=3.2 Hz, 1H), 7.19 (d, J=2.5 Hz, 1H), 7.12 (dd, J=8.1, 7.4 Hz, 1H), 6.88 (dd, J=3.2, 0.9 Hz, 1H), 5.06 (hept, J=6.1 Hz, 1H), 1.83 (tt, J=8.5, 5.2 Hz, 1H), 1.51 (q, J=3.8 Hz, 2H), 1.18-1.09 (m, 6H), 0.97-0.86 (m, 2H), 0.84 (q, J=3.9 Hz, 2H), 0.66-0.56 (m, 2H). MS (ESI+) m/z 440 (M+H)$^+$.

Example GI-62

1-{2-[(propan-2-yl)oxy]-5-(pyrrolidin-1-yl)pyridin-3-yl}-N-(quinoline-5-sulfonyl)cyclopropane-1-carboxamide Into a vial, a solution of 1-(2-isopropoxy-5-pyrrolidin-1-yl-3-pyridyl)cyclopropanecarboxylic acid (70 mg, 0.24 mmol), 1-(3-dimethylaminopropyl)-3-ethylcarbodiimide hydrochloride (CAS #25952-53-8) (55 mg, 0.288 mmol) and 4-dimethylaminopyridine (CAS #1122-58-3) (35 mg, 0.288 mmol) in anhydrous dichloromethane (2 mL) was added to quinoline-5-sulfonamide (CAS #415913-05-2) (50 mg, 0.24 mmol). The reaction mixture was stirred at reflux overnight. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.18 (ddd, J=8.7, 1.7, 0.9 Hz, 1H), 8.88 (dd, J=4.3, 1.7 Hz, 1H), 8.27 (dd, J=7.3, 1.2 Hz, 1H), 8.12 (dt, J=8.5, 1.1 Hz, 1H), 7.78 (dd, J=8.5, 7.3 Hz, 1H), 7.57 (dd, J=8.8, 4.3 Hz, 1H), 7.22 (d, J=3.0 Hz, 1H), 6.92 (d, J=3.0 Hz, 1H), 4.75 (h, J=6.1 Hz, 1H), 3.24-3.16 (m, 4H), 2.03-1.97 (m, 4H), 1.46 (q, J=3.8 Hz, 2H), 0.89 (d, J=6.1 Hz, 6H), 0.85 (q, J=3.9 Hz, 2H). MS (ESI+) m/z 481 (M+H)$^+$.

Example GI-63

N-(2-methylquinoline-5-sulfonyl)-1-{2-[(propan-2-yl)oxy]-5-(pyrrolidin-1-yl)pyridin-3-yl}cyclopropane-1-carboxamide Into a vial, a solution of 1-(2-isopropoxy-5-pyrrolidin-1-yl-3-pyridyl)cyclopropanecarboxylic acid (70 mg, 0.24 mmol), 1-(3-dimethylaminopropyl)-3-ethylcarbodiimide hydrochloride (CAS #25952-53-8) (55 mg, 0.288 mmol) and 4-dimethylaminopyridine (CAS #1122-58-3) (35 mg, 0.288 mmol) in anhydrous dichloromethane (2 mL) was added on 2-methylquinoline-5-sulfonamide (53 mg, 0.24 mmol). The reaction mixture was stirred at reflux overnight.

The reaction mixture was quenched with saturated aqueous NH₄Cl solution, and the aqueous layer was extracted with dichloromethane. The organic layers were combined, dried over MgSO₄, filtered and concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. $^1$H NMR (400 MHz, methanol-$d_4$) δ ppm 9.04 (dd, J=8.8, 0.8 Hz, 1H), 8.18 (dd, J=7.3, 1.2 Hz, 1H), 8.04 (dt, J=8.5, 1.1 Hz, 1H), 7.72 (dd, J=8.5, 7.3 Hz, 1H), 7.45 (d, J=8.9 Hz, 1H), 7.23 (d, J=3.0 Hz, 1H), 6.92 (d, J=3.0 Hz, 1H), 4.77 (h, J=6.1 Hz, 1H), 3.24-3.16 (m, 4H), 2.74 (s, 3H), 2.07-1.95 (m, 4H), 1.46 (q, J=3.8 Hz, 2H), 0.90 (d, J=6.1 Hz, 6H), 0.86 (q, J=3.9 Hz, 2H). MS (ESI+) m/z 495 (M+H)⁺.

Example GI-64

N-(1H-indole-4-sulfonyl)-1-{2-[(propan-2-yl)oxy]-5-(pyrrolidin-1-yl)pyridin-3-yl}cyclopropane-1-carboxamide Into a vial, a solution of 1-(2-isopropoxy-5-pyrrolidin-1-yl-3-pyridyl)cyclopropanecarboxylic acid (70 mg, 0.24 mmol), 1-(3-dimethylaminopropyl)-3-ethylcarbodiimide hydrochloride (CAS #25952-53-8) (55 mg, 0.288 mmol) and 4-dimethylaminopyridine (CAS #1122-58-3) (35 mg, 0.288 mmol) in anhydrous dichloromethane (2 mL) was added on 1H-indole-4-sulfonamide (47 mg, 0.24 mmol). The reaction mixture was stirred at reflux for 4 hours. The reaction mixture was quenched with saturated aqueous NH₄Cl solution, and the aqueous layer was extracted with dichloromethane. The organic layers were combined, dried over MgSO₄, filtered and concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. $^1$H NMR (400 MHz, methanol-$d_4$) δ ppm 7.64 (dd, J=7.5, 0.9 Hz, 1H), 7.52 (dt, J=8.1, 0.9 Hz, 1H), 7.32 (d, J=3.1 Hz, 1H), 7.26 (d, J=3.0 Hz, 1H), 7.13 (t, J=7.8 Hz, 1H), 6.97 (d, J=3.0 Hz, 1H), 6.89 (dd, J=3.1, 0.9 Hz, 1H), 5.20 (s, 1H), 4.59 (s, 2H), 3.50-3.41 (m, 1H), 3.23-3.19 (m, 4H), 3.16 (s, 3H), 3.13 (d, J=7.2 Hz, 1H), 3.10 (s, 2H), 2.07-1.97 (m, 5H), 1.97-1.87 (m, 1H), 1.49 (q, J=3.9 Hz, 2H), 1.15-1.05 (m, 8H), 0.88 (q, J=3.9 Hz, 2H). MS (ESI+) m/z 469 (M+H)⁺.

Example GI-65

1-{2,5-bis[(propan-2-yl)oxy]pyridin-3-yl}-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (92 mg, 0.48 mmol) and 4-dimethylaminopyridine (CAS #1122-58-3) (32 mg, 0.26 mmol) in anhydrous dichloromethane (2 mL), 1-(2,5-diisopropoxy-3-pyridyl)cyclopropanecarboxylic acid (69 mg, 0.24 mmol) was added and the mixture was stirred at ambient temperature for 10 minutes. Quinoline-5-sulfonamide (CAS #415913-05-2) (54 mg, 0.24 mmol) was added and the reaction mixture was stirred at reflux overnight. The reaction mixture was treated with water. The organic layer was separated on a phase separator and was concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. $^1$H NMR (400 MHz, methanol-$d_4$) δ ppm 9.16 (ddd, J=8.7, 1.7, 0.9 Hz, 1H), 8.88 (dd, J=4.3, 1.7 Hz, 1H), 8.25 (dd, J=7.3, 1.3 Hz, 1H), 8.13 (dt, J=8.5, 1.1 Hz, 1H), 7.78 (dd, J=8.5, 7.3 Hz, 1H), 7.57 (dd, J=8.7, 4.3 Hz, 1H), 7.53 (d, J=3.0 Hz, 1H), 7.12 (d, J=3.0 Hz, 1H), 4.92-4.78 (m, 1H), 4.41 (hept, J=6.1 Hz, 1H), 1.45 (q, J=3.9 Hz, 2H), 1.26 (d, J=6.1 Hz, 6H), 0.92 (d, J=6.1 Hz, 6H), 0.84 (q, J=3.9 Hz, 2H). MS (ESI+) m/z 470 (M+H)⁺.

Example GI-66

1-{2,5-bis[(propan-2-yl)oxy]pyridin-3-yl}-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (92 mg, 0.48 mmol) and 4-dimethylaminopyridine (CAS #1122-58-3) (32 mg, 0.26 mmol) in anhydrous dichloromethane (2 mL), 1-(2,5-diisopropoxy-3-pyridyl)cyclopropanecarboxylic acid (69 mg, 0.24 mmol) was added and the mixture was stirred at ambient temperature for 10 minutes. 1H-Indole-4-sulfonamide (51 mg, 0.24 mmol) was added and the reaction mixture was stirred at reflux overnight. The reaction was treated with water. The organic layer was separated on a phase separator and was concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. $^1$H NMR (400 MHz, methanol-$d_4$) δ ppm 7.60 (d, J=7.4 Hz, 1H), 7.55 (d, J=2.9 Hz, 1H), 7.52-7.48 (m, 1H), 7.31 (d, J=3.1 Hz, 1H), 7.16 (d, J=2.9 Hz, 1H), 7.11 (t, J=7.7 Hz, 1H), 6.91-6.86 (m, 1H), 5.02 (dq, J=12.3, 6.2 Hz, 3H), 4.43 (hept, J=5.9, 5.5 Hz, 1H), 3.30 (s, 1H), 1.51 (q, J=3.8 Hz, 2H), 1.28 (d, J=6.1 Hz, 6H), 1.19-1.09 (m, 6H), 0.86 (q, J=3.8 Hz, 2H). MS (ESI+) m/z 458 (M+H)⁺.

Example GI-67

1-{2,5-bis[(propan-2-yl)oxy]pyridin-3-yl}-N-(2-methylquinoline-5-sulfonyl)cyclopropane-1-carboxamide Into a vial, a solution of 1-(3-dimethylaminopropyl)-3-ethylcarbodiimide hydrochloride (CAS #25952-53-8) (92 mg, 0.48 mmol) and 4-dimethylaminopyridine (CAS #1122-58-3) (32 mg, 0.26 mmol) in anhydrous dichloromethane (2 mL), 1-(2,5-diisopropoxy-3-pyridyl)cyclopropanecarboxylic acid (69 mg, 0.24 mmol) was added and the mixture was stirred at ambient temperature for 10 minutes. 2-Methylquinoline-5-sulfonamide (58 mg, 0.24 mmol) was added and the reaction mixture was stirred at reflux overnight. The reaction was treated with water. The organic layer was separated on a phase separator and concentrated. The crude material was purified by reverse-phase HPLC Waters XBridge™ C18 5 µm OBD column, 30×100 mm, flow rate 50 mL/minute, H₂O+0.1% diethylamine/acetonitrile+0.1% diethylamine to give the title compound. $^1$H NMR (400 MHz, methanol-$d_4$) δ ppm 8.91 (dd, J=8.8, 0.9 Hz, 1H), 8.05 (dd, J=7.3, 1.2 Hz, 1H), 7.92 (dt, J=8.4, 1.1 Hz, 1H), 7.60 (dd, J=8.5, 7.3 Hz, 1H), 7.42 (d, J=2.9 Hz, 1H), 7.34 (d, J=8.9 Hz, 1H), 7.00 (d, J=3.0 Hz, 1H), 4.83-4.66 (m, 1H), 4.30 (hept, J=6.1 Hz, 1H), 2.62 (s, 3H), 1.35 (q, J=3.9 Hz, 2H), 1.15 (d, J=6.1 Hz, 6H), 0.81 (d, J=6.1 Hz, 6H), 0.72 (q, J=3.9 Hz, 2H). MS (ESI+) m/z 484 (M+H)⁺.

Example GI-68

1-[2-(2-methylpropoxy)-5-(pyrrolidin-1-yl)pyridin-3-yl]-N-(quinoline-5-sulfonyl)cyclopropane-1-carboxamide Into a vial, a solution of 1-(2-isobutoxy-5-pyrrolidin-1-yl-3-pyridyl)cyclopropanecarboxylic acid (44 mg, 0.144 mmol), 1-(3-dimethylaminopropyl)-3-ethylcarbodiimide hydrochloride (CAS #25952-53-8) (363 mg, 0.173 mmol) and 4-dimethylaminopyridine (CAS #1122-58-3) (21 mg, 0.173 mmol) in anhydrous dichloromethane (2 mL) was added to quinoline-5-sulfonamide (CAS #415913-05-2) (30 mg, 0.144 mmol). The reaction mixture was stirred at reflux overnight. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 8.97 (dd, J=4.3, 1.5 Hz, 1H), 8.93 (d, J=8.7 Hz, 1H), 8.44 (dd, J=7.4, 1.2 Hz, 1H), 8.31 (d, J=8.5 Hz, 1H), 7.90 (dd, J=8.5, 7.4 Hz, 1H), 7.61 (dd, J=8.7, 4.3 Hz, 1H), 7.32 (d, J=2.7 Hz, 1H), 6.96 (d, J=2.9 Hz, 1H), 3.41 (d, J=6.6 Hz, 2H), 3.24 (h, J=3.6 Hz, 4H), 2.08-1.95 (m, 4H), 1.40 (q, J=4.3 Hz, 2H), 1.18-1.08 (m, 1H), 1.01 (q, J=3.6, 2.9 Hz, 2H), 0.61 (d, J=6.7 Hz, 6H). MS (ESI+) m/z 495 (M+H)$^+$.

Example GI-69

1-[2-(2-methylpropoxy)-5-(pyrrolidin-1-yl)pyridin-3-yl]-N-(2-methylquinoline-5-sulfonyl)cyclopropane-1-carboxamide Into a vial, a solution of 1-(2-isobutoxy-5-pyrrolidin-1-yl-3-pyridyl)cyclopropanecarboxylic acid (44 mg, 0.144 mmol), 1-(3-dimethylaminopropyl)-3-ethylcarbodiimide hydrochloride (CAS #25952-53-8) (363 mg, 0.173 mmol) and 4-dimethylaminopyridine (CAS #1122-58-3) (21 mg, 0.173 mmol) in anhydrous dichloromethane (2 mL) was added to 2-methylquinoline-5-sulfonamide (32 mg, 0.144 mmol). The reaction mixture was stirred at reflux overnight. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 8.94 (dd, J=8.8, 0.8 Hz, 1H), 8.18 (dd, J=7.3, 1.2 Hz, 1H), 8.03 (dt, J=8.5, 1.1 Hz, 1H), 7.71 (dd, J=8.5, 7.3 Hz, 1H), 7.40 (d, J=8.9 Hz, 1H), 7.19 (d, J=2.9 Hz, 1H), 6.96 (d, J=3.0 Hz, 1H), 3.48 (d, J=6.6 Hz, 2H), 3.25-3.17 (m, 4H), 2.74 (s, 3H), 2.06-1.95 (m, 4H), 1.44 (q, J=3.8 Hz, 2H), 1.32 (dq, J=13.3, 6.7 Hz, 1H), 0.83 (q, J=3.8 Hz, 2H), 0.66 (d, J=6.7 Hz, 6H). MS (ESI+) m/z 509 (M+H)$^+$.

Example GI-70

N-(1H-indole-4-sulfonyl)-1-[2-(2-methylpropoxy)-5-(pyrrolidin-1-yl)pyridin-3-yl]cyclopropane-1-carboxamide Into a vial, a solution of 1-(2-isobutoxy-5-pyrrolidin-1-yl-3-pyridyl)cyclopropanecarboxylic acid (44 mg, 0.144 mmol), 1-(3-dimethylaminopropyl)-3-ethylcarbodiimide hydrochloride (CAS #25952-53-8) (363 mg, 0.173 mmol) and 4-dimethylaminopyridine (CAS #1122-58-3) (21 mg, 0.173 mmol) in anhydrous dichloromethane (2 mL) was added to 1H-indole-4-sulfonamide (32 mg, 0.144 mmol). The reaction mixture was stirred at reflux overnight. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 7.59 (dd, J=7.4, 0.9 Hz, 1H), 7.49 (dt, J=8.1, 1.0 Hz, 1H), 7.28 (d, J=3.1 Hz, 1H), 7.20 (d, J=2.9 Hz, 1H), 7.10 (t, J=7.8 Hz, 1H), 6.98 (d, J=3.0 Hz, 1H), 6.83 (dd, J=3.1, 0.9 Hz, 1H), 3.72 (d, J=6.6 Hz, 2H), 3.24-3.16 (m, 4H), 2.04-1.93 (m, 4H), 1.68 (dh, J=13.7, 6.9 Hz, 1H), 1.50 (q, J=3.8 Hz, 2H), 0.90-0.82 (m, 8H). MS (ESI+) m/z 483 (M+H)$^+$.

Example GI-71

1-{5-(dimethylamino)-2-[(propan-2-yl)oxy]pyridin-3-yl}-N-(quinoline-5-sulfonyl)cyclopropane-1-carboxamide Into a vial, a solution of 1-[5-(dimethylamino)-2-isopropoxy-3-pyridyl]cyclopropanecarboxylic acid (41 mg, 0.155 mmol), 1-(3-dimethylaminopropyl)-3-ethylcarbodiimide hydrochloride (CAS #25952-53-8) (36 mg, 0.186 mmol) and 4-dimethylaminopyridine (CAS #1122-58-3) (23 mg, 0.186 mmol) in anhydrous dichloromethane (2 mL) was added to quinoline-5-sulfonamide (CAS #415913-05-2) (32 mg, 0.155 mmol). The reaction mixture was stirred at reflux overnight. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.17 (ddd, J=8.7, 1.7, 0.8 Hz, 1H), 8.87 (dd, J=4.3, 1.7 Hz, 1H), 8.25 (dd, J=7.3, 1.2 Hz, 1H), 8.11 (dt, J=8.5, 1.1 Hz, 1H), 7.77 (dd, J=8.5, 7.3 Hz, 1H), 7.57 (dd, J=8.7, 4.3 Hz, 1H), 7.42 (d, J=3.1 Hz, 1H), 7.14 (d, J=3.0 Hz, 1H), 4.79 (h, J=6.1 Hz, 1H), 2.81 (s, 6H), 1.46 (q, J=3.8 Hz, 2H), 0.89 (d, J=6.1 Hz, 6H), 0.84 (q, J=3.9 Hz, 2H). MS (ESI+) m/z 455 (M+H)$^+$.

Example GI-71

1-{5-(dimethylamino)-2-[(propan-2-yl)oxy]pyridin-3-yl}-N-(2-methylquinoline-5-sulfonyl)cyclopropane-1-carboxamide Into a vial, a solution of 1-[5-(dimethylamino)-2-isopropoxy-3-pyridyl]cyclopropanecarboxylic acid (41 mg, 0.155 mmol), 1-(3-dimethylaminopropyl)-3-ethylcarbodiimide hydrochloride (CAS #25952-53-8) (36 mg, 0.186 mmol) and 4-dimethylaminopyridine (CAS #1122-58-3) (23 mg, 0.186 mmol) in anhydrous dichloromethane (2 mL) was added to 2-methylquinoline-5-sulfonamide (32 mg, 0.155 mmol). The reaction mixture was stirred at reflux overnight. The reaction mixture was quenched with saturated aqueous $NH_4Cl$ solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.02 (dd, J=8.8, 0.9 Hz, 1H), 8.17 (dd, J=7.3, 1.2 Hz, 1H), 8.01 (dt, J=8.5, 1.0 Hz, 1H), 7.70 (dd, J=8.5, 7.3 Hz, 1H), 7.47-7.38 (m, 2H), 7.13 (d, J=3.1 Hz, 1H), 4.79 (p, J=6.1 Hz, 2H), 2.80 (s, 6H), 2.73 (s, 3H), 1.44 (q, J=3.8 Hz, 2H), 0.88 (d, J=6.1 Hz, 6H), 0.82 (q, J=3.9 Hz, 2H). MS (ESI+) m/z 469 (M+H)$^+$.

Example GI-73

1-{5-(dimethylamino)-2-[(propan-2-yl)oxy]pyridin-3-yl}-N-(1H-indole-4-sulfonyl)cyclopropane-1-carboxamide Into a vial, a solution of 1-[5-(dimethylamino)-2-isopropoxy-3-pyridyl]cyclopropanecarboxylic acid (41 mg, 0.155 mmol), 1-(3-dimethylaminopropyl)-3-ethylcarbodiimide hydrochloride (CAS #25952-53-8) (36 mg, 0.186 mmol) and 4-dimethylaminopyridine (CAS #1122-58-3) (23 mg, 0.186 mmol) in anhydrous dichloromethane (2 mL) was added to 1H-indole-4-sulfonamide (32 mg, 0.155 mmol). The reaction mixture was stirred at reflux overnight. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.60 (dd, J=7.4, 0.9 Hz, 1H), 7.49 (dt, J=8.2, 0.9 Hz, 1H), 7.43 (d, J=3.0 Hz, 1H), 7.29 (d, J=3.1 Hz, 1H), 7.18 (d, J=3.1 Hz, 1H), 7.10 (dd, J=8.2, 7.4 Hz, 1H), 6.89 (dd, J=3.1, 0.9 Hz, 1H), 4.97 (h, J=6.1 Hz, 1H), 2.82 (s, 6H), 1.50 (q, J=3.9 Hz, 2H), 1.18 (t, J=7.3 Hz, 6H), 1.12 (d, J=6.1 Hz, 6H), 0.85 (q, J=3.9 Hz, 2H). MS (ESI+) m/z 443 (M+H)$^+$.

Example GI-74

1-{5-methoxy-2-[(propan-2-yl)oxy]pyridin-3-yl}-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (96 mg, 0.50 mmol) and 4-dimethylaminopyridine (CAS #1122-58-3) (33 mg, 0.27 mmol) in anhydrous dichloromethane (2 mL), 1-(2-isobutoxy-5-methoxy-3-pyridyl)cyclopropanecarboxylic acid (63 mg, 0.25 mmol) was added and the mixture was stirred at ambient temperature for 10 minutes. Quinoline-5-sulfonamide (CAS #415913-05-2) (52 mg, 0.25 mmol) was added and the reaction mixture was stirred at reflux overnight. The reaction was treated with water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.18 (ddd, J=8.7, 1.7, 0.9 Hz, 1H), 8.90 (dd, J=4.3, 1.7 Hz, 1H), 8.26 (dd, J=7.3, 1.2 Hz, 1H), 8.13 (dt, J=8.5, 1.1 Hz, 1H), 7.78 (dd, J=8.5, 7.3 Hz, 1H), 7.61-7.54 (m, 2H), 7.14 (d, J=3.0 Hz, 1H), 4.85 (h, J=6.1 Hz, 1H), 3.77 (s, 3H), 1.47 (q, J=3.9 Hz, 2H), 0.92 (d, J=6.2 Hz, 6H), 0.85 (q, J=3.9 Hz, 2H). MS (ESI+) m/z 442 (M+H)$^+$.

Example GI-75

N-(1H-indole-4-sulfonyl)-1-{5-methoxy-2-[(propan-2-yl)oxy]pyridin-3-yl}cyclopropane-1-carboxamide Into a vial, to a solution of 1-(3-dimethylaminopropyl)-3-ethylcarbodiimide hydrochloride (CAS #25952-53-8) (96 mg, 0.50 mmol) and 4-dimethylaminopyridine (CAS #1122-58-3) (33 mg, 0.27 mmol) in anhydrous dichloromethane (2 mL), 1-(2-isobutoxy-5-methoxy-3-pyridyl)cyclopropanecarboxylic acid (63 mg, 0.25 mmol) was added and the mixture was stirred at ambient temperature for 10 minutes. 1H-Indole-4-sulfonamide (49 mg, 0.25 mmol) was added and the reaction mixture was stirred at reflux overnight. The reaction was treated with water. The organic layer was separated on a phase separator and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.61 (dd, J=7.4, 0.9 Hz, 1H), 7.55 (d, J=3.0 Hz, 1H), 7.47 (dt, J=8.1, 0.9 Hz, 1H), 7.30 (d, J=3.1 Hz, 1H), 7.17 (d, J=3.0 Hz, 1H), 7.09 (t, J=7.8 Hz, 1H), 6.90 (dd, J=3.1, 0.9 Hz, 1H), 5.04 (hept, J=6.1 Hz, 1H), 3.74 (s, 3H), 1.53 (q, J=3.9 Hz, 2H), 1.17 (d, J=6.2 Hz, 6H), 0.88 (q, J=3.9 Hz, 2H). MS (ESI+) m/z 430 (M+H)$^+$.

Example GI-76

1-{5-methoxy-2-[(propan-2-yl)oxy]pyridin-3-yl}-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (96 mg, 0.50 mmol) and 4-dimethylaminopyridine (CAS #1122-58-3) (33 mg, 0.27 mmol) in anhydrous dichloromethane (2 mL), 1-(2-isobutoxy-5-methoxy-3-pyridyl)cyclopropanecarboxylic acid (63 mg, 0.25 mmol) was added and the mixture was stirred at ambient temperature for 10 minutes. 2-Methylquinoline-5-sulfonamide (56 mg, 0.25 mmol) was added and the reaction mixture was stirred at reflux overnight. The reaction was treated with water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.02 (dd, J=8.8, 0.8 Hz, 1H), 8.16 (dd, J=7.3, 1.2 Hz, 1H), 8.02 (dt, J=8.5, 1.1 Hz, 1H), 7.70 (dd, J=8.5, 7.3 Hz, 1H), 7.54 (d, J=3.0 Hz, 1H), 7.44 (d, J=8.8 Hz, 1H), 7.12 (d, J=3.0 Hz, 1H), 4.84 (h, J=6.1 Hz, 4H), 3.75 (s, 3H), 2.72 (s, 3H), 1.45 (q, J=3.9 Hz, 2H), 0.90 (d, J=6.2 Hz, 6H), 0.83 (q, J=3.9 Hz, 2H). MS (ESI+) m/z 456 (M+H)$^+$.

Example GI-77

1-[5-methoxy-2-(2-methylpropoxy)pyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8)

(134 mg, 0.70 mmol) and 4-dimethylaminopyridine (CAS #1122-58-3) (47 mg, 0.38 mmol) in anhydrous dichloromethane (2 mL), 1-(2-isobutoxy-5-methoxy-3-pyridyl)cyclopropanecarboxylic acid (93 mg, 0.35 mmol) was added and the mixture was stirred at ambient temperature for 10 minutes. Quinoline-5-sulfonamide (CAS #415913-05-2) (72 mg, 0.35 mmol) was added and the reaction mixture was stirred at reflux overnight. The reaction was treated with water. The organic layer was separated on a phase separator and was concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 8.89-8.82 (m, 2H), 8.22 (d, J=7.3 Hz, 1H), 8.11 (d, J=8.5 Hz, 1H), 7.83-7.75 (m, 1H), 7.57-7.49 (m, 2H), 7.20 (d, J=4.4 Hz, 1H), 3.78 (s, 3H), 3.27 (d, J=6.5 Hz, 2H), 1.37 (d, J=6.2 Hz, 2H), 0.97 (dt, J=13.3, 6.6 Hz, 1H), 0.79-0.75 (m, 2H), 0.48 (d, J=6.8 Hz, 6H). MS (ESI+) m/z 456 (M+H)$^+$.

Example GI-78

N-(1H-indole-4-sulfonyl)-1-[5-methoxy-2-(2-methylpropoxy)pyridin-3-yl]cyclopropane-1-carboxamide Into a vial, to a solution of 1-(3-dimethylaminopropyl)-3-ethylcarbodiimide hydrochloride (CAS #25952-53-8) (134 mg, 0.70 mmol) and 4-dimethylaminopyridine (CAS #1122-58-3) (47 mg, 0.38 mmol) in anhydrous dichloromethane (2 mL), 1-(2-isobutoxy-5-methoxy-3-pyridyl)cyclopropanecarboxylic acid (93 mg, 0.35 mmol) was added and the mixture was stirred at ambient temperature for 10 minutes. 1H-Indole-4-sulfonamide (68 mg, 0.35 mmol) was added and the reaction mixture was stirred at reflux overnight. The reaction was treated with water. The organic layer was separated on a phase separator and was concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 7.57 (dd, J=7.4, 0.9 Hz, 1H), 7.54 (d, J=3.0 Hz, 1H), 7.48 (dt, J=8.1, 1.0 Hz, 1H), 7.28 (d, J=3.2 Hz, 1H), 7.19 (d, J=3.0 Hz, 1H), 7.08 (t, J=7.8 Hz, 1H), 6.83 (dd, J=3.2, 0.9 Hz, 1H), 3.80 (d, J=6.6 Hz, 2H), 3.74 (s, 3H), 1.82-1.69 (m, J=6.7 Hz, 1H), 1.53 (q, J=3.8 Hz, 2H), 0.92-0.84 (m, 8H). MS (ESI+) m/z 444 (M+H)$^+$.

Example GI-79

1-[5-methoxy-2-(2-methylpropoxy)pyridin-3-yl]-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (134 mg, 0.70 mmol) and 4-dimethylaminopyridine (CAS #1122-58-3) (47 mg, 0.38 mmol) in anhydrous dichloromethane (2 mL) 1-(2-isobutoxy-5-methoxy-3-pyridyl)cyclopropanecarboxylic acid (93 mg, 0.35 mmol) was added and the mixture was stirred at ambient temperature for 10 minutes. 2-Methylquinoline-5-sulfonamide (77 mg, 0.35 mmol) was added and the reaction mixture was stirred at reflux overnight. The reaction was treated with water. The organic layer was separated on a phase separator and was concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 8.94 (dd, J=8.8, 0.8 Hz, 1H), 8.17 (dd, J=7.3, 1.2 Hz, 1H), 8.04 (dt, J=8.5, 1.1 Hz, 1H), 7.71 (dd, J=8.5, 7.3 Hz, 1H), 7.54 (d, J=3.0 Hz, 1H), 7.42 (d, J=8.9 Hz, 1H), 7.16 (d, J=3.0 Hz, 1H), 3.77 (s, 3H), 3.53 (d, J=6.6 Hz, 2H), 2.74 (s, 3H), 1.44 (q, J=3.9 Hz, 2H), 1.35 (dp, J=13.3, 6.6 Hz, 1H), 0.84 (q, J=3.9 Hz, 2H), 0.68 (d, J=6.7 Hz, 6H). MS (ESI+) m/z 470 (M+H)$^+$.

Example GI-80

1-{6-methyl-2-[(propan-2-yl)oxy]pyridin-3-yl}-N-(quinoline-5-sulfonyl)cyclopropane-1-carboxamide To a solution of 1-(2-isopropoxy-6-methyl-3-pyridyl)cyclopropanecarboxylic acid (80 mg, 0.34 mmol) in anhydrous dichloromethane (3 mL), 1-(3-dimethylaminopropyl)-3-ethylcarbodiimide hydrochloride (CAS #25952-53-8) (130 mg, 0.68 mmol) and 4-dimethylaminopyridine (CAS #1122-58-3) (42 mg, 0.34 mmol) were added, followed by quinoline-5-sulfonamide (CAS #415913-05-2) (64 mg, 0.306 mmol). The reaction mixture was stirred at reflux for 2 hours. The reaction mixture was quenched with saturated aqueous $NH_4Cl$ solution. The organic layer was separated on a phase separator and was concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, chloroform-d) δ ppm 8.97 (dd, J=4.2, 1.6 Hz, 1H), 8.81 (ddd, J=8.7, 1.6, 0.9 Hz, 1H), 8.47 (dd, J=7.5, 1.3 Hz, 1H), 8.35 (d, J=8.5 Hz, 1H), 7.81 (t, J=8.0 Hz, 1H), 7.45 (dd, J=8.8, 4.2 Hz, 1H), 7.25 (d, J=7.3 Hz, 1H), 6.64-6.57 (m, 1H), 5.38 (p, J=6.1 Hz, 1H), 2.41 (s, 3H), 1.43 (q, J=4.3 Hz, 2H), 1.31-1.24 (m, 7H), 0.90 (q, J=4.3 Hz, 2H). MS (ESI+) m/z 426 (M+H)$^+$.

Example GI-81

1-{6-methyl-2-[(propan-2-yl)oxy]pyridin-3-yl}-N-(2-methylquinoline-5-sulfonyl)cyclopropane-1-carboxamide To a solution of 1-(2-isopropoxy-6-methyl-3-pyridyl)cyclopropanecarboxylic acid (80 mg, 0.34 mmol) in anhydrous dichloromethane (3 mL), 1-(3-dimethylaminopropyl)-3-ethylcarbodiimide hydrochloride (CAS #25952-53-8) (130 mg, 0.68 mmol) and 4-dimethylaminopyridine (CAS #1122-58-3) (42 mg, 0.34 mmol) were added, followed by 2-methylquinoline-5-sulfonamide (68 mg, 0.306 mmol). The reaction mixture was stirred at reflux for 2 hours. The reaction mixture was quenched with saturated aqueous $NH_4Cl$ solution. The organic layer was separated on a phase separator and concentrated. The crude material was purified by reverse-phase HPLC Waters XBridge™ C18 5 μm OBD column, 30×100 mm, flow rate 50 mL/minute, $H_2O$+0.1% formic acid/acetonitrile+0.1% formic acid to give the title compound. $^1$H NMR (400 MHz, chloroform-d) δ ppm 8.70 (dd, J=8.8, 0.9 Hz, 1H), 8.39 (dd, J=7.5, 1.2 Hz, 1H), 8.27 (dt, J=8.5, 1.1 Hz, 1H), 7.77 (dd, J=8.5, 7.5 Hz, 1H), 7.34 (d, J=8.9 Hz, 1H), 7.29 (d, J=7.4 Hz, 2H), 6.67 (dd, J=7.4, 0.7 Hz, 1H), 5.42 (hept, J=6.2 Hz, 1H), 2.76 (s, 3H), 2.47 (s, 3H), 1.48-1.41 (m, 2H), 1.30 (d, J=6.2 Hz, 6H), 0.95-0.87 (m, 2H). MS (ESI+) m/z 440 (M+H)$^+$.

Example GI-82

N-(1H-indole-4-sulfonyl)-1-{6-methyl-2-[(propan-2-yl)oxy]pyridin-3-yl}cyclopropane-1-carboxamide To a solution of 1-(2-isopropoxy-6-methyl-3-pyridyl)cyclopropanecarboxylic acid (80 mg, 0.34 mmol) in anhydrous dichloromethane (3 mL), 1-(3-dimethylaminopropyl)-3-ethylcarbodiimide hydrochloride (CAS #25952-53-8) (130 mg, 0.68 mmol) and 4-dimethylaminopyridine (CAS #1122-58-3) (42 mg, 0.34 mmol) were added, followed by 1H-indole-4-sulfonamide (60 mg, 0.306 mmol). The reaction mixture was stirred at reflux for 2 hours. The reaction mixture was quenched with saturated aqueous NH$_4$Cl solution. The organic layer was separated on a phase separator and concentrated. The crude material was purified by reverse-phase HPLC Waters XBridge™ C18 5 µm OBD column, 30×100 mm, flow rate 50 mL/minute, H$_2$O+0.1% formic acid/acetonitrile+0.1% formic acid to give the title compound. $^1$H NMR (400 MHz, chloroform-d) δ ppm 8.61 (s, 1H), 8.50 (s, 1H), 7.88 (dd, J=7.6, 0.9 Hz, 1H), 7.60 (dt, J=8.1, 0.9 Hz, 1H), 7.37-7.31 (m, 2H), 7.26 (d, J=15.8 Hz, 1H), 6.84 (ddd, J=3.2, 2.0, 0.9 Hz, 1H), 5.41 (hept, J=6.2 Hz, 1H), 2.46 (s, 3H), 1.47 (q, J=4.2 Hz, 2H), 1.30 (d, J=6.2 Hz, 6H), 0.91 (q, J=4.3 Hz, 2H). MS (ESI+) m/z 414 (M+H)$^+$.

Example GI-83

1-{5-(azetidin-1-yl)-2-[(propan-2-yl)oxy]pyridin-3-yl}-N-(quinoline-5-sulfonyl)cyclopropane-1-carboxamide Into a vial, a solution of 1-[5-(azetidin-1-yl)-2-isopropoxy-3-pyridyl]cyclopropanecarboxylic acid (60 mg, 0.217 mmol), 1-(3-dimethylaminopropyl)-3-ethylcarbodiimide hydrochloride (CAS #25952-53-8) (50 mg, 0.26 mmol) and 4-dimethylaminopyridine (CAS #1122-58-3) (32 mg, 0.26 mmol) in anhydrous dichloromethane (2 mL) was added on quinoline-5-sulfonamide (CAS #415913-05-2) (45 mg, 0.217 mmol). The reaction mixture was stirred at reflux for 3 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound with N,N-dimethylaminopyridine. The compound was dissolved in ethyl acetate and washed with saturated aqueous NH$_4$Cl solution (3 times), dried over Na$_2$SO$_4$, filtered and concentrated to give the title compound. $^1$H NMR (400 MHz, methanol-d$_4$) δ ppm 9.06 (ddd, J=8.8, 1.6, 0.9 Hz, 1H), 8.99 (dd, J=4.3, 1.6 Hz, 1H), 8.47 (dd, J=7.5, 1.2 Hz, 1H), 8.34 (dt, J=8.5, 1.1 Hz, 1H), 7.93 (dd, J=8.5, 7.4 Hz, 1H), 7.66 (dd, J=8.8, 4.3 Hz, 1H), 7.31 (d, J=2.9 Hz, 1H), 6.80 (d, J=2.9 Hz, 1H), 4.92 ((h, J=6.1 Hz, 1H), 3.86 (t, J=7.2 Hz, 4H), 2.45-2.34 (m, 2H), 1.39-1.31 (m, 2H), 1.04-0.96 (m, 8H). MS (ESI+) m/z 467 (M+H)$^+$.

Example GI-84

1-{5-(azetidin-1-yl)-2-[(propan-2-yl)oxy]pyridin-3-yl}-N-(2-methylquinoline-5-sulfonyl)cyclopropane-1-carboxamide Into a vial, a solution of 1-[5-(azetidin-1-yl)-2-isopropoxy-3-pyridyl]cyclopropanecarboxylic acid (60 mg, 0.217 mmol), 1-(3-dimethylaminopropyl)-3-ethylcarbodiimide hydrochloride (CAS #25952-53-8) (50 mg, 0.26 mmol) and 4-dimethylaminopyridine (CAS #1122-58-3) (32 mg, 0.26 mmol) in anhydrous dichloromethane (2 mL) was added to 2-methylquinoline-5-sulfonamide (48 mg, 0.217 mmol). The reaction mixture was stirred at reflux for 3 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound with N,N-dimethylaminopyridine. The compound was dissolved in ethyl acetate and washed with saturated aqueous NH$_4$Cl solution (3 times), dried over Na$_2$SO$_4$, filtered and concentrated to give the title compound. $^1$H NMR (400 MHz, methanol-d$_4$) δ ppm 8.96-8.89 (m, 1H), 8.37 (dd, J=7.5, 1.2 Hz, 1H), 8.24 (dt, J=8.5, 1.1 Hz, 1H), 7.87 (dd, J=8.5, 7.5 Hz, 1H), 7.55 (d, J=8.9 Hz, 1H), 7.31 (d, J=2.9 Hz, 1H), 6.80 (d, J=2.9 Hz, 1H), 4.92 ((h, J=6.1 Hz, 1H), 3.86 (t, J=7.2 Hz, 4H), 2.78 (s, 3H), 2.45-2.34 (m, 2H), 1.40-1.32 (m, 2H), 1.01 (d, J=6.2 Hz, 8H). MS (ESI+) m/z 481 (M+H)$^+$.

Example GI-85

1-{5-(azetidin-1-yl)-2-[(propan-2-yl)oxy]pyridin-3-yl}-N-(1H-indole-4-sulfonyl)cyclopropane-1-carboxamide Into a vial, a solution of 1-[5-(azetidin-1-yl)-2-isopropoxy-3-pyridyl]cyclopropanecarboxylic acid (60 mg, 0.217 mmol), 1-(3-dimethylaminopropyl)-3-ethylcarbodiimide hydrochloride (CAS #25952-53-8) (50 mg, 0.26 mmol) and 4-dimethylaminopyridine (CAS #1122-58-3) (32 mg, 0.26 mmol) in anhydrous dichloromethane (2 mL) was added on 1H-indole-4-sulfonamide (42 mg, 0.217 mmol). The reaction mixture was stirred at reflux for 3 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound with N,N-dimethylaminopyridine. The compound was dissolved in ethyl acetate and washed with saturated aqueous NH$_4$Cl solution (3 times), dried over Na$_2$SO$_4$, filtered and concentrated to give the title compound. $^1$H NMR (400 MHz, methanol-d$_4$) δ ppm 7.76 (dd, J=7.6, 0.9 Hz, 1H), 7.70 (dt, J=8.2, 1.0 Hz, 1H), 7.44 (d, J=3.2 Hz, 1H), 7.32 (d, J=2.9 Hz, 1H), 7.24 (t, J=7.9 Hz, 1H), 6.84-6.76 (m, 2H), 5.04 (p, J=6.1 Hz, 1H), 3.85 (t, J=7.2 Hz, 4H), 2.39 (p, J=7.2 Hz, 2H), 1.41-1.33 (m, 2H), 1.12 (d, J=6.1 Hz, 6H), 0.98 (q, J=4.5 Hz, 2H). MS (ESI+) m/z 455 (M+H)$^+$.

Example GI-86

1-{6-(2-methylpropoxy)-3-[(propan-2-yl)oxy]pyridin-2-yl}-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (53 mg, 0.28 mmol) and 4-dimethylaminopyridine (CAS #1122-

58-3) (18 mg, 0.15 mmol) in anhydrous dichloromethane (2 mL), 1-(6-isobutoxy-3-isopropoxy-2-pyridyl)cyclopropanecarboxylic acid (41 mg, 0.14 mmol) was added and the mixture was stirred at ambient temperature for 10 minutes. Quinoline-5-sulfonamide (CAS #415913-05-2) (29 mg, 0.14 mmol) was added and the reaction mixture was stirred at reflux overnight. The reaction mixture was quenched with aqueous HCl (1N, 280 µL, 0.28 mmol) and water. The organic layer was separated on a phase separator and was concentrated. The crude material was purified by reverse-phase HPLC Waters XBridge™ C18 5 µm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.23 (ddd, J=8.8, 1.7, 0.9 Hz, 1H), 8.88 (dd, J=4.3, 1.6 Hz, 1H), 8.31 (dd, J=7.3, 1.3 Hz, 1H), 8.12 (dt, J=8.5, 1.1 Hz, 1H), 7.78 (dd, J=8.5, 7.3 Hz, 1H), 7.59 (dd, J=8.7, 4.3 Hz, 1H), 7.14 (d, J=8.8 Hz, 1H), 6.52 (d, J=8.7 Hz, 1H), 4.16 (hept, J=6.1 Hz, 1H), 3.91 (d, J=6.6 Hz, 2H), 2.09-1.95 (m, 1H), 1.42 (q, J=3.8 Hz, 2H), 1.04 (q, J=3.8 Hz, 2H), 1.00 (d, J=6.8 Hz, 6H), 0.86 (d, J=6.0 Hz, 6H). MS (ESI+) m/z 484 (M+H)$^+$.

Example GI-87

1-[2-(cyclopropylmethoxy)-5-methoxypyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (134 mg, 0.70 mmol) and 4-dimethylaminopyridine (CAS #1122-58-3) (47 mg, 0.38 mmol) in anhydrous dichloromethane (2 mL), 1-[2-(cyclopropylmethoxy)-5-methoxy-3-pyridyl]cyclopropanecarboxylic acid (92 mg, 0.35 mmol) was added and the mixture was stirred at ambient temperature for 10 minutes. Quinoline-5-sulfonamide (CAS #415913-05-2) (72 mg, 0.35 mmol) was added and the reaction mixture was stirred at reflux overnight. The reaction mixture was quenched with aqueous HCl (1N, 700 µL, 0.70 mmol) and water. The organic layer was separated on a phase separator and was concentrated. The crude material was purified by reverse-phase HPLC Waters XBridge™ C18 5 µm OBD column, 30×100 mm, flow rate 50 mL/minute, $H_2O$+0.1% formic acid/acetonitrile+0.1% formic acid to give the title compound. $^1$H NMR (400 MHz, methanol-$d_4$) δ ppm 9.10 (ddd, J=8.7, 1.7, 0.9 Hz, 1H), 8.86 (dd, J=4.3, 1.7 Hz, 1H), 8.28 (dd, J=7.3, 1.2 Hz, 1H), 8.11 (dt, J=8.5, 1.1 Hz, 1H), 7.77 (dd, J=8.5, 7.3 Hz, 1H), 7.58-7.50 (m, 2H), 7.16 (d, J=3.0 Hz, 1H), 3.78 (s, 3H), 3.69 (d, J=6.3 Hz, 2H), 1.41 (q, J=3.9 Hz, 2H), 0.82 (q, J=3.9 Hz, 2H), 0.74-0.62 (m, 1H), 0.27-0.16 (m, 2H), −0.01-0.03 (m, 2H). MS (ESI+) m/z 454 (M+H)$^+$.

Example GI-88

1-[2-(cyclopropylmethoxy)-5-methoxypyridin-3-yl]-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (134 mg, 0.70 mmol) and 4-dimethylaminopyridine (CAS #1122-58-3) (47 mg, 0.38 mmol) in anhydrous dichloromethane (2 mL), 1-[2-(cyclopropylmethoxy)-5-methoxy-3-pyridyl]cyclopropanecarboxylic acid (92 mg, 0.35 mmol) was added and the mixture was stirred at ambient temperature for 10 minutes. 1H-Indole-4-sulfonamide (68 mg, 0.35 mmol) was added and the reaction mixture was stirred at reflux overnight. The reaction mixture was quenched with aqueous HCl (1N, 700 µL, 0.70 mmol) and water. The organic layer was separated on a phase separator and concentrated. The crude material was purified by reverse-phase HPLC Waters XBridge™ C18 5 µm OBD column, 30×100 mm, flow rate 50 mL/minute, $H_2O$+0.1% formic acid/acetonitrile+0.1% formic acid to give the title compound. $^1$H NMR (400 MHz, methanol-$d_4$) δ ppm 7.63 (dd, J=7.5, 0.9 Hz, 1H), 7.54 (d, J=3.0 Hz, 1H), 7.49 (dt, J=8.1, 1.0 Hz, 1H), 7.29 (d, J=3.1 Hz, 1H), 7.19 (d, J=3.0 Hz, 1H), 7.12 (t, J=7.8 Hz, 1H), 6.85 (dd, J=3.2, 0.9 Hz, 1H), 3.89 (d, J=6.6 Hz, 2H), 3.78 (s, 3H), 1.49 (q, J=3.9 Hz, 2H), 1.01-0.89 (m, 1H), 0.86 (q, J=3.9 Hz, 2H), 0.43-0.32 (m, 2H), 0.18 (dt, J=6.1, 4.4 Hz, 2H). MS (ESI+) m/z 442 (M+H)$^+$.

Example GI-89

N-(1H-indole-4-sulfonyl)-1-{6-(2-methylpropoxy)-3-[(propan-2-yl)oxy]pyridin-2-yl}cyclopropane-1-carboxamide Into a vial, to a solution of 1-(3-dimethylaminopropyl)-3-ethylcarbodiimide hydrochloride (CAS #25952-53-8) (53 mg, 0.28 mmol) and 4-dimethylaminopyridine (CAS #1122-58-3) (18 mg, 0.15 mmol) in anhydrous dichloromethane (2 mL), 1-(6-isobutoxy-2-isopropoxy-2-pyridyl)cyclopropanecarboxylic acid (41 mg, 0.14 mmol) was added and the mixture was stirred at ambient temperature for 10 minutes. 1H-Indole-4-sulfonamide (27 mg, 0.14 mmol) was added and the reaction mixture was stirred at reflux overnight. The reaction mixture was quenched with aqueous HCl (1N, 280 µL, 0.28 mmol) and water. The organic layer was separated on a phase separator and concentrated. The crude material was purified by reverse-phase HPLC Waters XBridge™ C18 5 µm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 7.69 (d, J=7.4 Hz, 1H), 7.54 (d, J=8.1 Hz, 1H), 7.33 (d, J=3.2 Hz, 1H), 7.22 (d, J=8.8 Hz, 1H), 7.15 (t, J=7.8 Hz, 1H), 6.92 (dd, J=3.2, 0.9 Hz, 1H), 6.57 (d, J=8.7 Hz, 1H), 4.32 (hept, J=6.1 Hz, 1H), 3.95 (d, J=6.6 Hz, 2H), 2.11-1.96 (m, 1H), 1.45-1.40 (m, 2H), 1.13-1.09 (m, 2H), 1.08 (d, J=6.1 Hz, 6H), 1.01 (d, J=6.7 Hz, 6H). MS (ESI+) m/z 472 (M+H)$^+$.

Example GI-90

1-{6-(2-methylpropoxy)-3-[(propan-2-yl)oxy]pyridin-2-yl}-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (53 mg, 0.28 mmol) and 4-dimethylaminopyridine (CAS #1122-58-3) (18 mg, 0.15 mmol) in anhydrous dichloromethane (2 mL), 1-(6-isobutoxyd-3-isopropoxy-2-pyridyl)cyclopropanecarboxylic acid (41 mg, 0.14 mmol) was added and the mixture was stirred at ambient temperature for 10 minutes. 2-Methylquinoline-5-sulfonamide (31 mg, 0.14 mmol) was added and the reaction mixture was stirred at reflux overnight. The reaction mixture was quenched with aqueous HCl (1N, 280 µL, 0.28 mmol) and water. The organic layer was separated on a phase separator and was concentrated. The crude material was purified by reverse-phase HPLC Waters XBridge™ C18 5 µm OBD column, 30×100 mm, flow rate 50 mL/minute, $H_2O$+0.1% diethylamine/acetonitrile+0.1% diethylamine to give the title compound. $^1$H NMR (400 MHz, methanol-d$_4$) δ ppm 9.10 (dd, J=8.9, 0.9 Hz, 1H), 8.23 (dd, J=7.3, 1.3 Hz, 1H), 8.03 (dt, J=8.4, 1.0 Hz, 1H), 7.72 (dd, J=8.5, 7.3 Hz, 1H), 7.48 (d, J=8.9 Hz, 1H), 7.14 (d, J=8.8 Hz, 1H), 6.52 (d, J=8.8 Hz, 1H), 4.18 (hept, J=6.0 Hz, 1H), 3.91 (d, J=6.6 Hz, 2H), 2.75 (s, 3H), 2.08-1.95 (m, 1H), 1.42 (q, J=3.8 Hz, 2H), 1.04 (q, J=3.8 Hz, 2H), 1.00 (d, J=6.7 Hz, 6H), 0.88 (d, J=6.0 Hz, 6H). MS (ESI+) m/z 498 (M+H)$^+$.

Example GI-91

1-[5-(cyclopropylmethoxy)-2-methoxypyridin-4-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (77 mg, 0.40 mmol) and 4-dimethylaminopyridine (CAS #1122-58-3) (26 mg, 0.22 mmol) in anhydrous dichloromethane (2 mL), 1-[5-(cyclopropylmethoxy)-2-methoxy-4-pyridyl]cyclopropanecarboxylic acid (53 mg, 0.20) was added and the mixture was stirred at ambient temperature for 10 minutes. Quinoline-5-sulfonamide (CAS #415913-05-2) (42 mg, 0.20 mmol) was added and the reaction mixture was stirred at reflux overnight. The reaction mixture was quenched with aqueous HCl 1N (400 µL, 0.4 mmol) and water. The organic layer was separated on a phase separator and was concentrated. The crude material was purified by reverse-phase HPLC Waters XBridge™ C18 5 OBD column, 30×100 mm, flow rate 50 mL/minute, H$_2$O+0.1% formic acid/acetonitrile+0.1% formic acid to give the compound with impurities. The residue was purified by flash chromatography on silica gel (10 g ultra Biotage®) eluting with a gradient of 0-3% methanol in dichloromethane to give the title compound. $^1$H NMR (400 MHz, methanol-d$_4$) δ ppm 9.03-8.96 (m, 2H), 8.47 (dd, J=7.5, 1.2 Hz, 1H), 8.35 (d, J=8.5 Hz, 1H), 7.93 (dd, J=8.5, 7.4 Hz, 1H), 7.67 (dd, J=8.7, 4.4 Hz, 1H), 7.58 (s, 1H), 6.66 (s, 1H), 5.49 (s, 1H), 3.87 (s, 3H), 3.41 (d, J=6.4 Hz, 2H), 1.39 (q, J=4.5 Hz, 2H), 1.06 (q, J=4.5 Hz, 2H), 0.30-0.19 (m, 2H), −0.05-0.02 (m, 2H). MS (ESI+) m/z 454 (M+H)$^+$.

Example GI-92

1-[2-(cyclopropylmethoxy)-5-methoxypyridin-3-yl]-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (134 mg, 0.70 mmol) and 4-dimethylaminopyridine (CAS #1122-58-3) (47 mg, 0.38 mmol) in anhydrous dichloromethane (2 mL), 1-[2-(cyclopropylmethoxy)-5-methoxy-3-pyridyl]cyclopropanecarboxylic acid (92 mg, 0.35 mmol) was added and the mixture was stirred at ambient temperature for 10 minutes. 2-Methylquinoline-5-sulfonamide (77 mg, 0.35 mmol) was added and the reaction mixture was stirred at reflux overnight. The reaction mixture was quenched with aqueous HCl (1N, 700 µL, 0.70 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% formic acid/acetonitrile+0.1% formic acid to give the title compound. $^1$H NMR (400 MHz, DMSO-d$_6$) δ ppm 8.84 (d, J=8.9 Hz, 1H), 8.22 (d, J=7.9 Hz, 2H), 7.87 (t, J=7.9 Hz, 1H), 7.75 (d, J=3.0 Hz, 1H), 7.59 (d, J=8.9 Hz, 1H), 7.20 (d, J=3.0 Hz, 1H), 3.78 (s, 3H), 3.76 (d, J=6.4 Hz, 2H), 2.71 (s, 3H), 1.27 (q, J=4.3 Hz, 2H), 1.02 (s, 2H), 0.76-0.64 (m, 1H), 0.26-0.19 (m, 2H), −0.02-0.07 (m, 2H). MS (ESI+) m/z 468 (M+H)$^+$.

Example GI-93

1-[5-(cyclopropylmethoxy)-2-methoxypyridin-4-yl]-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (77 mg, 0.40 mmol) and 4-dimethylaminopyridine (CAS #1122-58-3) (26 mg, 0.22 mmol) in anhydrous dichloromethane (2 mL), 1-[5-(cyclopropylmethoxy)-2-methoxy-4-pyridyl]cyclopropanecarboxylic acid (53 mg, 0.20) was added and the mixture was stirred at ambient temperature for 10 minutes. 2-Methylquinoline-5-sulfonamide (44 mg, 0.20 mmol) was added and the reaction mixture was stirred at reflux overnight. The reaction mixture was quenched with aqueous HCl (1N, 400 µL, 0.4 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the compound with N,N-dimethylaminopyridine. The residue was washed with saturated aqueous NH$_4$Cl solution and extracted with ethyl acetate. The organic layer was separated, dried over Na$_2$SO$_4$, filtered and concentrated to give the title compound. $^1$H NMR (400 MHz, methanol-d$_4$) δ ppm 9.03-8.96 (m, 2H), 8.47 (dd, J=7.5, 1.2 Hz, 1H), 8.35 (d, J=8.5 Hz, 1H), 7.93 (dd, J=8.5, 7.4 Hz, 1H), 7.67 (dd, J=8.7, 4.4 Hz, 1H), 7.58 (s, 1H), 6.66 (s, 1H), 5.49 (s, 1H), 3.87 (s, 3H), 3.41 (d, J=6.4 Hz, 2H), 1.39 (q, J=4.5 Hz, 2H), 1.06 (q, J=4.5 Hz, 2H), 0.30-0.19 (m, 2H), −0.05-0.02 (m, 2H). MS (ESI+) m/z 454 (M+H)$^+$.

Example GI-94

1-[5-cyclobutyl-2-(2-methoxyethoxy)pyridin-3-yl]-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (115 mg, 0.60 mmol) and 4-dimethylaminopyridine (CAS #1122-58-3) (40 mg, 0.33 mmol) in anhydrous dichloromethane (2 mL), 1-[5-cyclobutyl-2-(2-methoxyethoxy)-3-pyridyl]cyclopropanecarboxylic acid (87 mg, 0.30 mmol) was added and the mixture was stirred at ambient temperature for 10 minutes. 2-Methylquinoline-5-sulfonamide (66 mg, 0.30 mmol) was added and the reaction mixture was stirred at reflux for 2 hours. The reaction mixture was quenched with aqueous HCl (1N, 600 µL, 0.60 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 8.93 (d, J=8.8 Hz, 1H), 8.16 (dd, J=7.4, 1.2 Hz, 1H), 8.11 (dt, J=8.5, 1.1 Hz, 1H), 7.80 (dd, J=2.4, 0.8 Hz, 1H), 7.64 (dd, J=8.5, 7.3 Hz, 1H), 7.32 (d, J=8.8 Hz, 1H), 7.25 (d, J=2.4 Hz, 4H), 4.34-4.27 (m, 2H), 3.61-3.54 (m, 2H), 3.39 (d, J=8.2 Hz, 1H), 3.35 (s, 3H), 2.75 (s, 3H), 2.31-2.20 (m, 2H), 2.07-1.94 (m, 3H), 1.88-1.78 (m, 1H), 1.51 (q, J=3.9 Hz, 2H), 0.89 (q, J=3.9 Hz, 2H). MS (ESI+) m/z 496 (M+H)$^+$.

Example GI-95

1-[5-(cyclopropylmethoxy)-2-methoxypyridin-4-yl]-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (96 mg, 0.50 mmol) and 4-dimethylaminopyridine (CAS #1122-58-3) (33 mg, 0.27 mmol) in anhydrous dichloromethane (2 mL), 1-[5-(cyclopropylmethoxy)-2-methoxy-4-pyridyl]cyclopropanecarboxylic acid (66 mg, 0.25) was added and the mixture was stirred at ambient temperature for 10 minutes. 1H-Indol-4-sulfonamide (49 mg, 0.25 mmol) was added and the reaction mixture was stirred at reflux overnight. The reaction mixture was quenched with aqueous HCl (1N, 400 µL, 0.4 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.61 (dd, J=7.4, 0.9 Hz, 1H), 7.53 (s, 1H), 7.48 (dt, J=8.1, 0.9 Hz, 1H), 7.28 (d, J=3.1 Hz, 1H), 7.10 (t, J=7.8 Hz, 1H), 6.83 (dd, J=3.1, 0.9 Hz, 1H), 6.63 (s, 1H), 3.80 (s, 3H), 3.61 (d, J=6.5 Hz, 2H), 1.47 (q, J=4.0 Hz, 2H), 0.92-0.80 (m, 3H), 0.41-0.30 (m, 2H), 0.19-0.11 (m, 2H). MS (ESI+) m/z 442 (M+H)$^+$.

Example GI-96

1-[2-(cyclopropylmethoxy)-5-methylpyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (96 mg, 0.50 mmol) and 4-dimethylaminopyridine (CAS #1122-58-3) (33 mg, 0.27 mmol) in anhydrous dichloromethane (2 mL), 1-[2-(cyclopropylmethoxy)-5-methyl-3-pyridyl]cyclopropanecarboxylic acid (62 mg, 0.25 mmol) was added and the mixture was stirred at ambient temperature for 10 minutes. Quinoline-5-sulfonamide (CAS #415913-05-2) (52 mg, 0.25 mmol) was added and the reaction mixture was stirred at reflux for 2 hours. The reaction mixture was quenched with aqueous HCl (1N, 500 µL, 0.50 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.11 (ddd, J=8.7, 1.7, 0.9 Hz, 1H), 8.86 (dd, J=4.3, 1.7 Hz, 1H), 8.28 (dd, J=7.4, 1.3 Hz, 1H), 8.11 (dt, J=8.5, 1.1 Hz, 1H), 7.78 (dd, J=8.5, 7.3 Hz, 1H), 7.68 (dd, J=2.4, 0.9 Hz, 1H), 7.54 (dd, J=8.7, 4.3 Hz, 1H), 7.33 (dd, J=2.4, 0.6 Hz, 1H), 3.70 (d, J=6.3 Hz, 2H), 2.20 (t, J=0.7 Hz, 3H), 1.41 (q, J=3.9 Hz, 2H), 0.80 (q, J=3.9 Hz, 2H), 0.74-0.62 (m, 1H), 0.27-0.16 (m, 2H), 0.06-−0.04 (m, 2H). MS (ESI+) m/z 438 (M+H)$^+$.

Example GI-97

1-[2-(cyclopropylmethoxy)-5-methylpyridin-3-yl]-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (96 mg, 0.50 mmol) and 4-dimethylaminopyridine (CAS #1122-58-3) (33 mg, 0.27 mmol) in anhydrous dichloromethane (2 mL), 1-[2-(cyclopropylmethoxy)-5-methyl-3-pyridyl]cyclopropanecarboxylic acid (62 mg, 0.25 mmol) was added and the mixture was stirred at ambient temperature for 10 minutes. 1H-Indole-4-sulfonamide (49 mg, 0.25 mmol) was added and the reaction mixture was stirred at reflux for 2 hours. The reaction mixture was quenched with aqueous HCl (1N, 500 µL, 0.50 mmol) and water. The organic layer was separated on a phase separator and was concentrated. The crude material was purified by reverse-phase HPLC Waters XBridge™ C18 5 OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.68 (dd, J=2.4, 1.0 Hz, 1H), 7.62 (dd, J=7.5, 0.9 Hz, 1H), 7.49 (dt, J=8.1, 1.0 Hz, 1H), 7.38-7.33 (m, 1H), 7.29 (d, J=3.2 Hz, 1H), 7.11 (t, J=7.8 Hz, 1H), 6.83 (dd, J=3.1, 0.9 Hz, 1H), 3.89 (d, J=6.6 Hz, 2H), 2.20 (d, J=0.7 Hz, 3H), 1.48 (q, J=3.9 Hz, 2H), 1.00-0.88 (m, 1H), 0.84 (q, J=3.9 Hz, 2H), 0.42-0.32 (m, 2H), 0.22-0.14 (m, 2H). MS (ESI+) m/z 426 (M+H)$^+$.

Example GI-98

1-[5-cyclobutyl-2-(cyclopropylmethoxy)pyridin-3-yl]-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (88 mg, 0.46 mmol) and 4-dimethylaminopyridine (CAS #1122-58-3) (30 mg, 0.25 mmol) in anhydrous dichloromethane (2 mL), 1-[5-cyclobutyl-2-(cyclopropylmethoxy)-3-pyridyl]cyclopropanecarboxylic acid (66 mg, 0.23 mmol) was added and the mixture was stirred at ambient temperature for 10 minutes. 1H-Indole-4-sulfonamide (45 mg, 0.23 mmol) was added and the reaction mixture was stirred at reflux for 2 hours. The reaction mixture was quenched with aqueous HCl (1N, 460 µL, 0.46 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 8.51 (s, 1H), 7.96 (dd, J=2.4, 0.7 Hz, 1H), 7.89 (dd, J=7.6, 0.9 Hz, 1H), 7.62 (dt, J=8.0, 0.9 Hz, 1H), 7.37 (dd, J=2.4, 0.6 Hz, 1H), 7.34 (t, J=2.9 Hz, 1H), 7.29 (t, J=7.9 Hz, 1H), 6.83 (ddd, J=3.2, 2.1, 0.9 Hz, 1H), 4.10 (d, J=7.0 Hz, 2H), 3.46 (p, J=8.5 Hz, 1H), 2.40-2.29 (m, 2H), 2.15-2.05 (m, 2H), 1.92-1.82 (m, 2H), 1.54 (q, J=4.2 Hz, 2H), 1.10-1.01 (m, 1H), 0.97 (q, J=4.3 Hz, 2H), 0.51-0.42 (m, 2H), 0.22 (dt, J=6.1, 4.6 Hz, 2H). MS (ESI+) m/z 466 (M+H)$^+$.

Example GI-99

1-[5-cyclobutyl-2-(2-methoxyethoxy)pyridin-3-yl]-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (115 mg, 0.60 mmol) and 4-dimethylaminopyridine (CAS #1122-58-3) (40 mg, 0.33 mmol) in anhydrous dichloromethane (2 mL), 1-[5-cyclobutyl-2-(2-methoxyethoxy)-3-pyridyl]cyclopropanecarboxylic acid (87 mg, 0.30 mmol) was added and the mixture was stirred at ambient temperature for 10 minutes. 1H-Indole-4-sulfonamide (58 mg, 0.30 mmol) was added and the reaction mixture was stirred at reflux for 2 hours. The reaction mixture was quenched with aqueous HCl (1N, 600 μL, 0.60 mmol) and water. The organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.73 (dd, J=2.4, 0.7 Hz, 1H), 7.62 (dd, J=7.4, 0.9 Hz, 1H), 7.51 (dt, J=8.1, 0.9 Hz, 1H), 7.43 (dd, J=2.4, 0.6 Hz, 1H), 7.29 (d, J=3.1 Hz, 1H), 7.13 (t, J=7.8 Hz, 1H), 6.81 (dd, J=3.1, 0.9 Hz, 1H), 4.17-4.05 (m, 2H), 3.47 (p, J=8.5 Hz, 1H), 3.37-3.33 (m, 2H), 3.27 (s, 3H), 2.31 (dtd, J=10.5, 8.0, 2.4 Hz, 2H), 2.21-1.95 (m, 3H), 1.93-1.81 (m, 1H), 1.47 (q, J=3.9 Hz, 2H), 0.85 (q, J=3.9 Hz, 2H). MS (ESI+) m/z 470 (M+H)$^+$.

Example GI-100

1-[5-cyclobutyl-2-(cyclopropylmethoxy)pyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (88 mg, 0.46 mmol) and 4-dimethylaminopyridine (CAS #1122-58-3) (30 mg, 0.25 mmol) in anhydrous dichloromethane (2 mL), 1-[5-cyclobutyl-2-(cyclopropylmethoxy)-3-pyridyl]cyclopropanecarboxylic acid (66 mg, 0.23 mmol) was added and the mixture was stirred at ambient temperature for 10 minutes. Quinoline-5-sulfonamide (CAS #415913-05-2) (48 mg, 0.23 mmol) was added and the reaction mixture was stirred at reflux for 2 hours. The reaction mixture was quenched with aqueous HCl (1N, 460 μL, 0.46 mmol) and water. The organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 8.99 (d, J=8.7 Hz, 1H), 8.95 (dd, J=4.2, 1.7 Hz, 1H), 8.26 (ddd, J=16.8, 7.8, 1.2 Hz, 2H), 7.82 (dd, J=2.4, 0.8 Hz, 1H), 7.71 (dd, J=8.5, 7.3 Hz, 1H), 7.43 (dd, J=8.7, 4.2 Hz, 1H), 7.27 (d, J=2.4 Hz, 8H), 3.98 (d, J=6.5 Hz, 2H), 3.39 (p, J=9.0 Hz, 1H), 2.32-2.22 (m, 3H), 2.02-1.94 (m, 2H), 1.84 (dd, J=7.5, 5.4 Hz, 1H), 1.50 (q, J=3.9 Hz, 2H), 1.04-0.94 (m, 1H), 0.94-0.89 (m, 2H), 0.44-0.33 (m, 2H), 0.20 (dt, J=6.1, 4.5 Hz, 2H). MS (ESI+) m/z 478 (M+H)$^+$.

Example GI-101

1-[2-(cyclopropylmethoxy)-5-methylpyridin-3-yl]-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (96 mg, 0.50 mmol) and 4-dimethylaminopyridine (CAS #1122-58-3) (33 mg, 0.27 mmol) in anhydrous dichloromethane (2 mL), 1-[2-(cyclopropylmethoxy)-5-methyl-3-pyridyl]cyclopropanecarboxylic acid (62 mg, 0.25 mmol) was added and the mixture was stirred at ambient temperature for 10 minutes. 2-Methylquinoline-5-sulfonamide (56 mg, 0.25 mmol) was added and the reaction mixture was stirred at reflux for 2 hours. The reaction mixture was quenched with aqueous HCl (1N, 500 4, 0.50 mmol) and water. The organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 8.96 (dd, J=8.8, 0.9 Hz, 1H), 8.20 (dd, J=7.4, 1.2 Hz, 1H), 8.03 (dt, J=8.5, 1.1 Hz, 1H), 7.76-7.65 (m, 2H), 7.42 (d, J=8.9 Hz, 1H), 7.33 (dd, J=2.4, 0.6 Hz, 1H), 3.70 (d, J=6.3 Hz, 2H), 2.73 (s, 3H), 2.20 (t, J=0.7 Hz, 3H), 1.41 (q, J=3.9 Hz, 2H), 0.80 (q, J=3.9 Hz, 2H), 0.71-0.59 (m, 1H), 0.27-0.16 (m, 2H), 0.05--0.04 (m, 2H). MS (ESI+) m/z 452 (M+H)$^+$.

Example GI-102

1-(5-ethyl-2-{4-[(propan-2-yl)oxy]piperidin-1-yl}pyridin-3-yl)-N-(1H-indole-4-sulfonyl)cyclopropane-1-carboxamide Into a vial, a solution of 1-[5-ethyl-2-(4-isopropoxy-1-piperidyl)-3-pyridyl]cyclopropanecarboxylic acid (60 mg, 0.18 mmol), 1-(3-dimethylaminopropyl)-3-ethylcarbodiimide hydrochloride (CAS #25952-53-8) (42 mg, 0.22 mmol) and 4-dimethylaminopyridine (CAS #1122-58-3) (27 mg, 0.22 mmol) in anhydrous dichloromethane (2 mL) was added to 1H-indole-4-sulfonamide (35 mg, 0.18 mmol). The reaction mixture was stirred at reflux for 3.5 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 7.82 (d, J=2.4 Hz, 1H), 7.60 (dd, J=7.4, 0.9 Hz, 1H), 7.54-7.47 (m, 2H), 7.31 (d, J=3.2 Hz, 1H), 7.11 (t, J=7.8 Hz, 1H), 6.87 (dd, J=3.1, 0.9 Hz, 1H), 3.74 (hept, J=6.1 Hz, 1H), 3.40 (dq, J=13.3, 4.3 Hz, 3H), 2.71 (ddd, J=13.0, 10.3, 2.7 Hz, 2H), 2.54 (q, J=7.6 Hz, 2H), 1.70-1.60 (m, 2H), 1.58 (q, J=3.6 Hz, 2H), 1.43 (dtd, J=13.0, 9.8, 3.6 Hz, 2H), 1.23-1.12 (m, 9H), 0.99 (q, J=3.7 Hz, 2H). MS (ESI+) m/z 511 (M+H)$^+$.

Example GI-104

1-(5-cyclobutyl-2-{4-[(propan-2-yl)oxy]piperidin-1-yl}pyridin-3-yl)-N-(1H-indole-4-sulfonyl)cyclopropane-1-carboxamide Into a vial, a solution of 1-[5-cyclobutyl-2-(4-isopropoxy-1-piperidyl)-3-pyridyl]cyclopropanecarboxylic acid (60 mg, 0.167 mmol), 1-(3-dimethylaminopropyl)-3-ethylcarbodiimide hydrochloride (CAS #25952-53-8) (38 mg, 0.20 mmol) and 4-dimethylaminopyridine (CAS #1122-58-3) (24 mg, 0.20 mmol) in anhydrous dichloromethane (2 mL) was added to 1H-indole-4-sulfonamide (33 mg, 0.167 mmol). The reaction mixture was stirred at reflux for 72 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$)

δ ppm 7.80 (d, J=2.4 Hz, 1H), 7.61 (dd, J=7.5, 0.9 Hz, 1H), 7.54 (d, J=2.4 Hz, 1H), 7.50 (d, J=8.1 Hz, 1H), 7.30 (d, J=3.1 Hz, 1H), 7.11 (t, J=7.8 Hz, 1H), 6.87 (dd, J=3.2, 0.9 Hz, 1H), 3.73 (hept, J=6.1 Hz, 1H), 3.52-3.34 (m, 4H), 2.70 (ddd, J=13.0, 10.4, 2.7 Hz, 2H), 2.29 (pt, J=10.1, 4.4 Hz, 2H), 2.19-1.95 (m, 3H), 1.92-1.81 (m, 1H), 1.64 (dd, J=13.2, 3.9 Hz, 2H), 1.57 (q, J=3.6 Hz, 2H), 1.42 (qd, J=9.6, 4.9 Hz, 2H), 1.15 (d, J=6.1 Hz, 6H), 0.97 (q, J=3.7 Hz, 2H). MS (ESI+) m/z 537 (M+H)+.

Example GI-105

1-(5-cyclobutyl-2-{4-[(propan-2-yl)oxy]piperidin-1-yl}pyridin-3-yl)-N-(quinoline-5-sulfonyl)cyclopropane-1-carboxamide Into a vial, a solution of 1-[5-cyclobutyl-2-(4-isopropoxy-1-piperidyl)-3-pyridyl]cyclopropanecarboxylic acid (60 mg, 0.18 mmol), 1-(3-dimethylaminopropyl)-3-ethylcarbodiimide hydrochloride (CAS #25952-53-8) (42 mg, 0.22 mmol) and 4-dimethylaminopyridine (CAS #1122-58-3) (27 mg, 0.22 mmol) in anhydrous dichloromethane (2 mL) was added to quinoline-5-sulfonamide (CAS #415913-05-2) (35 mg, 0.18 mmol). The reaction mixture was stirred at reflux for 3.5 hours. The reaction mixture was quenched with saturated aqueous NH$_4$Cl solution, and the aqueous layer was extracted with dichloromethane. The organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 9.19 (ddd, J=8.7, 1.6, 0.8 Hz, 1H), 8.88 (dd, J=4.3, 1.7 Hz, 1H), 8.27 (dd, J=7.3, 1.2 Hz, 1H), 8.12 (dt, J=8.5, 1.1 Hz, 1H), 7.83-7.74 (m, 2H), 7.57 (dd, J=8.7, 4.2 Hz, 1H), 7.48 (dd, J=2.4, 0.6 Hz, 1H), 3.68 (hept, J=6.1 Hz, 1H), 3.50-3.38 (m, 1H), 3.35 (dt, J=8.8, 4.2 Hz, 1H), 3.30-3.22 (m, 2H), 2.62 (ddd, J=12.9, 10.1, 2.7 Hz, 2H), 2.34-2.21 (m, 2H), 2.14-1.94 (m, 3H), 1.91-1.79 (m, 1H), 1.56-1.45 (m, 4H), 1.38-1.27 (m, 2H), 1.13 (d, J=6.1 Hz, 6H), 0.96 (q, J=3.8 Hz, 2H). MS (ESI+) m/z 549 (M+H)+.

Example GI-106

1-[2-(cyclopropylmethoxy)-5-ethylpyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (115 mg, 0.60 mmol) and 4-dimethylaminopyridine (CAS #1122-58-3) (40 mg, 0.33 mmol) in anhydrous dichloromethane (2 mL), 1-[5-ethyl-2-(2-methoxyethoxy)-3-pyridyl]cyclopropanecarboxylic acid (78 mg, 0.30 mmol) was added and the mixture was stirred at ambient temperature for 10 minutes. Quinoline-5-sulfonamide (CAS #415913-05-2) (62 mg, 0.30 mmol) was added and the reaction mixture was stirred at reflux for 2 hours. The reaction mixture was quenched with aqueous HCl (1N, 600 4, 0.60 mmol) and water. The organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 9.03 (ddd, J=8.7, 1.7, 0.8 Hz, 1H), 8.94 (dd, J=4.2, 1.7 Hz, 1H), 8.28-8.18 (m, 2H), 7.79 (d, J=2.3 Hz, 1H), 7.69 (dd, J=8.5, 7.3 Hz, 1H), 7.44 (dd, J=8.7, 4.2 Hz, 1H), 7.22 (d, J=2.4 Hz, 1H), 3.94 (d, J=6.5 Hz, 2H), 2.48 (q, J=7.6 Hz, 2H), 1.49 (q, J=3.9 Hz, 2H), 1.14 (t, J=7.6 Hz, 3H), 1.00-0.92 (m, 1H), 0.90 (q, J=3.9 Hz, 2H), 0.41-0.30 (m, 2H), 0.18 (dt, J=6.2, 4.5 Hz, 2H). MS (ESI+) m/z 452 (M+H)+.

Example GI-107

1-[2-(cyclopropylmethoxy)-5-ethylpyridin-3-yl]-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (115 mg, 0.60 mmol) and 4-dimethylaminopyridine (CAS #1122-58-3) (40 mg, 0.33 mmol) in anhydrous dichloromethane (2 mL), 1-[5-ethyl-2-(2-methoxyethoxy)-3-pyridyl]cyclopropanecarboxylic acid (78 mg, 0.30 mmol) was added and the mixture was stirred at ambient temperature for 10 minutes. 2-Methylquinoline-5-sulfonamide (66 mg, 0.30 mmol) was added and the reaction mixture was stirred at reflux for 2 hours. The reaction mixture was quenched with aqueous HCl (1N, 600 μL, 0.60 mmol) and water. The organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 8.93 (dd, J=8.8, 0.8 Hz, 1H), 8.15 (dd, J=7.3, 1.2 Hz, 1H), 8.11 (dt, J=8.5, 1.1 Hz, 1H), 7.77 (d, J=2.4 Hz, 1H), 7.63 (dd, J=8.5, 7.3 Hz, 1H), 7.32 (d, J=8.9 Hz, 1H), 7.21 (d, J=2.4 Hz, 1H), 3.92 (d, J=6.4 Hz, 2H), 2.75 (s, 3H), 2.48 (q, J=7.6 Hz, 2H), 1.49 (q, J=3.8 Hz, 2H), 1.13 (t, J=7.6 Hz, 3H), 0.96-0.90 (m, 1H), 0.89 (q, J=3.8 Hz, 2H), 0.39-0.28 (m, 2H), 0.16 (dt, J=6.1, 4.4 Hz, 2H). MS (ESI+) m/z 466 (M+H)+.

Example GI-108

1-[2-(cyclopropylmethoxy)-5-ethylpyridin-3-yl]-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (115 mg, 0.60 mmol) and 4-dimethylaminopyridine (CAS #1122-58-3) (40 mg, 0.33 mmol) in anhydrous dichloromethane (2 mL), 1-[5-ethyl-2-(2-methoxyethoxy)-3-pyridyl]cyclopropanecarboxylic acid (78 mg, 0.30 mmol) was added and the mixture was stirred at ambient temperature for 10 minutes. 1H-Indole-4-sulfonamide (58 mg, 0.30 mmol) was added and the reaction mixture was stirred at reflux for 2 hours. The reaction mixture was quenched with aqueous HCl (1N, 600 μL, 0.60 mmol) and water. The organic layer was separated on a phase separator and was concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 8.49 (s, 1H), 7.96 (d, J=2.4 Hz, 1H), 7.90 (dd, J=7.6, 0.9 Hz, 1H), 7.63 (dt, J=8.1, 1.0 Hz, 1H), 7.37-7.32 (m, 2H), 7.30 (t, J=7.9 Hz, 1H), 6.83 (ddd, J=3.2, 2.1, 1.0 Hz, 1H), 4.10 (d, J=6.9 Hz, 2H), 2.57 (q, J=7.6 Hz, 2H), 1.53 (q, J=4.2 Hz, 2H), 1.23 (t, J=7.6 Hz, 3H), 1.09-1.02 (m, 1H), 0.96 (q, J=4.3 Hz, 2H), 0.52-0.43 (m, 2H), 0.26-0.18 (m, 2H). MS (ESI+) m/z 440 (M+H)+.

Example GI-109

1-[5-ethyl-2-(2-methoxyethoxy)pyridin-3-yl]-N-(1H-indole-4-sulfonyl)cyclopropane-1-carboxamide Into a vial, to a solution of 1-(3-dimethylaminopropyl)-3-ethylcarbodiimide hydrochloride (CAS #25952-53-8) (118 mg, 0.62 mmol) and 4-dimethylaminopyridine (CAS #1122-58-3) (41 mg, 0.34 mmol) in anhydrous dichloromethane (2 mL), 1-[5-ethyl-2-(2-methoxyethoxy)-3-pyridyl]cyclopropanecarboxylic acid (82 mg, 0.31 mmol) was added and the mixture was stirred at ambient temperature for 10 minutes. 1H-Indole-4-sulfonamide (60 mg, 0.31 mmol) was added and the reaction mixture was stirred at reflux for 2 hours. The reaction mixture was quenched with aqueous HCl (1N, 620 µL, 0.62 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 8.54 (s, 1H), 7.93 (d, J=2.4 Hz, 1H), 7.85 (dd, J=7.6, 0.9 Hz, 1H), 7.59 (dt, J=8.2, 1.0 Hz, 1H), 7.36-7.22 (m, 7H), 6.86 (ddd, J=3.1, 2.1, 1.0 Hz, 1H), 4.39-4.32 (m, 2H), 3.53-3.46 (m, 2H), 3.30 (s, 3H), 2.56 (q, J=7.6 Hz, 2H), 1.54 (q, J=4.2 Hz, 2H), 1.21 (t, J=7.6 Hz, 3H), 0.96 (q, J=4.2 Hz, 2H). MS (ESI+) m/z 444 (M+H)+.

Example GI-110

1-[5-cyclobutyl-2-(cyclopropylmethoxy)pyridin-3-yl]-N-(2-methylquinoline-5-sulfonyl)cyclopropane-1-carboxamide Into a vial, to a solution of 1-(3-dimethylaminopropyl)-3-ethylcarbodiimide hydrochloride (CAS #25952-53-8) (88 mg, 0.46 mmol) and 4-dimethylaminopyridine (CAS #1122-58-3) (30 mg, 0.25 mmol) in anhydrous dichloromethane (2 mL), 1-[5-cyclobutyl-2-(cyclopropylmethoxy)-3-pyridyl]cyclopropanecarboxylic acid (66 mg, 0.23 mmol) was added and the mixture was stirred at ambient temperature for 10 minutes. 2-Methylquinoline-5-sulfonamide (51 mg, 0.23 mmol) was added and the reaction mixture was stirred at reflux for 2 hours. The reaction mixture was quenched with aqueous HCl (1N, 460 4, 0.46 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 8.92-8.86 (m, 1H), 8.18 (dd, J=7.3, 1.2 Hz, 1H), 8.13 (dt, J=8.5, 1.1 Hz, 1H), 7.81 (dd, J=2.4, 0.7 Hz, 1H), 7.65 (dd, J=8.5, 7.3 Hz, 1H), 7.32 (d, J=8.8 Hz, 1H), 7.27 (d, J=0.5 Hz, 1H), 3.96 (d, J=6.4 Hz, 2H), 3.39 (p, J=9.0 Hz, 1H), 2.75 (s, 3H), 2.31-2.21 (m, 2H), 2.04-1.94 (m, 3H), 1.88-1.80 (m, 1H), 1.50 (q, J=3.9 Hz, 2H), 1.00-0.93 (m, 1H), 0.91 (q, J=4.0 Hz, 2H), 0.42-0.31 (m, 2H), 0.18 (dt, J=6.2, 4.5 Hz, 2H). MS (ESI+) m/z 492 (M+H)+.

Example GI-111

1-[5-cyclobutyl-2-(2-methoxyethoxy)pyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (115 mg, 0.60 mmol) and 4-dimethylaminopyridine (CAS #1122-58-3) (40 mg, 0.33 mmol) in anhydrous dichloromethane (2 mL), 1-[5-cyclobutyl-2-(2-methoxyethoxy)-3-pyridyl]cyclopropanecarboxylic acid (87 mg, 0.30 mmol) was added and the mixture was stirred at ambient temperature for 10 minutes. Quinoline-5-sulfonamide (CAS #415913-05-2) (62 mg, 0.30 mmol) was added and the reaction mixture was stirred at reflux for 2 hours. The reaction mixture was quenched with aqueous HCl (1N, 600 µL, 0.60 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 9.10-9.02 (m, 1H), 8.94 (dd, J=4.2, 1.7 Hz, 1H), 8.27-8.17 (m, 2H), 7.80 (d, J=2.3 Hz, 1H), 7.69 (dd, J=8.5, 7.3 Hz, 1H), 7.44 (dd, J=8.7, 4.2 Hz, 1H), 7.25 (d, J=2.4 Hz, 1H), 4.36-4.29 (m, 2H), 3.65-3.58 (m, 2H), 3.44-3.31 (m, 4H), 2.32-2.20 (m, 2H), 2.02-1.93 (m, 3H), 1.88-1.78 (m, 1H), 1.52 (q, J=3.9 Hz, 2H), 0.90 (q, J=3.9 Hz, 2H). MS (ESI+) m/z 482 (M+H)+.

Example GI-112

1-[5-ethyl-2-(2-methoxyethoxy)pyridin-3-yl]-N-(quinoline-5-sulfonyl)cyclopropane-1-carboxamide Into a vial, to a solution of 1-(3-dimethylaminopropyl)-3-ethylcarbodiimide hydrochloride (CAS #25952-53-8) (118 mg, 0.62 mmol) and 4-dimethylaminopyridine (CAS #1122-58-3) (41 mg, 0.34 mmol) in anhydrous dichloromethane (2 mL), 1-[5-ethyl-2-(2-methoxyethoxy)-3-pyridyl]cyclopropanecarboxylic acid (82 mg, 0.31 mmol) was added and the mixture was stirred at ambient temperature for 10 minutes. Quinoline-5-sulfonamide (CAS #415913-05-2) (64 mg, 0.31 mmol) was added and the reaction mixture was stirred at reflux for 2 hours. The reaction mixture was quenched with aqueous HCl (1N, 620 µL, 0.62 mmol) and water. The organic layer was separated on a phase separator and was concentrated. The crude material was purified by reverse-phase HPLC Waters XBridge™ C18 5 µm OBD column, 30×100 mm, flow rate 50 mL/minute, H$_2$O+0.1% diethylamine/acetonitrile+0.1% diethylamine to give the title compound. $^1$H NMR (400 MHz, chloroform-d) δ ppm 9.09-9.03 (m, 1H), 8.94 (dd, J=4.2, 1.7 Hz, 1H), 8.24 (dd, J=7.3, 1.3 Hz, 1H), 8.21 (d, J=8.4 Hz, 1H), 7.80 (d, J=2.3 Hz, 1H), 7.69 (dd, J=8.5, 7.3 Hz, 1H), 7.44 (dd, J=8.7, 4.2 Hz, 1H), 7.22 (d, J=2.4 Hz, 1H), 4.37-4.30 (m, 2H), 3.67-3.60 (m, 2H), 3.38 (s, 3H), 2.48 (q, J=7.6 Hz, 2H), 1.52 (q, J=3.9 Hz, 2H), 1.14 (t, J=7.6 Hz, 3H), 0.90 (q, J=4.0 Hz, 2H). MS (ESI+) m/z 456 (M+H)+.

Example GI-113

1-(5-cyclobutyl-2-{4-[(propan-2-yl)oxy]piperidin-1-yl}pyridin-3-yl)-N-(2-methylquinoline-5-sulfonyl)cyclopropane-1-carboxamide Into a vial, a solution of 1-[5-cyclobutyl-2-(4-isopropoxy-1-piperidyl)-3-pyridyl]cyclopropanecarboxylic acid (60 mg, 0.18 mmol), 1-(3-dimethylaminopropyl)-3-ethylcarbodiimide hydrochloride (CAS #25952-53-8) (42 mg, 0.22 mmol) and 4-dimethylaminopyridine (CAS #1122-58-3) (27 mg, 0.22 mmol) in anhydrous dichloromethane (2 mL) was added to 2-methylquinoline-5-sulfonamide (37 mg, 0.18 mmol). The reaction mixture was stirred at reflux for 3.5 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% diethylamine/acetonitrile+0.1% diethylamine to give the title compound. $^1$H NMR (400 MHz, methanol-$d_4$) δ ppm 9.06 (dd, J=8.8, 0.8 Hz, 1H), 8.21 (dd, J=7.3, 1.2 Hz, 1H), 8.04 (dt, J=8.5, 1.1 Hz, 1H), 7.81 (dd, J=2.4, 0.7 Hz, 1H), 7.73 (dd, J=8.5, 7.3 Hz, 1H), 7.50 (dd, J=2.4, 0.6 Hz, 1H), 7.46 (d, J=8.8 Hz, 1H), 3.70 (hept, J=6.1 Hz, 1H), 3.52-3.40 (m, 1H), 3.37 (dd, J=9.0, 4.2 Hz, 1H), 3.31-3.23 (m, 2H), 2.75 (s, 3H), 2.63 (ddd, J=12.9, 10.2, 2.7 Hz, 2H), 2.30 (dddt, J=8.2, 6.7, 5.3, 3.3 Hz, 2H), 2.16-1.99 (m, 3H), 1.93-1.81 (m, 1H), 1.57-1.47 (m, 4H), 1.40-1.30 (m, 2H), 1.14 (d, J=6.1 Hz, 6H), 0.97 (q, J=3.7 Hz, 2H). MS (ESI+) m/z 563 (M+H)$^+$.

Example GI-114

1-(5-cyclobutyl-2-ethoxypyridin-3-yl)-N-(quinoline-5-sulfonyl)cyclopropane-1-carboxamide Into a vial, a solution of 1-(5-cyclobutyl-2-ethoxy-3-pyridyl)cyclopropanecarboxylic acid (60 mg, 0.23 mmol), 1-(3-dimethylaminopropyl)-3-ethylcarbodiimide hydrochloride (CAS #25952-53-8) (53 mg, 0.276 mmol) and 4-dimethylaminopyridine (CAS #1122-58-3) (34 mg, 0.276 mmol) in anhydrous dichloromethane (2 mL) was added to quinoline-5-sulfonamide (CAS #415913-05-2) (48 mg, 0.23 mmol). The reaction mixture was stirred at reflux for 3.5 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% formic acid/acetonitrile+0.1% formic acid to give the title compound. $^1$H NMR (400 MHz, methanol-$d_4$) δ ppm 9.02-8.93 (m, 2H), 8.46 (dd, J=7.5, 1.3 Hz, 1H), 8.34 (dt, J=8.5, 1.1 Hz, 1H), 7.93 (dd, J=8.5, 7.4 Hz, 1H), 7.88 (dd, J=2.4, 0.7 Hz, 1H), 7.63 (dd, J=8.7, 4.3 Hz, 1H), 7.46 (d, J=2.4 Hz, 1H), 3.85 (q, J=7.0 Hz, 2H), 3.52 (p, J=9.3, 8.8 Hz, 1H), 2.40-2.27 (m, 2H), 2.24-2.10 (m, 2H), 2.10-1.98 (m, 1H), 1.95-1.83 (m, 1H), 1.41-1.35 (m, 2H), 1.01 (q, J=4.4 Hz, 2H), 0.80 (t, J=7.0 Hz, 3H). MS (ESI+) m/z 452 (M+H)$^+$.

Example GI-115

1-(5-cyclobutyl-2-ethoxypyridin-3-yl)-N-(2-methylquinoline-5-sulfonyl)cyclopropane-1-carboxamide Into a vial, a solution of 1-(5-cyclobutyl-2-ethoxy-3-pyridyl)cyclopropanecarboxylic acid (60 mg, 0.23 mmol), 1-(3-dimethylaminopropyl)-3-ethylcarbodiimide hydrochloride (CAS #25952-53-8) (53 mg, 0.276 mmol) and 4-dimethylaminopyridine (CAS #1122-58-3) (34 mg, 0.276 mmol) in anhydrous dichloromethane (2 mL) was added to 2-methylquinoline-5-sulfonamide (51 mg, 0.23 mmol). The reaction mixture was stirred at reflux for 3.5 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% formic acid/acetonitrile+0.1% formic acid to give the title compound. $^1$H NMR (400 MHz, methanol-$d_4$) δ ppm 8.83 (dd, J=8.9, 0.9 Hz, 1H), 8.38 (dd, J=7.4, 1.2 Hz, 1H), 8.24 (dt, J=8.5, 1.1 Hz, 1H), 7.91-7.83 (m, 2H), 7.52 (d, J=8.9 Hz, 1H), 7.46 (dd, J=2.4, 0.6 Hz, 1H), 3.85 (q, J=7.0 Hz, 2H), 3.58-3.44 (m, 1H), 2.77 (s, 3H), 2.40-2.27 (m, 2H), 2.23-2.04 (m, 3H), 1.95-1.83 (m, 1H), 1.41-1.30 (m, 2H), 1.04-0.97 (m, 2H), 0.80 (t, J=7.0 Hz, 3H). MS (ESI+) m/z 466 (M+H)$^+$.

Example GI-116

1-(2-ethoxy-5-ethylpyridin-3-yl)-N-(quinoline-5-sulfonyl)cyclopropane-1-carboxamide Into a vial, a solution of 1-(2-ethoxy-5-ethyl-3-pyridyl)cyclopropanecarboxylic acid (60 mg, 0.255 mmol), 1-(3-dimethylaminopropyl)-3-ethylcarbodiimide hydrochloride (CAS #25952-53-8) (59 mg, 0.306 mmol) and 4-dimethylaminopyridine (CAS #1122-58-3) (37 mg, 0.306 mmol) in anhydrous dichloromethane (2 mL) was added to quinoline-5-sulfonamide (CAS #415913-05-2) (53 mg, 0.255 mmol). The reaction mixture was stirred at reflux for 3.5 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% formic acid/acetonitrile+0.1% formic acid to give the title compound. $^1$H NMR (400 MHz, methanol-$d_4$) δ ppm 9.02-8.93 (m, 2H), 8.47 (dd, J=7.5, 1.2 Hz, 1H), 8.34 (dt, J=8.5, 1.1 Hz, 1H), 7.93 (dd, J=8.5, 7.4 Hz, 1H), 7.89-7.84 (m, 1H), 7.63 (dd, J=8.8, 4.3 Hz, 1H), 7.42 (d, J=2.4 Hz, 1H), 3.85 (q, J=7.0 Hz, 2H), 2.59 (q, J=7.6 Hz, 2H), 1.41-1.32 (m, 2H), 1.23 (t, J=7.6 Hz, 3H), 1.04-0.97 (m, 2H), 0.81 (t, J=7.1 Hz, 3H). MS (ESI+) m/z 426 (M+H)$^+$.

Example GI-117

1-(2-ethoxy-5-ethylpyridin-3-yl)-N-(2-methylquinoline-5-sulfonyl)cyclopropane-1-carboxamide Into a vial, a solution of 1-(2-ethoxy-5-ethyl-3-pyridyl)cyclopropanecarboxylic acid (60 mg, 0.255 mmol), 1-(3-dimethylaminopropyl)-3-ethylcarbodiimide hydrochloride (CAS #25952-53-8) (59 mg, 0.306 mmol) and 4-dimethylaminopyridine (CAS #1122-58-3) (37 mg, 0.306 mmol) in anhydrous dichloromethane (2 mL) was added to 2-methylquinoline-5-sulfonamide (57 mg, 0.255 mmol). The reaction mixture was stirred at reflux for 3.5 hours. The reaction mixture was quenched with saturated aqueous $NH_4Cl$ solution, and the aqueous layer was extracted with dichloromethane. The organic layers were combined, dried over $MgSO_4$, filtered and concentrated. The crude material was purified by reverse-phase HPLC Waters XBridge™ C18 5 μm OBD column, 30×100 mm, flow rate 50 mL/minute, $H_2O$+0.1% formic acid/acetonitrile+0.1% formic acid to give the title compound. $^1$H NMR (400 MHz, methanol-$d_4$)

δ ppm 8.83 (dd, J=8.9, 0.9 Hz, 1H), 8.38 (dd, J=7.5, 1.2 Hz, 1H), 8.24 (dt, J=8.5, 1.1 Hz, 1H), 7.91-7.83 (m, 2H), 7.52 (d, J=8.9 Hz, 1H), 7.42 (d, J=2.3 Hz, 1H), 3.85 (q, J=7.0 Hz, 2H), 2.77 (s, 3H), 2.59 (q, J=7.6 Hz, 2H), 1.40-1.33 (m, 2H), 1.23 (t, J=7.6 Hz, 3H), 1.04-0.96 (m, 2H), 0.81 (t, J=7.0 Hz, 3H). MS (ESI+) m/z 440 (M+H)$^+$.

Example GI-118

1-{5-cyclobutyl-2-[4-(methoxymethyl)piperidin-1-yl]pyridin-3-yl}-N-(1H-indole-4-sulfonyl)cyclopropane-1-carboxamide Into a vial, to a solution of 1-[5-cyclobutyl-2-[4-(methoxymethyl)-1-piperidyl]-3-pyridyl]cyclopropanecarboxylic acid (29 mg, 0.084 mmol) in anhydrous dichloromethane (2 mL), 1-(3-dimethylaminopropyl)-3-ethylcarbodiimide hydrochloride (CAS #25952-53-8) (32 mg, 0.168 mmol) and 4-dimethylaminopyridine (CAS #1122-58-3) (10 mg, 0.084 mmol) were added, followed by 1H-indole-4-sulfonamide (15 mg, 0.076 mmol). The reaction mixture was stirred at reflux overnight. The reaction mixture was dried under N2 flow and the crude material was purified by reverse-phase HPLC Waters XBridge™ C18 5 μm OBD column, 30×100 mm, flow rate 50 mL/minute, H$_2$O+0.1% formic acid/acetonitrile+0.1% formic acid to give the title compound. $^1$H NMR (400 MHz, chloroform-d) δ ppm 8.96 (dd, J=4.2, 1.6 Hz, 1H), 8.86 (dt, J=8.8, 1.2 Hz, 1H), 8.50 (dd, J=7.5, 1.2 Hz, 1H), 8.37 (dt, J=8.5, 1.1 Hz, 1H), 8.21 (d, J=2.3 Hz, 1H), 8.11 (s, 1H), 7.83 (dd, J=8.5, 7.5 Hz, 1H), 7.41 (dd, J=8.8, 4.2 Hz, 1H), 7.32 (d, J=2.3 Hz, 1H), 3.48 (dq, J=10.7, 7.4, 5.2 Hz, 3H), 3.36 (s, 3H), 3.25 (d, J=6.0 Hz, 2H), 2.94 (td, J=12.5, 2.3 Hz, 2H), 2.34 (dddd, J=9.9, 7.1, 5.1, 2.9 Hz, 2H), 2.13-2.01 (m, 3H), 1.95-1.83 (m, 1H), 1.81-1.71 (m, 3H), 1.56 (q, J=4.3 Hz, 2H), 1.53-1.38 (m, 2H), 1.12 (q, J=4.3 Hz, 2H). MS (ESI+) m/z 523 (M+H)$^+$.

Example GI-119

1-{5-[1-(methoxymethyl)cyclopropyl]-2-[(propan-2-yl)oxy]pyridin-3-yl}-N-(naphthalene-1-sulfonyl)cyclopropane-1-carboxamide Into a vial, to a solution of 1-(3-dimethylaminopropyl)-3-ethylcarbodiimide hydrochloride (CAS #25952-53-8) (28 mg, 0.149 mmol), 4-dimethylaminopyridine (CAS #1122-58-3) (18 mg, 0.149 mmol) and 1-[2-isopropoxy-5-[1-(methoxymethyl)cyclopropyl]-3-pyridyl]cyclopropanecarboxylic acid (38 mg, 0.124 mmol) in anhydrous dichloromethane (2 mL), was added naphthalene-1-sulfonamide (CAS #606-25-7) (26 mg, 0.124 mmol) and the reaction mixture was stirred at reflux for 2 hours. The reaction mixture was quenched with saturated aqueous NH$_4$Cl solution. The aqueous layer was extracted with dichloromethane, and the organic layers were combined, dried over MgSO$_4$, filtered and concentrated. The crude material was purified by reverse-phase HPLC Waters XBridge™ C18 5 μm OBD column, 30×100 mm, flow rate 50 mL/minute, H$_2$O+0.1% diethylamine/acetonitrile+0.1% diethylamine to give the title compound. $^1$H NMR (400 MHz, methanol-d$_4$) δ ppm 8.80-8.73 (m, 1H), 8.21 (dd, J=7.3, 1.3 Hz, 1H), 8.00 (d, J=8.2 Hz, 1H), 7.97-7.92 (m, 1H), 7.89 (d, J=2.4 Hz, 1H), 7.62-7.53 (m, 2H), 7.51 (dd, J=8.2, 7.3 Hz, 1H), 7.45 (d, J=2.4 Hz, 1H), 4.97 (p, J=6.1 Hz, 2H), 3.45 (s, 2H), 3.31 (s, 3H), 1.51 (q, J=3.9 Hz, 2H), 1.00 (d, J=6.1 Hz, 6H), 0.88-0.81 (m, 6H). MS (ESI+) m/z 495 (M+H)$^+$.

Example GI-120

1-{5-ethyl-2-[4-(methoxymethyl)piperidin-1-yl]pyridin-3-yl}-N-(1H-indole-4-sulfonyl)cyclopropane-1-carboxamide Into a vial, to a solution of 1-[5-ethyl-2-[4-(methoxymethyl)-1-piperidyl]-3-pyridyl]cyclopropanecarboxylic acid (50 mg, 0.157 mmol) in anhydrous dichloromethane (3 mL), 1-(3-dimethylaminopropyl)-3-ethylcarbodiimide hydrochloride (CAS #25952-53-8) (60 mg, 0.314 mmol) and 4-dimethylaminopyridine (CAS #1122-58-3) (19 mg, 0.157 mmol) were added, followed by 1H-indole-4-sulfonamide (28 mg, 0.141 mmol). The reaction mixture was stirred at reflux for 2 hours. The reaction mixture was quenched with saturated aqueous NH$_4$Cl solution, and the organic layer was separated on a phase separator and concentrated. The crude material was purified by reverse-phase HPLC Waters XBridge™ C18 5 μm OBD column, 30×100 mm, flow rate 50 mL/minute, H$_2$O+0.1% formic acid/acetonitrile+0.1% formic acid to give the title compound. $^1$H NMR (400 MHz, chloroform-d) δ ppm 8.76 (s, 1H), 8.14 (d, J=2.3 Hz, 1H), 7.91 (dd, J=7.7, 0.9 Hz, 1H), 7.66-7.58 (m, 1H), 7.36 (d, J=2.4 Hz, 1H), 7.32 (t, J=2.9 Hz, 1H), 7.27 (t, J=7.9 Hz, 1H), 6.80 (ddd, J=3.1, 2.0, 0.9 Hz, 1H), 3.34 (s, 5H), 3.17 (d, J=6.5 Hz, 2H), 2.73 (td, J=12.3, 2.4 Hz, 2H), 2.58 (q, J=7.6 Hz, 2H), 1.65 (tq, J=11.2, 4.2, 3.7 Hz, 1H), 1.57 (dt, J=7.1, 3.4 Hz, 4H), 1.27-1.15 (m, 5H), 1.12 (q, J=4.2 Hz, 2H). MS (ESI+) m/z 497 (M+H)$^+$.

Example GI-121

1-{5-cyclobutyl-2-[4-(methoxymethyl)piperidin-1-yl]pyridin-3-yl}-N-(quinoline-5-sulfonyl)cyclopropane-1-carboxamide To a solution of 1-[5-cyclobutyl-2-[4-(methoxymethyl)-1-piperidyl]-3-pyridyl]cyclopropanecarboxylic acid (118 mg, 0.179 mmol) in anhydrous dichloromethane (3 mL), N,N-diisopropylethylamine (125 μL, 0.716 mmol), 1-(3-dimethylaminopropyl)-3-ethylcarbodiimide hydrochloride (CAS #25952-53-8) (73 mg, 0.358 mmol) and 4-dimethylaminopyridine (CAS #1122-58-3) (23 mg, 0.179 mmol) were added, followed by quinoline-5-sulfonamide (CAS #415913-05-2) (36 mg, 0.16 mmol). The reaction mixture was stirred at ambient temperature overnight. The reaction mixture was quenched with saturated aqueous NH$_4$Cl solution, and the organic layer was separated on phase separator and concentrated. The crude material was purified by reverse-phase HPLC Waters XBridge™ C18 5 μm OBD column, 30×100 mm, flow rate 50 mL/minute, H$_2$O+0.1% formic acid/acetonitrile+0.1% formic acid to give the title compound. $^1$H NMR (400 MHz, chloroform-d) δ ppm 8.96 (dd, J=4.2, 1.6 Hz, 1H), 8.86 (dt, J=8.8, 1.2 Hz, 1H), 8.50 (dd, J=7.5, 1.2 Hz, 1H), 8.37 (dt, J=8.5, 1.1 Hz, 1H), 8.21 (d, J=2.3 Hz, 1H), 8.11 (s, 1H), 7.83 (dd, J=8.5, 7.5 Hz, 1H), 7.41 (dd, J=8.8, 4.2 Hz, 1H), 7.32 (d, J=2.3 Hz, 1H), 3.48 (dq, J=10.7, 7.4, 5.2 Hz, 3H), 3.36 (s, 3H), 3.25 (d, J=6.0 Hz, 2H), 2.94 (td, J=12.5, 2.3 Hz, 2H), 2.34 (dddd, J=9.9, 7.1, 5.1, 2.9 Hz, 2H), 2.13-2.01 (m, 3H), 1.95-1.83 (m, 1H), 1.81-1.71 (m, 3H), 1.56 (q, J=4.3 Hz, 2H), 1.53-1.38 (m, 2H), 1.12 (q, J=4.3 Hz, 2H). MS (ESI+) m/z 535 (M+H)$^+$.

TABLE 4

|  | Name | NMR | MS |
|---|---|---|---|
| Example GII-1 | 1-(2,4-dimethoxypyrimidin-5-yl)-N-(naphthalene-1-sulfonyl)cyclopropane-1-carboxamide | $^1$H NMR (400 MHz, methanol-$d_4$) δ ppm 8.73-8.64 (m, 1H), 8.18 (dd, J = 7.3, 1.3 Hz, 1H), 8.03-7.94 (m, 2H), 7.94-7.86 (m, 1H), 7.57-7.52 (m, 2H), 7.50 (dd, J = 8.2, 7.3 Hz, 1H), 3.94 (s, 3H), 3.68 (s, 3H), 1.38 (q, J = 3.8 Hz, 2H), 0.81 (q, J = 3.9 Hz, 2H). | MS (ESI+) m/z 414 (M + H)$^+$. |
| Example GII-2 | N-(naphthalene-1-sulfonyl)-1-{2-[(propan-2-yl)oxy]pyridin-3-yl}cyclopropane-1-carboxamide | $^1$H NMR (400 MHz, methanol-$d_4$) δ ppm 8.78-8.69 (m, 1H), 8.17 (dd, J = 7.3, 1.3 Hz, 1H), 7.96 (dt, J = 8.3, 1.1 Hz, 1H), 7.89 (ddd, J = 9.0, 4.7, 1.8 Hz, 2H), 7.57-7.50 (m, 2H), 7.49-7.41 (m, 2H), 6.77 (dd, J = 7.3, 5.1 Hz, 1H), 4.97 (hept, J = 6.1 Hz, 1H), 1.49 (q, J = 3.8 Hz, 2H), 0.96 (d, J = 6.2 Hz, 6H), 0.82 (q, J = 3.9 Hz, 2H). | MS (ESI+) m/z 411 (M + H)$^+$. |
| Example GII-3 | 1-{2-[(propan-2-yl)oxy]pyridin-3-yl}-N-(quinoline-5-sulfonyl)cyclopropane-1-carboxamide | $^1$H NMR (400 MHz, methanol-$d_4$) δ ppm 9.16 (ddd, J = 8.8, 1.7, 0.9 Hz, 1H), 8.88 (dd, J = 4.3, 1.7 Hz, 1H), 8.25 (dd, J = 7.3, 1.2 Hz, 1H), 8.11 (dt, J = 8.5, 1.1 Hz, 1H), 7.87 (dd, J = 5.1, 1.9 Hz, 1H), 7.77 (dd, J = 8.5, 7.3 Hz, 1H), 7.57 (dd, J = 8.7, 4.3 Hz, 1H), 7.45 (dd, J = 7.2, 1.9 Hz, 1H), 6.78 (dd, J = 7.2, 5.1 Hz, 1H), 4.94 (h, J = 6.1 Hz, 1H), 1.46 (q, J = 3.9 Hz, 2H), 0.90 (d, J = 6.2 Hz, 6H), 0.82 (q, J = 3.9 Hz, 2H). | MS (ESI+) m/z 412 (M + H)$^+$. |
| Example GII-4 | 1-{2-[(propan-2-yl)oxy]pyridin-3-yl}-N-(1,2,3,4-tetrahydroquinoline-5-sulfonyl)cyclopropane-1-carboxamide | $^1$H NMR (400 MHz, methanol-$d_4$) δ ppm 7.91 (dd, J = 5.1, 1.9 Hz, 1H), 7.51 (dd, J = 7.2, 2.0 Hz, 1H), 7.20 (dd, J = 7.8, 1.3 Hz, 1H), 6.89 (dd, J = 7.9 Hz, 1H), 6.81 (dd, J = 7.2, 5.1 Hz, 1H), 6.57 (dd, J = 8.0, 1.2 Hz, 1H), 5.19 (hept, J = 6.2 Hz, 1H), 3.26-3.19 (m, 2H), 3.08 (t, J = 6.4 Hz, 2H), 1.90-1.79 (m, 2H), 1.52 (q, J = 3.8 Hz, 2H), 1.28 (d, J = 6.2 Hz, 6H), 0.87 (q, J = 3.9 Hz, 2H). | MS (ESI+) m/z 416 (M + H)$^+$. |
| Example GII-5 | 1-[5-chloro-2-(trifluoromethyl)pyridin-3-yl]-N-(naphthalene-1-sulfonyl)cyclopropane-1-carboxamide | $^1$H NMR (400 MHz, chloroform-d) δ ppm 8.52-8.44 (m, 2H), 8.29-8.22 (m, 1H), 8.18 (d, J = 8.2 Hz, 1H), 8.12 (s, 1H), 8.04-7.96 (m, 1H), 7.75 (d, J = 2.2 Hz, 1H), 7.72-7.59 (m, 3H), 1.56-1.52 (m, 2H), 1.13 (d, J = 3.6 Hz, 2H). | MS (ESI+) m/z 455 (M + H)$^+$. |
| Example GII-6 | 1-(5-chloro-2-methoxypyridin-4-yl)-N-(quinoline-5-sulfonyl)cyclopropane-1-carboxamide | $^1$H NMR (400 MHz, chloroform-d) δ ppm 9.05 (dd, J = 4.2, 1.6 Hz, 1H), 8.82 (dd, J = 8.7, 1.6, 0.9 Hz, 1H), 8.52 (dd, J = 7.5, 1.3 Hz, 1H), 8.43 (dt, J = 8.5, 1.1 Hz, 1H), 8.12-8.07 (m, 1H), 7.86 (dd, J = 8.5, 7.5 Hz, 1H), 7.58 (dd, J = 8.8, 4.2 Hz, 1H), 6.70 (d, J = 0.5 Hz, 1H), 3.91 (s, 3H), 1.64-1.60 (m, 2H), 1.08 (q, J = 4.4 Hz, 2H). | MS (ESI+) m/z 418 (M + H)$^+$. |
| Example GII-7 | 1-(5-chloro-2-methoxypyridin-4-yl)-N-(1,2,3,4-tetrahydroquinoline-5-sulfonyl)cyclopropane-1-carboxamide | $^1$H NMR (400 MHz, chloroform-d) δ ppm 8.00 (s, 1H), 7.48 (dd, J = 7.9, 1.6 Hz, 1H), 6.91 (dd, J = 7.3, 1.6 Hz, 1H), 6.65 (s, 1H), 6.42 (t, J = 7.6 Hz, 1H), 3.86 (s, 3H), 3.27-3.20 (m, 3H), 2.71 (t, J = 6.3 Hz, 2H), 1.88-1.79 (m, 2H), 1.55 (q, J = 3.8 Hz, 2H), 0.93 (q, J = 3.8 Hz, 2H). | MS (ESI+) m/z 422 (M + H)$^+$. |
| Example GII-8 | 1-[5-methyl-2-(morpholin-4-yl)pyridin-4-yl]-N-(quinoline-5-sulfonyl)cyclopropane-1-carboxamide | $^1$H NMR (400 MHz, methanol-$d_4$) δ ppm 9.11 (ddd, J = 8.8, 1.7, 0.9 Hz, 1H), 8.91 (dd, J = 4.3, 1.7 Hz, 1H), 8.32 (dd, J = 7.4, 1.2 Hz, 1H), 8.18 (dt, J = 8.5, 1.1 Hz, 1H), 8.12 (s, 1H), 7.83 (dd, J = 8.5, 7.3 Hz, 1H), 7.64-7.56 (m, 2H), 6.97 (s, 1H), 3.82 (dt, J = 8.2, 4.9 Hz, 4H), 3.57-3.49 (m, 4H), 2.67 (s, 3H), 1.48 (q, J = 3.6 Hz, 2H), 0.98 (q, J = 3.9 Hz, 2H). | MS (ESI+) m/z 453 (M + H)$^+$. |
| Example GII-9 | 1-[5-methyl-2-(pyrrolidin-1-yl)pyridin-4-yl]-N-(quinoline-5-sulfonyl)cyclopropane-1-carboxamide | $^1$H NMR (400 MHz, methanol-$d_4$) δ ppm 9.13 (dt, J = 8.6, 1.4 Hz, 1H), 8.90 (dd, J = 4.3, 1.7 Hz, 1H), 8.31 (dd, J = 7.3, 1.2 Hz, 1H), 8.15 (dt, J = 8.5, 1.1 Hz, 1H), 7.81 (dd, J = 8.5, 7.3 Hz, 1H), 7.58 (dd, J = 8.7, 4.3 Hz, 1H), 7.47 (s, 1H), 6.67 (s, 1H), 3.57-3.44 (m, 4H), 2.19-2.05 (m, 4H), 1.87 (d, J = 0.9 Hz, 3H), 1.47 (d, J = 3.0 Hz, 2H), 0.94 (q, J = 3.8 Hz, 2H). | MS (ESI+) m/z 437 (M + H)$^+$. |
| Example GII-10 | 1-[2-methoxy-6-(trifluoromethyl)pyridin-3-yl]-N-(quinoline-5-sulfonyl)cyclopropane-1-carboxamide | $^1$H NMR (400 MHz, methanol-$d_4$) δ ppm 9.09 (ddd, J = 8.7, 1.7, 0.9 Hz, 1H), 8.89 (dd, J = 4.3, 1.7 Hz, 1H), 8.29 (dd, J = 7.3, 1.2 Hz, 1H), 8.14 (dt, J = 8.5, 1.1 Hz, 1H), 7.80 (dd, J = 8.5, 7.3 Hz, 1H), 7.62 (dd, J = 7.5, 0.8 Hz, 1H), 7.55 (dd, J = 8.8, 4.3 Hz, 1H), 7.22 (d, J = 7.4 Hz, 1H), 3.58 (s, 3H), 1.41 (q, J = 4.0 Hz, 2H), 0.85 (q, J = 4.0 Hz, 2H). | MS (ESI+) m/z 452 (M + H)$^+$. |
| Example GII-11 | 1-[2-(dimethylamino)-5-methylpyridin-4-yl]-N-(quinoline-5-sulfonyl)cyclopropane-1-carboxamide | $^1$H NMR (400 MHz, methanol-$d_4$) δ ppm 9.12 (ddd, J = 8.7, 1.7, 0.9 Hz, 1H), 8.86 (dd, J = 4.3, 1.7 Hz, 1H), 8.26 (dd, J = 7.3, 1.3 Hz, 1H), 8.11 (dt, J = 8.5, 1.1 Hz, 1H), 7.77 (dd, J = 8.5, 7.3 Hz, 1H), 7.61 (t, J = 0.7 Hz, 1H), 7.53 (dd, J = 8.8, 4.3 Hz, 1H), 6.47 (s, 1H), 2.99 (s, 6H), 1.78 (d, J = 0.8 Hz, 3H), 1.41 (q, J = 3.6 Hz, 2H), 1.25 (t, J = 7.3 Hz, 7H), 0.84 (q, J = 3.6 Hz, 2H). | MS (ESI+) m/z 411 (M + H)$^+$. |
| Example GII-12 | 1-[2-methoxy-6-(trifluoromethyl)pyridin-3-yl]-N-(1,2,3,4- | $^1$H NMR (400 MHz, methanol-$d_4$) δ ppm 7.79 (d, J = 7.5 Hz, 1H), 7.35 (d, J = 7.5 Hz, 1H), 7.26 (dd, J = 7.8, 1.2 Hz, 1H), 7.04 (t, J = 8.0 Hz, 1H), 6.75 (dd, J = 8.1, | MS (ESI+) m/z 456 |

TABLE 4-continued

|  | Name | NMR | MS |
| --- | --- | --- | --- |
|  | tetrahydroquinoline-5-sulfonyl)cyclopropane-1-carboxamide | 1.2 Hz, 1H), 3.92 (s, 3H), 3.30-3.24 (m, 2H), 2.92 (t, J = 6.4 Hz, 2H), 1.92-1.82 (m, 2H), 1.57-1.51 (m, 2H), 1.15 (q, J = 4.5 Hz, 2H). | (M + H)$^+$. |
| Example GII-13 | 1-(2-methoxy-5-methylpyridin-4-yl)-N-(quinoline-5-sulfonyl)cyclopropane-1-carboxamide | $^1$H NMR (400 MHz, methanol-d$_4$) δ ppm 9.04-8.95 (m, 2H), 8.44 (dd, J = 7.4, 1.2 Hz, 1H), 8.32 (dt, J = 8.5, 1.1 Hz, 1H), 7.91 (dd, J = 8.5, 7.4 Hz, 1H), 7.81-7.76 (m, 1H), 7.64 (dd, J = 8.8, 4.3 Hz, 1H), 6.72 (s, 1H), 3.90 (s, 3H), 1.77 (d, J = 0.9 Hz, 3H), 1.46-1.39 (m, 2H), 1.10-1.02 (m, 2H). | MS (ESI+) m/z 398 (M + H)$^+$. |
| Example GII-14 | 1-[2-cyclobutyl-6-(trifluoromethyl)pyridin-3-yl]-N-(quinoline-5-sulfonyl)cyclopropane-1-carboxamide | $^1$H NMR (400 MHz, methanol-d$_4$) δ ppm 9.14 (ddd, J = 8.7, 1.6, 0.9 Hz, 1H), 8.90 (dd, J = 4.3, 1.7 Hz, 1H), 8.27 (dd, J = 7.3, 1.2 Hz, 1H), 8.13 (dt, J = 8.5, 1.1 Hz, 1H), 7.78 (dd, J = 8.5, 7.3 Hz, 1H), 7.63 (dd, J = 7.9, 0.8 Hz, 1H), 7.58 (dd, J = 8.7, 4.3 Hz, 1H), 7.41 (d, J = 7.9 Hz, 1H), 3.78-3.65 (m, 1H), 2.26-2.12 (m, 2H), 1.82-1.60 (m, 4H), 1.58 (q, J = 4.5, 3.1 Hz, 2H), 0.88 (d, J = 4.3 Hz, 2H). | MS (ESI+) m/z 476 (M + H)$^+$. |
| Example GII-15 | 1-(2-cyclopropyl-5-methoxypyridin-3-yl)-N-(quinoline-5-sulfonyl)cyclopropane-1-carboxamide | $^1$H NMR (400 MHz, methanol-d$_4$) δ ppm 9.08-9.02 (m, 1H), 8.97 (dd, J = 4.3, 1.6 Hz, 1H), 8.42 (dd, J = 7.4, 1.2 Hz, 1H), 8.29 (dt, J = 8.5, 1.1 Hz, 1H), 7.98 (d, J = 2.8 Hz, 1H), 7.93-7.87 (m, 1H), 7.62 (dd, J = 8.8, 4.3 Hz, 1H), 7.44 (d, J = 2.8 Hz, 1H), 3.90 (s, 3H), 1.88 (tt, J = 8.3, 5.1 Hz, 1H), 1.57 (q, J = 4.1 Hz, 2H), 1.16 (q, J = 4.0 Hz, 2H), 0.76 (dt, J = 6.2, 3.1 Hz, 2H), 0.64 (dt, J = 8.3, 3.2 Hz, 2H). | MS (ESI+) m/z 424 (M + H)$^+$. |
| Example GII-16 | 1-{2-ethyl-5-[(propan-2-yl)oxy]pyridin-3-yl}-N-(quinoline-5-sulfonyl)cyclopropane-1-carboxamide | $^1$H NMR (400 MHz, methanol-d$_4$) δ ppm 9.21-9.11 (m, 1H), 8.90 (dd, J = 4.3, 1.7 Hz, 1H), 8.31-8.23 (m, 1H), 8.13 (dt, J = 8.5, 1.1 Hz, 1H), 7.88 (d, J = 2.8 Hz, 1H), 7.83-7.75 (m, 1H), 7.61-7.53 (m, 1H), 7.13 (d, J = 2.8 Hz, 1H), 4.65-4.51 (m, J = 6.1 Hz, 1H), 2.47 (q, J = 7.6 Hz, 2H), 1.53 (p, J = 3.6 Hz, 2H), 1.34-1.23 (m, 6H), 0.89 (t, J = 7.5 Hz, 5H). | MS (ESI+) m/z 440 (M + H)$^+$. |
| Example GII-17 | 1-(2-ethyl-5-methoxypyridin-3-yl)-N-(quinoline-5-sulfonyl)cyclopropane-1-carboxamide | $^1$H NMR (400 MHz, methanol-d$_4$) δ ppm 9.13 (ddd, J = 8.7, 1.7, 0.9 Hz, 1H), 8.89 (dd, J = 4.3, 1.7 Hz, 1H), 8.25 (dd, J = 7.3, 1.2 Hz, 1H), 8.12 (dt, J = 8.5, 1.1 Hz, 1H), 7.92 (d, J = 2.9 Hz, 1H), 7.78 (dd, J = 8.5, 7.3 Hz, 1H), 7.57 (dd, J = 8.7, 4.3 Hz, 1H), 7.15 (d, J = 2.9 Hz, 1H), 3.81 (s, 3H), 2.46 (q, J = 7.5 Hz, 2H), 1.56-1.49 (m, 2H), 0.95-0.90 (m, 2H), 0.88 (t, J = 7.6 Hz, 3H). | MS (ESI+) m/z 412 (M + H)$^+$. |
| Example GII-18 | 1-[6-(dimethylamino)-2-methoxypyridin-3-yl]-N-(quinoline-5-sulfonyl)cyclopropane-1-carboxamide | $^1$H NMR (400 MHz, methanol-d$_4$) δ ppm 9.17 (ddd, J = 8.7, 1.7, 0.9 Hz, 1H), 8.87 (dd, J = 4.3, 1.6 Hz, 1H), 8.27 (dd, J = 7.4, 1.2 Hz, 1H), 8.11 (dt, J = 8.5, 1.1 Hz, 1H), 7.77 (dd, J = 8.5, 7.3 Hz, 1H), 7.56 (dd, J = 8.7, 4.3 Hz, 1H), 7.20 (d, J = 8.1 Hz, 1H), 5.96 (d, J = 8.1 Hz, 1H), 3.53 (s, 3H), 2.98 (s, 6H), 1.32 (q, J = 3.7 Hz, 2H), 0.74 (q, J = 3.7 Hz, 2H). | MS (ESI+) m/z 427 (M + H)$^+$. |
| Example GII-19 | 1-(6-methoxy-2-methylpyridin-3-yl)-N-(naphthalene-1-sulfonyl)cyclopropane-1-carboxamide | $^1$H NMR (400 MHz, methanol-d$_4$) δ ppm 8.76-8.69 (m, 1H), 8.17 (dd, J = 7.3, 1.3 Hz, 1H), 8.76-8.69 (dt, J = 8.3, 1.1 Hz, 1H), 7.89-7.83 (m, 2H), 7.56-7.48 (m, 2H), 7.45 (dd, J = 8.2, 7.3 Hz, 1H), 7.40 (d, J = 8.3 Hz, 1H), 6.46 (d, J = 8.4 Hz, 1H), 3.80 (s, 3H), 2.16 (s, 3H), 1.49 (q, J = 3.4 Hz, 2H), 0.81 (q, J = 3.4 Hz, 2H). (M + H)$^+$. | MS (ESI+) m/z 387 |
| Example GII-20 | 1-(4-ethylpyridin-3-yl)-N-(naphthalene-1-sulfonyl)cyclopropane-1-carboxamide | $^1$H NMR (400 MHz, methanol-d$_4$) δ ppm 8.74-8.66 (m, 1H), 8.24-8.19 (m, 2H), 8.17 (dd, J = 7.3, 1.3 Hz, 1H7.94 (dt, J = 8.5, 1.2 Hz, 1H), 7.91-7.84 (m, 1H), 7.53 (ddd, J = 5.5, 4.6, 3.3 Hz, 2H), 7.45 (dd, J = 8.2, 7.3 Hz, 1H), 7.15-7.09 (m, 1H), 3.10 (s, 3H), 2.45 (q, J = 7.5 Hz, 2H), 1.55 (d, J = 3.6 Hz, 2H), 0.93 (t, J = 7.5 Hz, 3H), 0.88 (q, J = 3.3 Hz, 2H). | MS (ESI+) m/z 381 (M + H)$^+$. |
| Example GII-21 | 1-(4-ethylpyridin-3-yl)-N-(1,2,3,4-tetrahydroquinoline-5-sulfonyl)cyclopropane-1-carboxamide | $^1$H NMR (400 MHz, methanol-d$_4$) δ ppm 8.30 (s, 1H), 8.26 (d, J = 5.2 Hz, 1H), 7.24 (d, J = 5.2 Hz, 1H), 7.20 (dd, J = 7.8, 1.3 Hz, 1H), 6.90 (t, J = 7.9 Hz, 1H), 6.58 (dd, J = 8.0, 1.2 Hz, 1H), 3.26-3.19 (m, 2H), 3.05 (t, J = 6.4 Hz, 2H), 2.78 (q, J = 7.5 Hz, 2H), 1.89-1.78 (m, 2H), 1.60 (d, J = 3.6 Hz, 2H), 1.21 (t, J = 7.6 Hz, 3H), 0.96 (q, J = 3.3 Hz, 2H). | MS (ESI+) m/z 386 (M + H)$^+$. |
| Example GII-22 | 1-(6-methoxy-4-methylpyridin-3-yl)-N-(naphthalene-1-sulfonyl)cyclopropane-1-carboxamide | $^1$H NMR (400 MHz, methanol-d$_4$) δ ppm 8.74-8.69 (m, 1H), 8.18 (dd, J = 7.3, 1.3 Hz, 1H), 7.97-7.92 (m, 1H), 7.91-7.86 (m, 1H), 7.80 (s, 1H), 7.55-7.50 (m, 2H), 7.47 (dd, J = 8.2, 7.3 Hz, 1H), 6.50-6.45 (m, 1H), 3.81 (s, 3H), 2.00 (d, J = 0.8 Hz, 3H), 1.49 (d, J = 3.4 Hz, 2H), 0.83 (q, J = 3.2 Hz, 2H). | MS (ESI+) m/z 397 (M + H)$^+$. |
| Example GII-23 | 1-(6-methoxy-4-methylpyridin-3-yl)-N-(quinoline-5-sulfonyl)cyclopropane-1-carboxamide | $^1$H NMR (400 MHz, methanol-d$_4$) δ ppm 9.15 (ddd, J = 8.7, 1.7, 0.9 Hz, 1H), 8.89 (dd, J = 4.3, 1.7 Hz, 1H), 8.26 (dd, J = 7.3, 1.3 Hz, 1H), 8.13 (dt, J = 8.5, 1.1 Hz, 1H), 7.83-7.75 (m, 2H), 7.58 (dd, J = 8.8, 4.3 Hz, 1H), 6.52-6.47 (m, 1H), 3.84 (s, 3H), 2.00 (d, J = 0.8 | MS (ESI+) m/z 398 (M + H)$^+$. |

TABLE 4-continued

| | Name | NMR | MS |
|---|---|---|---|
| | | Hz, 3H), 1.47 (d, J = 3.5 Hz, 2H), 0.86 (q, J = 3.2 Hz, 2H). | |
| Example GII-24 | 1-{6-methoxy-4-[(propan-2-yl)oxy]pyridin-3-yl}-N-(1,2,3,4-tetrahydroquinoline-5-sulfonyl)cyclopropane-1-carboxamide | $^1$H NMR (400 MHz, methanol-d$_4$) δ ppm 7.74 (s, 1H), 7.18 (dd, J = 7.8, 1.2 Hz, 1H), 6.88 (t, J = 7.9 Hz, 1H), 6.56 (dd, J = 8.0, 1.2 Hz, 1H), 6.21 (s, 1H), 4.59 (hept, J = 6.0 Hz, 1H), 3.84 (s, 3H), 3.25-3.18 (m, 2H), 3.14-3.05 (m, 2H), 1.89-1.79 (m, 2H), 1.48 (q, J = 3.7 Hz, 2H), 1.22 (t, J = 7.3 Hz, 6H), 0.84 (q, J = 3.8 Hz, 2H). | MS (ESI+) m/z 446 (M + H)$^+$. |
| Example GII-25 | 1-{5-cyclobutyl-2-[(propan-2-yl)oxy]pyridin-3-yl}-N-(1,2,3,4-tetrahydroquinoline-5-sulfonyl)cyclopropane-1-carboxamide | $^1$H NMR (400 MHz, methanol-d$_4$) δ ppm 7.74 (dd, J = 2.4, 0.7 Hz, 1H), 7.43 (d, J = 2.5 Hz, 1H), 7.20 (dd, J = 7.8, 1.2 Hz, 1H), 6.89 (t, J = 7.9 Hz, 1H), 6.56 (dd, J = 8.1, 1.2 Hz, 1H), 5.13 (hept, J = 6.1 Hz, 1H), 3.47 (p, J = 8.5 Hz, 1H), 3.40-3.33 (m, 1H), 3.24-3.19 (m, 2H), 3.05 (t, J = 6.4 Hz, 2H), 2.32-2.25 (m, 2H), 2.18-1.98 (m, 3H), 1.91-1.79 (m, 3H), 1.50 (q, J = 3.9 Hz, 2H), 1.27-1.24 (m, 6H), 0.87 (q, J = 3.9 Hz, 2H). | MS (ESI+) m/z 470 (M + H)$^+$. |
| Example GII-26 | 1-{2-cyclobutyl-5-[(propan-2-yl)oxy]pyridin-4-yl}-N-(1,2,3,4-tetrahydroquinoline-5-sulfonyl)cyclopropane-1-carboxamide | $^1$H NMR (400 MHz, methanol-d$_4$) δ ppm 7.96 (s, 1H), 7.20 (dd, J = 7.7, 1.2 Hz, 1H), 7.14 (s, 1H), 6.88 (t, J = 7.9 Hz, 1H), 6.56 (dd, J = 8.0, 1.2 Hz, 1H), 4.58 (hept, J = 6.0 Hz, 1H), 3.59 (tt, J = 10.0, 8.2 Hz, 1H), 3.23-3.18 (m, 2H), 3.03 (t, J = 6.4 Hz, 2H), 2.36-2.18 (m, 4H), 2.12-1.95 (m, 1H), 1.92-1.77 (m, 3H), 1.50 (q, J = 3.9 Hz, 2H), 1.29-1.24 (m, 6H), 0.90 (q, J = 4.0 Hz, 2H). | MS (ESI+) m/z 470 (M+H)$^+$. |
| Example GII-27 | 1-{5-cyclobutyl-3-[(propan-2-yl)oxy]pyridin-2-yl}-N-(quinoline-5-sulfonyl)cyclopropane-1-carboxamide | $^1$H NMR (400 MHz, methanol-d$_4$) δ ppm 9.18 (ddd, J = 8.8, 1.7, 0.9 Hz, 1H), 8.87 (dd, J = 4.3, 1.6 Hz, 1H), 8.24 (dd, J = 7.3, 1.2 Hz, 1H), 8.10 (dt, J = 8.5, 1.1 Hz, 1H), 7.76 (dd, J = 8.5, 7.3 Hz, 1H), 7.72 (d, J = 1.7 Hz, 1H), 7.57 (dd, J = 8.7, 4.3 Hz, 1H), 7.04 (d, J = 1.8 Hz, 1H), 4.39 (hept, J = 6.0 Hz, 1H), 3.58-3.45 (m, 1H), 2.39-2.26 (m, 2H), 2.19-1.98 (m, 3H), 1.92-1.83 (m, 1H), 1.48 (q, J = 3.9 Hz, 2H), 1.0-0.92 (m, 8H). | MS (ESI+) m/z 466 (M+H)$^+$. |
| Example GII-28 | 1-[5-cyclobutyl-2-(morpholin-4-yl)pyridin-3-yl]-N-(quinoline-5-sulfonyl)cyclopropane-1-carboxamide | $^1$H NMR (400 MHz, methanol-d$_4$) δ ppm 9.18 (ddd, J = 8.7, 1.7, 0.9 Hz, 1H), 8.88 (dd, J = 4.3, 1.7 Hz, 1H), 8.28 (dd, J = 7.3, 1.2 Hz, 1H), 8.15 (dt, J = 8.5, 1.1 Hz, 1H), 7.85 (dd, J = 2.4, 0.7 Hz, 1H), 7.78 (dd, J = 8.5, 7.3 Hz, 1H), 7.57 (dd, J = 8.7, 4.3 Hz, 1H), 7.49 (dd, J = 2.4, 0.6 Hz, 1H), 3.46 (t, J = 4.7 Hz, 5H), 2.96-2.91 (m, 4H), 2.35-2.25 (m, 2H), 2.16-1.98 (m, 3H), 1.92-1.80 (m, 1H), 1.49 (q, J = 3.7 Hz, 2H), 0.99 (q, J = 3.8 Hz, 2H). | MS (ESI+) m/z 493 (M+H)$^+$. |
| Example GII-29 | 1-[5-cyclopropyl-2-(pyrrolidin-1-yl)pyridin-3-yl]-N-(1,2,3,4-tetrahydroquinoline-5-sulfonyl)cyclopropane-1-carboxamide | $^1$H NMR (400 MHz, methanol-d$_4$) δ ppm 7.65 (d, J = 2.4 Hz, 1H), 7.25-7.18 (m, 2H), 6.89 (t, J = 7.9 Hz, 1H), 6.56 (dd, J = 8.0, 1.3 Hz, 1H), 3.56-3.40 (m, 4H), 3.22 (t, J = 5.6 Hz, 2H), 3.11 (t, J = 6.5 Hz, 2H), 1.90-1.69 (m, 7H), 1.55 (q, J = 3.6 Hz, 2H), 0.95 (q, J = 3.6 Hz, 2H), 0.90-0.79 (m, 2H), 0.60-0.52 (m, 2H). | MS (ESI+) m/z 467 (M + H)$^+$. |
| Example GII-30 | 1-[5-ethyl-2-(pyrrolidin-1-yl)pyridin-3-yl]-N-(quinoline-5-sulfonyl)cyclopropane-1-carboxamide | $^1$H NMR (400 MHz, methanol-d$_4$) δ ppm 9.19-9.12 (m, 1H), 8.91 (dd, J = 4.3, 1.6 Hz, 1H), 8.31 (dd, J = 7.3, 1.2 Hz, 1H), 8.15 (dt, J = 8.5, 1.1 Hz, 1H), 7.84-7.79 (m, 1H), 7.74 (d, J = 2.2 Hz, 1H), 7.60 (dd, J = 8.7, 4.3 Hz, 1H), 7.44 (dd, J = 2.2, 1.0 Hz, 1H), 3.47-3.40 (m, 4H), 2.55 (q, J = 7.6 Hz, 2H), 1.65-1.57 (m, 6H), 1.20 (t, J = 7.6 Hz, 3H), 1.17-1.12 (m, 2H). | MS (ESI+) m/z 451 (M + H)$^+$. |
| Example GII-31 | 1-[5-ethyl-2-(pyrrolidin-1-yl)pyridin-3-yl]-N-(2-methylquinoline-5-sulfonyl)cyclopropane-1-carboxamide | $^1$H NMR (400 MHz, DMSO-d$_6$) δ ppm 8.91 (d, J = 8.8 Hz, 1H), 8.06-7.91 (m, 2H), 7.70 (t, J = 7.9 Hz, 1H), 7.64-7.57 (m, 2H), 7.46 (d, J = 8.8 Hz, 1H), 3.30-3.15 (m, 4H), 2.67 (s, 3H), 2.55-2.45 (m, 2H), 1.55-1.32 (m, 6H), 1.13 (t, J = 7.5 Hz, 3H), 1.09-0.98 (m, 2H). | MS (ESI+) m/z 465 (M + H)$^+$. |
| Example GII-32 | 1-[5-ethyl-2-(morpholin-4-yl)pyridin-3-yl]-N-(2-methylquinoline-5-sulfonyl)cyclopropane-1-carboxamide | $^1$H NMR (400 MHz, methanol-d$_4$) δ ppm 9.04 (d, J = 8.8 Hz, 1H), 8.22-8.15 (m, 1H), 8.04 (d, J = 8.4 Hz, 1H), 7.86 (d, J = 2.5 Hz, 1H), 7.77-7.68 (m, 1H), 7.49-7.43 (m, 2H), 3.50-3.43 (m, 4H), 2.98-2.88 (m, 4H), 2.74 (s, 3H), 2.54 (q, J = 7.6 Hz, 2H), 1.50 (q, J = 3.7 Hz, 2H), 1.18 (t, J = 7.6 Hz, 3H), 1.00 (q, J = 3.8 Hz, 2H). | MS (ESI+) m/z 481 (M + H)$^+$. |
| Example GII-33 | 1-[2-(pyrrolidin-1-yl)pyridin-3-yl]-N-(quinoline-5-sulfonyl)cyclopropane-1-carboxamide | $^1$H NMR (400 MHz, methanol-d$_4$) δ ppm 9.17 (ddd, J = 8.7, 1.7, 0.9 Hz, 1H), 8.84 (dd, J = 4.3, 1.7 Hz, 1H), 8.24 (dd, J = 7.3, 1.2 Hz, 1H), 8.08 (dt, J = 8.5, 1.1 Hz, 1H), 7.79-7.69 (m, 2H), 7.54 (dd, J = 8.7, 4.3 Hz, 1H), 7.38 (dd, J = 7.3, 1.9 Hz, 1H), 6.52 (dd, J = 7.4, 5.0 Hz, 1H), 3.15 (d, J = 6.3 Hz, 4H), 1.50 (q, J = 3.6 Hz, 2H), 1.41-1.31 (m, 4H), 0.90 (q, J = 3.2 Hz, 2H). | MS (ESI+) m/z 423 (M + H)$^+$. |
| Example GII-34 | N-(2-methylquinoline-5-sulfonyl)-1-[2- | $^1$H NMR (400 MHz, methanol-d$_4$) δ ppm 9.06 (d, J = 8.8 Hz, 1H), 8.25 (d, J = 7.3 Hz, 1H), 7.85-7.75 (m, | MS (ESI+) |

TABLE 4-continued

| Name | NMR | MS |
|---|---|---|
| | (pyrrolidin-1-yl)pyridin-3-yl]cyclopropane-1-carboxamide | 3H), 7.68 (d, J = 6.3 Hz, 1H), 7.54 (d, J = 8.9 Hz, 1H), 6.82 (t, J = 6.7 Hz, 1H), 3.54-3.40 (d, J = 6.3 Hz, 4H), 2.76 (s, 3H), 1.69-1.57 (m, 6H), 1.20-1.13 (m, 2H). | m/z 437 (M + H)$^+$. |
| Example GII-35 | 1-[5-ethyl-2-(pyrrolidin-1-yl)pyridin-3-yl]-N-(1,2,3,4-tetrahydroquinoline-5-sulfonyl)cyclopropane-1-carboxamide | $^1$H NMR (400 MHz, methanol-d$_4$) δ ppm 7.65 (d, J = 2.3 Hz, 1H), 7.42 (d, J = 2.4 Hz, 1H), 7.20 (dd, J = 7.7, 1.2 Hz, 1H), 6.89 (t, J = 7.9 Hz, 1H), 6.57 (dd, J = 8.1, 1.2 Hz, 1H), 3.57-3.44 (m, 4H), 3.25-3.18 (m, 2H), 3.11 (t, J = 6.4 Hz, 2H), 2.49 (q, J = 7.6 Hz, 2H), 1.85-1.79 (m, 4H), 1.68 (dd, J = 5.9, 1.9 Hz, 2H), 1.58 (q, J = 3.6 Hz, 2H), 1.17 (t, J = 7.6 Hz, 3H), 1.02-0.99 (m, 2H). | MS (ESI+) m/z 455 (M + H)$^+$. |
| Example GII-36 | 1-[5-methyl-2-(pyrrolidin-1-yl)pyridin-3-yl]-N-(2-methylquinoline-5-sulfonyl)cyclopropane-1-carboxamide | $^1$H NMR (400 MHz, methanol-d$_4$) δ ppm 9.07 (dd, J = 8.8, 0.8 Hz, 1H), 8.21 (dd, J = 7.3, 1.2 Hz, 1H), 8.04 (dt, J = 8.5, 1.1 Hz, 1H), 7.73 (dd, J = 8.5, 7.3 Hz, 1H), 7.61 (dd, J = 2.3, 0.9 Hz, 1H), 7.47 (d, J = 8.9 Hz, 1H), 7.34 (d, J = 2.3 Hz, 1H), 3.22-3.14 (m, 4H), 2.74 (s, 3H), 2.14 (s, 3H), 1.54 (q, J = 3.6 Hz, 2H), 1.47-1.39 (m, 4H), 0.95 (q, J = 3.5 Hz, 2H). | MS (ESI+) m/z 451 (M + H)$^+$. |
| Example GII-37 | N-(1H-indole-4-sulfonyl)-1-[5-methyl-2-(pyrrolidin-1-yl)pyridin-3-yl]cyclopropane-1-carboxamide | $^1$H NMR (400 MHz, methanol-d$_4$) δ ppm 7.65-7.56 (m, 2H), 7.49 (dt, J = 8.1, 0.9 Hz, 1H), 7.36 (d, J = 2.3 Hz, 1H), 7.31 (d, J = 3.1 Hz, 1H), 7.11 (t, J = 7.8 Hz, 1H), 6.86 (dd, J = 3.1, 0.9 Hz, 1H), 3.27 (t, J = 5.4 Hz, 4H), 2.13 (s, 3H), 1.60 (q, J = 3.6 Hz, 2H), 1.52 (dq, J = 9.1, 5.7, 4.5 Hz, 4H), 0.95 (q, J = 3.6 Hz, 2H). | MS (ESI+) m/z 425 (M + H)$^+$. |
| Example GII-38 | 1-[5-methyl-2-(pyrrolidin-1-yl)pyridin-3-yl]-N-(quinoline-5-sulfonyl)cyclopropane-1-carboxamide | $^1$H NMR (400 MHz, methanol-d$_4$) δ ppm 9.24-9.17 (m, 1H), 8.89 (dd, J = 4.3, 1.7 Hz, 1H), 8.29 (dd, J = 7.3, 1.3 Hz, 1H), 8.12 (d, J = 8.5 Hz, 1H), 7.79 (dd, J = 8.5, 7.3 Hz, 1H), 7.63-7.55 (m, 2H), 7.35 (d, J = 2.3 Hz, 1H), 3.18 (d, J = 6.3 Hz, 4H), 2.14 (s, 3H), 1.55 (q, J = 3.6 Hz, 2H), 1.48-1.37 (m, 4H), 0.96 (q, J = 3.5 Hz, 2H). | MS (ESI+) m/z 437 (M + H)$^+$. |
| Example GII-39 | 1-(3-cyclopropyl-5-methylpyridin-2-yl)-N-(1H-indole-4-sulfonyl)cyclopropane-1-carboxamide | $^1$H NMR (400 MHz, methanol-d$_4$) δ ppm 7.92 (dd, J = 2.2, 0.9 Hz, 1H), 7.59 (dd, J = 7.4, 0.9 Hz, 1H), 7.48 (dt, J = 8.1, 1.0 Hz, 1H), 7.29 (d, J = 3.2 Hz, 1H), 7.09 (t, J = 7.8 Hz, 1H), 6.95 (d, J = 2.1 Hz, 1H), 6.89 (d, J = 3.1, 0.9 Hz, 1H), 2.21 (s, 3H), 1.92 (tt, J = 8.5, 5.3 Hz, 1H), 1.67 (q, J = 3.7 Hz, 2H), 1.09 (q, J = 3.7 Hz, 2H), 0.72-0.61 (m, 2H), 0.55-0.46 (m, 2H). | MS (ESI+) m/z 396 (M + H)$^+$. |
| Example GII-40 | 1-[5-methoxy-2-(pyrrolidin-1-yl)pyridin-3-yl]-N-(quinoline-5-sulfonyl)cyclopropane-1-carboxamide | $^1$H NMR (400 MHz, methanol-d$_4$) δ ppm 9.23 (ddd, J = 8.8, 1.7, 0.9 Hz, 1H), 8.90 (dd, J = 4.3, 1.7 Hz, 1H), 8.30 (dd, J = 7.3, 1.2 Hz, 1H), 8.13 (dt, J = 8.5, 1.1 Hz, 1H), 7.79 (dd, J = 8.5, 7.3 Hz, 1H), 7.63-7.54 (m, 2H), 7.17 (d, J = 3.0 Hz, 1H), 3.75 (s, 3H), 3.12 (q, J = 5.8, 4.6 Hz, 4H), 1.55 (q, J = 3.7 Hz, 2H), 1.48-1.37 (m, 4H), 0.98 (q, J = 3.7 Hz, 2H). | MS (ESI+) m/z 453 (M + H)$^+$. |
| Example GII-41 | 1-[2-(dimethylamino)-5-methylpyridin-3-yl]-N-(quinoline-5-sulfonyl)cyclopropane-1-carboxamide | $^1$H NMR (400 MHz, DMSO-d$_6$) δ ppm 9.04 (dd, J = 8.8, 1.7 Hz, 1H), 8.96-8.91 (m, 1H), 8.16-8.06 (m, 2H), 7.85-7.70 (m, 2H), 7.61-7.53 (m, 1H), 7.31 (s, 1H), 2.74 (s, 3H), 2.60 (s, 6H), 1.29 (q, J = 3.6 Hz, 2H), 0.89-0.83 (m, 2H). | MS (ESI+) m/z 411 (M + H)$^+$. |
| Example GII-42 | 1-[5-methoxy-2-(2-methoxyethoxy)pyridin-3-yl]-N-(2-methylquinoline-5-sulfonyl)cyclopropane-1-carboxamide | $^1$H NMR (400 MHz, methanol-d$_4$) δ ppm 8.86 (dd, J = 8.9, 0.9 Hz, 1H), 8.40 (dd, J = 7.4, 1.3 Hz, 1H), 8.27 (dt, J = 8.5, 1.1 Hz, 1H), 7.90 (dd, J = 8.5, 7.4 Hz, 1H), 7.74 (d, J = 2.9 Hz, 1H), 7.55 (d, J = 8.9 Hz, 1H), 7.24 (d, J = 3.0 Hz, 1H), 4.01-3.94 (m, 2H), 3.84 (s, 3H), 3.22 (s, 3H), 3.21-3.17 (m, 2H), 2.79 (s, 3H), 1.43-1.35 (m, 2H), 1.08-1.01 (m, 2H). | MS (ESI+) m/z 472 (M + H)$^+$. |
| Example GII-43 | N-(1H-indole-4-sulfonyl)-1-[5-methoxy-2-(2-methoxyethoxy)pyridin-3-yl]cyclopropane-1-carboxamide | $^1$H NMR (400 MHz, methanol-d$_4$) δ ppm 7.78 (dd, J = 7.5, 0.9 Hz, 1H), 7.76-7.70 (m, 2H), 7.45 (d, J = 3.1 Hz, 1H), 7.31-7.21 (m, 2H), 6.74 (d, J = 3.2, 0.9 Hz, 1H), 4.06-3.99 (m, 2H), 3.83 (s, 3H), 3.23 (s, 3H), 3.21-3.14 (m, 2H), 1.45-1.37 (m, 2H), 1.04 (q, J = 4.5 Hz, 2H). | MS (ESI+) m/z 446 (M + H)$^+$. |
| Example GII-44 | 1-[5-methoxy-2-(2-methoxyethoxy)pyridin-3-yl]-N-(quinoline-5-sulfonyl)cyclopropane-1-carboxamide | $^1$H NMR (400 MHz, methanol-d$_4$) δ ppm 9.03-8.96 (m, 2H), 8.48 (dd, J = 7.5, 1.2 Hz, 1H), 8.36 (d, J = 8.5 Hz, 1H), 7.95 (dd, J = 8.5, 7.4 Hz, 1H), 7.74 (d, J = 3.0 Hz, 1H), 7.69-7.61 (m, 1H), 7.24 (d, J = 3.0 Hz, 1H), 4.01-3.94 (m, 2H), 3.84 (s, 3H), 3.25-3.17 (m, 5H), 1.43-1.34 (m, 2H), 1.05 (q, J = 4.5 Hz, 2H). | MS (ESI+) m/z 458 (M + H)$^+$. |
| Example GII-45 | N-(1H-indole-4-sulfonyl)-1-[2-methoxy-5-(2-methoxyethoxy)pyridin-4-yl]cyclopropane-1-carboxamide | $^1$H NMR (400 MHz, methanol-d$_4$) δ ppm 7.79 (dd, J = 7.6, 0.9 Hz, 1H), 7.75 (dt, J = 8.1, 0.9 Hz, 1H), 7.65 (s, 1H), 7.47 (d, J = 3.1 Hz, 1H), 7.28 (t, J = 7.8 Hz, 1H), 6.77 (dd, J = 3.1, 0.9 Hz, 1H), 6.68 (s, 1H), 3.88 (s, 3H), 3.75-3.68 (m, 2H), 3.23 (s, 3H), 3.11-3.04 (m, 2H), 1.45-1.38 (m, 2H), 1.10-1.03 (m, 2H). | MS (ESI+) m/z 446 (M + H)$^+$. |
| Example GII-46 | 1-[2-methoxy-5-(2-methoxyethoxy)pyridin- | $^1$H NMR (400 MHz, methanol-d$_4$) δ ppm 8.88 (dd, J = 8.9, 0.9 Hz, 1H), 8.40 (dd, J = 7.5, 1.2 Hz, 1H), 8.27 | MS (ESI+) |

TABLE 4-continued

| | Name | NMR | MS |
|---|---|---|---|
| | 4-yl]-N-(2-methylquinoline-5-sulfonyl)cyclopropane-1-carboxamide | (dt, J = 8.5, 1.1 Hz, 1H), 7.90 (dd, J = 8.5, 7.4 Hz, 1H), 7.65 (s, 1H), 7.57 (d, J = 8.9 Hz, 1H), 6.66 (s, 1H), 3.88 (s, 3H), 3.75-3.68 (m, 2H), 3.22 (s, 3H), 3.16-3.09 (m, 2H), 2.80 (s, 3H), 1.42-1.35 (m, 2H), 1.10-1.03 (m, 2H). | m/z 472 (M + H)$^+$. |
| Example GII-47 | 1-[2-(dimethylamino)-5-ethylpyridin-3-yl]-N-(quinoline-5-sulfonyl)cyclopropane-1-carboxamide | $^1$H NMR (400 MHz, chloroform-d) δ ppm 8.99 (dd, J = 4.2, 1.6 Hz, 1H), 8.93 (dt, J = 8.8, 1.2 Hz, 1H), 8.50 (dd, J = 7.5, 1.2 Hz, 1H), 8.38 (dt, J = 8.4, 1.1 Hz, 1H), 8.18 (d, J = 2.3 Hz, 1H), 8.12 (s, 1H), 7.84 (dd, J = 8.5, 7.5 Hz, 1H), 7.48 (dd, J = 8.7, 4.2 Hz, 1H), 7.34 (d, J = 2.3 Hz, 1H), 5.30 (s, 1H), 2.94 (s, 6H), 2.58 (q, J = 7.6 Hz, 2H), 1.55 (q, J = 4.2 Hz, 2H), 1.21 (t, J = 7.6 Hz, 3H), 1.11 (q, J = 4.3 Hz, 2H). | MS (ESI+) m/z 425 (M + H)$^+$. |
| Example GII-48 | 1-[2-(dimethylamino)-5-ethylpyridin-3-yl]-N-(2-methylquinoline-5-sulfonyl)cyclopropane-1-carboxamide | $^1$H NMR (400 MHz, chloroform-d) δ ppm 8.76 (dd, J = 8.8, 0.9 Hz, 1H), 8.41 (dd, J = 7.5, 1.2 Hz, 1H), 8.26 (dt, J = 8.5, 1.1 Hz, 1H), 8.19 (d, J = 2.3 Hz, 1H), 7.78 (dd, J = 8.5, 7.5 Hz, 1H), 7.36-7.29 (m, 2H), 2.92 (s, 6H), 2.75 (s, 3H), 2.61-2.54 (m, 2H), 1.54 (q, J = 4.2 Hz, 2H), 1.22 (t, J = 7.6 Hz, 3H), 1.11 (q, J = 4.3 Hz, 2H). | MS (ESI+) m/z 439 (M + H)$^+$. |
| Example GII-49 | 1-[2-(dimethylamino)-5-ethylpyridin-3-yl]-N-(1H-indole-4-sulfonyl)cyclopropane-1-carboxamide | $^1$H NMR (400 MHz, DMSO-d$_6$) δ ppm 11.60 (s, 1H), 7.98 (d, J = 2.3 Hz, 1H), 7.69 (d, J = 8.1 Hz, 1H), 7.62-7.54 (m, 2H), 7.30 (d, J = 2.3 Hz, 1H), 7.21 (t, J = 7.8 Hz, 1H), 6.88-6.82 (m, 1H), 2.52 (s, 6H), 2.52-2.48 (m, 2H), 1.37 (q, J = 4.3 Hz, 2H), 1.17 (t, J = 7.6 Hz, 3H), 1.10 (q, J = 4.4 Hz, 2H). | MS (ESI+) m/z 413 (M + H)$^+$. |
| Example GII-50 | 1-[2-(2-methoxyethoxy)-5-methylpyridin-3-yl]-N-(2-methylquinoline-5-sulfonyl)cyclopropane-1-carboxamide | $^1$H NMR (400 MHz, methanol-d$_4$) δ ppm 8.83 (dd, J = 8.9, 0.9 Hz, 1H), 8.37 (dd, J = 7.5, 1.2 Hz, 1H), 8.24 (dt, J = 8.5, 1.1 Hz, 1H), 7.92-7.83 (m, 2H), 7.52 (d, J = 8.9 Hz, 1H), 7.42-7.37 (m, 1H), 4.01-3.94 (m, 2H), 3.19 (s, 3H), 3.19-3.15 (m, 2H), 2.77 (s, 3H), 2.24 (s, 3H), 1.36 (q, J = 4.4 Hz, 2H), 1.04-0.98 (m, 2H). | MS (ESI+) m/z 456 (M + H)$^+$. |
| Example GII-51 | 1-{2-(dimethylamino)-6-[(propan-2-yl)oxy]pyridin-3-yl}-N-(quinoline-5-sulfonyl)cyclopropane-1-carboxamide | $^1$H NMR (400 MHz, methanol-d$_4$,) δ ppm 9.08 (dt, J = 8.7, 1.3 Hz, 1H), 9.02-8.94 (m, 1H), 8.44 (dd, J = 7.4, 1.3 Hz, 1H), 8.30 (dt, J = 8.5, 1.1 Hz, 1H), 7.91 (dd, J = 8.6, 7.5 Hz, 1H), 7.64 (dd, J = 8.8, 4.3 Hz, 1H), 7.42 (d, J = 8.3 Hz, 1H), 6.34 (d, J = 8.3 Hz, 1H), 5.26 (hept, J = 6.2 Hz, 1H), 2.96 (s, 1H), 2.81 (s, 6H), 1.43 (q, J = 4.1 Hz, 2H), 1.35 (d, J = 6.2 Hz, 6H), 1.10 (q, J = 4.1 Hz, 2H). | MS (ESI+) m/z 455 (M + H)$^+$. |
| Example GII-52 | 1-[2-(2-methoxyethoxy)-5-methylpyridin-3-yl]-N-(quinoline-5-sulfonyl)cyclopropane-1-carboxamide | $^1$H NMR (400 MHz, methanol-d$_4$) δ ppm 9.04-8.96 (m, 2H), 8.49 (dd, J = 7.5, 1.3 Hz, 1H), 8.37 (dt, J = 8.5, 1.1 Hz, 1H), 7.95 (dd, J = 8.5, 7.4 Hz, 1H), 7.89 (dd, J = 2.4, 1.0 Hz, 1H), 7.65 (dd, J = 8.7, 4.4 Hz, 1H), 7.45-7.40 (m, 1H), 4.03-3.96 (m, 2H), 3.25-3.17 (m, 5H), 2.28 (s, 3H), 1.41-1.35 (m, 2H), 1.07-1.00 (m, 2H). | MS (ESI+) m/z 442 (M + H)$^+$. |
| Example GII-53 | N-(1H-indole-4-sulfonyl)-1-[2-(2-methoxyethoxy)-5-methylpyridin-3-yl]cyclopropane-1-carboxamide | $^1$H NMR (400 MHz, methanol-d$_4$) δ ppm 7.72 (dd, J = 2.4, 1.0 Hz, 1H), 7.64 (dd, J = 7.5, 0.9 Hz, 1H), 7.52 (dt, J = 8.1, 0.9 Hz, 1H), 7.40-7.35 (m, 1H), 7.31 (d, J = 3.2 Hz, 1H), 7.14 (t, J = 7.8 Hz, 1H), 6.83 (dd, J = 3.1, 0.9 Hz, 1H), 4.17-4.09 (m, 2H), 3.38-3.34 (m, 3H), 3.29 (s, 3H), 2.22 (d, J = 0.7 Hz, 3H), 1.47 (q, J = 3.9 Hz, 2H), 0.85 (q, J = 3.9 Hz, 2H). | MS (ESI+) m/z 430 (M + H)$^+$. |
| Example GII-54 | 1-(5-ethyl-2-{4-[(propan-2-yl)oxy]piperidin-1-yl}pyridin-3-yl)-N-(quinoline-5-sulfonyl)cyclopropane-1-carboxamide | $^1$H NMR (400 MHz, methanol-d$_4$) δ ppm 9.19 (ddd, J = 8.7, 1.7, 0.9 Hz, 1H), 8.88 (dd, J = 4.3, 1.7 Hz, 1H), 8.27 (dd, J = 7.3, 1.2 Hz, 1H), 8.12 (dt, J = 8.5, 1.1 Hz, 1H), 7.84-7.74 (m, 2H), 7.58 (dd, J = 8.7, 4.3 Hz, 1H), 7.45 (d, J = 2.4 Hz, 1H), 3.68 (hept, J = 6.1 Hz, 1H), 3.39-3.22 (m, 3H), 2.61 (ddd, J = 12.9, 10.2, 2.8 Hz, 2H), 2.53 (q, J = 7.6 Hz, 2H), 1.50 (dq, J = 14.3, 3.8 Hz, 4H), 1.32 (dtd, J = 12.9, 9.5, 3.6 Hz, 2H), 1.17 (t, J = 7.6 Hz, 3H), 1.13 (d, J = 6.1 Hz, 6H), 0.97 (q, J = 3.7 Hz, 2H). | MS (ESI+) m/z 523 (M + H)$^+$. |
| Example GII-55 | 1-(5-ethyl-2-{4-[(propan-2-yl)oxy]piperidin-1-yl}pyridin-3-yl)-N-(2-methylquinoline-5-sulfonyl)cyclopropane-1-carboxamide | $^1$H NMR (400 MHz, methanol-d$_4$) δ ppm 9.05 (dd, J = 8.9, 0.8 Hz, 1H), 8.20 (dd, J = 7.3, 1.2 Hz, 1H), 8.03 (dt, J = 8.5, 1.1 Hz, 1H), 7.80 (d, J = 2.4 Hz, 1H), 7.72 (dd, J = 8.5, 7.3 Hz, 1H), 7.49-7.43 (m, 2H), 3.69 (hept, J = 6.1 Hz, 1H), 3.35 (dt, J = 8.7, 4.2 Hz, 1H), 3.29-3.22 (m, 2H), 2.74 (s, 3H), 2.60 (ddd, J = 12.9, 10.3, 2.7 Hz, 2H), 2.53 (q, J = 7.6 Hz, 2H), 1.50 (dq, J = 14.7, 4.0 Hz, 4H), 1.37-1.29 (m, 2H), 1.18 (t, J = 7.6 Hz, 3H), 1.14 (d, J = 6.1 Hz, 6H), 0.97 (q, J = 3.7 Hz, 2H). | MS (ESI+) m/z 537 (M + H)$^+$. |
| Example GII-56 | 1-[5-ethyl-2-(2-methoxyethoxy)pyridin-3-yl]-N-(2- | $^1$H NMR (400 MHz, chloroform-d) δ ppm 8.70 (d, J = 8.9 Hz, 1H), 8.39-8.32 (m, 1H), 8.23 (dt, J = 8.5, 1.1 Hz, 1H), 7.91 (d, J = 2.4 Hz, 1H), 7.78-7.69 (m, 1H), | MS (ESI+) m/z 470 |

TABLE 4-continued

| | Name | NMR | MS |
|---|---|---|---|
| | methylquinoline-5-sulfonyl)cyclopropane-1-carboxamide | 7.32 (d, J = 8.9 Hz, 1H), 7.25 (d, J = 2.4 Hz, 1H), 4.42-4.35 (m, 2H), 3.56-3.49 (m, 2H), 3.32 (s, 3H), 2.74 (s, 3H), 2.50 (q, J = 7.6 Hz, 2H), 1.45 (q, J = 4.3 Hz, 2H), 1.16 (t, J = 7.6 Hz, 3H), 0.94 (q, J = 4.4 Hz, 2H). | (M + H)+. |
| Example GII-57 | 1-[5-ethyl-2-(4-methoxypiperidin-1-yl)pyridin-3-yl]-N-(quinoline-5-sulfonyl)cyclopropane-1-carboxamide | $^1$H NMR (400 MHz, chloroform-d) δ ppm 8.96 (dd, J = 4.2, 1.6 Hz, 1H), 8.83 (ddd, J = 8.8, 1.7, 0.9 Hz, 1H), 8.50 (dd, J = 7.5, 1.3 Hz, 1H), 8.35 (dt, J = 8.5, 1.1 Hz, 1H), 8.23-8.17 (m, 1H), 7.82 (dd, J = 8.5, 7.4 Hz, 1H), 7.42 (dd, J = 8.8, 4.2 Hz, 1H), 7.30 (d, J = 2.4 Hz, 1H), 3.45-3.37 (m, 3H), 3.37 (s, 3H), 3.02 (ddd, J = 12.2, 8.6, 3.3 Hz, 2H), 2.58 (q, J = 7.6 Hz, 2H), 2.03-1.91 (m, 2H), 1.74 (dtd, J = 12.7, 8.1, 3.5 Hz, 2H), 1.55 (q, J = 4.2 Hz, 2H), 1.21 (t, J = 7.6 Hz, 3H), 1.12 (q, J = 4.3 Hz, 2H). | MS (ESI+) m/z 495 (M + H)+. |
| Example GII-58 | 1-[5-ethyl-2-(4-methoxypiperidin-1-yl)pyridin-3-yl]-N-(1H-indole-4-sulfonyl)cyclopropane-1-carboxamide | $^1$H NMR (400 MHz, chloroform-d) δ ppm 8.57 (s, 1H), 8.16 (d, J = 2.3 Hz, 1H), 7.92 (dd, J = 7.6, 0.9 Hz, 1H), 7.64 (dt, J = 8.0, 1.0 Hz, 1H), 7.35 (dd, J = 2.8, 1.2 Hz, 1H), 7.30 (t, J = 7.9 Hz, 1H), 6.82 (ddd, J = 3.1, 2.0, 0.9 Hz, 1H), 3.33 (s, 3H), 3.28 (td, J = 8.1, 4.1 Hz, 2H), 2.87 (ddd, J = 12.4, 9.2, 3.1 Hz, 2H), 2.60 (q, J = 7.6 Hz, 2H), 1.85-1.76 (m, 2H), 1.56 (dq, J = 12.0, 4.0 Hz, 5H), 1.24 (t, J = 7.6 Hz, 3H), 1.14 (q, J = 4.2 Hz, 2H). | MS (ESI+) m/z 483 (M + H)+. |
| Example GII-59 | 1-{5-ethyl-2-[4-(methoxymethyl)piperidin-1-yl]pyridin-3-yl}-N-(quinoline-5-sulfonyl)cyclopropane-1-carboxamide | $^1$H NMR (400 MHz, chloroform-d) δ ppm 8.96 (dd, J = 4.3, 1.6 Hz, 1H), 8.92 (dt, J = 8.8, 1.3 Hz, 1H), 8.48 (dd, J = 7.5, 1.2 Hz, 1H), 8.37 (dt, J = 8.5, 1.1 Hz, 1H), 8.13 (d, J = 2.3 Hz, 1H), 7.83 (dd, J = 8.5, 7.4 Hz, 1H), 7.45 (dd, J = 8.8, 4.3 Hz, 1H), 7.37 (d, J = 2.3 Hz, 1H), 3.47 (dd, J = 13.0, 3.5 Hz, 2H), 3.34 (s, 3H), 3.23 (d, J = 6.1 Hz, 2H), 2.95 (td, J = 12.4, 2.4 Hz, 2H), 2.55 (q, J = 7.6 Hz, 2H), 1.80-1.66 (m, 3H), 1.55 (q, J = 4.3 Hz, 2H), 1.48-1.33 (m, 2H), 1.18 (t, J = 7.6 Hz, 3H), 1.09 (q, J = 4.3 Hz, 2H). | MS (ESI+) m/z 509 (M + H)+. |

TABLE 5

| | | NMR | MS |
|---|---|---|---|
| Example GIII-1 | 1-[3-chloro-5-(trifluoromethyl)pyridin-2-yl]-N-(quinoline-5-sulfonyl)cyclopropane-1-carboxamide | $^1$H NMR (400 MHz, methanol-d$_4$) δ ppm 9.08 (dt, J = 8.8, 1.2 Hz, 1H), 8.99 (dd, J = 4.3, 1.6 Hz, 1H), 8.73 (dt, J = 2.8, 1.4 Hz, 1H), 8.46 (dd, J = 7.4, 1.2 Hz, 1H), 8.33 (dt, J = 8.5, 1.1 Hz, 1H), 8.17 (dd, J = 32.2, 2.1 Hz, 1H), 7.92 (dd, J = 8.5, 7.4 Hz, 1H), 7.69 (dd, J = 8.8, 4.3 Hz, 1H), 1.53 (q, J = 4.4, 4.0 Hz, 2H), 1.38 (q, J = 4.8, 4.4 Hz, 2H). | LC/MS (ESI+) m/z 456 and 458 (M + H)+. |
| Example GIII-2 | 1-[5-chloro-2-(trifluoromethyl)pyridin-3-yl]-N-(quinoline-5-sulfonyl)cyclopropane-1-carboxamide | $^1$H NMR (400 MHz, chloroform-d) δ ppm 9.10 (dd, J = 4.2, 1.6 Hz, 1H), 8.76 (dd, J = 8.7, 1.5 Hz, 1H), 8.55-8.47 (m, 2H), 7.90 (dd, J = 8.5, 7.5 Hz, 1H), 7.81 (d, J = 2.2 Hz, 1H), 7.61 (dd, J = 8.8, 4.2 Hz, 1H), 7.25 (s, 1H), 1.75-1.64 (m, 2H), 1.24-1.13 (m, 2H) | LC/MS (ESI+) m/z 456 (M + H)+. |
| Example GIII-3 | N-(1H-indole-4-sulfonyl)-1-{6-methoxy-4-[(propan-2-yl)oxy]pyridin-3-yl}cyclopropane-1-carboxamide | $^1$H NMR (400 MHz, methanol-d$_4$) δ ppm 7.74 (s, 1H), 7.61 (dd, J = 7.5, 1.0 Hz, 1H), 7.50 (dt, J = 8.1, 1.0 Hz, 1H), 7.31 (d, J = 3.2 Hz, 1H), 7.12 (t, J = 7.8 Hz, 1H), 6.90 (dd, J = 3.1, 1.0 Hz, 1H), 6.18 (s, 1H), 4.51 (hept, J = 6.0 Hz, 1H), 3.85 (s, 3H), 1.50 (q, J = 3.8 Hz, 2H), 1.13 (d, J = 6.0 Hz, 6H), 0.82 (q, J = 3.8 Hz, 2H). | LC/MS (ESI+) m/z 430 (M + H)+. |
| Example GIII-4 | 1-(3-cyclopropyl-5-methylpyridin-2-yl)-N-(quinoline-5-sulfonyl)cyclopropane-1-carboxamide | $^1$H NMR (400 MHz, methanol-d$_4$) δ ppm 9.19 (ddd, J = 8.8, 1.7, 0.9 Hz, 1H), 8.87 (dd, J = 4.3, 1.7 Hz, 1H), 8.28 (dd, J = 7.3, 1.3 Hz, 1H), 8.10 (dt, J = 8.5, 1.1 Hz, 1H), 7.94-7.87 (m, 1H), 7.77 (dd, J = 8.5, 7.3 Hz, 1H), 7.57 (dd, J = 8.7, 4.3 Hz, 1H), 6.94 (d, J = 2.1 Hz, 1H), 2.22 (s, 3H), 1.78 (tt, J = 8.4, 5.3 Hz, 1H), 1.57 (q, J = 3.7 Hz, 2H), 1.07 (q, J = 3.7 Hz, 2H), 0.63-0.53 (m, 2H), 0.51-0.43 (m, 2H). | LC/MS (ESI+) m/z 408 (M + H)+. |
| Example GIII-5 | 1-[2-chloro-5-(2-methylpropoxy)pyridin-3-yl]-N-(quinoline-5-sulfonyl)cyclopropane-1-carboxamide | $^1$H NMR (400 MHz, methanol-d$_4$) δ ppm 9.07 (dt, J = 8.8, 1.2 Hz, 1H), 9.00 (dd, J = 4.3, 1.6 Hz, 1H), 8.46 (dd, J = 7.5, 1.2 Hz, 1H), 8.34 (dt, J = 8.5, 1.1 Hz, 1H), 7.99 (d, J = 2.9 Hz, 1H), 7.92 (dd, J = 8.5, 7.4 Hz, 1H), 7.68 (dd, J = 8.8, 4.3 Hz, 1H), 7.39 (d, J = 2.9 Hz, 1H), 3.85 (d, J = 6.4 Hz, 2H), 2.10 (dp, J = 13.2, 6.6 Hz, 1H), 1.55 (q, J = 4.5 Hz, 2H), 1.17 (q, J = 4.5 Hz, 2H), 1.06 (d, J = 6.7 Hz, 6H).. | LC/MS (ESI+) m/z 460 and 462 (M + H)+. |
| Example GIII-6 | 1-(4-ethylpyridin-3-yl)-N-(quinoline-5-sulfonyl)cyclopropane- | $^1$H NMR (400 MHz, methanol-d$_4$) δ ppm 9.14 (ddd, J = 8.8, 1.7, 0.9 Hz, 1H), 8.91 (dd, J = 4.3, 1.7 Hz, 1H), 8.24 (dd, J = 3.8, 1.4 Hz, 2H), 8.14 (dd, J = 8.5, 1.1 Hz, | LC/MS (ESI+) m/z 381 |

TABLE 5-continued

| | | NMR | MS |
|---|---|---|---|
| | 1-carboxamide | 1H), 7.79 (dd, J = 8.5, 7.3 Hz, 1H), 7.59 (dd, J = 8.7, 4.3 Hz, 1H), 7.22-7.10 (m, 1H), 2.44 (q, J = 7.6 Hz, 2H), 1.58-1.50 (m, 2H), 1.02-0.88 (m, 5H). | (M + H)$^+$. |
| Example GIII-7 | 1-(2-fluoro-5-methylpyridin-4-yl)-N-(1,2,3,4-tetrahydroquinoline-5-sulfonyl)cyclopropane-1-carboxamide | $^1$H NMR (400 MHz, methanol-d$_4$) δ ppm 7.84 (s, 1H), 7.24 (dd, J = 7.8, 1.2 Hz, 1H), 6.96-6.86 (m, 2H), 6.59 (dd, J = 8.0, 1.3 Hz, 1H), 3.26-3.19 (m, 2H), 3.08-2.98 (m, 6H), 2.25 (d, J = 1.0 Hz, 3H), 1.89-1.79 (m, 2H), 1.56 (q, J = 3.8 Hz, 2H), 0.94 (q, J = 3.9 Hz, 2H). | LC/MS (ESI+) m/z 390 (M + H)$^+$. |
| Example GIII-8 | 1-(6-methoxy-2-methylpyridin-3-yl)-N-(quinoline-5-sulfonyl)cyclopropane-1-carboxamide | $^1$H NMR (400 MHz, methanol-d$_4$) δ ppm 9.15 (ddd, J = 8.8, 1.7, 0.9 Hz, 1H), 8.90 (dd, J = 4.3, 1.7 Hz, 1H), 8.26 (dd, J = 7.3, 1.2 Hz, 1H), 8.14 (dt, J = 8.5, 1.1 Hz, 1H), 7.80 (dd, J = 8.5, 7.3 Hz, 1H), 7.58 (dd, J = 8.7, 4.3 Hz, 1H), 7.43 (d, J = 8.3 Hz, 1H), 6.51 (dd, J = 8.3, 0.7 Hz, 1H), 3.85 (s, 3H), 2.14 (s, 3H), 1.48 (q, J = 3.4 Hz, 2H), 0.85 (q, J = 3.4 Hz, 2H). | LC/MS (ESI+) m/z 398 (M + H)$^+$. |
| Example GIII-9 | 1-[5-cyclopropyl-2-(4-methylpiperazin-1-yl)pyridin-3-yl]-N-(quinoline-5-sulfonyl)cyclopropane-1-carboxamide | $^1$H NMR (400 MHz, methanol-d$_4$) δ ppm 9.21 (ddd, J = 8.7, 1.7, 0.9 Hz, 1H), 8.91 (dd, J = 4.3, 1.7 Hz, 1H), 8.30 (dd, J = 7.3, 1.2 Hz, 1H), 8.13 (dt, J = 8.5, 1.1 Hz, 1H), 7.85-7.75 (m, 2H), 7.62 (dd, J = 8.7, 4.3 Hz, 1H), 7.27 (d, J = 2.4 Hz, 1H), 3.05-2.98 (m, 4H), ), 2.35-2.17 (m, 7H), 1.84 (tt, J = 8.5, 5.1 Hz, 1H), 1.51 (q, J = 3.7 Hz, 2H), 1.00-0.87 (m, 4H), 0.68-0.58 (m, 2H). | LC/MS (ESI+) m/z 492 (M + H)$^+$. |
| Example GIII-10 | 1-[5-cyclopropyl-2-(trifluoromethyl)pyridin-3-yl]-N-(quinoline-5-sulfonyl)cyclopropane-1-carboxamide | | LC/MS (ESI+) m/z 462 (M + H)$^+$. |
| Example GIII-11 | 1-[2-methoxy-5-(2-methoxyethoxy)pyridin-4-yl]-N-(quinoline-5-sulfonyl)cyclopropane-1-carboxamide | $^1$H NMR (400 MHz, methanol-d$_4$) δ ppm 9.07-8.97 (m, 2H), 8.48 (dd, J = 7.4, 1.2 Hz, 1H), 8.36 (d, J = 8.5 Hz, 1H), 7.95 (dd, J = 8.5, 7.4 Hz, 1H), 7.73-7.60 (m, 2H), 6.67 (s, 1H), 3.89 (s, 3H), 3.75-3.60 (m, 2H), 3.21 (s, 3H), 3.17-3.07 (m, 2H), 1.42-1.34 (m, 2H), 1.06 (q, J = 4.5 Hz, 2H). | LC/MS (ESI+) m/z 458 (M + H)$^+$. |
| Example GIII-12 | 1-(2,4-dimethoxypyrimidin-5-yl)-N-(1,2,3,4-tetrahydroquinoline-5-sulfonyl)cyclopropane-1-carboxamide | $^1$H NMR (400 MHz, DMSO-d$_6$) δ ppm 11.42 (s, 1H), 8.17 (s, 1H), 7.07-6.96 (m, 1H), 6.70 (dd, J = 6.9, 2.5 Hz, 1H), 3.91 (s, 3H), 3.88 (s, 3H), 3.19 (t, J = 6.1 Hz, 2H), 2.88 (t, J = 6.4 Hz, 2H), 1.78 (p, J = 6.1 Hz, 2H), 1.33 (q, J = 4.1 Hz, 2H), 1.06 (q, J = 4.2 Hz, 2H). | LC/MS (ESI+) m/z 419 (M + H)$^+$. |
| Example GIII-13 | 1-{2-chloro-5-[(propan-2-yl)oxy]pyridin-3-yl}-N-(quinoline-5-sulfonyl)cyclopropane-1-carboxamide | $^1$H NMR (400 MHz, methanol-d$_4$) δ ppm 9.11-9.03 (m, 1H), 8.99 (dd, J = 4.3, 1.6 Hz, 1H), 8.45 (dd, J = 7.4, 1.2 Hz, 1H), 8.33 (dt, J = 8.6, 1.1 Hz, 1H), 7.97-7.86 (m, 2H), 7.68 (dd, J = 8.8, 4.3 Hz, 1H), 7.35 (d, J = 2.9 Hz, 1H), 4.67 (p, J = 6.0 Hz, 1H), 1.54 (q, J = 4.5 Hz, 2H), 1.34 (d, J = 6.0 Hz, 6H), 1.15 (q, J = 4.5 Hz, 2H). | LC/MS (ESI+) m/z 446 and 448 (M + H)$^+$. |
| Example GIII-14 | 1-[5-(2,2-difluoroethoxy)-2-methoxypyridin-4-yl]-N-(2-methylquinoline-5-sulfonyl)cyclopropane-1-carboxamide | $^1$H NMR (400 MHz, chloroform-d) δ ppm 8.72 (d, J = 8.9 Hz, 1H), 8.45-8.39 (m, 1H), 8.33 (d, J = 8.4 Hz, 1H), 7.82 (dd, J = 8.5, 7.5 Hz, 1H), 7.78 (s, 1H), 7.44 (d, J = 8.9 Hz, 1H), 6.64 (s, 1H), 5.63 (tt, J = 54.9, 4.0 Hz, 2H), 4.01 (td, J = 12.7, 4.1 Hz, 2H), 3.95 (s, 3H), 2.81 (s, 3H), 1.54 (q, J = 4.4 Hz, 2H), 1.04 (q, J = 4.5 Hz, 2H). | LC/MS (ESI+) m/z 478 (M + H)$^+$. |
| Example GIII-15 | 1-(6-methoxy-2-methylpyridin-3-yl)-N-(1,2,3,4-tetrahydroquinoline-5-sulfonyl)cyclopropane-1-carboxamide | $^1$H NMR (400 MHz, methanol-d$_4$) δ ppm 7.48 (d, J = 8.4 Hz, 1H), 7.19 (dd, J = 7.8, 1.3 Hz, 1H), 6.90 (t, J = 7.9 Hz, 1H), 6.57 (dd, J = 8.1, 1.2 Hz, 1H), 6.52 (dd, J = 8.3, 0.7 Hz, 1H), 3.85 (s, 3H), 3.23-3.16 (m, 2H), 3.03 (t, J = 6.4 Hz, 2H), 2.39 (s, 3H), 1.88-1.74 (m, 2H), 1.55 (q, J = 3.4 Hz, 2H), 0.89 (q, J = 3.5 Hz, 2H). | LC/MS (ESI+) m/z 402 (M + H)$^+$. |
| Example GIII-16 | 1-(2-fluoro-5-methylpyridin-4-yl)-N-(quinoline-5-sulfonyl)cyclopropane-1-carboxamide | $^1$H NMR (400 MHz, methanol-d$_4$) δ ppm 9.11 (ddd, J = 8.7, 1.7, 0.9 Hz, 1H), 8.90 (dd, J = 4.2, 1.7 Hz, 1H), 8.28 (dd, J = 7.3, 1.2 Hz, 1H), 8.14 (dt, J = 8.5, 1.1 Hz, 1H), 7.84-7.76 (m, 2H), 7.58 (dd, J = 8.7, 4.3 Hz, 1H), 6.84 (d, J = 1.4 Hz, 1H), 1.97 (t, J = 1.0 Hz, 3H), 1.48 (q, J = 3.8 Hz, 2H), 0.90 (q, J = 3.8 Hz, 2H). | LC/MS (ESI+) m/z 386 (M + H)$^+$. |
| Example GIII-17 | 1-(6-methoxy-4-methylpyridin-3-yl)-N-(1,2,3,4-tetrahydroquinoline-5-sulfonyl)cyclopropane-1-carboxamide | $^1$H NMR (400 MHz, methanol-d$_4$) δ ppm 7.85 (s, 1H), 7.20 (dd, J = 7.8, 1.3 Hz, 1H), 6.89 (t, J = 7.9 Hz, 1H), 6.60-6.53 (m, 2H), 3.84 (s, 3H), 3.24-3.17 (m, 2H), 3.05 (t, J = 6.4 Hz, 2H), 2.27 (d, J = 0.8 Hz, 3H), 1.88-1.77 (m, 2H), 1.54 (d, J = 3.3 Hz, 2H), 0.89 (q, J = 3.3 Hz, 2H). | LC/MS (ESI+) m/z 402 (M + H)$^+$. |
| Example GIII-18 | 1-[5-(2,2-difluoroethoxy)-2-methoxypyridin-4-yl]-N-(quinoline-5-sulfonyl)cyclopropane- | $^1$H NMR (400 MHz, chloroform-d) δ ppm 9.06 (dd, J = 4.2, 1.6 Hz, 1H), 8.83 (ddd, J = 8.8, 1.6, 0.9 Hz, 1H), 8.53 (dd, J = 7.4, 1.3 Hz, 1H), 8.44 (dt, J = 8.4, 1.1 Hz, 1H), 7.88 (dd, J = 8.5, 7.5 Hz, 1H), 7.76 (s, 1H), 7.57 (dd, J = 8.8, 4.2 Hz, 1H), 6.61 (s, 1H), 5.63 (tt, J = 54.9, | LC/MS (ESI+) m/z 464 (M + H)$^+$. |

TABLE 5-continued

|  |  | NMR | MS |
|---|---|---|---|
|  | 1-carboxamide | 4.0 Hz, 1H), 3.98 (td, J = 12.7, 4.0 Hz, 2H), 3.90 (s, 3H), 1.54 (q, J = 4.5 Hz, 2H), 1.04 (q, J = 4.5 Hz, 2H). |  |
| Example GIII-19 | 1-[5-(difluoromethoxy)-2-methoxypyridin-4-yl]-N-(quinoline-5-sulfonyl)cyclopropane-1-carboxamide | $^1$H NMR (400 MHz, chloroform-d) δ ppm 9.04 (dd, J = 4.2, 1.6 Hz, 1H), 8.83 (ddd, J = 8.7, 1.6, 0.9 Hz, 1H), 8.51 (dd, J = 7.5, 1.3 Hz, 1H), 8.42 (dt, J = 8.5, 1.1 Hz, 1H), 7.99 (d, J = 1.3 Hz, 1H), 7.86 (d, J = 8.5, 7.5 Hz, 1H), 7.57 (dd, J = 8.8, 4.2 Hz, 1H), 6.61 (s, 1H), 6.14 (t, J = 72.5 Hz, 1H), 3.84 (s, 3H), 1.54 (q, J = 4.5 Hz, 2H), 1.06 (q, J = 4.5 Hz, 2H). | LC/MS (ESI+) m/z 450 (M + H)$^+$. |
| Example GIII-20 | 1-[5-cyclopropyl-2-(morpholin-4-yl)pyridin-3-yl]-N-(2-methylquinoline-5-sulfonyl)cyclopropane-1-carboxamide | $^1$H NMR (400 MHz, methanol-d$_4$) δ ppm 9.02 (dd, J = 8.9, 0.9 Hz, 1H), 8.18 (dd, J = 7.3, 1.2 Hz, 1H), 8.04 (dt, J = 8.5, 1.1 Hz, 1H), 7.82 (d, J = 2.4 Hz, 1H), 7.72 (dd, J = 8.5, 7.3 Hz, 1H), 7.47 (d, J = 8.9 Hz, 1H), 7.25 (d, J = 2.4 Hz, 1H), 3.50-3.43 (m, 4H), 2.95-2.89 (m, 4H), 2.74 (s, 3H), 1.82 (tt, J = 8.4, 5.1 Hz, 1H), 1.48 (q, J = 3.7 Hz, 2H), 0.98 (q, J = 3.8 Hz, 2H), 0.95-0.86 (m, 2H), 0.64-0.55 (m, 2H). | LC/MS (ESI+) m/z 493 (M + H)$^+$. |
| Example GIII-21 | 1-[2-chloro-6-(trifluoromethyl)pyridin-3-yl]-N-(naphthalene-1-sulfonyl)cyclopropane-1-carboxamide | $^1$H NMR (400 MHz, methanol-d$_4$) δ ppm 8.75-8.67 (m, 1H), 8.21 (dd, J = 7.3, 1.2 Hz, 1H), 7.99 (d, J = 8.2 Hz, 1H), 7.95-7.85 (m, 2H), 7.66 (d, J = 7.8 Hz, 1H), 7.59-7.46 (m, 3H), 1.57 (q, J = 4.0 Hz, 2H), 0.98 (q, J = 4.0 Hz, 2H). | LC/MS (ESI+) m/z 455 and 457 (M + H)$^+$. |
| Example GIII-22 | 1-[5-(difluoromethoxy)-2-methoxypyridin-4-yl]-N-(2-methylquinoline-5-sulfonyl)cyclopropane-1-carboxamide | $^1$H NMR (400 MHz, chloroform-d) δ ppm 8.91 (dd, J = 8.8, 0.8 Hz, 1H), 8.09 (ddd, J = 8.5, 3.0, 1.1 Hz, 2H), 7.86 (d, J = 1.2 Hz, 1H), 7.60 (dd, J = 8.4, 7.3 Hz, 1H), 7.29 (d, J = 8.8 Hz, 1H), 6.62-6.23 (m, 2H), 3.90 (s, 3H), 2.77 (s, 3H), 1.49 (q, J = 4.0 Hz, 2H), 0.92 (q, J = 4.0 Hz, 2H). | LC/MS (ESI+) m/z 464 (M + H)$^+$. |
| Example GIII-23 | 1-[5-ethyl-2-(morpholin-4-yl)pyridin-3-yl]-N-(quinoline-5-sulfonyl)cyclopropane-1-carboxamide | $^1$H NMR (400 MHz, methanol-d$_4$) δ ppm 9.19 (dd, J = 8.9, 1.7 Hz, 1H), 8.91 (dd, J = 4.3, 1.7 Hz, 1H), 8.32-8.25 (m, 1H), 8.15 (d, J = 8.5 Hz, 1H), 7.88 (d, J = 2.3 Hz, 1H), 7.84-7.76 (m, 1H), 7.60 (dd, J = 8.7, 4.3 Hz, 1H), 7.47 (d, J = 2.4 Hz, 1H), 3.52-3.45 (m, 4H), 2.99-2.92 (m, 4H), 2.56 (q, J = 7.6 Hz, 2H), 1.52 (q, J = 3.7 Hz, 2H), 1.19 (t, J = 7.6 Hz, 3H), 1.02 (q, J = 3.8 Hz, 2H). | LC/MS (ESI+) m/z 467 (M + H)$^+$. |
| Example GIII-24 | 1-(2,4-dimethoxypyrimidin-5-yl)-N-(quinoline-5-sulfonyl)cyclopropane-1-carboxamide | $^1$H NMR (400 MHz, methanol-d$_4$) δ ppm 9.14 (ddd, J = 8.7, 1.7, 0.9 Hz, 1H), 8.90 (dd, J = 4.3, 1.7 Hz, 1H), 8.27 (dd, J = 7.3, 1.2 Hz, 1H), 8.14 (dt, J = 8.5, 1.1 Hz, 1H), 7.96 (s, 1H), 7.80 (dd, J = 8.5, 7.3 Hz, 1H), 7.60 (dd, J = 8.7, 4.3 Hz, 1H), 3.95 (s, 3H), 3.71 (s, 3H), 1.36 (q, J = 3.9 Hz, 2H), 0.82 (q, J = 3.9 Hz, 2H). | LC/MS (ESI+) m/z 414 (M + H)$^+$. |
| Example GIII-25 | 1-[5-cyclopropyl-2-(morpholin-4-yl)pyridin-3-yl]-N-(quinoline-5-sulfonyl)cyclopropane-1-carboxamide | $^1$H NMR (400 MHz, methanol-d$_4$) δ ppm 9.18 (ddd, J = 8.8, 1.7, 0.9 Hz, 1H), 8.91 (dd, J = 4.3, 1.7 Hz, 1H), 8.28 (dd, J = 7.3, 1.2 Hz, 1H), 8.14 (dt, J = 8.5, 1.1 Hz, 1H), 7.84 (d, J = 2.4 Hz, 1H), 7.80 (dd, J = 8.5, 7.3 Hz, 1H), 7.60 (dd, J = 8.7, 4.2 Hz, 1H), 7.27 (d, J = 2.5 Hz, 1H), 3.51-3.44 (m, 4H), 2.97-2.92 (m, 4H), 1.84 (tt, J = 8.4, 5.1 Hz, 1H), 1.50 (q, J = 3.7 Hz, 2H), 1.00 (q, J = 3.8 Hz, 2H), 0.97-0.91 (m, 2H), 0.66-0.58 (m, 2H). | LC/MS (ESI+) m/z 479 (M + H)$^+$. |
| Example GIII-26 | 1-[5-methyl-2-(4-methylpiperazin-1-yl)pyridin-3-yl]-N-(quinoline-5-sulfonyl)cyclopropane-1-carboxamide | $^1$H NMR (400 MHz, methanol-d$_4$) δ ppm 9.21 (d, J = 8.7 Hz, 1H), 8.91 (dd, J = 4.3, 1.7 Hz, 1H), 8.34-8.28 (m, 1H), 8.14 (d, J = 8.4 Hz, 1H), 7.88 (d, J = 2.3 Hz, 1H), 7.85-7.77 (m, 1H), 7.61 (dd, J = 8.7, 4.3 Hz, 1H), 7.43 (d, J = 2.3 Hz, 1H), 3.18-3.08 (m, 4H), 2.70-2.52 (m, 4H), 2.52-2.40 (m, 3H), 2.24 (s, 3H), 1.47 (q, J = 3.8 Hz, 2H), 0.97 (q, J = 3.8 Hz, 2H). | LC/MS (ESI+) m/z 466 (M + H)$^+$. |
| Example GIII-27 | 1-[5-cyclopropyl-2-(4-methylpiperazin-1-yl)pyridin-3-yl]-N-(2-methylquinoline-5-sulfonyl)cyclopropane-1-carboxamide | $^1$H NMR (400 MHz, methanol-d$_4$) δ ppm 9.08-8.99 (m, 1H), 8.21 (dd, J = 7.3, 1.2 Hz, 1H), 8.04 (dt, J = 8.5, 1.1 Hz, 1H), 7.84 (d, J = 2.4 Hz, 1H), 7.73 (dd, J = 8.5, 7.3 Hz, 1H), 7.49 (d, J = 8.9 Hz, 1H), 7.23 (d, J = 2.4 Hz, 1H), 3.13-3.04 (m, 4H), 2.75 (s, 3H), 2.65-2.49 (m, 4H), 2.43 (s, 3H), 1.83 (ddd, J = 13.6, 8.5, 5.1 Hz, 1H), 1.47 (q, J = 3.7 Hz, 2H), 0.98-0.87 (m, 4H), 0.68-0.58 (m, 2H). | LC/MS (ESI+) m/z 506 (M + H)$^+$. |
| Example GIII-28 | 1-[2-chloro-6-(trifluoromethyl)pyridin-3-yl]-N-(1,2,3,4-tetrahydroquinoline-5-sulfonyl)cyclopropane-1-carboxamide | $^1$H NMR (400 MHz, methanol-d$_4$) δ ppm 7.94 (d, J = 7.8 Hz, 1H), 7.68 (d, J = 7.8 Hz, 1H), 7.26 (dd, J = 7.8, 1.2 Hz, 1H), 6.92 (t, J = 7.9 Hz, 1H), 6.59 (dd, J = 8.0, 1.2 Hz, 1H), 3.26-3.19 (m, 2H), 3.10-3.06 (m, 2H), 1.87 (p, J = 6.3 Hz, 2H), 1.63 (q, J = 3.9 Hz, 2H), 1.02 (q, J = 4.0 Hz, 2H). | LC/MS (ESI+) m/z 460 and 462 (M + H)$^+$. |
| Example GIII-29 | 1-[2-chloro-6-(trifluoromethyl)pyridin-3-yl]-N-(quinoline-5-sulfonyl)cyclopropane-1-carboxamide | $^1$H NMR (400 MHz, methanol-d$_4$) δ ppm 9.14 (dt, J = 8.5, 1.4 Hz, 1H), 8.89 (dd, J = 4.3, 1.7 Hz, 1H), 8.29 (dd, J = 7.4, 1.2 Hz, 1H), 8.14 (dt, J = 8.5, 1.1 Hz, 1H), 7.90 (d, J = 7.8 Hz, 1H), 7.80 (dd, J = 8.5, 7.3 Hz, 1H), 7.67 (d, J = 7.8 Hz, 1H), 7.58 (dd, J = 8.7, 4.3 Hz, 1H), 1.55 (q, J = 3.9 Hz, 2H), 0.98 (q, J = 4.0 Hz, 2H). | LC/MS (ESI+) m/z 456 and 458 (M + H)$^+$. |

TABLE 5-continued

| | | NMR | MS |
|---|---|---|---|
| Example GIII-30 | 1-(6-amino-2-methoxypyridin-3-yl)-N-(quinoline-5-sulfonyl)cyclopropane-1-carboxamide | $^1$H NMR (400 MHz, methanol-$d_4$) δ ppm 9.23-9.15 (m, 1H), 8.89 (dd, J = 4.3, 1.6 Hz, 1H), 8.27 (dd, J = 7.3, 1.2 Hz, 1H), 8.13 (dt, J = 8.5, 1.1 Hz, 1H), 7.80 (dd, J = 8.5, 7.3 Hz, 1H), 7.59 (dd, J = 8.7, 4.3 Hz, 1H), 7.17 (d, J = 7.9 Hz, 1H), 6.02 (d, J = 7.9 Hz, 1H), 3.52 (s, 3H), 1.34 (q, J = 3.7 Hz, 2H), 0.75 (q, J = 3.7 Hz, 2H). | LC/MS (ESI+) m/z 399 (M + H)$^+$. |
| Example GIII-31 | 1-[5-cyclobutyl-2-(4-methylpiperazin-1-yl)pyridin-3-yl]-N-(quinoline-5-sulfonyl)cyclopropane-1-carboxamide | $^1$H NMR (400 MHz, DMSO-$d_6$) δ ppm 9.16-9.07 (m, 1H), 8.97 (dd, J = 4.2, 1.7 Hz, 1H), 8.12-8.03 (m, 2H), 7.95 (d, J = 2.3 Hz, 1H), 7.77 (dd, J = 8.3, 7.3 Hz, 1H), 7.59 (dd, J = 8.7, 4.1 Hz, 1H), 7.35 (d, J = 2.4 Hz, 1H), 3.47 (p, J = 8.7 Hz, 1H), 3.27-3.12 (m, 4H), 2.79-2.63 (m, 4H), 2.31 (ddt, J = 11.0, 8.3, 4.7 Hz, 2H), 2.18-1.95 (m, 3H), 1.94-1.80 (m, 1H), 1.34 (q, J = 3.2 Hz, 2H), 0.86 (q, J = 3.5 Hz, 2H). | LC/MS (ESI+) m/z 506 (M + H)$^+$. |
| Example GIII-32 | 1-[5-cyclobutyl-2-(4-methylpiperazin-1-yl)pyridin-3-yl]-N-(2-methylquinoline-5-sulfonyl)cyclopropane-1-carboxamide | $^1$H NMR (400 MHz, methanol-$d_4$) δ ppm 9.06 (d, J = 8.8 Hz, 1H), 8.20 (d, J = 7.3 Hz, 1H), 8.03 (d, J = 8.4 Hz, 2H), 7.84 (d, J = 3.0 Hz, 1H), 7.72 (t, J = 7.9 Hz, 1H), 7.51-7.44 (m, 2H), 3.52-3.39 (m, 1H), 3.10-2.93 (m, 4H), 2.74 (s, 3H), 2.42-2.24 (m, 4H), 2.15-1.95 (m, 3H), 1.91-1.83 (m, 1H), 1.51 (q, J = 3.6 Hz, 2H), 0.96 (q, J = 3.8 Hz, 2H). | LC/MS (ESI+) m/z 520 (M + H)$^+$. |
| Example GIII-33 | 1-[5-ethyl-2-(4-methylpiperazin-1-yl)pyridin-3-yl]-N-(quinoline-5-sulfonyl)cyclopropane-1-carboxamide | $^1$H NMR (400 MHz, methanol-$d_4$) δ ppm 9.21 (ddd, J = 8.7, 1.7, 0.9 Hz, 1H), 8.91 (dd, J = 4.3, 1.7 Hz, 1H), 8.30 (dd, J = 7.3, 1.2 Hz, 1H), 8.14 (dt, J = 8.5, 1.1 Hz, 1H), 7.89 (d, J = 2.4 Hz, 1H), 7.80 (dd, J = 8.5, 7.3 Hz, 1H), 7.61 (dd, J = 8.7, 4.3 Hz, 1H), 7.45 (d, J = 2.4 Hz, 1H), 3.16-3.07 (s, 4H), 2.65-2.48 (m, 6H), 2.43 (s, 3H), 1.49 (q, J = 3.7 Hz, 2H), 1.20 (t, J = 7.6 Hz, 3H), 0.98 (q, J = 3.8 Hz, 2H). | LC/MS (ESI+) m/z 480 (M + H)$^+$. |
| Example GIII-34 | 1-(5-chloro-2-fluoropyridin-3-yl)-N-(quinoline-5-sulfonyl)cyclopropane-1-carboxamide | $^1$H NMR (400 MHz, chloroform-d) δ ppm 8.97 (d, J = 3.9 Hz, 1H), 8.79-8.64 (m, 1H), 8.34-8.16 (m, 2H), 7.97 (d, J = 10.6 Hz, 1H), 7.70-7.57 (s, 1H), 7.41-7.31 (m, 2H), 1.48-1.43 (m, 2H), 1.01-0.90 (m, 2H). | LC/MS (ESI+) m/z 406 and 408 (M + H)$^+$. |
| Example GIII-35 | 1-{5-(hydroxymethyl)-2-[(propan-2-yl)oxy]pyridin-3-yl}-N-(quinoline-5-sulfonyl)cyclopropane-1-carboxamide | $^1$H NMR (400 MHz, methanol-$d_4$) δ ppm 9.06 (ddd, J = 8.8, 1.6, 0.9 Hz, 1H), 8.98 (dd, J = 4.3, 1.6 Hz, 1H), 8.46 (dd, J = 7.5, 1.2 Hz, 1H), 8.33 (dt, J = 8.5, 1.1 Hz, 1H), 8.03 (d, J = 2.3 Hz, 1H), 7.92 (dd, J = 8.5, 7.5 Hz, 1H), 7.65 (dd, J = 8.8, 4.2 Hz, 1H), 7.53 (d, J = 2.4 Hz, 1H), 5.06 (hept, J = 6.1 Hz, 1H), 4.55 (s, 2H), 1.39-1.34 (m, 2H), 1.04 (d, J = 6.1 Hz, 6H), 1.03-0.98 (m, 2H). | LC/MS (ESI+) m/z 442 (M + H)$^+$. |
| Example GIII-36 | 1-[5-cyclopropyl-2-(4-methylpiperazin-1-yl)pyridin-3-yl]-N-(1H-indole-4-sulfonyl)cyclopropane-1-carboxamide | $^1$H NMR (400 MHz, methanol-$d_4$) δ ppm 7.83 (d, J = 2.4 Hz, 1H), 7.61 (dd, J = 7.4, 0.9 Hz, 1H), 7.50 (dt, J = 8.1, 1.0 Hz, 1H), 7.32 (d, J = 3.1 Hz, 1H), 7.28 (d, J = 2.4 Hz, 1H), 7.11 (t, J = 7.8 Hz, 1H), 6.85 (dd, J = 3.1, 0.9 Hz, 1H), 4.83 (s, 6H), 3.08 (d, J = 6.5 Hz, 4H), 2.48 (t, J = 4.9 Hz, 4H), 2.37 (s, 3H), 1.82 (tt, J = 8.4, 5.1 Hz, 1H), 1.55 (q, J = 3.7 Hz, 2H), 0.98-0.85 (m, 4H), 0.68-0.59 (m, 2H). | LC/MS (ESI+) m/z 480 (M + H)$^+$. |

BIOLOGICAL EXAMPLES

Determination of Biological Activity

Cell Surface Expression-Horse Radish Peroxidase (CSE-HRP) Assay

A cellular assay for measuring the F508delCFTR cell surface expression after correction with test compounds either without or with a co-corrector (2 µM of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid), was developed in human lung derived epithelial cell line (CFBE4lo−) (Veit G et al, (2012) Mol Biol Cell. 23(21): 4188-4202). The development was achieved by expressing the F508delCFTR mutation along with a horseradish peroxidase (HRP) in the fourth exofacial loop, and then measuring the HRP activity using luminescence readout from these cells, CFBE410-F508delCFTR-HRP, that were incubated overnight with the test corrector compounds, either without or with the co-corrector. For this primary assay, the CFBE410-F508delCFTR-HRP cells were plated in 384-well plates (Greiner Bio-one; Cat 781080) at 4,000 cells/well along with 0.5 µg/mL doxycycline to induce the F508delCFTR-HRP expression and further incubated at 37° C., 5% $CO_2$ for 68-72 hours. The test compounds were then added either without or with a co-corrector at the required concentrations and further incubated for 18-24 hours at 33° C. The highest concentration tested was 20 µM or 30 µM (GI-1 to GIII-36) with an 8-point concentration response curve using a 3-fold dilution in both the test compound without or with the co-corrector. Three replicate plates were run to determine one $EC_{50}$. All plates contained negative controls (dimethyl sulfoxide, DMSO) and positive control (2 µM or 3 µM (GI-1 to GIII-36) of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) as well as on-plate concentration response of the positive control. Post incubation, the plates were washed 5× times with Dulbecco's phosphate buffered saline (DPBS), followed by the addition of the HRP substrate, luminol (50 4), and measuring the HRP activity using luminescence readout on EnVision® Multilabel Plate Reader (Perkin Elmer; product number 2104-0010). The raw counts from the experiment were analyzed using Accelrys® Assay Explorer v3.3.

Z' greater than 0.5 was used as passing quality control criteria for the plates.

The Z' is defined as:

$$1-[3*SD_{Positive\ Control}+3*SD_{Negative\ Control}]/Absolute$$
$$(Mean_{Positive\ Control}-Mean_{Negative\ Control})]$$

wherein "SD" is standard deviation.

The % activity measured at each of the 8 test concentrations of the test compound added either without or with a co-corrector (2 μM or 3 μM (GI-1 to GIII-36) of 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) was normalized to the on-plate positive control using the following formulae:

% activity (Test compound without co-corrector)=
[(test compound without co-corrector response DMSO response)/(positive control response DMSO response)]*100

% activity (Test compound with co-corrector)=[(test compound with co-corrector response DMSO response)/(positive control response DMSO response)]*100

The maximum % activity achieved for the test compound either without or with a co-corrector at any tested concentration is presented in Table 6 along with the respective $EC_{50}$'s calculated using the following general sigmoidal curve with variable Hill slope equation (described as Model 42 in the Accelrys® Assay Explorer v3.3 software):

$$y=(a-d)/(1+(x/c)b)+d$$

General sigmoidal curve with concentration, response, top, bottom, $EC_{50}$ and Hill slope. This model describes a sigmoidal curve with an adjustable baseline, a. The equation can be used to fit curves where response is either increasing or decreasing with respect to the independent variable, "x".
"x" is a concentration of drug under test.
"y" is the response.
"a" is the maximum response, and "d" is the minimum response
"c" is the inflection point (EGO for the curve. That is, "y" is halfway between the lower and upper asymptotes when x=c.
"b" is the slope-factor or Hill coefficient. The sign of b is positive when the response increases with increasing dose and is negative when the response decreases with increasing dose (inhibition). The data is presented with the qualifiers shown below:

| Without/with co-corrector | EC50 (μM) | |
|---|---|---|
| | <3 | +++ |
| | ≥3 and <10 | ++ |
| | ≥10 | + |
| Without co-corrector | Maximum % activity (%) | |
| | <50 | + |
| | ≥50 and <150 | ++ |
| | ≥150 | +++ |
| With co-corrector | Maximum % activity (%) | |
| | <150 | + |
| | ≥150 and <350 | ++ |
| | ≥350 | +++ |

TABLE 6

| Example # | EC50 (without co-corrector) (μM) | Maximum % activity (without co-corrector) (%) | EC50 (with co-corrector) (μM) | Maximum % activity (with co-corrector) (%) |
|---|---|---|---|---|
| I-1 | +++ | +++ | +++ | +++ |
| I-2 | +++ | +++ | +++ | +++ |
| I-3 | +++ | +++ | +++ | +++ |
| I-4 | +++ | +++ | +++ | +++ |
| I-5 | ++ | +++ | +++ | +++ |
| I-6 | +++ | +++ | +++ | +++ |
| I-7 | ++ | +++ | +++ | +++ |
| I-8 | +++ | +++ | +++ | +++ |
| I-9 | +++ | +++ | +++ | +++ |
| I-10 | ++ | +++ | +++ | +++ |
| I-11 | +++ | +++ | +++ | +++ |
| I-12 | +++ | +++ | +++ | +++ |
| I-13 | +++ | +++ | +++ | +++ |
| I-14 | +++ | +++ | +++ | +++ |
| I-15 | ++ | +++ | ++ | +++ |
| I-16 | ++ | +++ | +++ | +++ |
| I-17 | +++ | +++ | +++ | +++ |
| I-18 | +++ | +++ | +++ | +++ |
| I-19 | +++ | +++ | +++ | +++ |
| I-20 | +++ | +++ | +++ | +++ |
| I-21 | +++ | +++ | +++ | +++ |
| I-22 | ++ | +++ | +++ | +++ |
| I-23 | ++ | +++ | +++ | +++ |
| I-24 | +++ | +++ | +++ | +++ |
| I-25 | +++ | +++ | +++ | +++ |
| I-26 | +++ | +++ | +++ | +++ |
| I-27 | ++ | +++ | +++ | +++ |
| I-28 | +++ | +++ | +++ | +++ |
| I-29 | +++ | +++ | +++ | +++ |
| I-30 | +++ | +++ | +++ | +++ |
| I-31 | +++ | +++ | +++ | +++ |
| I-32 | +++ | +++ | +++ | +++ |
| I-33 | ++ | +++ | +++ | +++ |
| I-34 | +++ | +++ | +++ | +++ |
| I-35 | +++ | +++ | +++ | +++ |
| I-36 | +++ | +++ | +++ | +++ |
| I-37 | +++ | +++ | +++ | +++ |
| I-38 | +++ | +++ | +++ | +++ |
| I-39 | +++ | +++ | +++ | +++ |
| I-40 | +++ | +++ | +++ | +++ |
| I-41 | +++ | +++ | +++ | +++ |
| I-42 | +++ | +++ | +++ | +++ |
| I-43 | +++ | +++ | +++ | +++ |
| I-44 | +++ | +++ | +++ | +++ |
| I-45 | +++ | +++ | +++ | +++ |
| I-46 | +++ | +++ | +++ | +++ |
| I-47 | +++ | +++ | +++ | +++ |
| I-48 | +++ | +++ | +++ | +++ |
| I-49 | +++ | +++ | +++ | +++ |
| I-50 | +++ | +++ | +++ | +++ |
| I-51 | +++ | +++ | +++ | +++ |
| I-52 | +++ | +++ | +++ | +++ |
| I-53 | ++ | +++ | +++ | +++ |
| I-54 | +++ | +++ | +++ | +++ |
| I-55 | +++ | +++ | +++ | +++ |
| I-56 | +++ | +++ | +++ | +++ |
| I-57 | +++ | +++ | +++ | +++ |
| I-58 | ++ | +++ | +++ | +++ |
| I-59 | +++ | +++ | +++ | +++ |
| I-60 | +++ | +++ | +++ | +++ |
| I-61 | +++ | +++ | +++ | +++ |
| I-62 | +++ | +++ | +++ | +++ |
| I-63 | +++ | +++ | +++ | +++ |
| I-64 | +++ | +++ | +++ | +++ |
| I-65 | ++ | +++ | +++ | +++ |
| I-66 | +++ | +++ | +++ | +++ |
| I-67 | ++ | +++ | +++ | +++ |

TABLE 6-continued

| Example # | EC50 (without co-corrector) (µM) | Maximum % activity (without co-corrector) (%) | EC50 (with co-corrector) (µM) | Maximum % activity (with co-corrector) (%) |
|---|---|---|---|---|
| I-68 | +++ | +++ | +++ | +++ |
| I-69 | +++ | +++ | +++ | +++ |
| I-70 | +++ | +++ | +++ | +++ |
| I-71 | +++ | +++ | +++ | +++ |
| I-72 | ++ | +++ | +++ | +++ |
| I-73 | +++ | +++ | +++ | +++ |
| I-74 | +++ | +++ | +++ | +++ |
| I-75 | ++ | +++ | +++ | +++ |
| I-76 | ++ | +++ | +++ | +++ |
| I-77 | +++ | +++ | +++ | +++ |
| I-78 | +++ | +++ | +++ | +++ |
| I-79 | +++ | +++ | +++ | +++ |
| I-80 | ++ | +++ | +++ | +++ |
| I-81 | +++ | +++ | +++ | +++ |
| I-82 | +++ | +++ | +++ | +++ |
| I-83 | +++ | +++ | +++ | +++ |
| I-84 | +++ | +++ | +++ | +++ |
| I-85 | + | + | ++ | ++ |
| I-86 | +++ | +++ | +++ | +++ |
| I-87 | +++ | +++ | +++ | +++ |
| I-88 | ++ | +++ | +++ | +++ |
| I-89 | +++ | +++ | +++ | +++ |
| I-90 | ++ | ++ | ++ | +++ |
| I-91 | +++ | +++ | +++ | +++ |
| I-92 | +++ | +++ | +++ | +++ |
| I-93 | ++ | +++ | +++ | +++ |
| I-94 | +++ | +++ | +++ | +++ |
| I-95 | +++ | +++ | +++ | +++ |
| I-96 | +++ | +++ | +++ | +++ |
| I-97 | +++ | +++ | +++ | +++ |
| I-98 | +++ | +++ | +++ | +++ |
| I-99 | +++ | +++ | +++ | +++ |
| I-100 | +++ | +++ | +++ | +++ |
| I-101 | +++ | +++ | +++ | +++ |
| I-102 | +++ | +++ | +++ | +++ |
| I-103 | +++ | +++ | +++ | +++ |
| I-104 | +++ | +++ | +++ | +++ |
| I-105 | +++ | +++ | +++ | +++ |
| I-106 | ++ | +++ | +++ | +++ |
| I-107 | +++ | +++ | +++ | +++ |
| I-108 | +++ | +++ | +++ | +++ |
| I-109 | +++ | +++ | +++ | +++ |
| I-110 | +++ | +++ | +++ | +++ |
| I-111 | +++ | +++ | +++ | +++ |
| I-112 | +++ | +++ | +++ | +++ |
| I-113 | +++ | +++ | +++ | +++ |
| I-114 | +++ | +++ | +++ | +++ |
| I-115 | +++ | +++ | +++ | +++ |
| I-116 | +++ | +++ | +++ | +++ |
| I-117 | +++ | +++ | +++ | +++ |
| I-118 | +++ | +++ | +++ | +++ |
| I-119 | +++ | +++ | +++ | +++ |
| I-122 | +++ | +++ | +++ | +++ |
| I-123 | +++ | +++ | +++ | +++ |
| I-124 | +++ | +++ | +++ | +++ |
| II-1 | ++ | +++ | ++ | +++ |
| II-2 | ++ | +++ | ++ | +++ |
| II-3 | ++ | +++ | +++ | +++ |
| II-4 | ++ | ++ | ++ | +++ |
| II-5 | ++ | + | ++ | ++ |
| II-6 | ++ | +++ | +++ | +++ |
| II-7 | ++ | +++ | +++ | +++ |
| II-8 | ++ | +++ | +++ | +++ |
| II-9 | ++ | +++ | +++ | +++ |
| II-10 | ++ | +++ | ++ | +++ |
| II-11 | ++ | +++ | +++ | +++ |
| II-12 | ++ | +++ | +++ | +++ |
| II-13 | +++ | +++ | +++ | +++ |
| II-14 | +++ | +++ | +++ | +++ |
| II-15 | ++ | +++ | +++ | +++ |
| II-16 | ++ | +++ | +++ | +++ |
| II-17 | +++ | +++ | +++ | +++ |
| II-18 | ++ | +++ | +++ | +++ |
| II-19 | ++ | ++ | ++ | +++ |
| II-20 | ++ | +++ | +++ | +++ |
| II-21 | +++ | +++ | +++ | +++ |
| II-22 | ++ | +++ | +++ | +++ |
| II-23 | ++ | ++ | ++ | +++ |
| II-24 | +++ | +++ | +++ | +++ |
| II-25 | ++ | +++ | +++ | +++ |
| II-26 | +++ | +++ | +++ | +++ |
| II-27 | +++ | +++ | +++ | +++ |
| II-28 | +++ | +++ | +++ | +++ |
| II-29 | +++ | +++ | +++ | +++ |
| II-30 | ++ | +++ | +++ | +++ |
| II-31 | ++ | +++ | +++ | +++ |
| II-32 | ++ | +++ | +++ | +++ |
| II-33 | ++ | +++ | +++ | +++ |
| II-35 | ++ | +++ | +++ | +++ |
| II-36 | +++ | +++ | +++ | +++ |
| II-37 | +++ | +++ | +++ | +++ |
| II-38 | ++ | +++ | +++ | +++ |
| II-39 | +++ | ++ | +++ | +++ |
| II-40 | ++ | +++ | ++ | +++ |
| II-41 | ++ | ++ | +++ | +++ |
| II-42 | ++ | ++ | +++ | +++ |
| II-43 | +++ | ++ | +++ | +++ |
| II-44 | +++ | +++ | +++ | +++ |
| II-45 | ++ | +++ | +++ | +++ |
| II-46 | +++ | +++ | +++ | +++ |
| II-47 | +++ | +++ | +++ | +++ |
| II-48 | + | + | ++ | ++ |
| II-49 | +++ | +++ | +++ | +++ |
| II-50 | ++ | +++ | +++ | +++ |
| II-51 | +++ | +++ | +++ | +++ |
| II-52 | +++ | +++ | +++ | +++ |
| II-53 | ++ | +++ | +++ | +++ |
| II-54 | +++ | +++ | +++ | +++ |
| II-55 | +++ | +++ | +++ | +++ |
| II-56 | ++ | +++ | ++ | +++ |
| II-57 | +++ | +++ | +++ | +++ |
| II-58 | +++ | +++ | +++ | +++ |
| II-59 | +++ | +++ | +++ | +++ |
| II-60 | +++ | +++ | +++ | +++ |
| II-61 | +++ | +++ | +++ | +++ |
| II-62 | +++ | +++ | +++ | +++ |
| II-63 | +++ | +++ | +++ | +++ |
| II-64 | ++ | +++ | +++ | +++ |
| II-65 | +++ | +++ | +++ | +++ |
| II-66 | +++ | +++ | +++ | +++ |
| II-67 | +++ | +++ | +++ | +++ |
| II-68 | ++ | +++ | +++ | +++ |
| II-69 | +++ | +++ | +++ | +++ |
| II-70 | +++ | +++ | +++ | +++ |
| II-71 | +++ | +++ | +++ | +++ |
| II-72 | +++ | +++ | +++ | +++ |
| II-73 | +++ | +++ | +++ | +++ |
| II-74 | +++ | +++ | +++ | +++ |
| II-75 | +++ | +++ | +++ | +++ |
| II-76 | ++ | +++ | ++ | +++ |
| II-77 | +++ | +++ | +++ | +++ |
| II-78 | +++ | +++ | +++ | +++ |
| II-79 | +++ | +++ | +++ | +++ |
| II-80 | ++ | +++ | +++ | +++ |
| II-81 | +++ | +++ | +++ | +++ |
| II-82 | ++ | +++ | +++ | +++ |
| II-83 | +++ | +++ | +++ | +++ |
| II-84 | +++ | +++ | +++ | +++ |
| II-85 | +++ | +++ | +++ | +++ |
| II-86 | ++ | +++ | +++ | +++ |
| II-87 | ++ | +++ | +++ | +++ |
| II-88 | ++ | +++ | +++ | +++ |
| II-89 | ++ | +++ | ++ | +++ |
| II-90 | ++ | +++ | ++ | +++ |
| II-91 | ++ | +++ | +++ | +++ |
| II-92 | +++ | +++ | +++ | +++ |
| II-93 | +++ | +++ | +++ | +++ |
| II-94 | +++ | +++ | +++ | +++ |

TABLE 6-continued

| Example # | EC50 (without co-corrector) (μM) | Maximum % activity (without co-corrector) (%) | EC50 (with co-corrector) (μM) | Maximum % activity (with co-corrector) (%) |
|---|---|---|---|---|
| II-95 | +++ | +++ | +++ | +++ |
| II-96 | +++ | +++ | +++ | +++ |
| II-97 | +++ | +++ | +++ | +++ |
| II-98 | +++ | +++ | +++ | +++ |
| II-99 | +++ | +++ | +++ | +++ |
| II-100 | ++ | +++ | +++ | +++ |
| II-101 | +++ | +++ | +++ | +++ |
| II-102 | ++ | +++ | +++ | +++ |
| II-103 | +++ | +++ | +++ | +++ |
| II-104 | +++ | +++ | +++ | +++ |
| II-105 | +++ | +++ | +++ | +++ |
| II-106 | ++ | +++ | ++ | +++ |
| II-107 | +++ | +++ | +++ | +++ |
| II-108 | ++ | +++ | ++ | +++ |
| II-109 | ++ | +++ | ++ | +++ |
| II-110 | +++ | +++ | +++ | +++ |
| II-111 | +++ | +++ | +++ | +++ |
| II-112 | +++ | +++ | +++ | +++ |
| II-113 | +++ | +++ | +++ | +++ |
| II-115 | +++ | +++ | +++ | +++ |
| II-117 | ++ | +++ | +++ | +++ |
| III-3 | ++ | ++ | ++ | +++ |
| III-5 | + | + | + | + |
| III-6 | + | + | ++ | ++ |
| III-7 | + | + | ++ | ++ |
| III-8 | + | + | ++ | ++ |
| III-9 | + | + | ++ | + |
| III-10 | + | + | + | + |
| III-11 | + | + | + | + |
| III-12 | + | + | ++ | ++ |
| III-13 | ++ | + | +++ | ++ |
| III-14 | + | + | + | + |
| III-15 | ++ | + | ++ | ++ |
| III-16 | + | + | + | + |
| III-17 | + | + | + | + |
| III-19 | + | + | + | + |
| III-20 | + | + | + | + |
| III-22 | + | + | ++ | ++ |
| III-23 | ++ | ++ | ++ | +++ |
| III-24 | + | + | + | ++ |
| III-25 | + | + | ++ | + |
| III-26 | ++ | + | ++ | ++ |
| III-27 | + | + | + | + |
| III-28 | + | + | ++ | + |
| III-29 | ++ | + | ++ | ++ |
| III-30 | + | + | ++ | ++ |
| III-31 | + | + | ++ | ++ |
| III-32 | + | + | ++ | ++ |
| III-33 | ++ | + | ++ | ++ |
| III-34 | + | + | + | ++ |
| III-35 | + | + | + | ++ |
| III-36 | + | + | + | + |
| III-37 | + | + | ++ | ++ |
| III-55 | + | + | + | + |
| III-56 | + | + | + | + |
| III-57 | + | + | + | + |
| III-58 | + | + | ++ | ++ |
| III-59 | + | + | ++ | + |
| III-61 | + | + | ++ | ++ |
| III-62 | + | + | + | + |
| III-63 | + | + | ++ | ++ |
| III-64 | + | + | + | + |
| III-66 | + | + | ++ | ++ |
| III-67 | + | + | + | + |
| III-68 | + | + | +++ | + |
| III-70 | + | + | + | + |
| III-71 | ++ | ++ | ++ | +++ |
| III-72 | + | + | + | + |
| III-73 | + | + | + | + |
| III-74 | + | + | + | + |
| III-75 | + | + | + | + |
| III-76 | + | + | + | + |
| III-77 | + | + | + | + |
| III-78 | + | + | + | + |
| III-79 | + | + | ++ | + |
| III-80 | + | + | + | + |
| III-81 | + | + | + | + |
| III-82 | + | + | + | + |
| III-83 | + | + | + | ++ |
| III-84 | + | + | + | + |
| III-85 | ++ | ++ | ++ | +++ |
| III-86 | ++ | + | ++ | ++ |
| III-87 | ++ | ++ | ++ | +++ |
| III-88 | ++ | + | ++ | ++ |
| III-89 | ++ | + | +++ | ++ |
| III-90 | + | + | + | + |
| III-91 | + | +++ | ++ | +++ |
| III-92 | ++ | +++ | ++ | +++ |
| III-93 | ++ | +++ | ++ | +++ |
| III-94 | + | + | + | + |
| III-95 | ++ | +++ | ++ | +++ |
| III-96 | ++ | ++ | ++ | +++ |
| III-97 | ++ | +++ | ++ | +++ |
| III-98 | ++ | +++ | ++ | +++ |
| III-99 | ++ | ++ | ++ | +++ |
| III-100 | ++ | +++ | ++ | +++ |
| III-101 | +++ | +++ | +++ | +++ |
| III-102 | ++ | +++ | ++ | +++ |
| III-103 | ++ | +++ | +++ | +++ |
| III-104 | + | + | ++ | ++ |
| III-105 | + | + | + | + |
| III-106 | + | + | + | + |
| III-107 | + | + | + | + |
| III-108 | + | + | ++ | ++ |
| III-109 | + | + | + | + |
| III-111 | + | + | ++ | ++ |
| III-112 | + | + | + | + |
| III-113 | + | + | ++ | ++ |
| III-114 | + | + | ++ | + |
| III-115 | + | + | + | + |
| III-116 | + | + | + | + |
| III-119 | + | + | + | + |
| III-120 | + | + | + | + |
| III-121 | + | + | + | + |
| III-122 | ++ | +++ | ++ | +++ |
| III-123 | ++ | +++ | +++ | +++ |
| III-124 | ++ | ++ | ++ | +++ |
| III-125 | ++ | +++ | ++ | +++ |
| III-126 | +++ | ++ | +++ | ++ |
| III-127 | ++ | +++ | +++ | +++ |
| III-128 | ++ | + | ++ | ++ |
| III-129 | ++ | +++ | ++ | +++ |
| III-130 | ++ | +++ | +++ | +++ |
| III-131 | ++ | +++ | ++ | +++ |
| III-132 | +++ | +++ | +++ | +++ |
| III-133 | +++ | +++ | +++ | +++ |
| III-134 | +++ | +++ | +++ | +++ |
| GI-1 | +++ | +++ | +++ | +++ |
| GI-2 | +++ | +++ | +++ | +++ |
| GI-3 | +++ | +++ | +++ | +++ |
| GI-4 | ++ | +++ | +++ | +++ |
| GI-5 | ++ | +++ | +++ | +++ |
| GI-6 | ++ | +++ | +++ | +++ |
| GI-7 | ++ | +++ | +++ | +++ |
| GI-8 | +++ | +++ | +++ | +++ |
| GI-9 | +++ | +++ | +++ | +++ |
| GI-10 | +++ | +++ | +++ | +++ |
| GI-11 | +++ | +++ | +++ | +++ |
| GI-12 | +++ | +++ | +++ | +++ |
| GI-13 | +++ | +++ | +++ | +++ |
| GI-14 | ++ | +++ | +++ | +++ |
| GI-15 | +++ | +++ | +++ | +++ |
| GI-16 | ++ | +++ | +++ | +++ |
| GI-17 | ++ | +++ | +++ | +++ |
| GI-18 | ++ | +++ | +++ | +++ |
| GI-19 | ++ | +++ | +++ | +++ |
| GI-20 | +++ | +++ | +++ | +++ |
| GI-21 | +++ | +++ | +++ | +++ |

TABLE 6-continued

| Example # | EC50 (without co-corrector) (μM) | Maximum % activity (without co-corrector) (%) | EC50 (with co-corrector) (μM) | Maximum % activity (with co-corrector) (%) |
|---|---|---|---|---|
| GI-22 | +++ | +++ | +++ | +++ |
| GI-23 | +++ | +++ | +++ | +++ |
| GI-24 | +++ | +++ | +++ | +++ |
| GI-25 | ++ | +++ | +++ | +++ |
| GI-26 | ++ | +++ | +++ | +++ |
| GI-27 | ++ | +++ | +++ | +++ |
| GI-28 | ++ | +++ | +++ | +++ |
| GI-29 | +++ | +++ | +++ | +++ |
| GI-30 | +++ | +++ | +++ | +++ |
| GI-31 | +++ | +++ | +++ | +++ |
| GI-32 | ++ | +++ | +++ | +++ |
| GI-33 | ++ | +++ | +++ | +++ |
| GI-34 | ++ | +++ | +++ | +++ |
| GI-35 | ++ | +++ | +++ | +++ |
| GI-36 | ++ | +++ | +++ | +++ |
| GI-37 | ++ | +++ | +++ | +++ |
| GI-38 | +++ | +++ | +++ | +++ |
| GI-39 | +++ | +++ | +++ | +++ |
| GI-40 | +++ | +++ | +++ | +++ |
| GI-41 | +++ | +++ | +++ | +++ |
| GI-42 | +++ | +++ | +++ | +++ |
| GI-43 | +++ | +++ | +++ | +++ |
| GI-44 | +++ | +++ | +++ | +++ |
| GI-45 | +++ | +++ | +++ | +++ |
| GI-46 | +++ | +++ | +++ | +++ |
| GI-47 | +++ | +++ | +++ | +++ |
| GI-48 | +++ | +++ | +++ | +++ |
| GI-49 | +++ | +++ | +++ | +++ |
| GI-50 | +++ | +++ | +++ | +++ |
| GI-51 | +++ | +++ | +++ | +++ |
| GI-52 | +++ | +++ | +++ | +++ |
| GI-53 | +++ | +++ | +++ | +++ |
| GI-54 | ++ | +++ | ++ | +++ |
| GI-55 | ++ | +++ | +++ | +++ |
| GI-56 | ++ | +++ | +++ | +++ |
| GI-57 | +++ | +++ | +++ | +++ |
| GI-58 | +++ | +++ | +++ | +++ |
| GI-59 | ++ | +++ | +++ | +++ |
| GI-60 | +++ | +++ | +++ | +++ |
| GI-61 | +++ | +++ | +++ | +++ |
| GI-62 | +++ | +++ | +++ | +++ |
| GI-63 | +++ | +++ | +++ | +++ |
| GI-64 | +++ | +++ | +++ | +++ |
| GI-65 | +++ | +++ | +++ | +++ |
| GI-66 | +++ | +++ | +++ | +++ |
| GI-67 | ++ | +++ | +++ | +++ |
| GI-68 | +++ | +++ | +++ | +++ |
| GI-69 | +++ | +++ | +++ | +++ |
| GI-70 | +++ | +++ | +++ | +++ |
| GI-71 | ++ | +++ | +++ | +++ |
| GI-72 | +++ | +++ | +++ | +++ |
| GI-73 | ++ | +++ | +++ | +++ |
| GI-74 | ++ | +++ | +++ | +++ |
| GI-75 | ++ | +++ | +++ | +++ |
| GI-76 | +++ | +++ | +++ | +++ |
| GI-77 | +++ | +++ | +++ | +++ |
| GI-78 | +++ | +++ | +++ | +++ |
| GI-79 | +++ | +++ | +++ | +++ |
| GI-80 | +++ | +++ | +++ | +++ |
| GI-81 | +++ | +++ | +++ | +++ |
| GI-82 | +++ | +++ | +++ | +++ |
| GI-83 | ++ | +++ | +++ | +++ |
| GI-84 | ++ | +++ | +++ | +++ |
| GI-85 | ++ | +++ | +++ | +++ |
| GI-86 | +++ | +++ | +++ | +++ |
| GI-87 | ++ | +++ | +++ | +++ |
| GI-88 | +++ | +++ | +++ | +++ |
| GI-89 | +++ | +++ | +++ | +++ |
| GI-90 | +++ | +++ | +++ | +++ |
| GI-91 | ++ | +++ | +++ | +++ |
| GI-92 | +++ | +++ | +++ | +++ |
| GI-93 | +++ | +++ | +++ | +++ |
| GI-94 | +++ | +++ | +++ | +++ |
| GI-95 | +++ | +++ | +++ | +++ |
| GI-96 | ++ | +++ | +++ | +++ |
| GI-97 | +++ | +++ | +++ | +++ |
| GI-98 | +++ | +++ | +++ | +++ |
| GI-99 | +++ | +++ | +++ | +++ |
| GI-100 | +++ | +++ | +++ | +++ |
| GI-101 | ++ | +++ | +++ | +++ |
| GI-102 | ++ | +++ | +++ | +++ |
| GI-104 | +++ | +++ | +++ | +++ |
| GI-105 | +++ | +++ | +++ | +++ |
| GI-106 | +++ | +++ | +++ | +++ |
| GI-107 | +++ | +++ | +++ | +++ |
| GI-108 | +++ | +++ | +++ | +++ |
| GI-109 | ++ | +++ | +++ | +++ |
| GI-110 | +++ | +++ | +++ | +++ |
| GI-111 | +++ | +++ | +++ | +++ |
| GI-112 | ++ | +++ | +++ | +++ |
| GI-113 | +++ | +++ | +++ | +++ |
| GI-114 | ++ | +++ | +++ | +++ |
| GI-115 | +++ | +++ | +++ | +++ |
| GI-116 | ++ | +++ | +++ | +++ |
| GI-117 | +++ | +++ | +++ | +++ |
| GI-118 | +++ | +++ | +++ | +++ |
| GI-119 | +++ | +++ | +++ | +++ |
| GI-120 | ++ | +++ | +++ | +++ |
| GI-121 | +++ | +++ | +++ | +++ |
| GII-1 | ++[a] | + | ++[a] | ++ |
| GII-2 | ++ | ++ | ++ | ++ |
| GII-3 | ++ | ++ | ++ | ++ |
| GII-4 | ++ | ++ | ++ | ++ |
| GII-5 | ++ | ++ | ++ | ++ |
| GII-6 | ++ | ++ | ++ | ++ |
| GII-7 | ++ | ++ | ++ | +++ |
| GII-8 | + | + | ++[a] | ++ |
| GII-9 | ++ | ++ | ++ | ++ |
| GII-10 | ++ | +++ | ++ | +++ |
| GII-11 | ++[a] | ++ | ++ | +++ |
| GII-12 | ++ | ++ | ++ | +++ |
| GII-13 | ++ | ++ | ++ | +++ |
| GII-14 | ++ | +++ | ++ | +++ |
| GII-15 | ++ | +++ | ++ | +++ |
| GII-16 | ++[a] | ++ | ++ | ++ |
| GII-17 | ++ | + | ++ | ++ |
| GII-18 | ++ | +++ | ++ | +++ |
| GII-19 | ++[a] | ++ | ++ | +++ |
| GII-20 | ++[a] | ++ | ++[a] | ++ |
| GII-21 | + | + | ++ | ++ |
| GII-22 | ++ | +++ | ++ | +++ |
| GII-23 | ++[a] | ++ | ++[a] | ++ |
| GII-24 | ++[a] | ++ | ++ | ++ |
| GII-25 | ++ | +++ | ++ | +++ |
| GII-26 | ++ | +++ | ++ | +++ |
| GII-27 | ++ | ++ | ++ | ++ |
| GII-28 | ++[a] | ++ | ++ | ++ |
| GII-29 | ++ | +++ | ++ | +++ |
| GII-30 | ++ | +++ | ++ | +++ |
| GII-31 | ++ | +++ | ++ | +++ |
| GII-32 | ++[a] | ++ | ++[a] | ++ |
| GII-33 | ++[a] | ++ | ++[a] | ++ |
| GII-34 | ++[a] | ++ | ++[a] | ++ |
| GII-35 | ++ | +++ | ++ | ++ |
| GII-36 | ++ | ++ | ++ | +++ |
| GII-37 | ++ | +++ | ++ | +++ |
| GII-38 | ++ | +++ | ++ | +++ |
| GII-39 | ++ | ++ | ++ | ++ |
| GII-40 | ++ | +++ | ++ | +++ |
| GII-41 | ++ | ++ | ++ | +++ |
| GII-42 | ++[a] | ++ | ++ | ++ |
| GII-43 | ++[a] | ++ | ++ | ++ |
| GII-44 | ++[a] | ++ | ++[a] | ++ |
| GII-45 | ++ | +++ | ++ | +++ |
| GII-46 | ++[a] | ++ | ++ | ++ |
| GII-47 | ++ | +++ | + | +++ |
| GII-48 | ++ | +++ | ++ | +++ |
| GII-49 | ++ | +++ | ++ | +++ |

TABLE 6-continued

| Example # | EC50 (without co-corrector) (μM) | Maximum % activity (without co-corrector) (%) | EC50 (with co-corrector) (μM) | Maximum % activity (with co-corrector) (%) |
| --- | --- | --- | --- | --- |
| GII-50 | ++$^a$ | +++ | ++ | +++ |
| GII-51 | ++$^a$ | ++ | ++ | ++ |
| GII-52 | ++ | ++ | ++ | ++ |
| GII-53 | ++ | +++ | ++ | +++ |
| GII-54 | ++ | +++ | ++ | +++ |
| GII-55 | ++ | +++ | ++ | +++ |
| GII-56 | ++ | +++ | ++ | +++ |
| GII-57 | ++ | +++ | ++ | +++ |
| GII-58 | ++ | +++ | ++ | +++ |
| GII-59 | ++ | +++ | ++ | +++ |
| GIII-1 | ++$^a$ | + | ++$^a$ | ++ |
| GIII-2 | + | + | + | + |
| GIII-3 | ++ | +++ | ++ | +++ |
| GIII-5 | ++$^a$ | + | ++$^a$ | ++ |
| GIII-6 | + | + | + | + |
| GIII-7 | ++$^a$ | + | ++$^a$ | ++ |
| GIII-8 | ++$^a$ | ++ | ++$^a$ | ++ |
| GIII-10 | ++$^a$ | ++ | ++$^a$ | ++ |
| GIII-11 | ++$^a$ | ++ | ++$^a$ | ++ |
| GIII-12 | + | + | + | + |
| GIII-13 | + | + | ++$^a$ | ++ |
| GIII-14 | ++ | +++ | ++ | +++ |
| GIII-15 | ++$^a$ | + | ++$^a$ | ++ |
| GIII-16 | + | + | + | + |
| GIII-17 | ++$^a$ | ++ | ++$^a$ | ++ |
| GIII-18 | ++$^a$ | ++ | ++$^a$ | ++ |
| GIII-19 | ++$^a$ | ++ | ++$^a$ | ++ |
| GIII-20 | ++$^a$ | ++ | ++$^a$ | ++ |
| GIII-21 | ++$^a$ | ++ | ++$^a$ | ++ |
| GIII-22 | ++$^a$ | ++ | ++$^a$ | ++ |
| GIII-23 | + | ++ | + | ++ |
| GIII-24 | + | + | + | + |
| GIII-25 | ++$^a$ | ++ | ++$^a$ | ++ |
| GIII-26 | + | + | + | ++ |
| GIII-28 | + | + | + | ++ |
| GIII-29 | + | + | + | + |
| GIII-30 | + | + | ++$^a$ | + |
| GIII-31 | + | + | + | + |
| GIII-32 | + | + | + | + |
| GIII-33 | + | + | + | + |
| GIII-34 | + | + | + | + |
| GIII-35 | + | + | + | + |
| GIII-36 | + | + | + | + |

++$^a$ = data was reported as >3.00 μM

The data provided in the present application demonstrate that the compounds of the invention demonstrate activity in vitro, and may be useful in vivo in the treatment of cystic fibrosis.

Further benefits of Applicants' invention will be apparent to one skilled in the art from reading this patent application.

It is understood that the foregoing detailed description and accompanying examples are merely illustrative and are not to be taken as limitations upon the scope of the invention, which is defined solely by the appended claims and their equivalents. Various changes and modifications to the embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

We claim:

1. 1-(5-ethyl-2-{[(2R)-1-methoxypropan-2-yl]oxy}phenyl)-N-(2-methylquinoline-5-sulfonyl)cyclopropane-1-carboxamide.

2. A compound 1-(5-ethyl-2-{[(2R)-1-methoxypropan-2-yl]oxy}phenyl)-N-(2-methylquinoline-5-sulfonyl)cyclopropane-1-carboxamide or a pharmaceutically acceptable salt thereof.

* * * * *